US008288536B2

(12) United States Patent
Dong et al.

(10) Patent No.: US 8,288,536 B2
(45) Date of Patent: Oct. 16, 2012

(54) KINASE INHIBITORS

(75) Inventors: Qing Dong, San Diego, CA (US); David J. Hosfield, Solana Beach, CA (US); Bheema R. Paraselli, San Diego, CA (US); Nicholas Scorah, San Diego, CA (US); Jeffrey A. Stafford, San Diego, CA (US); Michael B. Wallace, San Diego, CA (US); Zhiyuan Zhang, San Diego, CA (US)

(73) Assignee: Takeda Pharmaceutical Company Limited, Osaka (JP)

( * ) Notice: Subject to any disclaimer, the term of this patent is extended or adjusted under 35 U.S.C. 154(b) by 277 days.

(21) Appl. No.: 12/755,301

(22) Filed: Apr. 6, 2010

(65) Prior Publication Data
US 2010/0216765 A1    Aug. 26, 2010

Related U.S. Application Data

(62) Division of application No. 11/251,616, filed on Oct. 14, 2005, now Pat. No. 7,713,973.

(60) Provisional application No. 60/619,302, filed on Oct. 15, 2004, provisional application No. 60/679,690, filed on May 11, 2005.

(51) Int. Cl.
C07D 487/04    (2006.01)
A61K 31/517    (2006.01)
A61P 19/02     (2006.01)
(52) U.S. Cl. ..................... 544/281; 514/259.1
(58) Field of Classification Search .............. 544/281; 514/259.1
See application file for complete search history.

(56) References Cited

U.S. PATENT DOCUMENTS

| | | | |
|---|---|---|---|
| 4,260,776 A | 4/1981 | Harnisch | |
| 5,491,147 A | 2/1996 | Boyd | |
| 5,739,144 A | 4/1998 | Warrellow | |
| 5,859,034 A | 1/1999 | Warrellow | |
| 5,962,312 A | 10/1999 | Plowman | |
| 5,972,676 A | 10/1999 | Plowman | |
| 6,143,480 A | 11/2000 | Obayashi et al. | |
| 6,207,401 B1 | 3/2001 | Plowman | |
| 6,265,411 B1 | 7/2001 | Thomas et al. | |
| 6,294,532 B1 | 9/2001 | Thomas et al. | |
| 6,352,858 B1 | 3/2002 | Cowsert | |
| 6,455,559 B1 | 9/2002 | Pevarello | |
| 6,528,509 B1 | 3/2003 | Hale | |
| 6,593,357 B1 | 7/2003 | Green | |
| 6,610,677 B2 | 8/2003 | Davies | |
| 6,613,776 B2 | 9/2003 | Knegtel | |
| 6,638,926 B2 | 10/2003 | Davies | |
| 6,653,300 B2 | 11/2003 | Bebbington | |
| 6,653,301 B2 | 11/2003 | Bebbington | |
| 6,656,939 B2 | 12/2003 | Bebbington | |
| 6,660,731 B2 | 12/2003 | Bebbington | |
| 6,664,247 B2 | 12/2003 | Bebbington | |
| 6,696,452 B2 | 2/2004 | Davies | |
| 6,699,865 B2 | 3/2004 | Hale | |
| 6,706,491 B1 | 3/2004 | Chang | |
| 6,716,575 B2 | 4/2004 | Plowman | |
| 6,727,251 B2 | 4/2004 | Bebbington | |
| 6,743,791 B2 | 6/2004 | Cao | |
| 6,770,643 B2 | 8/2004 | Cox | |
| 6,784,195 B2 | 8/2004 | Hale | |
| 6,787,545 B1 * | 9/2004 | Ohtani et al. | 514/243 |
| 6,806,272 B2 | 10/2004 | Bauer | |
| 6,831,091 B2 | 12/2004 | Gant | |
| 6,841,579 B1 | 1/2005 | Plowman | |
| 6,846,928 B2 | 1/2005 | Bebbington | |
| 6,849,653 B2 | 2/2005 | Clare | |
| 6,858,638 B2 | 2/2005 | Damour | |
| 6,861,422 B2 | 3/2005 | Hoffmann | |
| 6,872,533 B2 | 3/2005 | Toland | |
| 6,890,927 B2 | 5/2005 | Bogle | |
| 6,897,207 B2 | 5/2005 | Cox | |
| 6,916,798 B2 | 7/2005 | Green | |
| 6,919,338 B2 | 7/2005 | Mortlock | |

(Continued)

FOREIGN PATENT DOCUMENTS

DE    28 44 606    4/1980
(Continued)

OTHER PUBLICATIONS

Bhatti, Inayat A. et al. "Prolysis of 1-substituted pyrazoles and chloroform at 550 C: formation of a-carboline from 1-benzylpyrazoles" Journal of Chemical Society, Perkin Transactions 1: Organic and Bio-Organic Chemistry, (24), 3581-3586 Coden: JCPRB4; ISSN: 0300-922X, 1997, XP002417212 p. 3583; examples 24-27.

Database Caplus, Chemical Abstracts Service, Columbus, Ohio, US: XP002368789 retrieved from STN, Database accession No. 135:332604/DN abstract RN369597-42-2, -43-3 & JP 2001 294772 A, Oct. 23, 2001.

Database HCaplus ACS; XP002368787, retrieved from STN, Database accession No. 57:76580/DN abstract RN95936-94-0 & Sabata, B.K. et al.: Journal of Scientific and Industrial Research, Section B: Physical Sciences, vol. 21B, 1962, pp. 227-229.

(Continued)

Primary Examiner — Venkataraman Balasubramanian
(74) Attorney, Agent, or Firm — Mitchell R. Brustein; C. Amy Smith; David M Stemerick

(57) ABSTRACT

Compounds, pharmaceutical compositions and kits are provided for use with kinases that comprise a compound selected from the group consisting of:

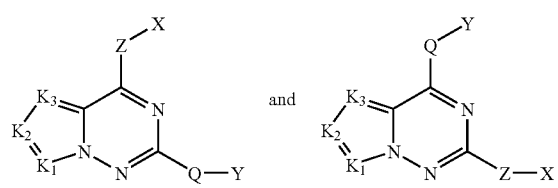

wherein the variables are as defined herein.

8 Claims, No Drawings

U.S. PATENT DOCUMENTS

| | | | |
|---|---|---|---|
| 6,982,265 B1 * | 1/2006 | Hunt et al. | 514/243 |
| 7,713,973 B2 * | 5/2010 | Dong et al. | 514/243 |
| 2002/0151573 A1 | 10/2002 | Gant | |
| 2002/0151574 A1 | 10/2002 | Hale | |
| 2003/0004161 A1 | 1/2003 | Bebbington | |
| 2003/0004164 A1 | 1/2003 | Bebbington | |
| 2003/0022885 A1 | 1/2003 | Bebbington | |
| 2003/0036543 A1 | 2/2003 | Bebbington | |
| 2003/0040536 A1 | 2/2003 | Hale | |
| 2003/0055044 A1 | 3/2003 | Davies | |
| 2003/0055068 A1 | 3/2003 | Bebbington | |
| 2003/0064981 A1 | 4/2003 | Knegtel | |
| 2003/0064982 A1 | 4/2003 | Davies | |
| 2003/0073687 A1 | 4/2003 | Bebbington | |
| 2003/0073692 A1 | 4/2003 | Pulici | |
| 2003/0078166 A1 | 4/2003 | Davies | |
| 2003/0078275 A1 | 4/2003 | Bebbington | |
| 2003/0083327 A1 | 5/2003 | Davies | |
| 2003/0092714 A1 | 5/2003 | Cao | |
| 2003/0105090 A1 | 6/2003 | Bebbington | |
| 2003/0105129 A1 | 6/2003 | Mortlock | |
| 2003/0109550 A1 | 6/2003 | Clare | |
| 2003/0109697 A1 | 6/2003 | Shepard | |
| 2003/0114432 A1 | 6/2003 | Clare | |
| 2003/0119856 A1 | 6/2003 | Cochran | |
| 2003/0125361 A1 | 7/2003 | Clare | |
| 2003/0171357 A1 | 9/2003 | Fancelli | |
| 2003/0171359 A1 | 9/2003 | Dahmann | |
| 2003/0187002 A1 | 10/2003 | Mortlock | |
| 2003/0187007 A1 | 10/2003 | Cao | |
| 2003/0208067 A1 | 11/2003 | Cao | |
| 2003/0225073 A1 | 12/2003 | Bebbington | |
| 2003/0225151 A1 | 12/2003 | Hale | |
| 2004/0002496 A1 | 1/2004 | Bebbington | |
| 2004/0009974 A1 | 1/2004 | Bebbington | |
| 2004/0009981 A1 | 1/2004 | Bebbington | |
| 2004/0009983 A1 | 1/2004 | Cox | |
| 2004/0010027 A1 | 1/2004 | Casuscelli | |
| 2004/0019046 A1 | 1/2004 | Pevarello | |
| 2004/0024040 A1 | 2/2004 | Green | |
| 2004/0029157 A1 | 2/2004 | Tatsuka | |
| 2004/0029857 A1 | 2/2004 | Hale | |
| 2004/0029885 A1 | 2/2004 | Bauer | |
| 2004/0049032 A1 | 3/2004 | Charrier | |
| 2004/0053931 A1 | 3/2004 | Cox | |
| 2004/0054179 A1 | 3/2004 | Yura et al. | |
| 2004/0063715 A1 | 4/2004 | Paruch et al. | |
| 2004/0082631 A1 | 4/2004 | Hale | |
| 2004/0097501 A1 | 5/2004 | Bebbington | |
| 2004/0097531 A1 | 5/2004 | Ledeboer | |
| 2004/0102360 A1 | 5/2004 | Barnett | |
| 2004/0102506 A1 | 5/2004 | Hale | |
| 2004/0106615 A1 | 6/2004 | Cochran | |
| 2004/0106667 A1 | 6/2004 | Damour | |
| 2004/0110741 A1 | 6/2004 | Bergmanis | |
| 2004/0116454 A1 | 6/2004 | Davies | |
| 2004/0147524 A1 | 7/2004 | Bauer | |
| 2004/0157893 A1 | 8/2004 | Bebbington | |
| 2004/0167121 A1 | 8/2004 | Aronov | |
| 2004/0167124 A1 | 8/2004 | Chen | |
| 2004/0167141 A1 | 8/2004 | Bebbington | |
| 2004/0176380 A1 | 9/2004 | Hoffmann | |
| 2004/0180881 A1 | 9/2004 | Berta | |
| 2004/0198737 A1 | 10/2004 | Cox | |
| 2004/0214814 A1 | 10/2004 | Bebbington | |
| 2004/0220200 A1 | 11/2004 | Maltais | |
| 2004/0224944 A1 | 11/2004 | Bebbington | |
| 2004/0229875 A1 | 11/2004 | Cao | |
| 2004/0235867 A1 | 11/2004 | Bilodeau | |
| 2004/0235919 A1 | 11/2004 | Pevarello | |
| 2004/0242559 A1 | 12/2004 | Ugolini | |
| 2004/0242613 A1 | 12/2004 | Cardozo | |
| 2004/0248853 A1 | 12/2004 | Dyckman | |
| 2004/0254177 A1 | 12/2004 | Amici | |
| 2004/0265852 A1 | 12/2004 | Plowman | |
| 2005/0002938 A1 | 1/2005 | Plowman | |
| 2005/0004110 A1 | 1/2005 | Bebbington | |
| 2005/0004152 A1 | 1/2005 | Cochran | |
| 2005/0004176 A1 | 1/2005 | Dyckman | |
| 2005/0009876 A1 | 1/2005 | Bhagwat | |
| 2005/0014760 A1 | 1/2005 | Hoffmann | |
| 2005/0014761 A1 | 1/2005 | Hoffmann | |
| 2005/0020583 A1 | 1/2005 | Pulici | |
| 2005/0026984 A1 | 2/2005 | Bigot | |
| 2005/0026991 A1 | 2/2005 | Cholody | |
| 2005/0032839 A1 | 2/2005 | Fancelli | |
| 2005/0032869 A1 | 2/2005 | Berta | |
| 2005/0038023 A1 | 2/2005 | Bebbington | |
| 2005/0043323 A1 | 2/2005 | Vanotti | |
| 2005/0043346 A1 | 2/2005 | Vanotti | |
| 2005/0059657 A1 | 3/2005 | Cavicchioli | |
| 2005/0059722 A1 | 3/2005 | Damour | |
| 2005/0065169 A1 | 3/2005 | Wang | |
| 2005/0065171 A1 | 3/2005 | Shakespeare | |
| 2005/0070561 A1 | 3/2005 | Jung | |
| 2005/0085490 A1 | 4/2005 | Wang | |
| 2005/0085531 A1 | 4/2005 | Hodge | |
| 2005/0107386 A1 | 5/2005 | Narla | |
| 2005/0113460 A1 | 5/2005 | Glick | |
| 2005/0124640 A1 | 6/2005 | Cardozo | |
| 2005/0125852 A1 | 6/2005 | Caenepeel | |
| 2005/0130977 A1 | 6/2005 | Lindsley | |
| 2005/0137171 A1 | 6/2005 | Cherrier | |
| 2005/0137199 A1 | 6/2005 | Jin | |
| 2005/0137201 A1 | 6/2005 | Aronov | |
| 2005/0143402 A1 | 6/2005 | Cheetham | |
| 2005/0170442 A1 | 8/2005 | Kupcho | |
| 2007/0117816 A1 | 5/2007 | Brown et al. | |

FOREIGN PATENT DOCUMENTS

| | | |
|---|---|---|
| EP | 1134221 A1 | 9/2001 |
| EP | 1209158 A1 | 5/2002 |
| EP | 1367058 A1 | 12/2003 |
| FR | 1 242 962 | 10/1960 |
| FR | 2 818 278 | 6/2002 |
| FR | 2876377 | 4/2006 |
| GB | 828 847 | 2/1960 |
| WO | WO 97/42187 | 11/1997 |
| WO | WO 98/18782 A1 | 5/1998 |
| WO | WO 98/28281 A1 | 7/1998 |
| WO | WO 98/41512 A1 | 9/1998 |
| WO | WO 99/10349 | 3/1999 |
| WO | WO 99/37788 | 7/1999 |
| WO | WO 01/07466 A1 | 2/2001 |
| WO | WO 01/21594 A1 | 3/2001 |
| WO | WO 01/21595 A1 | 3/2001 |
| WO | WO 01/21596 A1 | 3/2001 |
| WO | WO 01/21597 A1 | 3/2001 |
| WO | WO 01/25220 A | 4/2001 |
| WO | WO 01/32653 A1 | 5/2001 |
| WO | WO 01/47922 A2 | 7/2001 |
| WO | WO 01/47922 A3 | 7/2001 |
| WO | WO 01/55116 A2 | 8/2001 |
| WO | WO 01/55116 A3 | 8/2001 |
| WO | WO 01/56993 A2 | 8/2001 |
| WO | WO 01/56993 A3 | 8/2001 |
| WO | WO 01/57022 A2 | 8/2001 |
| WO | WO 01/57022 A3 | 8/2001 |
| WO | WO 01/98299 A1 | 12/2001 |
| WO | WO 02/00649 A1 | 1/2002 |
| WO | WO 02/12242 A2 | 2/2002 |
| WO | WO 02/22601 A1 | 3/2002 |
| WO | WO 02/22602 | 3/2002 |
| WO | WO 02/22602 A2 | 3/2002 |
| WO | WO 02/22602 A3 | 3/2002 |
| WO | WO 02/22603 A1 | 3/2002 |
| WO | WO 02/22604 A1 | 3/2002 |
| WO | WO 02/22605 A1 | 3/2002 |
| WO | WO 02/22606 A1 | 3/2002 |
| WO | WO 02/22607 A1 | 3/2002 |
| WO | WO 02/22608 A1 | 3/2002 |
| WO | WO 02/48114 A1 | 6/2002 |
| WO | WO 02/50065 A2 | 6/2002 |
| WO | WO 02/50065 A3 | 6/2002 |
| WO | WO 02/50066 A2 | 6/2002 |
| WO | WO 02/50066 A3 | 6/2002 |
| WO | WO 02/057259 A2 | 7/2002 |

| | | |
|---|---|---|
| WO | WO 02/057259 A3 | 7/2002 |
| WO | WO 02/059111 A2 | 8/2002 |
| WO | WO 02/059111 A3 | 8/2002 |
| WO | WO 02/059112 A2 | 8/2002 |
| WO | WO 02/059112 A3 | 8/2002 |
| WO | WO 02/062789 A1 | 8/2002 |
| WO | WO 02/062804 A1 | 8/2002 |
| WO | WO 02/064586 A2 | 8/2002 |
| WO | WO 02/064586 A3 | 8/2002 |
| WO | WO 02/066461 A1 | 8/2002 |
| WO | WO 02/068415 A1 | 9/2002 |
| WO | WO 02/079192 | 10/2002 |
| WO | WO 02/083654 | 10/2002 |
| WO | WO 02/094809 A1 | 11/2002 |
| WO | WO 02/096867 A2 | 12/2002 |
| WO | WO 02/096867 A3 | 12/2002 |
| WO | WO 02/096905 A1 | 12/2002 |
| WO | WO 03/000688 A1 | 1/2003 |
| WO | WO 03/000695 A1 | 1/2003 |
| WO | WO 03/008365 A2 | 1/2003 |
| WO | WO 03/009852 | 2/2003 |
| WO | WO 03/011287 A1 | 2/2003 |
| WO | WO 03/020276 A1 | 3/2003 |
| WO | WO 03/028720 A1 | 4/2003 |
| WO | WO 03/031606 A2 | 4/2003 |
| WO | WO 03/031606 A3 | 4/2003 |
| WO | WO 03/035625 A1 | 5/2003 |
| WO | WO 03/051358 A1 | 6/2003 |
| WO | WO 03/053330 A2 | 7/2003 |
| WO | WO 03/055491 A1 | 7/2003 |
| WO | WO 03/077921 A1 | 9/2003 |
| WO | WO 03/078402 A1 | 9/2003 |
| WO | WO 03/078423 | 9/2003 |
| WO | WO 03/078426 A1 | 9/2003 |
| WO | WO 03/078427 A1 | 9/2003 |
| WO | WO 03/082853 A1 | 10/2003 |
| WO | WO 03/087395 A2 | 10/2003 |
| WO | WO 03/087395 A3 | 10/2003 |
| WO | WO 03/091246 A1 | 11/2003 |
| WO | WO 03/092607 A2 | 11/2003 |
| WO | WO 03/092607 A3 | 11/2003 |
| WO | WO 03/097610 A1 | 11/2003 |
| WO | WO 03/106417 A1 | 12/2003 |
| WO | WO 03/106500 A1 | 12/2003 |
| WO | WO 03/107002 A1 | 12/2003 |
| WO | WO 2004/000833 A1 | 12/2003 |
| WO | WO 2004/005283 A1 | 1/2004 |
| WO | WO 2004/006838 A2 | 1/2004 |
| WO | WO 2004/007504 A1 | 1/2004 |
| WO | WO 2004/013144 A1 | 2/2004 |
| WO | WO 2004/013146 A1 | 2/2004 |
| WO | WO 2004/014374 A1 | 2/2004 |
| WO | WO 2004/037814 A1 | 5/2004 |
| WO | WO 2004/043953 A1 | 5/2004 |
| WO | WO 2004/055019 A1 | 7/2004 |
| WO | WO 2004/056812 A1 | 7/2004 |
| WO | WO 2004/056827 A1 | 7/2004 |
| WO | WO 2004/058752 A1 | 7/2004 |
| WO | WO 2004/058781 A1 | 7/2004 |
| WO | WO 2004/058782 A1 | 7/2004 |
| WO | WO 2004/066919 A2 | 8/2004 |
| WO | WO 2004/067516 A1 | 8/2004 |
| WO | WO 2004/070062 A2 | 8/2004 |
| WO | WO 2004/071390 A2 | 8/2004 |
| WO | WO 2004/071507 A1 | 8/2004 |
| WO | WO 2004/076454 A1 | 9/2004 |
| WO | WO 2004/080457 A1 | 9/2004 |
| WO | WO 2004/083203 A1 | 9/2004 |
| WO | WO 2004/087056 | 10/2004 |
| WO | WO 2004/087707 | 10/2004 |
| WO | WO 2004/090106 A2 | 10/2004 |
| WO | WO 2004/094410 A1 | 11/2004 |
| WO | WO 2004/096129 A2 | 11/2004 |
| WO | WO 2004/096130 A2 | 11/2004 |
| WO | WO 2004/096131 A2 | 11/2004 |
| WO | WO 2004/096135 A2 | 11/2004 |
| WO | WO 2004/098518 A2 | 11/2004 |
| WO | WO 2004/098528 A2 | 11/2004 |
| WO | WO 2004/099156 A1 | 11/2004 |
| WO | WO 2004/104007 A1 | 12/2004 |
| WO | WO 2004/105764 A1 | 12/2004 |
| WO | WO 2004/113324 A1 | 12/2004 |
| WO | WO 2005/002552 A2 | 1/2005 |
| WO | WO 2005/002571 A1 | 1/2005 |
| WO | WO 2005/002576 A2 | 1/2005 |
| WO | WO 2005/004988 A2 | 1/2005 |
| WO | WO 2005/005414 A2 | 1/2005 |
| WO | WO 2005/005427 A1 | 1/2005 |
| WO | WO 2005/005438 A1 | 1/2005 |
| WO | WO 2005/007641 A1 | 1/2005 |
| WO | WO 2005/009348 A2 | 2/2005 |
| WO | WO 2005/009987 A1 | 2/2005 |
| WO | WO 2005/011675 A1 | 2/2005 |
| WO | WO 2005/012262 A1 | 2/2005 |
| WO | WO 2005/012280 A1 | 2/2005 |
| WO | WO 2005/012298 A1 | 2/2005 |
| WO | WO 2005/012304 A2 | 2/2005 |
| WO | WO 2005/012307 A1 | 2/2005 |
| WO | WO 2005/016252 A2 | 2/2005 |
| WO | WO 2005/019190 A2 | 3/2005 |
| WO | WO 2005/026150 A1 | 3/2005 |
| WO | WO 2005/026155 A1 | 3/2005 |
| WO | WO 2005/026156 A1 | 3/2005 |
| WO | WO 2005/026157 A1 | 3/2005 |
| WO | WO 2005/027907 A1 | 3/2005 |
| WO | WO 2005/028475 A2 | 3/2005 |
| WO | WO 2005/033102 | 4/2005 |
| WO | WO 2005/034840 A2 | 4/2005 |
| WO | WO 2005/035527 A1 | 4/2005 |
| WO | WO 2005/037797 A1 | 4/2005 |
| WO | WO 2005/037825 A2 | 4/2005 |
| WO | WO 2005/037843 A1 | 4/2005 |
| WO | WO 2005/040133 A1 | 5/2005 |
| WO | WO 2005/040159 A1 | 5/2005 |
| WO | WO 2005/040368 | 5/2005 |
| WO | WO 2005/042525 A1 | 5/2005 |
| WO | WO 2005/044270 A1 | 5/2005 |
| WO | WO 2005/047266 A1 | 5/2005 |
| WO | WO 2005/049033 A1 | 6/2005 |
| WO | WO 2005/051308 | 6/2005 |
| WO | WO 2005/051942 | 6/2005 |
| WO | WO 2005/095400 | 10/2005 |
| WO | WO 2005/105788 A2 | 11/2005 |
| WO | WO 2005/123672 A2 | 12/2005 |
| WO | WO 2006/040451 A2 | 4/2006 |
| WO | WO 2006/131552 A1 | 12/2006 |
| WO | WO 2007/044779 | 2/2009 |

OTHER PUBLICATIONS

Database HCaplus ACS; XP002368788 retrieved from STN, Database accession No. 91:176650/DN abstract RN71811-83-1 & Vavrova, Jaroslava et al.: Collection of Czechoslovak Chemical Communications, vol. 44, 1979, pp. 1413-1422.
Database Registry ACS; Apr. 10, 2001; XP002368782, retrieved from STN, Database accession No. 330683-80-2/RN abstract.
Database Registry ACS; Feb. 8, 2001; XP002368783, retrieved from STN, Database accession No. 320741-28-4/RN abstract.
Database Registry ACS; Jan. 11, 2001; XP002368784, retrieved from STN, Database accession No. 313549-01-8/RN abstract.
Database Registry ACS; Jan. 11, 2001; XP002368785, retrieved from STN, Database accession No. 313522-23-5/RN abstract.
Database Registry ACS; Jan. 4, 2001; XP002368786, retrieved from STN, Database accession No. 312755-54-7/RN abstract.
Database Registry ACS; Mar. 18, 2002; XP002368781, retrieved from STN, Database accession No. 401622-65-9/RN abstract.
Database Registry ACS; Oct. 20, 2000; XP002368779, retrieved from STN, Database accession No. 297763-91-8/RN abstract.
Database Registry ACS; Oct. 9, 2000; XP002368780, retrieved from STN, Database accession No. 293763-18-5/RN abstract.
Drobnic-Kosorok, M. et al., "Transformations of Some Substituted Methylene Heterocycles with Some Nucleophiles (1)", Journal of Heterocyclic Chemistry, vol. 13, 1976, pp. 1279-1282, XP008060243.
Kurasawa, Y. et al., "A Facile Synthesis of Novel Heterocycle-Conjugated Quinoxalines", Heterocycles vol. 22, No. 5, 1984, pp. 1189-1193, XP008059222 ISSN: 0385-5414.

Kurasawa, Y. et al., "A New Synthesis of 1,5-Dihydropyridazino[3,4-*b*] quinoxalines and 2-(Pyrazol-4-yl) quinoxalines", J. Heterocyclic Chemistry, vol. 33, 1996, pp. 757-762, XP008060252.

Li Sun et al.: Identification of substituted 3-(4, 5, 6, 7-tetrahydro-1H-indol-2-yl)met hylene)-1, 3-dihydroindol-2-ones as growth factor receptor inhibitors for VEGF-R2 (Flk-1/KDR), FGF-R1 and PDGF-Rbeta tyroine kinases, Journal of Medicinal Chemistry, American Chemical Society, Washington, US, vol. 43, Jun. 23, 2000, pp. 2655-2663, XP002222716.

Li Sun et al.: Synthesis and biological evaluation of 3-substituted indolin-2-ones: a novel class of tyrosine kinase inhibitors that exhibit selectivity toward particular receptor tyrosine kinases. Journal of Medicinal and Pharmaceutical Chemistry, American Chemistry Society, Easton, US, vol. 41, No. 14, 1998, pp. 2588-2603, XP002184621.

Mehta, Lina K. et al. The Eliminatin of an Alkoxy Group in the Photo-Graebe-Ullmann Convension of 1-(2,5-Dialkoxyphenyl)triazolopyridines into Carbolines, and the Preparation of a-,u-and x-Carboine Quinones, J. Chem. Soc. Perkin Trans. 1263-1267, 1993.

P. Bruni, G. Guerra: Enolizable cylic ketones. I. Reaction with activated heteroaromatic N-oxides, Annali Di Chimica, vol. 57, No. 6, 1967, pp. 688-697, XP009048877 Rome p. 691, reaction scheme middle of page, last compound.

* cited by examiner

KINASE INHIBITORS

RELATED APPLICATIONS

This application is a divisional of U.S. application Ser. No. 11/251,616, filed Oct. 14, 2005, now U.S. Pat. No. 7,713,973, which claims the benefit of U.S. Provisional Application No. 60/619,302 filed Oct. 15, 2004 and U.S. Provisional Application No. 60/679,690 filed May 11, 2005, which are incorporated herein by reference.

FIELD OF THE INVENTION

The invention relates to compounds that may be used to inhibit kinases as well as compositions of matter and kits comprising these compounds. The present invention also relates to methods for inhibiting kinases as well as treatment methods using compounds according to the present invention.

BACKGROUND OF THE INVENTION

The invention relates to inhibitors of enzymes that catalyze phosphoryl transfer and/or that bind ATP/GTP nucleotides, compositions comprising the inhibitors, and methods of using the inhibitors and inhibitor compositions. The inhibitors and compositions comprising them are useful for treating or modulating disease in which phosphoryl transferases, including kinases, may be involved, symptoms of such disease, or the effect of other physiological events mediated by phosphoryl transferases, including kinases. The invention also provides for methods of making the inhibitor compounds and methods for treating diseases in which one or more phosphoryl transferase, including kinase, activities is involved.

Phosphoryl transferases are a large family of enzymes that transfer phosphorous-containing groups from one substrate to another. By the conventions set forth by the Nomenclature Committee of the International Union of Biochemistry and Molecular Biology (IUBMB) enzymes of this type have Enzyme Commission (EC) numbers starting with 2.7.-.- (See, Bairoch A., The ENZYME database in Nucleic Acids Res. 28:204-305 (2000)). Kinases are a class of enzymes that function in the catalysis of phosphoryl transfer. The protein kinases constitute the largest subfamily of structurally related phosphoryl transferases and are responsible for the control of a wide variety of signal transduction processes within the cell. (See, Hardie, G. and Hanks, S. (1995) The Protein Kinase Facts Book, I and II, Academic Press, San Diego, Calif.). Protein kinases are thought to have evolved from a common ancestral gene due to the conservation of their structure and catalytic function. Almost all kinases contain a similar 250-300 amino acid catalytic domain. The protein kinases may be categorized into families by the substrates they phosphorylate (e.g., protein-tyrosine, protein-serine/threonine, histidine, etc.). Protein kinase sequence motifs have been identified that generally correspond to each of these kinase families (See, for example, Hanks, S. K.; Hunter, T., FASEB J. 9:576-596 (1995); Kinghton et al., Science, 253:407-414 (1991); Hiles et al., Cell 70:419-429 (1992); Kunz et al., Cell, 73:585-596 (1993); Garcia-Bustos et al., EMBO J., 13:2352-2361 (1994)). Lipid kinases (e.g. PI3K) constitute a separate group of kinases with structural similarity to protein kinases.

Protein and lipid kinases regulate many different cell processes including, but not limited to, proliferation, growth, differentiation, metabolism, cell cycle events, apoptosis, motility, transcription, translation and other signaling processes, by adding phosphate groups to targets such as proteins or lipids. Phosphorylation events catalyzed by kinases act as molecular on/off switches that can modulate or regulate the biological function of the target protein. Phosphorylation of target proteins occurs in response to a variety of extracellular signals (hormones, neurotransmitters, growth and differentiation factors, etc.), cell cycle events, environmental or nutritional stresses, etc. Protein and lipid kinases can function in signaling pathways to activate or inactivate, or modulate the activity of (either directly or indirectly) the targets. These targets may include, for example, metabolic enzymes, regulatory proteins, receptors, cytoskeletal proteins, ion channels or pumps, or transcription factors. Uncontrolled signaling due to defective control of protein phosphorylation has been implicated in a number of diseases and disease conditions, including, for example, inflammation, cancer, allergy/asthma, diseases and conditions of the immune system, disease and conditions of the central nervous system (CNS), cardiovascular disease, dermatology, and angiogenesis.

Initial interest in protein kinases as pharmacological targets was stimulated by the findings that many viral oncogenes encode structurally modified cellular protein kinases with constitutive enzyme activity. These findings pointed to the potential involvement of oncogene related protein kinases in human proliferatives disorders. Subsequently, deregulated protein kinase activity, resulting from a variety of more subtle mechanisms, has been implicated in the pathophysiology of a number of important human disorders including, for example, cancer, CNS conditions, and immunologically related diseases. The development of selective protein kinase inhibitors that can block the disease pathologies and/or symptoms resulting from aberrant protein kinase activity has therefore generated much interest.

Cancer results from the deregulation of the normal processes that control cell division, differentiation and apoptotic cell death. Protein kinases play a critical role in this regulatory process. A partial non-limiting list of such kinases includes abl, Aurora-A, Aurora-B, Aurora-C, ATK, bcr-abl, Blk, Brk, Btk, c-Kit, c-Met, c-Src, CDK1, CDK2, CDK4, CDK6, cRaf1, CSF1R, CSK, EGFR, ErbB2, ErbB3, ErbB4, ERK, Fak, fes, FGFR1, FGFR2, FGFR3, FGFR4, FGFR5, Fgr, FLK-4, Flt-1, Fps, Frk, Fyn, Hck, IGF-1R, INS-R, Jak, KDR, Lck, Lyn, MEK, p38, PDGFR, PIK, PKC, PYK2, Ros, Tie1, Tie2, Trk, Yes and Zap70. In mammalian biology, such protein kinases comprise mitogen activated protein kinase (MAPK) signaling pathways. MAPK signaling pathways are inappropriately activated by a variety of common disease-associated mechanisms such as mutation of ras genes and deregulation of growth factor receptors (Magnuson et al., Seminars in Cancer Biology 5:247-252 (1994)). Therefore the inhibition of protein kinases is an object of the present invention.

Aurora kinases (Aurora-A, Aurora-B, Aurora-C) are serine/threonine protein kinases that have been implicated in human cancer, such as colon, breast and other solid tumors. Aurora-A (also sometimes referred to as AIK) is believed to be involved in protein phosphorylation events that regulate the cell cycle. Specifically, Aurora-A may play a role in controlling the accurate segregation of chromosomes during mitosis. Misregulation of the cell cycle can lead to cellular proliferation and other abnormalities. In human colon cancer tissue, Aurora-A, Aurora-B, Aurora-C have been found to be overexpressed (See, Bischoff et al., EMBO J., 17:3052-3065 (1998); Schumacher et al., J. Cell Biol. 143:1635-1646 (1998); Kimura et al., J. Biol. Chem., 272:13766-13771 (1997)).

There is a continued need to find new therapeutic agents to treat human diseases. The protein kinases, specifically but not limited to Aurora-A, Aurora-B and Aurora-C are especially attractive targets for the discovery of new therapeutics due to their important role in cancer, diabetes, Alzheimer's disease and other diseases.

SUMMARY OF THE INVENTION

The present invention relates to compounds that have activity for inhibiting kinases. The present invention also provides compositions, articles of manufacture and kits comprising these compounds.

In one embodiment, a pharmaceutical composition is provided that comprises a kinase inhibitor according to the present invention as an active ingredient. Pharmaceutical compositions according to the invention may optionally comprise 0.001%-100% of one or more kinase inhibitors of this invention. These pharmaceutical compositions may be administered or coadministered by a wide variety of routes, including for example, orally, parenterally, intraperitoneally, intravenously, intraarterially, transdermally, sublingually, intramuscularly, rectally, transbuccally, intranasally, liposomally, via inhalation, vaginally, intraoccularly, via local delivery (for example by catheter or stent), subcutaneously, intraadiposally, intraarticularly, or intrathecally. The compositions may also be administered or coadministered in slow release dosage forms.

The invention is also directed to kits and other articles of manufacture for treating disease states associated with kinases.

In one embodiment, a kit is provided that comprises a composition comprising at least one kinase inhibitor of the present invention in combination with instructions. The instructions may indicate the disease state for which the composition is to be administered, storage information, dosing information and/or instructions regarding how to administer the composition. The kit may also comprise packaging materials. The packaging material may comprise a container for housing the composition. The kit may also optionally comprise additional components, such as syringes for administration of the composition. The kit may comprise the composition in single or multiple dose forms.

In another embodiment, an article of manufacture is provided that comprises a composition comprising at least one kinase inhibitor of the present invention in combination with packaging materials. The packaging material may comprise a container for housing the composition. The container may optionally comprise a label indicating the disease state for which the composition is to be administered, storage information, dosing information and/or instructions regarding how to administer the composition. The kit may also optionally comprise additional components, such as syringes for administration of the composition. The kit may comprise the composition in single or multiple dose forms.

Also provided are methods for preparing compounds, compositions and kits according to the present invention. For example, several synthetic schemes are provided herein for synthesizing compounds according to the present invention.

Also provided are methods for using compounds, compositions, kits and articles of manufacture according to the present invention.

In one embodiment, the compounds, compositions, kits and articles of manufacture are used to inhibit kinases.

In another embodiment, the compounds, compositions, kits and articles of manufacture are used to treat a disease state for which kinases possesses activity that contributes to the pathology and/or symptomology of the disease state.

In another embodiment, a compound is administered to a subject wherein kinases activity within the subject is altered, preferably reduced.

In another embodiment, a prodrug of a compound is administered to a subject that is converted to the compound in vivo where it inhibits kinases.

In another embodiment, a method of inhibiting kinases is provided that comprises contacting kinases with a compound according to the present invention.

In another embodiment, a method of inhibiting kinases is provided that comprises causing a compound according to the present invention to be present in a subject in order to inhibit kinases in vivo.

In another embodiment, a method of inhibiting kinases is provided that comprises administering a first compound to a subject that is converted in vivo to a second compound wherein the second compound inhibits kinases in vivo. It is noted that the compounds of the present invention may be the first or second compounds.

In another embodiment, a therapeutic method is provided that comprises administering a compound according to the present invention.

In another embodiment, a method of inhibiting cell proliferation is provided that comprises contacting a cell with an effective amount of a compound according to the present invention.

In another embodiment, a method of inhibiting cell proliferation in a patient is provided that comprises administering to the patient a therapeutically effective amount of a compound according to the present invention.

In another embodiment, a method of treating a condition in a patient which is known to be mediated by kinases, or which is known to be treated by kinase inhibitors, comprising administering to the patient a therapeutically effective amount of a compound according to the present invention.

In another embodiment, a method is provided for using a compound according to the present invention in order to manufacture a medicament for use in the treatment of disease state which is known to be mediated by kinases, or which is known to be treated by kinase inhibitors.

In another embodiment, a method is provided for treating a disease state for which kinases possesses activity that contributes to the pathology and/or symptomology of the disease state, the method comprising: causing a compound according to the present invention to be present in a subject in a therapeutically effective amount for the disease state.

In another embodiment, a method is provided for treating a disease state for which kinases possesses activity that contributes to the pathology and/or symptomology of the disease state, the method comprising: administering a first compound to a subject that is converted in vivo to a second compound such that the second compound is present in the subject in a therapeutically effective amount for the disease state. It is noted that the compounds of the present invention may be the first or second compounds.

In another embodiment, a method is provided for treating a disease state for which kinases possesses activity that contributes to the pathology and/or symptomology of the disease state, the method comprising: administering a compound according to the present invention to a subject such that the compound is present in the subject in a therapeutically effective amount for the disease state.

It is noted in regard to all of the above embodiments that the present invention is intended to encompass all pharmaceutically acceptable ionized forms (e.g., salts) and solvates (e.g., hydrates) of the compounds, regardless of whether such ionized forms and solvates are specified since it is well know in the art to administer pharmaceutical agents in an ionized or solvated form. It is also noted that unless a particular stereochemistry is specified, recitation of a compound is intended to encompass all possible stereoisomers (e.g., enantiomers or diastereomers depending on the number of chiral centers), independent of whether the compound is present as an individual isomer or a mixture of isomers. Further, unless otherwise specified, recitation of a compound is intended to encompass all possible resonance forms and tautomers. With regard to the claims, the language "compound comprising the formula" is intended to encompass the compound and all pharmaceutically acceptable ionized forms and solvates, all possible stereoisomers, and all possible resonance forms and tautomers unless otherwise specifically specified in the particular claim.

It is further noted that prodrugs may also be administered which are altered in vivo and become a compound according to the present invention. The various methods of using the compounds of the present invention are intended, regardless of whether prodrug delivery is specified, to encompass the administration of a prodrug that is converted in vivo to a compound according to the present invention. It is also noted that certain compounds of the present invention may be altered in vivo prior to inhibiting kinases and thus may themselves be prodrugs for another compound. Such prodrugs of another compound may or may not themselves independently have kinase inhibitory activity.

DEFINITIONS

Unless otherwise stated, the following terms used in the specification and claims shall have the following meanings for the purposes of this Application.

"Alicyclic" means a moiety comprising a non-aromatic ring structure. Alicyclic moieties may be saturated or partially unsaturated with one, two or more double or triple bonds. Alicyclic moieties may also optionally comprise heteroatoms such as nitrogen, oxygen and sulfur. The nitrogen atoms can be optionally quaternerized or oxidized and the sulfur atoms can be optionally oxidized. Examples of alicyclic moieties include, but are not limited to moieties with $C_{3-8}$ rings such as cyclopropyl, cyclohexane, cyclopentane, cyclopentene, cyclopentadiene, cyclohexane, cyclohexene, cyclohexadiene, cycloheptane, cycloheptene, cycloheptadiene, cyclooctane, cyclooctene, and cyclooctadiene.

"Aliphatic" means a moiety characterized by a straight or branched chain arrangement of constituent carbon atoms and may be saturated or partially unsaturated with one, two or more double or triple bonds.

"Alkoxy" means an oxygen moiety having a further alkyl substituent. The alkoxy groups of the present invention can be optionally substituted.

"Alkyl" represented by itself means a straight or branched, saturated or unsaturated, aliphatic radical having a chain of carbon atoms, optionally with oxygen (See "oxaalkyl") or nitrogen atoms (See "aminoalkyl") between the carbon atoms. $C_X$alkyl and $C_{X-Y}$alkyl are typically used where X and Y indicate the number of carbon atoms in the chain. For example, $C_{1-6}$ alkyl includes alkyls that have a chain of between 1 and 6 carbons (e.g., methyl, ethyl, propyl, isopropyl, butyl, sec-butyl, isobutyl, tert-butyl, vinyl, allyl, 1-propenyl, isopropenyl, 1-butenyl, 2-butenyl, 3-butenyl, 2-methylallyl, ethynyl, 1-propynyl, 2-propynyl, and the like). Alkyl represented along with another radical (e.g., as in arylalkyl, heteroarylalkyl) means a straight or branched, saturated or unsaturated aliphatic divalent radical having the number of atoms indicated or when no atoms are indicated means a bond (e.g., $(C_{6-10})$aryl$(C_{1-3})$alkyl includes, benzyl, phenethyl, 1-phenylethyl, 3-phenylpropyl, 2-thienylmethyl, 2-pyridinylmethyl and the like).

"Alkenyl" means a straight or branched, carbon chain that contains at least one carbon-carbon double bond. Examples of alkenyl include vinyl, allyl, isopropenyl, pentenyl, hexenyl, heptenyl, 1-propenyl, 2-butenyl, 2-methyl-2-butenyl, and the like.

"Alkynyl" means a straight or branched, carbon chain that contains at least one carbon-carbon triple bond. Examples of alkynyl include ethynyl, propargyl, 3-methyl-1-pentynyl, 2-heptynyl and the like.

"Alkylene", unless indicated otherwise, means a straight or branched, saturated or unsaturated, aliphatic, divalent radical. $C_X$alkylene and $C_{X-Y}$alkylene are typically used where X and Y indicate the number of carbon atoms in the chain. For example, $C_{1-6}$ alkylene includes methylene (—$CH_2$—), ethylene (—$CH_2CH_2$—), trimethylene (—$CH_2CH_2CH_2$—), tetramethylene (—$CH_2CH_2CH_2CH_2$—) 2-butenylene (—$CH_2CH=CHCH_2$—), 2-methyltetramethylene (—$CH_2CH(CH_3)CH_2CH_2$—), pentamethylene (—$CH_2CH_2CH_2CH_2CH_2$—) and the like).

"Alkylidene" means a straight or branched saturated or unsaturated, aliphatic radical connected to the parent molecule by a double bond. $C_X$alkylidene and $C_{X-Y}$alkylidene are typically used where X and Y indicate the number of carbon atoms in the chain. For example, $C_{1-6}$ alkylidene includes methylene (=$CH_2$), ethylidene (=$CHCH_3$), isopropylidene (=$C(CH_3)_2$), propylidene (=$CHCH_2CH_3$), allylidene (=$CH$—$CH=CH_2$), and the like).

"Amino" means a nitrogen moiety having two further substituents where, for example, a hydrogen or carbon atom is attached to the nitrogen. For example, representative amino groups include —$NH_2$, —$NHCH_3$, —$N(CH_3)_2$, —$NHC_{1-10}$-alkyl, —$N(C_{1-10}$-alkyl$)_2$, —NHaryl, —NHheteroaryl, —$N(aryl)_2$, —$N(heteroaryl)_2$, and the like. Optionally, the two substituents together with the nitrogen may also form a ring. Unless indicated otherwise, the compounds of the invention containing amino moieties may include protected derivatives thereof. Suitable protecting groups for amino moieties include acetyl, tert-butoxycarbonyl, benzyloxycarbonyl, and the like.

"Aminoalkyl" means an alkyl, as defined above, except where one or more substituted or unsubstituted nitrogen atoms (—N—) are positioned between carbon atoms of the alkyl. For example, an $(C_{2-6})$aminoalkyl refers to a chain comprising between 2 and 6 carbons and one or more nitrogen atoms positioned between the carbon atoms.

"Animal" includes humans, non-human mammals (e.g., dogs, cats, rabbits, cattle, horses, sheep, goats, swine, deer, and the like) and non-mammals (e.g., birds, and the like).

"Aromatic" means a moiety wherein the constituent atoms make up an unsaturated ring system, all atoms in the ring system are $sp^2$ hybridized and the total number of pi electrons is equal to 4n+2. An aromatic ring may be such that the ring atoms are only carbon atoms or may include carbon and non-carbon atoms (see Heteroaryl).

"Aryl" means a monocyclic or polycyclic ring assembly wherein each ring is aromatic or when fused with one or more rings forms an aromatic ring assembly. If one or more ring atoms is not carbon (e.g., N, S), the aryl is a heteroaryl. $C_X$aryl and $C_{X-Y}$ aryl are typically used where X and Y indicate the number of atoms in the ring.

"Bicycloalkyl" means a saturated or partially unsaturated fused bicyclic or bridged polycyclic ring assembly.

"Bicycloaryl" means a bicyclic ring assembly wherein the rings are linked by a single bond or fused and at least one of the rings comprising the assembly is aromatic. $C_X$ bicycloaryl and $C_{X-Y}$ bicycloaryl are typically used where X and Y indicate the number of carbon atoms in the bicyclic ring assembly and directly attached to the ring.

"Bridging ring" as used herein refers to a ring that is bonded to another ring to form a compound having a bicyclic structure where two ring atoms that are common to both rings are not directly bound to each other. Non-exclusive examples of common compounds having a bridging ring include borneol, norbornane, 7-oxabicyclo[2.2.1]heptane, and the like. One or both rings of the bicyclic system may also comprise heteroatoms.

"Carbamoyl" means the radical —OC(O)NR$_a$R$_b$ where R$_a$ and R$_b$ are each independently two further substituents where a hydrogen or carbon atom is attached to the nitrogen.

"Carbocycle" means a ring consisting of carbon atoms.

"Carbocyclic ketone derivative" means a carbocyclic derivative wherein the ring contains a —CO— moiety.

"Carbonyl" means the radical —CO—. It is noted that the carbonyl radical may be further substituted with a variety of substituents to form different carbonyl groups including acids, acid halides, aldehydes, amides, esters, and ketones.

"Carboxy" means the radical —CO$_2$—. It is noted that compounds of the invention containing carboxy moieties may include protected derivatives thereof, i.e., where the oxygen is substituted with a protecting group. Suitable protecting groups for carboxy moieties include benzyl, tert-butyl, and the like.

"Cyano" means the radical —CN.

"Cycloalkyl" means a non-aromatic, saturated or partially unsaturated, monocyclic, fused bicyclic or bridged polycyclic ring assembly. $C_X$ cycloalkyl and $C_{X-Y}$ cycloalkyl are typically used where X and Y indicate the number of carbon atoms in the ring assembly. For example, $C_{3-10}$ cycloalkyl includes cyclopropyl, cyclobutyl, cyclopentyl, cyclohexyl, cyclohexenyl, 2,5-cyclohexadienyl, bicyclo[2.2.2]octyl, adamantan-1-yl, decahydronaphthyl, oxocyclohexyl, dioxocyclohexyl, thiocyclohexyl, 2-oxobicyclo[2.2.1]hept-1-yl, and the like.

"Cycloalkylene" means a divalent saturated or partially unsaturated, monocyclic or polycyclic ring assembly. $C_X$ cycloalkylene and $C_{X-Y}$ cycloalkylene are typically used where X and Y indicate the number of carbon atoms in the ring assembly.

"Disease" specifically includes any unhealthy condition of an animal or part thereof and includes an unhealthy condition that may be caused by, or incident to, medical or veterinary therapy applied to that animal, i.e., the "side effects" of such therapy.

"Fused ring" as used herein refers to a ring that is bonded to another ring to form a compound having a bicyclic structure when the ring atoms that are common to both rings are directly bound to each other. Non-exclusive examples of common fused rings include decalin, naphthalene, anthracene, phenanthrene, indole, furan, benzofuran, quinoline, and the like. Compounds having fused ring systems may be saturated, partially saturated, carbocyclics, heterocyclics, aromatics, heteroaromatics, and the like.

"Halo" means fluoro, chloro, bromo or iodo.

"Halo-substituted alkyl", as an isolated group or part of a larger group, means "alkyl" substituted by one or more "halo" atoms, as such terms are defined in this Application. Halo-substituted alkyl includes haloalkyl, dihaloalkyl, trihaloalkyl, perhaloalkyl and the like (e.g. halo-substituted ($C_{1-3}$)alkyl includes chloromethyl, dichloromethyl, difluoromethyl, trifluoromethyl, 2,2,2-trifluoroethyl, perfluoroethyl, 2,2,2-trifluoro-1,1-dichloroethyl, and the like).

"Heteroatom" refers to an atom that is not a carbon atom. Particular examples of heteroatoms include, but are not limited to nitrogen, oxygen, and sulfur.

"Heteroatom moiety" includes a moiety where the atom by which the moiety is attached is not a carbon. Examples of heteroatom moieties include —N=, —NR$_c$—, —N$^+$(O$^-$)=, —O—, —S— or —S(O)$_2$—, wherein R$_c$ is further substituent.

"Heterobicycloalkyl" means bicycloalkyl, as defined in this Application, provided that one or more of the atoms within the ring is a heteroatom. For example hetero($C_{9-12}$) bicycloalkyl as used in this application includes, but is not limited to, 3-aza-bicyclo[4.1.0]hept-3-yl, 2-aza-bicyclo [3.1.0]hex-2-yl, 3-aza-bicyclo[3.1.0]hex-3-yl, and the like.

"Heterocycloalkylene" means cycloalkylene, as defined in this Application, provided that one or more of the ring member carbon atoms is replaced by a heteroatom.

"Heteroaryl" means a cyclic aromatic group having five or six ring atoms, wherein at least one ring atom is a heteroatom and the remaining ring atoms are carbon. The nitrogen atoms can be optionally quaternerized and the sulfur atoms can be optionally oxidized. Heteroaryl groups of this invention include, but are not limited to, those derived from furan, imidazole, isothiazole, isoxazole, oxadiazole, oxazole, 1,2,3-oxadiazole, pyrazine, pyrazole, pyridazine, pyridine, pyrimidine, pyrroline, thiazole, 1,3,4-thiadiazole, triazole and tetrazole. "Heteroaryl" also includes, but is not limited to, bicyclic or tricyclic rings, wherein the heteroaryl ring is fused to one or two rings independently selected from the group consisting of an aryl ring, a cycloalkyl ring, a cycloalkenyl ring, and another monocyclic heteroaryl or heterocycloalkyl ring. These bicyclic or tricyclic heteroaryls include, but are not limited to, those derived from benzo[b]furan, benzo[b] thiophene, benzimidazole, imidazo[4,5-c]pyridine, quinazoline, thieno[2,3-c]pyridine, thieno[3,2-b]pyridine, thieno[2,3-b]pyridine, indolizine, imidazo[1,2a]pyridine, quinoline, isoquinoline, phthalazine, quinoxaline, naphthyridine, quinolizine, indole, isoindole, indazole, indoline, benzoxazole, benzopyrazole, benzothiazole, imidazo[1,5-a]pyridine, pyrazolo[1,5-a]pyridine, imidazo[1,2-a]pyrimidine, imidazo[1,2-c]pyrimidine, imidazo[1,5-a]pyrimidine, imidazo[1,5-c]pyrimidine, pyrrolo[2,3-b]pyridine, pyrrolo[2,3-c]pyridine, pyrrolo[3,2-c]pyridine, pyrrolo[3,2-b]pyridine, pyrrolo[2,3-d]pyrimidine, pyrrolo[3,2-d]pyrimidine, pyrrolo [2,3-b]pyrazine, pyrazolo[1,5-a]pyridine, pyrrolo[1,2-b]pyridazine, pyrrolo[1,2-c]pyrimidine, pyrrolo[1,2-a]pyrimidine, pyrrolo[1,2-a]pyrazine, triazo[1,5-a]pyridine, pteridine, purine, carbazole, acridine, phenazine, phenothiazene, phenoxazine, 1,2-dihydropyrrolo[3,2,1-hi]indole, indolizine, pyrido[1,2-a]indole and 2(1H)-pyridinone. The bicyclic or tricyclic heteroaryl rings can be attached to the parent molecule through either the heteroaryl group itself or the aryl, cycloalkyl, cycloalkenyl or heterocycloalkyl group to which it is fused. The heteroaryl groups of this invention can be substituted or unsubstituted.

"Heterobicycloaryl" means bicycloaryl, as defined in this Application, provided that one or more of the atoms within the ring is a heteroatom. For example, hetero($C_{4-12}$)bicycloaryl as used in this Application includes, but is not limited to, 2-amino-4-oxo-3,4-dihydropteridin-6-yl, tetrahydroisoquinolinyl, and the like.

"Heterocycloalkyl" means cycloalkyl, as defined in this Application, provided that one or more of the atoms forming the ring is a heteroatom selected, independently from N, O, or S. Non-exclusive examples of heterocycloalkyl include piperidyl, 4-morpholyl, 4-piperazinyl, pyrrolidinyl, perhydropyrrolizinyl, 1,4-diazaperhydroepinyl, 1,3-dioxanyl, 1,4-dioxanyl and the like.

"Hydroxy" means the radical —OH.

"Iminoketone derivative" means a derivative comprising the moiety —C(NR)—, wherein R comprises a hydrogen or carbon atom attached to the nitrogen.

"Isomers" mean any compound having an identical molecular formulae but differing in the nature or sequence of bonding of their atoms or in the arrangement of their atoms in space. Isomers that differ in the arrangement of their atoms in space are termed "stereoisomers." Stereoisomers that are not mirror images of one another are termed "diastereomers" and stereoisomers that are nonsuperimposable mirror images are termed "enantiomers" or sometimes "optical isomers." A carbon atom bonded to four nonidentical substituents is termed a "chiral center." A compound with one chiral center has two enantiomeric forms of opposite chirality. A mixture of the two enantiomeric forms is termed a "racemic mixture." A compound that has more than one chiral center has $2^{n-1}$ enantiomeric pairs, where n is the number of chiral centers. Compounds with more than one chiral center may exist as ether an individual diastereomer or as a mixture of diastereomers, termed a "diastereomeric mixture." When one chiral center is present a stereoisomer may be characterized by the absolute configuration of that chiral center. Absolute configuration refers to the arrangement in space of the substituents attached to the chiral center. Enantiomers are characterized by the absolute configuration of their chiral centers and described by the R- and S-sequencing rules of Cahn, Ingold and Prelog. Conventions for stereochemical nomenclature, methods for the determination of stereochemistry and the separation of stereoisomers are well known in the art (e.g., see "Advanced Organic Chemistry", 4th edition, March, Jerry, John Wiley & Sons, New York, 1992).

"Nitro" means the radical —NO$_2$.

"Oxaalkyl" means an alkyl, as defined above, except where one or more oxygen atoms (—O—) are positioned between carbon atoms of the alkyl. For example, an (C$_{2-6}$)oxaalkyl refers to a chain comprising between 2 and 6 carbons and one or more oxygen atoms positioned between the carbon atoms.

"Oxoalkyl" means an alkyl, further substituted with a carbonyl group. The carbonyl group may be an aldehyde, ketone, ester, amide, acid or acid chloride.

"Pharmaceutically acceptable" means that which is useful in preparing a pharmaceutical composition that is generally safe, non-toxic and neither biologically nor otherwise undesirable and includes that which is acceptable for veterinary use as well as human pharmaceutical use.

"Pharmaceutically acceptable salts" means salts of inhibitors of the present invention which are pharmaceutically acceptable, as defined above, and which possess the desired pharmacological activity. Such salts include acid addition salts formed with inorganic acids such as hydrochloric acid, hydrobromic acid, sulfuric acid, nitric acid, phosphoric acid, and the like; or with organic acids such as acetic acid, propionic acid, hexanoic acid, heptanoic acid, cyclopentanepropionic acid, glycolic acid, pyruvic acid, lactic acid, malonic acid, succinic acid, malic acid, maleic acid, fumaric acid, tartaric acid, citric acid, benzoic acid, o-(4-hydroxybenzoyl) benzoic acid, cinnamic acid, mandelic acid, methanesulfonic acid, ethanesulfonic acid, 1,2-ethanedisulfonic acid, 2-hydroxyethanesulfonic acid, benzenesulfonic acid, p-chlorobenzenesulfonic acid, 2-naphthalenesulfonic acid, p-toluenesulfonic acid, camphorsulfonic acid, 4-methylbicyclo [2.2.2]oct-2-ene-1-carboxylic acid, glucoheptonic acid, 4,4'-methylenebis(3-hydroxy-2-ene-1-carboxylic acid), 3-phenylpropionic acid, trimethylacetic acid, tertiary butylacetic acid, lauryl sulfuric acid, gluconic acid, glutamic acid, hydroxynaphthoic acid, salicylic acid, stearic acid, muconic acid and the like.

Pharmaceutically acceptable salts also include base addition salts which may be formed when acidic protons present are capable of reacting with inorganic or organic bases. Acceptable inorganic bases include sodium hydroxide, sodium carbonate, potassium hydroxide, aluminum hydroxide and calcium hydroxide. Acceptable organic bases include ethanolamine, diethanolamine, triethanolamine, tromethamine, N-methylglucamine and the like.

"Prodrug" means a compound that is convertible in vivo metabolically into an inhibitor according to the present invention. The prodrug itself may or may not also have kinase inhibitory activity. For example, an inhibitor comprising a hydroxy group may be administered as an ester that is converted by hydrolysis in vivo to the hydroxy compound. Suitable esters that may be converted in vivo into hydroxy compounds include acetates, citrates, lactates, tartrates, malonates, oxalates, salicylates, propionates, succinates, fumarates, maleates, methylene-bis-b-hydroxynaphthoates, gentisates, isethionates, di-p-toluoyltartrates, methanesulfonates, ethanesulfonates, benzenesulfonates, p-toluenesulfonates, cyclohexylsulfamates, quinates, esters of amino acids, and the like. Similarly, an inhibitor comprising an amine group may be administered as an amide that is converted by hydrolysis in vivo to the amine compound.

"Protected derivatives" means derivatives of inhibitors in which a reactive site or sites are blocked with protecting groups. Protected derivatives are useful in the preparation of inhibitors or in themselves may be active as inhibitors. A comprehensive list of suitable protecting groups can be found in T. W. Greene, *Protecting Groups in Organic Synthesis,* 3rd edition, John Wiley & Sons, Inc. 1999.

"Substituted or unsubstituted" means that a given moiety may consist of only hydrogen substituents through available valencies (unsubstituted) or may further comprise one or more non-hydrogen substituents through available valencies (substituted) that are not otherwise specified by the name of the given moiety. For example, isopropyl is an example of an ethylene moiety that is substituted by —CH$_3$. In general, a non-hydrogen substituent may be any substituent that may be bound to an atom of the given moiety that is specified to be substituted. Examples of substituents include, but are not limited to, aldehyde, alicyclic, aliphatic, (C$_{1-10}$)alkyl, alkylene, alkylidene, amide, amino, aminoalkyl, aromatic, aryl, bicycloalkyl, bicycloaryl, carbamoyl, carbocyclyl, carboxyl, carbonyl group, cycloalkyl, cycloalkylene, ester, halo, heterobicycloalkyl, heterocycloalkylene, heteroaryl, heterobicycloaryl, heterocycloalkyl, oxo, hydroxy, iminoketone, ketone, nitro, oxaalkyl, and oxoalkyl moieties, each of which may optionally also be substituted or unsubstituted.

"Sulfinyl" means the radical —SO—. It is noted that the sulfinyl radical may be further substituted with a variety of substituents to form different sulfinyl groups including sulfinic acids, sulfinamides, sulfinyl esters, and sulfoxides.

"Sulfonyl" means the radical —SO$_2$—. It is noted that the sulfonyl radical may be further substituted with a variety of substituents to form different sulfonyl groups including sulfonic acids, sulfonamides, sulfonate esters, and sulfones.

"Therapeutically effective amount" means that amount which, when administered to an animal for treating a disease, is sufficient to effect such treatment for the disease.

"Thiocarbonyl" means the radical —CS—. It is noted that the thiocarbonyl radical may be further substituted with a variety of substituents to form different thiocarbonyl groups including thioacids, thioamides, thioesters, and thioketones.

"Treatment" or "treating" means any administration of a compound of the present invention and includes:

(1) preventing the disease from occurring in an animal which may be predisposed to the disease but does not yet experience or display the pathology or symptomatology of the disease, (2) inhibiting the disease in an animal that is experiencing or displaying the pathology or symptomatology of the diseased (i.e., arresting further development of the pathology and/or symptomatology), or (3) ameliorating the disease in an animal that is experiencing or displaying the pathology or symptomatology of the diseased (i.e., reversing the pathology and/or symptomatology).

It is noted in regard to all of the definitions provided herein that the definitions should be interpreted as being open ended in the sense that further substituents beyond those specified may be included. Hence, a $C_1$ alkyl indicates that there is one carbon atom but does not indicate what are the substituents on the carbon atom. Hence, a $C_1$ alkyl comprises methyl (i.e., $-CH_3$) as well as $-CR_aR_bR_c$ where $R_a$, $R_b$, and $R_c$ may each independently be hydrogen or any other substituent where the atom attached to the carbon is a heteroatom or cyano. Hence, $CF_3$, $CH_2OH$ and $CH_2CN$, for example, are all $C_1$ alkyls.

Kinase Inhibitors

In one embodiment, kinase inhibitors of the present invention comprise the following formula:

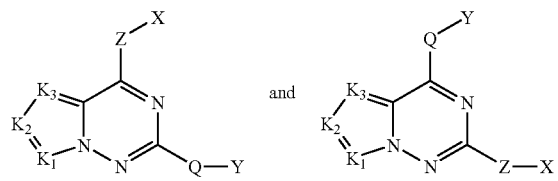

wherein:
l is selected from the group consisting of 1, 2, 3, 4 and 5;
$K_1$, $K_2$, and $K_3$ are each independently selected from the group consisting of $CR_3$ and N;
Q is selected from the group consisting of S, SO, $SO_2$, O, $NR_6$, $NR_6$—$(CR_{21}R_{22})_l$, $NR_6$—$(CR_{21}R_{22})_l$—O, and a substituted or unsubstituted $(C_{2-5})$alkylene, or Q is absent;
X is selected from the group consisting of $(C_{3-12})$cycloalkyl, hetero$(C_{3-12})$cycloalkyl, $(C_{9-12})$bicycloalkyl, hetero$(C_{3-12})$bicycloalkyl, aryl, heteroaryl, $(C_{9-12})$bicycloaryl and hetero$(C_{4-12})$bicycloaryl, each substituted or unsubstituted;
Y is selected from the group consisting of $(C_{3-12})$cycloalkyl, hetero$(C_{3-12})$cycloalkyl, $(C_{9-12})$bicycloalkyl, hetero$(C_{3-12})$bicycloalkyl, aryl, heteroaryl, $(C_{9-12})$bicycloaryl, and hetero$(C_{4-12})$bicycloaryl, each substituted or unsubstituted;
Z is selected from the group consisting of $NR_1$, S, SO, $SO_2$ and O;
$R_1$ is selected from the group consisting of hydrogen, nitro, thio, hydroxy, alkoxy, aryloxy, heteroaryloxy, carbonyl, amino, sulfonamido, imino, sulfonyl, sulfinyl, $(C_{1-10})$alkyl, $(C_{3-12})$cycloalkyl, hetero$(C_{3-12})$cycloalkyl, $(C_{9-12})$bicycloalkyl, hetero$(C_{3-12})$bicycloalkyl, aryl $(C_{1-10})$alkyl, heteroaryl$(C_{1-5})$alkyl, $(C_{3-12})$cycloalkyl $(C_{1-10})$alkyl, halo$(C_{1-10})$alkyl, carbonyl$(C_{1-3})$alkyl, thiocarbonyl$(C_{1-3})$alkyl, sulfonyl$(C_{1-3})$alkyl, sulfinyl $(C_{1-3})$alkyl, imino$(C_{1-3})$alkyl, aryl, heteroaryl, $(C_{9-12})$bicycloaryl, and hetero$(C_{4-12})$bicycloaryl, each substituted or unsubstituted;

each $R_3$ is independently selected from the group consisting of hydrogen, halo, nitro, cyano, thio, hydroxy, alkoxy, aryloxy, heteroaryloxy, carbonyl, amino, $(C_{1-10})$alkylamino, sulfonamido, imino, sulfonyl, sulfinyl, $(C_{1-10})$alkyl, $(C_{3-12})$cycloalkyl, hetero$(C_{3-12})$cycloalkyl, $(C_{9-12})$bicycloalkyl, hetero$(C_{3-12})$bicycloalkyl, aryl$(C_{1-10})$alkyl, heteroaryl$(C_{1-5})$alkyl, perhalo$(C_{1-10})$alkyl, carbonyl$(C_{1-3})$alkyl, thiocarbonyl $(C_{1-3})$alkyl, sulfonyl$(C_{1-3})$alkyl, sulfinyl$(C_{1-3})$alkyl, amino$(C_{1-10})$alkyl, imino$(C_{1-3})$alkyl, aryl, heteroaryl, $(C_{9-12})$bicycloaryl, and hetero$(C_{4-12})$bicycloaryl, each substituted or unsubstituted, or $R_2$ and one $R_3$, or two $R_3$ are taken together to form a substituted or unsubstituted ring;

$R_6$ is selected from the group consisting of hydrogen, nitro, thio, hydroxy, alkoxy, aryloxy, heteroaryloxy, carbonyl, amino, sulfonamido, imino, sulfonyl, sulfinyl, $(C_{1-10})$alkyl, $(C_{3-12})$cycloalkyl, hetero$(C_{3-12})$cycloalkyl, $(C_{9-12})$bicycloalkyl, hetero$(C_{3-12})$bicycloalkyl, aryl $(C_{1-10})$alkyl, heteroaryl$(C_{1-5})$alkyl, $(C_{3-12})$cycloalkyl $(C_{1-10})$alkyl, halo$(C_{1-10})$alkyl, carbonyl$(C_{1-3})$alkyl, thiocarbonyl$(C_{1-3})$alkyl, sulfonyl$(C_{1-3})$alkyl, sulfinyl $(C_{1-3})$alkyl, imino$(C_{1-3})$alkyl, aryl, heteroaryl, $(C_{9-12})$bicycloaryl, and hetero$(C_{4-12})$bicycloaryl, each substituted or unsubstituted; and $R_{21}$ and $R_{22}$ are each independently selected from the group consisting of hydrogen, halo, hydroxy, alkoxy, carbonyl, amino, $(C_{1-5})$alkylamino, $(C_{1-5})$alkyl, halo $(C_{1-5})$alkyl, carbonyl$(C_{1-3})$alkyl and amino$(C_{1-5})$alkyl, each substituted or unsubstituted.

In another embodiment, kinase inhibitors of the present invention comprise the following formula:

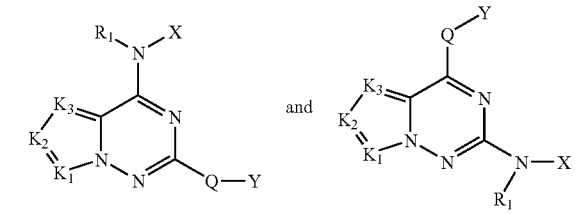

wherein:
l is selected from the group consisting of 1, 2, 3, 4 and 5;
$K_1$, $K_2$, and $K_3$ are each independently selected from the group consisting of $CR_3$ and N;
Q is selected from the group consisting of S, SO, $SO_2$, O, $NR_6$, $NR_6$—$(CR_{21}R_{22})_l$, $NR_6$—$(CR_{21}R_{22})_l$—O, and a substituted or unsubstituted $(C_{2-5})$alkylene, or Q is absent;
X is selected from the group consisting of $(C_{3-12})$cycloalkyl, hetero$(C_{3-12})$cycloalkyl, $(C_{9-12})$bicycloalkyl, hetero$(C_{3-12})$bicycloalkyl, aryl, heteroaryl, $(C_{9-12})$bicycloaryl and hetero$(C_{4-12})$bicycloaryl, each substituted or unsubstituted;
Y is selected from the group consisting of $(C_{3-12})$cycloalkyl, hetero$(C_{3-12})$cycloalkyl, $(C_{9-12})$bicycloalkyl, hetero$(C_{3-12})$bicycloalkyl, aryl, heteroaryl, $(C_{9-12})$bicycloaryl, and hetero$(C_{4-12})$bicycloaryl, each substituted or unsubstituted;
$R_1$ is selected from the group consisting of hydrogen, nitro, thio, hydroxy, alkoxy, aryloxy, heteroaryloxy, carbonyl, amino, sulfonamido, imino, sulfonyl, sulfinyl, $(C_{1-10})$ alkyl, (C$_{3-12}$)cycloalkyl, hetero(C$_{3-12}$)cycloalkyl, (C$_{9-12}$)bicycloalkyl, hetero(C$_{3-12}$)bicycloalkyl, aryl (C$_{1-10}$)alkyl, heteroaryl(C$_{1-5}$)alkyl, (C$_{3-12}$)cycloalkyl (C$_{1-10}$)alkyl, halo(C$_{1-10}$)alkyl, carbonyl(C$_{1-3}$)alkyl, thiocarbonyl(C$_{1-3}$)alkyl, sulfonyl(C$_{1-3}$)alkyl, sulfinyl (C$_{1-3}$)alkyl, imino(C$_{1-3}$)alkyl, aryl, heteroaryl, (C$_{9-12}$) bicycloaryl, and hetero(C$_{4-12}$)bicycloaryl, each substituted or unsubstituted;

each R$_3$ is independently selected from the group consisting of hydrogen, halo, nitro, cyano, thio, hydroxy, alkoxy, aryloxy, heteroaryloxy, carbonyl, amino, (C$_{1-10}$)alkylamino, sulfonamido, imino, sulfonyl, sulfinyl, (C$_{1-10}$)alkyl, (C$_{3-12}$)cycloalkyl, hetero(C$_{3-12}$)cycloalkyl, (C$_{9-12}$)bicycloalkyl, hetero(C$_{3-12}$)bicycloalkyl, aryl (C$_{1-10}$)alkyl, heteroaryl(C$_{1-5}$)alkyl, perhalo(C$_{1-10}$)alkyl, carbonyl(C$_{1-3}$)alkyl, thiocarbonyl(C$_{1-3}$)alkyl, sulfonyl (C$_{1-3}$)alkyl, sulfinyl(C$_{1-3}$)alkyl, amino(C$_{1-10}$)alkyl, imino(C$_{1-3}$)alkyl, aryl, heteroaryl, (C$_{9-12}$)bicycloaryl, and hetero(C$_{4-12}$)bicycloaryl, each substituted or unsubstituted, or R$_2$ and one R$_3$, or two R$_3$ are taken together to form a substituted or unsubstituted ring;

R$_6$ is selected from the group consisting of hydrogen, nitro, thio, hydroxy, alkoxy, aryloxy, heteroaryloxy, carbonyl, amino, sulfonamido, imino, sulfonyl, sulfinyl, (C$_{1-10}$) alkyl, (C$_{3-12}$)cycloalkyl, hetero(C$_{3-12}$)cycloalkyl, (C$_{9-12}$)bicycloalkyl, hetero(C$_{3-12}$)bicycloalkyl, aryl (C$_{1-10}$)alkyl, heteroaryl(C$_{1-5}$)alkyl, (C$_{3-12}$)cycloalkyl (C$_{1-10}$)alkyl, halo(C$_{1-10}$)alkyl, carbonyl(C$_{1-3}$)alkyl, thiocarbonyl(C$_{1-3}$)alkyl, sulfonyl(C$_{1-3}$)alkyl, sulfinyl (C$_{1-3}$)alkyl, imino(C$_{1-3}$)alkyl, aryl, heteroaryl, (C$_{9-12}$) bicycloaryl, and hetero(C$_{4-12}$)bicycloaryl, each substituted or unsubstituted; and R$_{21}$ and R$_{22}$ are each independently selected from the group consisting of hydrogen, halo, hydroxy, alkoxy, carbonyl, amino, (C$_{1-5}$)alkylamino, (C$_{1-5}$)alkyl, halo (C$_{1-5}$)alkyl, carbonyl(C$_{1-3}$)alkyl and amino(C$_{1-5}$)alkyl, each substituted or unsubstituted.

In a further embodiment, kinase inhibitors of the present invention comprise the following formula:

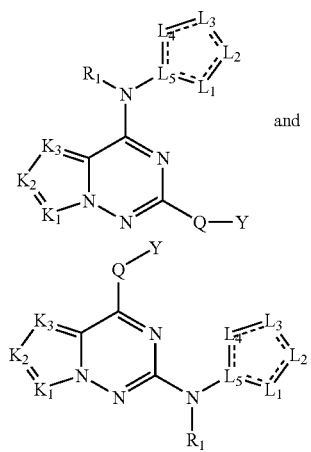

and wherein:
l is selected from the group consisting of 1, 2, 3, 4 and 5;
K$_1$, K$_2$, and K$_3$ are each independently selected from the group consisting of CR$_3$ and N;
L$_1$, L$_2$, L$_3$, L$_4$, and L$_5$ are each independently selected from the group consisting of CR$_4$ and NR$_5$, with the proviso that R$_5$ is absent when the atom to which it is attached forms part of a double bond;

Q is selected from the group consisting of S, SO, SO$_2$, O, NR$_6$, NR$_6$—(CR$_{21}$R$_{22}$)$_l$, NR$_6$—(CR$_{21}$R$_{22}$)$_l$—O, and a substituted or unsubstituted (C$_{2-5}$)alkylene, or Q is absent;

Y is selected from the group consisting of (C$_{3-12}$)cycloalkyl, hetero(C$_{3-12}$)cycloalkyl, (C$_{9-12}$)bicycloalkyl, hetero(C$_{3-12}$)bicycloalkyl, aryl, heteroaryl, (C$_{9-12}$)bicycloaryl, and hetero(C$_{4-12}$)bicycloaryl, each substituted or unsubstituted;

R$_1$ is selected from the group consisting of hydrogen, nitro, thio, hydroxy, alkoxy, aryloxy, heteroaryloxy, carbonyl, amino, sulfonamido, imino, sulfonyl, sulfinyl, (C$_{1-10}$) alkyl, (C$_{3-12}$)cycloalkyl, hetero(C$_{3-12}$)cycloalkyl, (C$_{9-12}$)bicycloalkyl, hetero(C$_{3-12}$)bicycloalkyl, aryl (C$_{1-10}$)alkyl, heteroaryl(C$_{1-5}$)alkyl, (C$_{3-12}$)cycloalkyl (C$_{1-10}$)alkyl, halo(C$_{1-10}$)alkyl, carbonyl(C$_{1-3}$)alkyl, thiocarbonyl(C$_{1-3}$)alkyl, sulfonyl(C$_{1-3}$)alkyl, sulfinyl (C$_{1-3}$)alkyl, imino(C$_{1-3}$)alkyl, aryl, heteroaryl, (C$_{9-12}$) bicycloaryl, and hetero(C$_{4-12}$)bicycloaryl, each substituted or unsubstituted;

each R$_3$ is independently selected from the group consisting of hydrogen, halo, nitro, cyano, thio, hydroxy, alkoxy, aryloxy, heteroaryloxy, carbonyl, amino, (C$_{1-10}$) alkylamino, sulfonamido, imino, sulfonyl, sulfinyl, (C$_{1-10}$)alkyl, (C$_{3-12}$)cycloalkyl, hetero(C$_{3-12}$)cycloalkyl, (C$_{9-12}$)bicycloalkyl, hetero(C$_{3-12}$)bicycloalkyl, aryl(C$_{1-10}$)alkyl, heteroaryl(C$_{1-5}$)alkyl, perhalo(C$_{1-10}$)alkyl, carbonyl(C$_{1-3}$)alkyl, thiocarbonyl (C$_{1-3}$)alkyl, sulfonyl(C$_{1-3}$)alkyl, sulfinyl(C$_{1-3}$)alkyl, amino(C$_{1-10}$)alkyl, imino(C$_{1-3}$)alkyl, aryl, heteroaryl, (C$_{9-12}$)bicycloaryl, and hetero(C$_{4-12}$)bicycloaryl, each substituted or unsubstituted, or R$_2$ and one R$_3$, or two R$_3$ are taken together to form a substituted or unsubstituted ring;

each R$_4$ is independently selected from the group consisting of hydrogen, halo, nitro, cyano, thio, hydroxy, alkoxy, aryloxy, heteroaryloxy, carbonyl, amino, (C$_{1-10}$) alkylamino, sulfonamido, imino, sulfonyl, sulfinyl, (C$_{1-10}$)alkyl, (C$_{3-12}$)cycloalkyl, hetero(C$_{3-12}$)cycloalkyl, (C$_{9-12}$)bicycloalkyl, hetero(C$_{3-12}$)bicycloalkyl, aryl(C$_{1-10}$)alkyl, heteroaryl(C$_{1-5}$)alkyl, perhalo(C$_{1-10}$)alkyl, carbonyl(C$_{1-3}$)alkyl, thiocarbonyl (C$_{1-3}$)alkyl, sulfonyl(C$_{1-3}$)alkyl, sulfinyl(C$_{1-3}$)alkyl, amino(C$_{1-10}$)alkyl, imino(C$_{1-3}$)alkyl, aryl, heteroaryl, (C$_{9-12}$)bicycloaryl, and hetero(C$_{4-12}$)bicycloaryl, each substituted or unsubstituted, or two R$_4$ are taken together to form part of a substituted or unsubstituted ring;

each R$_5$ is independently selected from the group consisting of hydrogen, nitro, thio, hydroxy, alkoxy, aryloxy, heteroaryloxy, carbonyl, amino, sulfonamido, imino, sulfonyl, sulfinyl, (C$_{1-10}$)alkyl, (C$_{3-12}$)cycloalkyl, hetero (C$_{3-12}$)cycloalkyl, (C$_{9-12}$)bicycloalkyl, hetero(C$_{3-12}$)bicycloalkyl, aryl(C$_{1-10}$)alkyl, heteroaryl(C$_{1-5}$)alkyl, (C$_{3-12}$)cycloalkyl(C$_{1-10}$)alkyl, halo(C$_{1-10}$)alkyl, carbonyl(C$_{1-3}$)alkyl, thiocarbonyl(C$_{1-3}$)alkyl, sulfonyl(C$_{1-3}$) alkyl, sulfinyl(C$_{1-3}$)alkyl, imino(C$_{1-3}$)alkyl, aryl, heteroaryl, (C$_{9-12}$)bicycloaryl, and hetero(C$_{4-12}$) bicycloaryl, each substituted or unsubstituted, or two R$_5$, or one R$_4$ and one R$_5$, are taken together to form part of a substituted or unsubstituted ring;

R$_6$ is selected from the group consisting of hydrogen, nitro, thio, hydroxy, alkoxy, aryloxy, heteroaryloxy, carbonyl, amino, sulfonamido, imino, sulfonyl, sulfinyl, (C$_{1-10}$) alkyl, (C$_{3-12}$)cycloalkyl, hetero(C$_{3-12}$)cycloalkyl, (C$_{9-12}$)bicycloalkyl, hetero(C$_{3-12}$)bicycloalkyl, aryl ($C_{1-10}$)alkyl, heteroaryl($C_{1-5}$)alkyl, ($C_{3-12}$)cycloalkyl ($C_{1-10}$)alkyl, halo($C_{1-10}$)alkyl, carbonyl($C_{1-3}$)alkyl, thiocarbonyl($C_{1-3}$)alkyl, sulfonyl($C_{1-3}$)alkyl, sulfinyl ($C_{1-3}$)alkyl, imino($C_{1-3}$)alkyl, aryl, heteroaryl, ($C_{9-12}$)bicycloaryl, and hetero($C_{4-12}$)bicycloaryl, each substituted or unsubstituted; and $R_{21}$ and $R_{22}$ are each independently selected from the group consisting of hydrogen, halo, hydroxy, alkoxy, carbonyl, amino, ($C_{1-5}$)alkylamino, ($C_{1-5}$)alkyl, halo($C_{1-5}$)alkyl, carbonyl($C_{1-3}$)alkyl and amino($C_{1-5}$)alkyl, each substituted or unsubstituted.

In another embodiment, kinase inhibitors of the present invention comprise the following formula:

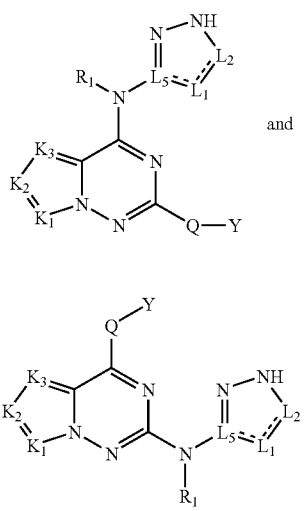

and wherein:
l is selected from the group consisting of 1, 2, 3, 4 and 5;
$K_1$, $K_2$, and $K_3$ are each independently selected from the group consisting of $CR_3$ and N;
$L_1$, $L_2$, and $L_5$ are each independently selected from the group consisting of $CR_4$ and $NR_5$, with the proviso that $R_5$ is absent when the atom to which it is attached forms part of a double bond;
Q is selected from the group consisting of S, SO, $SO_2$, O, $NR_6$, $NR_6$—$(CR_{21}R_{22})_l$, $NR_6$—$(CR_{21}R_{22})_l$—O, and a substituted or unsubstituted ($C_{2-5}$)alkylene, or Q is absent;
Y is selected from the group consisting of ($C_{3-12}$)cycloalkyl, hetero($C_{3-12}$)cycloalkyl, ($C_{9-12}$)bicycloalkyl, hetero($C_{3-12}$)bicycloalkyl, aryl, heteroaryl, ($C_{9-12}$)bicycloaryl, and hetero($C_{4-12}$)bicycloaryl, each substituted or unsubstituted;
$R_1$ is selected from the group consisting of hydrogen, nitro, thio, hydroxy, alkoxy, aryloxy, heteroaryloxy, carbonyl, amino, sulfonamido, imino, sulfonyl, sulfinyl, ($C_{1-10}$)alkyl, ($C_{3-12}$)cycloalkyl, hetero($C_{3-12}$)cycloalkyl, ($C_{9-12}$)bicycloalkyl, hetero($C_{3-12}$)bicycloalkyl, aryl ($C_{1-10}$)alkyl, heteroaryl($C_{1-5}$)alkyl, ($C_{3-12}$)cycloalkyl ($C_{1-10}$)alkyl, halo($C_{1-10}$)alkyl, carbonyl($C_{1-3}$)alkyl, thiocarbonyl($C_{1-3}$)alkyl, sulfonyl($C_{1-3}$)alkyl, sulfinyl ($C_{1-3}$)alkyl, imino($C_{1-3}$)alkyl, aryl, heteroaryl, ($C_{9-12}$)bicycloaryl, and hetero($C_{4-12}$)bicycloaryl, each substituted or unsubstituted;
each $R_3$ is independently selected from the group consisting of hydrogen, halo, nitro, cyano, thio, hydroxy, alkoxy, aryloxy, heteroaryloxy, carbonyl, amino, ($C_{1-10}$)alkylamino, sulfonamido, imino, sulfonyl, sulfinyl, ($C_{1-10}$)alkyl, ($C_{3-12}$)cycloalkyl, hetero($C_{3-12}$)cycloalkyl, ($C_{9-12}$)bicycloalkyl, hetero($C_{3-12}$)bicycloalkyl, aryl($C_{1-10}$)alkyl, heteroaryl($C_{1-5}$)alkyl, perhalo($C_{1-10}$)alkyl, carbonyl($C_{1-3}$)alkyl, thiocarbonyl($C_{1-3}$)alkyl, sulfonyl($C_{1-3}$)alkyl, sulfinyl($C_{1-3}$)alkyl, amino($C_{1-10}$)alkyl, imino($C_{1-3}$)alkyl, aryl, heteroaryl, ($C_{9-12}$)bicycloaryl, and hetero($C_{4-12}$)bicycloaryl, each substituted or unsubstituted, or $R_2$ and one $R_3$, or two $R_3$ are taken together to form a substituted or unsubstituted ring;
each $R_4$ is independently selected from the group consisting of hydrogen, halo, nitro, cyano, thio, hydroxy, alkoxy, aryloxy, heteroaryloxy, carbonyl, amino, ($C_{1-10}$)alkylamino, sulfonamido, imino, sulfonyl, sulfinyl, ($C_{1-10}$)alkyl, ($C_{3-12}$)cycloalkyl, hetero($C_{3-12}$)cycloalkyl, ($C_{9-12}$)bicycloalkyl, hetero($C_{3-12}$)bicycloalkyl, aryl ($C_{1-10}$)alkyl, heteroaryl($C_{1-5}$)alkyl, perhalo($C_{1-10}$)alkyl, carbonyl($C_{1-3}$)alkyl, thiocarbonyl($C_{1-3}$)alkyl, sulfonyl ($C_{1-3}$)alkyl, sulfinyl($C_{1-3}$)alkyl, amino($C_{1-10}$)alkyl, imino($C_{1-3}$)alkyl, aryl, heteroaryl, ($C_{9-12}$)bicycloaryl, and hetero($C_{4-12}$)bicycloaryl, each substituted or unsubstituted, or two $R_4$ are taken together to form part of a substituted or unsubstituted ring;
each $R_5$ is independently selected from the group consisting of hydrogen, nitro, thio, hydroxy, alkoxy, aryloxy, heteroaryloxy, carbonyl, amino, sulfonamido, imino, sulfonyl, sulfinyl, ($C_{1-10}$)alkyl, ($C_{3-12}$)cycloalkyl, hetero ($C_{3-12}$)cycloalkyl, ($C_{9-12}$)bicycloalkyl, hetero($C_{3-12}$)bicycloalkyl, aryl($C_{1-10}$)alkyl, heteroaryl($C_{1-5}$)alkyl, ($C_{3-12}$)cycloalkyl($C_{1-10}$)alkyl, halo($C_{1-10}$)alkyl, carbonyl($C_{1-3}$)alkyl, thiocarbonyl($C_{1-3}$)alkyl, sulfonyl($C_{1-3}$) alkyl, sulfinyl($C_{1-3}$)alkyl, imino($C_{1-3}$)alkyl, aryl, heteroaryl, ($C_{9-12}$)bicycloaryl, and hetero($C_{4-12}$) bicycloaryl, each substituted or unsubstituted, or two $R_5$, or one $R_4$ and one $R_5$, are taken together to form part of a substituted or unsubstituted ring;
$R_6$ is selected from the group consisting of hydrogen, nitro, thio, hydroxy, alkoxy, aryloxy, heteroaryloxy, carbonyl, amino, sulfonamido, imino, sulfonyl, sulfinyl, ($C_{1-10}$) alkyl, ($C_{3-12}$)cycloalkyl, hetero($C_{3-12}$)cycloalkyl, ($C_{9-12}$)bicycloalkyl, hetero($C_{3-12}$)bicycloalkyl, aryl ($C_{1-10}$)alkyl, heteroaryl($C_{1-5}$)alkyl, ($C_{3-12}$)cycloalkyl ($C_{1-10}$)alkyl, halo($C_{1-10}$)alkyl, carbonyl($C_{1-3}$)alkyl, thiocarbonyl($C_{1-3}$)alkyl, sulfonyl($C_{1-3}$)alkyl, sulfinyl ($C_{1-3}$)alkyl, imino($C_{1-3}$)alkyl, aryl, heteroaryl, ($C_{9-12}$) bicycloaryl, and hetero($C_{4-12}$)bicycloaryl, each substituted or unsubstituted; and
$R_{21}$ and $R_{22}$ are each independently selected from the group consisting of hydrogen, halo, hydroxy, alkoxy, carbonyl, amino, ($C_{1-5}$)alkylamino, ($C_{1-5}$)alkyl, halo ($C_{1-5}$)alkyl, carbonyl($C_{1-3}$)alkyl and amino($C_{1-5}$)alkyl, each substituted or unsubstituted.

In still another embodiment, kinase inhibitors of the present invention comprise the following formula:

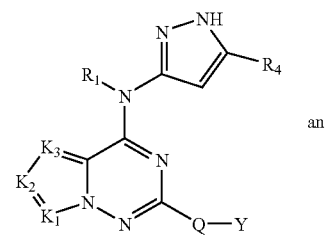

and

-continued

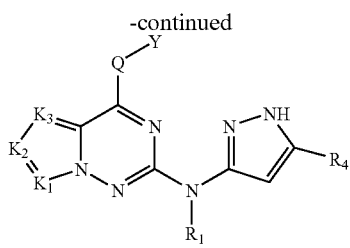

wherein:
l is selected from the group consisting of 1, 2, 3, 4 and 5;
$K_1$, $K_2$, and $K_3$ are each independently selected from the group consisting of $CR_3$ and N;
Q is selected from the group consisting of S, SO, $SO_2$, O, $NR_6$, $NR_6$—$(CR_{21}R_{22})_l$, $NR_6$—$(CR_{21}R_{22})_l$—O, and a substituted or unsubstituted ($C_{2-5}$)alkylene, or Q is absent;
Y is selected from the group consisting of ($C_{3-12}$)cycloalkyl, hetero($C_{3-12}$)cycloalkyl, ($C_{9-12}$)bicycloalkyl, hetero($C_{3-12}$)bicycloalkyl, aryl, heteroaryl, ($C_{9-12}$)bicycloaryl, and hetero($C_{4-12}$)bicycloaryl, each substituted or unsubstituted;
$R_1$ is selected from the group consisting of hydrogen, nitro, thio, hydroxy, alkoxy, aryloxy, heteroaryloxy, carbonyl, amino, sulfonamido, imino, sulfonyl, sulfinyl, ($C_{1-10}$) alkyl, ($C_{3-12}$)cycloalkyl, hetero($C_{3-12}$)cycloalkyl, ($C_{9-12}$)bicycloalkyl, hetero($C_{3-12}$)bicycloalkyl, aryl ($C_{1-10}$)alkyl, heteroaryl($C_{1-5}$)alkyl, ($C_{3-12}$)cycloalkyl ($C_{1-10}$)alkyl, halo($C_{1-10}$)alkyl, carbonyl($C_{1-3}$)alkyl, thiocarbonyl($C_{1-3}$)alkyl, sulfonyl($C_{1-3}$)alkyl, sulfinyl ($C_{1-3}$)alkyl, imino($C_{1-3}$)alkyl, aryl, heteroaryl, ($C_{9-12}$) bicycloaryl, and hetero($C_{4-12}$)bicycloaryl, each substituted or unsubstituted;
each $R_3$ is independently selected from the group consisting of hydrogen, halo, nitro, cyano, thio, hydroxy, alkoxy, aryloxy, heteroaryloxy, carbonyl, amino, ($C_{1-10}$) alkylamino, sulfonamido, imino, sulfonyl, sulfinyl, ($C_{1-10}$)alkyl, ($C_{3-12}$)cycloalkyl, hetero($C_{3-12}$)cycloalkyl, ($C_{9-12}$)bicycloalkyl, hetero($C_{3-12}$)bicycloalkyl, aryl($C_{1-10}$)alkyl, heteroaryl($C_{1-5}$)alkyl, perhalo($C_{1-10}$)alkyl, carbonyl($C_{1-3}$)alkyl, thiocarbonyl ($C_{1-3}$)alkyl, sulfonyl($C_{1-3}$)alkyl, sulfinyl($C_{1-3}$)alkyl, amino($C_{1-10}$)alkyl, imino($C_{1-3}$)alkyl, aryl, heteroaryl, ($C_{9-12}$)bicycloaryl, and hetero($C_{4-12}$)bicycloaryl, each substituted or unsubstituted, or $R_2$ and one $R_3$, or two $R_3$ are taken together to form a substituted or unsubstituted ring;
each $R_4$ is independently selected from the group consisting of hydrogen, halo, nitro, cyano, thio, hydroxy, alkoxy, aryloxy, heteroaryloxy, carbonyl, amino, ($C_{1-10}$) alkylamino, sulfonamido, imino, sulfonyl, sulfinyl, ($C_{1-10}$)alkyl, ($C_{3-12}$)cycloalkyl, hetero($C_{3-12}$)cycloalkyl, ($C_{9-12}$)bicycloalkyl, hetero($C_{3-12}$)bicycloalkyl, aryl($C_{1-10}$)alkyl, heteroaryl($C_{1-5}$)alkyl, perhalo($C_{1-10}$)alkyl, carbonyl($C_{1-3}$)alkyl, thiocarbonyl ($C_{1-3}$)alkyl, sulfonyl($C_{1-3}$)alkyl, sulfinyl($C_{1-3}$)alkyl, amino($C_{1-10}$)alkyl, imino($C_{1-3}$)alkyl, aryl, heteroaryl, ($C_{9-12}$)bicycloaryl, and hetero($C_{4-12}$)bicycloaryl, each substituted or unsubstituted, or two $R_4$ are taken together to form part of a substituted or unsubstituted ring;
$R_6$ is selected from the group consisting of hydrogen, nitro, thio, hydroxy, alkoxy, aryloxy, heteroaryloxy, carbonyl, amino, sulfonamido, imino, sulfonyl, sulfinyl, ($C_{1-10}$) alkyl, ($C_{3-12}$)cycloalkyl, hetero($C_{3-12}$)cycloalkyl, ($C_{9-12}$)bicycloalkyl, hetero($C_{3-12}$)bicycloalkyl, aryl ($C_{1-10}$)alkyl, heteroaryl($C_{1-5}$)alkyl, ($C_{3-12}$)cycloalkyl ($C_{1-10}$)alkyl, halo($C_{1-10}$)alkyl, carbonyl($C_{1-3}$)alkyl, thiocarbonyl($C_{1-3}$)alkyl, sulfonyl($C_{1-3}$)alkyl, sulfinyl ($C_{1-3}$)alkyl, imino($C_{1-3}$)alkyl, aryl, heteroaryl, ($C_{9-12}$) bicycloaryl, and hetero($C_{4-12}$)bicycloaryl, each substituted or unsubstituted; and
$R_{21}$ and $R_{22}$ are each independently selected from the group consisting of hydrogen, halo, hydroxy, alkoxy, carbonyl, amino, ($C_{1-5}$)alkylamino, ($C_{1-5}$)alkyl, halo ($C_{1-5}$)alkyl, carbonyl($C_{1-3}$)alkyl and amino($C_{1-5}$)alkyl, each substituted or unsubstituted.

In a further embodiment, kinase inhibitors of the present invention comprise the following formula:

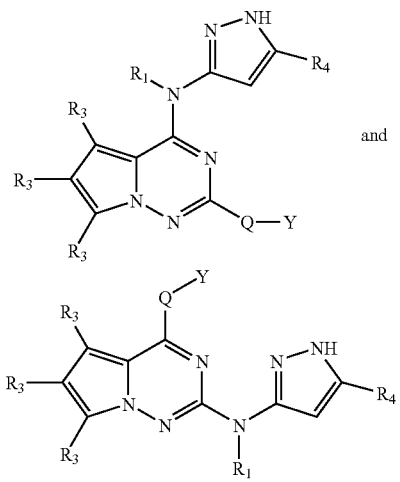

wherein:
l is selected from the group consisting of 1, 2, 3, 4 and 5;
Q is selected from the group consisting of S, SO, $SO_2$, O, $NR_6$, $NR_6$—$(CR_{21}R_{22})_l$, $NR_6$—$(CR_{21}R_{22})_l$—O, and a substituted or unsubstituted ($C_{2-5}$)alkylene, or Q is absent;
Y is selected from the group consisting of ($C_{3-12}$)cycloalkyl, hetero($C_{3-12}$)cycloalkyl, ($C_{9-12}$)bicycloalkyl, hetero($C_{3-12}$)bicycloalkyl, aryl, heteroaryl, ($C_{9-12}$)bicycloaryl, and hetero($C_{4-12}$)bicycloaryl, each substituted or unsubstituted;
$R_1$ is selected from the group consisting of hydrogen, nitro, thio, hydroxy, alkoxy, aryloxy, heteroaryloxy, carbonyl, amino, sulfonamido, imino, sulfonyl, sulfinyl, ($C_{1-10}$) alkyl, ($C_{3-12}$)cycloalkyl, hetero($C_{3-12}$)cycloalkyl, ($C_{9-12}$)bicycloalkyl, hetero($C_{3-12}$)bicycloalkyl, aryl ($C_{1-10}$)alkyl, heteroaryl($C_{1-5}$)alkyl, ($C_{3-12}$)cycloalkyl ($C_{1-10}$)alkyl, halo($C_{1-10}$)alkyl, carbonyl($C_{1-3}$)alkyl, thiocarbonyl($C_{1-3}$)alkyl, sulfonyl($C_{1-3}$)alkyl, sulfinyl ($C_{1-3}$)alkyl, imino($C_{1-3}$)alkyl, aryl, heteroaryl, ($C_{9-12}$) bicycloaryl, and hetero($C_{4-12}$)bicycloaryl, each substituted or unsubstituted;
each $R_3$ is independently selected from the group consisting of hydrogen, halo, nitro, cyano, thio, hydroxy, alkoxy, aryloxy, heteroaryloxy, carbonyl, amino, ($C_{1-10}$) alkylamino, sulfonamido, imino, sulfonyl, sulfinyl, ($C_{1-10}$)alkyl, ($C_{3-12}$)cycloalkyl, hetero($C_{3-12}$)cycloalkyl, ($C_{9-12}$)bicycloalkyl, hetero($C_{3-12}$)bicycloalkyl, aryl($C_{1-10}$)alkyl, heteroaryl($C_{1-5}$)alkyl, perhalo($C_{1-10}$)alkyl, carbonyl($C_{1-3}$)alkyl, thiocarbonyl ($C_{1-3}$)alkyl, sulfonyl($C_{1-3}$)alkyl, sulfinyl($C_{1-3}$)alkyl, amino($C_{1-10}$)alkyl, imino($C_{1-3}$)alkyl, aryl, heteroaryl, ($C_{9-12}$)bicycloaryl, and hetero($C_{4-12}$)bicycloaryl, each substituted or unsubstituted, or R₂ and one R₃, or two R₃ are taken together to form a substituted or unsubstituted ring;

each R₄ is independently selected from the group consisting of hydrogen, halo, nitro, cyano, thio, hydroxy, alkoxy, aryloxy, heteroaryloxy, carbonyl, amino, $(C_{1-10})$ alkylamino, sulfonamido, imino, sulfonyl, sulfinyl, $(C_{1-10})$alkyl, $(C_{3-12})$cycloalkyl, hetero$(C_{3-12})$cycloalkyl, $(C_{9-12})$bicycloalkyl, hetero$(C_{3-12})$bicycloalkyl, aryl$(C_{1-10})$alkyl, heteroaryl$(C_{1-5})$alkyl, perhalo$(C_{1-10})$alkyl, carbonyl$(C_{1-3})$alkyl, thiocarbonyl $(C_{1-3})$alkyl, sulfonyl$(C_{1-3})$alkyl, sulfinyl$(C_{1-3})$alkyl, amino$(C_{1-10})$alkyl, imino$(C_{1-3})$alkyl, aryl, heteroaryl, $(C_{9-12})$bicycloaryl, and hetero$(C_{4-12})$bicycloaryl, each substituted or unsubstituted, or two R₄ are taken together to form part of a substituted or unsubstituted ring;

R₆ is selected from the group consisting of hydrogen, nitro, thio, hydroxy, alkoxy, aryloxy, heteroaryloxy, carbonyl, amino, sulfonamido, imino, sulfonyl, sulfinyl, $(C_{1-10})$ alkyl, $(C_{3-12})$cycloalkyl, hetero$(C_{3-12})$cycloalkyl, $(C_{9-12})$bicycloalkyl, hetero$(C_{3-12})$bicycloalkyl, aryl $(C_{1-10})$alkyl, heteroaryl$(C_{1-5})$alkyl, $(C_{3-12})$cycloalkyl $(C_{1-10})$alkyl, halo$(C_{1-10})$alkyl, carbonyl$(C_{1-3})$alkyl, thiocarbonyl$(C_{1-3})$alkyl, sulfonyl$(C_{1-3})$alkyl, sulfinyl $(C_{1-3})$alkyl, imino$(C_{1-3})$alkyl, aryl, heteroaryl, $(C_{9-12})$ bicycloaryl, and hetero$(C_{4-12})$bicycloaryl, each substituted or unsubstituted; and R₂₁ and R₂₂ are each independently selected from the group consisting of hydrogen, halo, hydroxy, alkoxy, carbonyl, amino, $(C_{1-5})$alkylamino, $(C_{1-5})$alkyl, halo $(C_{1-5})$alkyl, carbonyl$(C_{1-3})$alkyl and amino$(C_{1-5})$alkyl, each substituted or unsubstituted.

In still a further embodiment, kinase inhibitors of the present invention comprise the following formula:

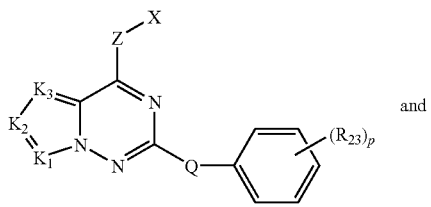

and

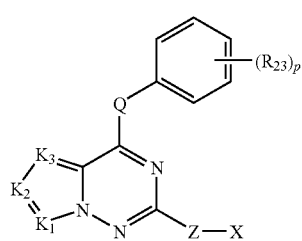

wherein:
l is selected from the group consisting of 1, 2, 3, 4 and 5;
p is selected from the group consisting of 0, 1, 2, 3, 4 and 5;
$K_1$, $K_2$, and $K_3$ are each independently selected from the group consisting of $CR_3$ and N;
Q is selected from the group consisting of S, SO, $SO_2$, O, $NR_6$, $NR_6$—$(CR_{21}R_{22})_l$, $NR_6$—$(CR_{21}R_{22})_l$—O, and a substituted or unsubstituted $(C_{2-5})$alkylene, or Q is absent;

X is selected from the group consisting of $(C_{3-12})$cycloalkyl, hetero$(C_{3-12})$cycloalkyl, $(C_{9-12})$bicycloalkyl, hetero$(C_{3-12})$bicycloalkyl, aryl, heteroaryl, $(C_{9-12})$bicycloaryl and hetero$(C_{4-12})$bicycloaryl, each substituted or unsubstituted;

Z is selected from the group consisting of $NR_1$, S, SO, $SO_2$ and O;

R₁ is selected from the group consisting of hydrogen, nitro, thio, hydroxy, alkoxy, aryloxy, heteroaryloxy, carbonyl, amino, sulfonamido, imino, sulfonyl, sulfinyl, $(C_{1-10})$ alkyl, $(C_{3-12})$cycloalkyl, hetero$(C_{3-12})$cycloalkyl, $(C_{9-12})$bicycloalkyl, hetero$(C_{3-12})$bicycloalkyl, aryl $(C_{1-10})$alkyl, heteroaryl$(C_{1-5})$alkyl, $(C_{3-12})$cycloalkyl $(C_{1-10})$alkyl, halo$(C_{1-10})$alkyl, carbonyl$(C_{1-3})$alkyl, thiocarbonyl$(C_{1-3})$alkyl, sulfonyl$(C_{1-3})$alkyl, sulfinyl $(C_{1-3})$alkyl, imino$(C_{1-3})$alkyl, aryl, heteroaryl, $(C_{9-12})$ bicycloaryl, and hetero$(C_{4-12})$bicycloaryl, each substituted or unsubstituted;

each R₃ is independently selected from the group consisting of hydrogen, halo, nitro, cyano, thio, hydroxy, alkoxy, aryloxy, heteroaryloxy, carbonyl, amino, $(C_{1-10})$ alkylamino, sulfonamido, imino, sulfonyl, sulfinyl, $(C_{1-10})$alkyl, $(C_{3-12})$cycloalkyl, hetero$(C_{3-12})$cycloalkyl, $(C_{9-12})$bicycloalkyl, hetero$(C_{3-12})$bicycloalkyl, aryl$(C_{1-10})$alkyl, heteroaryl$(C_{1-5})$alkyl, perhalo$(C_{1-10})$alkyl, carbonyl$(C_{1-3})$alkyl, thiocarbonyl $(C_{1-3})$alkyl, sulfonyl$(C_{1-3})$alkyl, sulfinyl$(C_{1-3})$alkyl, amino$(C_{1-10})$alkyl, imino$(C_{1-3})$alkyl, aryl, heteroaryl, $(C_{9-12})$bicycloaryl, and hetero$(C_{4-12})$bicycloaryl, each substituted or unsubstituted, or R₂ and one R₃, or two R₃ are taken together to form a substituted or unsubstituted ring;

R₆ is selected from the group consisting of hydrogen, nitro, thio, hydroxy, alkoxy, aryloxy, heteroaryloxy, carbonyl, amino, sulfonamido, imino, sulfonyl, sulfinyl, $(C_{1-10})$ alkyl, $(C_{3-12})$cycloalkyl, hetero$(C_{3-12})$cycloalkyl, $(C_{9-12})$bicycloalkyl, hetero$(C_{3-12})$bicycloalkyl, aryl $(C_{1-10})$alkyl, heteroaryl$(C_{1-5})$alkyl, $(C_{3-12})$cycloalkyl $(C_{1-10})$alkyl, halo$(C_{1-10})$alkyl, carbonyl$(C_{1-3})$alkyl, thiocarbonyl$(C_{1-3})$alkyl, sulfonyl$(C_{1-3})$alkyl, sulfinyl $(C_{1-3})$alkyl, imino$(C_{1-3})$alkyl, aryl, heteroaryl, $(C_{9-12})$ bicycloaryl, and hetero$(C_{4-12})$bicycloaryl, each substituted or unsubstituted;

R₂₁ and R₂₂ are each independently selected from the group consisting of hydrogen, halo, hydroxy, alkoxy, carbonyl, amino, $(C_{1-5})$alkylamino, $(C_{1-5})$alkyl, halo $(C_{1-5})$alkyl, carbonyl$(C_{1-3})$alkyl and amino$(C_{1-5})$alkyl, each substituted or unsubstituted; and R₂₃ is selected from the group consisting of hydrogen, halo, nitro, cyano, thio, oxy, hydroxy, carbonyloxy, alkoxy, aryloxy, heteroaryloxy, carbonyl, oxycarbonyl, aminocarbonyl, amino, $(C_{1-10})$alkylamino, sulfonamido, imino, sulfonyl, sulfinyl, $(C_{1-10})$alkyl, halo$(C_{1-10})$ alkyl, carbonyl$(C_{1-3})$alkyl, thiocarbonyl$(C_{1-3})$alkyl, sulfonyl$(C_{1-3})$alkyl, sulfinyl$(C_{1-3})$alkyl, amino$(C_{1-10})$ alkyl, imino$(C_{1-3})$alkyl, $(C_{3-12})$cycloalkyl$(C_{1-5})$alkyl, hetero$(C_{3-12})$cycloalkyl$(C_{1-5})$alkyl, aryl$(C_{1-10})$alkyl, heteroaryl$(C_{1-5})$alkyl, $(C_{9-12})$bicycloaryl$(C_{1-5})$alkyl, hetero$(C_{8-12})$bicycloaryl$(C_{1-5})$alkyl, $(C_{3-12})$cycloalkyl, hetero$(C_{3-12})$cycloalkyl, $(C_{9-12})$bicycloalkyl, hetero $(C_{3-12})$bicycloalkyl, aryl, heteroaryl, $(C_{9-12})$bicycloaryl and hetero$(C_{4-12})$bicycloaryl, each substituted or unsubstituted, or two R₂₃ are taken together to form a ring.

In another embodiment, kinase inhibitors of the present invention comprise the following formula:

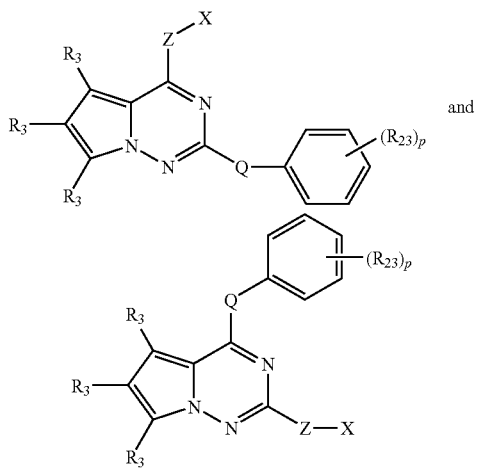

and wherein:
l is selected from the group consisting of 1, 2, 3, 4 and 5;
p is selected from the group consisting of 0, 1, 2, 3, 4 and 5;
Q is selected from the group consisting of S, SO, SO$_2$, O, NR$_6$, NR$_6$—(CR$_{21}$R$_{22}$)$_l$, NR$_6$—(CR$_{21}$R$_{22}$)$_l$—O, and a substituted or unsubstituted (C$_{2-5}$)alkylene, or Q is absent;
X is selected from the group consisting of (C$_{3-12}$)cycloalkyl, hetero(C$_{3-12}$)cycloalkyl, (C$_{9-12}$)bicycloalkyl, hetero(C$_{3-12}$)bicycloalkyl, aryl, heteroaryl, (C$_{9-12}$)bicycloaryl and hetero(C$_{4-12}$)bicycloaryl, each substituted or unsubstituted;
Z is selected from the group consisting of NR$_1$, S, SO, SO$_2$ and O;
R$_1$ is selected from the group consisting of hydrogen, nitro, thio, hydroxy, alkoxy, aryloxy, heteroaryloxy, carbonyl, amino, sulfonamido, imino, sulfonyl, sulfinyl, (C$_{1-10}$)alkyl, (C$_{3-12}$)cycloalkyl, hetero(C$_{3-12}$)cycloalkyl, (C$_{9-12}$)bicycloalkyl, hetero(C$_{3-12}$)bicycloalkyl, aryl(C$_{1-10}$)alkyl, heteroaryl(C$_{1-5}$)alkyl, (C$_{3-12}$)cycloalkyl(C$_{1-10}$)alkyl, halo(C$_{1-10}$)alkyl, carbonyl(C$_{1-3}$)alkyl, thiocarbonyl(C$_{1-3}$)alkyl, sulfonyl(C$_{1-3}$)alkyl, sulfinyl(C$_{1-3}$)alkyl, imino(C$_{1-3}$)alkyl, aryl, heteroaryl, (C$_{9-12}$)bicycloaryl, and hetero(C$_{4-12}$)bicycloaryl, each substituted or unsubstituted;
each R$_3$ is independently selected from the group consisting of hydrogen, halo, nitro, cyano, thio, hydroxy, alkoxy, aryloxy, heteroaryloxy, carbonyl, amino, (C$_{1-10}$)alkylamino, sulfonamido, imino, sulfonyl, sulfinyl, (C$_{1-10}$)alkyl, (C$_{3-12}$)cycloalkyl, hetero(C$_{3-12}$)cycloalkyl, (C$_{9-12}$)bicycloalkyl, hetero(C$_{3-12}$)bicycloalkyl, aryl(C$_{1-10}$)alkyl, heteroaryl(C$_{1-5}$)alkyl, perhalo(C$_{1-10}$)alkyl, carbonyl(C$_{1-3}$)alkyl, thiocarbonyl(C$_{1-3}$)alkyl, sulfonyl(C$_{1-3}$)alkyl, sulfinyl(C$_{1-3}$)alkyl, amino(C$_{1-10}$)alkyl, imino(C$_{1-3}$)alkyl, aryl, heteroaryl, (C$_{9-12}$)bicycloaryl, and hetero(C$_{4-12}$)bicycloaryl, each substituted or unsubstituted, or R$_2$ and one R$_3$, or two R$_3$ are taken together to form a substituted or unsubstituted ring;
R$_6$ is selected from the group consisting of hydrogen, nitro, thio, hydroxy, alkoxy, aryloxy, heteroaryloxy, carbonyl, amino, sulfonamido, imino, sulfonyl, sulfinyl, (C$_{1-10}$)alkyl, (C$_{3-12}$)cycloalkyl, hetero(C$_{3-12}$)cycloalkyl, (C$_{9-12}$)bicycloalkyl, hetero(C$_{3-12}$)bicycloalkyl, aryl(C$_{1-10}$)alkyl, heteroaryl(C$_{1-5}$)alkyl, (C$_{3-12}$)cycloalkyl(C$_{1-10}$)alkyl, halo(C$_{1-10}$)alkyl, carbonyl(C$_{1-3}$)alkyl, thiocarbonyl(C$_{1-3}$)alkyl, sulfonyl(C$_{1-3}$)alkyl, sulfinyl(C$_{1-3}$)alkyl, imino(C$_{1-3}$)alkyl, aryl, heteroaryl, (C$_{9-12}$)bicycloaryl, and hetero(C$_{4-12}$)bicycloaryl, each substituted or unsubstituted;
R$_{21}$ and R$_{22}$ are each independently selected from the group consisting of hydrogen, halo, hydroxy, alkoxy, carbonyl, amino, (C$_{1-5}$)alkylamino, (C$_{1-5}$)alkyl, halo(C$_{1-5}$)alkyl, carbonyl(C$_{1-3}$)alkyl and amino(C$_{1-5}$)alkyl, each substituted or unsubstituted; and
R$_{23}$ is selected from the group consisting of hydrogen, halo, nitro, cyano, thio, oxy, hydroxy, carbonyloxy, alkoxy, aryloxy, heteroaryloxy, carbonyl, oxycarbonyl, aminocarbonyl, amino, (C$_{1-10}$)alkylamino, sulfonamido, imino, sulfonyl, sulfinyl, (C$_{1-10}$)alkyl, halo(C$_{1-10}$)alkyl, carbonyl(C$_{1-3}$)alkyl, thiocarbonyl(C$_{1-3}$)alkyl, sulfonyl(C$_{1-3}$)alkyl, sulfinyl(C$_{1-3}$)alkyl, amino(C$_{1-10}$)alkyl, imino(C$_{1-3}$)alkyl, (C$_{3-12}$)cycloalkyl(C$_{1-5}$)alkyl, hetero(C$_{3-12}$)cycloalkyl(C$_{1-5}$)alkyl, aryl(C$_{1-10}$)alkyl, heteroaryl(C$_{1-5}$)alkyl, (C$_{9-12}$)bicycloaryl(C$_{1-5}$)alkyl, hetero(C$_{8-12}$)bicycloaryl(C$_{1-5}$)alkyl, (C$_{3-12}$)cycloalkyl, hetero(C$_{3-12}$)cycloalkyl, (C$_{9-12}$)bicycloalkyl, hetero(C$_{3-12}$)bicycloalkyl, aryl, heteroaryl, (C$_{9-12}$)bicycloaryl and hetero(C$_{4-12}$)bicycloaryl, each substituted or unsubstituted, or two R$_{23}$ are taken together to form a ring.

In yet another embodiment, kinase inhibitors of the present invention comprise the following formula:

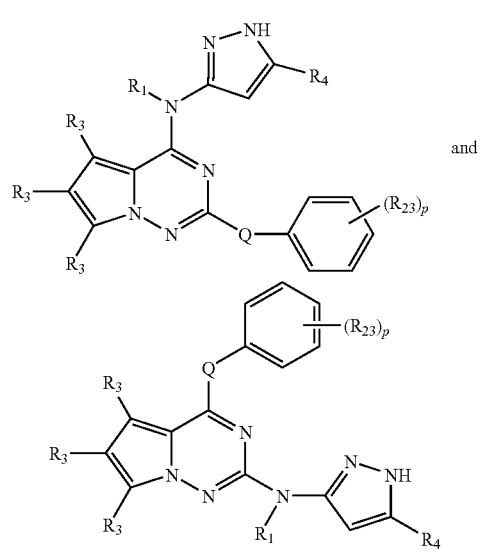

wherein:
l is selected from the group consisting of 1, 2, 3, 4 and 5;
p is selected from the group consisting of 0, 1, 2, 3, 4 and 5;
Q is selected from the group consisting of S, SO, SO$_2$, O, NR$_6$, NR$_6$—(CR$_{21}$R$_{22}$)$_l$, NR$_6$—(CR$_{21}$R$_{22}$)$_l$—O, and a substituted or unsubstituted (C$_{2-5}$)alkylene, or Q is absent;
R$_1$ is selected from the group consisting of hydrogen, nitro, thio, hydroxy, alkoxy, aryloxy, heteroaryloxy, carbonyl, amino, sulfonamido, imino, sulfonyl, sulfinyl, (C$_{1-10}$)alkyl, (C$_{3-12}$)cycloalkyl, hetero(C$_{3-12}$)cycloalkyl, (C$_{9-12}$)bicycloalkyl, hetero(C$_{3-12}$)bicycloalkyl, aryl(C$_{1-10}$)alkyl, heteroaryl(C$_{1-5}$)alkyl, (C$_{3-12}$)cycloalkyl(C$_{1-10}$)alkyl, halo(C$_{1-10}$)alkyl, carbonyl(C$_{1-3}$)alkyl, thiocarbonyl(C$_{1-3}$)alkyl, sulfonyl(C$_{1-3}$)alkyl, sulfinyl ($C_{1-3}$)alkyl, imino($C_{1-3}$)alkyl, aryl, heteroaryl, ($C_{9-12}$) bicycloaryl, and hetero($C_{4-12}$)bicycloaryl, each substituted or unsubstituted;

each $R_3$ is independently selected from the group consisting of hydrogen, halo, nitro, cyano, thio, hydroxy, alkoxy, aryloxy, heteroaryloxy, carbonyl, amino, ($C_{1-10}$) alkylamino, sulfonamido, imino, sulfonyl, sulfinyl, ($C_{1-10}$)alkyl, ($C_{3-12}$)cycloalkyl, hetero($C_{3-12}$)cycloalkyl, ($C_{9-12}$)bicycloalkyl, hetero($C_{3-12}$)bicycloalkyl, aryl($C_{1-10}$)alkyl, heteroaryl($C_{1-5}$)alkyl, perhalo($C_{1-10}$)alkyl, carbonyl($C_{1-3}$)alkyl, thiocarbonyl($C_{1-3}$)alkyl, sulfonyl($C_{1-3}$)alkyl, sulfinyl($C_{1-3}$)alkyl, amino($C_{1-10}$)alkyl, imino($C_{1-3}$)alkyl, aryl, heteroaryl, ($C_{9-12}$)bicycloaryl, and hetero($C_{4-12}$)bicycloaryl, each substituted or unsubstituted, or $R_2$ and one $R_3$, or two $R_3$ are taken together to form a substituted or unsubstituted ring;

$R_4$ is selected from the group consisting of hydrogen, halo, nitro, cyano, thio, hydroxy, alkoxy, aryloxy, heteroaryloxy, carbonyl, amino, ($C_{1-10}$)alkylamino, sulfonamido, imino, sulfonyl, sulfinyl, ($C_{1-10}$)alkyl, ($C_{3-12}$)cycloalkyl, hetero($C_{3-12}$)cycloalkyl, ($C_{9-12}$)bicycloalkyl, hetero($C_{3-12}$)bicycloalkyl, aryl($C_{1-10}$)alkyl, heteroaryl ($C_{1-5}$)alkyl, perhalo($C_{1-10}$)alkyl, carbonyl($C_{1-3}$)alkyl, thiocarbonyl($C_{1-3}$)alkyl, sulfonyl($C_{1-3}$)alkyl, sulfinyl ($C_{1-3}$)alkyl, amino($C_{1-10}$)alkyl, imino($C_{1-3}$)alkyl, aryl, heteroaryl, ($C_{9-12}$)bicycloaryl, and hetero($C_{4-12}$)bicycloaryl, each substituted or unsubstituted;

$R_6$ is selected from the group consisting of hydrogen, nitro, thio, hydroxy, alkoxy, aryloxy, heteroaryloxy, carbonyl, amino, sulfonamido, imino, sulfonyl, sulfinyl, ($C_{1-10}$) alkyl, ($C_{3-12}$)cycloalkyl, hetero($C_{3-12}$)cycloalkyl, ($C_{9-12}$)bicycloalkyl, hetero($C_{3-12}$)bicycloalkyl, aryl ($C_{1-10}$)alkyl, heteroaryl($C_{1-5}$)alkyl, ($C_{3-12}$)cycloalkyl ($C_{1-10}$)alkyl, halo($C_{1-10}$)alkyl, carbonyl($C_{1-3}$)alkyl, thiocarbonyl($C_{1-3}$)alkyl, sulfonyl($C_{1-3}$)alkyl, sulfinyl ($C_{1-3}$)alkyl, imino($C_{1-3}$)alkyl, aryl, heteroaryl, ($C_{9-12}$) bicycloaryl, and hetero($C_{4-12}$)bicycloaryl, each substituted or unsubstituted;

$R_{21}$ and $R_{22}$ are each independently selected from the group consisting of hydrogen, halo, hydroxy, alkoxy, carbonyl, amino, ($C_{1-5}$)alkylamino, ($C_{1-5}$)alkyl, halo ($C_{1-5}$)alkyl, carbonyl($C_{1-3}$)alkyl and amino($C_{1-5}$)alkyl, each substituted or unsubstituted; and $R_{23}$ is selected from the group consisting of hydrogen, halo, nitro, cyano, thio, oxy, hydroxy, carbonyloxy, alkoxy, aryloxy, heteroaryloxy, carbonyl, oxycarbonyl, aminocarbonyl, amino, ($C_{1-10}$)alkylamino, sulfonamido, imino, sulfonyl, sulfinyl, ($C_{1-10}$)alkyl, halo($C_{1-10}$) alkyl, carbonyl($C_{1-3}$)alkyl, thiocarbonyl($C_{1-3}$)alkyl, sulfonyl($C_{1-3}$)alkyl, sulfinyl($C_{1-3}$)alkyl, amino($C_{1-10}$) alkyl, imino($C_{1-3}$)alkyl, ($C_{3-12}$)cycloalkyl($C_{1-5}$)alkyl, hetero($C_{3-12}$)cycloalkyl($C_{1-5}$)alkyl, aryl($C_{1-10}$)alkyl, heteroaryl($C_{1-5}$)alkyl, ($C_{9-12}$)bicycloaryl($C_{1-5}$)alkyl, hetero($C_{8-12}$)bicycloaryl($C_{1-5}$)alkyl, ($C_{3-12}$)cycloalkyl, hetero($C_{3-12}$)cycloalkyl, ($C_{9-12}$)bicycloalkyl, hetero ($C_{3-12}$)bicycloalkyl, aryl, heteroaryl, ($C_{9-12}$)bicycloaryl and hetero($C_{4-12}$)bicycloaryl, each substituted or unsubstituted, or two $R_{23}$ are taken together to form a ring.

In another embodiment, kinase inhibitors of the present invention comprise one of the following formulae:

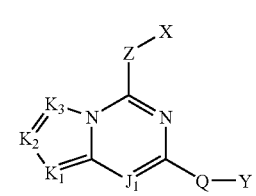

Ia

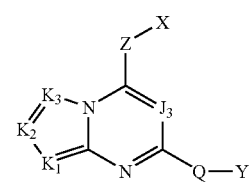

IIa

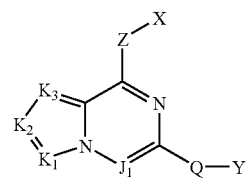

IIIa

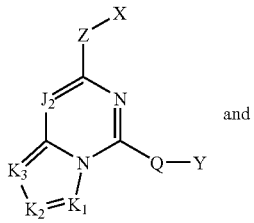

IVa and

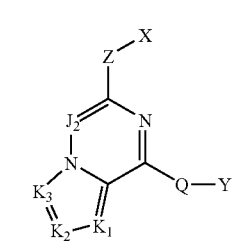

Va wherein:
l is selected from the group consisting of 1, 2, 3, 4 and 5;
$J_1$, $J_2$, and $J_3$ are selected from the group consisting of $CR_2$ and N;
$K_1$, $K_2$, and $K_3$ are each independently selected from the group consisting of $CR_3$ and N, with the proviso that $K_3$ is not N in Formula IIa when $K_1$ is $CR_2$, and $K_2$ and $J_3$ are each CH;
Q is selected from the group consisting of S, SO, $SO_2$, O, $NR_6$, $NR_6$—($CR_{21}R_{22}$)$_l$, $NR_6$—($CR_{21}R_{22}$)$_l$—O, and a substituted or unsubstituted ($C_{2-5}$)alkylene, or Q is absent, with the proviso that Q is not absent in Formula Ia when $J_1$ is CH, $K_1$ is N, $K_2$ is $CR_3$, and $K_3$ is CH or N;
X is selected from the group consisting of ($C_{3-12}$)cycloalkyl, hetero($C_{3-12}$)cycloalkyl, ($C_{9-12}$)bicycloalkyl, hetero($C_{3-12}$)bicycloalkyl, aryl, heteroaryl, ($C_{9-12}$)bicycloaryl and hetero($C_{4-12}$)bicycloaryl, each substituted or unsubstituted;
Y is selected from the group consisting of ($C_{3-12}$)cycloalkyl, hetero($C_{3-12}$)cycloalkyl, ($C_{9-12}$)bicycloalkyl, hetero($C_{3-12}$)bicycloalkyl, aryl, heteroaryl, ($C_{9-12}$)bicycloaryl, and hetero($C_{4-12}$)bicycloaryl, each substituted or unsubstituted;

Z is selected from the group consisting of $NR_1$, S, SO, $SO_2$ and O, with the provisos that Z is not NH or NC(O)—$CH_3$ in Formula IIIa when $K_3$ is N and $J_1$, $K_1$ and $K_2$ are all C; and Z is not NH or N—C(O)—O—C($CH_3$)$_3$ when $K_3$ is N and $J_1$, $K_1$ and $K_2$ are all C;

$R_1$ is selected from the group consisting of hydrogen, nitro, thio, hydroxy, alkoxy, aryloxy, heteroaryloxy, carbonyl, amino, sulfonamido, imino, sulfonyl, sulfinyl, ($C_{1-10}$) alkyl, ($C_{3-12}$)cycloalkyl, hetero($C_{3-12}$)cycloalkyl, ($C_{9-12}$)bicycloalkyl, hetero($C_{3-12}$)bicycloalkyl, aryl ($C_{1-10}$)alkyl, heteroaryl($C_{1-5}$)alkyl, ($C_{3-12}$)cycloalkyl ($C_{1-10}$)alkyl, halo($C_{1-10}$)alkyl, carbonyl($C_{1-3}$)alkyl, thiocarbonyl($C_{1-3}$)alkyl, sulfonyl($C_{1-3}$)alkyl, sulfinyl ($C_{1-3}$)alkyl, imino($C_{1-3}$)alkyl, aryl, heteroaryl, ($C_{9-12}$) bicycloaryl, and hetero($C_{4-12}$)bicycloaryl, each substituted or unsubstituted;

$R_2$ is selected from the group consisting of hydrogen, halo, nitro, cyano, thio, hydroxy, alkoxy, aryloxy, heteroaryloxy, carbonyl, amino, ($C_{1-10}$)alkylamino, sulfonamido, imino, sulfonyl, sulfinyl, ($C_{1-10}$)alkyl, ($C_{3-12}$)cycloalkyl, hetero($C_{3-12}$)cycloalkyl, ($C_{9-12}$)bicycloalkyl, hetero($C_{3-12}$)bicycloalkyl, aryl($C_{1-10}$)alkyl, heteroaryl ($C_{1-5}$)alkyl, perhalo($C_{1-10}$)alkyl, carbonyl($C_{1-3}$)alkyl, thiocarbonyl($C_{1-3}$)alkyl, sulfonyl($C_{1-3}$)alkyl, sulfinyl ($C_{1-3}$)alkyl, amino($C_{1-10}$)alkyl, imino($C_{1-3}$)alkyl, aryl, heteroaryl, ($C_{9-12}$)bicycloaryl, and hetero($C_{4-12}$)bicycloaryl, each substituted or unsubstituted;

each $R_3$ is independently selected from the group consisting of hydrogen, halo, nitro, cyano, thio, hydroxy, alkoxy, aryloxy, heteroaryloxy, carbonyl, amino, ($C_{1-10}$) alkylamino, sulfonamido, imino, sulfonyl, sulfinyl, ($C_{1-10}$)alkyl, ($C_{3-12}$)cycloalkyl, hetero($C_{3-12}$)cycloalkyl, ($C_{9-12}$)bicycloalkyl, hetero($C_{3-12}$)bicycloalkyl, aryl($C_{1-10}$)alkyl, heteroaryl($C_{1-5}$)alkyl, perhalo($C_{1-10}$)alkyl, carbonyl($C_{1-3}$)alkyl, thiocarbonyl ($C_{1-3}$)alkyl, sulfonyl($C_{1-3}$)alkyl, sulfinyl($C_{1-3}$)alkyl, amino($C_{1-10}$)alkyl, imino($C_{1-3}$)alkyl, aryl, heteroaryl, ($C_{9-12}$)bicycloaryl, and hetero($C_{4-12}$)bicycloaryl, each substituted or unsubstituted, or $R_2$ and one $R_3$, or two $R_3$ are taken together to form a substituted or unsubstituted ring;

$R_6$ is selected from the group consisting of hydrogen, nitro, thio, hydroxy, alkoxy, aryloxy, heteroaryloxy, carbonyl, amino, sulfonamido, imino, sulfonyl, sulfinyl, ($C_{1-10}$) alkyl, ($C_{3-12}$)cycloalkyl, hetero($C_{3-12}$)cycloalkyl, ($C_{9-12}$)bicycloalkyl, hetero($C_{3-12}$)bicycloalkyl, aryl ($C_{1-10}$)alkyl, heteroaryl($C_{1-5}$)alkyl, ($C_{3-12}$)cycloalkyl ($C_{1-10}$)alkyl, halo($C_{1-10}$)alkyl, carbonyl($C_{1-3}$)alkyl, thiocarbonyl($C_{1-3}$)alkyl, sulfonyl($C_{1-3}$)alkyl, sulfinyl ($C_{1-3}$)alkyl, imino($C_{1-3}$)alkyl, aryl, heteroaryl, ($C_{9-12}$) bicycloaryl, and hetero($C_{4-12}$)bicycloaryl, each substituted or unsubstituted; and $R_{21}$ and $R_{22}$ are each independently selected from the group consisting of hydrogen, halo, hydroxy, alkoxy, carbonyl, amino, ($C_{1-5}$)alkylamino, ($C_{1-5}$)alkyl, halo ($C_{1-5}$)alkyl, carbonyl($C_{1-3}$)alkyl and amino($C_{1-5}$)alkyl, each substituted or unsubstituted.

In another embodiment, kinase inhibitors of the present invention comprise one of the following formulae:

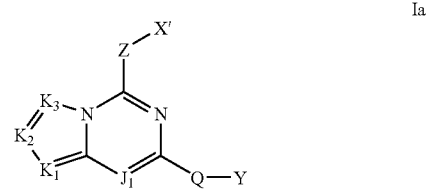

Ia

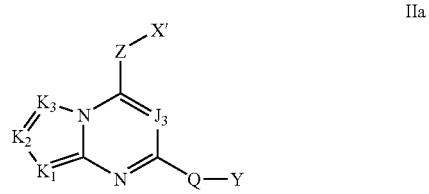

IIa

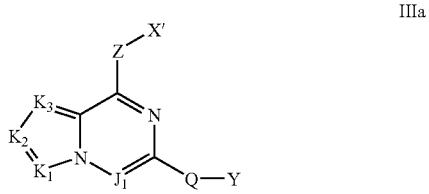

IIIa

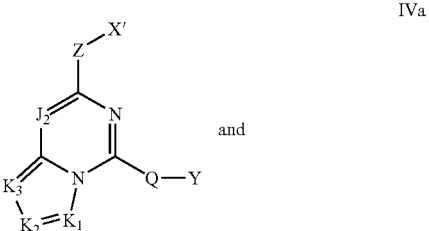

IVa and

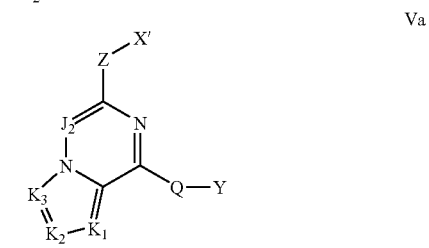

Va wherein:
l is selected from the group consisting of 1, 2, 3, 4 and 5;
$J_1$, $J_2$, and $J_3$ are selected from the group consisting of $CR_2$ and N;
$K_1$, $K_2$, and $K_3$ are each independently selected from the group consisting of $CR_3$ and N, with the proviso that $K_3$ is not N in Formula IIa when $K_1$ is $CR_2$, and $K_2$ and $J_3$ are each CH;
Q is selected from the group consisting of S, SO, $SO_2$, O, $NR_6$, $NR_6$—$(CR_{21}R_{22})_l$, $NR_6$—$(CR_{21}R_{22})_l$—O, and a substituted or unsubstituted ($C_{2-5}$)alkylene, or Q is absent, with the proviso that Q is not absent in Formula Ia when $J_1$ is CH, $K_1$ is N, $K_2$ is $CR_3$, and $K_3$ is CH or N;
X' is selected from the group consisting of pyrazolyl and indazolyl, each substituted or unsubstituted;
Y is selected from the group consisting of ($C_{3-12}$)cycloalkyl, hetero($C_{3-12}$)cycloalkyl, ($C_{9-12}$)bicycloalkyl, hetero($C_{3-12}$)bicycloalkyl, aryl, heteroaryl, ($C_{9-12}$)bicycloaryl, and hetero($C_{4-12}$)bicycloaryl, each substituted or unsubstituted;
Z is selected from the group consisting of $NR_1$, S, SO, $SO_2$ and O;

$R_1$ is selected from the group consisting of hydrogen, nitro, thio, hydroxy, alkoxy, aryloxy, heteroaryloxy, carbonyl, amino, sulfonamido, imino, sulfonyl, sulfinyl, $(C_{1-10})$alkyl, $(C_{3-12})$cycloalkyl, hetero$(C_{3-12})$cycloalkyl, $(C_{9-12})$bicycloalkyl, hetero$(C_{3-12})$bicycloalkyl, aryl$(C_{1-10})$alkyl, heteroaryl$(C_{1-5})$alkyl, $(C_{3-12})$cycloalkyl$(C_{1-10})$alkyl, halo$(C_{1-10})$alkyl, carbonyl$(C_{1-3})$alkyl, thiocarbonyl$(C_{1-3})$alkyl, sulfonyl$(C_{1-3})$alkyl, sulfinyl$(C_{1-3})$alkyl, imino$(C_{1-3})$alkyl, aryl, heteroaryl, $(C_{9-12})$bicycloaryl, and hetero$(C_{4-12})$bicycloaryl, each substituted or unsubstituted;

$R_2$ is selected from the group consisting of hydrogen, halo, nitro, cyano, thio, hydroxy, alkoxy, aryloxy, heteroaryloxy, carbonyl, amino, $(C_{1-10})$alkylamino, sulfonamido, imino, sulfonyl, sulfinyl, $(C_{1-10})$alkyl, $(C_{3-12})$cycloalkyl, hetero$(C_{3-12})$cycloalkyl, $(C_{9-12})$bicycloalkyl, hetero$(C_{3-12})$bicycloalkyl, aryl$(C_{1-10})$alkyl, heteroaryl$(C_{1-5})$alkyl, perhalo$(C_{1-10})$alkyl, carbonyl$(C_{1-3})$alkyl, thiocarbonyl$(C_{1-3})$alkyl, sulfonyl$(C_{1-3})$alkyl, sulfinyl$(C_{1-3})$alkyl, amino$(C_{1-10})$alkyl, imino$(C_{1-3})$alkyl, aryl, heteroaryl, $(C_{9-12})$bicycloaryl, and hetero$(C_{4-12})$bicycloaryl, each substituted or unsubstituted;

each $R_3$ is independently selected from the group consisting of hydrogen, halo, nitro, cyano, thio, hydroxy, alkoxy, aryloxy, heteroaryloxy, carbonyl, amino, $(C_{1-10})$alkylamino, sulfonamido, imino, sulfonyl, sulfinyl, $(C_{1-10})$alkyl, $(C_{3-12})$cycloalkyl, hetero$(C_{3-12})$cycloalkyl, $(C_{9-12})$bicycloalkyl, hetero$(C_{3-12})$bicycloalkyl, aryl$(C_{1-10})$alkyl, heteroaryl$(C_{1-5})$alkyl, perhalo$(C_{1-10})$alkyl, carbonyl$(C_{1-3})$alkyl, thiocarbonyl$(C_{1-3})$alkyl, sulfonyl$(C_{1-3})$alkyl, sulfinyl$(C_{1-3})$alkyl, amino$(C_{1-10})$alkyl, imino$(C_{1-3})$alkyl, aryl, heteroaryl, $(C_{9-12})$bicycloaryl, and hetero$(C_{4-12})$bicycloaryl, each substituted or unsubstituted, or $R_2$ and one $R_3$, or two $R_3$ are taken together to form a substituted or unsubstituted ring;

$R_6$ is selected from the group consisting of hydrogen, nitro, thio, hydroxy, alkoxy, aryloxy, heteroaryloxy, carbonyl, amino, sulfonamido, imino, sulfonyl, sulfinyl, $(C_{1-10})$alkyl, $(C_{3-12})$cycloalkyl, hetero$(C_{3-12})$cycloalkyl, $(C_{9-12})$bicycloalkyl, hetero$(C_{3-12})$bicycloalkyl, aryl$(C_{1-10})$alkyl, heteroaryl$(C_{1-5})$alkyl, $(C_{3-12})$cycloalkyl$(C_{1-10})$alkyl, halo$(C_{1-10})$alkyl, carbonyl$(C_{1-3})$alkyl, thiocarbonyl$(C_{1-3})$alkyl, sulfonyl$(C_{1-3})$alkyl, sulfinyl$(C_{1-3})$alkyl, imino$(C_{1-3})$alkyl, aryl, heteroaryl, $(C_{9-12})$bicycloaryl, and hetero$(C_{4-12})$bicycloaryl, each substituted or unsubstituted; and $R_{21}$ and $R_{22}$ are each independently selected from the group consisting of hydrogen, halo, hydroxy, alkoxy, carbonyl, amino, $(C_{1-5})$alkylamino, $(C_{1-5})$alkyl, halo$(C_{1-5})$alkyl, carbonyl$(C_{1-3})$alkyl and amino$(C_{1-5})$alkyl, each substituted or unsubstituted.

In a further embodiment, kinase inhibitors of the present invention comprise one of the following formulae:

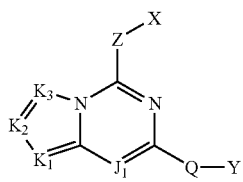

Ia

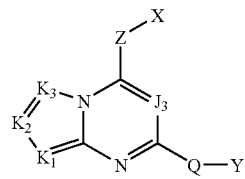

IIa

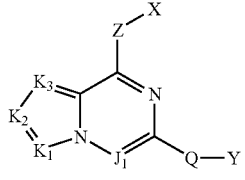

IIIa

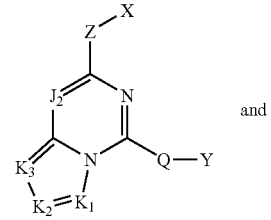

IVa and

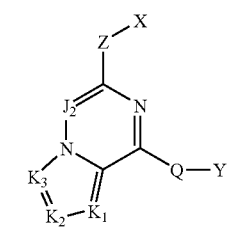

Va wherein:
l is selected from the group consisting of 1, 2, 3, 4 and 5;
$J_1$, $J_2$, and $J_3$ are selected from the group consisting of $CR_2$ and N;
$K_1$, $K_2$, and $K_3$ are each independently selected from the group consisting of $CR_3$ and N, with the proviso that $K_3$ is not N in Formula IIa when $K_1$ is $CR_2$, and $K_2$ and $J_3$ are each CH;
Q is selected from the group consisting of S, SO, $SO_2$, O, $NR_6$, $NR_6$—$(CR_{21}R_{22})_l$, $NR_6$—$(CR_{21}R_{22})_l$—O, and a substituted or unsubstituted $(C_{2-5})$alkylene, or Q is absent, with the proviso that Q is not absent in Formula Ia when $J_1$ is CH, $K_1$ is N, $K_2$ is $CR_3$, and $K_3$ is CH or N;
X is selected from the group consisting of $(C_{3-12})$cycloalkyl, hetero$(C_{3-12})$cycloalkyl, $(C_{9-12})$bicycloalkyl, hetero$(C_{3-12})$bicycloalkyl, aryl, heteroaryl, $(C_{9-12})$bicycloaryl and hetero$(C_{4-12})$bicycloaryl, each substituted or unsubstituted;
Y is selected from the group consisting of $(C_{3-12})$cycloalkyl, hetero$(C_{3-12})$cycloalkyl, $(C_{9-12})$bicycloalkyl, hetero$(C_{3-12})$bicycloalkyl, aryl, heteroaryl, $(C_{9-12})$bicycloaryl, and hetero$(C_{4-12})$bicycloaryl, each substituted or unsubstituted;
Z is selected from the group consisting of $NR_1'$, S, SO, $SO_2$ and O;
$R_1'$ is selected from the group consisting of hydrogen and unsubstituted or substituted $(C_{1-4})$alkyl;
$R_2$ is selected from the group consisting of hydrogen, halo, nitro, cyano, thio, hydroxy, alkoxy, aryloxy, heteroaryloxy, carbonyl, amino, $(C_{1-10})$alkylamino, sulfonamido, imino, sulfonyl, sulfinyl, $(C_{1-10})$alkyl, $(C_{3-12})$cycloalkyl, hetero($C_{3-12}$)cycloalkyl, ($C_{9-12}$)bicycloalkyl, hetero($C_{3-12}$)bicycloalkyl, aryl($C_{1-10}$)alkyl, heteroaryl ($C_{1-5}$)alkyl, perhalo($C_{1-10}$)alkyl, carbonyl($C_{1-3}$)alkyl, thiocarbonyl($C_{1-3}$)alkyl, sulfonyl($C_{1-3}$)alkyl, sulfinyl ($C_{1-3}$)alkyl, amino($C_{1-10}$)alkyl, imino($C_{1-3}$)alkyl, aryl, heteroaryl, ($C_{9-12}$)bicycloaryl, and hetero($C_{4-12}$)bicycloaryl, each substituted or unsubstituted;

each $R_3$ is independently selected from the group consisting of hydrogen, halo, nitro, cyano, thio, hydroxy, alkoxy, aryloxy, heteroaryloxy, carbonyl, amino, ($C_{1-10}$)alkylamino, sulfonamido, imino, sulfonyl, sulfinyl, ($C_{1-10}$)alkyl, ($C_{3-12}$)cycloalkyl, hetero($C_{3-12}$)cycloalkyl, ($C_{9-12}$)bicycloalkyl, hetero($C_{3-12}$)bicycloalkyl, aryl ($C_{1-10}$)alkyl, heteroaryl($C_{1-5}$)alkyl, perhalo($C_{1-10}$)alkyl, carbonyl($C_{1-3}$)alkyl, thiocarbonyl($C_{1-3}$)alkyl, sulfonyl ($C_{1-3}$)alkyl, sulfinyl($C_{1-3}$)alkyl, amino($C_{1-10}$)alkyl, imino($C_{1-3}$)alkyl, aryl, heteroaryl, ($C_{9-12}$)bicycloaryl, and hetero($C_{4-12}$)bicycloaryl, each substituted or unsubstituted, or $R_2$ and one $R_3$, or two $R_3$ are taken together to form a substituted or unsubstituted ring;

$R_6$ is selected from the group consisting of hydrogen, nitro, thio, hydroxy, alkoxy, aryloxy, heteroaryloxy, carbonyl, amino, sulfonamido, imino, sulfonyl, sulfinyl, ($C_{1-10}$) alkyl, ($C_{3-12}$)cycloalkyl, hetero($C_{3-12}$)cycloalkyl, ($C_{9-12}$)bicycloalkyl, hetero($C_{3-12}$)bicycloalkyl, aryl ($C_{1-10}$)alkyl, heteroaryl($C_{1-5}$)alkyl, ($C_{3-12}$)cycloalkyl ($C_{1-10}$)alkyl, halo($C_{1-10}$)alkyl, carbonyl($C_{1-3}$)alkyl, thiocarbonyl($C_{1-3}$)alkyl, sulfonyl($C_{1-3}$)alkyl, sulfinyl ($C_{1-3}$)alkyl, imino($C_{1-3}$)alkyl, aryl, heteroaryl, ($C_{9-12}$) bicycloaryl, and hetero($C_{4-12}$)bicycloaryl, each substituted or unsubstituted; and $R_{21}$ and $R_{22}$ are each independently selected from the group consisting of hydrogen, halo, hydroxy, alkoxy, carbonyl, amino, ($C_{1-5}$)alkylamino, ($C_{1-5}$)alkyl, halo ($C_{1-5}$)alkyl, carbonyl($C_{1-3}$)alkyl and amino($C_{1-5}$)alkyl, each substituted or unsubstituted.

In still another embodiment, kinase inhibitors of the present invention comprise one of the following formulae:

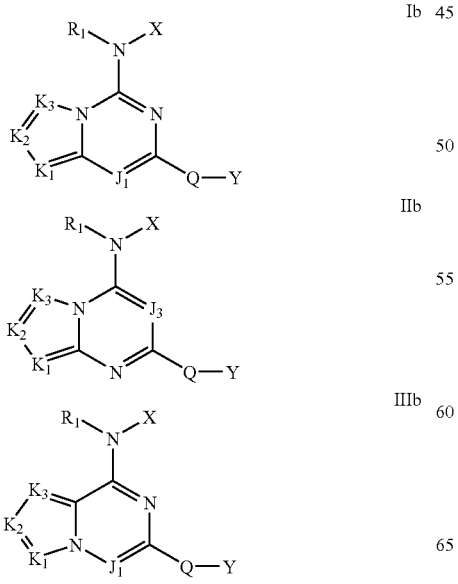

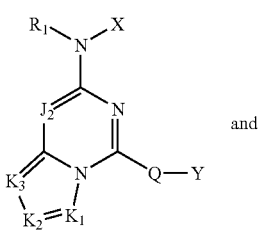

and

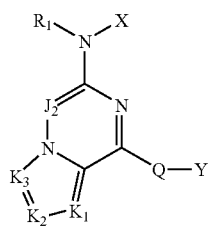

wherein:
l is selected from the group consisting of 1, 2, 3, 4 and 5;
$J_1$, $J_2$, and $J_3$ are selected from the group consisting of $CR_2$ and N;
$K_1$, $K_2$, and $K_3$ are each independently selected from the group consisting of $CR_3$ and N, with the proviso that $K_3$ is not N in Formula IIa when $K_1$ is $CR_2$, and $K_2$ and $J_3$ are each CH;
Q is selected from the group consisting of S, SO, $SO_2$, O, $NR_6$, $NR_6$—$(CR_{21}R_{22})_l$, $NR_6$—$(CR_{21}R_{22})_l$—O, and a substituted or unsubstituted ($C_{2-5}$)alkylene, or Q is absent, with the proviso that Q is not absent in Formula Ib when $J_1$ is CH, $K_1$ is N, $K_2$ is $CR_3$, and $K_3$ is CH or N;
X is selected from the group consisting of ($C_{3-12}$)cycloalkyl, hetero($C_{3-12}$)cycloalkyl, ($C_{9-12}$)bicycloalkyl, hetero($C_{3-12}$)bicycloalkyl, aryl, heteroaryl, ($C_{9-12}$)bicycloaryl and hetero($C_{4-12}$)bicycloaryl, each substituted or unsubstituted;
Y is selected from the group consisting of ($C_{3-12}$)cycloalkyl, hetero($C_{3-12}$)cycloalkyl, ($C_{9-12}$)bicycloalkyl, hetero($C_{3-12}$)bicycloalkyl, aryl, heteroaryl, ($C_{9-12}$)bicycloaryl, and hetero($C_{4-12}$)bicycloaryl, each substituted or unsubstituted;
$R_1$ is selected from the group consisting of hydrogen, nitro, thio, hydroxy, alkoxy, aryloxy, heteroaryloxy, carbonyl, amino, sulfonamido, imino, sulfonyl, sulfinyl, ($C_{1-10}$) alkyl, ($C_{3-12}$)cycloalkyl, hetero($C_{3-12}$)cycloalkyl, ($C_{9-12}$)bicycloalkyl, hetero($C_{3-12}$)bicycloalkyl, aryl ($C_{1-10}$)alkyl, heteroaryl($C_{1-5}$)alkyl, ($C_{3-12}$)cycloalkyl ($C_{1-10}$)alkyl, halo($C_{1-10}$)alkyl, carbonyl($C_{1-3}$)alkyl, thiocarbonyl($C_{1-3}$)alkyl, sulfonyl($C_{1-3}$)alkyl, sulfinyl ($C_{1-3}$)alkyl, imino($C_{1-3}$)alkyl, aryl, heteroaryl, ($C_{9-12}$) bicycloaryl, and hetero($C_{4-12}$)bicycloaryl, each substituted or unsubstituted;
$R_2$ is selected from the group consisting of hydrogen, halo, nitro, cyano, thio, hydroxy, alkoxy, aryloxy, heteroaryloxy, carbonyl, amino, ($C_{1-10}$)alkylamino, sulfonamido, imino, sulfonyl, sulfinyl, ($C_{1-10}$)alkyl, ($C_{3-12}$)cycloalkyl, hetero($C_{3-12}$)cycloalkyl, ($C_{9-12}$)bicycloalkyl, hetero($C_{3-12}$)bicycloalkyl, aryl($C_{1-10}$)alkyl, heteroaryl ($C_{1-5}$)alkyl, perhalo($C_{1-10}$)alkyl, carbonyl($C_{1-3}$)alkyl, thiocarbonyl($C_{1-3}$)alkyl, sulfonyl($C_{1-3}$)alkyl, sulfinyl ($C_{1-3}$)alkyl, amino($C_{1-10}$)alkyl, imino($C_{1-3}$)alkyl, aryl, heteroaryl, ($C_{9-12}$)bicycloaryl, and hetero($C_{4-12}$)bicycloaryl, each substituted or unsubstituted;

each $R_3$ is independently selected from the group consisting of hydrogen, halo, nitro, cyano, thio, hydroxy, alkoxy, aryloxy, heteroaryloxy, carbonyl, amino, $(C_{1-10})$ alkylamino, sulfonamido, imino, sulfonyl, sulfinyl, $(C_{1-10})$alkyl, $(C_{3-12})$cycloalkyl, hetero$(C_{3-12})$cycloalkyl, $(C_{9-12})$bicycloalkyl, hetero$(C_{3-12})$bicycloalkyl, aryl$(C_{1-10})$alkyl, heteroaryl$(C_{1-5})$alkyl, perhalo$(C_{1-10})$alkyl, carbonyl$(C_{1-3})$alkyl, thiocarbonyl$(C_{1-3})$alkyl, sulfonyl$(C_{1-3})$alkyl, sulfinyl$(C_{1-3})$alkyl, amino$(C_{1-10})$alkyl, imino$(C_{1-3})$alkyl, aryl, heteroaryl, $(C_{9-12})$bicycloaryl, and hetero$(C_{4-12})$bicycloaryl, each substituted or unsubstituted, or $R_2$ and one $R_3$, or two $R_3$ are taken together to form a substituted or unsubstituted ring;

$R_6$ is selected from the group consisting of hydrogen, nitro, thio, hydroxy, alkoxy, aryloxy, heteroaryloxy, carbonyl, amino, sulfonamido, imino, sulfonyl, sulfinyl, $(C_{1-10})$alkyl, $(C_{3-12})$cycloalkyl, hetero$(C_{3-12})$cycloalkyl, $(C_{9-12})$bicycloalkyl, hetero$(C_{3-12})$bicycloalkyl, aryl$(C_{1-10})$alkyl, heteroaryl$(C_{1-5})$alkyl, $(C_{3-12})$cycloalkyl$(C_{1-10})$alkyl, halo$(C_{1-10})$alkyl, carbonyl$(C_{1-3})$alkyl, thiocarbonyl$(C_{1-3})$alkyl, sulfonyl$(C_{1-3})$alkyl, sulfinyl$(C_{1-3})$alkyl, imino$(C_{1-3})$alkyl, aryl, heteroaryl, $(C_{9-12})$bicycloaryl, and hetero$(C_{4-12})$bicycloaryl, each substituted or unsubstituted; and $R_{21}$ and $R_{22}$ are each independently selected from the group consisting of hydrogen, halo, hydroxy, alkoxy, carbonyl, amino, $(C_{1-5})$alkylamino, $(C_{1-5})$alkyl, halo $(C_{1-5})$alkyl, carbonyl$(C_{1-3})$alkyl and amino$(C_{1-5})$alkyl, each substituted or unsubstituted.

In yet another embodiment, kinase inhibitors of the present invention comprise one of the following formulae:

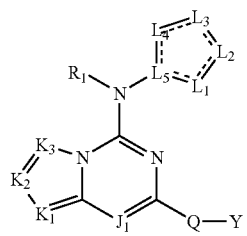

Ic

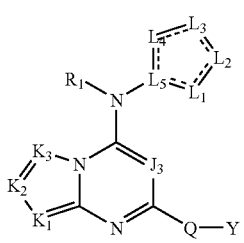

IIc

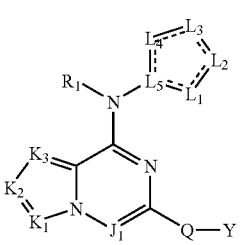

IIIc

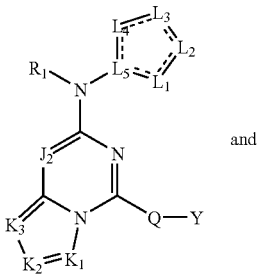

IVc and

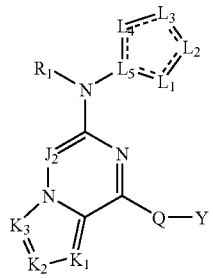

Vc wherein:
l is selected from the group consisting of 1, 2, 3, 4 and 5;
$J_1$, $J_2$ and $J_3$ are each independently selected from the group consisting of $CR_2$ and N;
$K_1$, $K_2$, and $K_3$ are each independently selected from the group consisting of $CR_3$ and N;
$L_1$, $L_2$, $L_3$, $L_4$, and $L_5$ are each independently selected from the group consisting of $CR_4$ and $NR_5$, with the proviso that $R_5$ is absent when the atom to which it is attached forms part of a double bond;
Q is selected from the group consisting of S, SO, $SO_2$, O, $NR_6$, $NR_6$—$(CR_{21}R_{22})_l$, $NR_6$—$(CR_{21}R_{22})_l$—O, and a substituted or unsubstituted $(C_{2-5})$alkylene, or Q is absent, with the proviso that Q is not absent in Formula Ic when $J_1$ is CH, $K_1$ is N, $K_2$ is $CR_3$, and $K_3$ is CH or N;
Y is selected from the group consisting of $(C_{3-12})$cycloalkyl, hetero$(C_{3-12})$cycloalkyl, $(C_{9-12})$bicycloalkyl, hetero$(C_{3-12})$bicycloalkyl, aryl, heteroaryl, $(C_{9-12})$bicycloaryl, and hetero$(C_{4-12})$bicycloaryl, each substituted or unsubstituted;
$R_1$ is selected from the group consisting of hydrogen, nitro, thio, hydroxy, alkoxy, aryloxy, heteroaryloxy, carbonyl, amino, sulfonamido, imino, sulfonyl, sulfinyl, $(C_{1-10})$alkyl, $(C_{3-12})$cycloalkyl, hetero$(C_{3-12})$cycloalkyl, $(C_{9-12})$bicycloalkyl, hetero$(C_{3-12})$bicycloalkyl, aryl $(C_{1-10})$alkyl, heteroaryl$(C_{1-5})$alkyl, $(C_{3-12})$cycloalkyl $(C_{1-10})$alkyl, halo$(C_{1-10})$alkyl, carbonyl$(C_{1-3})$alkyl, thiocarbonyl$(C_{1-3})$alkyl, sulfonyl$(C_{1-3})$alkyl, sulfinyl $(C_{1-3})$alkyl, imino$(C_{1-3})$alkyl, aryl, heteroaryl, $(C_{9-12})$ bicycloaryl, and hetero$(C_{4-12})$bicycloaryl, each substituted or unsubstituted;
$R_2$ is selected from the group consisting of hydrogen, halo, nitro, cyano, thio, hydroxy, alkoxy, aryloxy, heteroaryloxy, carbonyl, amino, $(C_{1-10})$alkylamino, sulfonamido, imino, sulfonyl, sulfinyl, $(C_{1-10})$alkyl, $(C_{3-12})$cycloalkyl, hetero$(C_{3-12})$cycloalkyl, $(C_{9-12})$bicycloalkyl, hetero$(C_{3-12})$bicycloalkyl, aryl$(C_{1-10})$alkyl, heteroaryl $(C_{1-5})$alkyl, perhalo$(C_{1-10})$alkyl, carbonyl$(C_{1-3})$alkyl, thiocarbonyl$(C_{1-3})$alkyl, sulfonyl$(C_{1-3})$alkyl, sulfinyl $(C_{1-3})$alkyl, amino$(C_{1-10})$alkyl, imino$(C_{1-3})$alkyl, aryl, heteroaryl, $(C_{9-12})$bicycloaryl, and hetero$(C_{4-12})$bicycloaryl, each substituted or unsubstituted;

each R₃ is independently selected from the group consisting of hydrogen, halo, nitro, cyano, thio, hydroxy, alkoxy, aryloxy, heteroaryloxy, carbonyl, amino, (C$_{1-10}$) alkylamino, sulfonamido, imino, sulfonyl, sulfinyl, (C$_{1-10}$)alkyl, (C$_{3-12}$)cycloalkyl, hetero(C$_{3-12}$)cycloalkyl, (C$_{9-12}$)bicycloalkyl, hetero(C$_{3-12}$)bicycloalkyl, aryl(C$_{1-10}$)alkyl, heteroaryl(C$_{1-5}$)alkyl, perhalo(C$_{1-10}$)alkyl, carbonyl(C$_{1-3}$)alkyl, thiocarbonyl(C$_{1-3}$)alkyl, sulfonyl(C$_{1-3}$)alkyl, sulfinyl(C$_{1-3}$)alkyl, amino(C$_{1-10}$)alkyl, imino(C$_{1-3}$)alkyl, aryl, heteroaryl, (C$_{9-12}$)bicycloaryl, and hetero(C$_{4-12}$)bicycloaryl, each substituted or unsubstituted, or R₂ and one R₃, or two R₃ are taken together to form a substituted or unsubstituted ring;

each R₄ is independently selected from the group consisting of hydrogen, halo, nitro, cyano, thio, hydroxy, alkoxy, aryloxy, heteroaryloxy, carbonyl, amino, (C$_{1-10}$) alkylamino, sulfonamido, imino, sulfonyl, sulfinyl, (C$_{1-10}$)alkyl, (C$_{3-12}$)cycloalkyl, hetero(C$_{3-12}$)cycloalkyl, (C$_{9-12}$)bicycloalkyl, hetero(C$_{3-12}$)bicycloalkyl, aryl(C$_{1-10}$)alkyl, heteroaryl(C$_{1-5}$)alkyl, perhalo(C$_{1-10}$)alkyl, carbonyl(C$_{1-3}$)alkyl, thiocarbonyl(C$_{1-3}$)alkyl, sulfonyl(C$_{1-3}$)alkyl, sulfinyl(C$_{1-3}$)alkyl, amino(C$_{1-10}$)alkyl, imino(C$_{1-3}$)alkyl, aryl, heteroaryl, (C$_{9-12}$)bicycloaryl, and hetero(C$_{4-12}$)bicycloaryl, each substituted or unsubstituted, or two R₄ are taken together to form part of a substituted or unsubstituted ring;

each R₅ is independently selected from the group consisting of hydrogen, nitro, thio, hydroxy, alkoxy, aryloxy, heteroaryloxy, carbonyl, amino, sulfonamido, imino, sulfonyl, sulfinyl, (C$_{1-10}$)alkyl, (C$_{3-12}$)cycloalkyl, hetero(C$_{3-12}$)cycloalkyl, (C$_{9-12}$)bicycloalkyl, hetero(C$_{3-12}$)bicycloalkyl, aryl(C$_{1-10}$)alkyl, heteroaryl(C$_{1-5}$)alkyl, (C$_{3-12}$)cycloalkyl(C$_{1-10}$)alkyl, halo(C$_{1-10}$)alkyl, carbonyl(C$_{1-3}$)alkyl, thiocarbonyl(C$_{1-3}$)alkyl, sulfonyl(C$_{1-3}$)alkyl, sulfinyl(C$_{1-3}$)alkyl, imino(C$_{1-3}$)alkyl, aryl, heteroaryl, (C$_{9-12}$)bicycloaryl, and hetero(C$_{4-12}$)bicycloaryl, each substituted or unsubstituted, or two R₅, or one R₄ and one R₅, are taken together to form part of a substituted or unsubstituted ring;

R₆ is selected from the group consisting of hydrogen, nitro, thio, hydroxy, alkoxy, aryloxy, heteroaryloxy, carbonyl, amino, sulfonamido, imino, sulfonyl, sulfinyl, (C$_{1-10}$)alkyl, (C$_{3-12}$)cycloalkyl, hetero(C$_{3-12}$)cycloalkyl, (C$_{9-12}$)bicycloalkyl, hetero(C$_{3-12}$)bicycloalkyl, aryl(C$_{1-10}$)alkyl, heteroaryl(C$_{1-5}$)alkyl, (C$_{3-12}$)cycloalkyl(C$_{1-10}$)alkyl, halo(C$_{1-10}$)alkyl, carbonyl(C$_{1-3}$)alkyl, thiocarbonyl(C$_{1-3}$)alkyl, sulfonyl(C$_{1-3}$)alkyl, sulfinyl(C$_{1-3}$)alkyl, imino(C$_{1-3}$)alkyl, aryl, heteroaryl, (C$_{9-12}$)bicycloaryl, and hetero(C$_{4-12}$)bicycloaryl, each substituted or unsubstituted; and R₂₁ and R₂₂ are each independently selected from the group consisting of hydrogen, halo, hydroxy, alkoxy, carbonyl, amino, (C$_{1-5}$)alkylamino, (C$_{1-5}$)alkyl, halo(C$_{1-5}$)alkyl, carbonyl(C$_{1-3}$)alkyl and amino(C$_{1-5}$)alkyl, each substituted or unsubstituted.

In another embodiment, kinase inhibitors of the present invention comprise one of the following formulae:

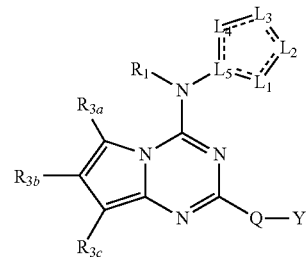

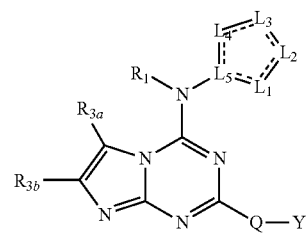

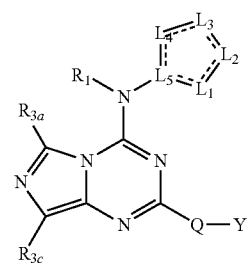

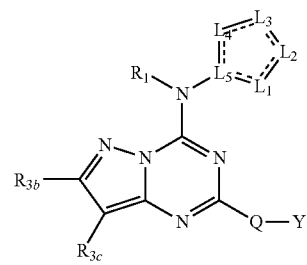

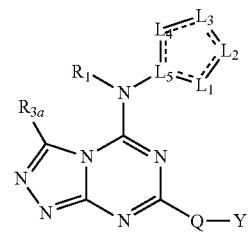

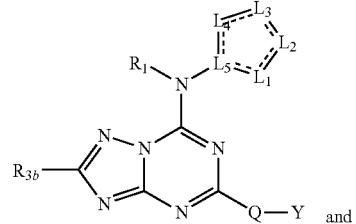

and

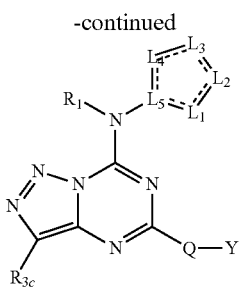

wherein:
- l is selected from the group consisting of 1, 2, 3, 4 and 5;
- $L_1$, $L_2$, $L_3$, $L_4$, and $L_5$ are each independently selected from the group consisting of $CR_4$ and $NR_5$, with the proviso that $R_5$ is absent when the atom to which it is attached forms part of a double bond;
- Q is selected from the group consisting of S, SO, $SO_2$, O, $NR_6$, $NR_6$—$(CR_{21}R_{22})_l$, $NR_6$—$(CR_{21}R_{22})_l$—O, and a substituted or unsubstituted $(C_{2-5})$alkylene, or Q is absent;
- Y is selected from the group consisting of $(C_{3-12})$cycloalkyl, hetero$(C_{3-12})$cycloalkyl, $(C_{9-12})$bicycloalkyl, hetero$(C_{3-12})$bicycloalkyl, aryl, heteroaryl, $(C_{9-12})$bicycloaryl, and hetero$(C_{4-12})$bicycloaryl, each substituted or unsubstituted;
- $R_1$ is selected from the group consisting of hydrogen, nitro, thio, hydroxy, alkoxy, aryloxy, heteroaryloxy, carbonyl, amino, sulfonamido, imino, sulfonyl, sulfinyl, $(C_{1-10})$alkyl, $(C_{3-12})$cycloalkyl, hetero$(C_{3-12})$cycloalkyl, $(C_{9-12})$bicycloalkyl, hetero$(C_{3-12})$bicycloalkyl, aryl$(C_{1-10})$alkyl, heteroaryl$(C_{1-5})$alkyl, $(C_{3-12})$cycloalkyl$(C_{1-10})$alkyl, halo$(C_{1-10})$alkyl, carbonyl$(C_{1-3})$alkyl, thiocarbonyl$(C_{1-3})$alkyl, sulfonyl$(C_{1-3})$alkyl, sulfinyl$(C_{1-3})$alkyl, imino$(C_{1-3})$alkyl, aryl, heteroaryl, $(C_{9-12})$bicycloaryl, and hetero$(C_{4-12})$bicycloaryl, each substituted or unsubstituted;
- $R_{3a}$, $R_{3b}$, and $R_{3c}$ are each independently selected from the group consisting of hydrogen, halo, nitro, cyano, thio, hydroxy, alkoxy, aryloxy, heteroaryloxy, carbonyl, amino, $(C_{1-10})$alkylamino, sulfonamido, imino, sulfonyl, sulfinyl, $(C_{1-10})$alkyl, $(C_{3-12})$cycloalkyl, hetero$(C_{3-12})$cycloalkyl, $(C_{9-12})$bicycloalkyl, hetero$(C_{3-12})$bicycloalkyl, aryl$(C_{1-10})$alkyl, heteroaryl$(C_{1-5})$alkyl, perhalo$(C_{1-10})$alkyl, carbonyl$(C_{1-3})$alkyl, thiocarbonyl$(C_{1-3})$alkyl, sulfonyl$(C_{1-3})$alkyl, sulfinyl$(C_{1-3})$alkyl, amino$(C_{1-10})$alkyl, imino$(C_{1-3})$alkyl, aryl, heteroaryl, $(C_{9-12})$bicycloaryl, and hetero$(C_{4-12})$bicycloaryl, each substituted or unsubstituted, or two $R_3$ are taken together to form a substituted or unsubstituted ring;
- each $R_4$ is independently selected from the group consisting of hydrogen, halo, nitro, cyano, thio, hydroxy, alkoxy, aryloxy, heteroaryloxy, carbonyl, amino, $(C_{1-10})$alkylamino, sulfonamido, imino, sulfonyl, sulfinyl, $(C_{1-10})$alkyl, $(C_{3-12})$cycloalkyl, hetero$(C_{3-12})$cycloalkyl, $(C_{9-12})$bicycloalkyl, hetero$(C_{3-12})$bicycloalkyl, aryl$(C_{1-10})$alkyl, heteroaryl$(C_{1-5})$alkyl, perhalo$(C_{1-10})$alkyl, carbonyl$(C_{1-3})$alkyl, thiocarbonyl$(C_{1-3})$alkyl, sulfonyl$(C_{1-3})$alkyl, sulfinyl$(C_{1-3})$alkyl, amino$(C_{1-10})$alkyl, imino$(C_{1-3})$alkyl, aryl, heteroaryl, $(C_{9-12})$bicycloaryl, and hetero$(C_{4-12})$bicycloaryl, each substituted or unsubstituted, or two $R_4$ are taken together to form part of a substituted or unsubstituted ring;
- each $R_5$ is independently selected from the group consisting of hydrogen, nitro, thio, hydroxy, alkoxy, aryloxy, heteroaryloxy, carbonyl, amino, sulfonamido, imino, sulfonyl, sulfinyl, $(C_{1-10})$alkyl, $(C_{3-12})$cycloalkyl, hetero$(C_{3-12})$cycloalkyl, $(C_{9-12})$bicycloalkyl, hetero$(C_{3-12})$bicycloalkyl, aryl$(C_{1-10})$alkyl, heteroaryl$(C_{1-5})$alkyl, $(C_{3-12})$cycloalkyl$(C_{1-10})$alkyl, halo$(C_{1-10})$alkyl, carbonyl$(C_{1-3})$alkyl, thiocarbonyl$(C_{1-3})$alkyl, sulfonyl$(C_{1-3})$alkyl, sulfinyl$(C_{1-3})$alkyl, imino$(C_{1-3})$alkyl, aryl, heteroaryl, $(C_{9-12})$bicycloaryl, and hetero$(C_{4-12})$bicycloaryl, each substituted or unsubstituted, or two $R_5$, or one $R_4$ and one $R_5$, are taken together to form part of a substituted or unsubstituted ring;
- $R_6$ is selected from the group consisting of hydrogen, nitro, thio, hydroxy, alkoxy, aryloxy, heteroaryloxy, carbonyl, amino, sulfonamido, imino, sulfonyl, sulfinyl, $(C_{1-10})$alkyl, $(C_{3-12})$cycloalkyl, hetero$(C_{3-12})$cycloalkyl, $(C_{9-12})$bicycloalkyl, hetero$(C_{3-12})$bicycloalkyl, aryl$(C_{1-10})$alkyl, heteroaryl$(C_{1-5})$alkyl, $(C_{3-12})$cycloalkyl$(C_{1-10})$alkyl, halo$(C_{1-10})$alkyl, carbonyl$(C_{1-3})$alkyl, thiocarbonyl$(C_{1-3})$alkyl, sulfonyl$(C_{1-3})$alkyl, sulfinyl$(C_{1-3})$alkyl, imino$(C_{1-3})$alkyl, aryl, heteroaryl, $(C_{9-12})$bicycloaryl, and hetero$(C_{4-12})$bicycloaryl, each substituted or unsubstituted; and
- $R_{21}$ and $R_{22}$ are each independently selected from the group consisting of hydrogen, halo, hydroxy, alkoxy, carbonyl, amino, $(C_{1-5})$alkylamino, $(C_{1-5})$alkyl, halo$(C_{1-5})$alkyl, carbonyl$(C_{1-3})$alkyl and amino$(C_{1-5})$alkyl, each substituted or unsubstituted.

In a further embodiment, kinase inhibitors of the present invention comprise one of the following formulae:

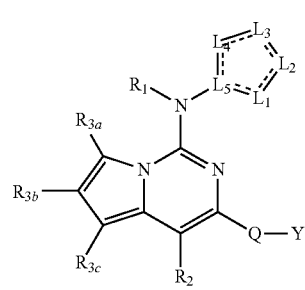

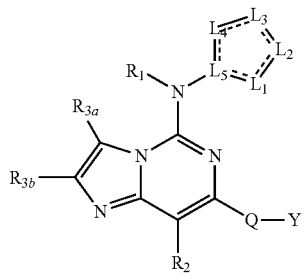

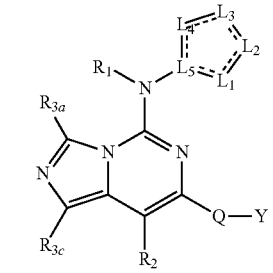

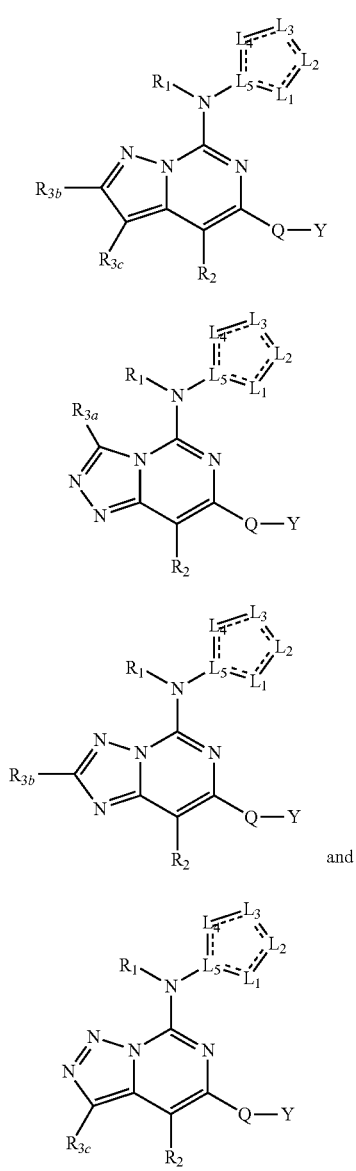

wherein:
l is selected from the group consisting of 1, 2, 3, 4 and 5;
$L_1$, $L_2$, $L_3$, $L_4$, and $L_5$ are each independently selected from the group consisting of $CR_4$ and $NR_5$, with the proviso that $R_5$ is absent when the atom to which it is attached forms part of a double bond;
Q is selected from the group consisting of S, SO, $SO_2$, O, $NR_6$, $NR_6$—$(CR_{21}R_{22})_l$, $NR_6$—$(CR_{21}R_{22})_l$—O, and a substituted or unsubstituted $(C_{2-5})$alkylene, or Q is absent, with the proviso that Q is not absent in Formula IId when $R_{3a}$ is H or in Formula VId;
Y is selected from the group consisting of $(C_{3-12})$cycloalkyl, hetero$(C_{3-12})$cycloalkyl, $(C_{9-12})$bicycloalkyl, hetero$(C_{3-12})$bicycloalkyl, aryl, heteroaryl, $(C_{9-12})$bicycloaryl, and hetero$(C_{4-12})$bicycloaryl, each substituted or unsubstituted;
$R_1$ is selected from the group consisting of hydrogen, nitro, thio, hydroxy, alkoxy, aryloxy, heteroaryloxy, carbonyl, amino, sulfonamido, imino, sulfonyl, sulfinyl, $(C_{1-10})$alkyl, $(C_{3-12})$cycloalkyl, hetero$(C_{3-12})$cycloalkyl, $(C_{9-12})$bicycloalkyl, hetero$(C_{3-12})$bicycloalkyl, aryl$(C_{1-10})$alkyl, heteroaryl$(C_{1-5})$alkyl, $(C_{3-12})$cycloalkyl $(C_{1-10})$alkyl, halo$(C_{1-10})$alkyl, carbonyl$(C_{1-3})$alkyl, thiocarbonyl$(C_{1-3})$alkyl, sulfonyl$(C_{1-3})$alkyl, sulfinyl $(C_{1-3})$alkyl, imino$(C_{1-3})$alkyl, aryl, heteroaryl, $(C_{9-12})$bicycloaryl, and hetero$(C_{4-12})$bicycloaryl, each substituted or unsubstituted;
$R_2$ is selected from the group consisting of hydrogen, halo, nitro, cyano, thio, hydroxy, alkoxy, aryloxy, heteroaryloxy, carbonyl, amino, $(C_{1-10})$alkylamino, sulfonamido, imino, sulfonyl, sulfinyl, $(C_{1-10})$alkyl, $(C_{3-12})$cycloalkyl, hetero$(C_{3-12})$cycloalkyl, $(C_{9-12})$bicycloalkyl, hetero$(C_{3-12})$bicycloalkyl, aryl$(C_{1-10})$alkyl, heteroaryl $(C_{1-5})$alkyl, perhalo$(C_{1-10})$alkyl, carbonyl$(C_{1-3})$alkyl, thiocarbonyl$(C_{1-3})$alkyl, sulfonyl$(C_{1-3})$alkyl, sulfinyl $(C_{1-3})$alkyl, amino$(C_{1-10})$alkyl, imino$(C_{1-3})$alkyl, aryl, heteroaryl, $(C_{9-12})$bicycloaryl, and hetero$(C_{4-12})$bicycloaryl, each substituted or unsubstituted;
$R_{3a}$, $R_{3b}$, and $R_{3c}$ are each independently selected from the group consisting of hydrogen, halo, nitro, cyano, thio, hydroxy, alkoxy, aryloxy, heteroaryloxy, carbonyl, amino, $(C_{1-10})$alkylamino, sulfonamido, imino, sulfonyl, sulfinyl, $(C_{1-10})$alkyl, $(C_{3-12})$cycloalkyl, hetero $(C_{3-12})$cycloalkyl, $(C_{9-12})$bicycloalkyl, hetero$(C_{3-12})$bicycloalkyl, aryl$(C_{1-10})$alkyl, heteroaryl$(C_{1-5})$alkyl, perhalo$(C_{1-10})$alkyl, carbonyl$(C_{1-3})$alkyl, thiocarbonyl $(C_{1-3})$alkyl, sulfonyl$(C_{1-3})$alkyl, sulfinyl$(C_{1-3})$alkyl, amino$(C_{1-10})$alkyl, imino$(C_{1-3})$alkyl, aryl, heteroaryl, $(C_{9-12})$bicycloaryl, and hetero$(C_{4-12})$bicycloaryl, each substituted or unsubstituted, or two $R_3$ are taken together to form a substituted or unsubstituted ring;
each $R_4$ is independently selected from the group consisting of hydrogen, halo, nitro, cyano, thio, hydroxy, alkoxy, aryloxy, heteroaryloxy, carbonyl, amino, $(C_{1-10})$ alkylamino, sulfonamido, imino, sulfonyl, sulfinyl, $(C_{1-10})$alkyl, $(C_{3-12})$cycloalkyl, hetero$(C_{3-12})$cycloalkyl, $(C_{9-12})$bicycloalkyl, hetero$(C_{3-12})$bicycloalkyl, aryl$(C_{1-10})$alkyl, heteroaryl$(C_{1-5})$alkyl, perhalo$(C_{1-10})$alkyl, carbonyl$(C_{1-3})$alkyl, thiocarbonyl $(C_{1-3})$alkyl, sulfonyl$(C_{1-3})$alkyl, sulfinyl$(C_{1-3})$alkyl, amino$(C_{1-10})$alkyl, imino$(C_{1-3})$alkyl, aryl, heteroaryl, $(C_{9-12})$bicycloaryl, and hetero$(C_{4-12})$bicycloaryl, each substituted or unsubstituted, or two $R_4$ are taken together to form part of a substituted or unsubstituted ring;
each $R_5$ is independently selected from the group consisting of hydrogen, nitro, thio, hydroxy, alkoxy, aryloxy, heteroaryloxy, carbonyl, amino, sulfonamido, imino, sulfonyl, sulfinyl, $(C_{1-10})$alkyl, $(C_{3-12})$cycloalkyl, hetero $(C_{3-12})$cycloalkyl, $(C_{9-12})$bicycloalkyl, hetero$(C_{3-12})$bicycloalkyl, aryl$(C_{1-10})$alkyl, heteroaryl$(C_{1-5})$alkyl, $(C_{3-12})$cycloalkyl$(C_{1-10})$alkyl, halo$(C_{1-10})$alkyl, carbonyl$(C_{1-3})$alkyl, thiocarbonyl$(C_{1-3})$alkyl, sulfonyl$(C_{1-3})$ alkyl, sulfinyl$(C_{1-3})$alkyl, imino$(C_{1-3})$alkyl, aryl, heteroaryl, $(C_{9-12})$bicycloaryl, and hetero$(C_{4-12})$ bicycloaryl, each substituted or unsubstituted, or two $R_5$, or one $R_4$ and one $R_5$, are taken together to form part of a substituted or unsubstituted ring;
$R_6$ is selected from the group consisting of hydrogen, nitro, thio, hydroxy, alkoxy, aryloxy, heteroaryloxy, carbonyl, amino, sulfonamido, imino, sulfonyl, sulfinyl, $(C_{1-10})$ alkyl, $(C_{3-12})$cycloalkyl, hetero$(C_{3-12})$cycloalkyl, $(C_{9-12})$bicycloalkyl, hetero$(C_{3-12})$bicycloalkyl, aryl $(C_{1-10})$alkyl, heteroaryl$(C_{1-5})$alkyl, $(C_{3-12})$cycloalkyl $(C_{1-10})$alkyl, halo$(C_{1-10})$alkyl, carbonyl$(C_{1-3})$alkyl, thiocarbonyl$(C_{1-3})$alkyl, sulfonyl$(C_{1-3})$alkyl, sulfinyl ($C_{1-3}$)alkyl, imino($C_{1-3}$)alkyl, aryl, heteroaryl, ($C_{9-12}$) bicycloaryl, and hetero($C_{4-12}$)bicycloaryl, each substituted or unsubstituted; and $R_{21}$ and $R_{22}$ are each independently selected from the group consisting of hydrogen, halo, hydroxy, alkoxy, carbonyl, amino, ($C_{1-5}$)alkylamino, ($C_{1-5}$)alkyl, halo ($C_{1-5}$)alkyl, carbonyl($C_{1-3}$)alkyl and amino($C_{1-5}$)alkyl, each substituted or unsubstituted.

In still another embodiment, kinase inhibitors of the present invention comprise one of the following formulae:

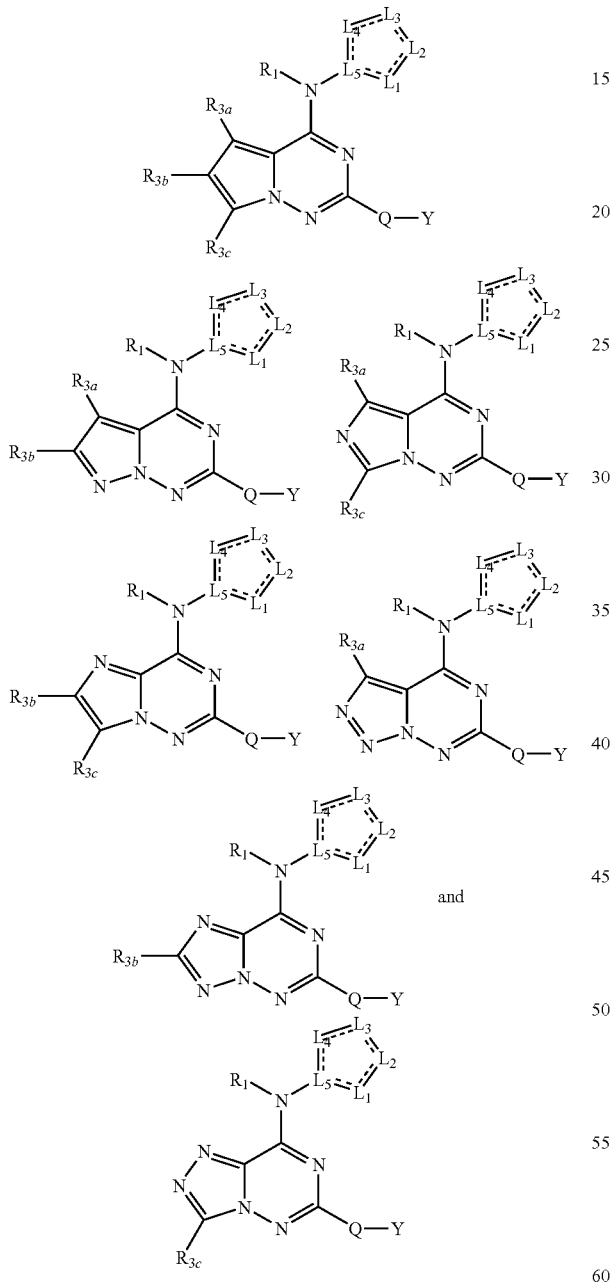

wherein:
l is selected from the group consisting of 1, 2, 3, 4 and 5;
$L_1$, $L_2$, $L_3$, $L_4$, and $L_5$ are each independently selected from the group consisting of $CR_4$ and $NR_5$, with the proviso that $R_5$ is absent when the atom to which it is attached forms part of a double bond;

Q is selected from the group consisting of S, SO, $SO_2$, O, $NR_6$, $NR_6$—$(CR_{21}R_{22})_l$, $NR_6$—$(CR_{21}R_{22})_l$—O, and a substituted or unsubstituted ($C_{2-5}$)alkylene, or Q is absent;

Y is selected from the group consisting of ($C_{3-12}$)cycloalkyl, hetero($C_{3-12}$)cycloalkyl, ($C_{9-12}$)bicycloalkyl, hetero($C_{3-12}$)bicycloalkyl, aryl, heteroaryl, ($C_{9-12}$)bicycloaryl, and hetero($C_{4-12}$)bicycloaryl, each substituted or unsubstituted;

$R_1$ is selected from the group consisting of hydrogen, nitro, thio, hydroxy, alkoxy, aryloxy, heteroaryloxy, carbonyl, amino, sulfonamido, imino, sulfonyl, sulfinyl, ($C_{1-10}$) alkyl, ($C_{3-12}$)cycloalkyl, hetero($C_{3-12}$)cycloalkyl, ($C_{9-12}$)bicycloalkyl, hetero($C_{3-12}$)bicycloalkyl, aryl ($C_{1-10}$)alkyl, heteroaryl($C_{1-5}$)alkyl, ($C_{3-12}$)cycloalkyl ($C_{1-10}$)alkyl, halo($C_{1-10}$)alkyl, carbonyl($C_{1-3}$)alkyl, thiocarbonyl($C_{1-3}$)alkyl, sulfonyl($C_{1-3}$)alkyl, sulfinyl ($C_{1-3}$)alkyl, imino($C_{1-3}$)alkyl, aryl, heteroaryl, ($C_{9-12}$) bicycloaryl, and hetero($C_{4-12}$)bicycloaryl, each substituted or unsubstituted;

$R_{3a}$, $R_{3b}$, and $R_{3c}$ are each independently selected from the group consisting of hydrogen, halo, nitro, cyano, thio, hydroxy, alkoxy, aryloxy, heteroaryloxy, carbonyl, amino, ($C_{1-10}$)alkylamino, sulfonamido, imino, sulfonyl, sulfinyl, ($C_{1-10}$)alkyl, ($C_{3-12}$)cycloalkyl, hetero ($C_{3-12}$)cycloalkyl, ($C_{9-12}$)bicycloalkyl, hetero($C_{3-12}$)bicycloalkyl, aryl($C_{1-10}$)alkyl, heteroaryl($C_{1-5}$)alkyl, perhalo($C_{1-10}$)alkyl, carbonyl($C_{1-3}$)alkyl, thiocarbonyl ($C_{1-3}$)alkyl, sulfonyl($C_{1-3}$)alkyl, sulfinyl($C_{1-3}$)alkyl, amino($C_{1-10}$)alkyl, imino($C_{1-3}$)alkyl, aryl, heteroaryl, ($C_{9-12}$)bicycloaryl, and hetero($C_{4-12}$)bicycloaryl, each substituted or unsubstituted, or two $R_3$ are taken together to form a substituted or unsubstituted ring;

each $R_4$ is independently selected from the group consisting of hydrogen, halo, nitro, cyano, thio, hydroxy, alkoxy, aryloxy, heteroaryloxy, carbonyl, amino, ($C_{1-10}$) alkylamino, sulfonamido, imino, sulfonyl, sulfinyl, ($C_{1-10}$)alkyl, ($C_{3-12}$)cycloalkyl, hetero($C_{3-12}$)cycloalkyl, ($C_{9-12}$)bicycloalkyl, hetero($C_{3-12}$)bicycloalkyl, aryl($C_{1-10}$)alkyl, heteroaryl($C_{1-5}$)alkyl, perhalo($C_{1-10}$)alkyl, carbonyl($C_{1-3}$)alkyl, thiocarbonyl ($C_{1-3}$)alkyl, sulfonyl($C_{1-3}$)alkyl, sulfinyl($C_{1-3}$)alkyl, amino($C_{1-10}$)alkyl, imino($C_{1-3}$)alkyl, aryl, heteroaryl, ($C_{9-12}$)bicycloaryl, and hetero($C_{4-12}$)bicycloaryl, each substituted or unsubstituted, or two $R_4$ are taken together to form part of a substituted or unsubstituted ring;

each $R_5$ is independently selected from the group consisting of hydrogen, nitro, thio, hydroxy, alkoxy, aryloxy, heteroaryloxy, carbonyl, amino, sulfonamido, imino, sulfonyl, sulfinyl, ($C_{1-10}$)alkyl, ($C_{3-12}$)cycloalkyl, hetero ($C_{3-12}$)cycloalkyl, ($C_{9-12}$)bicycloalkyl, hetero($C_{3-12}$)bicycloalkyl, aryl($C_{1-10}$)alkyl, heteroaryl($C_{1-5}$)alkyl, ($C_{3-12}$)cycloalkyl($C_{1-10}$)alkyl, halo($C_{1-10}$)alkyl, carbonyl($C_{1-3}$)alkyl, thiocarbonyl($C_{1-3}$)alkyl, sulfonyl($C_{1-3}$) alkyl, sulfinyl($C_{1-3}$)alkyl, imino($C_{1-3}$)alkyl, aryl, heteroaryl, ($C_{9-12}$)bicycloaryl, and hetero($C_{4-12}$) bicycloaryl, each substituted or unsubstituted, or two $R_5$, or one $R_4$ and one $R_5$, are taken together to form part of a substituted or unsubstituted ring;

$R_6$ is selected from the group consisting of hydrogen, nitro, thio, hydroxy, alkoxy, aryloxy, heteroaryloxy, carbonyl, amino, sulfonamido, imino, sulfonyl, sulfinyl, ($C_{1-10}$) alkyl, ($C_{3-12}$)cycloalkyl, hetero($C_{3-12}$)cycloalkyl, ($C_{9-12}$)bicycloalkyl, hetero($C_{3-12}$)bicycloalkyl, aryl ($C_{1-10}$)alkyl, heteroaryl($C_{1-5}$)alkyl, ($C_{3-12}$)cycloalkyl ($C_{1-10}$)alkyl, halo($C_{1-10}$)alkyl, carbonyl($C_{1-3}$)alkyl, thiocarbonyl($C_{1-3}$)alkyl, sulfonyl($C_{1-3}$)alkyl, sulfinyl ($C_{1-3}$)alkyl, imino($C_{1-3}$)alkyl, aryl, heteroaryl, ($C_{9-12}$) bicycloaryl, and hetero($C_{4-12}$)bicycloaryl, each substituted or unsubstituted; and $R_{21}$ and $R_{22}$ are each independently selected from the group consisting of hydrogen, halo, hydroxy, alkoxy, carbonyl, amino, ($C_{1-5}$)alkylamino, ($C_{1-5}$)alkyl, halo($C_{1-5}$)alkyl, carbonyl($C_{1-3}$)alkyl and amino($C_{1-5}$)alkyl, each substituted or unsubstituted.

In yet another embodiment, kinase inhibitors of the present invention comprise one of the following formulae:

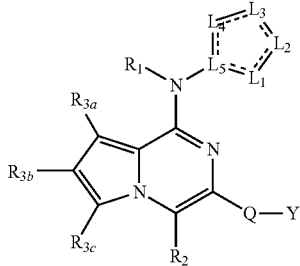

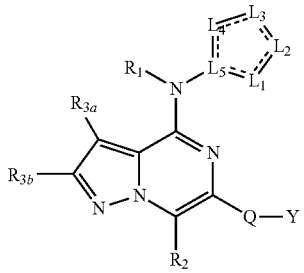

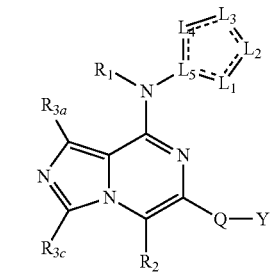

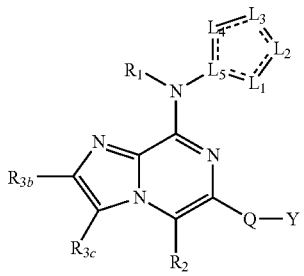

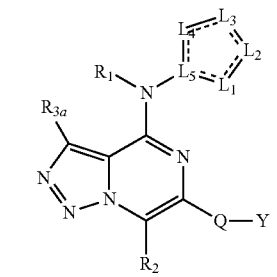

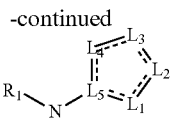

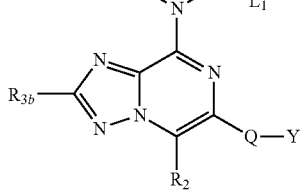

and

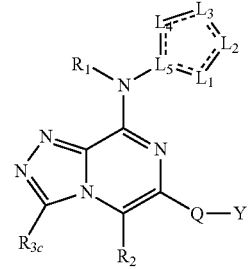

wherein:

l is selected from the group consisting of 1, 2, 3, 4 and 5;

$L_1$, $L_2$, $L_3$, $L_4$, and $L_5$ are each independently selected from the group consisting of $CR_4$ and $NR_5$, with the proviso that $R_5$ is absent when the atom to which it is attached forms part of a double bond;

Q is selected from the group consisting of S, SO, $SO_2$, O, $NR_6$, $NR_6$—$(CR_{21}R_{22})_j$, $NR_6$—$(CR_{21}R_{22})_j$—O, and a substituted or unsubstituted ($C_{2-5}$)alkylene, or Q is absent;

Y is selected from the group consisting of ($C_{3-12}$)cycloalkyl, hetero($C_{3-12}$)cycloalkyl, ($C_{9-12}$)bicycloalkyl, hetero($C_{3-12}$)bicycloalkyl, aryl, heteroaryl, ($C_{9-12}$)bicycloaryl, and hetero($C_{4-12}$)bicycloaryl, each substituted or unsubstituted;

$R_1$ is selected from the group consisting of hydrogen, nitro, thio, hydroxy, alkoxy, aryloxy, heteroaryloxy, carbonyl, amino, sulfonamido, imino, sulfonyl, sulfinyl, ($C_{1-10}$) alkyl, ($C_{3-12}$)cycloalkyl, hetero($C_{3-12}$)cycloalkyl, ($C_{9-12}$)bicycloalkyl, hetero($C_{3-12}$)bicycloalkyl, aryl($C_{1-10}$)alkyl, heteroaryl($C_{1-5}$)alkyl, ($C_{3-12}$)cycloalkyl ($C_{1-10}$)alkyl, halo($C_{1-10}$)alkyl, carbonyl($C_{1-3}$)alkyl, thiocarbonyl($C_{1-3}$)alkyl, sulfonyl($C_{1-3}$)alkyl, sulfinyl ($C_{1-3}$)alkyl, imino($C_{1-3}$)alkyl, aryl, heteroaryl, ($C_{9-12}$) bicycloaryl, and hetero($C_{4-12}$)bicycloaryl, each substituted or unsubstituted;

$R_2$ is selected from the group consisting of hydrogen, halo, nitro, cyano, thio, hydroxy, alkoxy, aryloxy, heteroaryloxy, carbonyl, amino, ($C_{1-10}$)alkylamino, sulfonamido, imino, sulfonyl, sulfinyl, ($C_{1-10}$)alkyl, ($C_{3-12}$)cycloalkyl, hetero($C_{3-12}$)cycloalkyl, ($C_{9-12}$)bicycloalkyl, hetero($C_{3-12}$)bicycloalkyl, aryl($C_{1-10}$)alkyl, heteroaryl ($C_{1-5}$)alkyl, perhalo($C_{1-10}$)alkyl, carbonyl($C_{1-3}$)alkyl, thiocarbonyl($C_{1-3}$)alkyl, sulfonyl($C_{1-3}$)alkyl, sulfinyl ($C_{1-3}$)alkyl, amino($C_{1-10}$)alkyl, imino($C_{1-3}$)alkyl, aryl, heteroaryl, ($C_{9-12}$)bicycloaryl, and hetero($C_{4-12}$)bicycloaryl, each substituted or unsubstituted;

$R_{3a}$, $R_{3b}$, and $R_{3c}$ are each independently selected from the group consisting of hydrogen, halo, nitro, cyano, thio, hydroxy, alkoxy, aryloxy, heteroaryloxy, carbonyl, amino, ($C_{1-10}$)alkylamino, sulfonamido, imino, sulfonyl, sulfinyl, ($C_{1-10}$)alkyl, ($C_{3-12}$)cycloalkyl, hetero ($C_{3-12}$)cycloalkyl, ($C_{9-12}$)bicycloalkyl, hetero($C_{3-12}$)bicycloalkyl, aryl($C_{1-10}$)alkyl, heteroaryl($C_{1-5}$)alkyl, perhalo($C_{1-10}$)alkyl, carbonyl($C_{1-3}$)alkyl, thiocarbonyl ($C_{1-3}$)alkyl, sulfonyl($C_{1-3}$)alkyl, sulfinyl($C_{1-3}$)alkyl, amino($C_{1-10}$)alkyl, imino($C_{1-3}$)alkyl, aryl, heteroaryl, ($C_{9-12}$)bicycloaryl, and hetero($C_{4-12}$)bicycloaryl, each substituted or unsubstituted, or two $R_3$ are taken together to form a substituted or unsubstituted ring;

each $R_4$ is independently selected from the group consisting of hydrogen, halo, nitro, cyano, thio, hydroxy, alkoxy, aryloxy, heteroaryloxy, carbonyl, amino, ($C_{1-10}$) alkylamino, sulfonamido, imino, sulfonyl, sulfinyl, ($C_{1-10}$)alkyl, ($C_{3-12}$)cycloalkyl, hetero($C_{3-12}$)cycloalkyl, ($C_{9-12}$)bicycloalkyl, hetero($C_{3-12}$)bicycloalkyl, aryl($C_{1-10}$)alkyl, heteroaryl($C_{1-5}$)alkyl, perhalo($C_{1-10}$)alkyl, carbonyl($C_{1-3}$)alkyl, thiocarbonyl ($C_{1-3}$)alkyl, sulfonyl($C_{1-3}$)alkyl, sulfinyl($C_{1-3}$)alkyl, amino($C_{1-10}$)alkyl, imino($C_{1-3}$)alkyl, aryl, heteroaryl, ($C_{9-12}$)bicycloaryl, and hetero($C_{4-12}$)bicycloaryl, each substituted or unsubstituted, or two $R_4$ are taken together to form part of a substituted or unsubstituted ring;

each $R_5$ is independently selected from the group consisting of hydrogen, nitro, thio, hydroxy, alkoxy, aryloxy, heteroaryloxy, carbonyl, amino, sulfonamido, imino, sulfonyl, sulfinyl, ($C_{1-10}$)alkyl, ($C_{3-12}$)cycloalkyl, hetero ($C_{3-12}$)cycloalkyl, ($C_{9-12}$)bicycloalkyl, hetero($C_{3-12}$)bicycloalkyl, aryl($C_{1-10}$)alkyl, heteroaryl($C_{1-5}$)alkyl, ($C_{3-12}$)cycloalkyl($C_{1-10}$)alkyl, halo($C_{1-10}$)alkyl, carbonyl($C_{1-3}$)alkyl, thiocarbonyl($C_{1-3}$)alkyl, sulfonyl($C_{1-3}$) alkyl, sulfinyl($C_{1-3}$)alkyl, imino($C_{1-3}$)alkyl, aryl, heteroaryl, ($C_{9-12}$)bicycloaryl, and hetero($C_{4-12}$) bicycloaryl, each substituted or unsubstituted, or two $R_5$, or one $R_4$ and one $R_5$, are taken together to form part of a substituted or unsubstituted ring;

$R_6$ is selected from the group consisting of hydrogen, nitro, thio, hydroxy, alkoxy, aryloxy, heteroaryloxy, carbonyl, amino, sulfonamido, imino, sulfonyl, sulfinyl, ($C_{1-10}$) alkyl, ($C_{3-12}$)cycloalkyl, hetero($C_{3-12}$)cycloalkyl, ($C_{9-12}$)bicycloalkyl, hetero($C_{3-12}$)bicycloalkyl, aryl ($C_{1-10}$)alkyl, heteroaryl($C_{1-5}$)alkyl, ($C_{3-12}$)cycloalkyl ($C_{1-10}$)alkyl, halo($C_{1-10}$)alkyl, carbonyl($C_{1-3}$)alkyl, thiocarbonyl($C_{1-3}$)alkyl, sulfonyl($C_{1-3}$)alkyl, sulfinyl ($C_{1-3}$)alkyl, imino($C_{1-3}$)alkyl, aryl, heteroaryl, ($C_{9-12}$) bicycloaryl, and hetero($C_{4-12}$)bicycloaryl, each substituted or unsubstituted; and $R_{21}$ and $R_{22}$ are each independently selected from the group consisting of hydrogen, halo, hydroxy, alkoxy, carbonyl, amino, ($C_{1-5}$)alkylamino, ($C_{1-5}$)alkyl, halo ($C_{1-5}$)alkyl, carbonyl($C_{1-3}$)alkyl and amino($C_{1-5}$)alkyl, each substituted or unsubstituted.

In one embodiment, kinase inhibitors of the present invention comprise one of the following formulae:

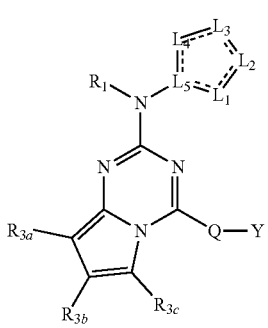

-continued

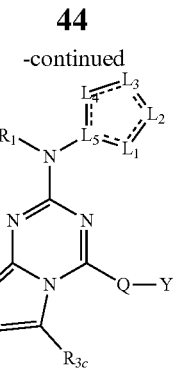

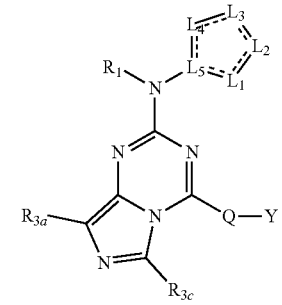

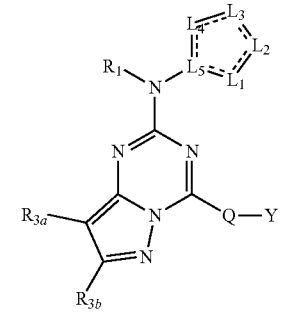

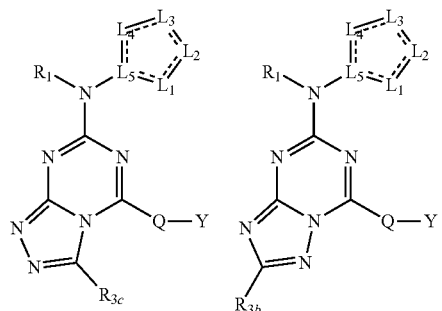

and

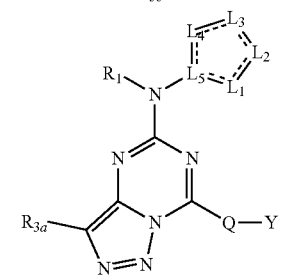

wherein:

l is selected from the group consisting of 1, 2, 3, 4 and 5;

$L_1$, $L_2$, $L_3$, $L_4$, and $L_5$ are each independently selected from the group consisting of $CR_4$ and $NR_5$, with the proviso that $R_5$ is absent when the atom to which it is attached forms part of a double bond;

Q is selected from the group consisting of S, SO, SO$_2$, O, NR$_6$, NR$_6$—(CR$_{21}$R$_{22}$)$_j$, NR$_6$—(CR$_{21}$R$_{22}$)$_j$—O, and a substituted or unsubstituted (C$_{2-5}$)alkylene, or Q is absent;

Y is selected from the group consisting of (C$_{3-12}$)cycloalkyl, hetero(C$_{3-12}$)cycloalkyl, (C$_{9-12}$)bicycloalkyl, hetero(C$_{3-12}$)bicycloalkyl, aryl, heteroaryl, (C$_{9-12}$)bicycloaryl, and hetero(C$_{4-12}$)bicycloaryl, each substituted or unsubstituted;

R$_1$ is selected from the group consisting of hydrogen, nitro, thio, hydroxy, alkoxy, aryloxy, heteroaryloxy, carbonyl, amino, sulfonamido, imino, sulfonyl, sulfinyl, (C$_{1-10}$)alkyl, (C$_{3-12}$)cycloalkyl, hetero(C$_{3-12}$)cycloalkyl, (C$_{9-12}$)bicycloalkyl, hetero(C$_{3-12}$)bicycloalkyl, aryl(C$_{1-10}$)alkyl, heteroaryl(C$_{1-5}$)alkyl, (C$_{3-12}$)cycloalkyl(C$_{1-10}$)alkyl, halo(C$_{1-10}$)alkyl, carbonyl(C$_{1-3}$)alkyl, thiocarbonyl(C$_{1-3}$)alkyl, sulfonyl(C$_{1-3}$)alkyl, sulfinyl(C$_{1-3}$)alkyl, imino(C$_{1-3}$)alkyl, aryl, heteroaryl, (C$_{9-12}$)bicycloaryl, and hetero(C$_{4-12}$)bicycloaryl, each substituted or unsubstituted;

R$_{3a}$, R$_{3b}$, and R$_{3c}$ are each independently selected from the group consisting of hydrogen, halo, nitro, cyano, thio, hydroxy, alkoxy, aryloxy, heteroaryloxy, carbonyl, amino, (C$_{1-10}$)alkylamino, sulfonamido, imino, sulfonyl, sulfinyl, (C$_{1-10}$)alkyl, (C$_{3-12}$)cycloalkyl, hetero(C$_{3-12}$)cycloalkyl, (C$_{9-12}$)bicycloalkyl, hetero(C$_{3-12}$)bicycloalkyl, aryl(C$_{1-10}$)alkyl, heteroaryl(C$_{1-5}$)alkyl, perhalo(C$_{1-10}$)alkyl, carbonyl(C$_{1-3}$)alkyl, thiocarbonyl(C$_{1-3}$)alkyl, sulfonyl(C$_{1-3}$)alkyl, sulfinyl(C$_{1-3}$)alkyl, amino(C$_{1-10}$)alkyl, imino(C$_{1-3}$)alkyl, aryl, heteroaryl, (C$_{9-12}$)bicycloaryl, and hetero(C$_{4-12}$)bicycloaryl, each substituted or unsubstituted, or two R$_3$ are taken together to form a substituted or unsubstituted ring;

each R$_4$ is independently selected from the group consisting of hydrogen, halo, nitro, cyano, thio, hydroxy, alkoxy, aryloxy, heteroaryloxy, carbonyl, amino, (C$_{1-10}$)alkylamino, sulfonamido, imino, sulfonyl, sulfinyl, (C$_{1-10}$)alkyl, (C$_{3-12}$)cycloalkyl, hetero(C$_{3-12}$)cycloalkyl, (C$_{9-12}$)bicycloalkyl, hetero(C$_{3-12}$)bicycloalkyl, aryl(C$_{1-10}$)alkyl, heteroaryl(C$_{1-5}$)alkyl, perhalo(C$_{1-10}$)alkyl, carbonyl(C$_{1-3}$)alkyl, thiocarbonyl(C$_{1-3}$)alkyl, sulfonyl(C$_{1-3}$)alkyl, sulfinyl(C$_{1-3}$)alkyl, amino(C$_{1-10}$)alkyl, imino(C$_{1-3}$)alkyl, aryl, heteroaryl, (C$_{9-12}$)bicycloaryl, and hetero(C$_{4-12}$)bicycloaryl, each substituted or unsubstituted, or two R$_4$ are taken together to form part of a substituted or unsubstituted ring;

each R$_5$ is independently selected from the group consisting of hydrogen, nitro, thio, hydroxy, alkoxy, aryloxy, heteroaryloxy, carbonyl, amino, sulfonamido, imino, sulfonyl, sulfinyl, (C$_{1-10}$)alkyl, (C$_{3-12}$)cycloalkyl, hetero(C$_{3-12}$)cycloalkyl, (C$_{9-12}$)bicycloalkyl, hetero(C$_{3-12}$)bicycloalkyl, aryl(C$_{1-10}$)alkyl, heteroaryl(C$_{1-5}$)alkyl, (C$_{3-12}$)cycloalkyl(C$_{1-10}$)alkyl, halo(C$_{1-10}$)alkyl, carbonyl(C$_{1-3}$)alkyl, thiocarbonyl(C$_{1-3}$)alkyl, sulfonyl(C$_{1-3}$)alkyl, sulfinyl(C$_{1-3}$)alkyl, imino(C$_{1-3}$)alkyl, aryl, heteroaryl, (C$_{9-12}$)bicycloaryl, and hetero(C$_{4-12}$)bicycloaryl, each substituted or unsubstituted, or two R$_5$, or one R$_4$ and one R$_5$, are taken together to form part of a substituted or unsubstituted ring;

R$_6$ is selected from the group consisting of hydrogen, nitro, thio, hydroxy, alkoxy, aryloxy, heteroaryloxy, carbonyl, amino, sulfonamido, imino, sulfonyl, sulfinyl, (C$_{1-10}$)alkyl, (C$_{3-12}$)cycloalkyl, hetero(C$_{3-12}$)cycloalkyl, (C$_{9-12}$)bicycloalkyl, hetero(C$_{3-12}$)bicycloalkyl, aryl(C$_{1-10}$)alkyl, heteroaryl(C$_{1-5}$)alkyl, (C$_{3-12}$)cycloalkyl(C$_{1-10}$)alkyl, halo(C$_{1-10}$)alkyl, carbonyl(C$_{1-3}$)alkyl, thiocarbonyl(C$_{1-3}$)alkyl, sulfonyl(C$_{1-3}$)alkyl, sulfinyl(C$_{1-3}$)alkyl, imino(C$_{1-3}$)alkyl, aryl, heteroaryl, (C$_{9-12}$)bicycloaryl, and hetero(C$_{4-12}$)bicycloaryl, each substituted or unsubstituted; and R$_{21}$ and R$_{22}$ are each independently selected from the group consisting of hydrogen, halo, hydroxy, alkoxy, carbonyl, amino, (C$_{1-5}$)alkylamino, (C$_{1-5}$)alkyl, halo(C$_{1-5}$)alkyl, carbonyl(C$_{1-3}$)alkyl and amino(C$_{1-5}$)alkyl, each substituted or unsubstituted.

In another embodiment, kinase inhibitors of the present invention comprise one of the following formulae:

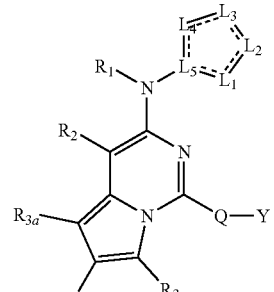

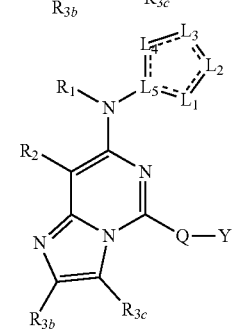

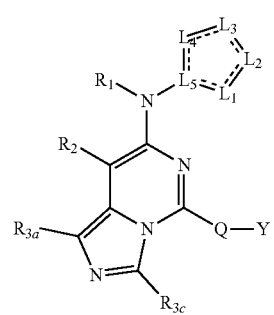

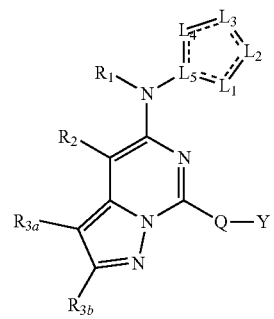

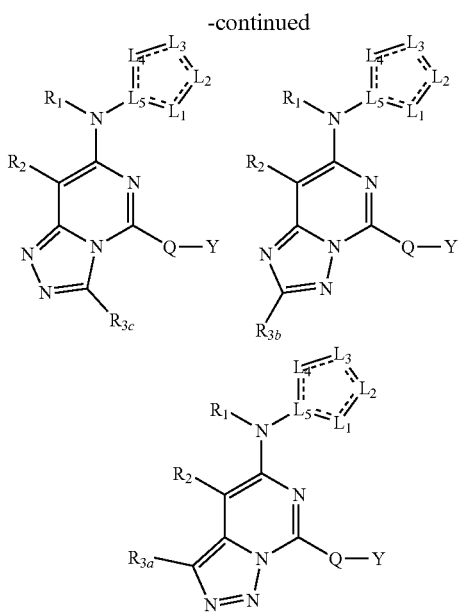

wherein:
- l is selected from the group consisting of 1, 2, 3, 4 and 5;
- $L_1$, $L_2$, $L_3$, $L_4$, and $L_5$ are each independently selected from the group consisting of $CR_4$ and $NR_5$, with the proviso that $R_5$ is absent when the atom to which it is attached forms part of a double bond;
- Q is selected from the group consisting of S, SO, $SO_2$, O, $NR_6$, $NR_6$—$(CR_{21}R_{22})_l$, $NR_6$—$(CR_{21}R_{22})_l$—O, and a substituted or unsubstituted $(C_{2-5})$alkylene, or Q is absent;
- Y is selected from the group consisting of $(C_{3-12})$cycloalkyl, hetero$(C_{3-12})$cycloalkyl, $(C_{9-12})$bicycloalkyl, hetero$(C_{3-12})$bicycloalkyl, aryl, heteroaryl, $(C_{9-12})$bicycloaryl, and hetero$(C_{4-12})$bicycloaryl, each substituted or unsubstituted;
- $R_1$ is selected from the group consisting of hydrogen, nitro, thio, hydroxy, alkoxy, aryloxy, heteroaryloxy, carbonyl, amino, sulfonamido, imino, sulfonyl, sulfinyl, $(C_{1-10})$alkyl, $(C_{3-12})$cycloalkyl, hetero$(C_{3-12})$cycloalkyl, $(C_{9-12})$bicycloalkyl, hetero$(C_{3-12})$bicycloalkyl, aryl$(C_{1-10})$alkyl, heteroaryl$(C_{1-5})$alkyl, $(C_{3-12})$cycloalkyl$(C_{1-10})$alkyl, halo$(C_{1-10})$alkyl, carbonyl$(C_{1-3})$alkyl, thiocarbonyl$(C_{1-3})$alkyl, sulfonyl$(C_{1-3})$alkyl, sulfinyl$(C_{1-3})$alkyl, imino$(C_{1-3})$alkyl, aryl, heteroaryl, $(C_{9-12})$bicycloaryl, and hetero$(C_{4-12})$bicycloaryl, each substituted or unsubstituted;
- $R_2$ is selected from the group consisting of hydrogen, halo, nitro, cyano, thio, hydroxy, alkoxy, aryloxy, heteroaryloxy, carbonyl, amino, $(C_{1-10})$alkylamino, sulfonamido, imino, sulfonyl, sulfinyl, $(C_{1-10})$alkyl, $(C_{3-12})$cycloalkyl, hetero$(C_{3-12})$cycloalkyl, $(C_{9-12})$bicycloalkyl, hetero$(C_{3-12})$bicycloalkyl, aryl$(C_{1-10})$alkyl, heteroaryl$(C_{1-5})$alkyl, perhalo$(C_{1-10})$alkyl, carbonyl$(C_{1-3})$alkyl, thiocarbonyl$(C_{1-3})$alkyl, sulfonyl$(C_{1-3})$alkyl, sulfinyl$(C_{1-3})$alkyl, amino$(C_{1-10})$alkyl, imino$(C_{1-3})$alkyl, aryl, heteroaryl, $(C_{9-12})$bicycloaryl, and hetero$(C_{4-12})$bicycloaryl, each substituted or unsubstituted;
- $R_{3a}$, $R_{3b}$, and $R_{3c}$ are each independently selected from the group consisting of hydrogen, halo, nitro, cyano, thio, hydroxy, alkoxy, aryloxy, heteroaryloxy, carbonyl, amino, $(C_{1-10})$alkylamino, sulfonamido, imino, sulfonyl, sulfinyl, $(C_{1-10})$alkyl, $(C_{3-12})$cycloalkyl, hetero $(C_{3-12})$cycloalkyl, $(C_{9-12})$bicycloalkyl, hetero$(C_{3-12})$bicycloalkyl, aryl$(C_{1-10})$alkyl, heteroaryl$(C_{1-5})$alkyl, perhalo$(C_{1-10})$alkyl, carbonyl$(C_{1-3})$alkyl, thiocarbonyl$(C_{1-3})$alkyl, sulfonyl$(C_{1-3})$alkyl, sulfinyl$(C_{1-3})$alkyl, amino$(C_{1-10})$alkyl, imino$(C_{1-3})$alkyl, aryl, heteroaryl, $(C_{9-12})$bicycloaryl, and hetero$(C_{4-12})$bicycloaryl, each substituted or unsubstituted, or two $R_3$ are taken together to form a substituted or unsubstituted ring;
- each $R_4$ is independently selected from the group consisting of hydrogen, halo, nitro, cyano, thio, hydroxy, alkoxy, aryloxy, heteroaryloxy, carbonyl, amino, $(C_{1-10})$alkylamino, sulfonamido, imino, sulfonyl, sulfinyl, $(C_{1-10})$alkyl, $(C_{3-12})$cycloalkyl, hetero$(C_{3-12})$cycloalkyl, $(C_{9-12})$bicycloalkyl, hetero$(C_{3-12})$bicycloalkyl, aryl$(C_{1-10})$alkyl, heteroaryl$(C_{1-5})$alkyl, perhalo$(C_{1-10})$alkyl, carbonyl$(C_{1-3})$alkyl, thiocarbonyl$(C_{1-3})$alkyl, sulfonyl$(C_{1-3})$alkyl, sulfinyl$(C_{1-3})$alkyl, amino$(C_{1-10})$alkyl, imino$(C_{1-3})$alkyl, aryl, heteroaryl, $(C_{9-12})$bicycloaryl, and hetero$(C_{4-12})$bicycloaryl, each substituted or unsubstituted, or two $R_4$ are taken together to form part of a substituted or unsubstituted ring;
- each $R_5$ is independently selected from the group consisting of hydrogen, nitro, thio, hydroxy, alkoxy, aryloxy, heteroaryloxy, carbonyl, amino, sulfonamido, imino, sulfonyl, sulfinyl, $(C_{1-10})$alkyl, $(C_{3-12})$cycloalkyl, hetero $(C_{3-12})$cycloalkyl, $(C_{9-12})$bicycloalkyl, hetero$(C_{3-12})$bicycloalkyl, aryl$(C_{1-10})$alkyl, heteroaryl$(C_{1-5})$alkyl, $(C_{3-12})$cycloalkyl$(C_{1-10})$alkyl, halo$(C_{1-10})$alkyl, carbonyl$(C_{1-3})$alkyl, thiocarbonyl$(C_{1-3})$alkyl, sulfonyl$(C_{1-3})$alkyl, sulfinyl$(C_{1-3})$alkyl, imino$(C_{1-3})$alkyl, aryl, heteroaryl, $(C_{9-12})$bicycloaryl, and hetero$(C_{4-12})$bicycloaryl, each substituted or unsubstituted, or two $R_5$, or one $R_4$ and one $R_5$, are taken together to form part of a substituted or unsubstituted ring;
- $R_6$ is selected from the group consisting of hydrogen, nitro, thio, hydroxy, alkoxy, aryloxy, heteroaryloxy, carbonyl, amino, sulfonamido, imino, sulfonyl, sulfinyl, $(C_{1-10})$alkyl, $(C_{3-12})$cycloalkyl, hetero$(C_{3-12})$cycloalkyl, $(C_{9-12})$bicycloalkyl, hetero$(C_{3-12})$bicycloalkyl, aryl $(C_{1-10})$alkyl, heteroaryl$(C_{1-5})$alkyl, $(C_{3-12})$cycloalkyl $(C_{1-10})$alkyl, halo$(C_{1-10})$alkyl, carbonyl$(C_{1-3})$alkyl, thiocarbonyl$(C_{1-3})$alkyl, sulfonyl$(C_{1-3})$alkyl, sulfinyl $(C_{1-3})$alkyl, imino$(C_{1-3})$alkyl, aryl, heteroaryl, $(C_{9-12})$ bicycloaryl, and hetero$(C_{4-12})$bicycloaryl, each substituted or unsubstituted; and
- $R_{21}$ and $R_{22}$ are each independently selected from the group consisting of hydrogen, halo, hydroxy, alkoxy, carbonyl, amino, $(C_{1-5})$alkylamino, $(C_{1-5})$alkyl, halo $(C_{1-5})$alkyl, carbonyl$(C_{1-3})$alkyl and amino$(C_{1-5})$alkyl, each substituted or unsubstituted.

In a further embodiment, kinase inhibitors of the present invention comprise one of the following formulae:

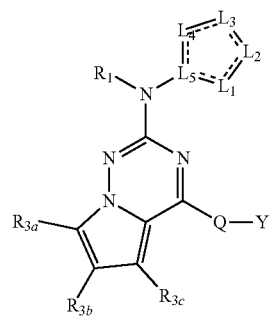

-continued

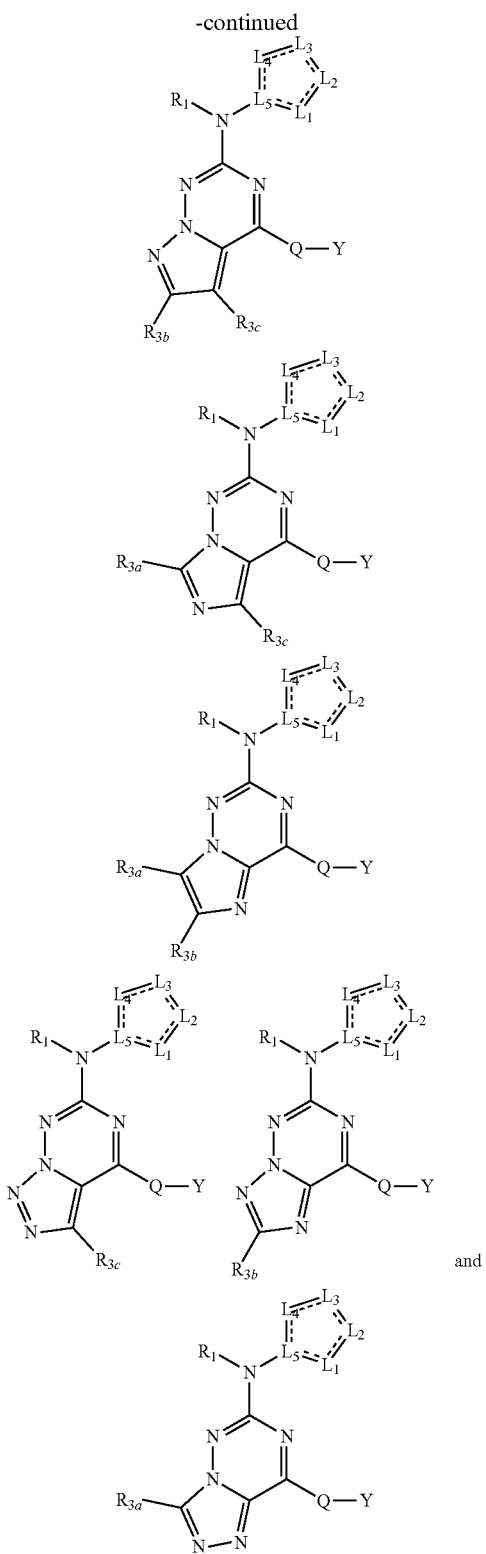

wherein:
l is selected from the group consisting of 1, 2, 3, 4 and 5;
$L_1, L_2, L_3, L_4,$ and $L_5$ are each independently selected from the group consisting of $CR_4$ and $NR_5$, with the proviso that $R_5$ is absent when the atom to which it is attached forms part of a double bond;

Q is selected from the group consisting of S, SO, $SO_2$, O, $NR_6$, $NR_6$—$(CR_{21}R_{22})_l$, $NR_6$—$(CR_{21}R_{22})_l$—O, and a substituted or unsubstituted $(C_{2-5})$alkylene, or Q is absent;

Y is selected from the group consisting of $(C_{3-12})$cycloalkyl, hetero$(C_{3-12})$cycloalkyl, $(C_{9-12})$bicycloalkyl, hetero$(C_{3-12})$bicycloalkyl, aryl, heteroaryl, $(C_{9-12})$bicycloaryl, and hetero$(C_{4-12})$bicycloaryl, each substituted or unsubstituted;

$R_1$ is selected from the group consisting of hydrogen, nitro, thio, hydroxy, alkoxy, aryloxy, heteroaryloxy, carbonyl, amino, sulfonamido, imino, sulfonyl, sulfinyl, $(C_{1-10})$alkyl, $(C_{3-12})$cycloalkyl, hetero$(C_{3-12})$cycloalkyl, $(C_{9-12})$bicycloalkyl, hetero$(C_{3-12})$bicycloalkyl, aryl$(C_{1-10})$alkyl, heteroaryl$(C_{1-5})$alkyl, $(C_{3-12})$cycloalkyl$(C_{1-10})$alkyl, halo$(C_{1-10})$alkyl, carbonyl$(C_{1-3})$alkyl, thiocarbonyl$(C_{1-3})$alkyl, sulfonyl$(C_{1-3})$alkyl, sulfinyl$(C_{1-3})$alkyl, imino$(C_{1-3})$alkyl, aryl, heteroaryl, $(C_{9-12})$bicycloaryl, and hetero$(C_{4-12})$bicycloaryl, each substituted or unsubstituted;

$R_{3a}$, $R_{3b}$, and $R_{3c}$ are each independently selected from the group consisting of hydrogen, halo, nitro, cyano, thio, hydroxy, alkoxy, aryloxy, heteroaryloxy, carbonyl, amino, $(C_{1-10})$alkylamino, sulfonamido, imino, sulfonyl, sulfinyl, $(C_{1-10})$alkyl, $(C_{3-12})$cycloalkyl, hetero$(C_{3-12})$cycloalkyl, $(C_{9-12})$bicycloalkyl, hetero$(C_{3-12})$bicycloalkyl, aryl$(C_{1-10})$alkyl, heteroaryl$(C_{1-5})$alkyl, perhalo$(C_{1-10})$alkyl, carbonyl$(C_{1-3})$alkyl, thiocarbonyl$(C_{1-3})$alkyl, sulfonyl$(C_{1-3})$alkyl, sulfinyl$(C_{1-3})$alkyl, amino$(C_{1-10})$alkyl, imino$(C_{1-3})$alkyl, aryl, heteroaryl, $(C_{9-12})$bicycloaryl, and hetero$(C_{4-12})$bicycloaryl, each substituted or unsubstituted, or two $R_3$ are taken together to form a substituted or unsubstituted ring;

each $R_4$ is independently selected from the group consisting of hydrogen, halo, nitro, cyano, thio, hydroxy, alkoxy, aryloxy, heteroaryloxy, carbonyl, amino, $(C_{1-10})$alkylamino, sulfonamido, imino, sulfonyl, sulfinyl, $(C_{1-10})$alkyl, $(C_{3-12})$cycloalkyl, hetero$(C_{3-12})$cycloalkyl, $(C_{9-12})$bicycloalkyl, hetero$(C_{3-12})$bicycloalkyl, aryl$(C_{1-10})$alkyl, heteroaryl$(C_{1-5})$alkyl, perhalo$(C_{1-10})$alkyl, carbonyl$(C_{1-3})$alkyl, thiocarbonyl$(C_{1-3})$alkyl, sulfonyl$(C_{1-3})$alkyl, sulfinyl$(C_{1-3})$alkyl, amino$(C_{1-10})$alkyl, imino$(C_{1-3})$alkyl, aryl, heteroaryl, $(C_{9-12})$bicycloaryl, and hetero$(C_{4-12})$bicycloaryl, each substituted or unsubstituted, or two $R_4$ are taken together to form part of a substituted or unsubstituted ring;

each $R_5$ is independently selected from the group consisting of hydrogen, nitro, thio, hydroxy, alkoxy, aryloxy, heteroaryloxy, carbonyl, amino, sulfonamido, imino, sulfonyl, sulfinyl, $(C_{1-10})$alkyl, $(C_{3-12})$cycloalkyl, hetero$(C_{3-12})$cycloalkyl, $(C_{9-12})$bicycloalkyl, hetero$(C_{3-12})$bicycloalkyl, aryl$(C_{1-10})$alkyl, heteroaryl$(C_{1-5})$alkyl, $(C_{3-12})$cycloalkyl$(C_{1-10})$alkyl, halo$(C_{1-10})$alkyl, carbonyl$(C_{1-3})$alkyl, thiocarbonyl$(C_{1-3})$alkyl, sulfonyl$(C_{1-3})$alkyl, sulfinyl$(C_{1-3})$alkyl, imino$(C_{1-3})$alkyl, aryl, heteroaryl, $(C_{9-12})$bicycloaryl, and hetero$(C_{4-12})$bicycloaryl, each substituted or unsubstituted, or two $R_5$, or one $R_4$ and one $R_5$, are taken together to form part of a substituted or unsubstituted ring;

$R_6$ is selected from the group consisting of hydrogen, nitro, thio, hydroxy, alkoxy, aryloxy, heteroaryloxy, carbonyl, amino, sulfonamido, imino, sulfonyl, sulfinyl, $(C_{1-10})$alkyl, $(C_{3-12})$cycloalkyl, hetero$(C_{3-12})$cycloalkyl, $(C_{9-12})$bicycloalkyl, hetero$(C_{3-12})$bicycloalkyl, aryl$(C_{1-10})$alkyl, heteroaryl$(C_{1-5})$alkyl, $(C_{3-12})$cycloalkyl$(C_{1-10})$alkyl, halo$(C_{1-10})$alkyl, carbonyl$(C_{1-3})$alkyl, thiocarbonyl$(C_{1-3})$alkyl, sulfonyl$(C_{1-3})$alkyl, sulfinyl ($C_{1-3}$)alkyl, imino($C_{1-3}$)alkyl, aryl, heteroaryl, ($C_{9-12}$) bicycloaryl, and hetero($C_{4-12}$)bicycloaryl, each substituted or unsubstituted; and $R_{21}$ and $R_{22}$ are each independently selected from the group consisting of hydrogen, halo, hydroxy, alkoxy, carbonyl, amino, ($C_{1-5}$)alkylamino, ($C_{1-5}$)alkyl, halo ($C_{1-5}$)alkyl, carbonyl($C_{1-3}$)alkyl and amino($C_{1-5}$)alkyl, each substituted or unsubstituted.

In still another embodiment, kinase inhibitors of the present invention comprise one of the following formulae:

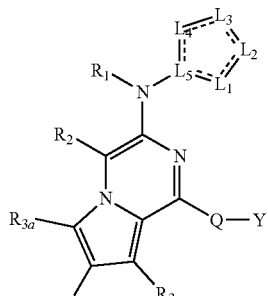

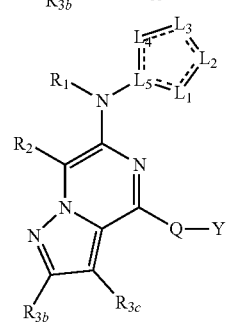

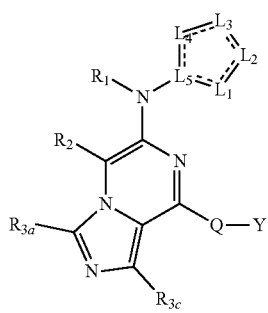

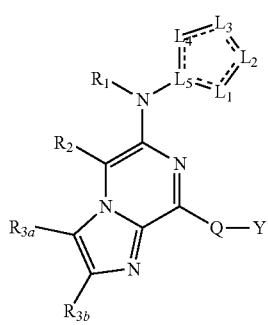

-continued

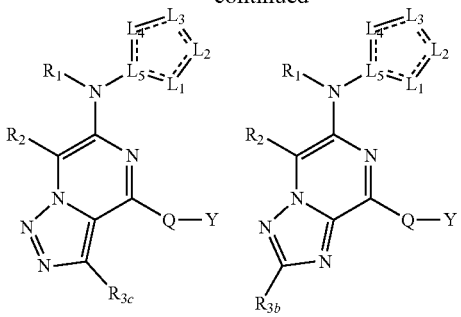

and

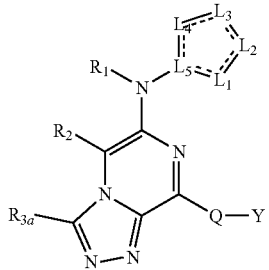

wherein:

l is selected from the group consisting of 1, 2, 3, 4 and 5;

$L_1, L_2, L_3, L_4$, and $L_5$ are each independently selected from the group consisting of $CR_4$ and $NR_5$, with the proviso that $R_5$ is absent when the atom to which it is attached forms part of a double bond;

Q is selected from the group consisting of S, SO, $SO_2$, O, $NR_6$, $NR_6$—$(CR_{21}R_{22})_l$, $NR_6$—$(CR_{21}R_{22})_l$—O, and a substituted or unsubstituted ($C_{2-5}$)alkylene, or Q is absent;

Y is selected from the group consisting of ($C_{3-12}$)cycloalkyl, hetero($C_{3-12}$)cycloalkyl, ($C_{9-12}$)bicycloalkyl, hetero($C_{3-12}$)bicycloalkyl, aryl, heteroaryl, ($C_{9-12}$)bicycloaryl, and hetero($C_{4-12}$)bicycloaryl, each substituted or unsubstituted;

$R_1$ is selected from the group consisting of hydrogen, nitro, thio, hydroxy, alkoxy, aryloxy, heteroaryloxy, carbonyl, amino, sulfonamido, imino, sulfonyl, sulfinyl, ($C_{1-10}$) alkyl, ($C_{3-12}$)cycloalkyl, hetero($C_{3-12}$)cycloalkyl, ($C_{9-12}$)bicycloalkyl, hetero($C_{3-12}$)bicycloalkyl, aryl ($C_{1-10}$)alkyl, heteroaryl($C_{1-5}$)alkyl, ($C_{3-12}$)cycloalkyl ($C_{1-10}$)alkyl, halo($C_{1-10}$)alkyl, carbonyl($C_{1-3}$)alkyl, thiocarbonyl($C_{1-3}$)alkyl, sulfonyl($C_{1-3}$)alkyl, sulfinyl ($C_{1-3}$)alkyl, imino($C_{1-3}$)alkyl, aryl, heteroaryl, ($C_{9-12}$) bicycloaryl, and hetero($C_{4-12}$)bicycloaryl, each substituted or unsubstituted;

$R_2$ is selected from the group consisting of hydrogen, halo, nitro, cyano, thio, hydroxy, alkoxy, aryloxy, heteroaryloxy, carbonyl, amino, ($C_{1-10}$)alkylamino, sulfonamido, imino, sulfonyl, sulfinyl, ($C_{1-10}$)alkyl, ($C_{3-12}$)cycloalkyl, hetero($C_{3-12}$)cycloalkyl, ($C_{9-12}$)bicycloalkyl, hetero($C_{3-12}$)bicycloalkyl, aryl($C_{1-10}$)alkyl, heteroaryl ($C_{1-5}$)alkyl, perhalo($C_{1-10}$)alkyl, carbonyl($C_{1-3}$)alkyl, thiocarbonyl($C_{1-3}$)alkyl, sulfonyl($C_{1-3}$)alkyl, sulfinyl ($C_{1-3}$)alkyl, amino($C_{1-10}$)alkyl, imino($C_{1-3}$)alkyl, aryl, heteroaryl, ($C_{9-12}$)bicycloaryl, and hetero($C_{4-12}$)bicycloaryl, each substituted or unsubstituted;

$R_{3a}, R_{3b}$, and $R_{3c}$ are each independently selected from the group consisting of hydrogen, halo, nitro, cyano, thio, hydroxy, alkoxy, aryloxy, heteroaryloxy, carbonyl, amino, ($C_{1-10}$)alkylamino, sulfonamido, imino, sulfonyl, sulfinyl, ($C_{1-10}$)alkyl, ($C_{3-12}$)cycloalkyl, hetero ($C_{3-12}$)cycloalkyl, ($C_{9-12}$)bicycloalkyl, hetero($C_{3-12}$)bicycloalkyl, aryl($C_{1-10}$)alkyl, heteroaryl($C_{1-5}$)alkyl, perhalo($C_{1-10}$)alkyl, carbonyl($C_{1-3}$)alkyl, thiocarbonyl($C_{1-3}$)alkyl, sulfonyl($C_{1-3}$)alkyl, sulfinyl($C_{1-3}$)alkyl, amino($C_{1-10}$)alkyl, imino($C_{1-3}$)alkyl, aryl, heteroaryl, ($C_{9-12}$)bicycloaryl, and hetero($C_{4-12}$)bicycloaryl, each substituted or unsubstituted, or two of $R_{3a}$, $R_{3b}$, and $R_{3c}$ are taken together to form a substituted or unsubstituted ring;

each $R_4$ is independently selected from the group consisting of hydrogen, halo, nitro, cyano, thio, hydroxy, alkoxy, aryloxy, heteroaryloxy, carbonyl, amino, ($C_{1-10}$)alkylamino, sulfonamido, imino, sulfonyl, sulfinyl, ($C_{1-10}$)alkyl, ($C_{3-12}$)cycloalkyl, hetero($C_{3-12}$)cycloalkyl, ($C_{9-12}$)bicycloalkyl, hetero($C_{3-12}$)bicycloalkyl, aryl($C_{1-10}$)alkyl, heteroaryl($C_{1-5}$)alkyl, perhalo($C_{1-10}$)alkyl, carbonyl($C_{1-3}$)alkyl, thiocarbonyl($C_{1-3}$)alkyl, sulfonyl($C_{1-3}$)alkyl, sulfinyl($C_{1-3}$)alkyl, amino($C_{1-10}$)alkyl, imino($C_{1-3}$)alkyl, aryl, heteroaryl, ($C_{9-12}$)bicycloaryl, and hetero($C_{4-12}$)bicycloaryl, each substituted or unsubstituted, or two $R_4$ are taken together to form part of a substituted or unsubstituted ring;

each $R_5$ is independently selected from the group consisting of hydrogen, nitro, thio, hydroxy, alkoxy, aryloxy, heteroaryloxy, carbonyl, amino, sulfonamido, imino, sulfonyl, sulfinyl, ($C_{1-10}$)alkyl, ($C_{3-12}$)cycloalkyl, hetero($C_{3-12}$)cycloalkyl, ($C_{9-12}$)bicycloalkyl, hetero($C_{3-12}$)bicycloalkyl, aryl($C_{1-10}$)alkyl, heteroaryl($C_{1-5}$)alkyl, ($C_{3-12}$)cycloalkyl($C_{1-10}$)alkyl, halo($C_{1-10}$)alkyl, carbonyl($C_{1-3}$)alkyl, thiocarbonyl($C_{1-3}$)alkyl, sulfonyl($C_{1-3}$)alkyl, sulfinyl($C_{1-3}$)alkyl, imino($C_{1-3}$)alkyl, aryl, heteroaryl, ($C_{9-12}$)bicycloaryl, and hetero($C_{4-12}$)bicycloaryl, each substituted or unsubstituted, or two $R_5$, or one $R_4$ and one $R_5$, are taken together to form part of a substituted or unsubstituted ring;

$R_6$ is selected from the group consisting of hydrogen, nitro, thio, hydroxy, alkoxy, aryloxy, heteroaryloxy, carbonyl, amino, sulfonamido, imino, sulfonyl, sulfinyl, ($C_{1-10}$)alkyl, ($C_{3-12}$)cycloalkyl, hetero($C_{3-12}$)cycloalkyl, ($C_{9-12}$)bicycloalkyl, hetero($C_{3-12}$)bicycloalkyl, aryl($C_{1-10}$)alkyl, heteroaryl($C_{1-5}$)alkyl, ($C_{3-12}$)cycloalkyl($C_{1-10}$)alkyl, halo($C_{1-10}$)alkyl, carbonyl($C_{1-3}$)alkyl, thiocarbonyl($C_{1-3}$)alkyl, sulfonyl($C_{1-3}$)alkyl, sulfinyl($C_{1-3}$)alkyl, imino($C_{1-3}$)alkyl, aryl, heteroaryl, ($C_{9-12}$)bicycloaryl, and hetero($C_{4-12}$)bicycloaryl, each substituted or unsubstituted; and $R_{21}$ and $R_{22}$ are each independently selected from the group consisting of hydrogen, halo, hydroxy, alkoxy, carbonyl, amino, ($C_{1-5}$)alkylamino, ($C_{1-5}$)alkyl, halo ($C_{1-5}$)alkyl, carbonyl($C_{1-3}$)alkyl and amino($C_{1-5}$)alkyl, each substituted or unsubstituted.

In yet another embodiment, kinase inhibitors of the present invention comprise one of the following formulae:

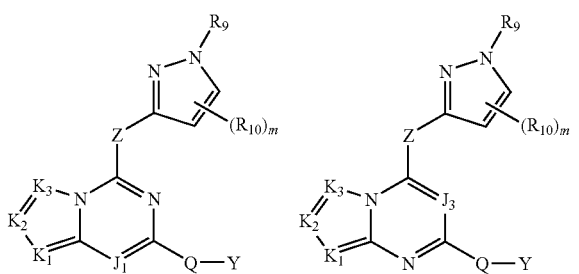

-continued

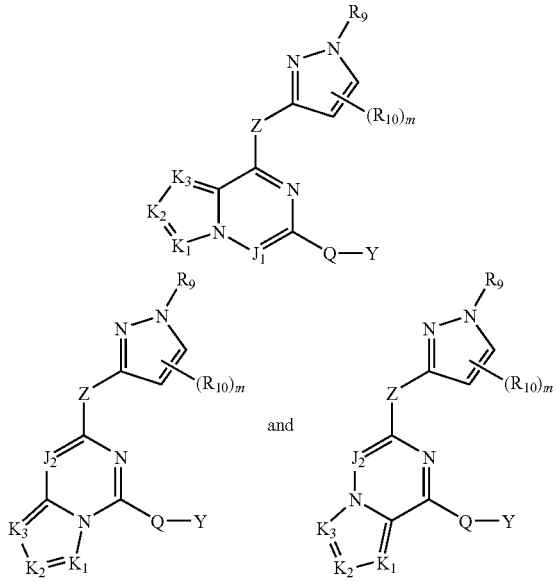

and wherein:
l is selected from the group consisting of 1, 2, 3, 4 and 5;
m is selected from the group consisting of 0, 1 and 2;
$J_1$, $J_2$ and $J_3$ are each independently selected from the group consisting of $CR_2$ and N;
$K_1$, $K_2$, and $K_3$ are each independently selected from the group consisting of $CR_3$ and N;
Q is selected from the group consisting of S, SO, $SO_2$, O, $NR_6$, $NR_6$—$(CR_{21}R_{22})_l$, $NR_6$—$(CR_{21}R_{22})_l$—O, and a substituted or unsubstituted ($C_{2-5}$)alkylene, or Q is absent;
Y is selected from the group consisting of ($C_{3-12}$)cycloalkyl, hetero($C_{3-12}$)cycloalkyl, ($C_{9-12}$)bicycloalkyl, hetero($C_{3-12}$)bicycloalkyl, aryl, heteroaryl, ($C_{9-12}$)bicycloaryl, and hetero($C_{4-12}$)bicycloaryl, each substituted or unsubstituted;
Z is selected from the group consisting of $NR_1$, S, SO, $SO_2$ and O;
$R_1$ is selected from the group consisting of hydrogen, nitro, thio, hydroxy, alkoxy, aryloxy, heteroaryloxy, carbonyl, amino, sulfonamido, imino, sulfonyl, sulfinyl, ($C_{1-10}$)alkyl, ($C_{3-12}$)cycloalkyl, hetero($C_{3-12}$)cycloalkyl, ($C_{9-12}$)bicycloalkyl, hetero($C_{3-12}$)bicycloalkyl, aryl($C_{1-10}$)alkyl, heteroaryl($C_{1-5}$)alkyl, ($C_{3-12}$)cycloalkyl($C_{1-10}$)alkyl, halo($C_{1-10}$)alkyl, carbonyl($C_{1-3}$)alkyl, thiocarbonyl($C_{1-3}$)alkyl, sulfonyl($C_{1-3}$)alkyl, sulfinyl($C_{1-3}$)alkyl, imino($C_{1-3}$)alkyl, aryl, heteroaryl, ($C_{9-12}$)bicycloaryl, and hetero($C_{4-12}$)bicycloaryl, each substituted or unsubstituted;
$R_2$ is selected from the group consisting of hydrogen, halo, nitro, cyano, thio, hydroxy, alkoxy, aryloxy, heteroaryloxy, carbonyl, amino, ($C_{1-10}$)alkylamino, sulfonamido, imino, sulfonyl, sulfinyl, ($C_{1-10}$)alkyl, ($C_{3-12}$)cycloalkyl, hetero($C_{3-12}$)cycloalkyl, ($C_{9-12}$)bicycloalkyl, hetero($C_{3-12}$)bicycloalkyl, aryl($C_{1-10}$)alkyl, heteroaryl($C_{1-5}$)alkyl, perhalo($C_{1-10}$)alkyl, carbonyl($C_{1-3}$)alkyl, thiocarbonyl($C_{1-3}$)alkyl, sulfonyl($C_{1-3}$)alkyl, sulfinyl($C_{1-3}$)alkyl, amino($C_{1-10}$)alkyl, imino($C_{1-3}$)alkyl, aryl, heteroaryl, ($C_{9-12}$)bicycloaryl, and hetero($C_{4-12}$)bicycloaryl, each substituted or unsubstituted;
each $R_3$ is independently selected from the group consisting of hydrogen, halo, nitro, cyano, thio, hydroxy, alkoxy, aryloxy, heteroaryloxy, carbonyl, amino, ($C_{1-10}$)alkylamino, sulfonamido, imino, sulfonyl, sulfinyl, ($C_{1-10}$)alkyl, ($C_{3-12}$)cycloalkyl, hetero($C_{3-12}$)cycloalkyl, ($C_{9-12}$)bicycloalkyl, hetero($C_{3-12}$)bicycloalkyl, aryl($C_{1-10}$)alkyl, heteroaryl($C_{1-5}$)alkyl, perhalo($C_{1-10}$)alkyl, carbonyl($C_{1-3}$)alkyl, thiocarbonyl($C_{1-3}$)alkyl, sulfonyl($C_{1-3}$)alkyl, sulfinyl($C_{1-3}$)alkyl, amino($C_{1-10}$)alkyl, imino($C_{1-3}$)alkyl, aryl, heteroaryl, ($C_{9-12}$)bicycloaryl, and hetero($C_{4-12}$)bicycloaryl, each substituted or unsubstituted, or $R_2$ and one $R_3$, or two $R_3$ are taken together to form a substituted or unsubstituted ring;

$R_6$ is selected from the group consisting of hydrogen, nitro, thio, hydroxy, alkoxy, aryloxy, heteroaryloxy, carbonyl, amino, sulfonamido, imino, sulfonyl, sulfinyl, ($C_{1-10}$) alkyl, ($C_{3-12}$)cycloalkyl, hetero($C_{3-12}$)cycloalkyl, ($C_{9-12}$)bicycloalkyl, hetero($C_{3-12}$)bicycloalkyl, aryl ($C_{1-10}$)alkyl, heteroaryl($C_{1-5}$)alkyl, ($C_{3-12}$)cycloalkyl ($C_{1-10}$)alkyl, halo($C_{1-10}$)alkyl, carbonyl($C_{1-3}$)alkyl, thiocarbonyl($C_{1-3}$)alkyl, sulfonyl($C_{1-3}$)alkyl, sulfinyl ($C_{1-3}$)alkyl, imino($C_{1-3}$)alkyl, aryl, heteroaryl, ($C_{9-12}$) bicycloaryl, and hetero($C_{4-12}$)bicycloaryl, each substituted or unsubstituted;

$R_9$ is selected from the group consisting of hydrogen, nitro, thio, hydroxy, alkoxy, aryloxy, heteroaryloxy, carbonyl, amino, sulfonamido, imino, sulfonyl, sulfinyl, ($C_{1-10}$) alkyl, ($C_{3-12}$)cycloalkyl, hetero($C_{3-12}$)cycloalkyl, ($C_{9-12}$)bicycloalkyl, hetero($C_{3-12}$)bicycloalkyl, aryl ($C_{1-10}$)alkyl, heteroaryl($C_{1-5}$)alkyl, ($C_{3-12}$)cycloalkyl ($C_{1-10}$)alkyl, halo($C_{1-10}$)alkyl, carbonyl($C_{1-3}$)alkyl, thiocarbonyl($C_{1-3}$)alkyl, sulfonyl($C_{1-3}$)alkyl, sulfinyl ($C_{1-3}$)alkyl, imino($C_{1-3}$)alkyl, aryl, heteroaryl, ($C_{9-12}$) bicycloaryl, and hetero($C_{4-12}$)bicycloaryl, each substituted or unsubstituted;

$R_{10}$ is selected from the group consisting of hydrogen, halo, nitro, cyano, thio, hydroxy, alkoxy, aryloxy, heteroaryloxy, carbonyl, amino, ($C_{1-10}$)alkylamino, sulfonamido, imino, sulfonyl, sulfinyl, ($C_{1-10}$)alkyl, ($C_{3-12}$) cycloalkyl, hetero($C_{3-12}$)cycloalkyl, ($C_{9-12}$) bicycloalkyl, hetero($C_{3-12}$)bicycloalkyl, aryl($C_{1-10}$) alkyl, heteroaryl($C_{1-5}$)alkyl, perhalo($C_{1-10}$)alkyl, carbonyl($C_{1-3}$)alkyl, thiocarbonyl($C_{1-3}$)alkyl, sulfonyl ($C_{1-3}$)alkyl, sulfinyl($C_{1-3}$)alkyl, amino($C_{1-10}$)alkyl, imino($C_{1-3}$)alkyl, aryl, heteroaryl, ($C_{9-12}$)bicycloaryl, and hetero($C_{4-12}$)bicycloaryl, each substituted or unsubstituted, or $R_9$ and $R_{10}$ are taken together to form a ring; and $R_{21}$ and $R_{22}$ are each independently selected from the group consisting of hydrogen, halo, hydroxy, alkoxy, carbonyl, amino, ($C_{1-5}$)alkylamino, ($C_{1-5}$)alkyl, halo ($C_{1-5}$)alkyl, carbonyl($C_{1-3}$)alkyl and amino($C_{1-5}$)alkyl, each substituted or unsubstituted.

In another embodiment, kinase inhibitors of the present invention comprise one of the following formulae:

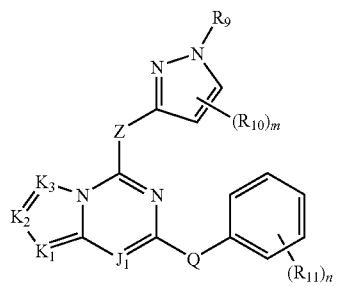

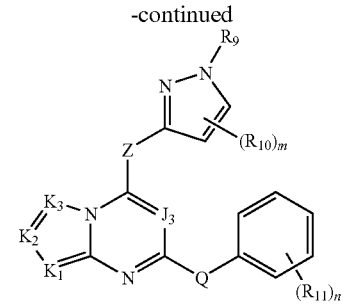

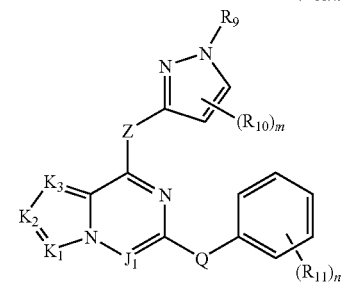

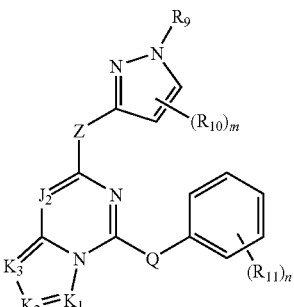

and

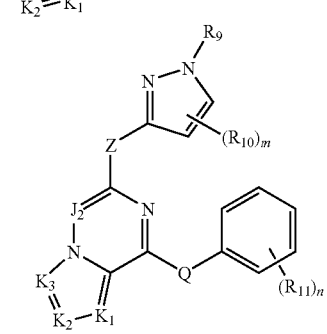

wherein:
  l is selected from the group consisting of 1, 2, 3, 4 and 5;
  m is selected from the group consisting of 0, 1 and 2;
  n is selected from the group consisting of 0, 1, 2, 3, 4, and 5;
  $J_1$, $J_2$ and $J_3$ are each independently selected from the group consisting of $CR_2$ and N;
  $K_1$, $K_2$, and $K_3$ are each independently selected from the group consisting of $CR_3$ and N;
  Q is selected from the group consisting of S, SO, $SO_2$, O, $NR_6$, $NR_6$—$(CR_{21}R_{22})_l$, $NR_6$—$(CR_{21}R_{22})_l$—O, and a substituted or unsubstituted ($C_{2-5}$)alkylene, or Q is absent;
  Z is selected from the group consisting of $NR_1$, S, SO, $SO_2$ and O;
  $R_1$ is selected from the group consisting of hydrogen, nitro, thio, hydroxy, alkoxy, aryloxy, heteroaryloxy, carbonyl, amino, sulfonamido, imino, sulfonyl, sulfinyl, ($C_{1-10}$) alkyl, ($C_{3-12}$)cycloalkyl, hetero($C_{3-12}$)cycloalkyl, ($C_{9-12}$)bicycloalkyl, hetero($C_{3-12}$)bicycloalkyl, aryl($C_{1-10}$)alkyl, heteroaryl($C_{1-5}$)alkyl, ($C_{3-12}$)cycloalkyl($C_{1-10}$)alkyl, halo($C_{1-10}$)alkyl, carbonyl($C_{1-3}$)alkyl, thiocarbonyl($C_{1-3}$)alkyl, sulfonyl($C_{1-3}$)alkyl, sulfinyl($C_{1-3}$)alkyl, imino($C_{1-3}$)alkyl, aryl, heteroaryl, ($C_{9-12}$)bicycloaryl, and hetero($C_{4-12}$)bicycloaryl, each substituted or unsubstituted;

$R_2$ is selected from the group consisting of hydrogen, halo, nitro, cyano, thio, hydroxy, alkoxy, aryloxy, heteroaryloxy, carbonyl, amino, ($C_{1-10}$)alkylamino, sulfonamido, imino, sulfonyl, sulfinyl, ($C_{1-10}$)alkyl, ($C_{3-12}$)cycloalkyl, hetero($C_{3-12}$)cycloalkyl, ($C_{9-12}$)bicycloalkyl, hetero($C_{3-12}$)bicycloalkyl, aryl($C_{1-10}$)alkyl, heteroaryl($C_{1-5}$)alkyl, perhalo($C_{1-10}$)alkyl, carbonyl($C_{1-3}$)alkyl, thiocarbonyl($C_{1-3}$)alkyl, sulfonyl($C_{1-3}$)alkyl, sulfinyl($C_{1-3}$)alkyl, amino($C_{1-10}$)alkyl, imino($C_{1-3}$)alkyl, aryl, heteroaryl, ($C_{9-12}$)bicycloaryl, and hetero($C_{4-12}$)bicycloaryl, each substituted or unsubstituted;

each $R_3$ is independently selected from the group consisting of hydrogen, halo, nitro, cyano, thio, hydroxy, alkoxy, aryloxy, heteroaryloxy, carbonyl, amino, ($C_{1-10}$)alkylamino, sulfonamido, imino, sulfonyl, sulfinyl, ($C_{1-10}$)alkyl, ($C_{3-12}$)cycloalkyl, hetero($C_{3-12}$)cycloalkyl, ($C_{9-12}$)bicycloalkyl, hetero($C_{3-12}$)bicycloalkyl, aryl($C_{1-10}$)alkyl, heteroaryl($C_{1-5}$)alkyl, perhalo($C_{1-10}$)alkyl, carbonyl($C_{1-3}$)alkyl, thiocarbonyl($C_{1-3}$)alkyl, sulfonyl($C_{1-3}$)alkyl, sulfinyl($C_{1-3}$)alkyl, amino($C_{1-10}$)alkyl, imino($C_{1-3}$)alkyl, aryl, heteroaryl, ($C_{9-12}$)bicycloaryl, and hetero($C_{4-12}$)bicycloaryl, each substituted or unsubstituted, or $R_2$ and one $R_3$, or two $R_3$ are taken together to form a substituted or unsubstituted ring;

$R_9$ is selected from the group consisting of hydrogen, nitro, thio, hydroxy, alkoxy, aryloxy, heteroaryloxy, carbonyl, amino, sulfonamido, imino, sulfonyl, sulfinyl, ($C_{1-10}$) alkyl, ($C_{3-12}$)cycloalkyl, hetero($C_{3-12}$)cycloalkyl, ($C_{9-12}$)bicycloalkyl, hetero($C_{3-12}$)bicycloalkyl, aryl ($C_{1-10}$)alkyl, heteroaryl($C_{1-5}$)alkyl, ($C_{3-12}$)cycloalkyl ($C_{1-10}$)alkyl, halo($C_{1-10}$)alkyl, carbonyl($C_{1-3}$)alkyl, thiocarbonyl($C_{1-3}$)alkyl, sulfonyl($C_{1-3}$)alkyl, sulfinyl ($C_{1-3}$)alkyl, imino($C_{1-3}$)alkyl, aryl, heteroaryl, ($C_{9-12}$) bicycloaryl, and hetero($C_{4-12}$)bicycloaryl, each substituted or unsubstituted;

each $R_{10}$ is independently selected from the group consisting of hydrogen, halo, nitro, cyano, thio, hydroxy, alkoxy, aryloxy, heteroaryloxy, carbonyl, amino, ($C_{1-10}$) alkylamino, sulfonamido, imino, sulfonyl, sulfinyl, ($C_{1-10}$)alkyl, ($C_{3-12}$)cycloalkyl, hetero($C_{3-12}$)cycloalkyl, ($C_{9-12}$)bicycloalkyl, hetero($C_{3-12}$)bicycloalkyl, aryl($C_{1-10}$)alkyl, heteroaryl($C_{1-5}$)alkyl, perhalo($C_{1-10}$)alkyl, carbonyl($C_{1-3}$)alkyl, thiocarbonyl ($C_{1-3}$)alkyl, sulfonyl($C_{1-3}$)alkyl, sulfinyl($C_{1-3}$)alkyl, amino($C_{1-10}$)alkyl, imino($C_{1-3}$)alkyl, aryl, heteroaryl, ($C_{9-12}$)bicycloaryl, and hetero($C_{4-12}$)bicycloaryl, each substituted or unsubstituted, or $R_9$ and $R_{10}$ are taken together to form a ring;

each $R_{11}$ is independently selected from the group consisting of hydrogen, halo, nitro, cyano, thio, hydroxy, alkoxy, aryloxy, heteroaryloxy, carbonyl, amino, ($C_{1-10}$) alkylamino, sulfonamido, imino, sulfonyl, sulfinyl, ($C_{1-10}$)alkyl, ($C_{3-12}$)cycloalkyl, hetero($C_{3-12}$)cycloalkyl, ($C_{9-12}$)bicycloalkyl, hetero($C_{3-12}$)bicycloalkyl, aryl($C_{1-10}$)alkyl, heteroaryl($C_{1-5}$)alkyl, perhalo($C_{1-10}$)alkyl, carbonyl($C_{1-3}$)alkyl, thiocarbonyl ($C_{1-3}$)alkyl, sulfonyl($C_{1-3}$)alkyl, sulfinyl($C_{1-3}$)alkyl, amino($C_{1-10}$)alkyl, imino($C_{1-3}$)alkyl, aryl, heteroaryl, ($C_{9-12}$)bicycloaryl, and hetero($C_{4-12}$)bicycloaryl, each substituted or unsubstituted, or two $R_{11}$ are taken together to form a ring; and $R_{21}$ and $R_{22}$ are each independently selected from the group consisting of hydrogen, halo, hydroxy, alkoxy, carbonyl, amino, ($C_{1-5}$)alkylamino, ($C_{1-5}$)alkyl, halo ($C_{1-5}$)alkyl, carbonyl($C_{1-3}$)alkyl and amino($C_{1-5}$)alkyl, each substituted or unsubstituted.

In a further embodiment, kinase inhibitors of the present invention comprise the following formula:

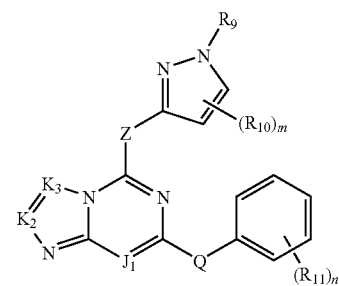

wherein:

l is selected from the group consisting of 1, 2, 3, 4 and 5;

m is selected from the group consisting of 0, 1 and 2;

n is selected from the group consisting of 0, 1, 2, 3, 4, and 5;

$J_1$ is selected from the group consisting of $CR_2$ and N;

$K_2$ and $K_3$ are each independently selected from the group consisting of $CR_3$ and N;

Q is selected from the group consisting of S, SO, $SO_2$, O, $NR_6$, $NR_6$—$(CR_{21}R_{22})_l$, $NR_6$—$(CR_{21}R_{22})_l$—O, and a substituted or unsubstituted ($C_{2-5}$)alkylene, or Q is absent;

Z is selected from the group consisting of $NR_1$, S, SO, $SO_2$ and O;

$R_1$ is selected from the group consisting of hydrogen, nitro, thio, hydroxy, alkoxy, aryloxy, heteroaryloxy, carbonyl, amino, sulfonamido, imino, sulfonyl, sulfinyl, ($C_{1-10}$) alkyl, ($C_{3-12}$)cycloalkyl, hetero($C_{3-12}$)cycloalkyl, ($C_{9-12}$)bicycloalkyl, hetero($C_{3-12}$)bicycloalkyl, aryl ($C_{1-10}$)alkyl, heteroaryl($C_{1-5}$)alkyl, ($C_{3-12}$)cycloalkyl ($C_{1-10}$)alkyl, halo($C_{1-10}$)alkyl, carbonyl($C_{1-3}$)alkyl, thiocarbonyl($C_{1-3}$)alkyl, sulfonyl($C_{1-3}$)alkyl, sulfinyl ($C_{1-3}$)alkyl, imino($C_{1-3}$)alkyl, aryl, heteroaryl, ($C_{9-12}$) bicycloaryl, and hetero($C_{4-12}$)bicycloaryl, each substituted or unsubstituted;

$R_2$ is selected from the group consisting of hydrogen, halo, nitro, cyano, thio, hydroxy, alkoxy, aryloxy, heteroaryloxy, carbonyl, amino, ($C_{1-10}$)alkylamino, sulfonamido, imino, sulfonyl, sulfinyl, ($C_{1-10}$)alkyl, ($C_{3-12}$)cycloalkyl, hetero($C_{3-12}$)cycloalkyl, ($C_{9-12}$)bicycloalkyl, hetero($C_{3-12}$)bicycloalkyl, aryl($C_{1-10}$)alkyl, heteroaryl ($C_{1-5}$)alkyl, perhalo($C_{1-10}$)alkyl, carbonyl($C_{1-3}$)alkyl, thiocarbonyl($C_{1-3}$)alkyl, sulfonyl($C_{1-3}$)alkyl, sulfinyl ($C_{1-3}$)alkyl, amino($C_{1-10}$)alkyl, imino($C_{1-3}$)alkyl, aryl, heteroaryl, ($C_{9-12}$)bicycloaryl, and hetero($C_{4-12}$)bicycloaryl, each substituted or unsubstituted;

each $R_3$ is independently selected from the group consisting of hydrogen, halo, nitro, cyano, thio, hydroxy, alkoxy, aryloxy, heteroaryloxy, carbonyl, amino, ($C_{1-10}$) alkylamino, sulfonamido, imino, sulfonyl, sulfinyl, ($C_{1-10}$)alkyl, ($C_{3-12}$)cycloalkyl, hetero($C_{3-12}$)cycloalkyl, ($C_{9-12}$)bicycloalkyl, hetero($C_{3-12}$)bicycloalkyl, aryl($C_{1-10}$)alkyl, heteroaryl($C_{1-5}$)alkyl, perhalo($C_{1-10}$)alkyl, carbonyl($C_{1-3}$)alkyl, thiocarbonyl ($C_{1-3}$)alkyl, sulfonyl($C_{1-3}$)alkyl, sulfinyl($C_{1-3}$)alkyl, amino($C_{1-10}$)alkyl, imino($C_{1-3}$)alkyl, aryl, heteroaryl, ($C_{9-12}$)bicycloaryl, and hetero($C_{4-12}$)bicycloaryl, each substituted or unsubstituted, or $R_2$ and one $R_3$, or two $R_3$ are taken together to form a substituted or unsubstituted ring;

$R_9$ is selected from the group consisting of hydrogen, nitro, thio, hydroxy, alkoxy, aryloxy, heteroaryloxy, carbonyl, amino, sulfonamido, imino, sulfonyl, sulfinyl, ($C_{1-10}$)alkyl, ($C_{3-12}$)cycloalkyl, hetero($C_{3-12}$)cycloalkyl, ($C_{9-12}$)bicycloalkyl, hetero($C_{3-12}$)bicycloalkyl, aryl($C_{1-10}$)alkyl, heteroaryl($C_{1-5}$)alkyl, ($C_{3-12}$)cycloalkyl($C_{1-10}$)alkyl, halo($C_{1-10}$)alkyl, carbonyl($C_{1-3}$)alkyl, thiocarbonyl($C_{1-3}$)alkyl, sulfonyl($C_{1-3}$)alkyl, sulfinyl($C_{1-3}$)alkyl, imino($C_{1-3}$)alkyl, aryl, heteroaryl, ($C_{9-12}$)bicycloaryl, and hetero($C_{4-12}$)bicycloaryl, each substituted or unsubstituted;

each $R_{10}$ is independently selected from the group consisting of hydrogen, halo, nitro, cyano, thio, hydroxy, alkoxy, aryloxy, heteroaryloxy, carbonyl, amino, ($C_{1-10}$)alkylamino, sulfonamido, imino, sulfonyl, sulfinyl, ($C_{1-10}$)alkyl, ($C_{3-12}$)cycloalkyl, hetero($C_{3-12}$)cycloalkyl, ($C_{9-12}$)bicycloalkyl, hetero($C_{3-12}$)bicycloalkyl, aryl($C_{1-10}$)alkyl, heteroaryl($C_{1-5}$)alkyl, perhalo($C_{1-10}$)alkyl, carbonyl($C_{1-3}$)alkyl, thiocarbonyl($C_{1-3}$)alkyl, sulfonyl($C_{1-3}$)alkyl, sulfinyl($C_{1-3}$)alkyl, amino($C_{1-10}$)alkyl, imino($C_{1-3}$)alkyl, aryl, heteroaryl, ($C_{9-12}$)bicycloaryl, and hetero($C_{4-12}$)bicycloaryl, each substituted or unsubstituted, or $R_9$ and $R_{10}$ are taken together to form a ring;

each $R_{11}$ is independently selected from the group consisting of hydrogen, halo, nitro, cyano, thio, hydroxy, alkoxy, aryloxy, heteroaryloxy, carbonyl, amino, ($C_{1-10}$)alkylamino, sulfonamido, imino, sulfonyl, sulfinyl, ($C_{1-10}$)alkyl, ($C_{3-12}$)cycloalkyl, hetero($C_{3-12}$)cycloalkyl, ($C_{9-12}$)bicycloalkyl, hetero($C_{3-12}$)bicycloalkyl, aryl($C_{1-10}$)alkyl, heteroaryl($C_{1-5}$)alkyl, perhalo($C_{1-10}$)alkyl, carbonyl($C_{1-3}$)alkyl, thiocarbonyl($C_{1-3}$)alkyl, sulfonyl($C_{1-3}$)alkyl, sulfinyl($C_{1-3}$)alkyl, amino($C_{1-10}$)alkyl, imino($C_{1-3}$)alkyl, aryl, heteroaryl, ($C_{9-12}$)bicycloaryl, and hetero($C_{4-12}$)bicycloaryl, each substituted or unsubstituted, or two $R_{11}$ are taken together to form a ring; and $R_{21}$ and $R_{22}$ are each independently selected from the group consisting of hydrogen, halo, hydroxy, alkoxy, carbonyl, amino, ($C_{1-5}$)alkylamino, ($C_{1-5}$)alkyl, halo($C_{1-5}$)alkyl, carbonyl($C_{1-3}$)alkyl and amino($C_{1-5}$)alkyl, each substituted or unsubstituted.

In still another embodiment, kinase inhibitors of the present invention comprise the following formula:

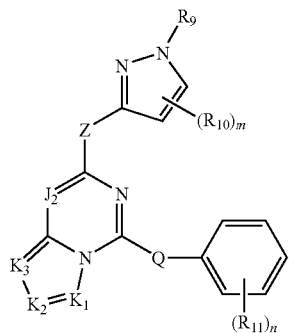

wherein:
l is selected from the group consisting of 1, 2, 3, 4 and 5;
m is selected from the group consisting of 0, 1 and 2;
n is selected from the group consisting of 0, 1, 2, 3, 4, and 5;
$J_2$ is selected from the group consisting of $CR_2$ and N;
$K_1$, $K_2$, and $K_3$ are each independently selected from the group consisting of $CR_3$ and N;
Q is selected from the group consisting of S, SO, $SO_2$, O, $NR_6$, $NR_6$—$(CR_{21}R_{22})_l$, $NR_6$—$(CR_{21}R_{22})_l$—O, and a substituted or unsubstituted ($C_{2-5}$)alkylene, or Q is absent;
Z is selected from the group consisting of $NR_1$, S, SO, $SO_2$ and O;
$R_1$ is selected from the group consisting of hydrogen, nitro, thio, hydroxy, alkoxy, aryloxy, heteroaryloxy, carbonyl, amino, sulfonamido, imino, sulfonyl, sulfinyl, ($C_{1-10}$)alkyl, ($C_{3-12}$)cycloalkyl, hetero($C_{3-12}$)cycloalkyl, ($C_{9-12}$)bicycloalkyl, hetero($C_{3-12}$)bicycloalkyl, aryl($C_{1-10}$)alkyl, heteroaryl($C_{1-5}$)alkyl, ($C_{3-12}$)cycloalkyl($C_{1-10}$)alkyl, halo($C_{1-10}$)alkyl, carbonyl($C_{1-3}$)alkyl, thiocarbonyl($C_{1-3}$)alkyl, sulfonyl($C_{1-3}$)alkyl, sulfinyl($C_{1-3}$)alkyl, imino($C_{1-3}$)alkyl, aryl, heteroaryl, ($C_{9-12}$)bicycloaryl, and hetero($C_{4-12}$)bicycloaryl, each substituted or unsubstituted;

$R_2$ is selected from the group consisting of hydrogen, halo, nitro, cyano, thio, hydroxy, alkoxy, aryloxy, heteroaryloxy, carbonyl, amino, ($C_{1-10}$)alkylamino, sulfonamido, imino, sulfonyl, sulfinyl, ($C_{1-10}$)alkyl, ($C_{3-12}$)cycloalkyl, hetero($C_{3-12}$)cycloalkyl, ($C_{9-12}$)bicycloalkyl, hetero($C_{3-12}$)bicycloalkyl, aryl($C_{1-10}$)alkyl, heteroaryl($C_{1-5}$)alkyl, perhalo($C_{1-10}$)alkyl, carbonyl($C_{1-3}$)alkyl, thiocarbonyl($C_{1-3}$)alkyl, sulfonyl($C_{1-3}$)alkyl, sulfinyl($C_{1-3}$)alkyl, amino($C_{1-10}$)alkyl, imino($C_{1-3}$)alkyl, aryl, heteroaryl, ($C_{9-12}$)bicycloaryl, and hetero($C_{4-12}$)bicycloaryl, each substituted or unsubstituted;

each $R_3$ is independently selected from the group consisting of hydrogen, halo, nitro, cyano, thio, hydroxy, alkoxy, aryloxy, heteroaryloxy, carbonyl, amino, ($C_{1-10}$)alkylamino, sulfonamido, imino, sulfonyl, sulfinyl, ($C_{1-10}$)alkyl, ($C_{3-12}$)cycloalkyl, hetero($C_{3-12}$)cycloalkyl, ($C_{9-12}$)bicycloalkyl, hetero($C_{3-12}$)bicycloalkyl, aryl($C_{1-10}$)alkyl, heteroaryl($C_{1-5}$)alkyl, perhalo($C_{1-10}$)alkyl, carbonyl($C_{1-3}$)alkyl, thiocarbonyl($C_{1-3}$)alkyl, sulfonyl($C_{1-3}$)alkyl, sulfinyl($C_{1-3}$)alkyl, amino($C_{1-10}$)alkyl, imino($C_{1-3}$)alkyl, aryl, heteroaryl, ($C_{9-12}$)bicycloaryl, and hetero($C_{4-12}$)bicycloaryl, each substituted or unsubstituted, or $R_2$ and one $R_3$, or two $R_3$ are taken together to form a substituted or unsubstituted ring;

$R_9$ is selected from the group consisting of hydrogen, nitro, thio, hydroxy, alkoxy, aryloxy, heteroaryloxy, carbonyl, amino, sulfonamido, imino, sulfonyl, sulfinyl, ($C_{1-10}$)alkyl, ($C_{3-12}$)cycloalkyl, hetero($C_{3-12}$)cycloalkyl, ($C_{9-12}$)bicycloalkyl, hetero($C_{3-12}$)bicycloalkyl, aryl($C_{1-10}$)alkyl, heteroaryl($C_{1-5}$)alkyl, ($C_{3-12}$)cycloalkyl($C_{1-10}$)alkyl, halo($C_{1-10}$)alkyl, carbonyl($C_{1-3}$)alkyl, thiocarbonyl($C_{1-3}$)alkyl, sulfonyl($C_{1-3}$)alkyl, sulfinyl($C_{1-3}$)alkyl, imino($C_{1-3}$)alkyl, aryl, heteroaryl, ($C_{9-12}$)bicycloaryl, and hetero($C_{4-12}$)bicycloaryl, each substituted or unsubstituted;

each $R_{10}$ is independently selected from the group consisting of hydrogen, halo, nitro, cyano, thio, hydroxy, alkoxy, aryloxy, heteroaryloxy, carbonyl, amino, ($C_{1-10}$)alkylamino, sulfonamido, imino, sulfonyl, sulfinyl, ($C_{1-10}$)alkyl, ($C_{3-12}$)cycloalkyl, hetero($C_{3-12}$)cycloalkyl, ($C_{9-12}$)bicycloalkyl, hetero($C_{3-12}$)bicycloalkyl, aryl($C_{1-10}$)alkyl, heteroaryl($C_{1-5}$)alkyl, perhalo($C_{1-10}$)alkyl, carbonyl($C_{1-3}$)alkyl, thiocarbonyl($C_{1-3}$)alkyl, sulfonyl($C_{1-3}$)alkyl, sulfinyl($C_{1-3}$)alkyl, amino($C_{1-10}$)alkyl, imino($C_{1-3}$)alkyl, aryl, heteroaryl, ($C_{9-12}$)bicycloaryl, and hetero(C$_{4-12}$)bicycloaryl, each substituted or unsubstituted, or R$_9$ and R$_{10}$ are taken together to form a ring;

each R$_{11}$ is independently selected from the group consisting of hydrogen, halo, nitro, cyano, thio, hydroxy, alkoxy, aryloxy, heteroaryloxy, carbonyl, amino, (C$_{1-10}$) alkylamino, sulfonamido, imino, sulfonyl, sulfinyl, (C$_{1-10}$)alkyl, (C$_{3-12}$)cycloalkyl, hetero(C$_{3-12}$)cycloalkyl, (C$_{9-12}$)bicycloalkyl, hetero(C$_{3-12}$)bicycloalkyl, aryl(C$_{1-10}$)alkyl, heteroaryl(C$_{1-5}$)alkyl, perhalo(C$_{1-10}$)alkyl, carbonyl(C$_{1-3}$)alkyl, thiocarbonyl(C$_{1-3}$)alkyl, sulfonyl(C$_{1-3}$)alkyl, sulfinyl(C$_{1-3}$)alkyl, amino(C$_{1-10}$)alkyl, imino(C$_{1-3}$)alkyl, aryl, heteroaryl, (C$_{9-12}$)bicycloaryl, and hetero(C$_{4-12}$)bicycloaryl, each substituted or unsubstituted, or two R$_{11}$ are taken together to form a ring; and R$_{21}$ and R$_{22}$ are each independently selected from the group consisting of hydrogen, halo, hydroxy, alkoxy, carbonyl, amino, (C$_{1-5}$)alkylamino, (C$_{1-5}$)alkyl, halo (C$_{1-5}$)alkyl, carbonyl(C$_{1-3}$)alkyl and amino(C$_{1-5}$)alkyl, each substituted or unsubstituted.

In yet another embodiment, kinase inhibitors of the present invention comprise the following formula:

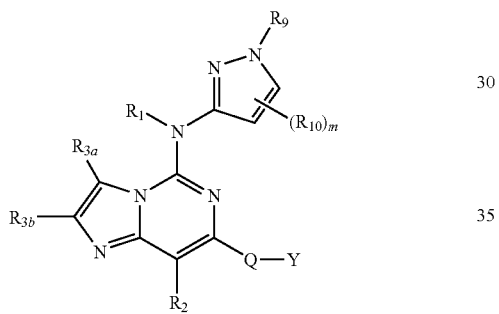

wherein:
l is selected from the group consisting of 1, 2, 3, 4 and 5;
m is selected from the group consisting of 0, 1 and 2;
Q is selected from the group consisting of S, SO, SO$_2$, O, NR$_6$, NR$_6$—(CR$_{21}$R$_{22}$)$_l$, NR$_6$—(CR$_{21}$R$_{22}$)$_l$—O, and a substituted or unsubstituted (C$_{2-5}$)alkylene, or Q is absent;

Y is selected from the group consisting of (C$_{3-12}$)cycloalkyl, hetero(C$_{3-12}$)cycloalkyl, (C$_{9-12}$)bicycloalkyl, hetero(C$_{3-12}$)bicycloalkyl, aryl, heteroaryl, (C$_{9-12}$)bicycloaryl, and hetero(C$_{4-12}$)bicycloaryl, each substituted or unsubstituted;

R$_1$ is selected from the group consisting of hydrogen, nitro, thio, hydroxy, alkoxy, aryloxy, heteroaryloxy, carbonyl, amino, sulfonamido, imino, sulfonyl, sulfinyl, (C$_{1-10}$) alkyl, (C$_{3-12}$)cycloalkyl, hetero(C$_{3-12}$)cycloalkyl, (C$_{9-12}$)bicycloalkyl, hetero(C$_{3-12}$)bicycloalkyl, aryl (C$_{1-10}$)alkyl, heteroaryl(C$_{1-5}$)alkyl, (C$_{3-12}$)cycloalkyl (C$_{1-10}$)alkyl, halo(C$_{1-10}$)alkyl, carbonyl(C$_{1-3}$)alkyl, thiocarbonyl(C$_{1-3}$)alkyl, sulfonyl(C$_{1-3}$)alkyl, sulfinyl (C$_{1-3}$)alkyl, imino(C$_{1-3}$)alkyl, aryl, heteroaryl, (C$_{9-12}$) bicycloaryl, and hetero(C$_{4-12}$)bicycloaryl, each substituted or unsubstituted;

R$_2$ is selected from the group consisting of hydrogen, halo, nitro, cyano, thio, hydroxy, alkoxy, aryloxy, heteroaryloxy, carbonyl, amino, (C$_{1-10}$)alkylamino, sulfonamido, imino, sulfonyl, sulfinyl, (C$_{1-10}$)alkyl, (C$_{3-12}$)cycloalkyl, hetero(C$_{3-12}$)cycloalkyl, (C$_{9-12}$)bicycloalkyl, hetero(C$_{3-12}$)bicycloalkyl, aryl(C$_{1-10}$)alkyl, heteroaryl (C$_{1-5}$)alkyl, perhalo(C$_{1-10}$)alkyl, carbonyl(C$_{1-3}$)alkyl, thiocarbonyl(C$_{1-3}$)alkyl, sulfonyl(C$_{1-3}$)alkyl, sulfinyl (C$_{1-3}$)alkyl, amino(C$_{1-10}$)alkyl, imino(C$_{1-3}$)alkyl, aryl, heteroaryl, (C$_{9-12}$)bicycloaryl, and hetero(C$_{4-12}$)bicycloaryl, each substituted or unsubstituted;

R$_{3a}$ and R$_{3b}$ are each independently selected from the group consisting of hydrogen, halo, nitro, cyano, thio, hydroxy, alkoxy, aryloxy, heteroaryloxy, carbonyl, amino, (C$_{1-10}$)alkylamino, sulfonamido, imino, sulfonyl, sulfinyl, (C$_{1-10}$)alkyl, (C$_{3-12}$)cycloalkyl, hetero (C$_{3-12}$)cycloalkyl, (C$_{9-12}$)bicycloalkyl, hetero(C$_{3-12}$)bicycloalkyl, aryl(C$_{1-10}$)alkyl, heteroaryl(C$_{1-5}$)alkyl, perhalo(C$_{1-10}$)alkyl, carbonyl(C$_{1-3}$)alkyl, thiocarbonyl (C$_{1-3}$)alkyl, sulfonyl(C$_{1-3}$)alkyl, sulfinyl(C$_{1-3}$)alkyl, amino(C$_{1-10}$)alkyl, imino(C$_{1-3}$)alkyl, aryl, heteroaryl, (C$_{9-12}$)bicycloaryl, and hetero(C$_{4-12}$)bicycloaryl, each substituted or unsubstituted, or R$_{3a}$ and R$_{3b}$ are taken together to form a substituted or unsubstituted ring;

R$_6$ is selected from the group consisting of hydrogen, nitro, thio, hydroxy, alkoxy, aryloxy, heteroaryloxy, carbonyl, amino, sulfonamido, imino, sulfonyl, sulfinyl, (C$_{1-10}$) alkyl, (C$_{3-12}$)cycloalkyl, hetero(C$_{3-12}$)cycloalkyl, (C$_{9-12}$)bicycloalkyl, hetero(C$_{3-12}$)bicycloalkyl, aryl (C$_{1-10}$)alkyl, heteroaryl(C$_{1-5}$)alkyl, (C$_{3-12}$)cycloalkyl (C$_{1-10}$)alkyl, halo(C$_{1-10}$)alkyl, carbonyl(C$_{1-3}$)alkyl, thiocarbonyl(C$_{1-3}$)alkyl, sulfonyl(C$_{1-3}$)alkyl, sulfinyl (C$_{1-3}$)alkyl, imino(C$_{1-3}$)alkyl, aryl, heteroaryl, (C$_{9-12}$) bicycloaryl, and hetero(C$_{4-12}$)bicycloaryl, each substituted or unsubstituted;

R$_9$ is selected from the group consisting of hydrogen, nitro, thio, hydroxy, alkoxy, aryloxy, heteroaryloxy, carbonyl, amino, sulfonamido, imino, sulfonyl, sulfinyl, (C$_{1-10}$) alkyl, (C$_{3-12}$)cycloalkyl, hetero(C$_{3-12}$)cycloalkyl, (C$_{9-12}$)bicycloalkyl, hetero(C$_{3-12}$)bicycloalkyl, aryl (C$_{1-10}$)alkyl, heteroaryl(C$_{1-5}$)alkyl, (C$_{3-12}$)cycloalkyl (C$_{1-10}$)alkyl, halo(C$_{1-10}$)alkyl, carbonyl(C$_{1-3}$)alkyl, thiocarbonyl(C$_{1-3}$)alkyl, sulfonyl(C$_{1-3}$)alkyl, sulfinyl (C$_{1-3}$)alkyl, imino(C$_{1-3}$)alkyl, aryl, heteroaryl, (C$_{9-12}$) bicycloaryl, and hetero(C$_{4-12}$)bicycloaryl, each substituted or unsubstituted;

each R$_{10}$ is independently selected from the group consisting of hydrogen, halo, nitro, cyano, thio, hydroxy, alkoxy, aryloxy, heteroaryloxy, carbonyl, amino, (C$_{1-10}$) alkylamino, sulfonamido, imino, sulfonyl, sulfinyl, (C$_{1-10}$)alkyl, (C$_{3-12}$)cycloalkyl, hetero(C$_{3-12}$)cycloalkyl, (C$_{9-12}$)bicycloalkyl, hetero(C$_{3-12}$)bicycloalkyl, aryl(C$_{1-10}$)alkyl, heteroaryl(C$_{1-5}$)alkyl, perhalo(C$_{1-10}$)alkyl, carbonyl(C$_{1-3}$)alkyl, thiocarbonyl (C$_{1-3}$)alkyl, sulfonyl(C$_{1-3}$)alkyl, sulfinyl(C$_{1-3}$)alkyl, amino(C$_{1-10}$)alkyl, imino(C$_{1-3}$)alkyl, aryl, heteroaryl, (C$_{9-12}$)bicycloaryl, and hetero(C$_{4-12}$)bicycloaryl, each substituted or unsubstituted, or R$_9$ and R$_{10}$ are taken together to form a ring; and R$_{21}$ and R$_{22}$ are each independently selected from the group consisting of hydrogen, halo, hydroxy, alkoxy, carbonyl, amino, (C$_{1-5}$)alkylamino, (C$_{1-5}$)alkyl, halo (C$_{1-5}$)alkyl, carbonyl(C$_{1-3}$)alkyl and amino(C$_{1-5}$)alkyl, each substituted or unsubstituted.

In a further embodiment, kinase inhibitors of the present invention comprise the following formula:

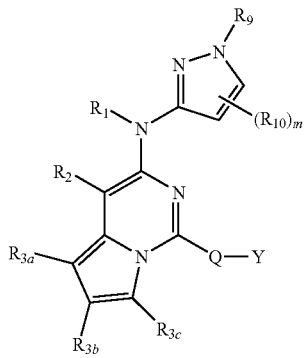

wherein:
l is selected from the group consisting of 1, 2, 3, 4 and 5;
m is selected from the group consisting of 0, 1 and 2;
Q is selected from the group consisting of S, SO, $SO_2$, O, $NR_6$, $NR_6$—$(CR_{21}R_{22})_l$, $NR_6$—$(CR_{21}R_{22})_l$—O, and a substituted or unsubstituted ($C_{2-5}$)alkylene, or Q is absent;
Y is selected from the group consisting of ($C_{3-12}$)cycloalkyl, hetero($C_{3-12}$)cycloalkyl, ($C_{9-12}$)bicycloalkyl, hetero($C_{3-12}$)bicycloalkyl, aryl, heteroaryl, ($C_{9-12}$)bicycloaryl, and hetero($C_{4-12}$)bicycloaryl, each substituted or unsubstituted;
$R_1$ is selected from the group consisting of hydrogen, nitro, thio, hydroxy, alkoxy, aryloxy, heteroaryloxy, carbonyl, amino, sulfonamido, imino, sulfonyl, sulfinyl, ($C_{1-10}$) alkyl, ($C_{3-12}$)cycloalkyl, hetero($C_{3-12}$)cycloalkyl, ($C_{9-12}$)bicycloalkyl, hetero($C_{3-12}$)bicycloalkyl, aryl ($C_{1-10}$)alkyl, heteroaryl($C_{1-5}$)alkyl, ($C_{3-12}$)cycloalkyl ($C_{1-10}$)alkyl, halo($C_{1-10}$)alkyl, carbonyl($C_{1-3}$)alkyl, thiocarbonyl($C_{1-3}$)alkyl, sulfonyl($C_{1-3}$)alkyl, sulfinyl ($C_{1-3}$)alkyl, imino($C_{1-3}$)alkyl, aryl, heteroaryl, ($C_{9-12}$) bicycloaryl, and hetero($C_{4-12}$)bicycloaryl, each substituted or unsubstituted;
$R_2$ is selected from the group consisting of hydrogen, halo, nitro, cyano, thio, hydroxy, alkoxy, aryloxy, heteroaryloxy, carbonyl, amino, ($C_{1-10}$)alkylamino, sulfonamido, imino, sulfonyl, sulfinyl, ($C_{1-10}$)alkyl, ($C_{3-12}$)cycloalkyl, hetero($C_{3-12}$)cycloalkyl, ($C_{9-12}$)bicycloalkyl, hetero($C_{3-12}$)bicycloalkyl, aryl($C_{1-10}$)alkyl, heteroaryl ($C_{1-5}$)alkyl, perhalo($C_{1-10}$)alkyl, carbonyl($C_{1-3}$)alkyl, thiocarbonyl($C_{1-3}$)alkyl, sulfonyl($C_{1-3}$)alkyl, sulfinyl ($C_{1-3}$)alkyl, amino($C_{1-10}$)alkyl, imino($C_{1-3}$)alkyl, aryl, heteroaryl, ($C_{9-12}$)bicycloaryl, and hetero($C_{4-12}$)bicycloaryl, each substituted or unsubstituted;
$R_{3a}$, $R_{3b}$ and $R_{3c}$ are each independently selected from the group consisting of hydrogen, halo, nitro, cyano, thio, hydroxy, alkoxy, aryloxy, heteroaryloxy, carbonyl, amino, ($C_{1-10}$)alkylamino, sulfonamido, imino, sulfonyl, sulfinyl, ($C_{1-10}$)alkyl, ($C_{3-12}$)cycloalkyl, hetero ($C_{3-12}$)cycloalkyl, ($C_{9-12}$)bicycloalkyl, hetero($C_{3-12}$)bicycloalkyl, aryl($C_{1-10}$)alkyl, heteroaryl($C_{1-5}$)alkyl, perhalo($C_{1-10}$)alkyl, carbonyl($C_{1-3}$)alkyl, thiocarbonyl ($C_{1-3}$)alkyl, sulfonyl($C_{1-3}$)alkyl, sulfinyl($C_{1-3}$)alkyl, amino($C_{1-10}$)alkyl, imino($C_{1-3}$)alkyl, aryl, heteroaryl, ($C_{9-12}$)bicycloaryl, and hetero($C_{4-12}$)bicycloaryl, each substituted or unsubstituted, or any two of $R_{3a}$, $R_{3b}$ and $R_{3c}$ are taken together to form a substituted or unsubstituted ring;

$R_6$ is selected from the group consisting of hydrogen, nitro, thio, hydroxy, alkoxy, aryloxy, heteroaryloxy, carbonyl, amino, sulfonamido, imino, sulfonyl, sulfinyl, ($C_{1-10}$) alkyl, ($C_{3-12}$)cycloalkyl, hetero($C_{3-12}$)cycloalkyl, ($C_{9-12}$)bicycloalkyl, hetero($C_{3-12}$)bicycloalkyl, aryl ($C_{1-10}$)alkyl, heteroaryl($C_{1-5}$)alkyl, ($C_{3-12}$)cycloalkyl ($C_{1-10}$)alkyl, halo($C_{1-10}$)alkyl, carbonyl($C_{1-3}$)alkyl, thiocarbonyl($C_{1-3}$)alkyl, sulfonyl($C_{1-3}$)alkyl, sulfinyl ($C_{1-3}$)alkyl, imino($C_{1-3}$)alkyl, aryl, heteroaryl, ($C_{9-12}$) bicycloaryl, and hetero($C_{4-12}$)bicycloaryl, each substituted or unsubstituted;
$R_9$ is selected from the group consisting of hydrogen, nitro, thio, hydroxy, alkoxy, aryloxy, heteroaryloxy, carbonyl, amino, sulfonamido, imino, sulfonyl, sulfinyl, ($C_{1-10}$) alkyl, ($C_{3-12}$)cycloalkyl, hetero($C_{3-12}$)cycloalkyl, ($C_{9-12}$)bicycloalkyl, hetero($C_{3-12}$)bicycloalkyl, aryl ($C_{1-10}$)alkyl, heteroaryl($C_{1-5}$)alkyl, ($C_{3-12}$)cycloalkyl ($C_{1-10}$)alkyl, halo($C_{1-10}$)alkyl, carbonyl($C_{1-3}$)alkyl, thiocarbonyl($C_{1-3}$)alkyl, sulfonyl($C_{1-3}$)alkyl, sulfinyl ($C_{1-3}$)alkyl, imino($C_{1-3}$)alkyl, aryl, heteroaryl, ($C_{9-12}$) bicycloaryl, and hetero($C_{4-12}$)bicycloaryl, each substituted or unsubstituted;
each $R_{10}$ is independently selected from the group consisting of hydrogen, halo, nitro, cyano, thio, hydroxy, alkoxy, aryloxy, heteroaryloxy, carbonyl, amino, ($C_{1-10}$) alkylamino, sulfonamido, imino, sulfonyl, sulfinyl, ($C_{1-10}$)alkyl, ($C_{3-12}$)cycloalkyl, hetero($C_{3-12}$)cycloalkyl, ($C_{9-12}$)bicycloalkyl, hetero($C_{3-12}$)bicycloalkyl, aryl($C_{1-10}$)alkyl, heteroaryl($C_{1-5}$)alkyl, perhalo($C_{1-10}$)alkyl, carbonyl($C_{1-3}$)alkyl, thiocarbonyl ($C_{1-3}$)alkyl, sulfonyl($C_{1-3}$)alkyl, sulfinyl($C_{1-3}$)alkyl, amino($C_{1-10}$)alkyl, imino($C_{1-3}$)alkyl, aryl, heteroaryl, ($C_{9-12}$)bicycloaryl, and hetero($C_{4-12}$)bicycloaryl, each substituted or unsubstituted, or $R_9$ and $R_{10}$ are taken together to form a ring; and
$R_{21}$ and $R_{22}$ are each independently selected from the group consisting of hydrogen, halo, hydroxy, alkoxy, carbonyl, amino, ($C_{1-5}$)alkylamino, ($C_{1-5}$)alkyl, halo ($C_{1-5}$)alkyl, carbonyl($C_{1-3}$)alkyl and amino($C_{1-5}$)alkyl, each substituted or unsubstituted.

In another embodiment, kinase inhibitors of the present invention comprise the following formula:

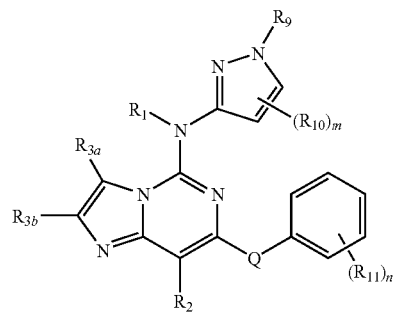

wherein:
l is selected from the group consisting of 1, 2, 3, 4 and 5;
m is selected from the group consisting of 0, 1 and 2;
n is selected from the group consisting of 0, 1, 2, 3, 4, and 5;
Q is selected from the group consisting of S, SO, $SO_2$, O, $NR_6$, $NR_6$—$(CR_{21}R_{22})_l$, $NR_6$—$(CR_{21}R_{22})_l$—O, and a substituted or unsubstituted ($C_{2-5}$)alkylene, or Q is absent;

R₁ is selected from the group consisting of hydrogen, nitro, thio, hydroxy, alkoxy, aryloxy, heteroaryloxy, carbonyl, amino, sulfonamido, imino, sulfonyl, sulfinyl, $(C_{1-10})$alkyl, $(C_{3-12})$cycloalkyl, hetero$(C_{3-12})$cycloalkyl, $(C_{9-12})$bicycloalkyl, hetero$(C_{3-12})$bicycloalkyl, aryl $(C_{1-10})$alkyl, heteroaryl$(C_{1-5})$alkyl, $(C_{3-12})$cycloalkyl $(C_{1-10})$alkyl, halo$(C_{1-10})$alkyl, carbonyl$(C_{1-3})$alkyl, thiocarbonyl$(C_{1-3})$alkyl, sulfonyl$(C_{1-3})$alkyl, sulfinyl $(C_{1-3})$alkyl, imino$(C_{1-3})$alkyl, aryl, heteroaryl, $(C_{9-12})$bicycloaryl, and hetero$(C_{4-12})$bicycloaryl, each substituted or unsubstituted;

R₂ is selected from the group consisting of hydrogen, halo, nitro, cyano, thio, hydroxy, alkoxy, aryloxy, heteroaryloxy, carbonyl, amino, $(C_{1-10})$alkylamino, sulfonamido, imino, sulfonyl, sulfinyl, $(C_{1-10})$alkyl, $(C_{3-12})$cycloalkyl, hetero$(C_{3-12})$cycloalkyl, $(C_{9-12})$bicycloalkyl, hetero$(C_{3-12})$bicycloalkyl, aryl$(C_{1-10})$alkyl, heteroaryl $(C_{1-5})$alkyl, perhalo$(C_{1-10})$alkyl, carbonyl$(C_{1-3})$alkyl, thiocarbonyl$(C_{1-3})$alkyl, sulfonyl$(C_{1-3})$alkyl, sulfinyl $(C_{1-3})$alkyl, amino$(C_{1-10})$alkyl, imino$(C_{1-3})$alkyl, aryl, heteroaryl, $(C_{9-12})$bicycloaryl, and hetero$(C_{4-12})$bicycloaryl, each substituted or unsubstituted;

$R_{3a}$ and $R_{3b}$ are each independently selected from the group consisting of hydrogen, halo, nitro, cyano, thio, hydroxy, alkoxy, aryloxy, heteroaryloxy, carbonyl, amino, $(C_{1-10})$alkylamino, sulfonamido, imino, sulfonyl, sulfinyl, $(C_{1-10})$alkyl, $(C_{3-12})$cycloalkyl, hetero $(C_{3-12})$cycloalkyl, $(C_{9-12})$bicycloalkyl, hetero$(C_{3-12})$bicycloalkyl, aryl$(C_{1-10})$alkyl, heteroaryl$(C_{1-5})$alkyl, perhalo$(C_{1-10})$alkyl, carbonyl$(C_{1-3})$alkyl, thiocarbonyl $(C_{1-3})$alkyl, sulfonyl$(C_{1-3})$alkyl, sulfinyl$(C_{1-3})$alkyl, amino$(C_{1-10})$alkyl, imino$(C_{1-3})$alkyl, aryl, heteroaryl, $(C_{9-12})$bicycloaryl, and hetero$(C_{4-12})$bicycloaryl, each substituted or unsubstituted, or $R_{3a}$ and $R_{3b}$ are taken together to form a substituted or unsubstituted ring;

R₉ is selected from the group consisting of hydrogen, nitro, thio, hydroxy, alkoxy, aryloxy, heteroaryloxy, carbonyl, amino, sulfonamido, imino, sulfonyl, sulfinyl, $(C_{1-10})$alkyl, $(C_{3-12})$cycloalkyl, hetero$(C_{3-12})$cycloalkyl, $(C_{9-12})$bicycloalkyl, hetero$(C_{3-12})$bicycloalkyl, aryl $(C_{1-10})$alkyl, heteroaryl$(C_{1-5})$alkyl, $(C_{3-12})$cycloalkyl $(C_{1-10})$alkyl, halo$(C_{1-10})$alkyl, carbonyl$(C_{1-3})$alkyl, thiocarbonyl$(C_{1-3})$alkyl, sulfonyl$(C_{1-3})$alkyl, sulfinyl $(C_{1-3})$alkyl, imino$(C_{1-3})$alkyl, aryl, heteroaryl, $(C_{9-12})$bicycloaryl, and hetero$(C_{4-12})$bicycloaryl, each substituted or unsubstituted;

R₁₀ is selected from the group consisting of hydrogen, halo, nitro, cyano, thio, hydroxy, alkoxy, aryloxy, heteroaryloxy, carbonyl, amino, $(C_{1-10})$alkylamino, sulfonamido, imino, sulfonyl, sulfinyl, $(C_{1-10})$alkyl, $(C_{3-12})$cycloalkyl, hetero$(C_{3-12})$cycloalkyl, $(C_{9-12})$bicycloalkyl, hetero$(C_{3-12})$bicycloalkyl, aryl$(C_{1-10})$alkyl, heteroaryl$(C_{1-5})$alkyl, perhalo$(C_{1-10})$alkyl, carbonyl$(C_{1-3})$alkyl, thiocarbonyl$(C_{1-3})$alkyl, sulfonyl $(C_{1-3})$alkyl, sulfinyl$(C_{1-3})$alkyl, amino$(C_{1-10})$alkyl, imino$(C_{1-3})$alkyl, aryl, heteroaryl, $(C_{9-12})$bicycloaryl, and hetero$(C_{4-12})$bicycloaryl, each substituted or unsubstituted, or R₉ and R₁₀ are taken together to form a ring;

R₁₁ is selected from the group consisting of hydrogen, halo, nitro, cyano, thio, hydroxy, alkoxy, aryloxy, heteroaryloxy, carbonyl, amino, $(C_{1-10})$alkylamino, sulfonamido, imino, sulfonyl, sulfinyl, $(C_{1-10})$alkyl, $(C_{3-12})$cycloalkyl, hetero$(C_{3-12})$cycloalkyl, $(C_{9-12})$bicycloalkyl, hetero$(C_{3-12})$bicycloalkyl, aryl$(C_{1-10})$alkyl, heteroaryl$(C_{1-5})$alkyl, perhalo$(C_{1-10})$alkyl, carbonyl$(C_{1-3})$alkyl, thiocarbonyl$(C_{1-3})$alkyl, sulfonyl $(C_{1-3})$alkyl, sulfinyl$(C_{1-3})$alkyl, amino$(C_{1-10})$alkyl, imino$(C_{1-3})$alkyl, aryl, heteroaryl, $(C_{9-12})$bicycloaryl, and hetero$(C_{4-12})$bicycloaryl, each substituted or unsubstituted, or two R₁₁ are taken together to form a ring; and $R_{21}$ and $R_{22}$ are each independently selected from the group consisting of hydrogen, halo, hydroxy, alkoxy, carbonyl, amino, $(C_{1-5})$alkylamino, $(C_{1-5})$alkyl, halo $(C_{1-5})$alkyl, carbonyl$(C_{1-3})$alkyl and amino$(C_{1-5})$alkyl, each substituted or unsubstituted.

In yet another embodiment, kinase inhibitors of the present invention comprise the following formula:

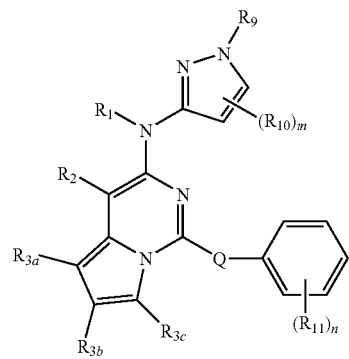

wherein:
l is selected from the group consisting of 1, 2, 3, 4 and 5;
m is selected from the group consisting of 0, 1 and 2;
n is selected from the group consisting of 0, 1, 2, 3, 4, and 5;
Q is selected from the group consisting of S, SO, SO₂, O, NR₆, NR₆—(CR₂₁R₂₂)ₗ, NR₆—(CR₂₁R₂₂)ₗ—O, and a substituted or unsubstituted $(C_{2-5})$alkylene, or Q is absent;

R₁ is selected from the group consisting of hydrogen, nitro, thio, hydroxy, alkoxy, aryloxy, heteroaryloxy, carbonyl, amino, sulfonamido, imino, sulfonyl, sulfinyl, $(C_{1-10})$alkyl, $(C_{3-12})$cycloalkyl, hetero$(C_{3-12})$cycloalkyl, $(C_{9-12})$bicycloalkyl, hetero$(C_{3-12})$bicycloalkyl, aryl $(C_{1-10})$alkyl, heteroaryl$(C_{1-5})$alkyl, $(C_{3-12})$cycloalkyl $(C_{1-10})$alkyl, halo$(C_{1-10})$alkyl, carbonyl$(C_{1-3})$alkyl, thiocarbonyl$(C_{1-3})$alkyl, sulfonyl$(C_{1-3})$alkyl, sulfinyl $(C_{1-3})$alkyl, imino$(C_{1-3})$alkyl, aryl, heteroaryl, $(C_{9-12})$bicycloaryl, and hetero$(C_{4-12})$bicycloaryl, each substituted or unsubstituted;

R₂ is selected from the group consisting of hydrogen, halo, nitro, cyano, thio, hydroxy, alkoxy, aryloxy, heteroaryloxy, carbonyl, amino, $(C_{1-10})$alkylamino, sulfonamido, imino, sulfonyl, sulfinyl, $(C_{1-10})$alkyl, $(C_{3-12})$cycloalkyl, hetero$(C_{3-12})$cycloalkyl, $(C_{9-12})$bicycloalkyl, hetero$(C_{3-12})$bicycloalkyl, aryl$(C_{1-10})$alkyl, heteroaryl $(C_{1-5})$alkyl, perhalo$(C_{1-10})$alkyl, carbonyl$(C_{1-3})$alkyl, thiocarbonyl$(C_{1-3})$alkyl, sulfonyl$(C_{1-3})$alkyl, sulfinyl $(C_{1-3})$alkyl, amino$(C_{1-10})$alkyl, imino$(C_{1-3})$alkyl, aryl, heteroaryl, $(C_{9-12})$bicycloaryl, and hetero$(C_{4-12})$bicycloaryl, each substituted or unsubstituted;

$R_{3a}$, $R_{3b}$ and $R_{3c}$ are each independently selected from the group consisting of hydrogen, halo, nitro, cyano, thio, hydroxy, alkoxy, aryloxy, heteroaryloxy, carbonyl, amino, $(C_{1-10})$alkylamino, sulfonamido, imino, sulfonyl, sulfinyl, $(C_{1-10})$alkyl, $(C_{3-12})$cycloalkyl, hetero $(C_{3-12})$cycloalkyl, $(C_{9-12})$bicycloalkyl, hetero$(C_{3-12})$bicycloalkyl, aryl$(C_{1-10})$alkyl, heteroaryl$(C_{1-5})$alkyl, perhalo$(C_{1-10})$alkyl, carbonyl$(C_{1-3})$alkyl, thiocarbonyl $(C_{1-3})$alkyl, sulfonyl$(C_{1-3})$alkyl, sulfinyl$(C_{1-3})$alkyl, amino($C_{1-10}$)alkyl, imino($C_{1-3}$)alkyl, aryl, heteroaryl, ($C_{9-12}$)bicycloaryl, and hetero($C_{4-12}$)bicycloaryl, each substituted or unsubstituted, or any two of $R_{3a}$, $R_{3b}$ and $R_{3c}$ are taken together to form a substituted or unsubstituted ring;

$R_9$ is selected from the group consisting of hydrogen, nitro, thio, hydroxy, alkoxy, aryloxy, heteroaryloxy, carbonyl, amino, sulfonamido, imino, sulfonyl, sulfinyl, ($C_{1-10}$)alkyl, ($C_{3-12}$)cycloalkyl, hetero($C_{3-12}$)cycloalkyl, ($C_{9-12}$)bicycloalkyl, hetero($C_{3-12}$)bicycloalkyl, aryl($C_{1-10}$)alkyl, heteroaryl($C_{1-5}$)alkyl, ($C_{3-12}$)cycloalkyl($C_{1-10}$)alkyl, halo($C_{1-10}$)alkyl, carbonyl($C_{1-3}$)alkyl, thiocarbonyl($C_{1-3}$)alkyl, sulfonyl($C_{1-3}$)alkyl, sulfinyl($C_{1-3}$)alkyl, imino($C_{1-3}$)alkyl, aryl, heteroaryl, ($C_{9-12}$)bicycloaryl, and hetero($C_{4-12}$)bicycloaryl, each substituted or unsubstituted;

$R_{10}$ is selected from the group consisting of hydrogen, halo, nitro, cyano, thio, hydroxy, alkoxy, aryloxy, heteroaryloxy, carbonyl, amino, ($C_{1-10}$)alkylamino, sulfonamido, imino, sulfonyl, sulfinyl, ($C_{1-10}$)alkyl, ($C_{3-12}$)cycloalkyl, hetero($C_{3-12}$)cycloalkyl, ($C_{9-12}$)bicycloalkyl, hetero($C_{3-12}$)bicycloalkyl, aryl($C_{1-10}$)alkyl, heteroaryl($C_{1-5}$)alkyl, perhalo($C_{1-10}$)alkyl, carbonyl($C_{1-3}$)alkyl, thiocarbonyl($C_{1-3}$)alkyl, sulfonyl($C_{1-3}$)alkyl, sulfinyl($C_{1-3}$)alkyl, amino($C_{1-10}$)alkyl, imino($C_{1-3}$)alkyl, aryl, heteroaryl, ($C_{9-12}$)bicycloaryl, and hetero($C_{4-12}$)bicycloaryl, each substituted or unsubstituted, or $R_9$ and $R_{10}$ are taken together to form a ring;

$R_{11}$ is selected from the group consisting of hydrogen, halo, nitro, cyano, thio, hydroxy, alkoxy, aryloxy, heteroaryloxy, carbonyl, amino, ($C_{1-10}$)alkylamino, sulfonamido, imino, sulfonyl, sulfinyl, ($C_{1-10}$)alkyl, ($C_{3-12}$)cycloalkyl, hetero($C_{3-12}$)cycloalkyl, ($C_{9-12}$)bicycloalkyl, hetero($C_{3-12}$)bicycloalkyl, aryl($C_{1-10}$)alkyl, heteroaryl($C_{1-5}$)alkyl, perhalo($C_{1-10}$)alkyl, carbonyl($C_{1-3}$)alkyl, thiocarbonyl($C_{1-3}$)alkyl, sulfonyl($C_{1-3}$)alkyl, sulfinyl($C_{1-3}$)alkyl, amino($C_{1-10}$)alkyl, imino($C_{1-3}$)alkyl, aryl, heteroaryl, ($C_{9-12}$)bicycloaryl, and hetero($C_{4-12}$)bicycloaryl, each substituted or unsubstituted, or two $R_{11}$ are taken together to form a ring; and $R_{21}$ and $R_{22}$ are each independently selected from the group consisting of hydrogen, halo, hydroxy, alkoxy, carbonyl, amino, ($C_{1-5}$)alkylamino, ($C_{1-5}$)alkyl, halo($C_{1-5}$)alkyl, carbonyl($C_{1-3}$)alkyl and amino($C_{1-5}$)alkyl, each substituted or unsubstituted.

In still another embodiment, kinase inhibitors of the present invention comprise the following formula:

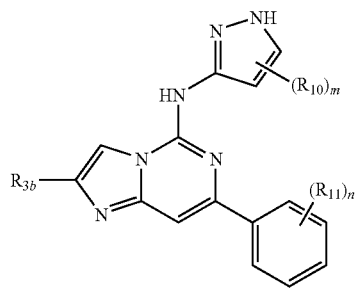

wherein:
m is selected from the group consisting of 0, 1 and 2;
n is selected from the group consisting of 0, 1, 2, 3, 4, and 5;

$R_{3b}$ is selected from the group consisting of hydrogen, halo, nitro, cyano, thio, hydroxy, alkoxy, aryloxy, heteroaryloxy, carbonyl, amino, ($C_{1-10}$)alkylamino, sulfonamido, imino, sulfonyl, sulfinyl, ($C_{1-10}$)alkyl, ($C_{3-12}$)cycloalkyl, hetero($C_{3-12}$)cycloalkyl, ($C_{9-12}$)bicycloalkyl, hetero($C_{3-12}$)bicycloalkyl, aryl($C_{1-10}$)alkyl, heteroaryl($C_{1-5}$)alkyl, perhalo($C_{1-10}$)alkyl, carbonyl($C_{1-3}$)alkyl, thiocarbonyl($C_{1-3}$)alkyl, sulfonyl($C_{1-3}$)alkyl, sulfinyl($C_{1-3}$)alkyl, amino($C_{1-10}$)alkyl, imino($C_{1-3}$)alkyl, aryl, heteroaryl, ($C_{9-12}$)bicycloaryl, and hetero($C_{4-12}$)bicycloaryl, each substituted or unsubstituted;

$R_{10}$ is selected from the group consisting of hydrogen, halo, nitro, cyano, thio, hydroxy, alkoxy, aryloxy, heteroaryloxy, carbonyl, amino, ($C_{1-10}$)alkylamino, sulfonamido, imino, sulfonyl, sulfinyl, ($C_{1-10}$)alkyl, ($C_{3-12}$)cycloalkyl, hetero($C_{3-12}$)cycloalkyl, ($C_{9-12}$)bicycloalkyl, hetero($C_{3-12}$)bicycloalkyl, aryl($C_{1-10}$)alkyl, heteroaryl($C_{1-5}$)alkyl, perhalo($C_{1-10}$)alkyl, carbonyl($C_{1-3}$)alkyl, thiocarbonyl($C_{1-3}$)alkyl, sulfonyl($C_{1-3}$)alkyl, sulfinyl($C_{1-3}$)alkyl, amino($C_{1-10}$)alkyl, imino($C_{1-3}$)alkyl, aryl, heteroaryl, ($C_{9-12}$)bicycloaryl, and hetero($C_{4-12}$)bicycloaryl, each substituted or unsubstituted, or $R_9$ and $R_{10}$ are taken together to form a ring; and $R_{11}$ is selected from the group consisting of hydrogen, halo, nitro, cyano, thio, hydroxy, alkoxy, aryloxy, heteroaryloxy, carbonyl, amino, ($C_{1-10}$)alkylamino, sulfonamido, imino, sulfonyl, sulfinyl, ($C_{1-10}$)alkyl, ($C_{3-12}$)cycloalkyl, hetero($C_{3-12}$)cycloalkyl, ($C_{9-12}$)bicycloalkyl, hetero($C_{3-12}$)bicycloalkyl, aryl($C_{1-10}$)alkyl, heteroaryl($C_{1-5}$)alkyl, perhalo($C_{1-10}$)alkyl, carbonyl($C_{1-3}$)alkyl, thiocarbonyl($C_{1-3}$)alkyl, sulfonyl($C_{1-3}$)alkyl, sulfinyl($C_{1-3}$)alkyl, amino($C_{1-10}$)alkyl, imino($C_{1-3}$)alkyl, aryl, heteroaryl, ($C_{9-12}$)bicycloaryl, and hetero($C_{4-12}$)bicycloaryl, each substituted or unsubstituted, or two $R_{11}$ are taken together to form a ring.

In a further embodiment, kinase inhibitors of the present invention comprise the following formula:

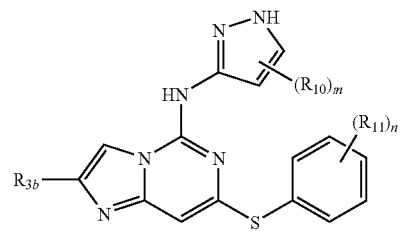

wherein:
m is selected from the group consisting of 0, 1 and 2;
n is selected from the group consisting of 0, 1, 2, 3, 4, and 5;

$R_{3b}$ is selected from the group consisting of hydrogen, halo, nitro, cyano, thio, hydroxy, alkoxy, aryloxy, heteroaryloxy, carbonyl, amino, ($C_{1-10}$)alkylamino, sulfonamido, imino, sulfonyl, sulfinyl, ($C_{1-10}$)alkyl, ($C_{3-12}$)cycloalkyl, hetero($C_{3-12}$)cycloalkyl, ($C_{9-12}$)bicycloalkyl, hetero($C_{3-12}$)bicycloalkyl, aryl($C_{1-10}$)alkyl, heteroaryl($C_{1-5}$)alkyl, perhalo($C_{1-10}$)alkyl, carbonyl($C_{1-3}$)alkyl, thiocarbonyl($C_{1-3}$)alkyl, sulfonyl($C_{1-3}$)alkyl, sulfinyl($C_{1-3}$)alkyl, amino($C_{1-10}$)alkyl, imino($C_{1-3}$)alkyl, aryl, heteroaryl, ($C_{9-12}$)bicycloaryl, and hetero($C_{4-12}$)bicycloaryl, each substituted or unsubstituted;

$R_{10}$ is selected from the group consisting of hydrogen, halo, nitro, cyano, thio, hydroxy, alkoxy, aryloxy, heteroaryloxy, carbonyl, amino, $(C_{1-10})$alkylamino, sulfonamido, imino, sulfonyl, sulfinyl, $(C_{1-10})$alkyl, $(C_{3-12})$cycloalkyl, hetero$(C_{3-12})$cycloalkyl, $(C_{9-12})$bicycloalkyl, hetero$(C_{3-12})$bicycloalkyl, aryl$(C_{1-10})$alkyl, heteroaryl$(C_{1-5})$alkyl, perhalo$(C_{1-10})$alkyl, carbonyl$(C_{1-3})$alkyl, thiocarbonyl$(C_{1-3})$alkyl, sulfonyl$(C_{1-3})$alkyl, sulfinyl$(C_{1-3})$alkyl, amino$(C_{1-10})$alkyl, imino$(C_{1-3})$alkyl, aryl, heteroaryl, $(C_{9-12})$bicycloaryl, and hetero$(C_{4-12})$bicycloaryl, each substituted or unsubstituted, or $R_9$ and $R_{10}$ are taken together to form a ring; and $R_{11}$ is selected from the group consisting of hydrogen, halo, nitro, cyano, thio, hydroxy, alkoxy, aryloxy, heteroaryloxy, carbonyl, amino, $(C_{1-10})$alkylamino, sulfonamido, imino, sulfonyl, sulfinyl, $(C_{1-10})$alkyl, $(C_{3-12})$cycloalkyl, hetero$(C_{3-12})$cycloalkyl, $(C_{9-12})$bicycloalkyl, hetero$(C_{3-12})$bicycloalkyl, aryl$(C_{1-10})$alkyl, heteroaryl$(C_{1-5})$alkyl, perhalo$(C_{1-10})$alkyl, carbonyl$(C_{1-3})$alkyl, thiocarbonyl$(C_{1-3})$alkyl, sulfonyl$(C_{1-3})$alkyl, sulfinyl$(C_{1-3})$alkyl, amino$(C_{1-10})$alkyl, imino$(C_{1-3})$alkyl, aryl, heteroaryl, $(C_{9-12})$bicycloaryl, and hetero$(C_{4-12})$bicycloaryl, each substituted or unsubstituted, or two $R_{11}$ are taken together to form a ring.

In yet another embodiment, kinase inhibitors of the present invention comprise the following formula:

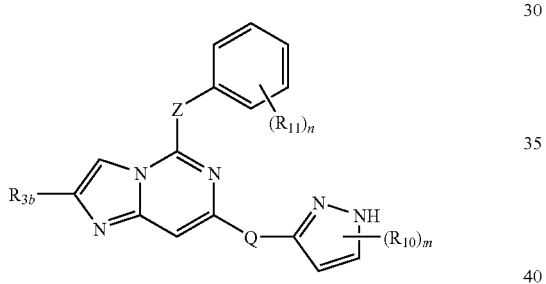

wherein:
l is selected from the group consisting of 1, 2, 3, 4 and 5;
m is selected from the group consisting of 0, 1 and 2;
n is selected from the group consisting of 0, 1, 2, 3, 4 and 5;
Q is selected from the group consisting of S, SO, $SO_2$, O, $NR_6$, $NR_6$—$(CR_{21}R_{22})_l$, $NR_6$—$(CR_{21}R_{22})_l$—O, and a substituted or unsubstituted $(C_{2-5})$alkylene, or Q is absent;
Z is selected from the group consisting of $NR_1$, S, SO, $SO_2$ and O, with the provisos that Z is not NH, NC(O)—$CH_3$ or N—C(O)—O—C$(CH_3)_3$;
$R_1$ is selected from the group consisting of hydrogen, nitro, thio, hydroxy, alkoxy, aryloxy, heteroaryloxy, carbonyl, amino, sulfonamido, imino, sulfonyl, sulfinyl, $(C_{1-10})$alkyl, $(C_{3-12})$cycloalkyl, hetero$(C_{3-12})$cycloalkyl, $(C_{9-12})$bicycloalkyl, hetero$(C_{3-12})$bicycloalkyl, aryl$(C_{1-10})$alkyl, heteroaryl$(C_{1-5})$alkyl, $(C_{3-12})$cycloalkyl$(C_{1-10})$alkyl, halo$(C_{1-10})$alkyl, carbonyl$(C_{1-3})$alkyl, thiocarbonyl$(C_{1-3})$alkyl, sulfonyl$(C_{1-3})$alkyl, sulfinyl$(C_{1-3})$alkyl, imino$(C_{1-3})$alkyl, aryl, heteroaryl, $(C_{9-12})$bicycloaryl, and hetero$(C_{4-12})$bicycloaryl, each substituted or unsubstituted;
$R_{3b}$ is selected from the group consisting of hydrogen, halo, nitro, cyano, thio, hydroxy, alkoxy, aryloxy, heteroaryloxy, carbonyl, amino, $(C_{1-10})$alkylamino, sulfonamido, imino, sulfonyl, sulfinyl, $(C_{1-10})$alkyl, $(C_{3-12})$cycloalkyl, hetero$(C_{3-12})$cycloalkyl, $(C_{9-12})$bicycloalkyl, hetero$(C_{3-12})$bicycloalkyl, aryl$(C_{1-10})$alkyl, heteroaryl$(C_{1-5})$alkyl, perhalo$(C_{1-10})$alkyl, carbonyl$(C_{1-3})$alkyl, thiocarbonyl$(C_{1-3})$alkyl, sulfonyl$(C_{1-3})$alkyl, sulfinyl$(C_{1-3})$alkyl, amino$(C_{1-10})$alkyl, imino$(C_{1-3})$alkyl, aryl, heteroaryl, $(C_{9-12})$bicycloaryl, and hetero$(C_{4-12})$bicycloaryl, each substituted or unsubstituted;

$R_6$ is selected from the group consisting of hydrogen, nitro, thio, hydroxy, alkoxy, aryloxy, heteroaryloxy, carbonyl, amino, sulfonamido, imino, sulfonyl, sulfinyl, $(C_{1-10})$alkyl, $(C_{3-12})$cycloalkyl, hetero$(C_{3-12})$cycloalkyl, $(C_{9-12})$bicycloalkyl, hetero$(C_{3-12})$bicycloalkyl, aryl$(C_{1-10})$alkyl, heteroaryl$(C_{1-5})$alkyl, $(C_{3-12})$cycloalkyl$(C_{1-10})$alkyl, halo$(C_{1-10})$alkyl, carbonyl$(C_{1-3})$alkyl, thiocarbonyl$(C_{1-3})$alkyl, sulfonyl$(C_{1-3})$alkyl, sulfinyl$(C_{1-3})$alkyl, imino$(C_{1-3})$alkyl, aryl, heteroaryl, $(C_{9-12})$bicycloaryl, and hetero$(C_{4-12})$bicycloaryl, each substituted or unsubstituted;

$R_{10}$ is selected from the group consisting of hydrogen, halo, nitro, cyano, thio, hydroxy, alkoxy, aryloxy, heteroaryloxy, carbonyl, amino, $(C_{1-10})$alkylamino, sulfonamido, imino, sulfonyl, sulfinyl, $(C_{1-10})$alkyl, $(C_{3-12})$cycloalkyl, hetero$(C_{3-12})$cycloalkyl, $(C_{9-12})$bicycloalkyl, hetero$(C_{3-12})$bicycloalkyl, aryl$(C_{1-10})$alkyl, heteroaryl$(C_{1-5})$alkyl, perhalo$(C_{1-10})$alkyl, carbonyl$(C_{1-3})$alkyl, thiocarbonyl$(C_{1-3})$alkyl, sulfonyl$(C_{1-3})$alkyl, sulfinyl$(C_{1-3})$alkyl, amino$(C_{1-10})$alkyl, imino$(C_{1-3})$alkyl, aryl, heteroaryl, $(C_{9-12})$bicycloaryl, and hetero$(C_{4-12})$bicycloaryl, each substituted or unsubstituted, or $R_9$ and $R_{10}$ are taken together to form a ring;

$R_{11}$ is selected from the group consisting of hydrogen, halo, nitro, cyano, thio, hydroxy, alkoxy, aryloxy, heteroaryloxy, carbonyl, amino, $(C_{1-10})$alkylamino, sulfonamido, imino, sulfonyl, sulfinyl, $(C_{1-10})$alkyl, $(C_{3-12})$cycloalkyl, hetero$(C_{3-12})$cycloalkyl, $(C_{9-12})$bicycloalkyl, hetero$(C_{3-12})$bicycloalkyl, aryl$(C_{1-10})$alkyl, heteroaryl$(C_{1-5})$alkyl, perhalo$(C_{1-10})$alkyl, carbonyl$(C_{1-3})$alkyl, thiocarbonyl$(C_{1-3})$alkyl, sulfonyl$(C_{1-3})$alkyl, sulfinyl$(C_{1-3})$alkyl, amino$(C_{1-10})$alkyl, imino$(C_{1-3})$alkyl, aryl, heteroaryl, $(C_{9-12})$bicycloaryl, and hetero$(C_{4-12})$bicycloaryl, each substituted or unsubstituted, or two $R_{11}$ are taken together to form a ring; and $R_{21}$ and $R_{22}$ are each independently selected from the group consisting of hydrogen, halo, hydroxy, alkoxy, carbonyl, amino, $(C_{1-5})$alkylamino, $(C_{1-5})$alkyl, halo$(C_{1-5})$alkyl, carbonyl$(C_{1-3})$alkyl and amino$(C_{1-5})$alkyl, each substituted or unsubstituted.

In a further embodiment, kinase inhibitors of the present invention comprise the following formula:

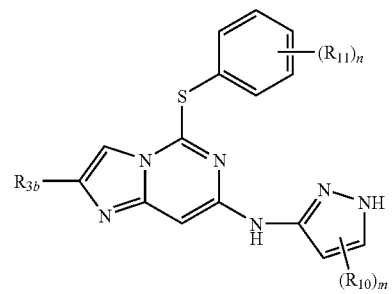

wherein:
    m is selected from the group consisting of 0, 1 and 2;
    n is selected from the group consisting of 0, 1, 2, 3, 4 and 5;
    $R_{3b}$ is selected from the group consisting of hydrogen, halo, nitro, cyano, thio, hydroxy, alkoxy, aryloxy, heteroaryloxy, carbonyl, amino, $(C_{1-10})$alkylamino, sulfonamido, imino, sulfonyl, sulfinyl, $(C_{1-10})$alkyl, $(C_{3-12})$cycloalkyl, hetero$(C_{3-12})$cycloalkyl, $(C_{9-12})$bicycloalkyl, hetero$(C_{3-12})$bicycloalkyl, aryl$(C_{1-10})$alkyl, heteroaryl$(C_{1-5})$alkyl, perhalo$(C_{1-10})$alkyl, carbonyl$(C_{1-3})$alkyl, thiocarbonyl$(C_{1-3})$alkyl, sulfonyl$(C_{1-3})$alkyl, sulfinyl$(C_{1-3})$alkyl, amino$(C_{1-10})$alkyl, imino$(C_{1-3})$alkyl, aryl, heteroaryl, $(C_{9-12})$bicycloaryl, and hetero$(C_{4-12})$bicycloaryl, each substituted or unsubstituted;
    $R_{10}$ is selected from the group consisting of hydrogen, halo, nitro, cyano, thio, hydroxy, alkoxy, aryloxy, heteroaryloxy, carbonyl, amino, $(C_{1-10})$alkylamino, sulfonamido, imino, sulfonyl, sulfinyl, $(C_{1-10})$alkyl, $(C_{3-12})$cycloalkyl, hetero$(C_{3-12})$cycloalkyl, $(C_{9-12})$bicycloalkyl, hetero$(C_{3-12})$bicycloalkyl, aryl$(C_{1-10})$alkyl, heteroaryl$(C_{1-5})$alkyl, perhalo$(C_{1-10})$alkyl, carbonyl$(C_{1-3})$alkyl, thiocarbonyl$(C_{1-3})$alkyl, sulfonyl$(C_{1-3})$alkyl, sulfinyl$(C_{1-3})$alkyl, amino$(C_{1-10})$alkyl, imino$(C_{1-3})$alkyl, aryl, heteroaryl, $(C_{9-12})$bicycloaryl, and hetero$(C_{4-12})$bicycloaryl, each substituted or unsubstituted, or $R_9$ and $R_{10}$ are taken together to form a ring; and
    $R_{11}$ is selected from the group consisting of hydrogen, halo, nitro, cyano, thio, hydroxy, alkoxy, aryloxy, heteroaryloxy, carbonyl, amino, $(C_{1-10})$alkylamino, sulfonamido, imino, sulfonyl, sulfinyl, $(C_{1-10})$alkyl, $(C_{3-12})$cycloalkyl, hetero$(C_{3-12})$cycloalkyl, $(C_{9-12})$bicycloalkyl, hetero$(C_{3-12})$bicycloalkyl, aryl$(C_{1-10})$alkyl, heteroaryl$(C_{1-5})$alkyl, perhalo$(C_{1-10})$alkyl, carbonyl$(C_{1-3})$alkyl, thiocarbonyl$(C_{1-3})$alkyl, sulfonyl$(C_{1-3})$alkyl, sulfinyl$(C_{1-3})$alkyl, amino$(C_{1-10})$alkyl, imino$(C_{1-3})$alkyl, aryl, heteroaryl, $(C_{9-12})$bicycloaryl, and hetero$(C_{4-12})$bicycloaryl, each substituted or unsubstituted, or two $R_{11}$ are taken together to form a ring.

In another embodiment, kinase inhibitors of the present invention comprise the following formula:

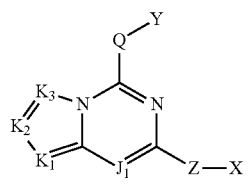

Ia

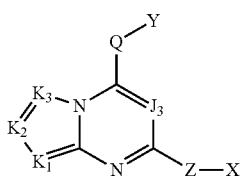

IIa

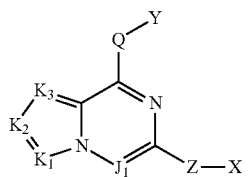

IIIa

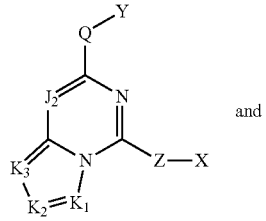

IVa and

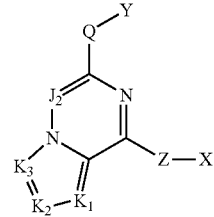

Va wherein:
    l is selected from the group consisting of 1, 2, 3, 4 and 5;
    $J_1$, $J_2$, and $J_3$ are selected from the group consisting of $CR_2$ and N;
    $K_1$, $K_2$, and $K_3$ are each independently selected from the group consisting of $CR_3$ and N, with the proviso that $K_3$ is not N in Formula IIa when $K_1$ is $CR_2$, and $K_2$ and $J_3$ are each CH;
    Q is selected from the group consisting of S, SO, $SO_2$, O, $NR_6$, $NR_6$—$(CR_{21}R_{22})_l$, $NR_6$—$(CR_{21}R_{22})_l$—O, and a substituted or unsubstituted $(C_{2-5})$alkylene, or Q is absent, with the proviso that Q is not absent in Formula Ia when $J_1$ is CH, $K_1$ is N, $K_2$ is $CR_3$, and $K_3$ is CH or N;
    X is selected from the group consisting of $(C_{3-12})$cycloalkyl, hetero$(C_{3-12})$cycloalkyl, $(C_{9-12})$bicycloalkyl, hetero$(C_{3-12})$bicycloalkyl, aryl, heteroaryl, $(C_{9-12})$bicycloaryl and hetero$(C_{4-12})$bicycloaryl, each substituted or unsubstituted;
    Y is selected from the group consisting of $(C_{3-12})$cycloalkyl, hetero$(C_{3-12})$cycloalkyl, $(C_{9-12})$bicycloalkyl, hetero$(C_{3-12})$bicycloalkyl, aryl, heteroaryl, $(C_{9-12})$bicycloaryl, and hetero$(C_{4-12})$bicycloaryl, each substituted or unsubstituted;
    Z is selected from the group consisting of $NR_1$, S, SO, $SO_2$ and O, with the provisos that Z is not NH or NC(O)—$CH_3$ in Formula Ma when $K_3$ is N and $J_1$, $K_1$ and $K_2$ are all C; and Z is not NH or N—C(O)—O—C(CH$_3$)$_3$ when $K_3$ is N and $J_1$, $K_1$ and $K_2$ are all C;
    $R_1$ is selected from the group consisting of hydrogen, nitro, thio, hydroxy, alkoxy, aryloxy, heteroaryloxy, carbonyl, amino, sulfonamido, imino, sulfonyl, sulfinyl, $(C_{1-10})$alkyl, $(C_{3-12})$cycloalkyl, hetero$(C_{3-12})$cycloalkyl, $(C_{9-12})$bicycloalkyl, hetero$(C_{3-12})$bicycloalkyl, aryl$(C_{1-10})$alkyl, heteroaryl$(C_{1-5})$alkyl, $(C_{3-12})$cycloalkyl$(C_{1-10})$alkyl, halo$(C_{1-10})$alkyl, carbonyl$(C_{1-3})$alkyl, thiocarbonyl$(C_{1-3})$alkyl, sulfonyl$(C_{1-3})$alkyl, sulfinyl$(C_{1-3})$alkyl, imino$(C_{1-3})$alkyl, aryl, heteroaryl, $(C_{9-12})$bicycloaryl, and hetero$(C_{4-12})$bicycloaryl, each substituted or unsubstituted;
    $R_2$ is selected from the group consisting of hydrogen, halo, nitro, cyano, thio, hydroxy, alkoxy, aryloxy, heteroaryloxy, carbonyl, amino, $(C_{1-10})$alkylamino, sulfonamido, imino, sulfonyl, sulfinyl, $(C_{1-10})$alkyl, $(C_{3-12})$cycloalkyl, hetero$(C_{3-12})$cycloalkyl, $(C_{9-12})$bicycloalkyl, hetero$(C_{3-12})$bicycloalkyl, aryl$(C_{1-10})$alkyl, heteroaryl$(C_{1-5})$alkyl, perhalo$(C_{1-10})$alkyl, carbonyl$(C_{1-3})$alkyl, thiocarbonyl(C$_{1-3}$)alkyl, sulfonyl(C$_{1-3}$)alkyl, sulfinyl (C$_{1-3}$)alkyl, amino(C$_{1-10}$)alkyl, imino(C$_{1-3}$)alkyl, aryl, heteroaryl, (C$_{9-12}$)bicycloaryl, and hetero(C$_{4-12}$)bicycloaryl, each substituted or unsubstituted;

each R$_3$ is independently selected from the group consisting of hydrogen, halo, nitro, cyano, thio, hydroxy, alkoxy, aryloxy, heteroaryloxy, carbonyl, amino, (C$_{1-10}$) alkylamino, sulfonamido, imino, sulfonyl, sulfinyl, (C$_{1-10}$)alkyl, (C$_{3-12}$)cycloalkyl, hetero(C$_{3-12}$)cycloalkyl, (C$_{9-12}$)bicycloalkyl, hetero(C$_{3-12}$)bicycloalkyl, aryl(C$_{1-10}$)alkyl, heteroaryl(C$_{1-5}$)alkyl, perhalo(C$_{1-10}$)alkyl, carbonyl(C$_{1-3}$)alkyl, thiocarbonyl(C$_{1-3}$)alkyl, sulfonyl(C$_{1-3}$)alkyl, sulfinyl(C$_{1-3}$)alkyl, amino(C$_{1-10}$)alkyl, imino(C$_{1-3}$)alkyl, aryl, heteroaryl, (C$_{9-12}$)bicycloaryl, and hetero(C$_{4-12}$)bicycloaryl, each substituted or unsubstituted, or R$_2$ and one R$_3$, or two R$_3$ are taken together to form a substituted or unsubstituted ring;

R$_6$ is selected from the group consisting of hydrogen, nitro, thio, hydroxy, alkoxy, aryloxy, heteroaryloxy, carbonyl, amino, sulfonamido, imino, sulfonyl, sulfinyl, (C$_{1-10}$) alkyl, (C$_{3-12}$)cycloalkyl, hetero(C$_{3-12}$)cycloalkyl, (C$_{9-12}$)bicycloalkyl, hetero(C$_{3-12}$)bicycloalkyl, aryl (C$_{1-10}$)alkyl, heteroaryl(C$_{1-5}$)alkyl, (C$_{3-12}$)cycloalkyl (C$_{1-10}$)alkyl, halo(C$_{1-10}$)alkyl, carbonyl(C$_{1-3}$)alkyl, thiocarbonyl(C$_{1-3}$)alkyl, sulfonyl(C$_{1-3}$)alkyl, sulfinyl (C$_{1-3}$)alkyl, imino(C$_{1-3}$)alkyl, aryl, heteroaryl, (C$_{9-12}$) bicycloaryl, and hetero(C$_{4-12}$)bicycloaryl, each substituted or unsubstituted; and R$_{21}$ and R$_{22}$ are each independently selected from the group consisting of hydrogen, halo, hydroxy, alkoxy, carbonyl, amino, (C$_{1-5}$)alkylamino, (C$_{1-5}$)alkyl, halo (C$_{1-5}$)alkyl, carbonyl(C$_{1-3}$)alkyl and amino(C$_{1-5}$)alkyl, each substituted or unsubstituted.

In one variation of each of the above embodiments, m is selected from the group consisting of 1 and 2.

In another variation of each of the above embodiments and variations, one R$_{10}$ is bound at the 5-position of the pyrazole ring to which it is attached to form:

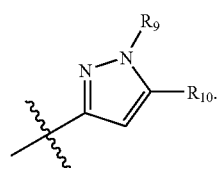

In one variation of each of the above embodiments and variations, X is selected from the group consisting of:

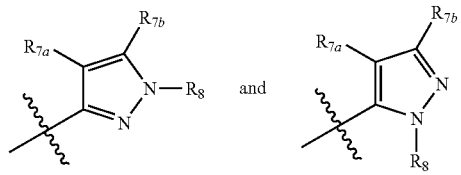

wherein
R$_{7a}$ and R$_{7b}$ are each independently selected from the group consisting of hydrogen, cyano, alkyl, hydroxyalkyl, alkoxyalkyl, aminoalkyl, cycloalkyl, and aryl, each unsubstituted or substituted, or R$_{7a}$ and R$_{7b}$ are taken together to form part of an unsubstituted or substituted ring; and R$_8$ is selected from the group consisting of hydrogen, nitro, cyano, thio, hydroxy, alkoxy, aryloxy, heteroaryloxy, carbonyl, amino, (C$_{1-10}$)alkylamino, sulfonamido, imino, sulfonyl, sulfinyl, (C$_{1-10}$)alkyl, (C$_{3-12}$)cycloalkyl, hetero(C$_{3-12}$)cycloalkyl, (C$_{9-12}$)bicycloalkyl, hetero(C$_{3-12}$)bicycloalkyl, aryl(C$_{1-10}$)alkyl, heteroaryl (C$_{1-5}$)alkyl, perhalo(C$_{1-10}$)alkyl, (C$_{3-12}$)cycloalkyl (C$_{1-10}$)alkyl, halo(C$_{1-10}$)alkyl, carbonyl(C$_{1-3}$)alkyl, thiocarbonyl(C$_{1-3}$)alkyl, sulfonyl(C$_{1-3}$)alkyl, sulfinyl (C$_{1-3}$)alkyl, amino(C$_{1-10}$)alkyl, imino(C$_{1-3}$)alkyl, aryl, heteroaryl, (C$_{9-12}$)bicycloaryl, and hetero(C$_{4-12}$)bicycloaryl, each substituted or unsubstituted.

In a particular variation of the above embodiments and variations, R$_{7a}$ and R$_{7b}$ are each independently selected from the group consisting of —H, —CN, —CH$_3$, —CH$_2$CH$_3$, —CH$_2$CH$_2$CH$_3$, —CH(CH$_3$)$_2$, —CH$_2$CH$_2$OH, —CH$_2$CH$_2$OCH$_3$, —CH$_2$CH$_2$CH$_2$OCH$_2$Ph, —CH$_2$CH$_2$CH$_2$NHBoc, cyclopropyl, cyclobutyl, cyclopentyl, and phenyl, each substituted or unsubstituted.

In another variation of each of the above embodiments and variations, X is selected from the group consisting of pyrazolyl and indazolyl, each substituted or unsubstituted.

In a further variation of each of the above embodiments and variations, Y is selected from the group consisting of phenyl, cyclohexyl, pyridinyl, piperidinyl, hexahydroazepinyl, indolinyl, isoindolinyl, tetrahydroquinolinyl, and tetrahydroisoquinolinyl, each unsubstituted or substituted.

In still a further variation of each of the above embodiments and variations, Y is phenyl, unsubstituted or substituted with one or more substituents selected from the group consisting of halo, cyano, amino, alkyl, haloalkyl, alkoxy, alkylcarboxy, alkylsulfinyl, aryl, and aryloxy, each unsubstituted or substituted.

In yet a further variation of each of the above embodiments and variations, Y is selected from the group consisting of:

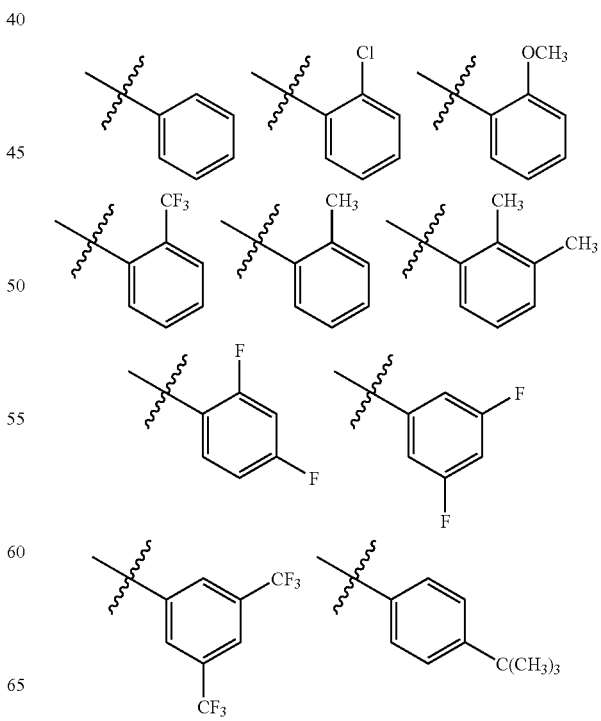

In another variation of each of the above embodiments and variations, Y is selected from the group consisting of:

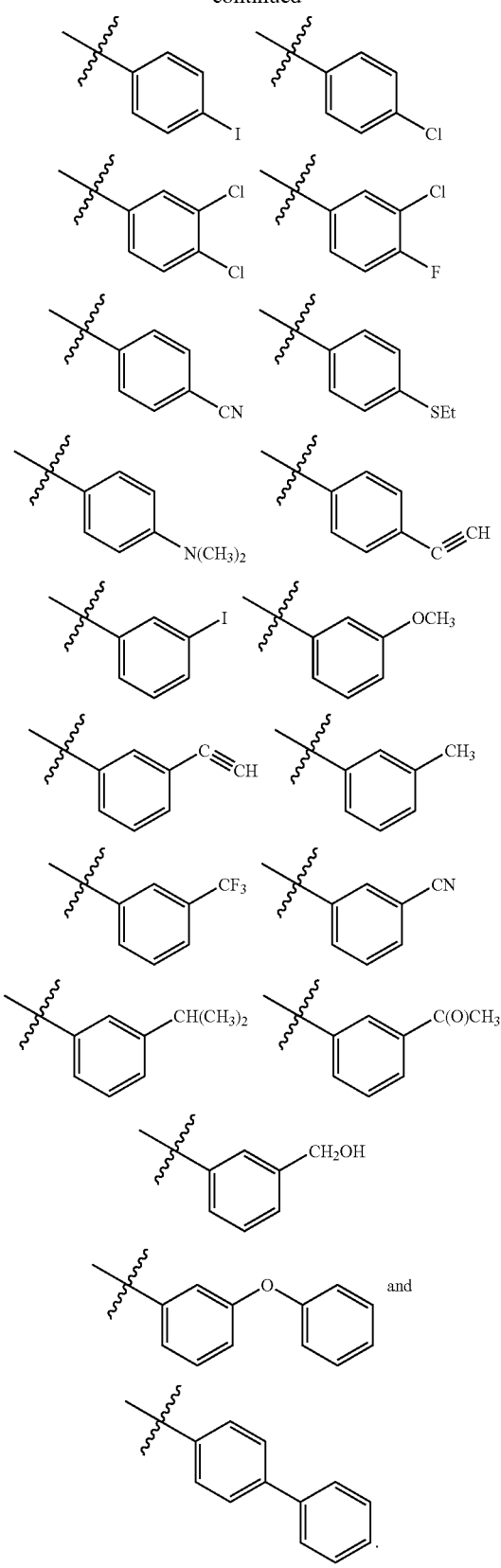

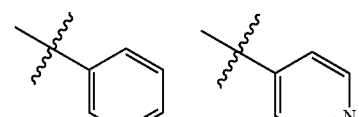
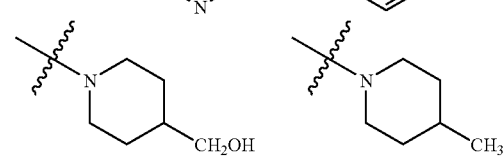
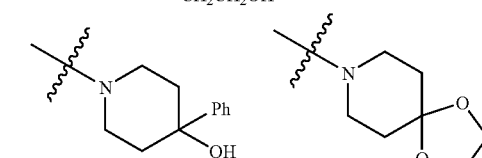
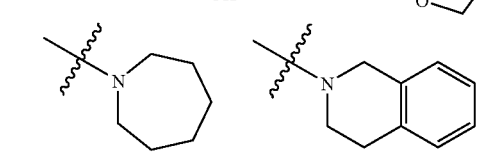
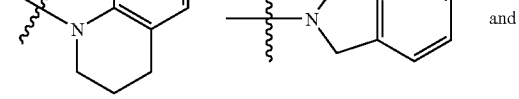
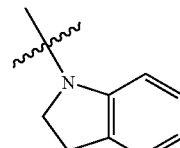
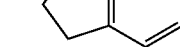

In still another variation of each of the above embodiments and variations, Y is selected from the group consisting of carboxyaminoaryl, carboxyaminoheteroaryl, aminocarboxyaryl, aminocarboxyheteroaryl, sulfinylaminoary, sulfinylaminoheteroaryl, aminosulfinylaryl and aminosulfinylheteroaryl, each unsubstituted or substituted.

In a further variation of each of the above embodiments and variations, Y is selected from the group consisting of acetamidophenyl and cyclopropylcarboxyaminophenyl, each substituted or unsubstituted.

In yet another variation of each of the above embodiments and variations, Y is substituted with a substituent selected from the group consisting of amino, alkylamino, alkyl, aminoalkyl, cycloalkyl, heterocycloalkyl, aryl, heteroaryl, alkoxy, cycloalkyloxy and heterocycloalkyloxy, each unsubstituted or substituted.

In still a further variation of each of the above embodiments and variations, Q is selected from the group consisting of S, SO, SO$_2$, O and NR$_6$, or Q is absent. In another variation, Q is S. In yet another variation of each of the above embodiments and variations, Q is N. In a further variation of each of the above embodiments and variations, Q is absent.

In yet a further variation of each of the above embodiments and variations, R$_1$ is selected from the group consisting of H and a substituted or unsubstituted C$_{1-4}$ alkyl.

In another variation of each of the above embodiments and variations, at least one of $L_1$, $L_2$, $L_3$, $L_4$, and $L_5$ is $NR_6$. In still another variation of each of the above embodiments and variations, at least two of $L_1$, $L_2$, $L_3$, $L_4$, and $L_5$ are $NR_6$. In yet another variation of each of the above embodiments and variations, $L_3$ and $L_4$ are $NR_6$.

In a further variation of each of the above embodiments and variations, each $R_3$ is independently selected from the group consisting of hydrogen, halo, amino, aminocarboxy, alkyl, hydroxyalkyl, aminoalkyl, cycloalkylalkyl, and heterocycloalkylalkyl, each unsubstituted or substituted. Similarly, in a further variation of each of the above embodiments and variations, each $R_{3a}$, $R_{3b}$ and $R_{3c}$ is independently selected from the group consisting of hydrogen, halo, amino, aminocarboxy, alkyl, hydroxyalkyl, aminoalkyl, cycloalkylalkyl, and heterocycloalkylalkyl, each unsubstituted or substituted.

In another variation of each of the above embodiments and variations, $R_{3b}$ is selected from the group consisting of hydrogen, halo, amino, $(C_{1-6})$alkyl, hydroxy$(C_{1-6})$alkyl, alkoxy $(C_{1-6})$alkyl, hetero$(C_{3-12})$cycloalkyl$(C_{1-6})$alkyl and aryl, each substituted or unsubstituted. In yet another variation of each of the above embodiments and variations, $R_{3b}$ is selected from the group consisting of methyl, ethyl, isopropyl, cyclopropyl, fluoromethyl, difluoromethyl, methylamino and dimethylamino In still a further variation of each of the above embodiments and variations, two $R_5$ are taken together to from part of a substituted or unsubstituted ring.

In another variation of each of the above embodiments and variations, $R_{10}$ is selected from the group consisting of hydrogen, $(C_{1-6})$alkyl, $(C_{3-12})$cycloalkyl and heteroaryl, each substituted or unsubstituted. In yet another variation of each of the above embodiments and variations, $R_{10}$ is selected from the group consisting of $(C_{1-4})$alkyl and $(C_{3-10})$cycloalkyl, each substituted or unsubstituted. In yet another variation of each of the above embodiments and variations, $R_{10}$ is selected from the group consisting of methyl, ethyl, isopropyl and cyclopropyl, each substituted or unsubstituted. In a further variation of each of the above embodiments and variations, $R_{10}$ is a substituted or unsubstituted cyclopropyl. In another variation of each of the above embodiments and variations, $R_{10}$ is selected from the group consisting of —$CH_2$—$NHR_{17}$ and —$CO_2$—$NHR_{17}$, wherein $R_{17}$ is selected from the group consisting of hydrogen, nitro, thio, hydroxy, alkoxy, aryloxy, heteroaryloxy, amino, $(C_{1-10})$alkylamino, sulfonamido, imino, sulfonyl, sulfinyl, $(C_{1-10})$alkyl, halo$(C_{1-10})$alkyl, carbonyl$(C_{1-3})$alkyl, thiocarbonyl$(C_{1-3})$alkyl, sulfonyl$(C_{1-3})$alkyl, sulfinyl$(C_{1-3})$alkyl, amino $(C_{1-10})$alkyl, imino $(C_{1-3})$alkyl, $(C_{3-12})$cycloalkyl$(C_{1-5})$alkyl, hetero$(C_{3-12})$cycloalkyl$(C_{1-5})$alkyl, aryl$(C_{1-10})$alkyl, heteroaryl$(C_{1-5})$alkyl, $(C_{9-12})$bicycloaryl$(C_{1-5})$alkyl, hetero$(C_{8-12})$bicycloaryl$(C_{1-5})$alkyl, $(C_{3-12})$cycloalkyl, hetero$(C_{3-12})$cycloalkyl, $(C_{9-12})$bicycloalkyl, hetero$(C_{3-12})$bicycloalkyl, aryl, heteroaryl, $(C_{9-12})$bicycloaryl and hetero$(C_{4-12})$bicycloaryl, each substituted or unsubstituted.

In another variation of each of the above embodiments and variations, $R_{11}$ is selected from the group consisting of hydrogen, halo, cyano, alkoxy, amino, imino, sulfonyl, carbonyl, $(C_{1-6})$alkyl, hetero$(C_{3-12})$cycloalkyl and heteroaryl, each substituted or unsubstituted. In a further variation of each of the above embodiments and variations, $R_{11}$ is —CO—$NR_{12}R_{13}$, wherein $R_{12}$ and $R_{13}$ are each independently selected from the group consisting of hydrogen, nitro, thio, hydroxy, alkoxy, aryloxy, heteroaryloxy, carbonyl, amino, $(C_{1-10})$alkylamino, sulfonamido, imino, sulfonyl, sulfinyl, $(C_{1-10})$alkyl, halo$(C_{1-10})$alkyl, carbonyl$(C_{1-3})$alkyl, thiocarbonyl$(C_{1-3})$alkyl, sulfonyl$(C_{1-3})$alkyl, sulfinyl$(C_{1-3})$alkyl, amino$(C_{1-10})$alkyl, imino$(C_{1-3})$alkyl, $(C_{3-12})$cycloalkyl$(C_{1-5})$alkyl, hetero$(C_{3-12})$cycloalkyl$(C_{1-5})$alkyl, aryl$(C_{1-10})$alkyl, heteroaryl$(C_{1-5})$alkyl, $(C_{9-12})$bicycloaryl$(C_{1-5})$alkyl, hetero$(C_{8-12})$bicycloaryl$(C_{1-5})$alkyl, $(C_{3-12})$cycloalkyl, hetero$(C_{3-12})$cycloalkyl, $(C_{9-12})$bicycloalkyl, hetero$(C_{3-12})$bicycloalkyl, aryl, heteroaryl, $(C_{9-12})$bicycloaryl and hetero$(C_{4-12})$bicycloaryl, each substituted or unsubstituted.

In yet another variation of each of the above embodiments and variations, $R_{11}$ is —NH—CO—$R_{14}$, wherein $R_{14}$ is selected from the group consisting of hydrogen, halo, nitro, cyano, thio, hydroxy, alkoxy, aryloxy, heteroaryloxy, carbonyl, amino, $(C_{1-10})$alkylamino, sulfonamido, imino, sulfonyl, sulfinyl, $(C_{1-10})$alkyl, halo$(C_{1-10})$alkyl, carbonyl$(C_{1-3})$alkyl, thiocarbonyl$(C_{1-3})$alkyl, sulfonyl$(C_{1-3})$alkyl, sulfinyl$(C_{1-3})$alkyl, amino$(C_{1-10})$alkyl, imino$(C_{1-3})$alkyl, $(C_{3-12})$cycloalkyl$(C_{1-5})$alkyl, hetero$(C_{3-12})$cycloalkyl$(C_{1-5})$alkyl, aryl$(C_{1-10})$alkyl, heteroaryl$(C_{1-5})$alkyl, $(C_{9-12})$bicycloaryl$(C_{1-5})$alkyl, hetero$(C_{8-12})$bicycloaryl$(C_{1-5})$alkyl, $(C_{3-12})$cycloalkyl, hetero$(C_{3-12})$cycloalkyl, $(C_{9-12})$bicycloalkyl, hetero$(C_{3-12})$bicycloalkyl, aryl, heteroaryl, $(C_{9-12})$bicycloaryl and hetero$(C_{4-12})$bicycloaryl, each substituted or unsubstituted.

In a further variation of each of the above embodiments and variations, $R_{11}$ is —NH—$SO_2$—$R_{20}$, wherein $R_{20}$ is selected from the group consisting of hydrogen, halo, nitro, cyano, thio, hydroxy, alkoxy, aryloxy, heteroaryloxy, carbonyl, amino, $(C_{1-10})$alkylamino, sulfonamido, imino, sulfonyl, sulfinyl, $(C_{1-10})$alkyl, halo$(C_{1-10})$alkyl, carbonyl$(C_{1-3})$alkyl, thiocarbonyl$(C_{1-3})$alkyl, sulfonyl$(C_{1-3})$alkyl, sulfinyl$(C_{1-3})$alkyl, amino$(C_{1-10})$alkyl, imino$(C_{1-3})$alkyl, $(C_{3-12})$cycloalkyl$(C_{1-5})$alkyl, hetero$(C_{3-12})$cycloalkyl$(C_{1-5})$alkyl, aryl$(C_{1-10})$alkyl, heteroaryl$(C_{1-5})$alkyl, $(C_{9-12})$bicycloaryl$(C_{1-5})$alkyl, hetero$(C_{8-12})$bicycloaryl$(C_{1-5})$alkyl, $(C_{3-12})$cycloalkyl, hetero$(C_{3-12})$cycloalkyl, $(C_{9-12})$bicycloalkyl, hetero$(C_{3-12})$bicycloalkyl, aryl, heteroaryl, $(C_{9-12})$bicycloaryl and hetero$(C_{4-12})$bicycloaryl, each substituted or unsubstituted.

In still another variation of each of the above embodiments and variations, $R_{11}$ is —SO—$R_{15}$, wherein $R_{15}$ is selected from the group consisting of hydrogen, halo, nitro, cyano, thio, hydroxy, alkoxy, aryloxy, heteroaryloxy, carbonyl, amino, $(C_{1-10})$alkylamino, sulfonamido, imino, sulfonyl, sulfinyl, $(C_{1-10})$alkyl, halo$(C_{1-10})$alkyl, carbonyl$(C_{1-3})$alkyl, thiocarbonyl$(C_{1-3})$alkyl, sulfonyl$(C_{1-3})$alkyl, sulfinyl$(C_{1-3})$alkyl, amino$(C_{1-10})$alkyl, imino$(C_{1-3})$alkyl, $(C_{3-12})$cycloalkyl$(C_{1-5})$alkyl, hetero$(C_{3-12})$cycloalkyl$(C_{1-5})$alkyl, aryl$(C_{1-10})$alkyl, heteroaryl$(C_{1-5})$alkyl, $(C_{9-12})$bicycloaryl$(C_{1-5})$alkyl, hetero$(C_{8-12})$bicycloaryl$(C_{1-5})$alkyl, $(C_{3-12})$cycloalkyl, hetero$(C_{3-12})$cycloalkyl, $(C_{9-12})$bicycloalkyl, hetero$(C_{3-12})$bicycloalkyl, aryl, heteroaryl, $(C_{9-12})$bicycloaryl and hetero$(C_{4-12})$bicycloaryl, each substituted or unsubstituted.

In yet another variation of each of the above embodiments and variations, $R_{11}$ is —$SO_2$—$R_{16}$, wherein $R_{16}$ is selected from the group consisting of hydrogen, halo, nitro, cyano, thio, hydroxy, alkoxy, aryloxy, heteroaryloxy, carbonyl, amino, $(C_{1-10})$alkylamino, sulfonamido, imino, sulfonyl, sulfinyl, $(C_{1-10})$alkyl, halo$(C_{1-10})$alkyl, carbonyl$(C_{1-3})$alkyl, thiocarbonyl$(C_{1-3})$alkyl, sulfonyl$(C_{1-3})$alkyl, sulfinyl$(C_{1-3})$alkyl, amino$(C_{1-10})$alkyl, imino$(C_{1-3})$alkyl, $(C_{3-12})$cycloalkyl$(C_{1-5})$alkyl, hetero$(C_{3-12})$cycloalkyl$(C_{1-5})$alkyl, aryl$(C_{1-10})$alkyl, heteroaryl$(C_{1-5})$alkyl, $(C_{9-12})$bicycloaryl$(C_{1-5})$alkyl, hetero$(C_{8-12})$bicycloaryl$(C_{1-5})$alkyl, $(C_{3-12})$cycloalkyl, hetero$(C_{3-12})$cycloalkyl, $(C_{9-12})$bicycloalkyl, hetero$(C_{3-12})$bicycloalkyl, aryl, heteroaryl, $(C_{9-12})$bicycloaryl and hetero$(C_{4-12})$bicycloaryl, each substituted or unsubstituted.

In a further variation of each of the above embodiments and variations, $R_{11}$ is —$SO_2$—$NHR_{18}$, wherein $R_{18}$ is selected from the group consisting of hydrogen, nitro, thio, hydroxy, alkoxy, aryloxy, heteroaryloxy, carbonyl, amino, $(C_{1-10})$alkylamino, sulfonamido, imino, sulfonyl, sulfinyl, $(C_{1-10})$alkyl, halo$(C_{1-10})$alkyl, carbonyl$(C_{1-3})$alkyl, thiocarbonyl$(C_{1-3})$alkyl, sulfonyl$(C_{1-3})$alkyl, sulfinyl$(C_{1-3})$alkyl, amino$(C_{1-10})$alkyl, imino$(C_{1-3})$alkyl, $(C_{3-12})$cycloalkyl$(C_{1-5})$alkyl, hetero$(C_{3-12})$cycloalkyl$(C_{1-5})$alkyl, aryl$(C_{1-10})$alkyl, heteroaryl$(C_{1-5})$alkyl, $(C_{9-12})$bicycloaryl$(C_{1-5})$alkyl, hetero$(C_{8-12})$bicycloaryl$(C_{1-5})$alkyl, $(C_{3-12})$cycloalkyl, hetero$(C_{3-12})$cycloalkyl, $(C_{9-12})$bicycloalkyl, hetero$(C_{3-12})$bicycloalkyl, aryl, heteroaryl, $(C_{9-12})$bicycloaryl and hetero$(C_{4-12})$bicycloaryl, each substituted or unsubstituted.

In still another variation of each of the above embodiments and variations, $R_{11}$ is —$CH_2$—$NHR_{19}$, wherein $R_{19}$ is selected from the group consisting of hydrogen, nitro, thio, hydroxy, alkoxy, aryloxy, heteroaryloxy, carbonyl, amino, $(C_{1-10})$alkylamino, sulfonamido, imino, sulfonyl, sulfinyl, $(C_{1-10})$alkyl, halo$(C_{1-10})$alkyl, carbonyl$(C_{1-3})$alkyl, thiocarbonyl$(C_{1-3})$alkyl, sulfonyl$(C_{1-3})$alkyl, sulfinyl$(C_{1-3})$alkyl, amino$(C_{1-10})$alkyl, imino$(C_{1-3})$alkyl, $(C_{3-12})$cycloalkyl$(C_{1-5})$alkyl, hetero$(C_{3-12})$cycloalkyl$(C_{1-5})$alkyl, aryl$(C_{1-10})$alkyl, heteroaryl$(C_{1-5})$alkyl, $(C_{9-12})$bicycloaryl$(C_{1-5})$alkyl, hetero$(C_{8-12})$bicycloaryl$(C_{1-5})$alkyl, $(C_{3-12})$cycloalkyl, hetero$(C_{3-12})$cycloalkyl, $(C_{9-12})$bicycloalkyl, hetero$(C_{3-12})$bicycloalkyl, aryl, heteroaryl, $(C_{9-12})$bicycloaryl and hetero$(C_{4-12})$bicycloaryl, each substituted or unsubstituted.

In a further variation of each of the above embodiments and variations, $R_{11}$ is selected from the group consisting of —NH—C(O)H, —NH—CO-cyclopropyl, —NH—$SO_2$—$CH_3$, —NH—$SO_2$—$CH_2CH_3$, —CO—NH—$CH_2CH_3$, —$SO_2$—NH—$CH_3$, —$SO_2$—NH—$CH_2CH_3$, —$SO_2$—NH-cyclopropyl, —$SO_2$—$CH_3$ and —$SO_2$—$CH_2CH_3$, each substituted or unsubstituted.

In another variation of each of the above embodiments and variations, two $R_{11}$ are taken together to form a ring selected from the group consisting of:

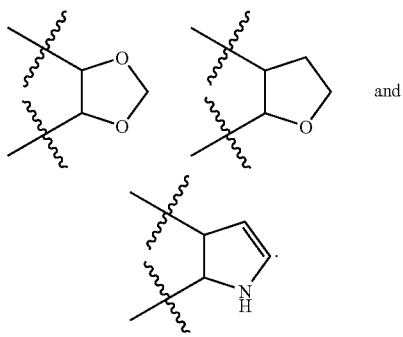

Particular examples of kinase inhibitors according to the present invention include, but are not limited to:
2-(3-(ethylsulfonyl)phenyl)-6-methyl-N-(5-methyl-1H-pyrazol-3-yl)pyrrolo[1,2-f][1,2,4]triazin-4-amine;
2-(3-(ethylsulfonyl)phenyl)-N-(5-methyl-1H-pyrazol-3-yl)pyrrolo[1,2-f][1,2,4]triazin-4-amine;
N-(5-methyl-1H-pyrazol-3-yl)-2-(3-(methylsulfonyl)phenyl)pyrrolo[1,2-f][1,2,4]triazin-4-amine;
N-(5-methyl-1H-pyrazol-3-yl)-2-phenylpyrrolo[1,2-f][1,2,4]triazin-4-amine;
2-(1-(Ethylsulfonyl)-1H-indol-6-yl)-N-(5-methyl-1H-pyrazol-3-yl)pyrrolo[1,2-f][1,2,4]triazin-4-amine;
2-(1-(Ethylsulfonyl)-1H-indol-6-yl)-6-methyl-N-(5-methyl-1H-pyrazol-3-yl)pyrrolo[1,2-f][1,2,4]triazin-4-amine;
2-(3-((dimethylamino)methyl)-1-(ethylsulfonyl)-1H-indol-6-yl)-6-methyl-N-(5-methyl-1H-pyrazol-3-yl)pyrrolo[1,2-f][1,2,4]triazin-4-amine;
2(3-(dimethylamino)methyl-1-(ethylsulfonyl)-1H-indol-6-yl)-N-(5-methyl-1H-pyrazol-3-yl)pyrrolo[1,2-f][1,2,4]triazin-4-amine; and
N-(4-(4-(5-methyl-1H-pyrazol-3-ylamino)pyrrolo[1,2-f][1,2,4]triazin-2-ylthio)phenyl)acetamide.

Particular examples of kinase inhibitors according to the present invention also include, but are not limited to:
N-(5-cyclopropyl-1H-pyrazol-3-yl)-7-phenylimidazo[1,2-f]pyrimidin-5-amine;
N-cyclopentyl-3-(5-(5-cyclopropyl-1H-pyrazol-3-ylamino)imidazo[1,2-f]pyrimidin-7-yl)benzamide;
N-(5-cyclopropyl-1H-pyrazol-3-yl)-7-(3-(piperazin-1-ylmethyl)phenyl) imidazo[1,2-f]pyrimidin-5-amine;
4-((3-(5-(5-Cyclopropyl-1H-pyrazol-3-ylamino)imidazo[1,2-f]pyrimidin-7-yl)phenyl)methyl)piperazin-2-one;
4-((3-(5-(5-Methyl-1H-pyrazol-3-ylamino)imidazo[1,2-f]pyrimidin-7-yl)phenyl)methyl)piperazin-2-one;
(5-Cyclopropyl-1H-pyrazol-3-yl)-[7-(2,3-dihydro-benzofuran-5-yl)-imidazo[1,2-c]pyrimidin-5-yl]-amine;
N-{3-[5-(5-Cyclopropyl-1H-pyrazol-3-ylamino)-imidazo[1,2-c]pyrimidin-7-yl]-benzyl}-acetamide;
3-{3-[5-(5-Cyclopropyl-1H-pyrazol-3-ylamino)-imidazo[1,2-c]pyrimidin-7-yl]-benzyl}-imidazolidine-2,4-dione;
(5-Cyclopropyl-1H-pyrazol-3-yl)-{7-[3-(3-methyl-3H-imidazol-4-yl)-phenyl]-imidazo[1,2-c]pyrimidin-5-yl}-amine;
N-{3-[5-(5-Cyclopropyl-1H-pyrazol-3-ylamino)-imidazo[1,2-c]pyrimidin-7-yl]-benzyl}-methanesulfonamide;
Cyclopropanecarboxylic acid 3-[5-(5-cyclopropyl-1H-pyrazol-3-ylamino)-imidazo[1,2-c]pyrimidin-7-yl]-benzylamide;
1-{3-[5-(5-Cyclopropyl-1H-pyrazol-3-ylamino)-imidazo[1,2-c]pyrimidin-7-yl]-benzyl}-imidazolidin-2-one;
Cyclopropanecarboxylic acid 3-[5-(5-methyl-1H-pyrazol-3-ylamino)-imidazo[1,2-c]pyrimidin-7-yl]-benzylamide;
N-(5-cyclopropyl-1H-pyrazol-3-yl)-7-(2-methoxyphenyl)imidazo[1,2-f]pyrimidin-5-amine;
3-(5-(5-cyclopropyl-1H-pyrazol-3-ylamino)imidazo[1,2-f]pyrimidin-7-yl)benzonitrile;
N-(5-cyclopropyl-1H-pyrazol-3-yl)-7-(3,5-dimethylphenyl)imidazo[1,2-f]pyrimidin-5-amine;
N-(5-cyclopropyl-1H-pyrazol-3-yl)-7-p-tolylimidazo[1,2-f]pyrimidin-5-amine;
7-(5-chloro-2-methoxyphenyl)-N-(5-cyclopropyl-1H-pyrazol-3-yl)imidazo[1,2-f]pyrimidin-5-amine;
N-(5-cyclopropyl-1H-pyrazol-3-yl)-7-(2-methoxy-5-methylphenyl)imidazo[1,2-f]pyrimidin-5-amine;
N-(5-cyclopropyl-1H-pyrazol-3-yl)-7-(3,5-dimethoxyphenyl)imidazo[1,2-f]pyrimidin-5-amine;
N-(5-cyclopropyl-1H-pyrazol-3-yl)-7-(4-methoxyphenyl)imidazo[1,2-f]pyrimidin-5-amine;
N-(5-cyclopropyl-1H-pyrazol-3-yl)-7-(pyrimidin-5-yl)imidazo[1,2-f]pyrimidin-5-amine;
N-(5-cyclopropyl-1H-pyrazol-3-yl)-7-(pyridin-3-yl)imidazo[1,2-f]pyrimidin-5-amine;
N-(5-cyclopropyl-1H-pyrazol-3-yl)-7-(3,4-dimethoxyphenyl)imidazo[1,2-f]pyrimidin-5-amine;
N-(5-cyclopropyl-1H-pyrazol-3-yl)-7-(2,3-dimethylphenyl)imidazo[1,2-f]pyrimidin-5-amine;
7-(benzo[d][1,3]dioxol-5-yl)-N-(5-cyclopropyl-1H-pyrazol-3-yl)imidazo[1,2-f]pyrimidin-5-amine;

N-(5-cyclopropyl-1H-pyrazol-3-yl)-7-(2,6-dimethylphenyl) imidazo[1,2-f]pyrimidin-5-amine;
N-(5-cyclopropyl-1H-pyrazol-3-yl)-7-(2,6-dimethoxyphenyl)imidazo[1,2-f]pyrimidin-5-amine;
N-(5-cyclopropyl-1H-pyrazol-3-yl)-7-(2-methoxypyridin-4-yl)imidazo[1,2-f]pyrimidin-5-amine;
N-(5-cyclopropyl-1H-pyrazol-3-yl)-7-(4-phenoxyphenyl) imidazo[1,2-f]pyrimidin-5-amine;
N-(5-cyclopropyl-1H-pyrazol-3-yl)-7-(3-biphenyl)imidazo[1,2-f]pyrimidin-5-amine;
N-(5-cyclopropyl-1H-pyrazol-3-yl)-7-(4-biphenyl)imidazo[1,2-f]pyrimidin-5-amine;
N-(5-cyclopropyl-1H-pyrazol-3-yl)-7-(2-biphenyl)imidazo[1,2-f]pyrimidin-5-amine;
N-(5-cyclopropyl-1H-pyrazol-3-yl)-7-(2-fluorophenyl)imidazo[1,2-f]pyrimidin-5-amine;
N-(5-cyclopropyl-1H-pyrazol-3-yl)-7-(3,5-difluorophenyl) imidazo[1,2-f]pyrimidin-5-amine;
3-(5-(5-cyclopropyl-1H-pyrazol-3-ylamino)imidazo[1,2-f] pyrimidin-7-yl)-N-methylbenzamide;
3-(5-(5-cyclopropyl-1H-pyrazol-3-ylamino)imidazo[1,2-f] pyrimidin-7-yl)-N-ethylbenzamide;
N-cyclopropyl-3-(5-(5-cyclopropyl-1H-pyrazol-3-ylamino) imidazo[1,2-f]pyrimidin-7-yl)benzamide;
N-(2-cyanoethyl)-3-(5-(5-cyclopropyl-1H-pyrazol-3-ylamino)imidazo[1,2-f]pyrimidin-7-yl)benzamide;
(3-(5-(5-cyclopropyl-1H-pyrazol-3-ylamino)imidazo[1,2-f] pyrimidin-7-yl)phenyl)(pyrrolidin-1-yl)methanone;
Methyl 3-(5-(5-cyclopropyl-1H-pyrazol-3-ylamino)imidazo[1,2-f]pyrimidin-7-yl)benzoate;
(3-(5-(5-cyclopropyl-1H-pyrazol-3-ylamino)imidazo[1,2-f] pyrimidin-7-yl)phenyl)methanol;
(E)-N-(5-cyclopropyl-1H-pyrazol-3-yl)-7-styrylimidazo[1,2-f]pyrimidin-5-amine;
N-(5-methyl-1H-pyrazol-3-yl)-7-phenylimidazo[1,2-f]pyrimidin-5-amine;
N-(4-(5-(5-cyclopropyl-1H-pyrazol-3-ylamino)imidazo[1,2-f]pyrimidin-7-yl)phenyl)acetamide;
7-(2-chlorophenyl)-N-(5-cyclopropyl-1H-pyrazol-3-yl)imidazo[1,2-f]pyrimidin-5-amine;
N-(5-cyclopropyl-1H-pyrazol-3-yl)-7-o-tolylimidazo[1,2-f] pyrimidin-5-amine;
N-(5-cyclopropyl-1H-pyrazol-3-yl)-7-m-tolylimidazo[1,2-f]pyrimidin-5-amine;
N-(5-cyclopropyl-1H-pyrazol-3-yl)-7-(4-(dimethylamino) phenyl)imidazo[1,2-f]pyrimidin-5-amine;
N-(5-cyclopropyl-1H-pyrazol-3-yl)-7-(1H-indol-5-yl)imidazo[1,2-f]pyrimidin-5-amine;
7-(3-chlorophenyl)-N-(5-cyclopropyl-1H-pyrazol-3-yl)imidazo[1,2-f]pyrimidin-5-amine;
7-(3-(1H-pyrazol-1-yl)phenyl)-N-(5-cyclopropyl-1H-pyrazol-3-yl)imidazo[1,2-f]pyrimidin-5-amine;
(3-(5-(5-cyclopropyl-1H-pyrazol-3-ylamino)imidazo[1,2-f] pyrimidin-7-yl)phenyl)(morpholino)methanone;
(4-(5-(5-cyclopropyl-1H-pyrazol-3-ylamino)imidazo[1,2-f] pyrimidin-7-yl)phenyl)(morpholino)methanone;
N-(5-cyclopropyl-1H-pyrazol-3-yl)-7-(4-morpholinophenyl)imidazo[1,2-f]pyrimidin-5-amine;
N-(5-cyclopropyl-1H-pyrazol-3-yl)-7-(3-morpholinophenyl)imidazo[1,2-f]pyrimidin-5-amine;
N-(5-cyclopropyl-1H-pyrazol-3-yl)-7-(4-(piperidin-1-yl) phenyl)imidazo[1,2-f]pyrimidin-5-amine;
N-(5-cyclopropyl-1H-pyrazol-3-yl)-7-(3-((4-methylpiperazin-1-yl)methyl)phenyl) imidazo[1,2-f]pyrimidin-5-amine;
N-{3-[5-(5-Cyclopropyl-2H-pyrazol-3-ylamino)-imidazo[1,2-c]pyrimidin-7-yl]-phenyl}-methanesulfonamide;
N-{3-[5-(5-Cyclopropyl-2H-pyrazol-3-ylamino)-imidazo[1,2-c]pyrimidin-7-yl]-phenyl}-acetamide;
N-{3-[5-(5-Methyl-2H-pyrazol-3-ylamino)-imidazo[1,2-c] pyrimidin-7-yl]-phenyl}-methanesulfonamide;
[7-(3-Ethanesulfonyl-phenyl)-imidazo[1,2-c]pyrimidin-5-yl]-(5-methyl-2H-pyrazol-3-yl)-amine;
N-{3-[5-(5-Cyclopropyl-2H-pyrazol-3-ylamino)-2-hydroxymethyl-imidazo[1,2-c]pyrimidin-7-yl]-phenyl}-methanesulfonamide;
(5-Cyclopropyl-2H-pyrazol-3-yl)-[7-(3-ethanesulfonyl-phenyl)-imidazo[1,2-c]pyrimidin-5-yl]-amine;
[7-(4-Methyl-piperazin-1-yl)-imidazo[1,2-c]pyrimidin-5-yl]-(5-methyl-1H-pyrazol-3-yl)-amine;
(5-Methyl-1H-pyrazol-3-yl)-(7-piperidin-1-yl-imidazo[1,2-c]pyrimidin-5-yl)-amine;
(5-Cyclopropyl-1H-pyrazol-3-yl)-[7-(2,3-dihydro-indol-1-yl)-imidazo[1,2-c]pyrimidin-5-yl]-amine;
(5-Cyclopropyl-1H-pyrazol-3-yl)-[7-(3,4-dihydro-1H-isoquinolin-2-yl)-imidazo[1,2-c]pyrimidin-5-yl]-amine;
Ethyl 5-(5-cyclopropyl-1H-pyrazol-3-ylamino)-7-(4-((2,5-dioxoimidazolidin-1-yl)methyl)phenyl) imidazo[1,2-f] pyrimidine-2-carboxylate;
Ethyl 5-(5-cyclopropyl-1H-pyrazol-3-ylamino)-7-(4-(pyrrolidine-1-carbonyl)phenyl) imidazo[1,2-f]pyrimidine-2-carboxylate;
Ethyl 5-(5-cyclopropyl-1H-pyrazol-3-ylamino)-7-(4-(cyclopropylcarbamoyl)phenyl) imidazo[1,2-f]pyrimidine-2-carboxylate;
Cyclopentanecarboxylic acid 3-[5-(5-cyclopropyl-1H-pyrazol-3-ylamino)-imidazo[1,2-c]pyrimidin-7-yl]-benzylamide;
N-(5-cyclopropyl-1H-pyrazol-3-yl)-7-phenylimidazo[1,2-f] pyrimidin-5-amine;
N-cyclopropyl-3-(5-(5-methyl-1H-pyrazol-3-ylamino)imidazo[1,2-f]pyrimidin-7-yl)benzamide;
(3-(5-(5-methyl-1H-pyrazol-3-ylamino)imidazo[1,2-f]pyrimidin-7-yl)phenyl)(4-methylpiperazin-1-yl)methanone;
(4-aminopiperidin-1-yl)(3-(5-(5-methyl-1H-pyrazol-3-ylamino)imidazo[1,2-f]pyrimidin-7-yl)phenyl)methanone;
3-(5-(5-Methyl-1H-pyrazol-3-ylamino)imidazo[1,2-f]pyrimidin-7-yl)-N-(piperidin-4-yl)benzamide;
(3-(5-(5-Cyclopropyl-1H-pyrazol-3-ylamino)imidazo[1,2-f] pyrimidin-7-yl)phenyl)(piperazin-1-yl)methanone;
(S)-Pyrrolidine-2-carboxylic acid 3-[5-(5-methyl-1H-pyrazol-3-ylamino)-imidazo[1,2-c]pyrimidin-7-yl]-benzylamide;
N-{3-[5-(5-Cyclopropyl-1H-pyrazol-3-ylamino)-2-(4-methyl-piperazin-1-ylmethyl)-imidazo[1,2-c]pyrimidin-7-yl]-phenyl}-methanesulfonamide;
[7-(3-Methanesulfonyl-phenyl)-imidazo[1,2-c]pyrimidin-5-yl]-(5-methyl-1H-pyrazol-3-yl)-amine;
[5-(5-Cyclopropyl-1H-pyrazol-3-ylamino)-7-(3-ethanesulfonyl-phenyl)-imidazo[1,2-c]pyrimidin-2-yl]-methanol;
(5-Cyclopropyl-1H-pyrazol-3-yl)-[7-(3-ethanesulfonyl-phenyl)-2-(4-methyl-piperazin-1-ylmethyl)-imidazo[1,2-c] pyrimidin-5-yl]-amine;
[7-(3-Ethanesulfonyl-phenyl)-5-(5-methyl-1H-pyrazol-3-ylamino)-imidazo[1,2-c]pyrimidin-2-yl]-methanol;
[7-(3-Ethanesulfonyl-phenyl)-2-(4-methyl-piperazin-1-ylmethyl)-imidazo[1,2-c]pyrimidin-5-yl]-(5-methyl-1H-pyrazol-3-yl)-amine;
2-methyl-N-(5-methyl-1H-pyrazol-3-yl)-7-phenylimidazo [1,2-f]pyrimidin-5-amine;
N-cyclopropyl-2-(3-(2-methyl-5-(5-methyl-1H-pyrazol-3-ylamino)imidazo[1,2-f]pyrimidin-7-yl)phenyl)acetamide;

7-(3-(ethylsulfonyl)phenyl)-2-methyl-N-(5-methyl-1H-pyrazol-3-yl)imidazo[1,2-f]pyrimidin-5-amine;
2-methyl-N-(5-methyl-1H-pyrazol-3-yl)-7-(3-methylsulfonyl)phenyl) imidazo[1,2-f]pyrimidin-5-amine;
2-methoxy-N-methyl-5-(2-methyl-5-(5-methyl-1H-pyrazol-3-ylamino) imidazo[1,2-f]pyrimidin-7-yl)benzenesulfonamide;
2-methoxy-N-methyl-5-(2-methyl-5-(5-methyl-1H-pyrazol-3-ylamino) imidazo[1,2-f]pyrimidin-7-yl)benzenesulfonamide;
N-ethyl-N-methyl-3-(2-methyl-5-(5-methyl-1H-pyrazol-3-ylamino) imidazo[1,2-f]pyrimidin-7-yl)benzenesulfonamide;
N-ethyl-N-methyl-3-(2-methyl-5-(5-methyl-1H-pyrazol-3-ylamino) imidazo[1,2-f]pyrimidin-7-yl)benzenesulfonamide;
N-(3-(2-Methyl-5-(5-methyl-1H-pyrazol-3-ylamino)imidazo[1,2-f]pyrimidin-7-yl)phenyl)cyclopropanesulfonamide;
N-Ethyl-2-methoxy-5-(2-methyl-5-(5-methyl-1H-pyrazol-3-ylamino) imidazo[1,2-f]pyrimidin-7-yl)benzenesulfonamide;
N-(3-(2-Methyl-5-(5-methyl-1H-pyrazol-3-ylamino)imidazo[1,2-f]pyrimidin-7-yl)phenyl)ethanesulfonamide;
N-(2-Methoxy-5-(2-methyl-5-(5-methyl-1H-pyrazol-3-ylamino) imidazo[1,2-f]pyrimidin-7-yl)phenyl)cyclopropanesulfonamide;
N-(3-(2-Methyl-5-(5-methyl-1H-pyrazol-3-ylamino)imidazo[1,2-f]pyrimidin-7-yl)phenyl)methanesulfonamide;
N-(4-(2-Methyl-5-(5-methyl-1H-pyrazol-3-ylamino)imidazo[1,2-f]pyrimidin-7-yl)phenyl)methanesulfonamide;
Cyclopropanecarboxylic acid 4-fluoro-3-[5-(5-methyl-1H-pyrazol-3-ylamino)-imidazo[1,2-c]pyrimidin-7-yl]-benzylamide;
Cyclopropanecarboxylic acid 4-fluoro-3-[2-methyl-5-(5-methyl-1H-pyrazol-3-ylamino)-imidazo[1,2-c]pyrimidin-7-yl]-benzylamide;
5-[2-Methyl-5-(5-methyl-1H-pyrazol-3-ylamino)-imidazo[1,2-c]pyrimidin-7-yl]-1,3-dihydro-benzoimidazol-2-one;
Cyclopropanesulfonic acid methyl-{3-[2-methyl-5-(5-methyl-1H-pyrazol-3-ylamino)-imidazo[1,2-c]pyrimidin-7-yl]-phenyl}-amide;
(5-Methyl-1H-pyrazol-3-yl)-(2-methyl-7-pyridin-2-yl-imidazo[1,2-c]pyrimidin-5-yl]-amine;
[7-(1-Ethanesulfonyl-1H-indol-6-yl)-2-methyl-imidazo[1,2-c]pyrimidin-5-yl]-(5-(5-methyl-1H-pyrazol-3-yl)-amine;
Ethanesulfonic acid methyl-{3-[2-methyl-5-(5-methyl-1H-pyrazol-3-ylamino)-imidazo[1,2-c]pyrimidin-7-yl]-benzyl}-amide;
Ethanesulfonic acid {5-[2-methyl-5-(5-methyl-1H-pyrazol-3-ylamino)-imidazo[1,2-c]pyrimidin-7-yl]-1H-indol-7-yl}-amide;
N-ethyl-2-methoxy-N-methyl-5-(2-methyl-5-(5-methyl-1H-pyrazol-3-ylamino)imidazo[1,2-f]pyrimidin-7-yl)benzenesulfonamide;
N-(cyclopropylmethyl)-2-methoxy-5-(2-methyl-5-(5-methyl-1H-pyrazol-3-ylamino) imidazo[1,2-f]pyrimidin-7-yl)benzenesulfonamide;
N-cyclopropyl-3-(2-methyl-5-(5-methyl-1H-pyrazol-3-ylamino)imidazo[1,2-f]pyrimidin-7-yl)benzenesulfonamide;
N-ethyl-3-(2-methyl-5-(5-methyl-1H-pyrazol-3-ylamino) imidazo[1,2-f]pyrimidin-7-yl)benzenesulfonamide;
7-Chloro-N-(5-cyclopropyl-1H-pyrazol-3-yl)-2-(isopropoxymethyl) imidazo[1,2-f]pyrimidin-5-amine;
7-Chloro-N-(5-cyclopropyl-1H-pyrazol-3-yl)-2-(isopropoxymethyl) imidazo[1,2-f]pyrimidin-5-amine;
7-Chloro-N-(5-cyclopropyl-1H-pyrazol-3-yl)-2-(isopropoxymethyl) imidazo[1,2-f]pyrimidin-5-amine;
N-(5-methyl-1H-pyrazol-3-yl)-7-phenyl-2-(trifluoromethyl) imidazo[1,2-f]pyrimidin-5-amine;
3-(2-(Chloromethyl)-5-(5-methyl-1H-pyrazol-3-ylamino) imidazo[1,2-f]pyrimidin-7-yl0-N-cyclopropylbenzamide;
2-Ethyl-7-(3-(ethylsulfonyl)phenyl)-N-(5-methyl-1H-pyrazol-3-yl)imidazo[1,2-f]pyrimidin-5-amine;
7-(3-(ethylsulfonyl)phenyl)-2-isopropyl-N-(5-methyl-1H-pyrazol-3-yl) imidazo[1,2-f]pyrimidin-5-amine;
N-(5-ethyl-1H-pyrazol-3-yl)-7-(3-(ethylsulfonyl)phenyl)-2-methylimidazo[1,2-f]pyrimidin-5-amine;
N-(methyl-N-(3-(2-methyl-5-(5-methyl-1H-pyrazol-3-ylamino) imidazo[1,2-f]pyrimidin-7-yl)phenyl)cycloprpanesulfonamide;
2-(3-(ethylsulfonyl)phenyl)-6-methyl-N-(5-methyl-1H-pyrazol-3-yl)pyrrolo[1,2-f][1,2,4]triazin-4-amine;
2-(3-(ethylsulfonyl)phenyl)-N-(5-methyl-1H-pyrazol-3-yl) pyrrolo[1,2-f][1,2,4]triazin-4-amine;
N-(5-methyl-1H-pyrazol-3-yl)-2-(3-(methylsulfonyl)phenyl)pyrrolo[1,2-f][1,2,4]triazin-4-amine;
N-(5-methyl-1H-pyrazol-3-yl)-2-phenylpyrrolo[1,2-f][1,2,4]triazin-4-amine;
2-(1-(Ethylsulfonyl)-1H-indol-6-yl)-N-(5-methyl-1H-pyrazol-3-yl)pyrrolo[1,2-f][1,2,4]triazin-4-amine;
2-(1-(Ethylsulfonyl)-1H-indol-6-yl)-6-methyl-N-(5-methyl-1H-pyrazol-3-yl)pyrrolo[1,2-f][1,2,4]triazin-4-amine;
2-(3-((dimethylamino)methyl)-1-(ethylsulfonyl)-1H-indol-6-yl)-6-methyl-N-(5-methyl-1H-pyrazol-3-yl)pyrrolo[1,2-f][1,2,4]triazin-4-amine;
Cyclobutanecarboxylic acid 3-[5-(5-methyl-1H-pyrazol-3-ylamino)-imidazo[1,2-c]pyrimidin-7-yl]-benzylamide;
Azetidine-3-carboxylic acid 3-[5-(5-methyl-1H-pyrazol-3-ylamino)-imidazo[1,2-c]pyrimidin-7-yl]-benzylamide;
[7-(3-Aminomethyl-phenyl)-imidazo[1,2-c]pyrimidin-5-yl]-(5-methyl-1H-pyrazol-3-yl)-amine;
Cyclopropanesulfonic acid 3-[5-(5-methyl-1H-pyrazol-3-ylamino)-imidazo[1,2-c]pyrimidin-7-yl]-benzylamide;
(7-{3-[(Cyclopropylmethyl-amino)-methyl]-phenyl}-imidazo[1,2-c]pyrimidin-5-yl)-(5-methyl-1H-pyrazol-3-yl)-amine;
[7-(3-Methylaminomethyl-phenyl)-imidazo[1,2-c]pyrimidin-5-yl]-(5-methyl-1H-pyrazol-3-yl)-amine;
(5-Methyl-1H-pyrazol-3-yl)-[7-(1,2,3,4-tetrahydro-isoquinolin-7-yl)-imidazo[1,2-c]pyrimidin-5-yl]-amine;
[7-(2-Methanesulfonyl-1,2,3,4-tetrahydro-isoquinolin-7-yl)-imidazo[1,2-c]pyrimidin-5-yl]-(5-methyl-1H-pyrazol-3-yl)-amine;
[7-(3-Ethanesulfonylmethyl-phenyl)-2-methyl-imidazo[1,2-c]pyrimidin-5-yl]-(5-methyl-1H-pyrazol-3-yl)-amine;
[7-(3-Ethanesulfonylmethyl-phenyl)-2-methyl-imidazo[1,2-c]pyrimidin-5-yl]-(5-methyl-1H-pyrazol-3-yl)-amine;
{2-Methyl-7-[3-(3-methyl-pyridin-4-yl)-phenyl]-imidazo[1,2-c]pyrimidin-5-yl}-(5-methyl-1H-pyrazol-3-yl)-amine;
{7-[3-(3,5-Dimethyl-1H-pyrazol-4-yl)-phenyl]-2-methyl-imidazo[1,2-c]pyrimidin-5-yl}-(5-methyl-1H-pyrazol-3-yl)-amine;
{2-Methyl-7-[3-(3-methyl-3H-imidazol-4-yl)-phenyl]-imidazo[1,2-c]pyrimidin-5-yl}-(5-methyl-1H-pyrazol-3-yl)-amine;
(5-Methyl-1H-pyrazol-3-yl)-{2-methyl-7-[3-(1,3,5-trimethyl-1H-pyrazol-4-yl)-phenyl]-imidazo[1,2-c]pyrimidin-5-yl}-amine;

{7-[3-(3,5-Dimethyl-isoxazol-4-yl)-phenyl]-2-methyl-imidazo[1,2-c]pyrimidin-5-yl}-(5-methyl-1H-pyrazol-3-yl)-amine;

{7-[3-(5-Cyclopropyl-3-methyl-1H-pyrazol-4-yl)-phenyl]-2-methyl-imidazo[1,2-c]pyrimidin-5-yl}-(5-methyl-1H-pyrazol-3-yl)-amine;

(5-Methyl-1H-pyrazol-3-yl)-{2-methyl-7-[3-(thiazole-2-sulfonyl)-phenyl]-imidazo[1,2-c]pyrimidin-5-yl}-amine;

[7-(3-Dimethylaminomethyl-1-ethanesulfonyl-1H-indol-6-yl)-2-methyl-imidazo[1,2-c]pyrimidin-5-yl]-(5-methyl-1H-pyrazol-3-yl)-amine;

(5-Methyl-1H-pyrazol-3-yl)-{2-methyl-7-[3-(1H-pyrrolo[2,3-b]pyridin-4-yl)-phenyl]-imidazo[1,2-c]pyrimidin-5-yl}-amine;

(5-Methyl-1H-pyrazol-3-yl)-{2-methyl-7-[3-(S)-(pyrrolidine-3-sulfonyl)-phenyl]-imidazo[1,2-c]pyrimidin-5-yl}-amine;

{7-[3-(3-Amino-propane-1-sulfonyl)-phenyl]-2-methyl-imidazo[1,2-c]pyrimidin-5-yl}-(5-methyl-1H-pyrazol-3-yl)-amine;

[7-(3-Ethylsulfanyl-phenyl)-2-methyl-imidazo[1,2-c]pyrimidin-5-yl]-(5-methyl-1H-pyrazol-3-yl)-amine;

[7-(3-Ethanesulfinyl-phenyl)-2-methyl-imidazo[1,2-c]pyrimidin-5-yl]-(5-methyl-1H-pyrazol-3-yl)-amine;

7-(3-(ethylsulfonyl)phenyl)-N-(5-methyl-1H-pyrazol-3-yl)-[1,2,4]triazolo[1,5-c]pyrimidin-5-amine;

N-(5-(2-methyl-5-(5-methyl-1H-pyrazol-3-ylamino)imidazo[1,2-c]pyrimidin-7-yl)-2-(2-morpholinoethoxy)phenyl)cyclopropanesulfonamide;

4-methyl-5-(3-(2-methyl-5-(5-methyl-1H-pyrazol-3-ylamino)imidazo[1,2-c]pyrimidin-7-yl)phenyl)thiazol-2-amine;

3-(2-methyl-5-(5-methyl-1H-pyrazol-3-ylamino)imidazo[1,2-c]pyrimidin-7-yl)-N-phenylbenzenesulfonamide;

(4-hydroxypiperidin-1-yl)(3-(5-(5-methyl-1H-pyrazol-3-ylamino)imidazo[1,2-c]pyrimidin-7-yl)phenyl)methanone;

N-isobutyl-3-(5-(5-methyl-1H-pyrazol-3-ylamino)imidazo[1,2-c]pyrimidin-7-yl)benzamide;

N-cyclopentyl-3-(5-(5-methyl-1H-pyrazol-3-ylamino)imidazo[1,2-c]pyrimidin-7-yl)benzamide;

3-(5-(5-methyl-1H-pyrazol-3-ylamino)imidazo[1,2-c]pyrimidin-7-yl)-N-(pyrrolidin-3-ylmethyl)benzamide;

3-(5-(5-methyl-1H-pyrazol-3-ylamino)imidazo[1,2-c]pyrimidin-7-yl)-N-(pyrrolidin-2-ylmethyl)benzamide;

N-isopropyl-3-(5-(5-methyl-1H-pyrazol-3-ylamino)imidazo[1,2-c]pyrimidin-7-yl)benzamide;

3-(5-(5-methyl-1H-pyrazol-3-ylamino)imidazo[1,2-c]pyrimidin-7-yl)-N-phenylbenzamide;

N-benzyl-3-(5-(5-methyl-1H-pyrazol-3-ylamino)imidazo[1,2-c]pyrimidin-7-yl)benzamide;

3-(2-methyl-5-(5-methyl-1H-pyrazol-3-ylamino)imidazo[1,2-c]pyrimidin-7-yl)-N-(thiazol-2-yl)benzenesulfonamide;

N-(2-aminoethyl)-3-(2-methyl-5-(5-methyl-1H-pyrazol-3-ylamino)imidazo[1,2-c]pyrimidin-7-yl)benzenesulfonamide;

N-ethyl-N-(3-(2-isopropyl-5-(5-methyl-1H-pyrazol-3-ylamino)imidazo[1,2-c]pyrimidin-7-yl)phenyl)methanesulfonamide;

N-isopropyl-3-(5-(5-methyl-1H-pyrazol-3-ylamino)-2-(trifluoromethyl) imidazo[1,2-c]pyrimidin-7-yl)benzamide;

N-(5-methyl-1H-pyrazol-3-yl)-2,7-diphenylimidazo[1,2-c]pyrimidin-5-amine;

N-(4-(2-(hydroxymethyl)-5-(5-methyl-1H-pyrazol-3-ylamino)imidazo[1,2-c]pyrimidin-7-ylthio)phenyl)cyclopropanecarboxamide;

N-(3-(2-(hydroxymethyl)-5-(5-methyl-1H-pyrazol-3-ylamino)imidazo[1,2-c]pyrimidin-7-yl)phenyl)methanesulfonamide;

[7-(3-Ethanesulfonyl-phenyl)-2-methyl-imidazo[1,2-c]pyrimidin-5-yl]-(5-methyl-1H-pyrazol-3-yl)-amine;

[7-(3-Isopropoxy-phenyl)-2-methyl-imidazo[1,2-c]pyrimidin-5-yl]-(5-methyl-1H-pyrazol-3-yl)-amine;

[2-Methyl-7-(3-propoxy-phenyl)-imidazo[1,2-c]pyrimidin-5-yl]-(5-methyl-1H-pyrazol-3-yl)-amine;

[7-(3-Ethanesulfonyl-phenyl)-2-imidazol-1-ylmethyl-imidazo[1,2-c]pyrimidin-5-yl]-(5-methyl-1H-pyrazol-3-yl)-amine;

3-{3-[2-Methyl-5-(5-methyl-1H-pyrazol-3-ylamino)-imidazo[1,2-c]pyrimidin-7-yl]-phenyl}-propionic acid methyl ester;

3-{3-[2-Methyl-5-(5-methyl-1H-pyrazol-3-ylamino)-imidazo[1,2-c]pyrimidin-7-yl]-phenyl}-propionic acid;

5-[2-Methyl-5-(5-methyl-1H-pyrazol-3-ylamino)-imidazo[1,2-c]pyrimidin-7-yl]-thiophene-2-carboxylic acid cyclopropylamide;

[7-(1-Benzyl-1H-pyrazol-4-yl)-2-methyl-imidazo[1,2-c]pyrimidin-5-yl]-(5-cyclopropyl-1H-pyrazol-3-yl)-amine;

[7-(1-Benzyl-1H-pyrazol-4-yl)-2-methyl-imidazo[1,2-c]pyrimidin-5-yl]-(5-methyl-1H-pyrazol-3-yl)-amine;

N-{2-[2-Methyl-5-(5-methyl-1H-pyrazol-3-ylamino)-imidazo[1,2-c]pyrimidin-7-yl]-phenyl}-methanesulfonamide;

N-{2-[2-Methyl-5-(5-methyl-1H-pyrazol-3-ylamino)-imidazo[1,2-c]pyrimidin-7-yl]-phenyl}-acetamide;

[7-(1H-Indol-4-yl)-2-methyl-imidazo[1,2-c]pyrimidin-5-yl]-(5-methyl-1H-pyrazol-3-yl)-amine;

[7-(2-Amino-phenyl)-2-methyl-imidazo[1,2-c]pyrimidin-5-yl]-(5-methyl-1H-pyrazol-3-yl)-amine;

[7-(1-Isobutyl-1H-pyrazol-4-yl)-2-methyl-imidazo[1,2-c]pyrimidin-5-yl]-(5-methyl-1H-pyrazol-3-yl)-amine;

4-{4-[2-Methyl-5-(5-methyl-1H-pyrazol-3-ylamino)-imidazo[1,2-c]pyrimidin-7-yl]-pyrazol-1-ylmethyl}-benzoic acid methyl ester;

(5-Cyclopropyl-1H-pyrazol-3-yl)-{7-[1-(3-methoxy-benzyl)-1H-pyrazol-4-yl]-2-methyl-imidazo[1,2-c]pyrimidin-5-yl}-amine;

(5-Cyclopropyl-1H-pyrazol-3-yl)-[2-methyl-7-(1-quinolin-8-ylmethyl-1H-pyrazol-4-yl)-imidazo[1,2-c]pyrimidin-5-yl]-amine;

3-{4-[5-(5-Cyclopropyl-1H-pyrazol-3-ylamino)-2-methyl-imidazo[1,2-c]pyrimidin-7-yl]-pyrazol-1-ylmethyl}-benzoic acid methyl ester;

(5-Cyclopropyl-1H-pyrazol-3-yl)-{7-[1-(4-methanesulfonyl-benzyl)-1H-pyrazol-4-yl]-2-methyl-imidazo[1,2-c]pyrimidin-5-yl}-amine;

(5-Cyclopropyl-1H-pyrazol-3-yl)-{7-[1-(4-methoxy-benzyl)-1H-pyrazol-4-yl]-2-methyl-imidazo[1,2-c]pyrimidin-5-yl}-amine;

(5-Cyclopropyl-1H-pyrazol-3-yl)-{7-[1-(2,3-dimethoxy-benzyl)-1H-pyrazol-4-yl]-2-methyl-imidazo[1,2-c]pyrimidin-5-yl}-amine;

(5-Cyclopropyl-1H-pyrazol-3-yl)-{7-[1-(3,5-dimethoxy-benzyl)-1H-pyrazol-4-yl]-2-methyl-imidazo[1,2-c]pyrimidin-5-yl}-amine;

[7-(1-Benzo[1,2,5]oxadiazol-5-ylmethyl-1H-pyrazol-4-yl)-2-methyl-imidazo[1,2-c]pyrimidin-5-yl]-(5-cyclopropyl-1H-pyrazol-3-yl)-amine;

2-{4-[5-(5-Cyclopropyl-1H-pyrazol-3-ylamino)-2-methyl-imidazo[1,2-c]pyrimidin-7-yl]-pyrazol-1-ylmethyl}-benzonitrile;

(5-Cyclopropyl-1H-pyrazol-3-yl)-[2-methyl-7-(1-pyridin-2-ylmethyl-1H-pyrazol-4-yl)-imidazo[1,2-c]pyrimidin-5-yl]-amine;

3-{4-[5-(5-Cyclopropyl-1H-pyrazol-3-ylamino)-2-methyl-imidazo[1,2-c]pyrimidin-7-yl]-pyrazol-1-ylmethyl}-N-ethyl-benzamide;

3-{4-[5-(5-Cyclopropyl-1H-pyrazol-3-ylamino)-2-methyl-imidazo[1,2-c]pyrimidin-7-yl]-pyrazol-1-ylmethyl}-benzonitrile;

3-{4-[5-(5-Cyclopropyl-1H-pyrazol-3-ylamino)-2-methyl-imidazo[1,2-c]pyrimidin-7-yl]-pyrazol-1-ylmethyl}-N-thiazol-2-yl-benzamide;

(5-Cyclopropyl-1H-pyrazol-3-yl)-[2-methyl-7-(1-phenethyl-1H-pyrazol-4-yl)-imidazo[1,2-c]pyrimidin-5-yl]-amine;

(5-Cyclopropyl-1H-pyrazol-3-yl)-{2-methyl-7-[1-(4-pyrazol-1-yl-benzyl)-1H-pyrazol-4-yl]-imidazo[1,2-c]pyrimidin-5-yl}-amine;

2-{4-[2-Methyl-5-(5-methyl-1H-pyrazol-3-ylamino)-imidazo[1,2-c]pyrimidin-7-yl]-pyrazol-1-ylmethyl}-benzonitrile;

(5-Cyclopropyl-1H-pyrazol-3-yl)-{2-methyl-7-[1-(3-pyrrol-1-yl-benzyl)-1H-pyrazol-4-yl]-imidazo[1,2-c]pyrimidin-5-yl}-amine;

N-Ethyl-4-{4-[2-methyl-5-(5-methyl-1H-pyrazol-3-ylamino)-imidazo[1,2-c]pyrimidin-7-yl]-pyrazol-1-ylmethyl}-benzamide;

(5-Cyclopropyl-1H-pyrazol-3-yl)-{2-methyl-7-[1-(3-nitrobenzyl)-1H-pyrazol-4-yl]-imidazo[1,2-c]pyrimidin-5-yl}-amine;

(5-Cyclopropyl-1H-pyrazol-3-yl)-{2-methyl-7-[1-(2-morpholin-4-yl-ethyl)-1H-pyrazol-4-yl]-imidazo[1,2-c]pyrimidin-5-yl}-amine;

{7-[1-(3-Amino-benzyl)-1H-pyrazol-4-yl]-2-methyl-imidazo[1,2-c]pyrimidin-5-yl}-(5-cyclopropyl-1H-pyrazol-3-yl)-amine;

{7-[1-(2,5-Dichloro-benzyl)-1H-pyrazol-4-yl]-2-methyl-imidazo[1,2-c]pyrimidin-5-yl}-(5-methyl-1H-pyrazol-3-yl)-amine;

{2-Methyl-7-[1-(2-piperidin-1-yl-ethyl)-1H-pyrazol-4-yl]-imidazo[1,2-c]pyrimidin-5-yl}-(5-methyl-1H-pyrazol-3-yl)-amine;

2-{4-[2-Methyl-5-(5-methyl-1H-pyrazol-3-ylamino)-imidazo[1,2-c]pyrimidin-7-yl]-pyrazol-1-yl}-N-phenyl-acetamide;

{2-Methyl-7-[1-(1-methyl-2-phenyl-ethyl)-1H-pyrazol-4-yl]-imidazo[1,2-c]pyrimidin-5-yl}-(5-methyl-1H-pyrazol-3-yl)-amine;

N-(3-{4-[5-(5-Cyclopropyl-1H-pyrazol-3-ylamino)-2-methyl-imidazo[1,2-c]pyrimidin-7-yl]-pyrazol-1-ylmethyl}-phenyl)-2-methoxy-acetamide;

4-Fluoro-2-{4-[2-methyl-5-(5-methyl-1H-pyrazol-3-ylamino)-imidazo[1,2-c]pyrimidin-7-yl]-pyrazol-1-ylmethyl}-benzonitrile;

(5-Methyl-1H-pyrazol-3-yl)-{2-methyl-7-[1-(2-trifluoromethoxy-benzyl)-1H-pyrazol-4-yl]-imidazo[1,2-c]pyrimidin-5-yl}-amine;

N-(5-cyclopropyl-1H-pyrazol-3-yl)-7-(2-methoxyphenyl)imidazo[1,2-f]pyrimidin-5-amine;

3-(5-(5-cyclopropyl-1H-pyrazol-3-ylamino)imidazo[1,2-f]pyrimidin-7-yl)benzonitrile;

N-(5-cyclopropyl-1H-pyrazol-3-yl)-7-(3,5-dimethylphenyl)imidazo[1,2-f]pyrimidin-5-amine;

N-(5-cyclopropyl-1H-pyrazol-3-yl)-7-p-tolylimidazo[1,2-f]pyrimidin-5-amine;

7-(5-chloro-2-methoxyphenyl)-N-(5-cyclopropyl-1H-pyrazol-3-yl)imidazo[1,2-f]pyrimidin-5-amine;

N-(5-cyclopropyl-1H-pyrazol-3-yl)-7-(2-methoxy-5-methylphenyl)imidazo[1,2-f]pyrimidin-5-amine;

N-(5-cyclopropyl-1H-pyrazol-3-yl)-7-(3,5-dimethoxyphenyl)imidazo[1,2-f]pyrimidin-5-amine;

N-(5-cyclopropyl-1H-pyrazol-3-yl)-7-(4-methoxyphenyl)imidazo[1,2-f]pyrimidin-5-amine;

N-(5-cyclopropyl-1H-pyrazol-3-yl)-7-(pyrimidin-5-yl)imidazo[1,2-f]pyrimidin-5-amine;

N-(5-cyclopropyl-1H-pyrazol-3-yl)-7-(pyridin-3-yl)imidazo[1,2-f]pyrimidin-5-amine;

N-(5-cyclopropyl-1H-pyrazol-3-yl)-7-(3,4-dimethoxyphenyl)imidazo[1,2-f]pyrimidin-5-amine;

N-(5-cyclopropyl-1H-pyrazol-3-yl)-7-(2,3-dimethylphenyl)imidazo[1,2-f]pyrimidin-5-amine;

7-(benzo[d][1,3]dioxol-5-yl)-N-(5-cyclopropyl-1H-pyrazol-3-yl)imidazo[1,2-f]pyrimidin-5-amine;

N-(5-cyclopropyl-1H-pyrazol-3-yl)-7-(2,6-dimethylphenyl)imidazo[1,2-f]pyrimidin-5-amine;

N-(5-cyclopropyl-1H-pyrazol-3-yl)-7-(2,6-dimethoxyphenyl)imidazo[1,2-f]pyrimidin-5-amine;

N-(5-cyclopropyl-1H-pyrazol-3-yl)-7-(2-methoxypyridin-4-yl)imidazo[1,2-f]pyrimidin-5-amine;

N-(5-cyclopropyl-1H-pyrazol-3-yl)-7-(4-phenoxyphenyl)imidazo[1,2-f]pyrimidin-5-amine;

N-(5-cyclopropyl-1H-pyrazol-3-yl)-7-(3-biphenyl)imidazo[1,2-f]pyrimidin-5-amine;

N-(5-cyclopropyl-1H-pyrazol-3-yl)-7-(4-biphenyl)imidazo[1,2-f]pyrimidin-5-amine;

N-(5-cyclopropyl-1H-pyrazol-3-yl)-7-(2-biphenyl)imidazo[1,2-f]pyrimidin-5-amine;

N-(5-cyclopropyl-1H-pyrazol-3-yl)-7-(2-fluorophenyl)imidazo[1,2-f]pyrimidin-5-amine;

N-(5-cyclopropyl-1H-pyrazol-3-yl)-7-(3,5-difluorophenyl)imidazo[1,2-f]pyrimidin-5-amine;

3-(5-(5-cyclopropyl-1H-pyrazol-3-ylamino)imidazo[1,2-f]pyrimidin-7-yl)-N-methylbenzamide;

3-(5-(5-cyclopropyl-1H-pyrazol-3-ylamino)imidazo[1,2-f]pyrimidin-7-yl)-N-ethylbenzamide;

N-cyclopropyl-3-(5-(5-cyclopropyl-1H-pyrazol-3-ylamino)imidazo[1,2-f]pyrimidin-7-yl)benzamide;

N-(2-cyanoethyl)-3-(5-(5-cyclopropyl-1H-pyrazol-3-ylamino)imidazo[1,2-f]pyrimidin-7-yl)benzamide;

(3-(5-(5-cyclopropyl-1H-pyrazol-3-ylamino)imidazo[1,2-f]pyrimidin-7-yl)phenyl)(pyrrolidin-1-yl)methanone;

Methyl 3-(5-(5-cyclopropyl-1H-pyrazol-3-ylamino)imidazo[1,2-f]pyrimidin-7-yl)benzoate;

(3-(5-(5-cyclopropyl-1H-pyrazol-3-ylamino)imidazo[1,2-f]pyrimidin-7-yl)phenyl)methanol;

N-ethyl-2-methoxy-N-methyl-5-(2-methyl-5-(5-methyl-1H-pyrazol-3-ylamino)imidazo[1,2-f]pyrimidin-7-yl)benzenesulfonamide;

N-(cyclopropylmethyl)-2-methoxy-5-(2-methyl-5-(5-methyl-1H-pyrazol-3-ylamino) imidazo[1,2-f]pyrimidin-7-yl)benzenesulfonamide;

N-cyclopropyl-3-(2-methyl-5-(5-methyl-1H-pyrazol-3-ylamino)imidazo[1,2-f]pyrimidin-7-yl)benzenesulfonamide;

N-ethyl-3-(2-methyl-5-(5-methyl-1H-pyrazol-3-ylamino)imidazo[1,2-f]pyrimidin-7-yl)benzenesulfonamide;

N-(2-hydroxyethyl)-2-methoxy-5-(2-methyl-5-(5-methyl-1H-pyrazol-3-ylamino) imidazo[1,2-c]pyrimidin-7-yl)benzenesulfonamide;

7-(4-methoxy-3-(morpholinosulfonyl)phenyl)-2-methyl-N-(5-methyl-1H-pyrazol-3-yl)imidazo[1,2-c]pyrimidin-5-amine;

7-(4-methoxy-3-(tetrahydro-2H-pyran-4-ylsulfonyl)phenyl)-2-methyl-N-(5-methyl-1H-pyrazol-3-yl)imidazo[1,2-c]pyrimidin-5-amine;

N-(2-(2-(dimethylamino)ethoxy)-5-(2-methyl-5-(5-methyl-1H-pyrazol-3-ylamino) imidazo[1,2-c]pyrimidin-7-yl)phenyl)cyclopropanesulfonamide;

N-(2-hydroxyethyl)-3-(2-methyl-5-(5-methyl-1H-pyrazol-3-ylamino)imidazo[1,2-c]pyrimidin-7-yl)benzenesulfonamide;

3-(2-methyl-5-(5-methyl-1H-pyrazol-3-ylamino)imidazo[1,2-c]pyrimidin-7-yl)-N-(2,2,2-trifluoroethyl)benzenesulfonamide;

7-(3-(2-(dimethylamino)ethoxy)phenyl)-2-methyl-N-(5-methyl-1H-pyrazol-3-yl)imidazo[1,2-c]pyrimidin-5-amine;

2-methyl-N-(5-methyl-1H-pyrazol-3-yl)-7-(3-(pyrrolidin-1-ylsulfonyl)phenyl) imidazo[1,2-c]pyrimidin-5-amine;

7-(3-(3-aminopyrrolidin-1-ylsulfonyl)phenyl)-2-methyl-N-(5-methyl-1H-pyrazol-3-yl)imidazo[1,2-c]pyrimidin-5-amine;

3-(2-methyl-5-(5-methyl-1H-pyrazol-3-ylamino)imidazo[1,2-c]pyrimidin-7-yl)-N-(3-(pyrrolidin-1-yl)propyl)benzenesulfonamide;

3-(2-methyl-5-(5-methyl-1H-pyrazol-3-ylamino)imidazo[1,2-c]pyrimidin-7-yl)-N-p-tolylbenzenesulfonamide;

N-(5-methyl-1H-pyrazol-3-yl)-7-(3-(4-methylpiperazin-1-ylsulfonyl)phenyl)imidazo[1,2-c]pyrimidin-5-amine;

7-(1-(ethylsulfonyl)-1H-indol-6-yl)-2-methyl-N-(5-methyl-1H-pyrazol-3-yl)imidazo[1,2-c]pyrimidin-5-amine;

N-(6-(2-methyl-5-(5-methyl-1H-pyrazol-3-ylamino)imidazo[1,2-c]pyrimidin-7-yl)-1H-indol-3-yl)ethanesulfonamide;

(3-(7-phenylimidazo[1,2-c]pyrimidin-5-ylamino)-1H-pyrazol-5-yl)methanol;

7-(3-(5-amino-2-methylthiophen-3-yl)phenyl)-2-methyl-N-(5-methyl-1H-pyrazol-3-yl)imidazo[1,2-c]pyrimidin-5-amine;

2-Methyl-N-(5-methyl-1H-pyrazol-3-yl)-7-phenyl-2,3-dihydroimidazo[1,2-c]pyrimidin-5-amine;

7-(3-(Ethylsulfonyl)phenyl)-N-(5-methyl-1H-pyrazol-3-yl)imidazo[1,2-c]pyrimidin-5-amine;

2-Methyl-N-(5-methyl-1H-pyrazol-3-yl)-7-(3-(piperazin-1-ylmethyl)phenyl) imidazo[1,2-c]pyrimidin-5-amine;

(S)-1-(3-(2-Methyl-5-(5-methyl-1H-pyrazol-3-ylamino) imidazo[1,2-c]pyrimidin-7-yl)phenylsulfonyl)pyrrolidin-3-ol;

2-Methyl-N-(5-methyl-1H-pyrazol-3-yl)-7-(3-(3-(methylamino)pyrrolidin-1-ylsulfonyl)phenyl)imidazo[1,2-c]pyrimidin-5-amine;

2-Methyl-N-(5-methyl-1H-pyrazol-3-yl)-7-(3-(piperidin-1-ylmethyl)phenyl) imidazo[1,2-c]pyrimidin-5-amine;

N,4-Dimethyl-5-(3-(2-methyl-5-(5-methyl-1H-pyrazol-3-ylamino)imidazo[1,2-c]pyrimidin-7-yl)phenyl)thiazol-2-amine;

2-Methyl-N-(5-methyl-1H-pyrazol-3-yl)-7-(3-(piperazin-1-ylsulfonyl)phenyl) imidazo[1,2-c]pyrimidin-5-amine;

3-(2-Methyl-5-(5-methyl-1H-pyrazol-3-ylamino)imidazo[1,2-c]pyrimidin-7-yl)-N-(pyrrolidin-3-yl)benzenesulfonamide;

N-Cyclopropyl-2-(3-(7-phenylimidazo[1,2-c]pyrimidin-5-ylamino)-1H-pyrazol-5-yl)acetamide;

N-(5-cyclopropyl-1H-pyrazol-3-yl)-2-(ethoxymethyl)-7-(3-(ethylsulfonyl)phenyl)imidazo[1,2-c]pyrimidin-5-amine;

N1-(3-(5-(5-cyclopropyl-1H-pyrazol-3-ylamino)-2-methylimidazo[1,2-c]pyrimidin-7-yl)phenyl)-N4-ethylsuccinamide;

N-(5-cyclopropyl-1H-pyrazol-3-yl)-7-(1-isopentyl-1H-pyrazol-4-yl)-2-methylimidazo[1,2-c]pyrimidin-5-amine;

7-(3-(diethylamino)pyrrolidin-1-yl)-2-methyl-N-(5-methyl-1H-pyrazol-3-yl)imidazo[1,2-c]pyrimidin-5-amine;

2(3-(dimethylamino)methyl-1-(ethylsulfonyl)-1H-indol-6-yl)-N-(5-methyl-1H-pyrazol-3-yl)pyrrolo[1,2-f][1,2,4]triazin-4-amine;

7-(4-(dimethylamino)phenyl)-N-(5-methyl-1H-pyrazol-3-yl)imidazo[1,2-f]pyrimidin-5-amine;

N-(5-methyl-1H-pyrazol-3-yl)-7-(pyridin-3-yl)imidazo[1,2-f]pyrimidin-5-amine;

1-(5-(5-methyl-1H-pyrazol-3-ylamino)imidazo[1,2-f]pyrimidin-7-yl)piperidin-4-ol;

7-(azepan-1-yl)-N-(5-methyl-1H-pyrazol-3-yl)imidazo[1,2-f]pyrimidin-5-amine;

7-(isoindolin-2-yl)-N-(5-methyl-1H-pyrazol-3-yl)imidazo[1,2-f]pyrimidin-5-amine;

7-(3,4-dihydroisoquinolin-2(1H)-yl)-N-(5-methyl-1H-pyrazol-3-yl)imidazo[1,2-f]pyrimidin-5-amine;

N-(5-methyl-1H-pyrazol-3-yl)-7-phenyl-[1,2,4]triazolo[1,5-f]pyrimidin-5-amine;

N-(5-methyl-1H-pyrazol-3-yl)-7-(piperidin-1-yl)-[1,2,4]triazolo[1,5-f]pyrimidin-5-amine;

N-(5-methyl-1H-pyrazol-3-yl)-6-phenylimidazo[1,2-a]pyrazin-8-amine;

N-(5-methyl-1H-pyrazol-3-yl)-6-(piperidin-1-yl)imidazo[1,2-a]pyrazin-8-amine;

N-(5-methyl-1H-pyrazol-3-yl)-7-phenylimidazo[1,5-f]pyrimidin-5-amine; and

N-(5-methyl-1H-pyrazol-3-yl)-7-(piperidin-1-yl)imidazo[1,5-f]pyrimidin-5-amine

Particular examples of kinase inhibitors according to the present invention also include, but are not limited to:

$N^5$-(5-methyl-1H-pyrazol-3-yl)-$N^7$-(2-(piperidin-1-yl)ethyl)imidazo[1,2-f]pyrimidine-5,7-diamine;

$N^7$-(2-(diethylamino)ethyl)-$N^5$-(5-methyl-1H-pyrazol-3-yl)imidazo[1,2-f]pyrimidine-5,7-diamine;

$N^7$-(2,5-difluorobenzyl)-$N^5$-(5-methyl-1H-pyrazol-3-yl)imidazo[1,2-f]pyrimidine-5,7-diamine;

$N^5$-(5-methyl-1H-pyrazol-3-yl)-$N^7$-(thiophen-2-ylmethyl)imidazo[1,2-f]pyrimidine-5,7-diamine;

$N^7$-(2-chlorophenethyl)-$N^5$-(5-methyl-1H-pyrazol-3-yl)imidazo[1,2-f]pyrimidine-5,7-diamine;

$N^7$-(3-chlorophenethyl)-$N^5$-(5-methyl-1H-pyrazol-3-yl)imidazo[1,2-f]pyrimidine-5,7-diamine;

$N^7$-(4-chlorophenethyl)-$N^5$-(5-methyl-1H-pyrazol-3-yl)imidazo[1,2-f]pyrimidine-5,7-diamine;

$N^5$-(5-methyl-1H-pyrazol-3-yl)-$N^7$-phenethylimidazo[1,2-f]pyrimidine-5,7-diamine;

$N^5$-(5-methyl-1H-pyrazol-3-yl)-$N^7$-(3-phenylpropyl)imidazo[1,2-f]pyrimidine-5,7-diamine;

$N^5$-(5-methyl-1H-pyrazol-3-yl)-$N^7$-(2-phenoxyethyl)imidazo[1,2-f]pyrimidine-5,7-diamine;

(R)-2-(5-(5-methyl-1H-pyrazol-3-ylamino)imidazo[1,2-f]pyrimidin-7-ylamino)-1-phenylethanol;

(S)-2-(5-(5-methyl-1H-pyrazol-3-ylamino)imidazo[1,2-f]pyrimidin-7-ylamino)-1-phenylethanol;

2-(methyl(5-(5-methyl-1H-pyrazol-3-ylamino)imidazo[1,2-f]pyrimidin-7-yl)amino)-1-phenylethanol;

(R)-2-(5-(5-methyl-1H-pyrazol-3-ylamino)imidazo[1,2-f]pyrimidin-7-ylamino)-4-phenylbutan-1-ol;

$N^5$-(5-methyl-1H-pyrazol-3-yl)-$N^7$-(pyridin-2-ylmethyl)imidazo[1,2-f]pyrimidine-5,7-diamine;

$N^7$-(3-fluorobenzyl)-$N^7$-methyl-$N^5$-(5-methyl-1H-pyrazol-3-yl)imidazo[1,2-f]pyrimidine-5,7-diamine;

$N^7$-(3-chlorobenzyl)-$N^7$-methyl-$N^5$-(5-methyl-1H-pyrazol-3-yl)imidazo[1,2-f]pyrimidine-5,7-diamine;

N$^7$-(3,4-dimethoxybenzyl)-N$^5$-(5-methyl-1H-pyrazol-3-yl) imidazo[1,2-f]pyrimidine-5,7-diamine;

N$^7$-(2-Methoxy-benzyl)-N$^5$-(5-methyl-1H-pyrazol-3-yl)-imidazo[1,2-c]pyrimidine-5,7-diamine;

N$^7$-(4-Methoxy-benzyl)-N$^5$-(5-methyl-1H-pyrazol-3-yl) imidazo[1,2-f]pyrimidine-5,7-diamine;

N$^7$-(1-Benzyl-piperidin-4-yl)-2-methyl-N$^5$-(5-methyl-1H-pyrazol-3-yl)-imidazo[1,2-c]pyrimidine-5,7-diamine;

N7,2-dimethyl-N-5-(5-methyl-1H-pyrazol-3-yl)-N-7-(1-methylpyrrolidin-3-yl)imidazo[1,2-c]pyrimidine-5,7-diamine;

6-(5-(5-methyl-1H-pyrazol-3-ylamino)imidazo[1,2-f]pyrimidin-7-ylamino)-1,2-dihydroindazol-3-one;

N-(4-(7-(5-methyl-1H-pyrazol-3-ylamino)imidazo[1,5-f]pyrimidin-5-ylthio)phenyl)cyclopropane carboxamide;

N-(4-(7-(5-methyl-1H-pyrazol-3-ylamino)imidazo[1,5-f]pyrimidin-5-ylthio)phenyl)acetamide;

N-(4-(7-(5-methyl-1H-pyrazol-3-ylamino)imidazo[1,2-f]pyrimidin-5-ylthio)phenyl)cyclopropane carboxamide;

N-(4-(7-(5-methyl-1H-pyrazol-3-ylamino)imidazo[1,2-f]pyrimidin-5-ylthio)phenyl)acetamide;

N-(4-(6-(5-methyl-1H-pyrazol-3-ylamino)imidazo[1,2-a]pyrazin-8-ylthio)phenyl)cyclopropane carboxamide;

N-(4-(6-(5-methyl-1H-pyrazol-3-ylamino)imidazo[1,2-a]pyrazin-8-ylthio)phenyl)acetamide;

N-(4-(7-(5-methyl-1H-pyrazol-3-ylamino)-[1,2,4]triazolo[1,5-f]pyrimidin-5-ylthio)phenyl)cyclopropane carboxamide; and N-(4-(7-(5-methyl-1H-pyrazol-3-ylamino)-[1,2,4]triazolo[1,5-f]pyrimidin-5-ylthio)phenyl)acetamide.

Further, particular examples of kinase inhibitors according to the present invention include, but are not limited to:

N-(4-(5-(5-Methyl-1H-pyrazol-3-ylamino)imidazo[1,2-f]pyrimidin-7-ylthio)phenyl)cyclopropane carboxamide;

N-(4-(5-(5-Cyclopropyl-1H-pyrazol-3-ylamino)imidazo[1,2-f]pyrimidin-7-ylthio)phenyl)cyclopropane carboxamide;

N-(4-(5-(3-Cyclopropyl-1H-pyrazol-5-ylamino)imidazo[1,2-f]pyrimidin-7-ylthio)phenyl)acetamide;

N-(4-(5-(5-Methyl-1H-pyrazol-3-ylamino)imidazo[1,2-f]pyrimidin-7-ylthio)phenyl)acetamide;

7-(4-Aminophenylthio)-N-(5-methyl-1H-pyrazol-3-yl)imidazo[1,2-f]pyrimidin-5-amine;

N-(4-(5-(5-Methyl-1H-pyrazol-3-ylamino)-[1,2,4]triazolo[1,5-f]pyrimidin-7-ylthio)phenyl)cyclopropane carboxamide;

N-(4-(5-(5-Methyl-1H-pyrazol-3-ylamino)-[1,2,4]triazolo[1,5-f]pyrimidin-7-ylthio)phenyl)acetamide;

N-(4-(8-(5-Methyl-1H-pyrazol-3-ylamino)imidazo[1,2-a]pyrazin-6-ylthio)phenyl)cyclopropane carboxamide;

N-(4-(8-(5-Methyl-1H-pyrazol-3-ylamino)imidazo[1,2-a]pyrazin-6-ylthio)phenyl)acetamide;

N-(4-(5-(5-Methyl-1H-pyrazol-3-ylamino)imidazo[1,2-a]pyrimidin-7-ylthio)phenyl)cyclopropane carboxamide;

N-(4-(5-(5-Methyl-1H-pyrazol-3-ylamino)imidazo[1,2-a]pyrimidin-7-ylthio)phenyl)acetamide;

N-(4-(5-(5-methyl-1H-pyrazol-3-ylamino)imidazo[1,2-f]pyrimidin-7-ylthio)phenyl)thiophene-2-sulfonamide;

N-(4-(5-(5-methyl-1H-pyrazol-3-ylamino)imidazo[1,2-f]pyrimidin-7-ylthio)phenyl)cyclopropanesulfonamide;

N-(4-(5-(5-methyl-1H-pyrazol-3-ylamino)imidazo[1,2-f]pyrimidin-7-ylthio)phenyl)propane-2-sulfonamide;

1-amino-N-(4-(5-(5-methyl-1H-pyrazol-3-ylamino)imidazo[1,2-f]pyrimidin-7-ylthio)phenyl)cyclopropanecarboxamide;

(R)-2-amino-3-methyl-N-(4-(5-(5-methyl-1H-pyrazol-3-ylamino)imidazo[1,2-f]pyrimidin-7-ylthio)phenyl)butanamide;

N-(4-(5-(5-cyclopropyl-1H-pyrazol-3-ylamino)imidazo[1,2-f]pyrimidin-7-ylthio)phenyl)-2-methoxyacetamide;

N-(4-(5-(5-methyl-1H-pyrazol-3-ylamino)imidazo[1,2-f]pyrimidin-7-ylthio)phenyl)picolinamide;

N-(4-(5-(5-cyclopropyl-1H-pyrazol-3-ylamino)imidazo[1,2-f]pyrimidin-7-ylthio)phenyl)morpholine-4-carboxamide;

2-methoxyethyl 4-(5-(5-methyl-1H-pyrazol-3-ylamino)imidazo[1,2-f]pyrimidin-7-ylthio)phenylcarbamate;

Ethyl 4-(5-(5-methyl-1H-pyrazol-3-ylamino)imidazo[1,2-f]pyrimidin-7-ylthio)phenylcarbamate;

Isobutyl 4-(5-(5-methyl-1H-pyrazol-3-ylamino)imidazo[1,2-f]pyrimidin-7-ylthio)phenylcarbamate;

Ethyl 4-(5-(5-cyclopropyl-1H-pyrazol-3-ylamino)imidazo[1,2-f]pyrimidin-7-ylthio)phenylcarbamate;

{4-[5-(5-Cyclopropyl-1H-pyrazol-3-ylamino)-imidazo[1,2-c]pyrimidin-7-ylsulfanyl]-phenyl}-carbamic acid but-2-ynyl ester;

{4-[5-(5-Cyclopropyl-1H-pyrazol-3-ylamino)-imidazo[1,2-c]pyrimidin-7-ylsulfanyl]-phenyl}-carbamic acid allyl ester;

Propyl 4-(5-(5-cyclopropyl-1H-pyrazol-3-ylamino)imidazo[1,2-f]pyrimidin-7-ylthio)phenylcarbamate;

N-(4-(5-(5-methyl-1H-pyrazol-3-ylamino)imidazo[1,2-f]pyrimidin-7-ylthio)phenyl)pyrrolidine-2-carboxamide;

N-(4-(5-(5-methyl-1H-pyrazol-3-ylamino)imidazo[1,2-f]pyrimidin-7-ylthio)phenyl)butyramide;

N-(4-(5-(5-methyl-1H-pyrazol-3-ylamino)imidazo[1,2-f]pyrimidin-7-ylthio)phenyl)cyclobutanecarboxamide;

N-(4-(5-(5-methyl-1H-pyrazol-3-ylamino)imidazo[1,2-f]pyrimidin-7-ylthio)phenyl)isobutyramide;

2-methoxy-N-(4-(5-(5-methyl-1H-pyrazol-3-ylamino)imidazo[1,2-f]pyrimidin-7-ylthio)phenyl)acetamide;

N-(4-(5-(5-methyl-1H-pyrazol-3-ylamino)imidazo[1,2-f]pyrimidin-7-ylthio)phenyl)-2-propoxyacetamide;

2-ethoxy-N-(4-(5-(5-methyl-1H-pyrazol-3-ylamino)imidazo[1,2-f]pyrimidin-7-ylthio)phenyl)acetamide;

2-(allyloxy)-N-(4-(5-(5-methyl-1H-pyrazol-3-ylamino)imidazo[1,2-f]pyrimidin-7-ylthio)phenyl)acetamide;

2-(dimethylamino)-N-(4-(5-(5-methyl-1H-pyrazol-3-ylamino)imidazo[1,2-f]pyrimidin-7-ylthio)phenyl)acetamide;

2-(cyclopropylamino)-N-(4-(5-(5-methyl-1H-pyrazol-3-ylamino)imidazo[1,2-f]pyrimidin-7-ylthio)phenyl)acetamide;

2-(1H-imidazol-1-yl)-N-(4-(5-(5-methyl-1H-pyrazol-3-ylamino)imidazo[1,2-f]pyrimidin-7-ylthio)phenyl)acetamide;

N-(4-(5-(5-cyclopropyl-1H-pyrazol-3-ylamino)imidazo[1,2-f]pyrimidin-7-ylthio)phenyl)-2-(ethyl(methy)amino)acetamide;

N-(4-(5-(5-cyclopropyl-1H-pyrazol-3-ylamino)imidazo[1,2-f]pyrimidin-7-ylthio)phenyl)-2-(dimethylamino)acetamide;

N-(4-(5-(5-cyclopropyl-1H-pyrazol-3-ylamino)imidazo[1,2-f]pyrimidin-7-ylthio)phenyl)-2-(cyclopropylamino)acetamide;

N-(4-(5-(5-cyclopropyl-1H-pyrazol-3-ylamino)imidazo[1,2-f]pyrimidin-7-ylthio)phenyl)-2-ethoxyacetamide;

2-(ethyl(methyl)amino)-N-(4-(5-(5-methyl-1H-pyrazol-3-ylamino)imidazo[1,2-f]pyrimidin-7-ylthio)phenyl)acetamide;

N-(4-(2-(hydroxymethyl)-5-(5-methyl-1H-pyrazol-3-ylamino)imidazo[1,2-f]pyrimidin-7-ylthio)phenyl)-2-methoxyacetamide;
N-(4-(5-(5-cyclopropyl-1H-pyrazol-3-ylamino)imidazo[1,2-f]pyrimidin-7-ylthio) phenyl)nicotinamide;
N-(4-(5-(5-cyclopropyl-1H-pyrazol-3-ylamino)imidazo[1,2-f]pyrimidin-7-ylthio)phenyl)-2-methylcyclopropanecarboxamide;
N-(4-(5-(5-cyclopropyl-1H-pyrazol-3-ylamino)imidazo[1,2-f]pyrimidin-7-ylthio)phenyl)pyrrolidine-1-carboxamide;
N-(4-(5-(5-cyclopropyl-1H-pyrazol-3-ylamino)imidazo[1,2-f]pyrimidin-7-ylthio)phenyl)-3-methylbutanamide;
N-(4-(5-(5-cyclopropyl-1H-pyrazol-3-ylamino)-2-(methoxymethyl)imidazo[1,2-f]pyrimidin-7-ylthio)phenyl)acetamide;
N-(4-(5-(5-cyclopropyl-1H-pyrazol-3-ylamino)imidazo[1,2-f]pyrimidin-7-ylthio)phenyl) isonicotinamide;
6-chloro-N-(4-(5-(5-cyclopropyl-1H-pyrazol-3-ylamino)imidazo[1,2-f]pyrimidin-7-ylthio)phenyl)nicotinamide;
N-(4-(2-(Hydroxymethyl)-5-(5-methyl-1H-pyrazol-3-ylamino)imidazo[1,2-f]pyrimidin-7-ylthio)phenyl)acetamide;
N-(4-(2-(Hydroxymethyl)-5-(5-methyl-1H-pyrazol-3-ylamino)imidazo[1,2-f]pyrimidin-7-ylthio)phenyl)cyclopropanecarboxamide;
N-{4-[5-(5-Cyclopropyl-1H-pyrazol-3-ylamino)-2-dimethylaminomethyl-imidazo[1,2-c]pyrimidin-7-ylsulfanyl]-phenyl}acetamide;
N-(4-(5-(5-Cyclopropyl-1H-pyrazol-3-ylamino)-2-((4-methylpiperazin-1-yl)methyl)imidazo[1,2-f]pyrimidin-7-ylthio)phenyl)acetamide;
N-(5-methyl-1H-pyrazol-3-yl)-7-(o-tolylthio)imidazo[1,2-f]pyrimidin-5-amine;
((5-fluoro-2-(5-(5-methyl-1H-pyrazol-3-ylamino)imidazo[1,2-f]pyrimidin-7-ylthio)phenyl)methanol;
7-(3-aminophenylthio)-N-(5-methyl-1H-pyrazol-3-yl)imidazo[1,2-f]pyrimidin-5-amine;
Methyl 3-(5-(5-methyl-1H-pyrazol-3-ylamino)imidazo[1,2-f]pyrimidin-7-ylthio)benzoate;
3-(5-(5-methyl-1H-pyrazol-3-ylamino)imidazo[1,2-f]pyrimidin-7-ylthio)benzoic acid;
Methyl 4-(5-(5-methyl-1H-pyrazol-3-ylamino)imidazo[1,2-f]pyrimidin-7-ylthio)benzoate;
4-(5-(5-Methyl-1H-pyrazol-3-ylamino)imidazo[1,2-f]pyrimidin-7-ylthio)benzoic acid;
(E)-methyl 3-(4-(5-(5-methyl-1H-pyrazol-3-ylamino)imidazo[1,2-f]pyrimidin-7-ylthio)phenyl)acrylate;
3-(5-(5-methyl-1H-pyrazol-3-ylamino)imidazo[1,2-f]pyrimidin-7-ylthio)benzamide;
7-(2-Amino-4-chlorophenylthio)-N-(5-methyl-1H-pyrazol-3-yl)imidazo[1,2-f]pyrimidin-5-amine;
2-(3-(5-(5-methyl-1H-pyrazol-3-ylamino)imidazo[1,2-f]pyrimidin-7-ylthio)phenyl)acetic acid;
N-cyclopropyl-2-(3-(5-(5-methyl-1H-pyrazol-3-ylamino)imidazo[1,2-f]pyrimidin-7-ylthio)phenyl)acetamide;
N-methyl-2-(3-(5-(5-methyl-1H-pyrazol-3-ylamino)imidazo[1,2-f]pyrimidin-7-ylthio)phenyl)acetamide;
N-ethyl-2-(3-(5-(5-methyl-1H-pyrazol-3-ylamino)imidazo[1,2-f]pyrimidin-7-ylthio)phenyl)acetamide;
4-(5-(5-cyclopropyl-1H-pyrazol-3-ylamino)imidazo[1,2-f]pyrimidin-7-ylthio)-N-ethylbenzamide;
(4-(5-(5-cyclopropyl-1H-pyrazol-3-ylamino)imidazo[1,2-f]pyrimidin-7-ylthio)phenyl)(piperazin-1-yl)methanone;
N-cyclopropyl-4-(5-(5-cyclopropyl-1H-pyrazol-3-ylamino)imidazo[1,2-f]pyrimidin-7-ylthio)benzamide;
Azetidin-1-yl(4-(5-(5-cyclopropyl-1H-pyrazol-3-ylamino)imidazo[1,2-f]pyrimidin-7-ylthio)phenyl)methanone;
4-(5-(5-cyclopropyl-1H-pyrazol-3-ylamino)imidazo[1,2-f]pyrimidin-7-ylthio)-N-(pyrrolidin-3-yl)benzamide;
4-(5-(5-cyclopropyl-1H-pyrazol-3-ylamino)imidazo[1,2-f]pyrimidin-7-ylthio)-N-(piperidin-4-yl)benzamide;
4-(5-(5-cyclopropyl-1H-pyrazol-3-ylamino)imidazo[1,2-f]pyrimidin-7-ylthio)-N-(piperidin-3-yl)benzamide;
4-(5-(5-cyclopropyl-1H-pyrazol-3-ylamino)imidazo[1,2-f]pyrimidin-7-ylthio)-N-methoxybenzamide;
4-(5-(5-cyclopropyl-1H-pyrazol-3-ylamino)imidazo[1,2-f]pyrimidin-7-ylthio)-N',N'-dimethylbenzohydrazide;
4-(5-(5-cyclopropyl-1H-pyrazol-3-ylamino)imidazo[1,2-f]pyrimidin-7-ylthio)-N-(2-(dimethylamino)ethyl)benzamide;
4-(5-(5-cyclopropyl-1H-pyrazol-3-ylamino)imidazo[1,2-f]pyrimidin-7-ylthio)-N-(2-hydroxyethyl)benzamide;
(4-(5-(5-cyclopropyl-1H-pyrazol-3-ylamino)imidazo[1,2-f]pyrimidin-7-ylthio)phenyl)(morpholino)methanone;
N-cyclopropyl-4-(5-(5-methyl-1H-pyrazol-3-ylamino)imidazo[1,2-f]pyrimidin-7-ylthio)benzamide;
N-ethyl-4-(5-(5-methyl-1H-pyrazol-3-ylamino)imidazo[1,2-f]pyrimidin-7-ylthio)benzamide;
N-(5-cyclopropyl-1H-pyrazol-3-yl)-7-(4-(5-ethyl-1,3,4-oxadiazol-2-yl)phenylthio)imidazo[1,2-f]pyrimidin-5-amine;
7-(4-(5-ethyl-1,3,4-oxadiazol-2-yl)phenylthio)-N-(5-methyl-1H-pyrazol-3-yl)imidazo[1,2-f]pyrimidin-5-amine;
7-(4-(1,3,4-Oxadiazol-2-yl)phenylthio)-N-(5-cyclopropyl-1H-pyrazol-3-yl)imidazo[1,2-f]pyrimidin-5-amine;
7-(4-(1,3,4-oxadiazol-2-yl)phenylthio)-N-(5-methyl-1H-pyrazol-3-yl)imidazo[1,2-f]pyrimidin-5-amine;
7-(4-(5-Methyl-1,3,4-oxadiazol-2-yl)phenylthio)-N-(5-methyl-1H-pyrazol-3-yl)imidazo[1,2-f]pyrimidin-5-amine;
N-(5-Cyclopropyl-1H-pyrazol-3-yl)-7-(4-(5-methyl-1,3,4-oxadiazol-2-yl)phenylthio)imidazo[1,2-f]pyrimidin-5-amine;
N-{3-[5-(5-Cyclopropyl-1H-pyrazol-3-ylamino)-2-methyl-imidazo[1,2-c]pyrimidin-7-ylsulfanyl]-phenyl}-acetamide;
N-(4-(5-(5-cyclopropyl-1H-pyrazol-3-ylamino)-2-((dimethylamino)methyl)imidazo[1,2-c]pyrimidin-7-ylthio)phenyl)acetamide;
N-(4-(2-methyl-5-(5-methyl-1H-pyrazol-3-ylamino)imidazo[1,2-c]pyrimidin-7-ylthio)phenyl)cyclopropanecarboxamide;
N-(4-(2-ethyl-5-(5-methyl-1H-pyrazol-3-ylamino)imidazo[1,2-c]pyrimidin-7-ylthio)phenyl)cyclopropanecarboxamide;
N-(4-(2-((dimethylamino)methyl)-5-(5-methyl-1H-pyrazol-3-ylamino)imidazo[1,2-c]pyrimidin-7-ylthio)phenyl)cyclopropanecarboxamide;
N-(4-(5-(5-methyl-1H-pyrazol-3-ylamino)-2-((methylamino)methyl) imidazo[1,2-c]pyrimidin-7-ylthio)phenyl)cyclopropanecarboxamide;
N-(4-(2-((2-hydroxyethylamino)methyl)-5-(5-methyl-1H-pyrazol-3-ylamino)imidazo[1,2-c]pyrimidin-7-ylthio)phenyl)cyclopropanecarboxamide;
N-{4-[2-Methyl-5-(5-methyl-1H-pyrazol-3-ylamino)-imidazo[1,2-c]pyrimidin-7-ylsulfanyl]-phenyl}-acetamide;
N-(4-(5-(5-cyclopropyl-1H-pyrazol-3-ylamino)-2-(methoxymethyl)imidazo[1,2-c]pyrimidin-7-ylthio)phenyl)-2-methoxyacetamide;
Ethyl 2-(4-(5-(5-methyl-1H-pyrazol-3-ylamino)imidazo[1,2-c]pyrimidin-7-ylthio)phenylamino)-2-oxoacetate;

N-(4-(5-(5-methyl-1H-pyrazol-3-ylamino)imidazo[1,2-c]pyrimidin-7-ylthio)phenyl)tetrahydrofuran-2-carboxamide;
N-(4-(2-methyl-5-(5-methyl-1H-pyrazol-3-ylamino)imidazo[1,2-c]pyrimidin-7-ylthio)phenyl)furan-2-carboxamide;
(S)—N-(4-(2-methyl-5-(5-methyl-1H-pyrazol-3-ylamino)imidazo[1,2-c]pyrimidin-7-ylthio)phenyl)tetrahydrofuran-2-carboxamide;
N-(4-(2-methyl-5-(5-methyl-1H-pyrazol-3-ylamino)imidazo[1,2-c]pyrimidin-7-ylthio)phenyl)isoxazole-5-carboxamide;
5-methyl-N-(4-(2-methyl-5-(5-methyl-1H-pyrazol-3-ylamino)imidazo[1,2-c]pyrimidin-7-ylthio)phenyl)isoxazole-3-carboxamide;
4-methyl-N-(4-(2-methyl-5-(5-methyl-1H-pyrazol-3-ylamino)imidazo[1,2-c]pyrimidin-7-ylthio)phenyl)oxazole-5-carboxamide;
N-(4-(5-(5-cyclopropyl-1H-pyrazol-3-ylamino)-2-methylimidazo[1,2-c]pyrimidin-7-ylthio)phenyl)-5-methylfuran-2-carboxamide;
N-(4-(5-(5-cyclopropyl-1H-pyrazol-3-ylamino)-2-methylimidazo[1,2-c]pyrimidin-7-ylthio)phenyl)-1,5-dimethyl-1H-pyrazole-3-carboxamide;
N-(4-(5-(5-cyclopropyl-1H-pyrazol-3-ylamino)-2-methylimidazo[1,2-c]pyrimidin-7-ylthio)phenyl)-1,3-dimethyl-1H-pyrazole-5-carboxamide;
N1-(4-(5-(5-cyclopropyl-1H-pyrazol-3-ylamino)-2-methylimidazo[1,2-c]pyrimidin-7-ylthio)phenyl)-N2-ethyl-N2-methyloxalamide;
N1-(4-(5-(5-cyclopropyl-1H-pyrazol-3-ylamino)-2-methylimidazo[1,2-c]pyrimidin-7-ylthio)phenyl)-N2-(thiazol-2-yl)oxalamide;
N-(4-(4-(5-methyl-1H-pyrazol-3-ylamino)pyrrolo[1,2-f][1,2,4]triazin-2-ylthio)phenyl)acetamide;
N-(4-(5-(5-methyl-1H-1,2,4-triazol-3-ylamino)imidazo[1,2-f]pyrimidin-7-ylthio)phenyl)cyclopropane carboxamide;
N-(4-(5-(5-cyclopropyl-1H-pyrazol-3-ylamino)imidazo[1,2-f]pyrimidin-7-ylthio)phenyl)thiophene-2-sulfonamide;
N-(4-(5-(5-isopropyl-1H-pyrazol-3-ylamino)imidazo[1,2-f]pyrimidin-7-ylthio)phenyl)cyclopropane carboxamide;
N-(4-(5-(5-isopropyl-1H-pyrazol-3-ylamino)imidazo[1,2-f]pyrimidin-7-ylthio)phenyl)acetamide;
N-(4-(5-(5-ethyl-1H-pyrazol-3-ylamino)imidazo[1,2-f]pyrimidin-7-ylthio)phenyl)cyclopropane carboxamide;
N-(4-(5-(5-ethyl-1H-pyrazol-3-ylamino)imidazo[1,2-f]pyrimidin-7-ylthio)phenyl)acetamide;
N-(4-(5-(1H-pyrazol-3-ylamino)imidazo[1,2-f]pyrimidin-7-ylthio)phenyl)cyclopropane carboxamide;
N-(4-(5-(5-propyl-1H-pyrazol-3-ylamino)imidazo[1,2-f]pyrimidin-7-ylthio)phenyl)cyclopropane carboxamide;
N-(4-(5-(1H-indazol-3-ylamino)imidazo[1,2-f]pyrimidin-7-ylthio)phenyl)cyclopropane carboxamide;
N-(4-(5-(5-(3-hydroxypropyl)-1H-pyrazol-3-ylamino)imidazo[1,2-f]pyrimidin-7-ylthio)phenyl)cyclopropane carboxamide;
N-(4-(5-(5-(3-methoxypropyl)-1H-pyrazol-3-ylamino)imidazo[1,2-f]pyrimidin-7-ylthio)phenyl)cyclopropane carboxamide;
N-(4-(5-(5-cyclobutyl-1H-pyrazol-3-ylamino)imidazo[1,2-f]pyrimidin-7-ylthio)phenyl)cyclopropane carboxamide;
N-(4-(5-(5-cyclopentyl-1H-pyrazol-3-ylamino)imidazo[1,2-f]pyrimidin-7-ylthio)phenyl)cyclopropane carboxamide;
N-(4-(3-methyl-5-(5-methyl-1H-pyrazol-3-ylamino)imidazo[1,2-f]pyrimidin-7-ylthio)phenyl)cyclopropane carboxamide;
N-(4-(3-fluoro-5-(5-methyl-1H-pyrazol-3-ylamino)imidazo[1,2-f]pyrimidin-7-ylthio)phenyl)cyclopropane carboxamide;
N-(4-(3-chloro-5-(5-methyl-1H-pyrazol-3-ylamino)imidazo[1,2-f]pyrimidin-7-ylthio)phenyl)cyclopropane carboxamide;
N-(4-(3-bromo-5-(5-methyl-1H-pyrazol-3-ylamino)imidazo[1,2-f]pyrimidin-7-ylthio)phenyl)cyclopropane carboxamide;
N-(4-(5-(5-methyl-1H-pyrazol-3-ylamino)-2-((4-methylpiperazin-1-yl)methyl)imidazo[1,2-f]pyrimidin-7-ylthio)phenyl)cyclopropane carboxamide;
N-(4-(2-(aminomethyl)-5-(5-methyl-1H-pyrazol-3-ylamino)imidazo[1,2-f]pyrimidin-7-ylthio)phenyl)cyclopropane carboxamide;
N-(4-(5-(5-methyl-1H-pyrazol-3-ylamino)-2-(morpholinomethyl)imidazo[1,2-f]pyrimidin-7-ylthio)phenyl)cyclopropane carboxamide;
N-(4-(3-amino-5-(5-methyl-1H-pyrazol-3-ylamino)imidazo[1,2-f]pyrimidin-7-ylthio)phenyl)cyclopropane carboxamide;
N-(4-(2-amino-5-(5-methyl-1H-pyrazol-3-ylamino)imidazo[1,2-f]pyrimidin-7-ylthio)phenyl)cyclopropane carboxamide;
7-(4-(cyclopropanecarboxamido)phenylthio)-N-methyl-5-(5-methyl-1H-pyrazol-3-ylamino)imidazo[1,2-f]pyrimidine-2-carboxamide;
6-(5-(5-methyl-1H-pyrazol-3-ylamino)imidazo[1,2-f]pyrimidin-7-ylthio)-1,2-dihydroindazol-3-one;
N-(4-(5-(5-methyl-1H-pyrazol-3-ylamino)imidazo[1,2-f]pyrimidin-7-ylthio)phenyl)-2-morpholinoacetamide;
3-(dimethylamino)-N-(4-(5-(5-methyl-1H-pyrazol-3-ylamino)imidazo[1,2-f]pyrimidin-7-ylthio)phenyl)propanamide;
N-(4-(5-(5-methyl-1H-pyrazol-3-ylamino)imidazo[1,2-f]pyrimidin-7-ylthio)phenyl)-2-(methylamino)acetamide;
N-(2-(dimethylamino)ethyl)-4-(5-(5-methyl-1H-pyrazol-3-ylamino)imidazo[1,2-f]pyrimidin-7-ylthio)benzamide;
4-(5-(5-methyl-1H-pyrazol-3-ylamino)imidazo[1,2-f]pyrimidin-7-ylthio)-N-(2-morpholinoethyl)benzamide;
N-(5-methyl-1H-pyrazol-3-yl)-7-(4-(methylamino)phenylthio)imidazo[1,2-f]pyrimidin-5-amine;
7-(4-(cyclopropylmethylamino)phenylthio)-N-(5-methyl-1H-pyrazol-3-yl)imidazo[1,2-f]pyrimidin-5-amine;
2-amino-2-methyl-N-(4-(5-(5-methyl-1H-pyrazol-3-ylamino)imidazo[1,2-f]pyrimidin-7-ylthio)phenyl)propanamide;
N-(4-(5-(5-methyl-1H-pyrazol-3-ylamino)imidazo[1,2-f]pyrimidin-7-ylthio)phenyl)propionamide;
1-amino-N-(4-(5-(5-methyl-1H-pyrazol-3-ylamino)imidazo[1,2-f]pyrimidin-7-ylthio)phenyl)cyclobutanecarboxamide;
1-amino-N-(4-(5-(5-methyl-1H-pyrazol-3-ylamino)imidazo[1,2-f]pyrimidin-7-ylthio)phenyl)cyclopentanecarboxamide;
N-(4-(5-(5-methyl-1H-pyrazol-3-ylamino)imidazo[1,2-f]pyrimidin-7-ylthio)phenyl)pyrrolidine-3-carboxamide;
N-(4-(5-(5-methyl-1H-pyrazol-3-ylamino)imidazo[1,2-f]pyrimidin-7-ylthio)phenyl)-tetrahydro-2H-pyran-4-carboxamide;
N-(4-(5-(5-methyl-1H-pyrazol-3-ylamino)imidazo[1,2-f]pyrimidin-7-ylthio)phenyl)piperidine-4-carboxamide;
2-amino-N-(4-(5-(5-methyl-1H-pyrazol-3-ylamino)imidazo[1,2-f]pyrimidin-7-ylthio)phenyl)cyclopentanecarboxamide;

3-amino-N-(4-(5-(5-methyl-1H-pyrazol-3-ylamino)imidazo[1,2-f]pyrimidin-7-ylthio)phenyl)cyclopentanecarboxamide;
N-(4-(5-(5-methyl-1H-pyrazol-3-ylamino)imidazo[1,2-f]pyrimidin-7-ylthio)phenyl)piperidine-2-carboxamide;
N-(4-(5-(5-methyl-1H-pyrazol-3-ylamino)imidazo[1,2-f]pyrimidin-7-ylthio)phenyl)piperidine-3-carboxamide;
N-(4-(5-(5-methyl-1H-pyrazol-3-ylamino)imidazo[1,2-f]pyrimidin-7-ylthio)phenyl)morpholine-4-carboxamide;
N-(4-(5-(5-methyl-1H-pyrazol-3-ylamino)imidazo[1,2-f]pyrimidin-7-ylthio)phenyl)piperazine-1-carboxamide;
1-cyclopropyl-3-(4-(5-(5-methyl-1H-pyrazol-3-ylamino)imidazo[1,2-f]pyrimidin-7-ylthio)phenyl)urea;
1,1-diethyl-3-(4-(5-(5-methyl-1H-pyrazol-3-ylamino)imidazo[1,2-f]pyrimidin-7-ylthio)phenyl)urea;
1-ethyl-3-(4-(5-(5-methyl-1H-pyrazol-3-ylamino)imidazo[1,2-f]pyrimidin-7-ylthio)phenyl)urea;
1-isopropyl-3-(4-(5-(5-methyl-1H-pyrazol-3-ylamino)imidazo[1,2-f]pyrimidin-7-ylthio)phenyl)urea;
isopropyl 4-(5-(5-methyl-1H-pyrazol-3-ylamino)imidazo[1,2-f]pyrimidin-7-ylthio)phenylcarbamate;
cyclopropyl 4-(5-(5-methyl-1H-pyrazol-3-ylamino)imidazo[1,2-f]pyrimidin-7-ylthio)phenylcarbamate;
cyclobutyl 4-(5-(5-methyl-1H-pyrazol-3-ylamino)imidazo[1,2-f]pyrimidin-7-ylthio)phenylcarbamate;
cyclopentyl 4-(5-(5-methyl-1H-pyrazol-3-ylamino)imidazo[1,2-f]pyrimidin-7-ylthio)phenylcarbamate;
pyrrolidin-3-yl 4-(5-(5-methyl-1H-pyrazol-3-ylamino)imidazo[1,2-f]pyrimidin-7-ylthio)phenylcarbamate;
2-methyl-N-(4-(5-(5-methyl-1H-pyrazol-3-ylamino)imidazo[1,2-f]pyrimidin-7-ylthio)phenyl)propane-1-sulfonamide;
N-(4-(5-(5-methyl-1H-pyrazol-3-ylamino)imidazo[1,2-f]pyrimidin-7-ylthio)phenyl)benzenesulfonamide;
N-(4-(5-(5-methyl-1H-pyrazol-3-ylamino)imidazo[1,2-f]pyrimidin-7-ylthio)phenyl)thiazole-5-sulfonamide;
1-methyl-N-(4-(5-(5-methyl-1H-pyrazol-3-ylamino)imidazo[1,2-f]pyrimidin-7-ylthio)phenyl)-1H-imidazole-5-sulfonamide;
N-(4-(2-methyl-5-(5-methyl-1H-pyrazol-3-ylamino)-[1,2,4]triazolo[1,5-f]pyrimidin-7-ylthio)phenyl)acetamide;
N-(4-(2-methyl-5-(5-methyl-1H-pyrazol-3-ylamino)-[1,2,4]triazolo[1,5-f]pyrimidin-7-ylthio)phenyl)cyclopropane carboxamide;
N-(4-(5-(1H-indazol-3-ylamino)-[1,2,4]triazolo[1,5-f]pyrimidin-7-ylthio)phenyl)cyclopropane carboxamide;
N-(4-(2-amino-5-(5-methyl-1H-pyrazol-3-ylamino)-[1,2,4]triazolo[1,5-f]pyrimidin-7-ylthio)phenyl)cyclopropane carboxamide;
N-(4-(2-methyl-8-(5-methyl-1H-pyrazol-3-ylamino)imidazo[1,2-a]pyrazin-6-ylthio)phenyl)cyclopropane carboxamide;
N-(4-(3-methyl-8-(5-methyl-1H-pyrazol-3-ylamino)imidazo[1,2-a]pyrazin-6-ylthio)phenyl)cyclopropane carboxamide;
N-(4-(3-methyl-5-(5-methyl-1H-pyrazol-3-ylamino)imidazo[1,5-f]pyrimidin-7-ylthio)phenyl)cyclopropane carboxamide;
N-(4-(3-methyl-5-(5-methyl-1H-pyrazol-3-ylamino)imidazo[1,5-f]pyrimidin-7-ylthio)phenyl)acetamide;
N-(4-(5-(5-methyl-1H-pyrazol-3-ylamino)imidazo[1,5-f]pyrimidin-7-ylthio)phenyl)cyclopropane carboxamide;
N-(4-(5-(5-methyl-1H-pyrazol-3-ylamino)imidazo[1,5-f]pyrimidin-7-ylthio)phenyl)acetamide;
N-(4-(5-(1H-indazol-3-ylamino)imidazo[1,5-f]pyrimidin-7-ylthio)phenyl)cyclopropane carboxamide; and
N-(4-(3-chloro-5-(5-methyl-1H-pyrazol-3-ylamino)imidazo[1,5-f]pyrimidin-7-ylthio)phenyl)cyclopropane carboxamide.

Further, particular examples of kinase inhibitors according to the present invention include, but are not limited to N-(4-(5-(5-Methyl-1H-pyrazol-3-ylamino)imidazo[1,2-f]pyrimidin-7-yloxy)phenyl)acetamide.

It is noted that the compounds of the present invention may be in the form of a pharmaceutically acceptable salt, biohydrolyzable ester, biohydrolyzable amide, biohydrolyzable carbamate, solvate, hydrate or prodrug thereof. For example, the compound optionally comprises a substituent that is convertible in vivo to a different substituent such as a hydrogen.

It is further noted that the compounds of the present invention may optionally be solely or predominantly in the enol tautomer in its active state. It is further noted that the compound may be present in a mixture of stereoisomers, or the compound comprises a single stereoisomer.

The invention also provides pharmaceutical compositions comprising, as an active ingredient, a compound according to any one of the above embodiments and variations. In addition, the composition may be a solid or liquid formulation adapted for oral administration. In a further variation, the pharmaceutical composition may be a tablet. In yet another variation, the pharmaceutical composition may be a liquid formulation adapted for parenteral administration.

In one embodiment, there is provided the pharmaceutical composition comprising a compound according to any one of the above embodiments and variations wherein the composition is adapted for administration by a route selected from the group consisting of orally, parenterally, intraperitoneally, intravenously, intraarterially, transdermally, sublingually, intramuscularly, rectally, transbuccally, intranasally, liposomally, via inhalation, vaginally, intraoccularly, via local delivery (for example by catheter or stent), subcutaneously, intraadiposally, intraarticularly, and intrathecally.

The invention also provides a kit comprising a compound or composition according to any one of the above embodiments and variations, and instructions which comprise one or more forms of information selected from the group consisting of indicating a disease state for which the compound is to be administered, storage information for the compound, dosing information and instructions regarding how to administer the compound. In one variation, the kit comprises the compound or composition in a multiple dose form.

In another embodiment, the present invention provides an article of manufacture comprising a compound or composition according to any one of the above embodiments and variations, and packaging materials. In one variation, the packaging material comprises a container for housing the compound or composition. The container optionally comprises a label indicating a disease state for which the compound or composition is to be administered, storage information, dosing information and/or instructions regarding how to administer the compound or composition. In regard to the above embodiments and variations, the article of manufacture optionally comprises the compound or composition in a multiple dose form.

In another embodiment, the present invention provides a therapeutic method comprising administering a compound or composition according to any one of the above embodiments and variations to a subject.

In yet another embodiment, the present invention provides a method of inhibiting a kinase comprising contacting a kinase with a compound or composition according to any one of the above embodiments and variations.

In still another embodiment, there is provided a method of inhibiting kinase comprising causing a compound or composition according to any one of the above embodiments and variations to be present in a subject in order to inhibit kinase in vivo.

The present invention also provides a method of inhibiting kinase comprising administering a first compound to a subject that is converted in vivo to a second compound wherein the second compound inhibits kinase in vivo, the second compound being a compound according to any one of the above embodiments and variations.

In yet another embodiment, there is provided a method of preventing or treating a disease state for which kinase possesses activity that contributes to the pathology and/or symptomology of the disease state comprising causing a compound or composition according to any one of the above embodiments and variations to be present in a subject in a therapeutically effective amount for the disease state.

The present invention also provides a method of preventing or treating a disease state for which kinase possesses activity that contributes to the pathology and/or symptomology of the disease state comprising administering a first compound to a subject that is converted in vivo to a second compound according to any one of the above embodiments and variations wherein the second compound is present in a subject in a therapeutically effective amount for the disease state.

In addition, there is provided a method of preventing or treating a disease state for which kinase possesses activity that contributes to the pathology and/or symptomology of the disease state comprising administering a compound or composition according to any one of the above embodiments and variations, wherein the compound or composition is present in the subject in a therapeutically effective amount for the disease state.

In each of the above embodiments and variations, the kinase is optionally an Aurora kinase. In particular variations of each of the above embodiments and variations, the kinase is an Aurora-B kinase.

In another embodiment, there is provided a method for treating cancer comprising administering a therapeutically effective amount of a compound or composition of the present invention to a mammalian species in need thereof. In one embodiment, the cancer is selected from the group consisting of squamous cell carcinoma, astrocytoma, Kaposi's sarcoma, glioblastoma, non small-cell lung cancer, bladder cancer, head and neck cancer, melanoma, ovarian cancer, prostate cancer, breast cancer, small-cell lung cancer, glioma, colorectal cancer, genitourinary cancer, gastrointestinal cancer, thyroid cancer and skin cancer.

In another embodiment, there is provided a method for treating inflammation, inflammatory bowel disease, psoriasis, or transplant rejection, comprising administration to a mammalian species in need thereof of a therapeutically effective amount of a compound or composition according to the present invention.

In another embodiment, there is provided a method for preventing or treating amyotrophic lateral sclerosis, corticobasal degeneration, Down syndrome, Huntington's Disease, Parkinson's Disease, postencephelatic parkinsonism, progressive supranuclear palsy, Pick's Disease, Niemann-Pick's Disease, stroke, head trauma and other chronic neurodegenerative diseases, Bipolar Disease, affective disorders, depression, schizophrenia, cognitive disorders, hair loss and contraceptive medication, comprising administration to a mammalian species in need thereof of a therapeutically effective amount of a compound or composition according to any one of the above embodiments.

In yet another embodiment, there is provided a method for preventing or treating mild Cognitive Impairment, Age-Associated Memory Impairment, Age-Related Cognitive Decline, Cognitive Impairment No Dementia, mild cognitive decline, mild neurocognitive decline, Late-Life Forgetfulness, memory impairment and cognitive impairment and androgenetic alopecia, comprising administering to a mammal, including man in need of such prevention and/or treatment, a therapeutically effective amount of a compound or composition according to any one of the above embodiments.

In a further embodiment, there is provided a method for preventing or treating dementia related diseases, Alzheimer's Disease and conditions associated with kinases, comprising administration to a mammalian species in need thereof of a therapeutically effective amount of a compound or composition according to any one of the above embodiments. In one particular variation, the dementia related diseases are selected from the group consisting of Frontotemporal dementia Parkinson's Type, Parkinson dementia complex of Guam, HIV dementia, diseases with associated neurofibrillar tangle pathologies, predemented states, vascular dementia, dementia with Lewy bodies, Frontotemporal dementia and dementia pugilistica.

In another embodiment, there is provided a method for treating arthritis comprising administration to a mammalian species in need thereof of a therapeutically effective amount of a compound or composition according to any one of the above embodiment.

Salts, Hydrates, and Prodrugs of Kinase Inhibitors

It should be recognized that the compounds of the present invention may be present and optionally administered in the form of salts, hydrates and prodrugs that are converted in vivo into the compounds of the present invention. For example, it is within the scope of the present invention to convert the compounds of the present invention into and use them in the form of their pharmaceutically acceptable salts derived from various organic and inorganic acids and bases in accordance with procedures well known in the art.

When the compounds of the present invention possess a free base form, the compounds can be prepared as a pharmaceutically acceptable acid addition salt by reacting the free base form of the compound with a pharmaceutically acceptable inorganic or organic acid, e.g., hydrohalides such as hydrochloride, hydrobromide, hydroiodide; other mineral acids and their corresponding salts such as sulfate, nitrate, phosphate, etc.; and alkyl and monoarylsulfonates such as ethanesulfonate, toluenesulfonate and benzenesulfonate; and other organic acids and their corresponding salts such as acetate, tartrate, maleate, succinate, citrate, benzoate, salicylate and ascorbate. Further acid addition salts of the present invention include, but are not limited to: adipate, alginate, arginate, aspartate, bisulfate, bisulfite, bromide, butyrate, camphorate, camphorsulfonate, caprylate, chloride, chlorobenzoate, cyclopentanepropionate, digluconate, dihydrogenphosphate, dinitrobenzoate, dodecylsulfate, fumarate, galacterate (from mucic acid), galacturonate, glucoheptaoate, gluconate, glutamate, glycerophosphate, hemisuccinate, hemisulfate, heptanoate, hexanoate, hippurate, hydrochloride, hydrobromide, hydroiodide, 2-hydroxyethanesulfonate, iodide, isethionate, iso-butyrate, lactate, lactobionate, malate, malonate, mandelate, metaphosphate, methanesulfonate, methylbenzoate, monohydrogenphosphate, 2-naphthalenesulfonate, nicotinate, nitrate, oxalate, oleate, pamoate, pectinate, persulfate, phenylacetate, 3-phenylpropionate, phosphate, phosphonate and phthalate. It should be recognized that the free base forms will typically differ from their respective salt forms somewhat in physical properties such as solubility in polar solvents, but otherwise the salts are equivalent to their respective free base forms for the purposes of the present invention.

When the compounds of the present invention possess a free acid form, a pharmaceutically acceptable base addition salt can be prepared by reacting the free acid form of the compound with a pharmaceutically acceptable inorganic or organic base. Examples of such bases are alkali metal hydroxides including potassium, sodium and lithium hydroxides; alkaline earth metal hydroxides such as barium and calcium hydroxides; alkali metal alkoxides, e.g. potassium ethanolate and sodium propanolate; and various organic bases such as ammonium hydroxide, piperidine, diethanolamine and N-methylglutamine. Also included are the aluminum salts of the compounds of the present invention. Further base salts of the present invention include, but are not limited to: copper, ferric, ferrous, lithium, magnesium, manganic, manganous, potassium, sodium and zinc salts. Organic base salts include, but are not limited to, salts of primary, secondary and tertiary amines, substituted amines including naturally occurring substituted amines, cyclic amines and basic ion exchange resins, e.g., arginine, betaine, caffeine, chloroprocaine, choline, N,N'-dibenzylethylenediamine (benzathine), dicyclohexylamine, diethanolamine, 2-diethylaminoethanol, 2-dimethylaminoethanol, ethanolamine, ethylenediamine, N-ethylmorpholine, N-ethylpiperidine, glucamine, glucosamine, histidine, hydrabamine, iso-propylamine, lidocaine, lysine, meglumine, N-methyl-D-glucamine, morpholine, piperazine, piperidine, polyamine resins, procaine, purines, theobromine, triethanolamine, triethylamine, trimethylamine, tripropylamine and tris-(hydroxymethyl)-methylamine (tromethamine) It should be recognized that the free acid forms will typically differ from their respective salt forms somewhat in physical properties such as solubility in polar solvents, but otherwise the salts are equivalent to their respective free acid forms for the purposes of the present invention.

Compounds of the present invention that comprise basic nitrogen-containing groups may be quaternized with such agents as $(C_{1-4})$alkyl halides, e.g., methyl, ethyl, iso-propyl and tert-butyl chlorides, bromides and iodides; di$(C_{1-4})$alkyl sulfates, e.g., dimethyl, diethyl and diamyl sulfates; $(C_{10-18})$alkyl halides, e.g., decyl, dodecyl, lauryl, myristyl and stearyl chlorides, bromides and iodides; and aryl$(C_{1-4})$alkyl halides, e.g., benzyl chloride and phenethyl bromide. Such salts permit the preparation of both water-soluble and oil-soluble compounds of the present invention.

N-oxides of compounds according to the present invention can be prepared by methods known to those of ordinary skill in the art. For example, N-oxides can be prepared by treating an unoxidized form of the compound with an oxidizing agent (e.g., trifluoroperacetic acid, permaleic acid, perbenzoic acid, peracetic acid, meta-chloroperoxybenzoic acid, or the like) in a suitable inert organic solvent (e.g., a halogenated hydrocarbon such as dichloromethane) at approximately 0° C. Alternatively, the N-oxides of the compounds can be prepared from the N-oxide of an appropriate starting material.

Prodrug derivatives of compounds according to the present invention can be prepared by modifying substituents of compounds of the present invention that are then converted in vivo to a different substituent. It is noted that in many instances, the prodrugs themselves also fall within the scope of the range of compounds according to the present invention. For example, prodrugs can be prepared by reacting a compound with a carbamylating agent (e.g., 1,1-acyloxyalkylcarbonochloridate, para-nitrophenyl carbonate, or the like) or an acylating agent. Further examples of methods of making prodrugs are described in Saulnier et al. (1994), *Bioorganic and Medicinal Chemistry Letters*, Vol. 4, p. 1985.

Protected derivatives of compounds of the present invention can also be made. Examples of techniques applicable to the creation of protecting groups and their removal can be found in T. W. Greene, Protecting *Groups in Organic Synthesis*, $3^{rd}$ edition, John Wiley & Sons, Inc. 1999.

Compounds of the present invention may also be conveniently prepared, or formed during the process of the invention, as solvates (e.g. hydrates). Hydrates of compounds of the present invention may be conveniently prepared by recrystallization from an aqueous/organic solvent mixture, using organic solvents such as dioxin, tetrahydrofuran or methanol.

A "pharmaceutically acceptable salt", as used herein, is intended to encompass any compound according to the present invention that is utilized in the form of a salt thereof, especially where the salt confers on the compound improved pharmacokinetic properties as compared to the free form of compound or a different salt form of the compound. The pharmaceutically acceptable salt form may also initially confer desirable pharmacokinetic properties on the compound that it did not previously possess, and may even positively affect the pharmacodynamics of the compound with respect to its therapeutic activity in the body. An example of a pharmacokinetic property that may be favorably affected is the manner in which the compound is transported across cell membranes, which in turn may directly and positively affect the absorption, distribution, biotransformation and excretion of the compound. While the route of administration of the pharmaceutical composition is important, and various anatomical, physiological and pathological factors can critically affect bioavailability, the solubility of the compound is usually dependent upon the character of the particular salt form thereof, which it utilized. One of skill in the art will appreciate that an aqueous solution of the compound will provide the most rapid absorption of the compound into the body of a subject being treated, while lipid solutions and suspensions, as well as solid dosage forms, will result in less rapid absorption of the compound.

Preparation of Kinase Inhibitors

Various methods may be developed for synthesizing compounds according to the present invention. Representative methods for synthesizing these compounds are provided in the Examples. It is noted, however, that the compounds of the present invention may also be synthesized by other synthetic routes that others may devise.

It will be readily recognized that certain compounds according to the present invention have atoms with linkages to other atoms that confer a particular stereochemistry to the compound (e.g., chiral centers). It is recognized that synthesis of compounds according to the present invention may result in the creation of mixtures of different stereoisomers (enantiomers, diastereomers). Unless a particular stereochemistry is specified, recitation of a compound is intended to encompass all of the different possible stereoisomers.

Various methods for separating mixtures of different stereoisomers are known in the art. For example, a racemic mixture of a compound may be reacted with an optically active resolving agent to form a pair of diastereoisomeric compounds. The diastereomers may then be separated in order to recover the optically pure enantiomers. Dissociable complexes may also be used to resolve enantiomers (e.g., crystalline diastereoisomeric salts). Diastereomers typically have sufficiently distinct physical properties (e.g., melting points, boiling points, solubilities, reactivity, etc.) that they can be readily separated by taking advantage of these dissimilarities. For example, diastereomers can typically be separated by chromatography or by separation/resolution techniques based upon differences in solubility. A more detailed description of techniques that can be used to resolve stereoisomers of compounds from their racemic mixture can be found in Jean Jacques Andre Collet, Samuel H. Wilen, Enantiomers, Racemates and Resolutions, John Wiley & Sons, Inc. (1981).

Composition Comprising Kinase Inhibitors

A wide variety of compositions and administration methods may be used in conjunction with the kinase inhibitors of the present invention. Such compositions may include, in addition to the kinase inhibitors of the present invention, conventional pharmaceutical excipients, and other conventional, pharmaceutically inactive agents. Additionally, the compositions may include active agents in addition to the kinase inhibitors of the present invention. These additional active agents may include additional compounds according to the invention, and/or one or more other pharmaceutically active agents.

The compositions may be in gaseous, liquid, semi-liquid or solid form, formulated in a manner suitable for the route of administration to be used. For oral administration, capsules and tablets are typically used. For parenteral administration, reconstitution of a lyophilized powder, prepared as described herein, is typically used.

Compositions comprising kinase inhibitors of the present invention may be administered or coadministered orally, parenterally, intraperitoneally, intravenously, intraarterially, transdermally, sublingually, intramuscularly, rectally, transbuccally, intranasally, liposomally, via inhalation, vaginally, intraoccularly, via local delivery (for example by catheter or stent), subcutaneously, intraadiposally, intraarticularly, or intrathecally. The compounds and/or compositions according to the invention may also be administered or coadministered in slow release dosage forms.

The kinase inhibitors and compositions comprising them may be administered or coadministered in any conventional dosage form. Co-administration in the context of this invention is intended to mean the administration of more than one therapeutic agent, one of which includes a kinase inhibitor, in the course of a coordinated treatment to achieve an improved clinical outcome. Such co-administration may also be coextensive, that is, occurring during overlapping periods of time.

Solutions or suspensions used for parenteral, intradermal, subcutaneous, or topical application may optionally include one or more of the following components: a sterile diluent, such as water for injection, saline solution, fixed oil, polyethylene glycol, glycerine, propylene glycol or other synthetic solvent; antimicrobial agents, such as benzyl alcohol and methyl parabens; antioxidants, such as ascorbic acid and sodium bisulfate; chelating agents, such as ethylenediaminetetraacetic acid (EDTA); buffers, such as acetates, citrates and phosphates; agents for the adjustment of tonicity such as sodium chloride or dextrose, and agents for adjusting the acidity or alkalinity of the composition, such as alkaline or acidifying agents or buffers like carbonates, bicarbonates, phosphates, hydrochloric acid, and organic acids like acetic and citric acid. Parenteral preparations may optionally be enclosed in ampules, disposable syringes or single or multiple dose vials made of glass, plastic or other suitable material.

When kinase inhibitors according to the present invention exhibit insufficient solubility, methods for solubilizing the compounds may be used. Such methods are known to those of skill in this art, and include, but are not limited to, using cosolvents, such as dimethylsulfoxide (DMSO), using surfactants, such as TWEEN, or dissolution in aqueous sodium bicarbonate. Derivatives of the compounds, such as prodrugs of the compounds may also be used in formulating effective pharmaceutical compositions.

Upon mixing or adding kinase inhibitors according to the present invention to a composition, a solution, suspension, emulsion or the like may be formed. The form of the resulting composition will depend upon a number of factors, including the intended mode of administration, and the solubility of the compound in the selected carrier or vehicle. The effective concentration needed to ameliorate the disease being treated may be empirically determined.

Compositions according to the present invention are optionally provided for administration to humans and animals in unit dosage forms, such as tablets, capsules, pills, powders, dry powders for inhalers, granules, sterile parenteral solutions or suspensions, and oral solutions or suspensions, and oil-water emulsions containing suitable quantities of the compounds, particularly the pharmaceutically acceptable salts, preferably the sodium salts, thereof. The pharmaceutically therapeutically active compounds and derivatives thereof are typically formulated and administered in unit-dosage forms or multiple-dosage forms. Unit-dose forms, as used herein, refers to physically discrete units suitable for human and animal subjects and packaged individually as is known in the art. Each unit-dose contains a predetermined quantity of the therapeutically active compound sufficient to produce the desired therapeutic effect, in association with the required pharmaceutical carrier, vehicle or diluent. Examples of unit-dose forms include ampoules and syringes individually packaged tablet or capsule. Unit-dose forms may be administered in fractions or multiples thereof. A multiple-dose form is a plurality of identical unit-dosage forms packaged in a single container to be administered in segregated unit-dose form. Examples of multiple-dose forms include vials, bottles of tablets or capsules or bottles of pint or gallons. Hence, multiple dose form is a multiple of unit-doses that are not segregated in packaging.

In addition to one or more kinase inhibitors according to the present invention, the composition may comprise: a diluent such as lactose, sucrose, dicalcium phosphate, or carboxymethylcellulose; a lubricant, such as magnesium stearate, calcium stearate and talc; and a binder such as starch, natural gums, such as gum acaciagelatin, glucose, molasses, polyinylpyrrolidine, celluloses and derivatives thereof, povidone, crospovidones and other such binders known to those of skill in the art. Liquid pharmaceutically administrable compositions can, for example, be prepared by dissolving, dispersing, or otherwise mixing an active compound as defined above and optional pharmaceutical adjuvants in a carrier, such as, for example, water, saline, aqueous dextrose, glycerol, glycols, ethanol, and the like, to form a solution or suspension. If desired, the pharmaceutical composition to be administered may also contain minor amounts of auxiliary substances such as wetting agents, emulsifying agents, or solubilizing agents, pH buffering agents and the like, for example, acetate, sodium citrate, cyclodextrine derivatives, sorbitan monolaurate, triethanolamine sodium acetate, triethanolamine oleate, and other such agents. Actual methods of preparing such dosage forms are known in the art, or will be apparent, to those skilled in this art; for example, see Remington's Pharmaceutical Sciences, Mack Publishing Company, Easton, Pa., 15th Edition, 1975. The composition or formulation to be administered will, in any event, contain a sufficient quantity of a kinase inhibitor of the present invention to reduce kinases activity in vivo, thereby treating the disease state of the subject.

Dosage forms or compositions may optionally comprise one or more kinase inhibitors according to the present invention in the range of 0.005% to 100% (weight/weight) with the balance comprising additional substances such as those described herein. For oral administration, a pharmaceutically acceptable composition may optionally comprise any one or more commonly employed excipients, such as, for example pharmaceutical grades of mannitol, lactose, starch, magnesium stearate, talcum, cellulose derivatives, sodium crosscarmellose, glucose, sucrose, magnesium carbonate, sodium saccharin, talcum. Such compositions include solutions, suspensions, tablets, capsules, powders, dry powders for inhalers and sustained release formulations, such as, but not limited to, implants and microencapsulated delivery systems, and biodegradable, biocompatible polymers, such as collagen, ethylene vinyl acetate, polyanhydrides, polyglycolic acid, polyorthoesters, polylactic acid and others. Methods for preparing these formulations are known to those skilled in the art. The compositions may optionally contain 0.01%-100% (weight/weight) of one or more kinase inhibitors, optionally 0.1-95%, and optionally 1-95%.

Salts, preferably sodium salts, of the kinase inhibitors may be prepared with carriers that protect the compound against rapid elimination from the body, such as time release formulations or coatings. The formulations may further include other active compounds to obtain desired combinations of properties.

Formulations for Oral Administration

Oral pharmaceutical dosage forms may be as a solid, gel or liquid. Examples of solid dosage forms include, but are not limited to tablets, capsules, granules, and bulk powders. More specific examples of oral tablets include compressed, chewable lozenges and tablets that may be enteric-coated, sugar-coated or film-coated. Examples of capsules include hard or soft gelatin capsules. Granules and powders may be provided in non-effervescent or effervescent forms. Each may be combined with other ingredients known to those skilled in the art.

In certain embodiments, kinase inhibitors according to the present invention are provided as solid dosage forms, preferably capsules or tablets. The tablets, pills, capsules, troches and the like may optionally contain one or more of the following ingredients, or compounds of a similar nature: a binder; a diluent; a disintegrating agent; a lubricant; a glidant; a sweetening agent; and a flavoring agent.

Examples of binders that may be used include, but are not limited to, microcrystalline cellulose, gum tragacanth, glucose solution, acacia mucilage, gelatin solution, sucrose and starch paste.

Examples of lubricants that may be used include, but are not limited to, talc, starch, magnesium or calcium stearate, lycopodium and stearic acid.

Examples of diluents that may be used include, but are not limited to, lactose, sucrose, starch, kaolin, salt, mannitol and dicalcium phosphate.

Examples of glidants that may be used include, but are not limited to, colloidal silicon dioxide.

Examples of disintegrating agents that may be used include, but are not limited to, crosscarmellose sodium, sodium starch glycolate, alginic acid, corn starch, potato starch, bentonite, methylcellulose, agar and carboxymethylcellulose.

Examples of coloring agents that may be used include, but are not limited to, any of the approved certified water soluble FD and C dyes, mixtures thereof; and water insoluble FD and C dyes suspended on alumina hydrate.

Examples of sweetening agents that may be used include, but are not limited to, sucrose, lactose, mannitol and artificial sweetening agents such as sodium cyclamate and saccharin, and any number of spray-dried flavors.

Examples of flavoring agents that may be used include, but are not limited to, natural flavors extracted from plants such as fruits and synthetic blends of compounds that produce a pleasant sensation, such as, but not limited to peppermint and methyl salicylate.

Examples of wetting agents that may be used include, but are not limited to, propylene glycol monostearate, sorbitan monooleate, diethylene glycol monolaurate and polyoxyethylene lauryl ether.

Examples of anti-emetic coatings that may be used include, but are not limited to, fatty acids, fats, waxes, shellac, ammoniated shellac and cellulose acetate phthalates.

Examples of film coatings that may be used include, but are not limited to, hydroxyethylcellulose, sodium carboxymethylcellulose, polyethylene glycol 4000 and cellulose acetate phthalate.

If oral administration is desired, the salt of the compound may optionally be provided in a composition that protects it from the acidic environment of the stomach. For example, the composition can be formulated in an enteric coating that maintains its integrity in the stomach and releases the active compound in the intestine. The composition may also be formulated in combination with an antacid or other such ingredient.

When the dosage unit form is a capsule, it may optionally additionally comprise a liquid carrier such as a fatty oil. In addition, dosage unit forms may optionally additionally comprise various other materials that modify the physical form of the dosage unit, for example, coatings of sugar and other enteric agents.

Compounds according to the present invention may also be administered as a component of an elixir, suspension, syrup, wafer, sprinkle, chewing gum or the like. A syrup may optionally comprise, in addition to the active compounds, sucrose as a sweetening agent and certain preservatives, dyes and colorings and flavors.

The kinase inhibitors of the present invention may also be mixed with other active materials that do not impair the desired action, or with materials that supplement the desired action, such as antacids, H2 blockers, and diuretics. For example, if a compound is used for treating asthma or hypertension, it may be used with other bronchodilators and antihypertensive agents, respectively.

Examples of pharmaceutically acceptable carriers that may be included in tablets comprising kinase inhibitors of the present invention include, but are not limited to binders, lubricants, diluents, disintegrating agents, coloring agents, flavoring agents, and wetting agents. Enteric-coated tablets, because of the enteric-coating, resist the action of stomach acid and dissolve or disintegrate in the neutral or alkaline intestines. Sugar-coated tablets may be compressed tablets to which different layers of pharmaceutically acceptable substances are applied. Film-coated tablets may be compressed tablets that have been coated with polymers or other suitable coating. Multiple compressed tablets may be compressed tablets made by more than one compression cycle utilizing the pharmaceutically acceptable substances previously mentioned. Coloring agents may also be used in tablets. Flavoring and sweetening agents may be used in tablets, and are especially useful in the formation of chewable tablets and lozenges.

Examples of liquid oral dosage forms that may be used include, but are not limited to, aqueous solutions, emulsions, suspensions, solutions and/or suspensions reconstituted from non-effervescent granules and effervescent preparations reconstituted from effervescent granules.

Examples of aqueous solutions that may be used include, but are not limited to, elixirs and syrups. As used herein, elixirs refer to clear, sweetened, hydroalcoholic preparations. Examples of pharmaceutically acceptable carriers that may be used in elixirs include, but are not limited to solvents. Particular examples of solvents that may be used include glycerin, sorbitol, ethyl alcohol and syrup. As used herein, syrups refer to concentrated aqueous solutions of a sugar, for example, sucrose. Syrups may optionally further comprise a preservative.

Emulsions refer to two-phase systems in which one liquid is dispersed in the form of small globules throughout another liquid. Emulsions may optionally be oil-in-water or water-in-oil emulsions. Examples of pharmaceutically acceptable carriers that may be used in emulsions include, but are not limited to non-aqueous liquids, emulsifying agents and preservatives.

Examples of pharmaceutically acceptable substances that may be used in non-effervescent granules, to be reconstituted into a liquid oral dosage form, include diluents, sweeteners and wetting agents.

Examples of pharmaceutically acceptable substances that may be used in effervescent granules, to be reconstituted into a liquid oral dosage form, include organic acids and a source of carbon dioxide.

Coloring and flavoring agents may optionally be used in all of the above dosage forms.

Particular examples of preservatives that may be used include glycerin, methyl and propylparaben, benzoic add, sodium benzoate and alcohol.

Particular examples of non-aqueous liquids that may be used in emulsions include mineral oil and cottonseed oil.

Particular examples of emulsifying agents that may be used include gelatin, acacia, tragacanth, bentonite, and surfactants such as polyoxyethylene sorbitan monooleate.

Particular examples of suspending agents that may be used include sodium carboxymethylcellulose, pectin, tragacanth, Veegum and acacia. Diluents include lactose and sucrose. Sweetening agents include sucrose, syrups, glycerin and artificial sweetening agents such as sodium cyclamate and saccharin.

Particular examples of wetting agents that may be used include propylene glycol monostearate, sorbitan monooleate, diethylene glycol monolaurate and polyoxyethylene lauryl ether.

Particular examples of organic acids that may be used include citric and tartaric acid.

Sources of carbon dioxide that may be used in effervescent compositions include sodium bicarbonate and sodium carbonate. Coloring agents include any of the approved certified water soluble FD and C dyes, and mixtures thereof.

Particular examples of flavoring agents that may be used include natural flavors extracted from plants such fruits, and synthetic blends of compounds that produce a pleasant taste sensation.

For a solid dosage form, the solution or suspension, in for example propylene carbonate, vegetable oils or triglycerides, is preferably encapsulated in a gelatin capsule. Such solutions, and the preparation and encapsulation thereof, are disclosed in U.S. Pat. Nos. 4,328,245; 4,409,239; and 4,410,545. For a liquid dosage form, the solution, e.g., for example, in a polyethylene glycol, may be diluted with a sufficient quantity of a pharmaceutically acceptable liquid carrier, e.g. water, to be easily measured for administration.

Alternatively, liquid or semi-solid oral formulations may be prepared by dissolving or dispersing the active compound or salt in vegetable oils, glycols, triglycerides, propylene glycol esters (e.g. propylene carbonate) and other such carriers, and encapsulating these solutions or suspensions in hard or soft gelatin capsule shells. Other useful formulations include those set forth in U.S. Pat. Nos. Re 28,819 and 4,358,603.

Injectables, Solutions, and Emulsions

The present invention is also directed to compositions designed to administer the kinase inhibitors of the present invention by parenteral administration, generally characterized by injection, either subcutaneously, intramuscularly or intravenously. Injectables may be prepared in any conventional form, for example as liquid solutions or suspensions, solid forms suitable for solution or suspension in liquid prior to injection, or as emulsions.

Examples of excipients that may be used in conjunction with injectables according to the present invention include, but are not limited to water, saline, dextrose, glycerol or ethanol. The injectable compositions may also optionally comprise minor amounts of non-toxic auxiliary substances such as wetting or emulsifying agents, pH buffering agents, stabilizers, solubility enhancers, and other such agents, such as for example, sodium acetate, sorbitan monolaurate, triethanolamine oleate and cyclodextrins. Implantation of a slow-release or sustained-release system, such that a constant level of dosage is maintained (see, e.g., U.S. Pat. No. 3,710,795) is also contemplated herein. The percentage of active compound contained in such parenteral compositions is highly dependent on the specific nature thereof, as well as the activity of the compound and the needs of the subject.

Parenteral administration of the formulations includes intravenous, subcutaneous and intramuscular administrations. Preparations for parenteral administration include sterile solutions ready for injection, sterile dry soluble products, such as the lyophilized powders described herein, ready to be combined with a solvent just prior to use, including hypodermic tablets, sterile suspensions ready for injection, sterile dry insoluble products ready to be combined with a vehicle just prior to use and sterile emulsions. The solutions may be either aqueous or nonaqueous.

When administered intravenously, examples of suitable carriers include, but are not limited to physiological saline or phosphate buffered saline (PBS), and solutions containing thickening and solubilizing agents, such as glucose, polyethylene glycol, and polypropylene glycol and mixtures thereof.

Examples of pharmaceutically acceptable carriers that may optionally be used in parenteral preparations include, but are not limited to aqueous vehicles, nonaqueous vehicles, antimicrobial agents, isotonic agents, buffers, antioxidants, local anesthetics, suspending and dispersing agents, emulsifying agents, sequestering or chelating agents and other pharmaceutically acceptable substances.

Examples of aqueous vehicles that may optionally be used include Sodium Chloride Injection, Ringers Injection, Isotonic Dextrose Injection, Sterile Water Injection, Dextrose and Lactated Ringers Injection.

Examples of nonaqueous parenteral vehicles that may optionally be used include fixed oils of vegetable origin, cottonseed oil, corn oil, sesame oil and peanut oil.

Antimicrobial agents in bacteriostatic or fungistatic concentrations may be added to parenteral preparations, particularly when the preparations are packaged in multiple-dose containers and thus designed to be stored and multiple aliquots to be removed. Examples of antimicrobial agents that may be used include phenols or cresols, mercurials, benzyl alcohol, chlorobutanol, methyl and propyl p-hydroxybenzoic acid esters, thimerosal, benzalkonium chloride and benzethonium chloride.

Examples of isotonic agents that may be used include sodium chloride and dextrose. Examples of buffers that may be used include phosphate and citrate. Examples of antioxidants that may be used include sodium bisulfate. Examples of local anesthetics that may be used include procaine hydrochloride. Examples of suspending and dispersing agents that may be used include sodium carboxymethylcellulose, hydroxypropyl methylcellulose and polyvinylpyrrolidone. Examples of emulsifying agents that may be used include Polysorbate 80 (TWEEN 80). A sequestering or chelating agent of metal ions include EDTA.

Pharmaceutical carriers may also optionally include ethyl alcohol, polyethylene glycol and propylene glycol for water miscible vehicles and sodium hydroxide, hydrochloric acid, citric acid or lactic acid for pH adjustment.

The concentration of a kinase inhibitor in the parenteral formulation may be adjusted so that an injection administers a pharmaceutically effective amount sufficient to produce the desired pharmacological effect. The exact concentration of a kinase inhibitor and/or dosage to be used will ultimately depend on the age, weight and condition of the patient or animal as is known in the art.

Unit-dose parenteral preparations may be packaged in an ampoule, a vial or a syringe with a needle. All preparations for parenteral administration should be sterile, as is know and practiced in the art.

Injectables may be designed for local and systemic administration. Typically a therapeutically effective dosage is formulated to contain a concentration of at least about 0.1% w/w up to about 90% w/w or more, preferably more than 1% w/w of the kinase inhibitor to the treated tissue(s). The kinase inhibitor may be administered at once, or may be divided into a number of smaller doses to be administered at intervals of time. It is understood that the precise dosage and duration of treatment will be a function of the location of where the composition is parenterally administered, the carrier and other variables that may be determined empirically using known testing protocols or by extrapolation from in vivo or in vitro test data. It is to be noted that concentrations and dosage values may also vary with the age of the individual treated. It is to be further understood that for any particular subject, specific dosage regimens may need to be adjusted over time according to the individual need and the professional judgment of the person administering or supervising the administration of the formulations. Hence, the concentration ranges set forth herein are intended to be exemplary and are not intended to limit the scope or practice of the claimed formulations.

The kinase inhibitor may optionally be suspended in micronized or other suitable form or may be derivatized to produce a more soluble active product or to produce a prodrug. The form of the resulting mixture depends upon a number of factors, including the intended mode of administration and the solubility of the compound in the selected carrier or vehicle. The effective concentration is sufficient for ameliorating the symptoms of the disease state and may be empirically determined.

Lyophilized Powders

The kinase inhibitors of the present invention may also be prepared as lyophilized powders, which can be reconstituted for administration as solutions, emulsions and other mixtures. The lyophilized powders may also be formulated as solids or gels.

Sterile, lyophilized powder may be prepared by dissolving the compound in a sodium phosphate buffer solution containing dextrose or other suitable excipient. Subsequent sterile filtration of the solution followed by lyophilization under standard conditions known to those of skill in the art provides the desired formulation. Briefly, the lyophilized powder may optionally be prepared by dissolving dextrose, sorbitol, fructose, corn syrup, xylitol, glycerin, glucose, sucrose or other suitable agent, about 1-20%, preferably about 5 to 15%, in a suitable buffer, such as citrate, sodium or potassium phosphate or other such buffer known to those of skill in the art at, typically, about neutral pH. Then, a kinase inhibitor is added to the resulting mixture, preferably above room temperature, more preferably at about 30-35° C., and stirred until it dissolves. The resulting mixture is diluted by adding more buffer to a desired concentration. The resulting mixture is sterile filtered or treated to remove particulates and to insure sterility, and apportioned into vials for lyophilization. Each vial may contain a single dosage or multiple dosages of the kinase inhibitor.

Topical Administration

The kinase inhibitors of the present invention may also be administered as topical mixtures. Topical mixtures may be used for local and systemic administration. The resulting mixture may be a solution, suspension, emulsions or the like and are formulated as creams, gels, ointments, emulsions, solutions, elixirs, lotions, suspensions, tinctures, pastes, foams, aerosols, irrigations, sprays, suppositories, bandages, dermal patches or any other formulations suitable for topical administration.

The kinase inhibitors may be formulated as aerosols for topical application, such as by inhalation (see, U.S. Pat. Nos. 4,044,126, 4,414,209, and 4,364,923, which describe aerosols for delivery of a steroid useful for treatment inflammatory diseases, particularly asthma). These formulations for administration to the respiratory tract can be in the form of an aerosol or solution for a nebulizer, or as a microfine powder for insufflation, alone or in combination with an inert carrier such as lactose. In such a case, the particles of the formulation will typically have diameters of less than 50 microns, preferably less than 10 microns.

The kinase inhibitors may also be formulated for local or topical application, such as for topical application to the skin and mucous membranes, such as in the eye, in the form of gels, creams, and lotions and for application to the eye or for intracisternal or intraspinal application. Topical administration is contemplated for transdermal delivery and also for administration to the eyes or mucosa, or for inhalation therapies. Nasal solutions of the kinase inhibitor alone or in combination with other pharmaceutically acceptable excipients can also be administered.

Formulations for Other Routes of Administrations

Depending upon the disease state being treated, other routes of administration, such as topical application, transdermal patches, and rectal administration, may also be used. For example, pharmaceutical dosage forms for rectal administration are rectal suppositories, capsules and tablets for systemic effect. Rectal suppositories are used herein mean solid bodies for insertion into the rectum that melt or soften at body temperature releasing one or more pharmacologically or therapeutically active ingredients. Pharmaceutically acceptable substances utilized in rectal suppositories are bases or vehicles and agents to raise the melting point. Examples of bases include cocoa butter (theobroma oil), glycerin-gelatin, carbowax, (polyoxyethylene glycol) and appropriate mixtures of mono-, di- and triglycerides of fatty acids. Combinations of the various bases may be used. Agents to raise the melting point of suppositories include spermaceti and wax. Rectal suppositories may be prepared either by the compressed method or by molding. The typical weight of a rectal suppository is about 2 to 3 gm. Tablets and capsules for rectal administration may be manufactured using the same pharmaceutically acceptable substance and by the same methods as for formulations for oral administration.

Examples of Formulations

The following are particular examples of oral, intravenous and tablet formulations that may optionally be used with compounds of the present invention. It is noted that these formulations may be varied depending on the particular compound being used and the indication for which the formulation is going to be used.

Oral Formulation

| | |
|---|---|
| Compound of the Present Invention | 10-100 mg |
| Citric Acid Monohydrate | 105 mg |
| Sodium Hydroxide | 18 mg |
| Flavoring | |
| Water | q.s. to 100 mL |

Intravenous Formulation

| | |
|---|---|
| Compound of the Present Invention | 0.1-10 mg |
| Dextrose Monohydrate | q.s. to make isotonic |
| Citric Acid Monohydrate | 1.05 mg |
| Sodium Hydroxide | 0.18 mg |
| Water for Injection | q.s. to 1.0 mL |

Tablet Formulation

| | |
|---|---|
| Compound of the Present Invention | 1% |
| Microcrystalline Cellulose | 73% |
| Stearic Acid | 25% |
| Colloidal Silica | 1%. |

Kits Comprising Kinase Inhibitors

The invention is also directed to kits and other articles of manufacture for treating diseases associated with kinases. It is noted that diseases are intended to cover all conditions for which the kinases possesses activity that contributes to the pathology and/or symptomology of the condition.

In one embodiment, a kit is provided that comprises a composition comprising at least one kinase inhibitor of the present invention in combination with instructions. The instructions may indicate the disease state for which the composition is to be administered, storage information, dosing information and/or instructions regarding how to administer the composition. The kit may also comprise packaging materials. The packaging material may comprise a container for housing the composition. The kit may also optionally comprise additional components, such as syringes for administration of the composition. The kit may comprise the composition in single or multiple dose forms.

In another embodiment, an article of manufacture is provided that comprises a composition comprising at least one kinase inhibitor of the present invention in combination with packaging materials. The packaging material may comprise a container for housing the composition. The container may optionally comprise a label indicating the disease state for which the composition is to be administered, storage information, dosing information and/or instructions regarding how to administer the composition. The kit may also optionally comprise additional components, such as syringes for administration of the composition. The kit may comprise the composition in single or multiple dose forms.

It is noted that the packaging material used in kits and articles of manufacture according to the present invention may form a plurality of divided containers such as a divided bottle or a divided foil packet. The container can be in any conventional shape or form as known in the art which is made of a pharmaceutically acceptable material, for example a paper or cardboard box, a glass or plastic bottle or jar, a re-sealable bag (for example, to hold a "refill" of tablets for placement into a different container), or a blister pack with individual doses for pressing out of the pack according to a therapeutic schedule. The container that is employed will depend on the exact dosage form involved, for example a conventional cardboard box would not generally be used to hold a liquid suspension. It is feasible that more than one container can be used together in a single package to market a single dosage form. For example, tablets may be contained in a bottle that is in turn contained within a box. Typically the kit includes directions for the administration of the separate components. The kit form is particularly advantageous when the separate components are preferably administered in different dosage forms (e.g., oral, topical, transdermal and parenteral), are administered at different dosage intervals, or when titration of the individual components of the combination is desired by the prescribing physician.

One particular example of a kit according to the present invention is a so-called blister pack. Blister packs are well known in the packaging industry and are being widely used for the packaging of pharmaceutical unit dosage forms (tablets, capsules, and the like). Blister packs generally consist of a sheet of relatively stiff material covered with a foil of a preferably transparent plastic material. During the packaging process recesses are formed in the plastic foil. The recesses have the size and shape of individual tablets or capsules to be packed or may have the size and shape to accommodate multiple tablets and/or capsules to be packed. Next, the tablets or capsules are placed in the recesses accordingly and the sheet of relatively stiff material is sealed against the plastic foil at the face of the foil which is opposite from the direction in which the recesses were formed. As a result, the tablets or capsules are individually sealed or collectively sealed, as desired, in the recesses between the plastic foil and the sheet. Preferably the strength of the sheet is such that the tablets or capsules can be removed from the blister pack by manually applying pressure on the recesses whereby an opening is formed in the sheet at the place of the recess. The tablet or capsule can then be removed via said opening.

Another specific embodiment of a kit is a dispenser designed to dispense the daily doses one at a time in the order of their intended use. Preferably, the dispenser is equipped with a memory-aid, so as to further facilitate compliance with the regimen. An example of such a memory-aid is a mechanical counter that indicates the number of daily doses that has been dispensed. Another example of such a memory-aid is a battery-powered micro-chip memory coupled with a liquid crystal readout, or audible reminder signal which, for example, reads out the date that the last daily dose has been taken and/or reminds one when the next dose is to be taken.

EXAMPLES

1. Preparation of Kinase Inhibitors

Various methods may be developed for synthesizing compounds according to the present invention. Representative methods for synthesizing these compounds are provided in the Examples. It is noted, however, that the compounds of the present invention may also be synthesized by other synthetic routes that others may devise.

It will be readily recognized that certain compounds according to the present invention have atoms with linkages to other atoms that confer a particular stereochemistry to the compound (e.g., chiral centers). It is recognized that synthesis of compounds according to the present invention may result in the creation of mixtures of different stereoisomers (enantiomers, diastereomers). Unless a particular stereochemistry is specified, recitation of a compound is intended to encompass all of the different possible stereoisomers.

Various methods for separating mixtures of different stereoisomers are known in the art. For example, a racemic mixture of a compound may be reacted with an optically active resolving agent to form a pair of diastereoisomeric compounds. The diastereomers may then be separated in order to recover the optically pure enantiomers. Dissociable complexes may also be used to resolve enantiomers (e.g., crystalline diastereoisomeric salts). Diastereomers typically have sufficiently distinct physical properties (e.g., melting points, boiling points, solubilities, reactivity, etc.) that they can be readily separated by taking advantage of these dissimilarities. For example, diastereomers can typically be separated by chromatography or by separation/resolution techniques based upon differences in solubility. A more detailed description of techniques that can be used to resolve stereoisomers of compounds from their racemic mixture can be found in Jean Jacques Andre Collet, Samuel H. Wilen, Enantiomers, Racemates and Resolutions, John Wiley & Sons, Inc. (1981).

Compounds according to the present invention can also be prepared as a pharmaceutically acceptable acid addition salt by reacting the free base form of the compound with a pharmaceutically acceptable inorganic or organic acid. Alternatively, a pharmaceutically acceptable base addition salt of a compound can be prepared by reacting the free acid form of the compound with a pharmaceutically acceptable inorganic or organic base. Inorganic and organic acids and bases suitable for the preparation of the pharmaceutically acceptable salts of compounds are set forth in the definitions section of this Application. Alternatively, the salt forms of the compounds can be prepared using salts of the starting materials or intermediates.

The free acid or free base forms of the compounds can be prepared from the corresponding base addition salt or acid addition salt form. For example, a compound in an acid addition salt form can be converted to the corresponding free base by treating with a suitable base (e.g., ammonium hydroxide solution, sodium hydroxide, and the like). A compound in a base addition salt form can be converted to the corresponding free acid by treating with a suitable acid (e.g., hydrochloric acid, etc).

The N-oxides of compounds according to the present invention can be prepared by methods known to those of ordinary skill in the art. For example, N-oxides can be prepared by treating an unoxidized form of the compound with an oxidizing agent (e.g., trifluoroperacetic acid, permaleic acid, perbenzoic acid, peracetic acid, meta-chloroperoxybenzoic acid, or the like) in a suitable inert organic solvent (e.g., a halogenated hydrocarbon such as dichloromethane) at approximately 0° C. Alternatively, the N-oxides of the compounds can be prepared from the N-oxide of an appropriate starting material.

Compounds in an unoxidized form can be prepared from N-oxides of compounds by treating with a reducing agent (e.g., sulfur, sulfur dioxide, triphenyl phosphine, lithium borohydride, sodium borohydride, phosphorus trichloride, tribromide, or the like) in an suitable inert organic solvent (e.g., acetonitrile, ethanol, aqueous dioxane, or the like) at 0 to 80° C.

Prodrug derivatives of the compounds can be prepared by methods known to those of ordinary skill in the art (e.g., for further details see Saulnier et al. (1994), *Bioorganic and Medicinal Chemistry Letters*, Vol. 4, p. 1985). For example, appropriate prodrugs can be prepared by reacting a non-derivatized compound with a suitable carbamylating agent (e.g., 1,1-acyloxyalkylcarbonochloridate, para-nitrophenyl carbonate, or the like).

Protected derivatives of the compounds can be made by methods known to those of ordinary skill in the art. A detailed description of the techniques applicable to the creation of protecting groups and their removal can be found in T. W. Greene, *Protecting Groups in Organic Synthesis*, $3^{rd}$ edition, John Wiley & Sons, Inc. 1999.

Compounds according to the present invention may be conveniently prepared, or formed during the process of the invention, as solvates (e.g. hydrates). Hydrates of compounds of the present invention may be conveniently prepared by recrystallization from an aqueous/organic solvent mixture, using organic solvents such as dioxin, tetrahydrofuran or methanol.

Compounds according to the present invention can also be prepared as their individual stereoisomers by reacting a racemic mixture of the compound with an optically active resolving agent to form a pair of diastereoisomeric compounds, separating the diastereomers and recovering the optically pure enantiomer. While resolution of enantiomers can be carried out using covalent diastereomeric derivatives of compounds, dissociable complexes are preferred (e.g., crystalline diastereoisomeric salts). Diastereomers have distinct physical properties (e.g., melting points, boiling points, solubilities, reactivity, etc.) and can be readily separated by taking advantage of these dissimilarities. The diastereomers can be separated by chromatography or, preferably, by separation/resolution techniques based upon differences in solubility. The optically pure enantiomer is then recovered, along with the resolving agent, by any practical means that would not result in racemization. A more detailed description of the techniques applicable to the resolution of stereoisomers of compounds from their racemic mixture can be found in Jean Jacques Andre Collet, Samuel H. Wilen, Enantiomers, Racemates and Resolutions, John Wiley & Sons, Inc. (1981).

As used herein the symbols and conventions used in these processes, schemes and examples are consistent with those used in the contemporary scientific literature, for example, the Journal of the American Chemical Society or the Journal of Biological Chemistry. Standard single-letter or three-letter abbreviations are generally used to designate amino acid residues, which are assumed to be in the L-configuration unless otherwise noted. Unless otherwise noted, all starting materials were obtained from commercial suppliers and used without further purification. Specifically, the following abbreviations may be used in the examples and throughout the specification:

g (grams); mg (milligrams);
L (liters); mL (milliliters);

μL (microliters); psi (pounds per square inch);
M (molar); mM (millimolar);
i.v. (intravenous); Hz (Hertz);
MHz (megahertz); mol (moles);
mmol (millimoles); RT (ambient temperature);
min (minutes); h (hours);
mp (melting point); TLC (thin layer chromatography);
Tr (retention time); RP (reverse phase);
MeOH (methanol); i-PrOH (isopropanol);
TEA (triethylamine); TFA (trifluoroacetic acid);
TFAA (trifluoroacetic anhydride); THF (tetrahydrofuran);
DMSO (dimethylsulfoxide); EtOAc (ethyl acetate);
DME (1,2-dimethoxyethane); DCM (dichloromethane);
DCE (dichloroethane); DMF (N,N-dimethylformamide);
DMPU (N,N'-dimethylpropyleneurea); CDI (1,1-carbonyldiimidazole);
IBCF (isobutyl chloroformate); HOAc (acetic acid);
HOSu (N-hydroxysuccinimide); HOBT (1-hydroxybenzotriazole);
Et$_2$O (diethyl ether); EDCI (ethylcarbodiimide hydrochloride);
BOC (tert-butyloxycarbonyl); FMOC (9-fluorenylmethoxycarbonyl);
DCC (dicyclohexylcarbodiimide); CBZ (benzyloxycarbonyl);
Ac (acetyl); atm (atmosphere);
TMSE (2-(trimethylsilyl)ethyl); TMS (trimethylsilyl);
TIPS (triisopropylsilyl); TBS (t-butyldimethylsilyl);
DMAP (4-dimethylaminopyridine); Me (methyl);
OMe (methoxy); Et (ethyl);
Et (ethyl); tBu (tert-butyl);
HPLC (high pressure liquid chromatography);
BOP (bis(2-oxo-3-oxazolidinyl)phosphinic chloride);
TBAF (tetra-n-butylammonium fluoride);
mCPBA (meta-chloroperbenzoic acid.

All references to ether or Et$_2$O are to diethyl ether; brine refers to a saturated aqueous solution of NaCl. Unless otherwise indicated, all temperatures are expressed in ° C. (degrees Centigrade). All reactions conducted under an inert atmosphere at RT unless otherwise noted.

$^1$H NMR spectra were recorded on a Bruker Avance 400. Chemical shifts are expressed in parts per million (ppm). Coupling constants are in units of Hertz (Hz). Splitting patterns describe apparent multiplicities and are designated as s (singlet), d (doublet), t (triplet), q (quartet), m (multiplet), br (broad).

Low-resolution mass spectra (MS) and compound purity data were acquired on a Waters ZQ LC/MS single quadrupole system equipped with electrospray ionization (ESI) source, UV detector (220 and 254 nm), and evaporative light scattering detector (ELSD). Thin-layer chromatography was performed on 0.25 mm E Merck silica gel plates (60E-254), visualized with UV light, 5% ethanolic phosphomolybdic acid, Ninhydrin or p-anisaldehyde solution. Flash column chromatography was performed on silica gel (230-400 mesh, Merck).

The starting materials and reagents used in preparing these compounds are either available from commercial suppliers such as the Aldrich Chemical Company (Milwaukee, Wis.), Bachem (Torrance, Calif.), Sigma (St. Louis, Mo.), or may be prepared by methods well known to a person of ordinary skill in the art, following procedures described in such standard references as Fieser and Fieser's *Reagents for Organic Synthesis*, vols. 1-17, John Wiley and Sons, New York, N.Y., 1991; *Rodd's Chemistry of Carbon Compounds*, vols. 1-5 and supps., Elsevier Science Publishers, 1989; Organic Reactions, vols. 1-40, John Wiley and Sons, New York, N.Y., 1991; March J.: *Advanced Organic Chemistry*, 4th ed., John Wiley and Sons, New York, N.Y.; and Larock: *Comprehensive Organic Transformations*, VCH Publishers, New York, 1989.

The entire disclosure of all documents cited throughout this application are incorporated herein by reference.

2. Synthetic Schemes for Kinase Inhibitors of the Present Invention

Kinase inhibitors according to the present invention may be synthesized according to the reaction schemes shown below. Other reaction schemes could be readily devised by those skilled in the art. It should also be appreciated that a variety of different solvents, temperatures and other reaction conditions can be varied to optimize the yields of the reactions.

In the reactions described hereinafter it may be necessary to protect reactive functional groups, for example hydroxy, amino, imino, thio or carboxy groups, where these are desired in the final product, to avoid their unwanted participation in the reactions. Conventional protecting groups may be used in accordance with standard practice, for examples see T. W. Greene and P. G. M. Wuts in "Protective Groups in Organic Chemistry" John Wiley and Sons, 1991.

Kinase inhibitors according to the present invention may be synthesized according to the reaction scheme shown below. Other reaction schemes could be readily devised by those skilled in the art. It should also be appreciated that a variety of different solvents, temperatures and other reaction conditions can be varied to optimize the yields of the reactions.

In the reactions described hereinafter it may be necessary to protect reactive functional groups, for example hydroxy, amino, imino, thio or carboxy groups, where these are desired in the final product, to avoid their unwanted participation in the reactions. Conventional protecting groups may be used in accordance with standard practice, for examples see T. W. Greene and P. G. M. Wuts in "Protective Groups in Organic Chemistry" John Wiley and Sons, 1991.

Experimental Methods

A general synthetic route for producing compounds of the present invention is shown in Scheme 1. Cyclisation of Compound A with an aldehyde provides Compound B which, upon hydrolysis, produces Compound C. Halogenation gives Compound D. Compound D is then reacted with Compound E to produce Compound F. Microwave promoted addition of Compound G affords Compound H.

Scheme 1:

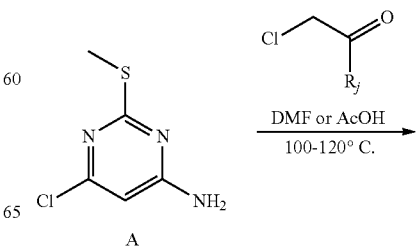

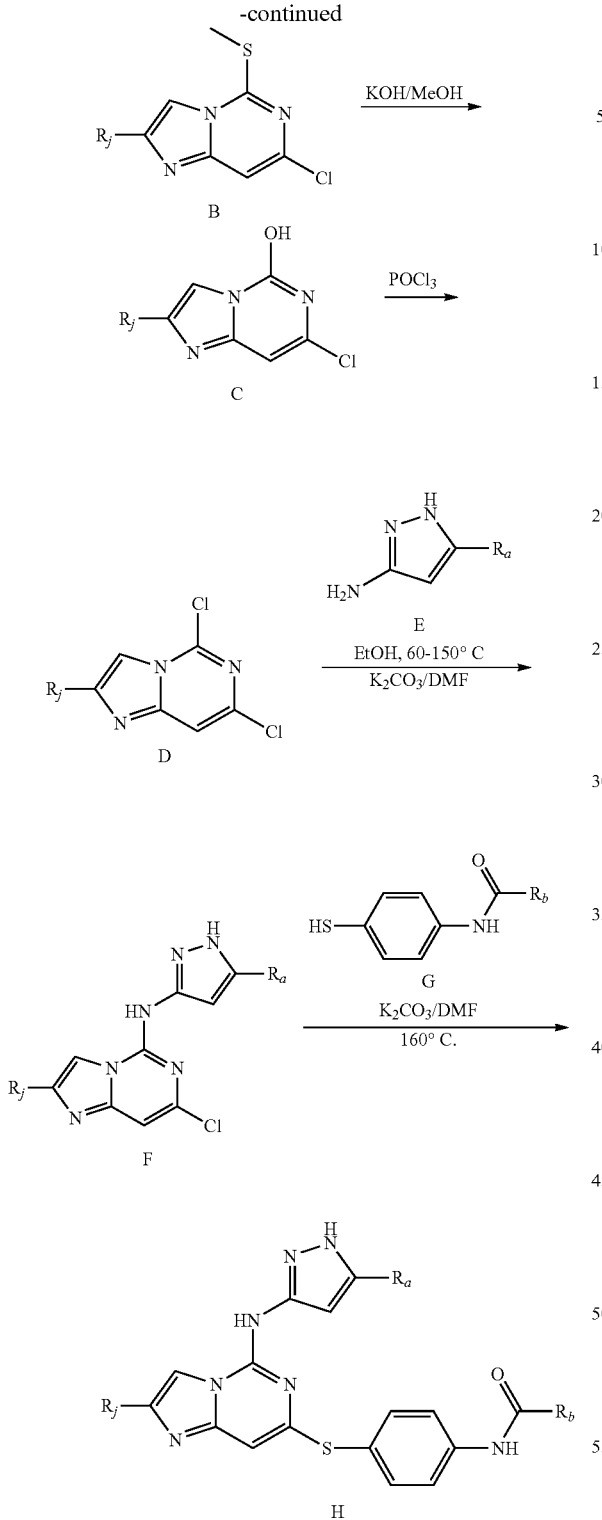

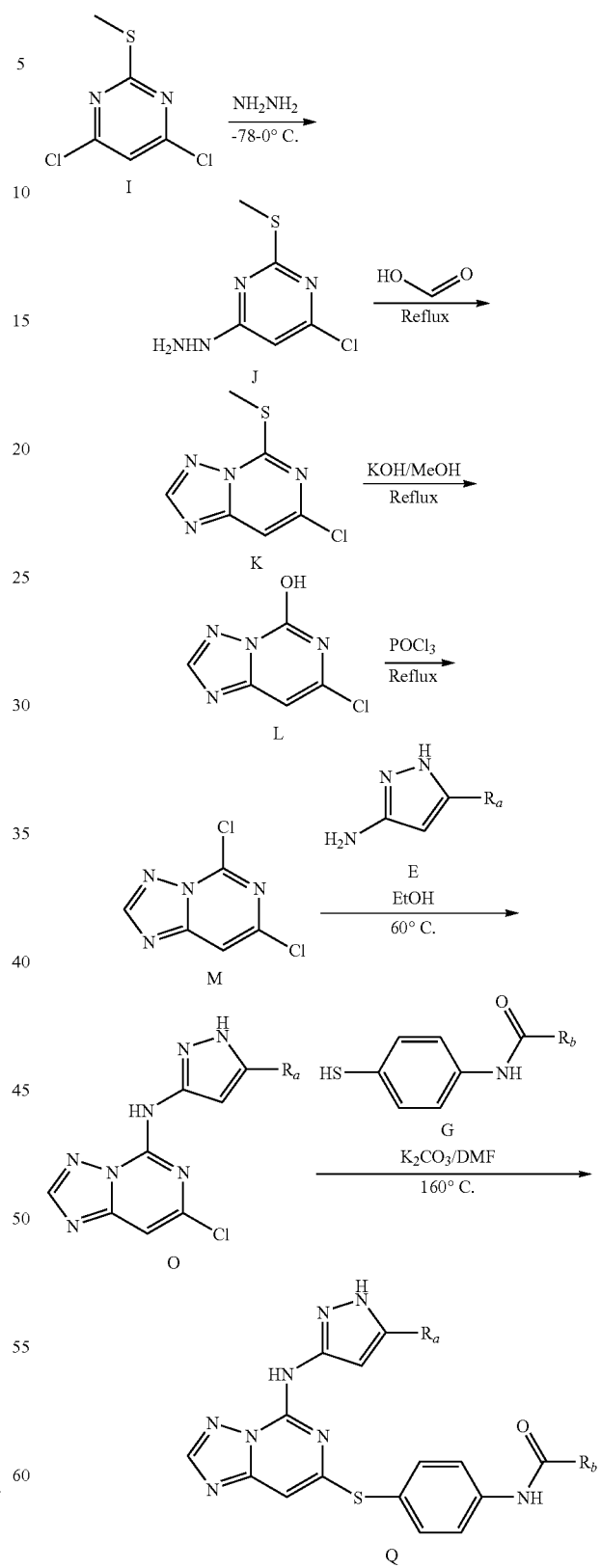

Scheme 2:

A synthetic route for producing other compounds of the present invention is shown in Scheme 2. Condensation of Compound I with hydrazine provides Compound J, which is then cyclized with formic acid to produce Compound K. Hydrolysis gives Compound L which, upon POCl₃ treatment, gives Compound M. Pyrazole displacement gives Compound O and microwave promoted addition of Compound G affords Compound Q.

A synthetic route for producing other compounds of the present invention is shown in Scheme 3. Bromination of Compound R with N-bromosuccinimide provides Compound S, which is cyclized with chloroacetaldehyde to form Compound T. Addition of pyrazole gives Compound V. Reaction with Compound G gives Compound X of the present invention.

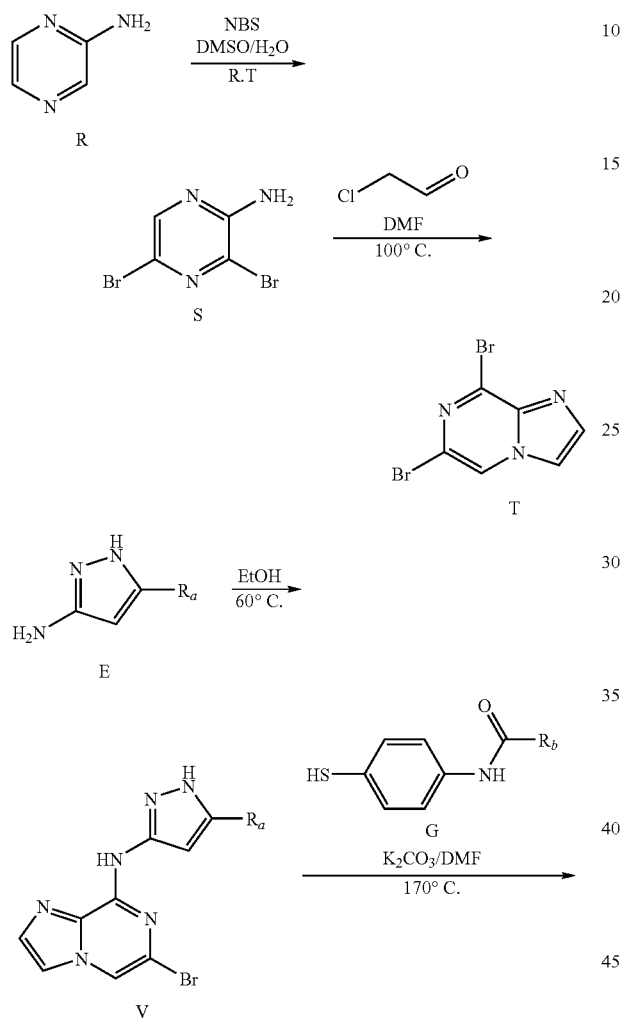

Scheme 4:

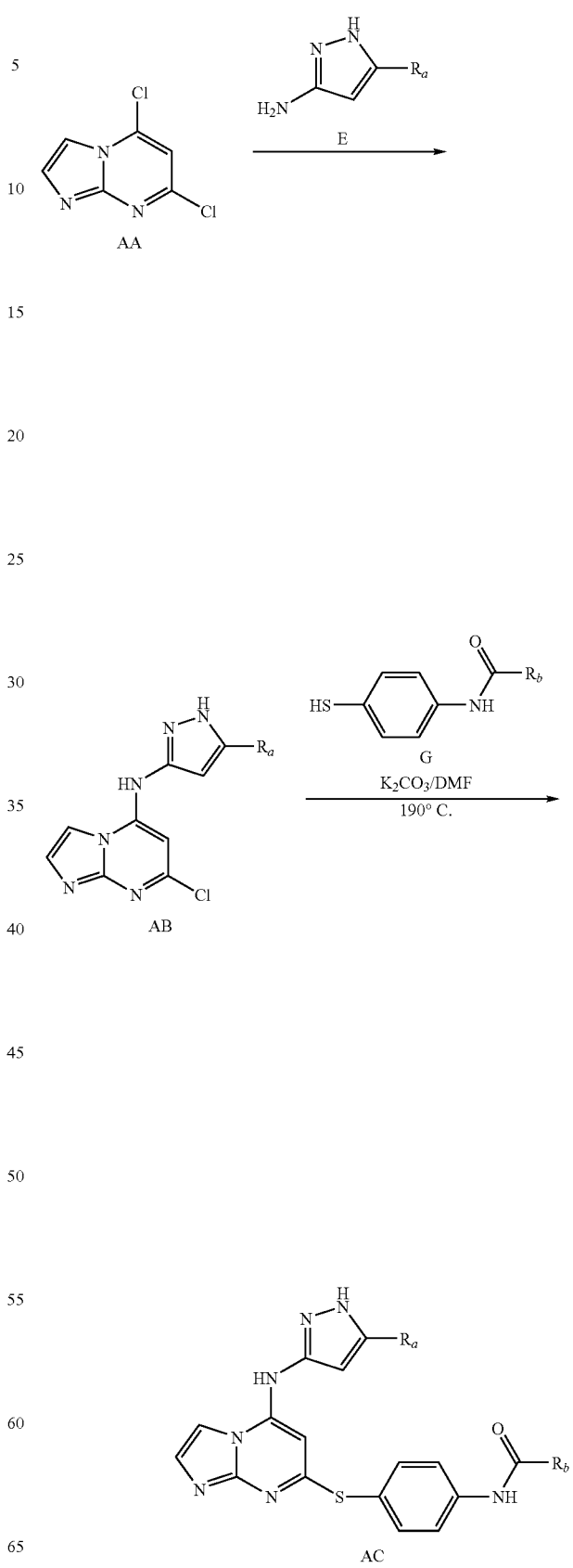

A synthetic route for producing other compounds of the present invention is shown in Scheme 4. Reaction of Compound AA (*Ann. N.Y. Acad. Sci.*, 1975, 255, 166-175) with compound E provides Compound AB, which is then reacted with Compound G to give Compound AC of the present invention.

A synthetic route for producing other compounds of the present invention is shown in Scheme 5. Reaction of Compound BA (*J. Heterocyclic Chemistry*, 1986, 23, 981-987) with Compound E provides Compound BB, which is then reacted with Compound G to give Compound BC of the present invention.

Scheme 5:

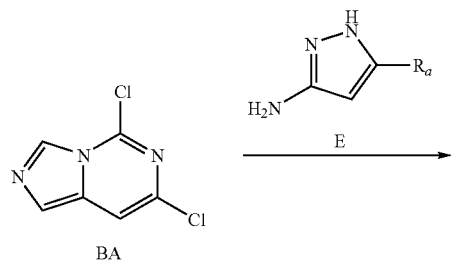

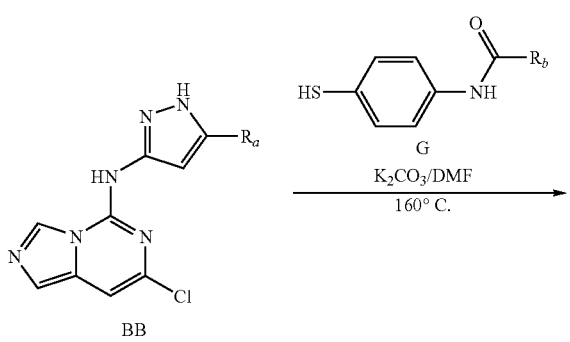

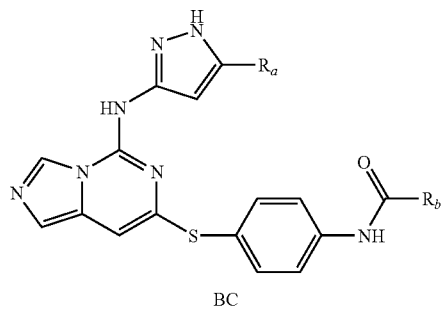

A synthetic route for producing other compounds of the present invention is shown in Scheme 6. 5,7-Dichloro-imidazo[1,2-c]pyrimidine (10 mol) may be dissolved in DMF and treated with solid $K_2CO_3$ (50 mol). The reaction may be stirred at 50-200° C. for 0-3 hours and then concentrated in vacuo. Product may be precipitated by adding water. Resulting solid may then be filtered and dried under vacuo to provide Compound F.

Reaction of Compound F (see Scheme 1) with Compound CA provides Compound CB. For example, Compound F (0.12 mol) and an amine (1.2 mol) may be dissolved in DMF (0.3 mL) This solution may then be heated at between 150-200° C. for 1-25 minutes using a microwave reactor. Purification by preparative HPLC may afford the product as a solid. Alternatively, Suzuki coupling of Compound F with Compound CC gives Compound CD of the present invention.

Additional compounds of the present invention can be prepared in an analogous manner using Compounds O, V, AB and BB in place of Compound F.

Scheme 6:

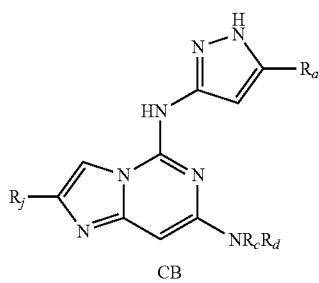

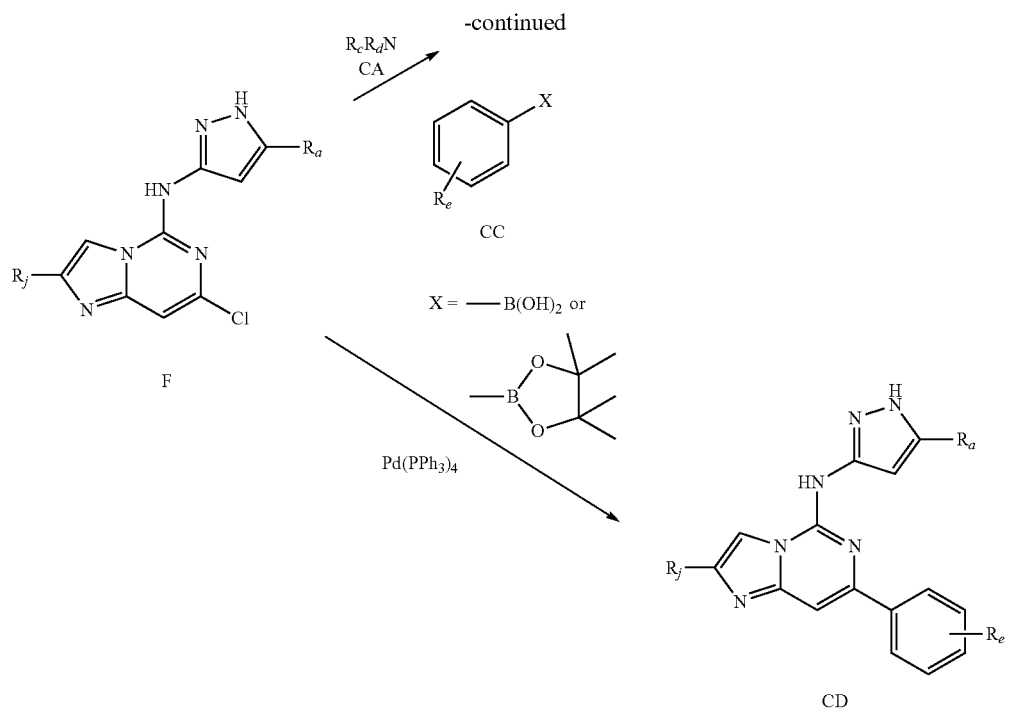

A synthetic route for producing other compounds of the present invention is shown in Scheme 7. Compound DA (9.5 mol) and a pyrrazole (10.5 mol) may be dissolved in ethanol (20 mL) This solution may then be heated at 30-75° C. for 1-90 minutes. Reaction mixture may be cooled to room temperature and resulting solid may be filtered and washed with small amount of alcohol then dried in vacuo to provide Compound DB.

Compound DB (1.66 mol) in anhydrous THF (3 mL) may be cooled to −20° C. under $N_2$. Solution of $LiAlH_4$ in THF (2.65 mol) may be added dropwise. This mixture may then be maintained at about 0° C. for 1-2 hours. The reaction mixture may be quenched with water (0.75 mL) and 1N NaOH (0.25 mL) Diluted with organic solvent such as ethyl acetate and resulting salts may be filtered off The filtrate then be transferred to a seperatory funnel and washed with water and brine, and then dried ($MgSO_4$) and concentrated in vacuo to provide Compound DC.

Compound DC (0.64 mol), a boronic acid (0.96 mol) and Pd $(PPh_3)_4$ (0.32 mol) may be taken up in dioxane (3 mL), and saturated $K_2CO_3$ (1.5 mL) added. This solution may then be heated at 120-180° C. for 1-30 minutes using a microwave reactor. If a solid is observed upon cooling, it may be filtered. Filtrate may then be further purified by preparative HPLC to provide Compound DD.

Chlorination: Compound DD (0.25 mol) may be treated with thionyl chloride (0.6 mL). Reaction mixture may be stirred at room temperature for 0-60 minutes, and then concentrated in vacuo to provide Compound DE.

Compound DE (0.25 mol) in dimethylformamide (0.5 mL) may be treated with excess amine. This solution may be stirred at room temperature for 0-60 minutes. Purification by preparative HPLC may afford the product, Compound DF, as a solid.

Scheme 7:

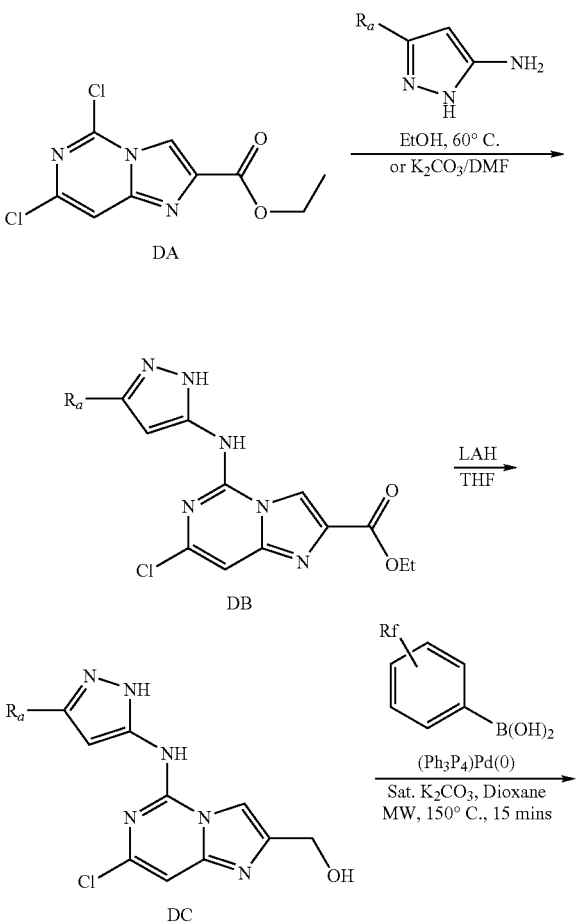

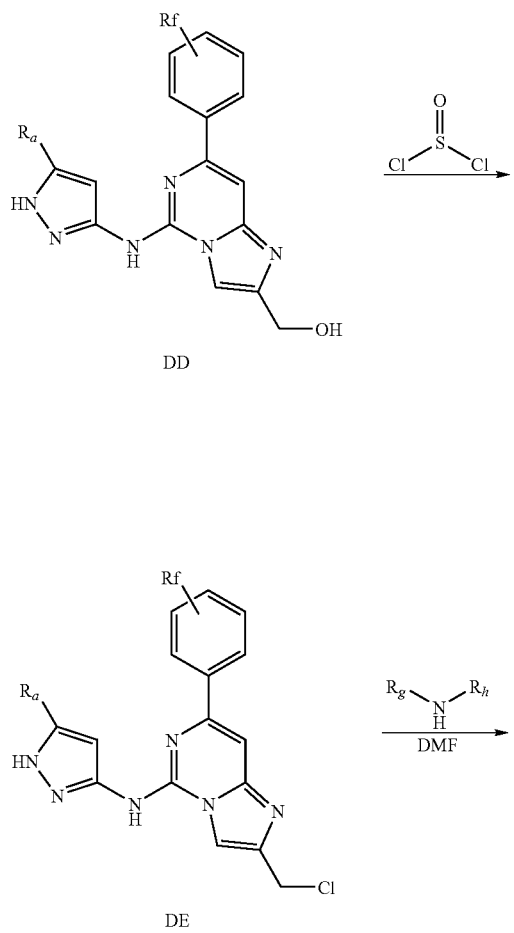

DD

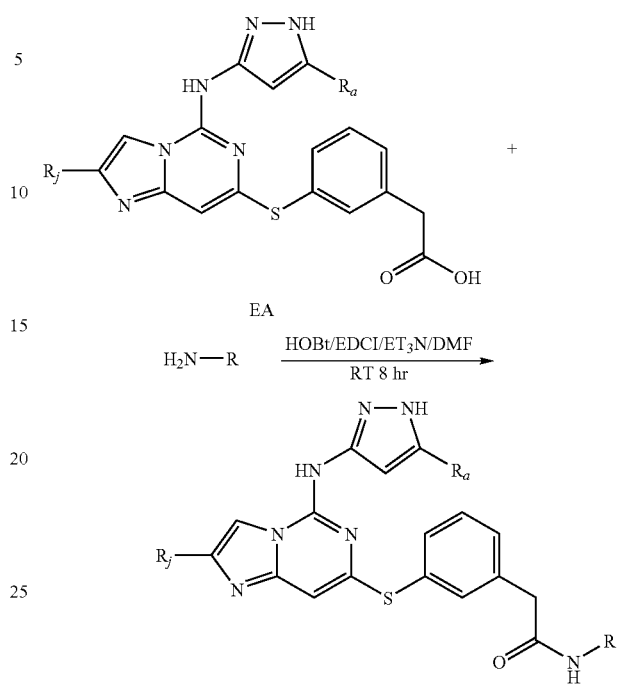

Scheme 8:

EA

EB

A synthetic route for producing other compounds of the present invention is shown in Scheme 8. Displacement of the carboxylic acid of Compound EA with various amines in the presence of the coupling agents hydroxybenzotriazole and 1-ethyl-(3-dimethylaminopropyl) carbodiimide hydrochloride under basic conditions provides Compound EB.

DE

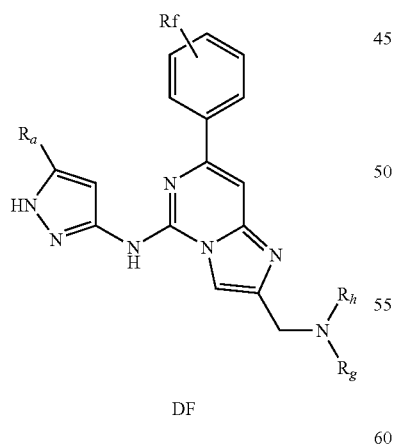

DF

A synthetic route for producing other compounds of the present invention is shown in Scheme 9. Microwave displacement of the chlorine atom of Compound F with 4-mercaptobenzoic acid provides Compound FB. This is then reacted with various amines using hydroxybenzotriazole and 1-ethyl-(3-dimethylaminopropyl)carbodiimide hydrochloride under basic conditions at room temperature to produce Compound FC. In reactions which showed little product, hydroxybenzotriazole and 1-ethyl-(3-dimethylaminopropyl)carbodiimide hydrochloride were replaced by 2 equivalents of PYBOP.

Scheme 9:

F

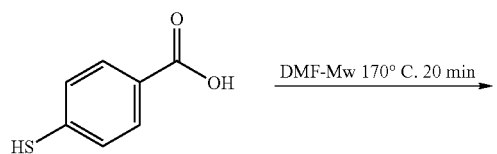

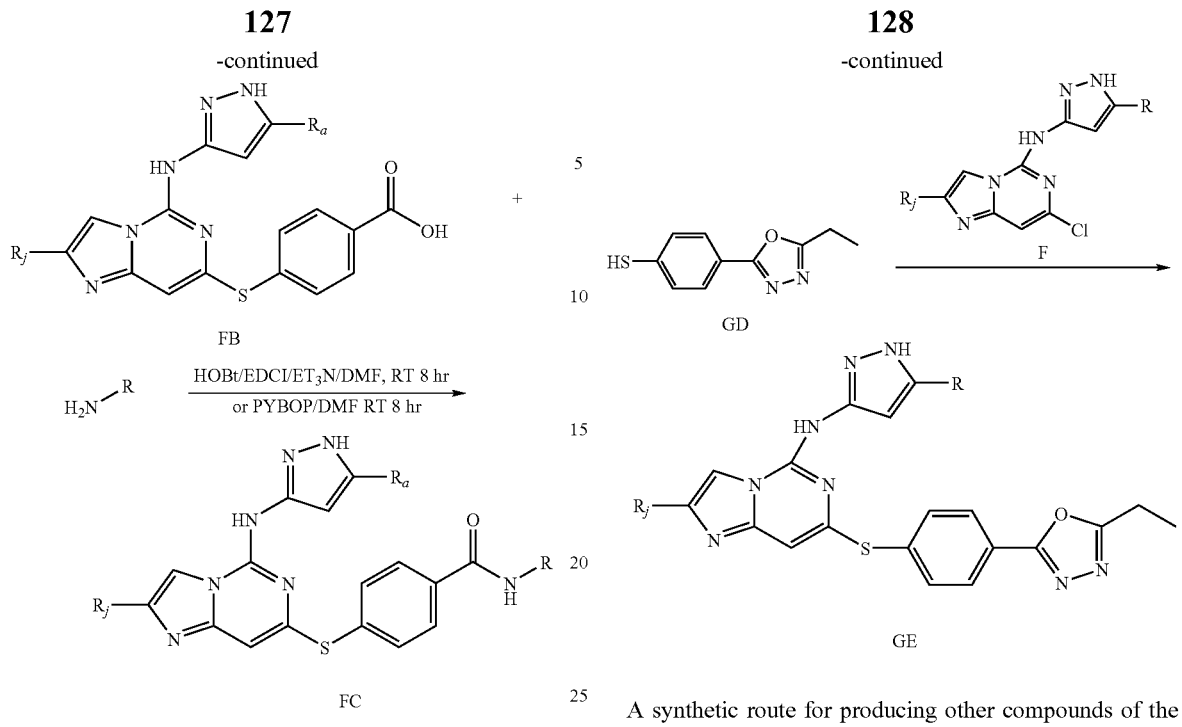

A synthetic route for producing other compounds of the present invention is shown in Scheme 10. Microwave condensation of Compound GA with triethyl orthopropionate provides HB, which is then cyclized in a microwave reactor with formic acid in dioxane to produce Compound GC. Removal of the trityl group with triethyl silane and trifluoroacetic acid gives Compound GD. Coupling to pyrazole linked imidazopyrimidine chloride, F, gives the title compound Compound GE.

Scheme 10:

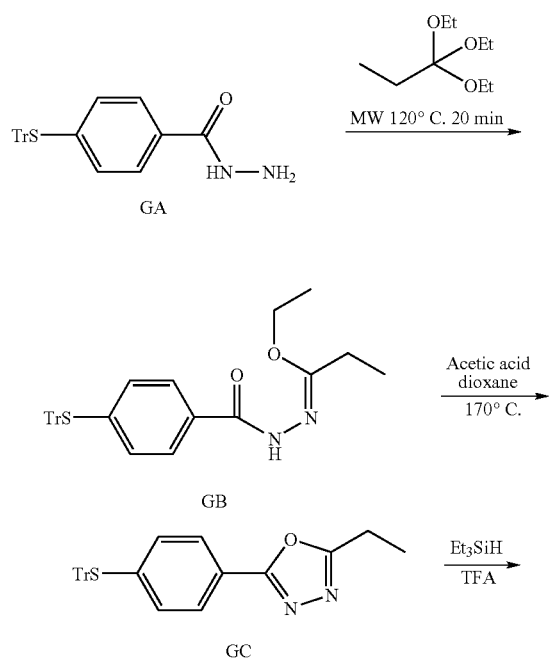

A synthetic route for producing other compounds of the present invention is shown in Scheme 11. An ethyl 7-chloro-5-(1H-pyrazol-3-ylamino)imidazo[1,2-f]pyrimidine-2-carboxylate (3.59 g, 10.4 ml 1 eq) is dissolved in anhydrous THF under nitrogen at 0° C. 1.0M lithium aluminum hydride in THF (15.5 ml, 15.5 mmol, 1.5 eq) is added dropwise. Upon completion of addition, the solution is stirred for 2 hours. The reaction can be seen to be complete by LCMS. Sodium sulfate decahydrate is slowly added until bubbling stops and the reaction mixture is filtered. The solid is triturated in 20% methanol in methylene chloride and filtered. This can be repeated a further two times. The solvent is removed in vacuo and the product purified by flash chromatography.

The (7-chloro-5-(1H-pyrazol-3-ylamino) imidazo[1,2-f]pyrimidin-2-yl)methanol (928 mg, 30.5 mmol, 1 eq), an N-(4-mercaptophenyl)acetamide (1.02 g, 61 mmol, 2 eq) and potassium carbonate (421 mg, 30.5 mmol, 1 eq) are dissolved in DMF. The mixture is placed in a microwave reactor at 160° C. for 15 minutes. LCMS can be used to confirm the product. The solvent can be evaporated and the residue purified by flash chromatography.

The N-(4-(5-(1H-pyrazol-3-ylamino)-2-(hydroxymethyl)imidazo[1,2-f]pyrimidin-7-ylthio)phenyl)acetamide (50 mg, 0.11 mmol, 1 eq) and 2.0M methylamine in THF (1 ml, 22 mmol, 180 eq) are mixed in DMF and stirred at room temperature. The reaction can be followed by LCMS. Upon completion, the reaction mixture can be evaporated and the residue purified by high-performance liquid chromatography.

Scheme 11:

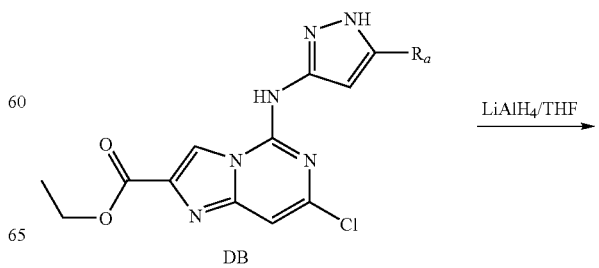

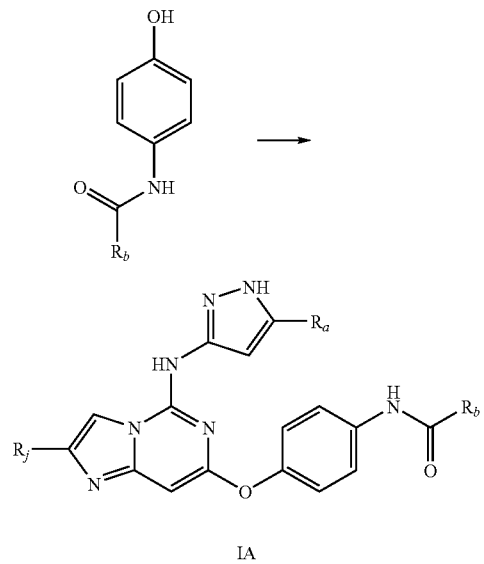

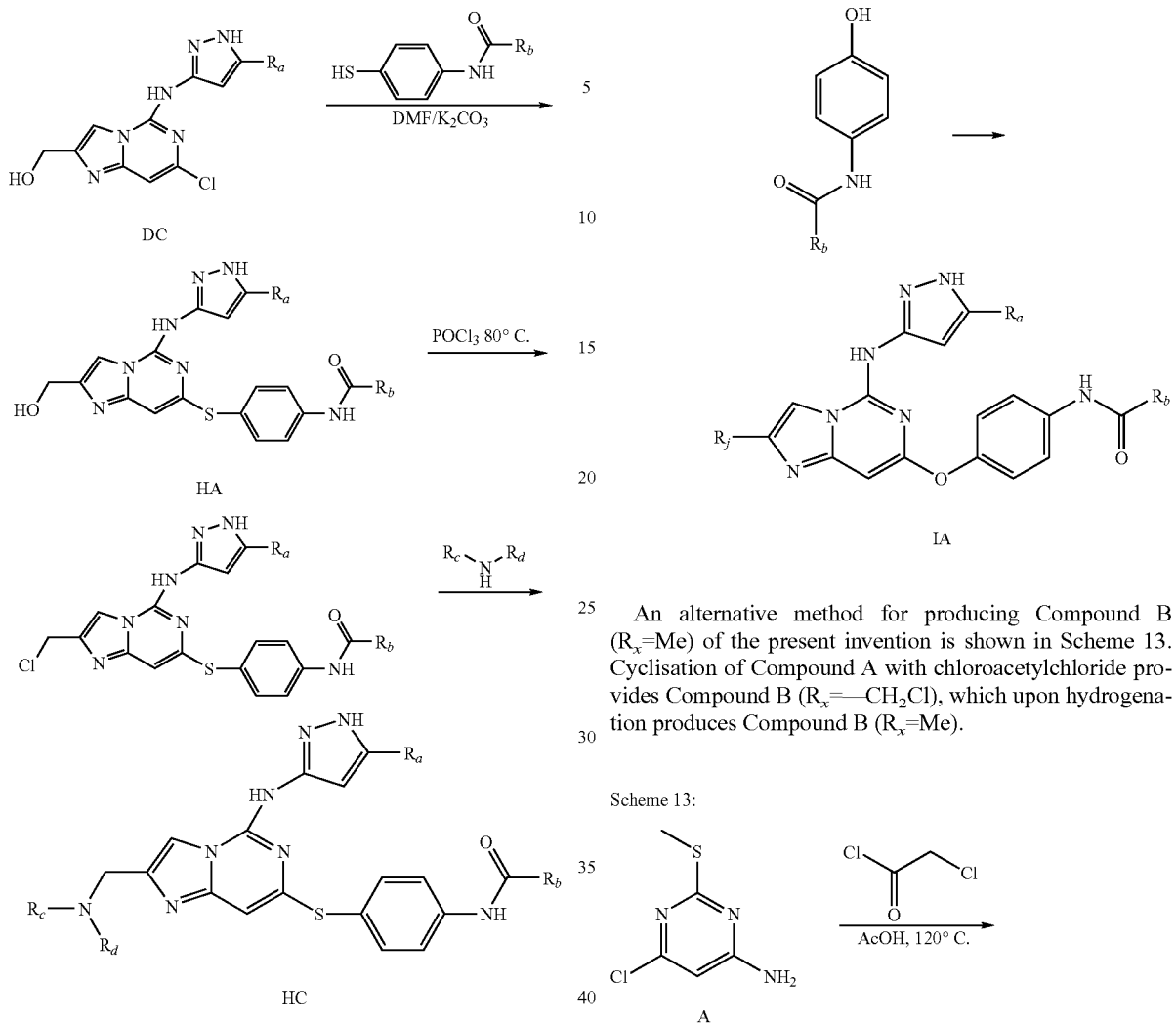

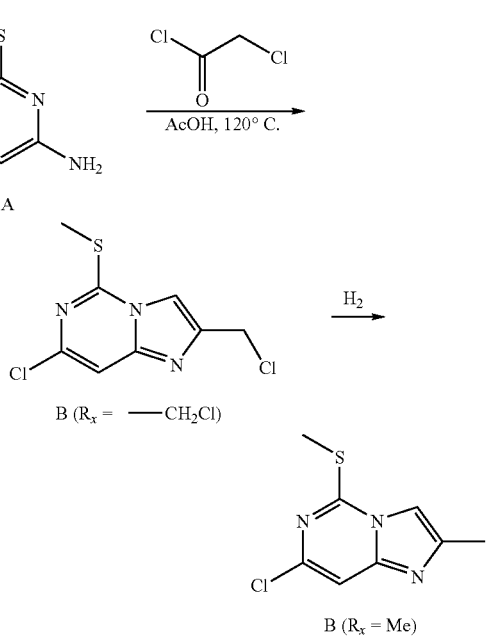

A synthetic route for producing other compounds of the present invention is shown in Scheme 12. A mixture of a (7-Chloro-imidazo[1,2-c]pyrimidin-5-yl)-(1H-pyrazol-3-yl)-amine (125 mg, 0.46 mmol), an N-(4-Hydroxy-phenyl)-acetamide (689 mg, 4.56 mmol) and K$_2$CO$_3$ (630 mg) are mixed in DMF (1 ml) and heated at 200° C. in a microwave for 15 minutes. The reaction mixture can then be purified with HPLC.

Scheme 12:

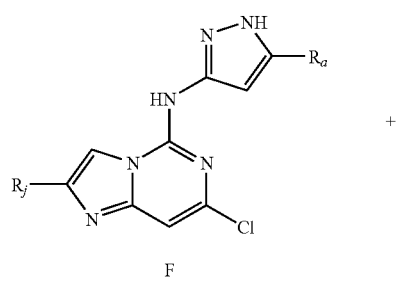

An alternative method for producing Compound B (R$_x$=Me) of the present invention is shown in Scheme 13. Cyclisation of Compound A with chloroacetylchloride provides Compound B (R$_x$=—CH$_2$Cl), which upon hydrogenation produces Compound B (R$_x$=Me).

Scheme 13:

An alternative method for producing Compound CD (R$_x$=Me) of the present invention is shown in Scheme 14. Reaction of Compound A with amino alcohol followed by treatment with methane sulfonylchloride provides Compound B (R$_x$=Me), which upon hydrolysis produces Compound C(R$_x$=Me). Halogenation gives Compound D (R$_x$=Me). Compound D (R$_x$=Me) is then reacted with Compound E to produce Compound F (R$_x$=Me). Suzuki coupling of Compound F (R$_x$=Me) with Compound CC gives Compound CD (R$_i$=Me), which upon oxidation provides Compound CD (R$_x$=Me).

Scheme 14:

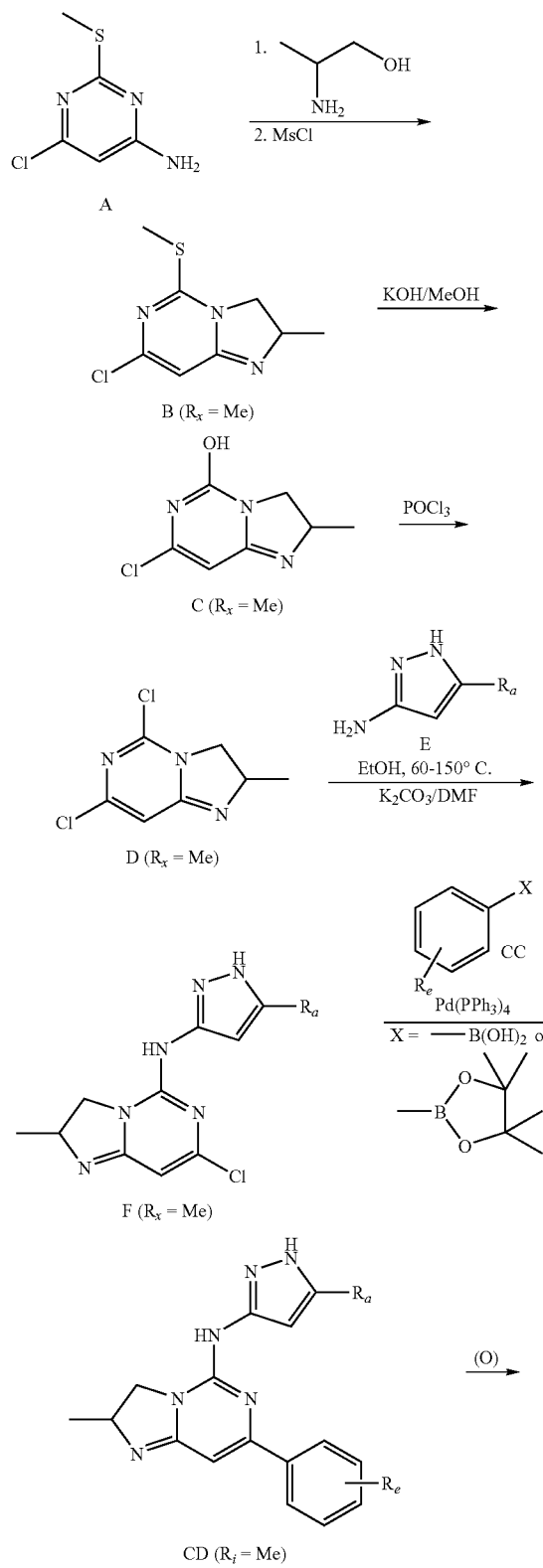

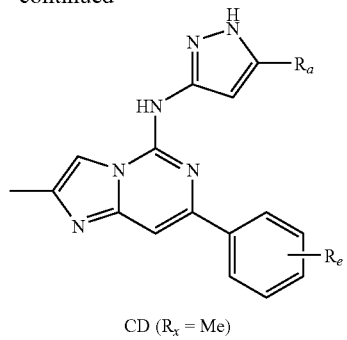

A synthetic route for producing other compounds of the present invention is shown in Scheme 15. Reaction of Compound JA with DMF and POCl$_3$ provides Compound JB, which is then treated with NH$_2$OSO$_3$H in presence of KOH to produce Compound JC. Hydrolysis gives Compound JD. Cyclization of Compound JD with the appropriate imidate provides Compound JE. Treatment of Compound JE with POCl$_3$, gives Compound JF, and pyrazole displacement affords Compound IG.

Scheme 15:

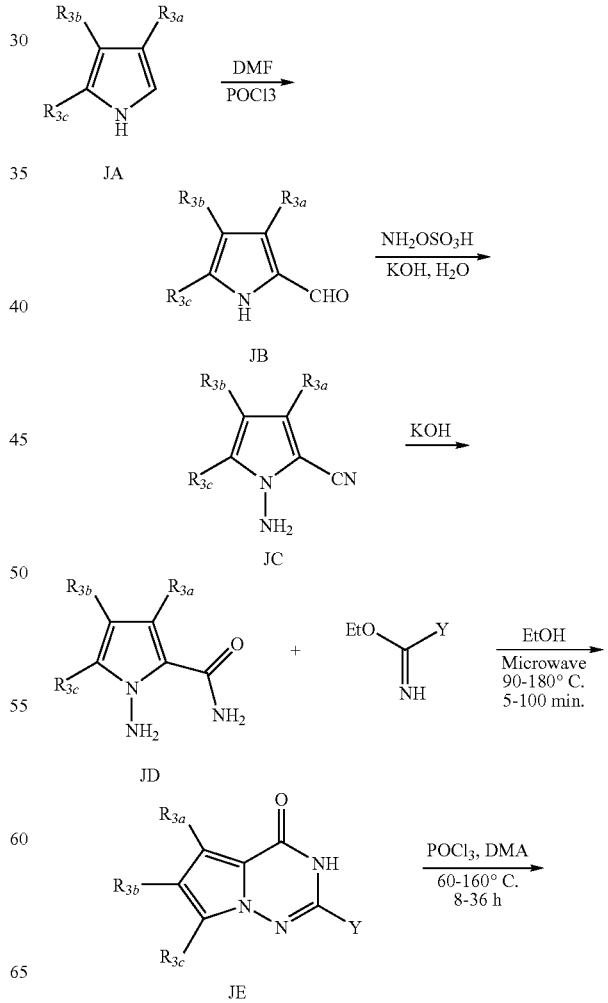

-continued

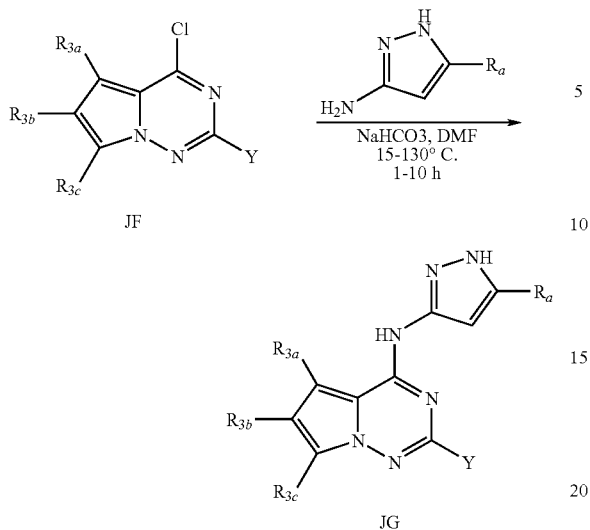

A synthetic route for producing still other compounds of the present invention is shown in Scheme 16. Cyclization of Compound KD with CDI provides Compound KH, which is then treated with (CF$_3$SO$_2$)$_2$O to produce Compound M. Pyrazole displacement gives Compound KJ. Suzuki coupling of Compound KJ with the appropriate boronic acid affords Compound KK. Alternatively, displacement of the OTf group on Compound KJ with the appropriate thiol affords Compound KL.

Scheme 16:

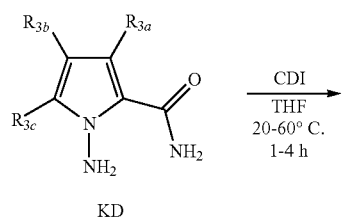

KD

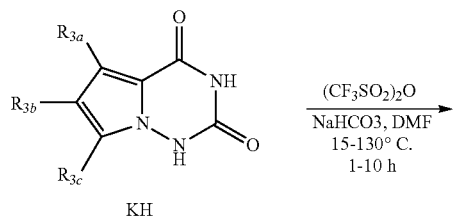

KH

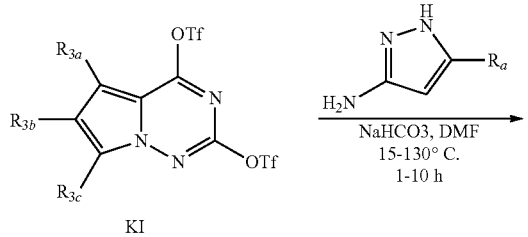

KI

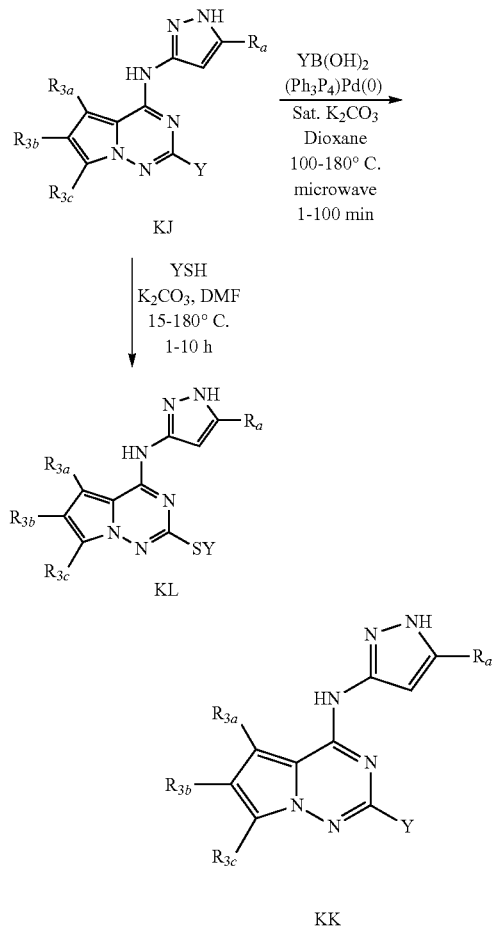

For example, the above reaction schemes, and variations thereof, can be used to prepare the following:

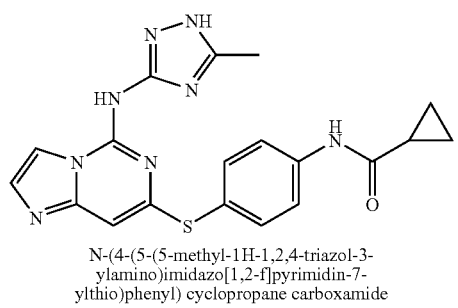

N-(4-(5-(5-methyl-1H-1,2,4-triazol-3-ylamino)imidazo[1,2-f]pyrimidin-7-ylthio)phenyl) cyclopropane carboxamide

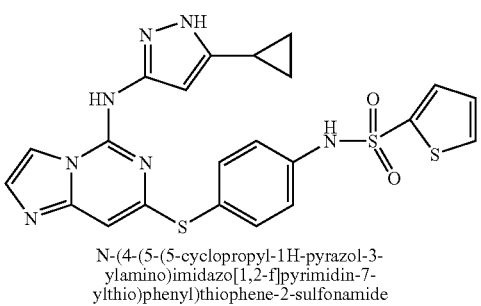

N-(4-(5-(5-cyclopropyl-1H-pyrazol-3-ylamino)imidazo[1,2-f]pyrimidin-7-ylthio)phenyl)thiophene-2-sulfonamide

135
-continued

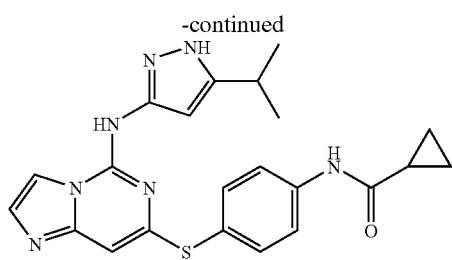
N-(4-(5-(5-isopropyl-1H-pyrazol-3-ylamino)imidazo[1,2-f]pyrimidin-7-ylthio)phenyl) cyclopropane carboxamide

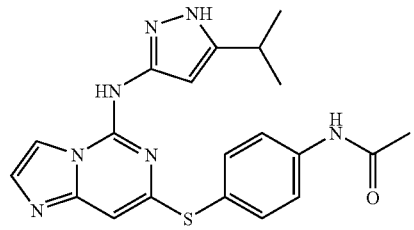
N-(4-(5-(5-isopropyl-1H-pyrazol-3-ylamino)imidazo[1,2-f]pyrimidin-7-ylthio)phenyl)acetamide

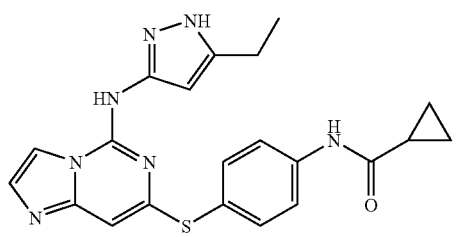
N-(4-(5-(5-ethyl-1H-pyrazol-3-ylamino)imidazo[1,2-f]pyrimidin-7-ylthio)phenyl) cyclopropane carboxamide

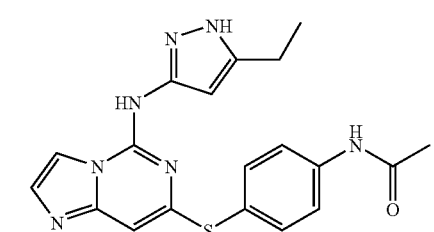
N-(4-(5-(5-ethyl-1H-pyrazol-3-ylamino)imidazo[1,2-f]pyrimidin-7-ylthio)phenyl)acetamide

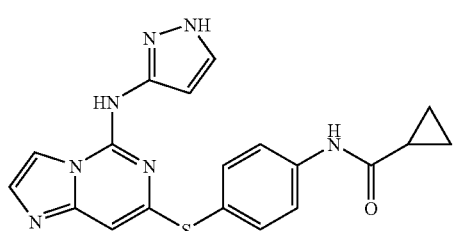
N-(4-(5-(1H-pyrazol-3-ylamino)imidazo[1,2-f]pyrimidin-7-ylthio)phenyl) cyclopropane carboxamide

136
-continued

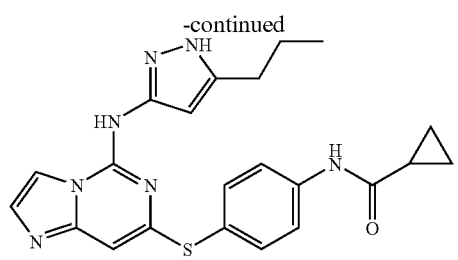
N-(4-(5-(5-propyl-1H-pyrazol-3-ylamino)imidazo[1,2-f]pyrimidin-7-ylthio)phenyl) cyclopropane carboxamide

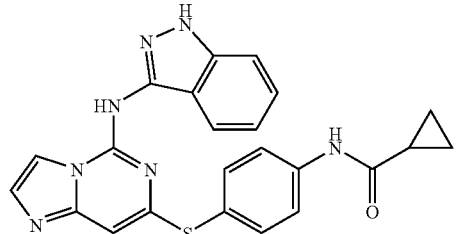
N-(4-(5-(1H-indazol-3-ylamino)imidaz[1,2-f]pyrimidin-7-ylthio)phenyl) cyclopropane carboxamide

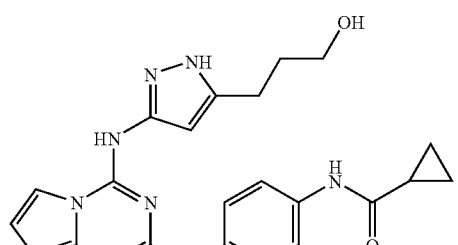
N-(4-(5-(3-hyroxypropyl-1H-pyrazol-3-ylamino)imidazo[1,2-f]pyrimidin-7-ylthio)phenyl) cyclopropane carboxamide

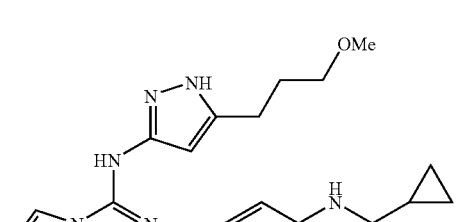
N-(4-(5-(3-methoxpropyl-1H-pyrazol-3-ylamino)imidazo[1,2-f]pyrimidin-7-ylthio)phenyl) cyclopropane carboxamide

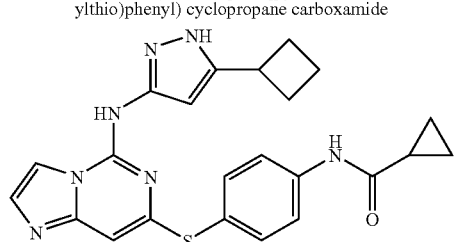
N-(4-(5-(5-cyclobutyl-1H-pyrazol-3-ylamino)imidazo[1,2-f]pyrimidin-7-ylthio)phenyl) cyclopropane carboxamide -continued

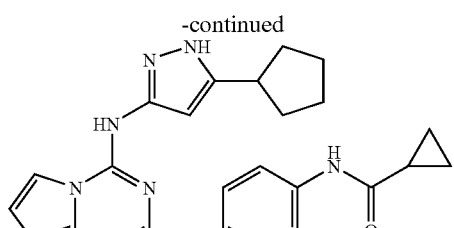

N-(4-(5-(5-cyclopentyl-1H-pyrazol-3-ylamino)imidazo[1,2-f]pyrimidin-7-ylthio)phenyl) cyclopropane carboxamide

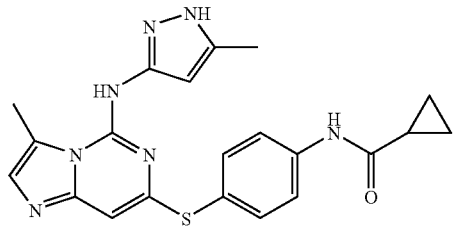

N-(4-(3-methyl-5-(5-methyl-1H-pyrazol-3-ylamino)imidazo[1,2-f]pyrimidin-7-ylthio)phenyl) cyclopropane carboxamide

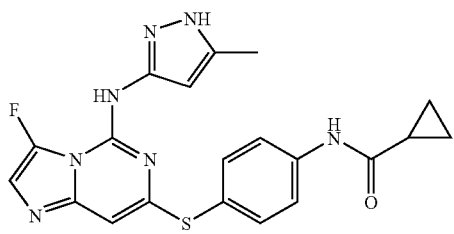

N-(4-(3-fluoro-5-(5-methyl-1H-pyrazol-3-ylamino)imidazo[1,2-f]pyrimidin-7-ylthio)phenyl) cyclopropane carboxamide

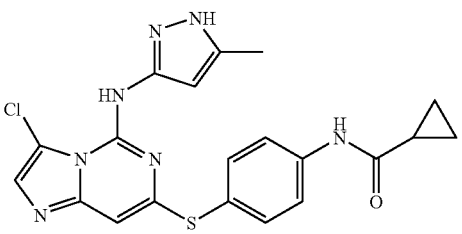

N-(4-(3-chloro-5-(5-methyl-1H-pyrazol-3-ylamino)imidazo[1,2-f]pyrimidin-7-ylthio)phenyl) cyclopropane carboxamide

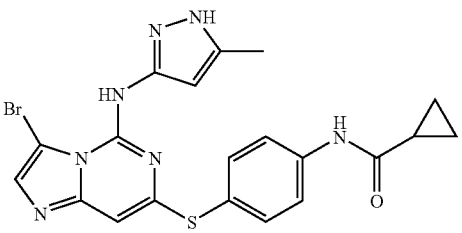

N-(4-(3-bromo-5-(5-methyl-1H-pyrazol-3-ylamino)imidazo[1,2-f]pyrimidin-7-ylthio)phenyl) cyclopropane carboxamide -continued

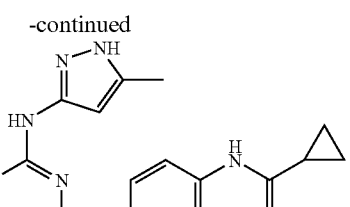

N-(4-(5-(5-methyl-1H-pyrazol-3-ylamino)-2-((4-methylpiperazin-1-yl)methyl)imidazo[1,2-f]pyrimidin-7-ylthio)phenyl) cyclopropane carboxamide

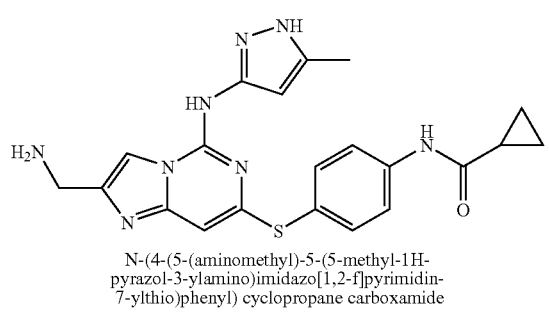

N-(4-(5-(aminomethyl)-5-(5-methyl-1H-pyrazol-3-ylamino)imidazo[1,2-f]pyrimidin-7-ylthio)phenyl) cyclopropane carboxamide

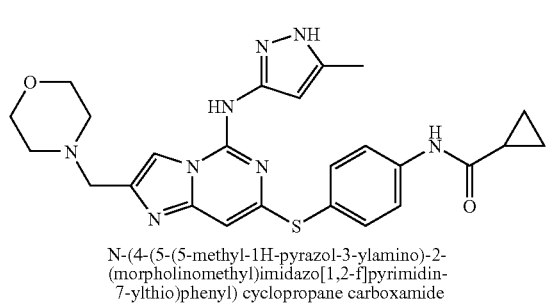

N-(4-(5-(5-methyl-1H-pyrazol-3-ylamino)-2-(morpholinomethyl)imidazo[1,2-f]pyrimidin-7-ylthio)phenyl) cyclopropane carboxamide

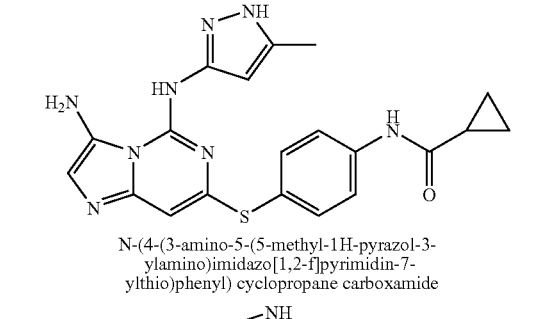

N-(4-(3-amino-5-(5-methyl-1H-pyrazol-3-ylamino)imidazo[1,2-f]pyrimidin-7-ylthio)phenyl) cyclopropane carboxamide

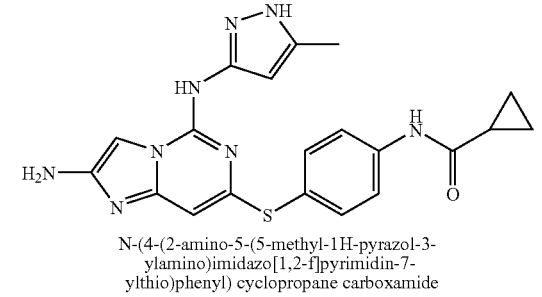

N-(4-(2-amino-5-(5-methyl-1H-pyrazol-3-ylamino)imidazo[1,2-f]pyrimidin-7-ylthio)phenyl) cyclopropane carboxamide -continued

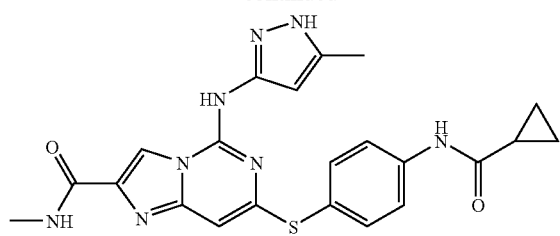

7-(4-(cyclopropanecarboxamido)phenylthio)-
N-methyl-5-(5-methyl-1H-pyrazol-3-
ylamino)imidazo[1,2-f]pyrimidine-2-
carboxamide

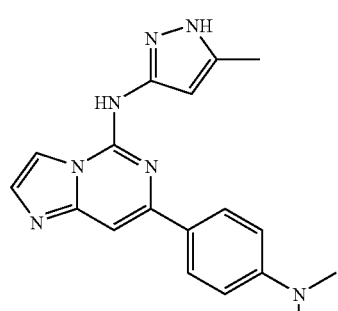

7-(4-(dimethylamino)phenyl)-N-(5-methyl-
1H-pyrazol-3-yl)imidazo[1,2-f]pyrimidin-5-
amine

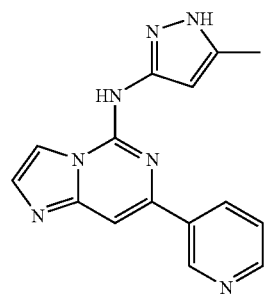

N-(5-methyl-1H-pyrazol-3-yl)-7-(pyridin-3-
yl)imidazo[1,2-f]pyrimidin-5-amine

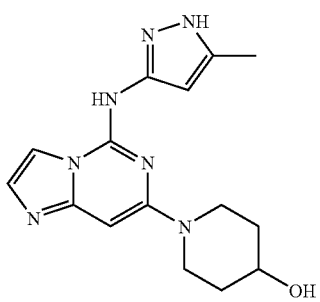

1-(5-(5-methyl-1H-pyrazol-3-
ylamino)imidazo[1,2-f]pyrimidin-7-
yl)piperidin-4-ol -continued

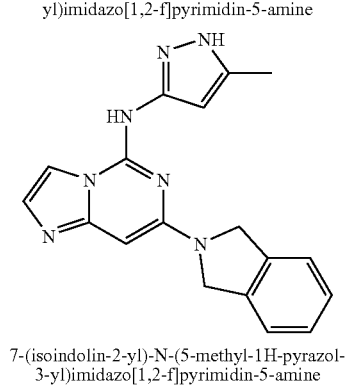

7-(azepan-1-yl)-N-(5-methyl-1H-pyrazol-3-
yl)imidazo[1,2-f]pyrimidin-5-amine

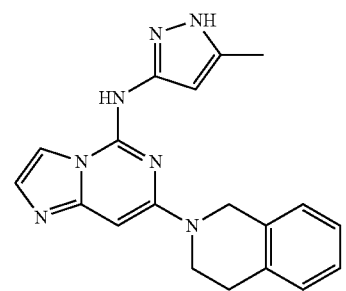

7-(isoindolin-2-yl)-N-(5-methyl-1H-pyrazol-
3-yl)imidazo[1,2-f]pyrimidin-5-amine

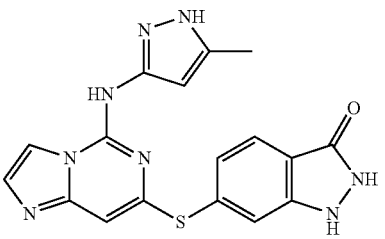

7-(3,4-dihydroisoquinolin-2(1H)-yl)-N-(5-
methyl-1H-pyrazol-3-yl)imidazo[1,2-
f]pyrimidin-5-amine

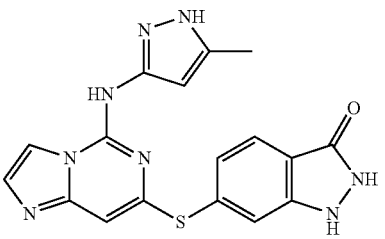

6-(5-(5-methyl-1H-pyrazol-3-
ylamino)imidaz[1,2-f]pyrimidin-7-ylthio)-
1,2-dihydroindazol-3-one

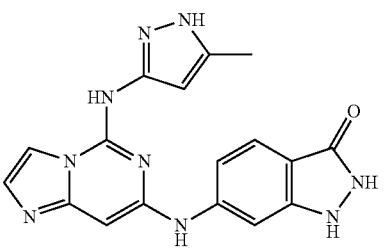

6-(5-(5-methyl-1H-pyrazol-3-
ylamino)imidazo[1,2-f]pyrimidin-7-
ylamino)-1,2-dihydroindazol-3-one

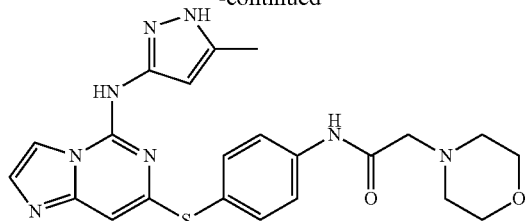

N-(4-(5-(5-methyl-1H-pyrazol-3-ylamino)imidazo[1,2-f]pyrimidin-7-ylthio)phenyl)-2-morpholinoacetamide

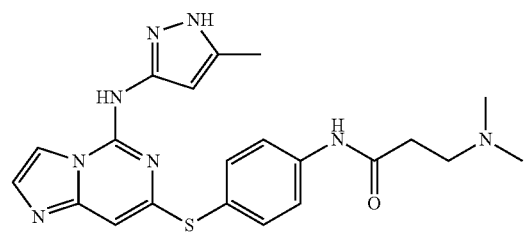

3-(dimethylamino)-N-(4-(5-(5-methyl-1H-pyrazol-3-ylamino)imidazo[1,2-f]ppyrimidin-7-ylthio)phenyl)propanamide

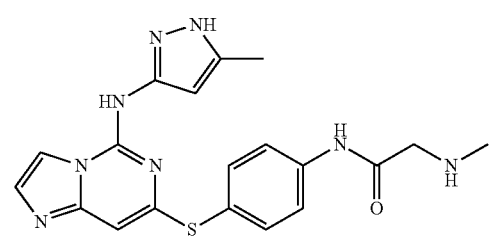

N-(4-(5-(5-methyl-1H-pyrazol-3-ylamino)imidazo[1,2-f]ppyrimidin-7-ylthio)phenyl)-2-(methylamino)acetamide

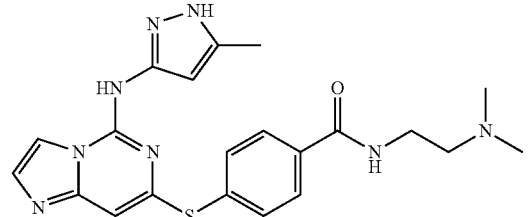

N-(2-(dimethylamino)ethyl)-4-(5-(5-methyl-1H-pyrazol-3-ylamino)imidazo[1,2-f]pyrimidin-7-ylthio)benzamide

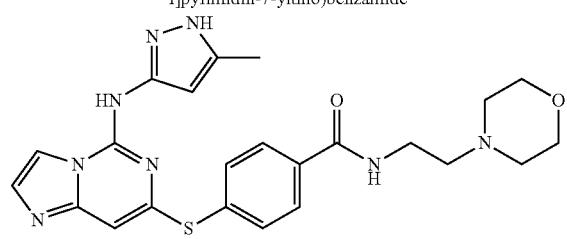

4-(5-(5-methyl-1H-pyrazol-3-ylamino)imidazo[1,2-f]pyrimidin-7-ylthio)-N-(2-morpholinoethyl)benzamide

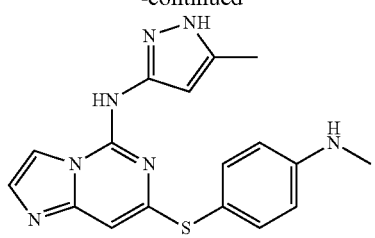

N-(5-methyl-1H-pyrazol-3-yl)-7-(4-(methylamino)phenylthio)imidazo[1,2-f]pyrimidin-5-amine

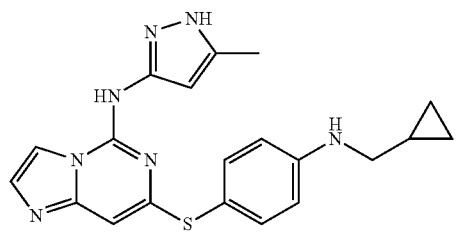

7-(4-(cyclopropylmethylamino)phenylthio)-N-(5-methyl-1H-pyrazol-3-yl)imidazo[1,2-f]pyrimidin-5-amine

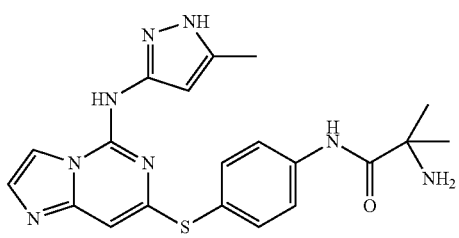

2-amino-2-methyl-N-(4-(5-(5-methyl-1H-pyrazol-3-ylamino)imidazo[1,2-f]pyridmidin-7-ylthio)phenyl)propanamide

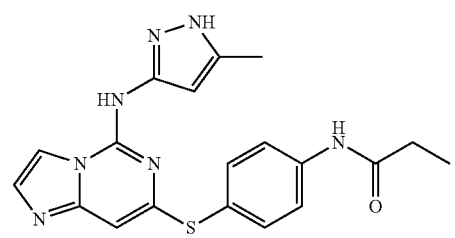

N-(4-(5-(5-methyl-1H-pyrazol-3-ylamino)imidazo[1,2-f]pyrimidin-7-ylthio)phenyl)propionamide

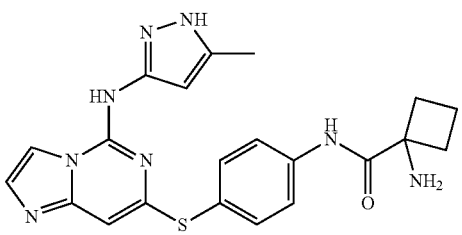

1-amino-N-(4-(5-(5-methyl-1H-pyrazol-3-ylamino)imidazo[1,2-f]pyrimidin-7-ylthio)phenyl)cyclobutanecarboxamide -continued

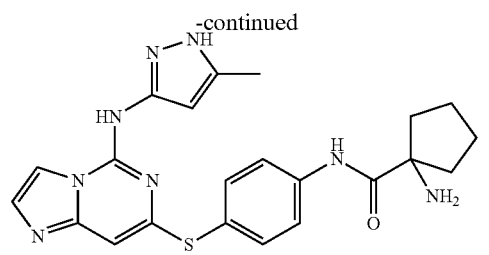

1-amino-N-(4-(5-(5-methyl-1H-pyrazol-3-ylamino)imidazo[1,2-f]pyrimidin-7-ylthio)phenyl)cyclpentanecarboxamide

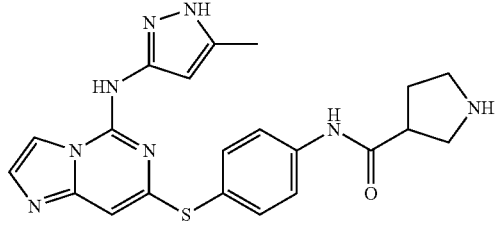

N-(4-(5-(5-methyl-1H-pyrazol-3-ylamino)imidazo[1,2-f]pyrimidin-7-ylthio)phenyl)pyrrolidine-3-carboxamide

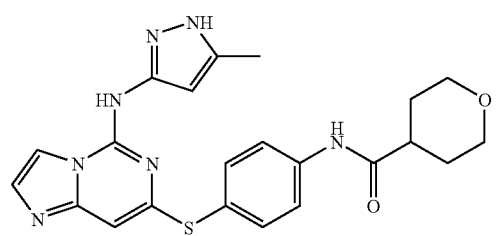

N-(4-(5-(5-methyl-1H-pyrazol-3-ylamino)imidazo[1,2-f]pyrimidin-7-ylthio)phenyl)-tetrahydro-2H-pyran-4-carboxamide

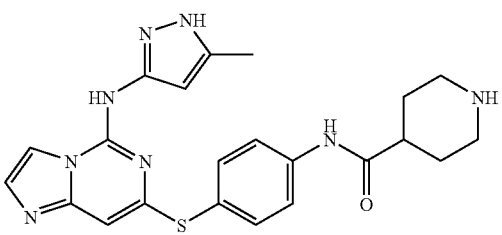

N-(4-(5-(5-methyl-1H-pyrazol-3-ylamino)imidazo[1,2-f]pyrimidin-7-ylthio)phenyl)piperidine-4-carboxamide

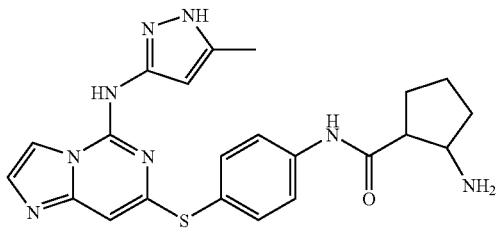

2-amino-N-(4-(5-(5-methyl-1H-pyrazol-3-ylamino)imidazo[1,2-f]pyrimidin-7-ylthio)phenyl)cyclopentanecarboxamide -continued

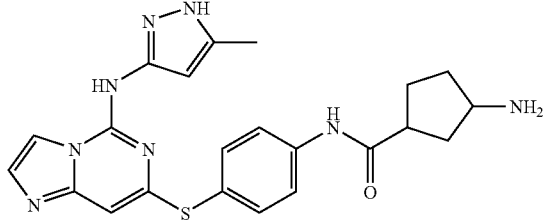

3-amino-N-(4-(5-(5-methyl-1H-pyrazol-3-ylamino)imidazo[1,2-f]pyrimidin-7-ylthio)phenyl)cyclopentanecarboxamide

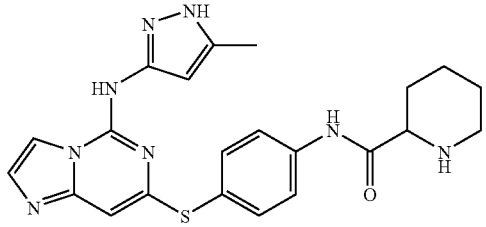

N-(4-(5-(5-methyl-1H-pyrazol-3-ylamino)imidazo[1,2-f]pyrimidin-7-ylthio)phenyl)piperidine-2-carboxamide

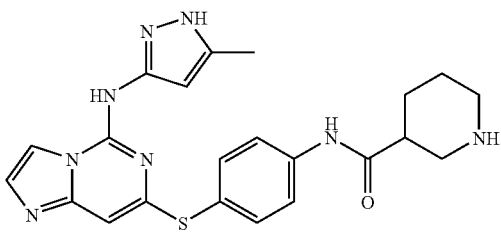

N-(4-(5-(5-methyl-1H-pyrazol-3-ylamino)imidazo[1,2-f]pyrimidin-7-ylthio)phenyl)piperidine-3-carboxamide

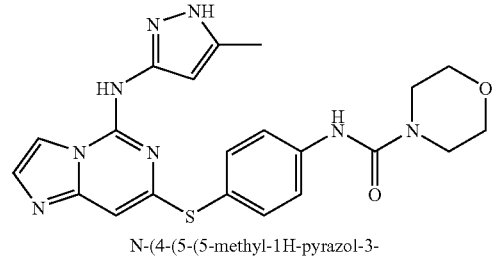

N-(4-(5-(5-methyl-1H-pyrazol-3-ylamino)imidazo[1,2-f]pyrimidin-7-ylthio)phenyl)morpholine-4-carboxamide

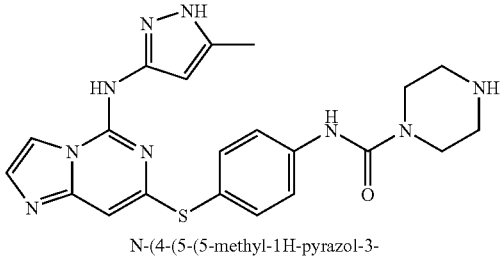

N-(4-(5-(5-methyl-1H-pyrazol-3-ylamino)imidazo[1,2-f]pyrimidin-7-ylthio)phenyl)piperazine-1-carboxamide -continued

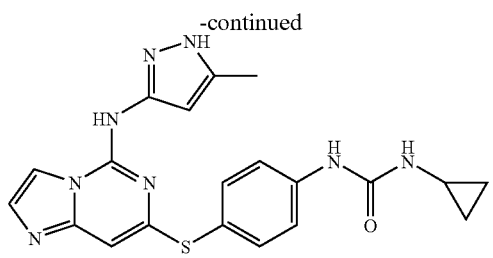

1-cyclopropyl-3-(4-(5-(5-methyl-1H-pyrazol-3-ylamino)imidazo[1,2-f]pyrimidine-7-ylthio)phenyl)urea

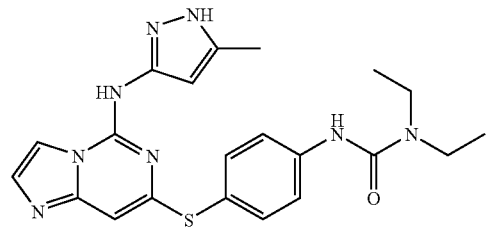

1,1-diethyl-3-(4-(5-(5-methyl-1H-pyrazol-3-ylamino)imidazo[1,2-f]pyrimidin-7-ylthio)phenyl)urea

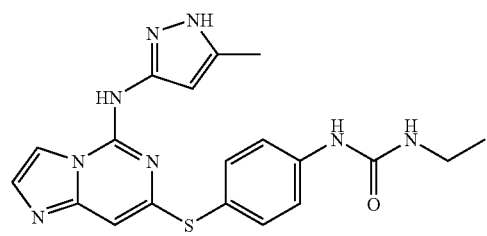

1-ethyl-3-(4-(5-(5-methyl-1H-pyrazol-3-ylamino)imidazo[1,2-f]pyrimidin-7-ylthio)phenyl)urea

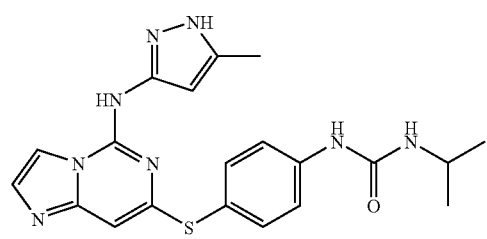

1-isopropyl-3-(4-(5-(5-methyl-1H-pyrazol-3-ylamino)imidazo[1,2-f]pyrimidin-7-ylthio)phenyl)urea

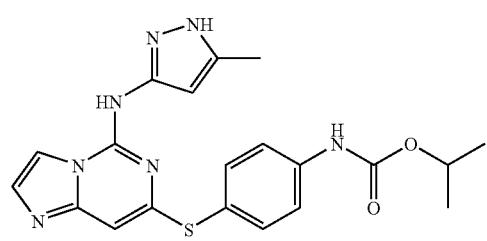

isopropyl 4-(5-(5-methyl-1H-pyrazol-3-ylamino)imidazo[1,2-f]pyrimidin-7-ylthio)phenylcarbamate -continued

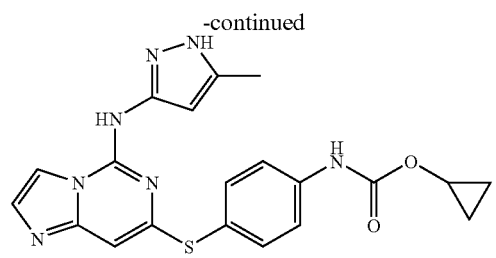

cyclopropyl 4-(5-(5-methyl-1H-pyrazol-3-ylamino)imidazo[1,2-f]pyrimidin-7-ylthio)phenylcarbamate

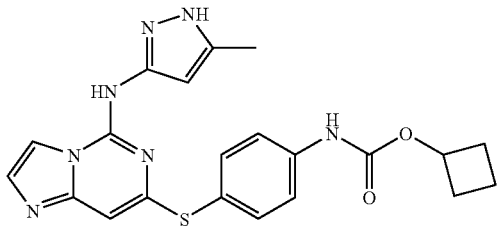

cyclobutyl 4-(5-(5-methyl-1H-pyrazol-3-ylamino)imidazo[1,2-f]pyrimidin-7-ylthio)phenylcarbamate

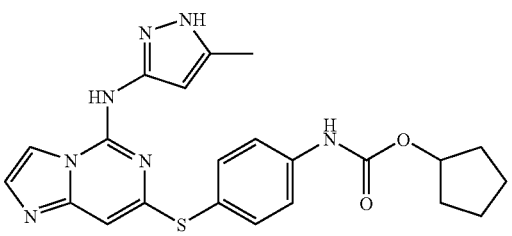

cyclopentyl 4-(5-(5-methyl-1H-pyrazol-3-ylamino)imidazo[1,2-f]pyrimidin-7-ylthio)phenylcarbamate

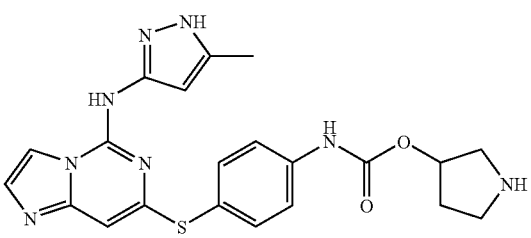

pyrrolidin-3-yl 4-(5-(5-methyl-1H-pyrazol-3-ylamino)imidazo[1,2-f]pyrimidin-7-ylthio)phenylcarbamate

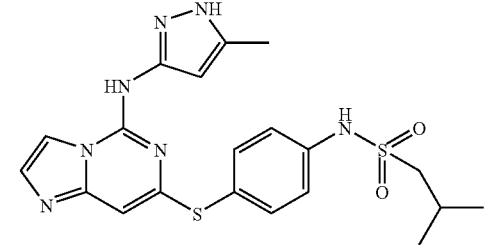

2-methyl-N-(4-(5-(5-methyl-1H-pyrazol-3-ylamino)imidazo[1,2-f]pyrimidin-7-ylthio)phenyl)propane-1-sulfonamide

147

-continued

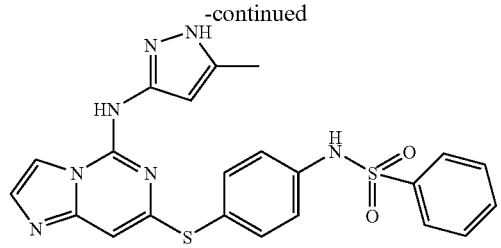

N-(4-(5-(5-methyl-1H-pyrazol-3-
ylamino)imidazo[1,2-f]pyrimidin-7-
ylthio)phenyl)benzenesulfonamide

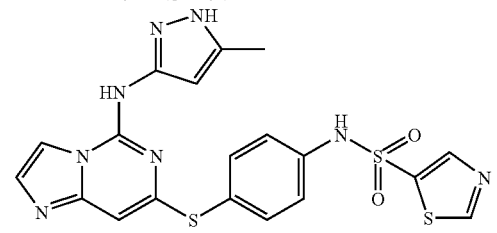

N-(4-(5-(5-methyl-1H-pyrazol-3-
ylamino)imidazo[1,2-f]pyrimidin-7-
ylthio)phenyl)thiazole-5-sulfonamide

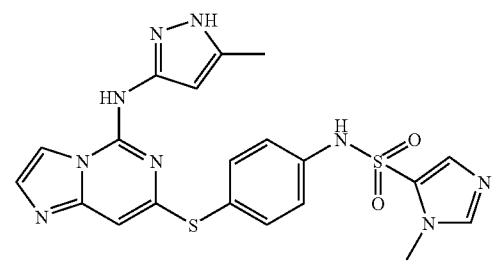

1-methyl-N-(4-(5-(5-methyl-1H-pyrazol-3-
ylamino)imidazo[1,2-f]pyrimidin-7-
ylthio)phenyl)-1H-imidazole-5-sulfonamide

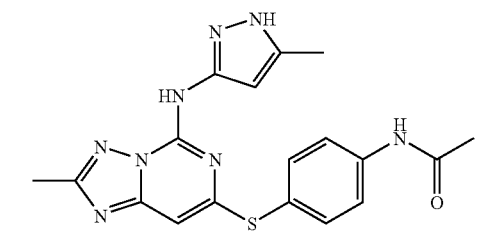

N-(4-(2-methyl-5-(5-methyl-1H-pyrazol-3-
ylamino)-[1,2,4]triazolo[1,5-f]pyrimidin-7-
ylthio)phenyl)acetamide

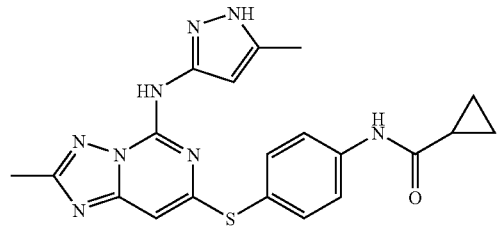

N-(4-(2-methyl-5-(5-methyl-1H-pyrazol-3-
ylamino)-[1,2,4]triazolo[1,5-f]pyrimidin-7-
ylthio)phenyl) cyclopropane carboxamide

148

-continued

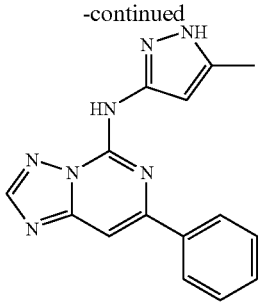

N-(5-methyl-1H-pyrazol-3-yl)-7-phenyl-
[1,2,4]triazolo[1,5-f]pyrimidin-5-amine

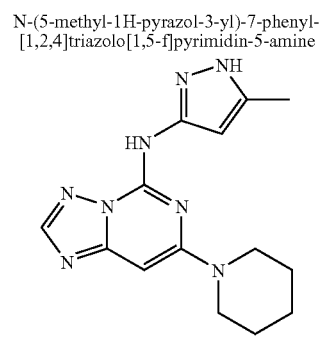

N-(5-methyl-1H-pyrazol-3-yl)-7-(piperidin-1-
yl)-[1,2,4]triazolo[1,5-f]pyrimidin-5-amine

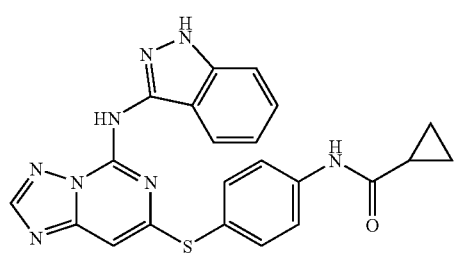

N-(4-(5-(5-methyl-1H-pyrazol-3-
ylamino)imidazo[1,2-f]pyrimidin-7-
ylthio)phenyl)thiazole-5-sulfonamide

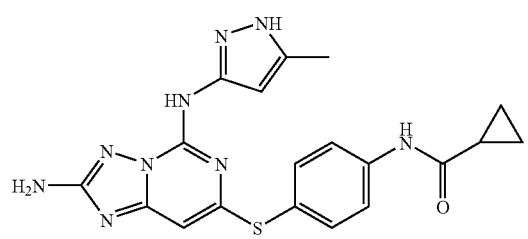

N-(4-(2-amino-5-(5-methyl-1H-pyrazol-3-
ylamino)-[1,2,4]triazolo[1,5-f]pyrimidin-7-
ylthio)phenyl) cyclopropane carboxamide

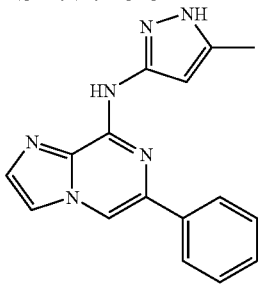

N-(5-methyl-1H-pyrazol-3-yl)-6-
phenylimidazo[1,2-a]pyrazin-8-amine

-continued

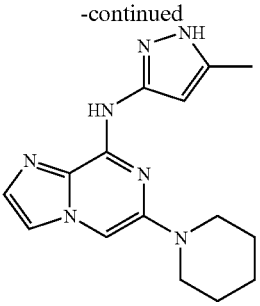

N-(5-methyl-1H-pyrazol-3-yl)-6-(pipersin-1-yl)imidazo[1,2-a]pyrazin-8-amine

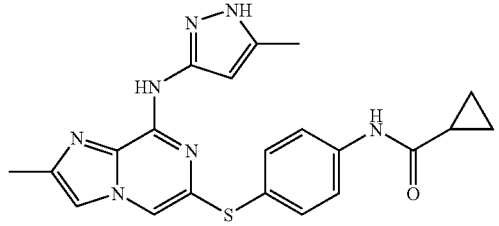

N-(4-(2-methyl-8-(5-methyl-1H-pyrazol-3-ylamino)imidazo[1,2-a]pyrazin-6-ylthio)phenyl) cyclopropane carboxamide

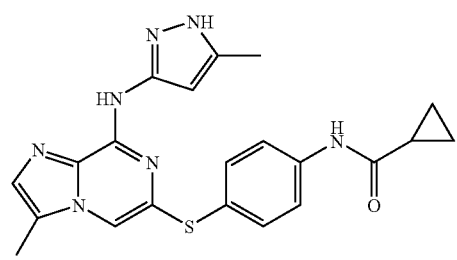

N-(4-(3-methyl-8-(5-methyl-1H-pyrazol-3-ylamino)imidazo[1,2-a]pyrazin-6-ylthio)phenyl) cyclopropane carboxamide

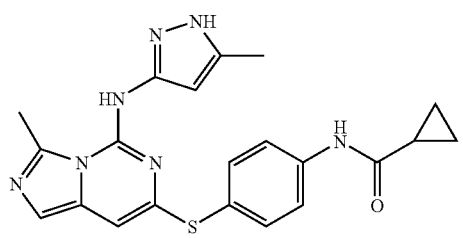

N-(4-(3-methyl-5-(5-methyl-1H-pyrazol-3-ylamino)imidazo[1,5-f]pyrimidin-7-ylthio)phenyl) cyclopropane carboxamide

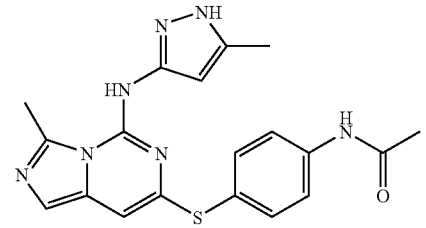

N-(4-(3-methyl-5-(5-methyl-1H-pyrazol-3-ylamino)imidazo[1,5-f]pyrimidin-7-ylthio)phenyl)acetamide -continued

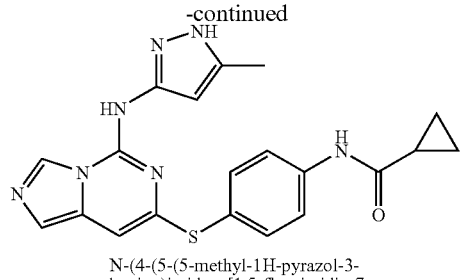

N-(4-(5-(5-methyl-1H-pyrazol-3-ylamino)imidazo[1,5-f]pyrimidin-7-ylthio)phenyl) cyclopropane carboxamide

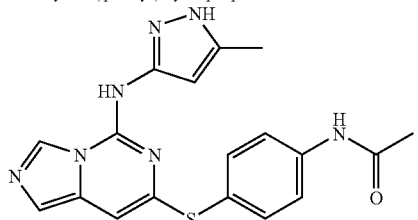

N-(4-(5-(5-methyl-1H-pyrazol-3-ylamino)imidazo[1,5-f]pyrimidin-7-ylthio)phenyl)acetamide

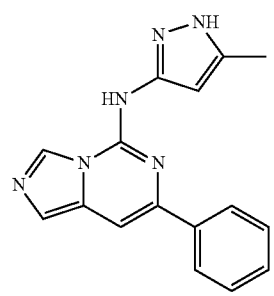

N-(5-methyl-1H-pyrazol-3-yl)-7-phenylimidazo[1,5-f]pyrimidin-5-amine

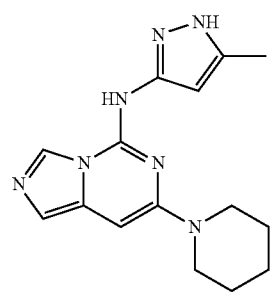

N-(5-methyl-1H-pyrazol-3-yl)-7-piperdine-1-yl)imidazo[1,5-f]pyrimidin-5-amine

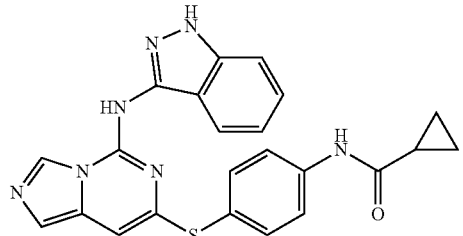

N-(4-(5-(1H-indazol-3-ylamino)imidazo[,5-f]pyrimidin-7-ylthio)phenyl) cyclopropane carboxamide -continued

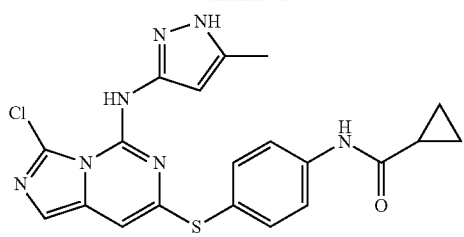

N-(4-(3-chloro-5-(5-methyl-1H-pyrazol-3-ylamino)imidazo[1,5-f]pyrimidine-7-ylthio)phenyl) cyclopropane carboxamide

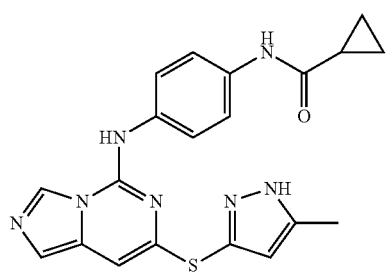

N-(4-(7-(5-methyl-1H-pyrazol-3-ylamino)imidazo[1,5-f]pyrimidine-5-ylthio)phenyl) cyclopropane carboxamide

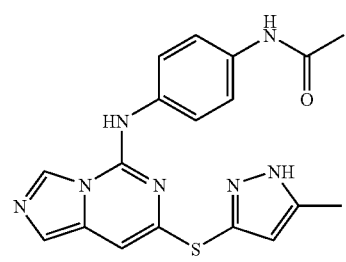

N-(4-(7-(5-methyl-1H-pyrazol-3-ylamino)imidazo[1,5-f]pyrimidine-5-ylthio)phenyl)acetamide

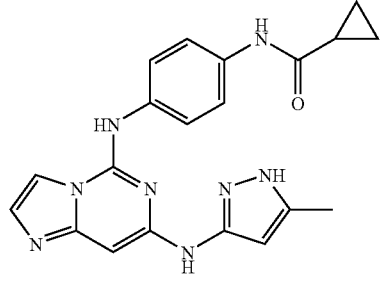

N-(4-(7-(5-methyl-1H-pyrazol-3-ylamino)imidazo[1,2-f]pyrimidine-5-ylthio)phenyl) cyclopropane carboxamide

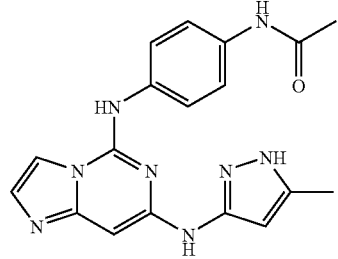

N-(4-(7-(5-methyl-1H-pyrazol-3-ylamino)imidazo[1,2-f]pyrimidine-5-ylthio)phenyl)acetamide -continued

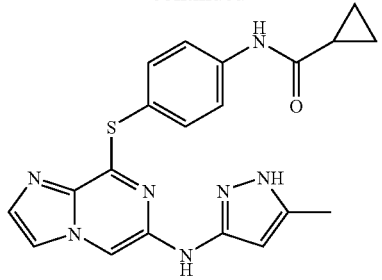

N-(4-(6-(5-methyl-1H-pyrazol-3-ylamino)imidazo[1,2-a]pyrazin-8-ylthio)phenyl) cyclopropane carboxamide

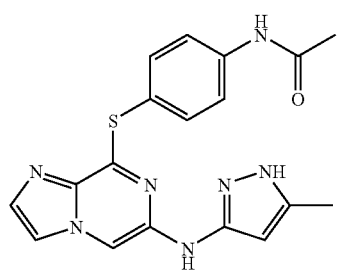

N-(4-(6-(5-methyl-1H-pyrazol-3-ylamino)imidazo[1,2-a]pyrazin-8-ylthio)phenyl)acetamide

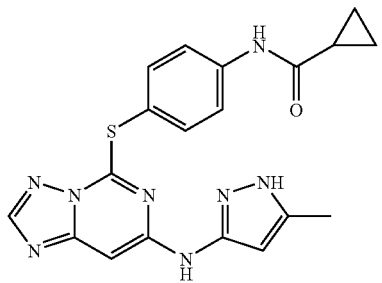

N-(4-(7-(5-methyl-1H-pyrazol-3-ylamino)-[1,2,4]triazolo[1,5-f]pyrimidin-5-ylthio)phenyl) cyclopropane carboxamide

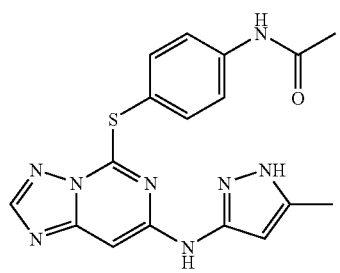

N-(4-(7-(5-methyl-1H-pyrazol-3-ylamino)-[1,2,4]triazolo[1,5-f]pyrimidin-5-ylthio)phenyl)acetamide In each of the above reaction procedures or schemes, the various substituents may be selected from among the various substituents otherwise taught herein.

Descriptions of the syntheses of particular compounds according to the present invention based on the above reaction scheme are set forth herein.

3. Examples of Kinase Inhibitors

The present invention is further exemplified, but not limited by, the following examples that describe the synthesis of particular compounds according to the invention.

Example 1

N-(4-(5-(5-Methyl-1H-pyrazol-3-ylamino)imidazo[1,2-f]pyrimidin-7-ylthio)phenyl)cyclopropane carboxamide

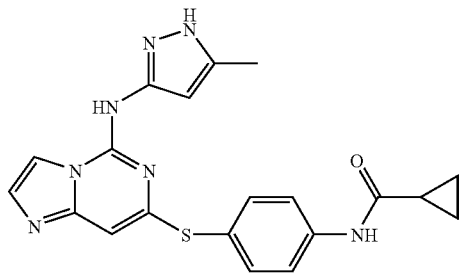

Referring to Scheme 1, 4-amino-6-chloro-2-(methylthio)-pyrimidine (1.0 g, 5.7 mmol) and chloroacetaldehyde (2 ml, 14.2 mmol) were mixed in DMF (5 ml). The solution was stirred overnight at 100° C. DMF was removed in vacuo and the residue was purified by flash chromatography with 1:10 MeOH:DCM to leave 7-chloro-5-(methylthio)imidazo[1,2-f]pyrimidine as a brown solid (68 mg, 60%). $^1$H NMR (400 MHz, CD$_3$OD) δ 7.93 (s, 1H) 7.74 (d, J=1.5 Hz, 1H) 7.62 (s, 1H) 3.27 (s, 3H). [M+H] calc'd for C$_7$H$_6$ClN$_3$S, 200; found, 200.

7-Chloro-5-(methylthio)imidazo[1,2-f]pyrimidine (500 mg, 2.5 mmol) was dissolved in methanol (5 ml). 2N KOH (15 ml) was added and the solution stirred at reflux overnight and the product confirmed by LC/MS. The solvent was removed in vacuo and the residue purified by flash chromatography with 1:10 MeOH:DCM to give 7-chloroimidazo[1,2-f]pyrimidin-5-ol (420 mg, 99%). $^1$H NMR (400 MHz, DMSO) δ 7.73 (d, J=2.0 Hz, 1H) 7.46 (s, 1H) 6.66 (s, 1H). [M+H] calc'd for C$_6$H$_4$ClN$_3$O, 170; found, 170.

Phosphorous oxychloride (20 ml) was added to 7-chloroimidazo[1,2-f]pyrimidin-5-ol (420 mg, 2.47 mmol) and the suspension stirred at reflux for 4 hours under nitrogen. The volatiles were evaporated and the residue was filtered through a silica plug. The filtrate was evaporated to leave brown oil that solidified under high vacuum. Purification by flash chromatography afforded 5,7-dichloroimidazo[1,2-f]pyrimidine as a light yellow solid. $^1$H NMR (300 MHz, CDCl$_3$) δ 7.72 (br.s, 2H) 7.55 (s, 1H). [M+H] calc'd for C$_6$H$_3$Cl$_2$N$_3$, 188; found, 188.

5,7-Dichloroimidazo[1,2-f]pyrimidine (100 mg, 0.5 mmol) and 3-amino-5-methyl pyrazole (52 mg, 0.5 mmol) were stirred in ethanol (1 ml) at 60° C. for 15 minutes. Alternatively, the pyrimidine and the pyrazole can be reacted in DMF at 100-150° C. for 15-30 minutes. The solvent was evaporated and the residue purified by flash chromatography using 1:1 EtOAc:Hexane then 1:10 MeOH/DCM. Evaporation of the solvent revealed 7-chloro-N-(5-methyl-1H-pyrazol-3-yl)imidazo[1,2-f]pyrimidin-5-amine (100 mg, 75%). $^1$H NMR (400 MHz, DMSO) δ 10.54 (s, 1H) 8.37 (s, 1H) 7.57 (s, 1H) 7.07 (s, 1H) 6.48 (s, 1H) 2.28 (s, 3H). [M+H] calc'd for C$_{10}$H$_9$ClN$_6$, 249; found, 249.

4-Aminothiophenol (5 g, 39.9 mmol) and triethylamine (4.44 g, 43.9 mmol) were stirred in chloroform (50 ml) at 0° C. Cyclopropanecarbonyl chloride (4 g, 39.9 mmol) was dissolved in chloroform (30 ml). The solution of cyclopropanecarbonyl chloride was added to the solution of 4-aminothiophenol drop wise over an hour. Once addition was complete, the mixture was stirred for an hour. Hydrochloric acid (50 ml) was added and the organic layer was separated. The aqueous layer was extracted with chloroform (2×30 ml). The organic extracts were combined and dried over MgSO$_4$, and the solvent removed in vacuo. LCMS confirmed the product N-(4-mercaptophenyl)cyclopropane carboxamide (3.63 g, 47%). $^1$H NMR (400 MHz, DMSO-D6) δ 10.16 (s, 1H) 7.46 (d, J=8.6, 2.0 Hz, 2H) 7.22 (d, J=8.8 Hz, 2H) 1.75-1.72 (m, 1H) 0.78 (m, 4H). [M+H] calc'd for C$_{10}$H$_{11}$NOS, 194; found, 194.

7-Chloro-N-(5-methyl-1H-pyrazol-3-yl)imidazo[1,2-f]pyrimidin-5-amine (100 mg, 0.4 mmol), N-(4-mercaptophenyl)cyclopropane carboxamide (155 mg, 0.8 mmol) and a catalytic amount of potassium carbonate (3 mg) were mixed in DMF (1 ml). This mixture was reacted in a microwave reactor at 160° C. for 15 minutes. DMF was removed in vacuo and the residue was purified by HPLC to afford Example 1 as a light yellow solid (84 mg, 51%). $^1$H NMR (400 MHz, CD$_3$OD) δ 8.23 (s, 1H) 7.80 (s, 1H) 7.79 (d, J=10.3 Hz, 2H) 7.60 (dd, J=8.8 Hz, 2H) 6.71 (s, 1H) 5.94 (s, 1H) 2.21 (s, 3H) 1.81 (m, 1H) 0.98 (m, 2H) 0.91 (m, 2H). [M+H] calc'd for C$_{20}$H$_{19}$N$_7$OS, 406; found, 406.

Example 2

N-(4-(5-(5-Cyclopropyl-1H-pyrazol-3-ylamino)imidazo[1,2-f]pyrimidin-7-ylthio)phenyl)cyclopropane carboxamide

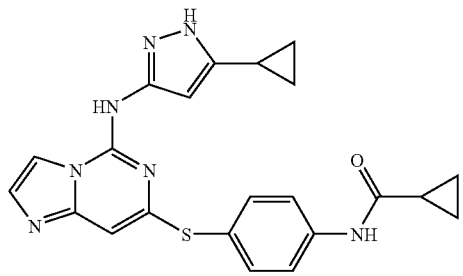

The title compound was synthesized using 3-cyclopropyl-1H-pyrazol-5-amine following the procedure described in the synthesis of Example 1. $^1$H NMR (400 MHz, CD$_3$OD) δ 8.23 (d, J=1.7, 1H) 7.80 (s, 1H) 7.79 (d, J=8.6, 2H) 7.61 (d, J=8.6 Hz, 2H), 6.67 (s, 1H) 5.98 (s, 1H), 1.83 (m, 1H) 1.80 (m, 1H)

1.30 (m, 2H) 0.97 (m, 2H) 0.90 (m, 2H) 0.68 (m, 2H). [M+H] calc'd for $C_{22}H_{21}N_7OS$, 432; found, 432.

Example 3

N-(4-(5-(3-Cyclopropyl-1H-pyrazol-5-ylamino)imidazo[1,2-f]pyrimidin-7-ylthio)phenyl)acetamide

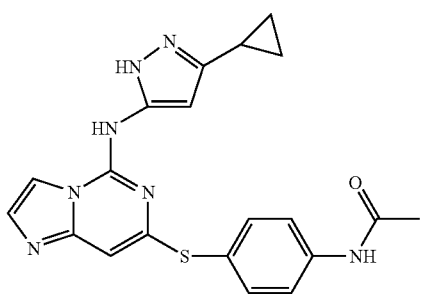

The title compound was synthesized using 3-cyclopropyl-1H-pyrazol-5-amine and N-(4-mercaptophenyl)acetamide following the procedure described in the synthesis of Example 1. $^1$H NMR (400 MHz, CD$_3$OD) δ 8.23 (s, 1H) 7.78-7.84 (m, 3H) 7.60 (d, J=8.6 Hz, 2H) 6.65 (s, 1H) 6.31 (s, 1H) 2.16 (s, 3H), 1.87 (m, 1H) 1.00 (m, 2H) 0.69 (m, 2H). [M+H] calc'd for $C_{20}H_{19}N_7OS$, 406; found, 406.

Example 4

N-(4-(5-(5-Methyl-1H-pyrazol-3-ylamino)imidazo[1,2-f]pyrimidin-7-ylthio)phenyl)acetamide

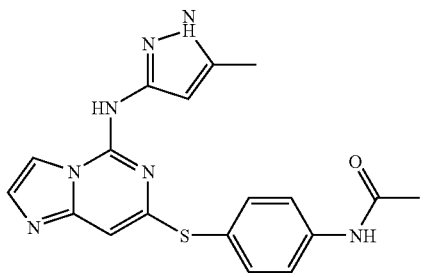

The title compound was synthesized using 5-methyl-1H-pyrazol-3-amine and N-(4-mercaptophenyl)acetamide following the procedure described in the synthesis of Example 1. $^1$H NMR (400 MHz, CD$_3$OD) δ 8.23 (s, 1H) 7.78-7.80 (m, 3H) 7.60 (d, J=9.0 Hz, 2H) 6.70 (s, 1H) 5.96 (s, 1H) 2.22 (s, 3H), 2.17 (s, 3H). [M+H] calc'd for $C_{18}H_{17}N_7OS$, 380; found, 380.

Example 5

7-(4-Aminophenylthio)-N-(5-methyl-1H-pyrazol-3-yl)imidazo[1,2-f]pyrimidin-5-amine

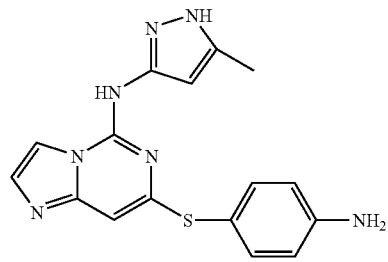

The title compound was synthesized using 5-methyl-1H-pyrazol-3-amine and 4-aminothiophenol following the procedure described in the synthesis of Example 1. $^1$H NMR (400 MHz, CD$_3$OD) δ 8.24 (d, J=2.5 Hz, 1H) 7.80 (d, J=2.0 Hz, 1H) 7.50 (d, J=8.3 Hz, 2H) 7.0 (d, J=8.3 Hz, 2H) 6.63 (s, 1H) 6.17 (s, 1H), 3.30 (m, 4H) 2.31 (s, 3H) [M+H] calc'd for $C_{16}H_{15}N_7S$, 338; found, 338.

Example 6

N-(4-(5-(5-Methyl-1H-pyrazol-3-ylamino)-[1,2,4]triazolo[1,5-f]pyrimidin-7-ylthio)phenyl)cyclopropane carboxamide

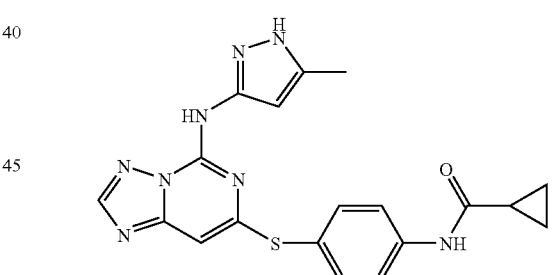

Referring to Scheme 2, anhydrous hydrazine (164 mg, 162 µl, 5.1 mmol) and dichloromethane (3 ml) were cooled to −78° C. 4,6-Dichloro-2-(methylthio)pyrimidine (1 g, 5.1 mmol) was slowly added. The mixture was allowed to stir for 10 minutes then the bath was replaced with an ice bath and the solution allowed to slowly reach 0° C. The precipitate was filtered and washed with DCM. 1-(6-Chloro-2-(methylthio)pyrimidin-4-yl)hydrazine (624 mg, 64%) was obtained. [M+H] calc'd for $C_5H_7ClN_4S$, 191; found, 191.

1-(6-chloro-2-(methylthio)pyrimidin-4-yl)hydrazine (300 mg, 1.6 mmol) was dissolved in formic acid (5 ml). The solution was stirred at reflux overnight LC/MS confirmed mass of intended product. The solution was evaporated in vacuo. The residue was purified by flash chromatography with 1:10 MeOH:DCM to leave 7-Chloro-5-methylsulfanyl-[1,2,4]triazolo[1,5-c]pyrimidine as a yellow oil (278 mg, 88%). ¹H NMR (400 MHz, CDCl₃) δ 8.78 (s, 1H) 7.45 (s, 2H) 2.85 (s, 3H). [M+H] calc'd for C₆H₅ClN₄S, 201; found, 201.

7-Chloro-5-methylsulfanyl-[1,2,4]triazolo[1,5-c]pyrimidine (181 mg, 0.91 mmol) was dissolved in MeOH (4 ml). 2N KOH (8 ml) was added and the mixture was stirred at reflux for 2 hours. The solvents were removed by a rotavap. The residue was added 4N HCl in dioxane and stirred for an hour before it was concentrated. Water was added and the mixture was extracted with DCM to give 7-Chloro-[1,2,4]triazolo[1,5-c]pyrimidin-5-ol (35 mg) as a solid. [M+H] calc'd for C₅H₃ClN₄O, 171; found, 171.

The mixture of 7-Chloro-[1,2,4]triazolo[1,5-c]pyrimidin-5-ol (35 mg) in POCl₃ was heated at reflux for 3 hours. After removal of the volatiles, the residue was purified by a short plug column eluting with 1:1 EtOAc/hexane to give 5,7-Dichloro-[1,2,4]triazolo[1,5-c]pyrimidine as an off-white solid (11 mg). ¹H NMR (400 MHz, CDCl₃) δ 8.49 (s, 1H) 7.72 (s, 1H). [M+H] calc'd for C₅H₂Cl₂N₄, 189; found, 189.

Example 6 was then prepared as follows. 5,7-Dichloro-[1,2,4]triazolo[1,5-c]pyrimidine (10 mg) and 3-amino-5-methylpyrazole (10 mg) were stirred in ethanol (1 ml) at 60° C. for 15 minutes. The solvent was evaporated and the residue purified by flash chromatography using 1:1 EtOAc:Hexane then 1:10 MeOH/DCM. Evaporation of the solvents provided 7-chloro-N-(5-methyl-1H-pyrazol-3-yl)-[1,2,4]triazolo[1,5-f]pyrimidin-5-amine as a white solid (11 mg). [M+H] calc'd for C₉H₈ClN₇, 250; found, 250.

7-Chloro-N-(5-methyl-1H-pyrazol-3-yl)-[1,2,4]triazolo[1,5-f]pyrimidin-5-amine (21 mg, 0.084 mmol), N-(4-mercaptophenyl)cyclopropane carboxamide (32 mg, 0.16 mmol) and potassium carbonate (17 mg) were mixed in DMF (1 ml). This mixture was reacted in a microwave reactor at 160° C. for 15 minutes. DMF was removed in vacuo and the residue was purified by HPLC to afford the title compound Example 6 as a white solid (14.9 mg). ¹H NMR (400 MHz, CD₃OD) δ 8.29 (s, 1H) 7.77 (d, J=8.4 Hz, 2H) 7.59 (d, J=8.4 Hz, 2H) 6.67 (s, 1H) 5.97 (s, 1H) 2.20 (s, 3H) 1.76-1.86 (m, 1H) 0.84-0.90 (m, 4H). [M+H] calc'd for C₁₉H₁₈N₈OS, 407; found, 407.

Example 7

N-(4-(5-(5-Methyl-1H-pyrazol-3-ylamino)-[1,2,4]triazolo[1,5-f]pyrimidin-7-ylthio)phenyl)acetamide

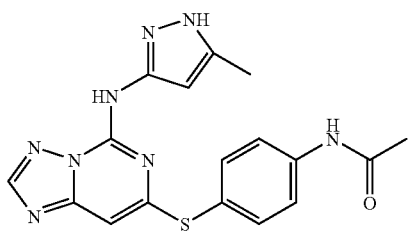

The title compound was synthesized following the procedure described in the synthesis of Example 6. ¹H NMR (400 MHz, CD₃OD) δ 8.37 (s, 1H) 7.79 (d, J=8.5 Hz, 2H) 7.61 (d, J=8.5 Hz, 2H) 6.68 (s, 1H) 6.06 (s, 1H) 2.25 (s, 3H) 2.17 (s, 3H). [M+H] calc'd for C17H₁₆N₈OS, 381; found, 381.

Example 8

N-(4-(8-(5-Methyl-1H-pyrazol-3-ylamino)imidazo[1,2-a]pyrazin-6-ylthio)phenyl)cyclopropane carboxamide

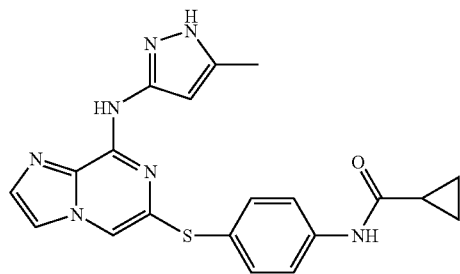

Referring to Scheme 3, pyrazin-2-ylamine (1 g, 10.5 mmol) was dissolved in a solution of DMSO (40 ml)/H₂O (1 ml) at 0° C. N-bromosuccinimide (3.93 g, 22 mmol) was added over an hour keeping the temperature below 5° C. Once addition was complete, the mixture was stirred for 6 hours at RT. The mixture was poured over ice water (150 ml) whilst stirring, then extracted with EtOAc (4×100 ml). The organic layers were combined, dried and evaporated to leave an orange oil, which solidified overnight under high vacuum. 3,5-dibromopyrazin-2-amine was produced as an orange/brown solid (2.24 g, 84%). The product was used for the next reaction without further purification. [M+H] calc'd for C₄H₃Br₂N₃, 254; found, 254.

3,5-Dibromopyrazin-2-amine (200 mg, 0.79 mmol) and chloroacetaldehyde (200 μl, 1.58 mmol) were dissolved in DMF (5 ml). The mixture was stirred at 100° C. overnight. LC/MS showed 6,8-dibromoimidazo[1,2-a]pyrazine plus the mass with one bromine displaced by chlorine. The crude material was used for the next step without further purification. ¹H NMR (400 MHz, CDCl₃) δ 8.28 (s, 1H) 7.88 (s, 1H) 7.80 (s, 1H). [M+H] calc'd for C₆H₃Br₂N₃, 276; found, 276.

Example 8 was then prepared as follows. 6,8-Dibromoimidazo[1,2-a]pyrazine (278 mg, 1 mmol) and 5-methyl-1H-pyrazol-3-amine (196 mg, 2 mmol) was suspended in EtOH (2 ml). The mixture was heated with microwave at 120° C. for four hours. The mixture was then purified with HPLC to give (6-Bromo-imidazo[1,2-a]pyrazin-8-yl)-(5-methyl-1H-pyrazol-3-yl)-amine as a solid (96 mg). ¹H NMR (400 MHz, DMSO) δ 8.29 (s, 1H) 7.98 (s, 1H) 7.70 (s, 1H) 6.48 (s, 1H) 2.27 (s, 3H). [M+H] calc'd for C₁₀H₉BrN₆, 293; found, 293.

(6-Bromo-imidazo[1,2-a]pyrazin-8-yl)-(5-methyl-1H-pyrazol-3-yl)-amine (21 mg, 0.072 mmol), N-(4-mercaptophenyl)cyclopropane carboxamide (28 mg, 0.145 mmol) and potassium carbonate (20 mg) were mixed in DMF (1 ml). This mixture was reacted in a microwave reactor at 170° C. for 15 minutes. DMF was removed in vacuo and the residue was purified by HPLC to afford the title compound Example 8 as an off-white solid. (11.9 mg). ¹H NMR (400 MHz, DMSO) δ 10.39 (s, 1H) 7.99 (d, J=0.8 Hz, 1H) 7.96 (s, 1H) 7.70 (s, 1H) 7.69 (d, J=8.4 Hz, 2H) 7.49 (d, J=8.4 Hz, 2H) 6.03

(s, 1H) 2.14 (s, 3H) 1.75-1.82 (m, 1H) 0.77-0.81 (m, 2H). [M+H] calc'd for $C_{20}H_{19}N_7OS$, 406; found, 406.

Example 9

N-(4-(8-(5-Methyl-1H-pyrazol-3-ylamino)imidazo[1,2-a]pyrazin-6-ylthio)phenyl)acetamide

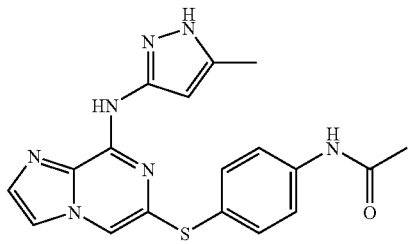

The title compound was synthesized using 3-methyl-1H-pyrazol-5-amine and N-(4-mercaptophenyl)acetamide following the procedure described in the synthesis of Example 8. $^1$H NMR (400 MHz, DMSO) δ 10.15 (s, 1H) 8.03 (d, J=0.8 Hz, 1H) 7.98 (s, 1H) 7.76 (s, 1H) 7.69 (d, J=8.8 Hz, 2H) 7.51 (d, J=8.4 Hz, 2H) 7.47 (d, J=8.8 Hz, 1H) 7.21 (d, J=8.8 Hz, 1H) 6.05 (s, 1H) 2.16 (s, 3H) 2.06 (s, 3H). [M+H] calc'd for $C_{18}H_{17}N_7OS$, 380; found, 380.

Example 10

N-(4-(5-(5-Methyl-1H-pyrazol-3-ylamino)imidazo[1,2-a]pyrimidin-7-ylthio)phenyl)cyclopropane carboxamide

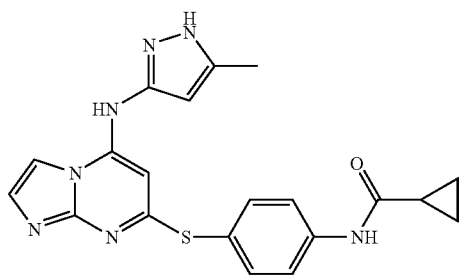

Referring to Scheme 4, $C_{5,7}$-Dichloro-imidazo[1,2-a]pyrimidine (206 mg, 1.1 mmol) and 5-methyl-1H-pyrazol-3-amine (213 mg, 2.19 mmol) was mixed in EtOH (5 ml). The mixture was heated at 80° C. for 10 minutes. The mixture was then cooled to RT and the solid was collected and washed with EtOAc to give (7-Chloro-imidazo[1,2-a]pyrimidin-5-yl)-(5-methyl-1H-pyrazol-3-yl)-amine as a white solid (182 mg, 0.73 mmol, 66%). $^1$H NMR (400 MHz, DMSO) δ 8.17 (s, 1H) 7.63 (s, 1H) 7.12 (s, 1H) 6.02 (s, 1H) 2.28 (s, 3H). [M+H] calc'd for $C_{10}H_9ClN_6$, 249; found, 249.

A mixture of (7-Chloro-imidazo[1,2-a]pyrimidin-5-yl)-(5-methyl-1H-pyrazol-3-yl)-amine (73 mg, 0.29 mmol), N-(4-mercaptophenyl)cyclopropane carboxamide (170 mg, 0.88 mmol), potassium carbonate (81 mg, 0.58 mmol) in DMF (1 ml) was heated with microwave at 190° C. for 30 minutes. The reaction mixture was then purified by HPLC to give the title compound Example 10 as an off-white solid (110 mg). $^1$H NMR (400 MHz, DMSO) δ 10.54 (s, 1H) 8.26 (d, J=2.8 Hz, 1H) 7.97 (d, J=2.4 Hz, 1H) 7.79 (d, J=8.8 Hz, 2H) 7.57 (d, J=8.8 Hz, 2H) 6.89 (s, 1H) 5.82 (s, 1H) 2.20 (s, 3H) 1.81-1.85 (m, 1H) 0.84-0.86 (m, 4H). [M+H] calc'd for $C_{20}H_{19}N_7OS$, 406; found, 406.

Example 11

N-(4-(5-(5-Methyl-1H-pyrazol-3-ylamino)imidazo[1,2-a]pyrimidin-7-ylthio)phenyl)acetamide

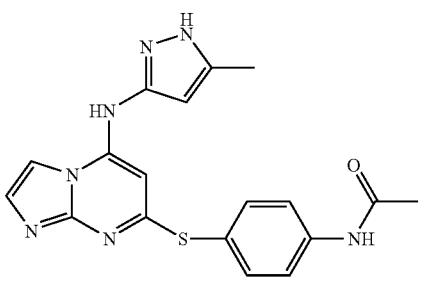

The title compound was synthesized using 3-methyl-1H-pyrazol-5-amine and N-(4-mercaptophenyl)acetamide following the procedure described in the synthesis of Example 10. $^1$H NMR (400 MHz, DMSO) δ 10.28 (s, 1H) 8.27 (d, J=2.7 Hz, 1H) 7.96 (d, J=2.4 Hz, 1H) 7.77 (d, J=8.8 Hz, 2H) 7.57 (d, J=8.8 Hz, 2H) 6.92 (s, 1H) 2.21 (s, 3H) 2.11 (s, 3H). [M+H] calc'd for $C_{18}H_{17}N_7OS$, 380; found, 380.

Example 12

N-(5-cyclopropyl-1H-pyrazol-3-yl)-7-phenylimidazo[1,2-f]pyrimidin-5-amine

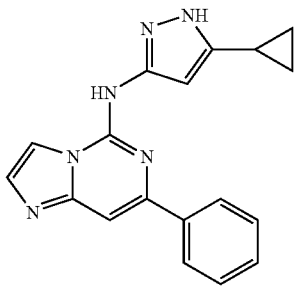

Referring to Scheme 6, (7-Chloro-imidazo[1,2-c]pyrimidin-5-yl)-(5-cyclopropyl-1H-pyrazol-3-yl)-amine (43 mg, 0.16 mmol), phenylboronic acid (28.7 mg, 0.24 mmol), and Tetrakis(triphenylphosphine)palladium (36 mg, 0.03 mmol) were added to a mixture of dioxane (1.5 ml) and saturated potassium carbonate solution (0.5 ml). The mixture was heated at 150° C. for 20 minutes in a microwave reactor. The mixture was then filtered, concentrated and purified by high performance liquid chromatography to give the title compound as a tan solid (15 mg, 0.05 mmol, 31%). $^1$H NMR (400 MHz, MeOD) δ 8.35 (s, 1H) 8.15-8.13 (m, 2H) 7.97 (d, J=2.5 Hz, 1H) 7.65 (s, 1H) 7.55-7.54 (m, 3H) 6.49 (s, 1H) 2.03-1.99

(m, 1H) 1.08-1.05 (m, 2H) 0.82-0.78 (m, 2H). [M+H] calc'd for $C_{18}H_{16}N_6$, 317; found, 317.

Example 13

N-cyclopentyl-3-(5-(5-cyclopropyl-1H-pyrazol-3-ylamino)imidazo[1,2-f]pyrimidin-7-yl)benzamide

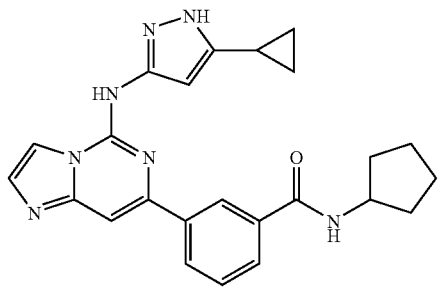

The title compound was synthesized in 37% yield using 3-(cyclopentylcarbamoyl)phenylboronic acid following the procedure described in the synthesis of Example 12. $^1$H NMR (400 MHz, MeOD-$d_4$) δ 8.55 (br.s, 1H), 8.37 (d, J=2.2 Hz, 1H), 8.25 (d, J=7.8 Hz, 1H), 7.99 (d, J=2.2 Hz, 1H), 7.92 (d, J=2.9 Hz, 1H), 7.71 (s, 1H), 7.60 (t, J=7.6 Hz, 1H), 7.18-7.22 (m, 1H), 6.48 (s, 1H), 4.32-4.38 (m, 1H), 1.95-2.10 (m, 4H), 1.55-1.90 (m, 5H), 1.03-1.08 (m, 2H), 0.80-0.84 (m, 2H). [M+H] calc'd for $C_{24}H_{26}N_7O$, 428; found, 428.

Example 14a tert-Butyl 4-(3-bromobenzyl)piperazine-1-carboxylate

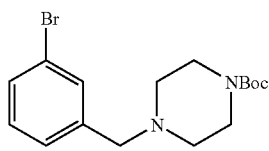

To a stirred solution of 1-bromo-3-(bromomethyl)benzene (677 mg, 2.71 mmol) in THF (10 ml) was added triethylamine (380 µL, 2.71 mmol), followed by tert-butyl piperazine-1-carboxylate (504 mg, 2.71 mmol). The mixture was allowed to stir at RT for one hour. The solvent was evaporated and the residue was purified with a silica gel column eluting with 1:10 EtOAc/hexanes to give the title compound as an oil (888 mg, 2.49 mmol, 92%). [M+H] calc'd for $C_{16}H_{24}BrN_2O_2$, 355; found, 355.

Example 14b tert-Butyl 4-(3-(4,4,5,5-tetramethyl-1,3,2-dioxaborolan-2-yl)benzyl)piperazine-1-carboxylate

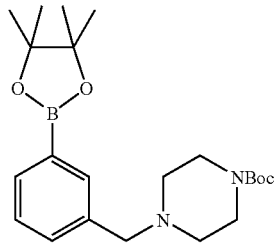

tert-Butyl 4-(3-bromobenzyl)piperazine-1-carboxylate (448 mg, 1.25 mmol), bis(pinacolato)diboron (352 mg, 1.38 mmol), potassium acetate (368 mg, 3.75 mmol), and [1,1'-bis(diphenylphosphino)ferrocene]dichloropalladium(II) (31 mg, 0.038 mmol) were combined in DMF (10 mL), and the reaction stirred at 80° C. under $N_2$ for 4 h. The cooled solution was partitioned between EtOAc and water. Organics were washed with brine, dried ($MgSO_4$), and concentrated in vacuo. Purification by silica gel chromatography (10% EtOAc/hexanes) gave 550 mg (90%) of the title compound as an oil. [M+H] calc'd for $C_{22}H_{36}BN_2O_4$, 403; found, 403.

Example 14

N-(5-cyclopropyl-1H-pyrazol-3-yl)-7-(3-(piperazin-1-ylmethyl)phenyl) imidazo[1,2-f]pyrimidin-5-amine

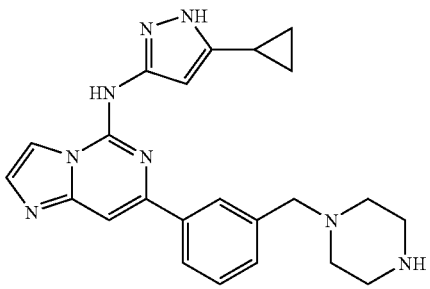

The title compound was synthesized using tert-butyl 4-(3-(4,4,5,5-tetramethyl-1,3,2-dioxaborolan-2-yl)benzyl)piperazine-1-carboxylate following a procedure analogous to that described in the synthesis of Example 12, except that the reaction product was further treated with TFA (30 min) to give the title compound as a foam (22 mg). $^1$H NMR (400 MHz, MeOD-$d_4$) δ 8.41 (s, 1H), 8.25-8.30 (m, 2H), 8.02 (t, J=2.0 Hz, 1H), 7.78 (s, 1H), 7.66-7.71 (m, 2H), 6.48 (s, 1H), 4.40 (s, 2H), 3.51-3.53 (m, 4H), 3.45-3.47 (m, 4H), 2.01-2.03

(m, 1H), 1.05-1.10 (m, 2H), 0.82-0.84 (m, 2H). [M+H] calc'd for $C_{23}H_{27}N_8$, 415; found, 415.

Example 15a 4-(3-Bromobenzyl)piperazin-2-one

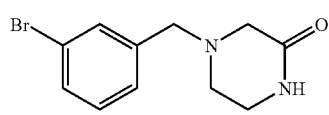

The title compound was synthesized using a procedure analogous to that described in Example 14a. [M+H] calc'd for $C_{11}H_{14}BrN_2O$, 269, 271; found, 269, 271.

Example 15b 4-(3-(4,4,5,5-Tetramethyl-1,3,2-dioxaborolan-2-yl)benzyl)piperazin-2-one

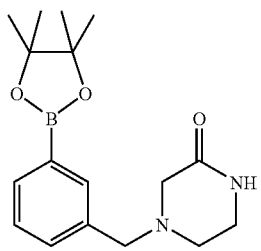

4-(3-Bromobenzyl)piperazin-2-one (356 mg, 1.32 mmol), bis(pinacolato)diboron (370 mg, 1.46 mmol), potassium acetate (388 mg, 3.95 mmol), and [1,1'-bis(diphenylphosphino)ferrocene]dichloropalladium(II) (32 mg, 0.039 mmol) were combined in DMF (10 mL), and the reaction stirred at 80° C. under $N_2$ for 4 h. The cooled solution was partitioned between EtOAc and water. Organics were washed with brine, dried (MgSO$_4$), and concentrated in vacuo. Purification by silica gel chromatography (50% EtOAc/hexanes then 10% MeOH/DCM) gave 261 mg (63%) of the title compound as a tan solid. [M+H] calc'd for $C_{17}H_{26}BN_2O_3$, 317; found, 317.

Example 15

4-((3-(5-(5-Cyclopropyl-1H-pyrazol-3-ylamino)imidazo[1,2-f]pyrimidin-7-yl)phenyl)methyl)piperazin-2-one

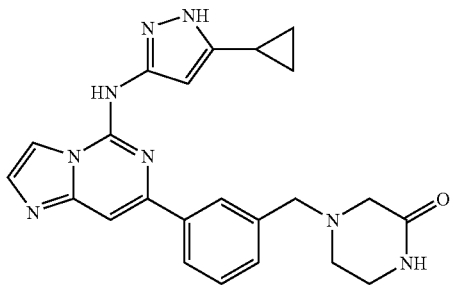

The title compound was synthesized in 34% yield using 4-(3-(4,4,5,5-tetramethyl-1,3,2-dioxaborolan-2-yl)benzyl)piperazin-2-one following the procedure described in the synthesis of Example 12. $^1$H NMR (400 MHz, MeOD-d$_4$) δ 8.41 (br.s, 1H), 8.30-8.32 (m, 2H), 8.01-8.03 (m, 1H), 7.79 (s, 1H), 7.67-7.75 (m, 2H), 6.46 (s, 1H), 4.58 (s, 2H), 3.89-3.90 (m, 2H), 3.61-3.62 (m, 4H), 2.00-2.06 (m, 1H), 1.04-1.11 (m, 2H), 0.79-0.84 (m, 2H). [M+H] calc'd for $C_{23}H_{25}N_8O$, 429; found, 429.

Example 16

4-((3-(5-(5-Methyl-1H-pyrazol-3-ylamino)imidazo[1,2-f]pyrimidin-7-yl)phenyl)methyl)piperazin-2-one

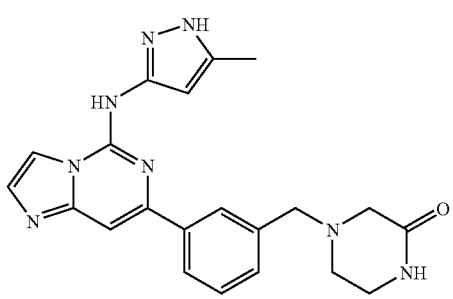

The title compound was synthesized in 41% yield using 4-(3-(4,4,5,5-tetramethyl-1,3,2-dioxaborolan-2-yl)benzyl)piperazin-2-one and 7-chloro-N-(5-methyl-1H-pyrazol-3-yl)imidazo[1,2-f]pyrimidin-5-amine following the procedure described in the synthesis of Example 12. $^1$H NMR (400 MHz, MeOD-d$_4$) δ 8.42 (d, J=2.3 Hz, 1H), 8.30-8.33 (m, 2H), 8.03 (d, J=2.3 Hz, 1H), 7.79 (s, 1H), 7.68-7.74 (m, 2H), 6.59

(s, 1H), 4.59 (s, 2H), 3.89 (s, 2H), 3.59-3.65 (m, 4H), 2.41 (s, 3H). [M+H] calc'd for $C_{21}H_{23}N_8O$, 403; found, 403.

Example 17

(5-Cyclopropyl-1H-pyrazol-3-yl)-[7-(2,3-dihydro-benzofuran-5-yl)-imidazo[1,2-c]pyrimidin-5-yl]-amine

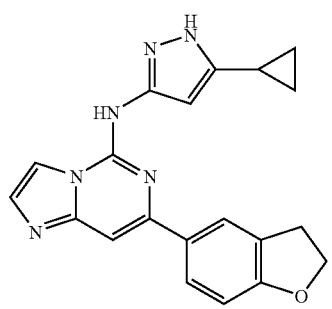

The title compound was synthesized in 39% yield using 2,3-dihydro-1-benzofuran-5-ylboronic acid following the procedure described in the synthesis of Example 12. $^1$H NMR (400 MHz, DMSO-d$_6$) δ 12.45 (br s, 1H), 10.92 (s, 1H), 8.55 (s, 1H), 7.94-8.09 (m, 3H), 7.61 (s, 1H), 6.93 (d, J=8.4 Hz, 1H), 6.49 (s, 1H), 4.64 (t, J=8.4 Hz, 2H), 3.28 (t, J=8.4 Hz, 2H), 1.91-1.99 (m, 1H), 0.92-1.01 (m, 2H), 0.68-0.78 (m, 2H). [M+H] calc'd for $C_{20}H_{18}N_6O$, 359; found, 359.

Example 18a 3-(Acetylamino-methyl)-phenylboronic acid

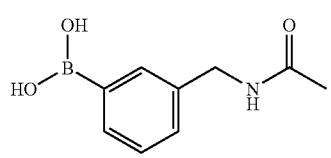

Acetic anhydride (76 μL, 0.80 mmol) was added dropwise to a stirred solution of (3-aminomethylphenyl)boronic acid, hydrochloride (150 mg, 0.80 mmol) and DIEA (560 μL, 3.2 mmol) in CH$_2$Cl$_2$ (5 mL) at 0° C. After 1 h, the solution was concentrated in vacuo and purified by preparatory HPLC to give 36 mg (23%) of the title compound as a white solid. [M+H] calc'd for $C_9H_{12}BNO_3$, 194; found, 194.

Example 18

N-{3-[5-(5-Cyclopropyl-1H-pyrazol-3-ylamino)-imidazo[1,2-c]pyrimidin-7-yl]-benzyl}-acetamide

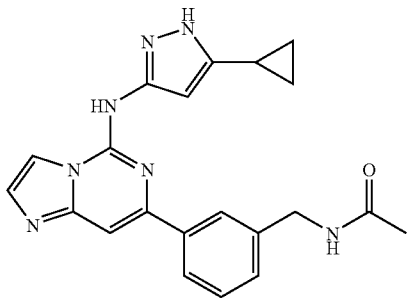

The title compound was synthesized in 33% yield using 3-(acetylamino-methyl)-phenylboronic acid following the procedure described in the synthesis of Example 12. $^1$H NMR (400 MHz, DMSO-d$_6$) δ 12.51 (br s, 1H), 11.01 (s, 1H), 8.63 (s, 1H), 8.45 (t, J=5.6 Hz, 1H), 8.11 (s, 1H), 8.01-8.06 (m, 2H), 7.72 (s, 1H), 7.53 (t, J=7.6 Hz, 1H), 7.42 (d, J=7.6 Hz, 1H), 6.58 (s, 1H), 4.36 (d, J=5.6 Hz, 2H), 1.99-2.07 (m, 1H), 1.89 (s, 3H), 0.93-1.01 (m, 2H), 0.72-0.80 (m, 2H). [M+H] calc'd for $C_{21}H_{21}N_9O$, 388; found, 388.

Example 19a 3-(3-Bromo-benzyl)-imidazolidine-2,4-dione

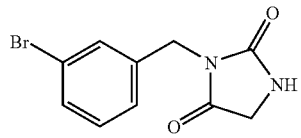

Hydantoin (300 mg, 3.0 mmol) was added to a solution of KOH (202 mg, 3.6 mmol) in 90% EtOH at r.t., and the reaction stirred for 30 min. 3-Bromobenzyl bromide (750 mg, 3.0 mmol) was added, and the reaction was heated at reflux for 18 h. The solution was diluted with EtOAc, washed with H$_2$O and brine, dried (MgSO$_4$) and concentrated in vacuo. Precipitation from 50% EtOAc/hexanes followed by collection by filtration gave 512 mg (63%) of the title compound as a white solid. $^1$H NMR (400 MHz, CDCl$_3$) δ 7.54 (s, 1H), 7.42 (d, J=7.6 Hz, 1H), 7.34 (d, J=7.6 Hz, 1H), 7.19 (t, J=7.6 Hz, 1H), 5.81 (s, 1H), 4.63 (s, 2H), 4.00 (s, 2H). [M+H] calc'd for C₁₀H₉BrN₂O₂, 269, 271; found, 269, 271.

Example 19b 3-(2,5-Dioxo-imidazolidin-lylmethyl)-phenylboronic acid, pinacol ester

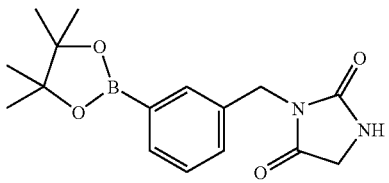

3-(3-Bromo-benzyl)-imidazolidine-2,4-dione (480 mg, 1.78 mmol), bis(pinacolato)diboron (475 mg, 1.97 mmol), potassium acetate (525 mg, 5.34 mmol), and [1,1'-bis(diphenylphosphino)ferrocene]dichloropalladium(II) (44 mg, 0.05 mmol) were combined in DMF (10 mL), and the reaction stirred at 80° C. under N₂ for 16 h. The cooled solution was partitioned between EtOAc and water. Organics were washed with brine, dried (MgSO₄), and concentrated in vacuo. Purification by silica gel chromatography (75% EtOAc/hexanes) gave 366 mg (65%) of the title compound as a tan solid. ¹H NMR (400 MHz, DMSO-d₆) δ 8.13 (s, 1H), 7.58 (s, 1H), 7.56 (d, J=7.6 Hz, 1H), 7.39 (d, J=7.6 Hz, 1H), 7.33 (t, J=7.6 Hz, 1H), 4.51 (s, 2H), 3.96 (s, 2H), 1.28 (s, 12H). [M+H] calc'd for C₁₆H₂₁BN₂O₄, 317; found, 317.

Example 19

3-{3-[5-(5-Cyclopropyl-1H-pyrazol-3-ylamino)-imidazo[1,2-c]pyrimidin-7-yl]-benzyl}-imidazolidine-2,4-dione

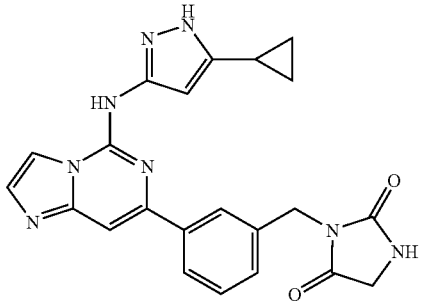

The title compound was synthesized in 13% yield using 3-(2,5-dioxo-imidazolidin-lylmethyl)-phenylboronic acid, pinacol ester following the procedure described in the synthesis of Example 12. ¹H NMR (400 MHz, MeOD-d₄) δ 8.37 (s, 1H), 8.19 (s, 1H), 8.07 (d, J=6.8 Hz, 1H), 7.98 (s, 1H), 7.64 (s, 1H), 7.50-7.56 (m, 2H), 6.56 (s, 1H), 4.75 (s, 2H), 4.00 (s, 2H), 2.00-2.08 (m, 1H), 1.00-1.08 (m, 2H), 0.79-0.86 (m, 2H). [M+H] calc'd for C₂₂H₂₀N₈O₂, 429; found, 429.

Example 20a 3-(3-Methyl-3H-imidazol-4-yl)-phenylboronic acid

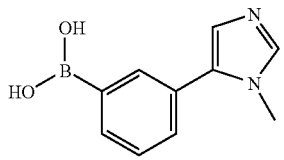

1,3-Benzenediboronic acid (300 mg, 1.8 mmol), 5-bromo-1-methylimidazole (291 mg, 1.8 mmol), potassium phosphate (1.15 g, 5.4 mmol), tris(dibenzylideneacetone)dipalladium(0) (164 mg, 0.18 mmol), and 2-dicyclohexylphosphino-2'-(N,N-dimethylamino)biphenyl (142 mg, 0.36 mmol) were combined with DMA (3 mL) in a sealed tube purged with N₂. The reaction was heated at 130° C. for 25 min in a microwave reactor. The solution was diluted with MeOH, filtered, and concentrated in vacuo. Purification by preparatory HPLC gave 166 mg (45%) of the title compound as a white solid. ¹H NMR (400 MHz, DMSO-d₆) δ 9.12 (s, 1H), 7.91-7.98 (m, 2H), 7.83 (s, 1H), 7.63 (d, J=7.6 Hz, 1H), 7.52 (t, J=7.6 Hz, 1H), 3.83 (s, 3H). [M+H] calc'd for C₁₀H₁₁BN₂O₂, 202; found, 202.

Example 20

(5-Cyclopropyl-1H-pyrazol-3-yl)-{7-[3-(3-methyl-3H-imidazol-4-yl)-phenyl]-imidazo[1,2-c]pyrimidin-5-yl}-amine

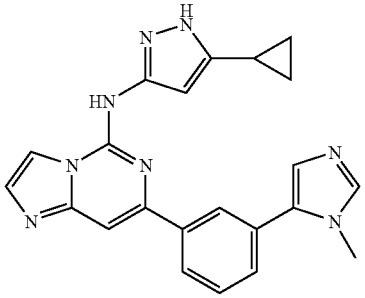

The title compound was synthesized in 23% yield using 3-(3-methyl-3H-imidazol-4-yl)-phenylboronic acid following the procedure described in the synthesis of Example 12. ¹H NMR (400 MHz, MeOD-d₄) δ 9.08 (s, 1H), 8.32-8.46 (m, 3H), 8.02 (s, 1H), 7.83 (s, 1H), 7.75-7.80 (m, 2H), 7.56 (s, 1H), 6.46 (s, 1H), 3.94 (s, 3H), 1.94-2.02 (m, 1H), 0.98-1.05 (m, 2H), 0.70-0.76 (m, 2H). [M+H] calc'd for $C_{22}H_{20}N_8$, 397; found, 397.

Example 21a 3-(Methanesulfonylamino-methyl)-phenylboronic acid, pinacol ester

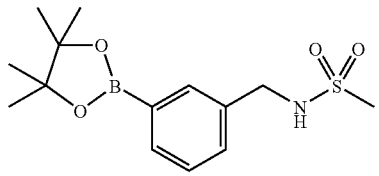

Methanesulfonyl chloride (60 µL, 0.78 mmol) was added to a stirred solution of (3-aminomethylphenyl)boronic acid pinacol ester, hydrochloride (200 mg, 0.74 mmol) and DIEA (260 µL, 1.48 mmol) in $CH_2Cl_2$ (5 mL) at r.t. After 1 h, the solution was washed with 0.5 N HCl and brine, dried ($MgSO_4$) and concentrated in vacuo to give 228 mg (99%) of the title compound as a clear oil. $^1$H NMR (400 MHz, MeOD-$d_4$) δ 7.75 (s, 1H), 7.66 (d, J=7.6 Hz, 1H), 7.48 (d, J=7.6 Hz, 1H), 7.36 (t, J=7.6 Hz, 1H), 4.24 (s, 2H), 2.85 (s, 3H), 1.34 (s, 12H). [M+H] calc'd for $C_{14}H_{22}BNO_4S$, 312; found, 312.

Example 21

N-{3-[5-(5-Cyclopropyl-1H-pyrazol-3-ylamino)-imidazo[1,2-c]pyrimidin-7-yl]-benzyl}-methanesulfonamide

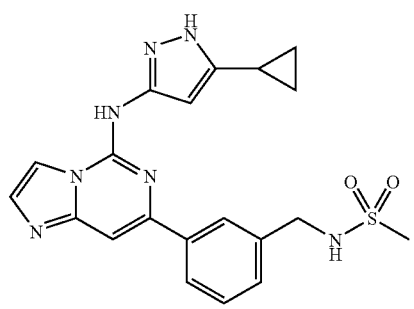

The title compound was synthesized in 32% yield using 3-(methanesulfonylamino-methyl)-phenylboronic acid, pinacol ester following the procedure described in the synthesis of Example 12. $^1$H NMR (400 MHz, MeOD-$d_4$) δ 8.34 (d, J=2.0 Hz, 1H), 8.18 (s, 1H), 8.06 (d, J=7.6 Hz, 1H), 7.97 (d, J=2.0 Hz, 1H), 7.65 (s, 1H), 7.50-7.57 (m, 2H), 6.51 (s, 1H), 4.35 (s, 2H), 2.92 (s, 3H), 2.00-2.08 (m, 1H), 1.00-1.08 (m, 2H), 0.78-0.85 (m, 2H). [M+H] calc'd for $C_{20}H_{21}N_7O_2S$, 424; found, 424.

Example 22a

3-[(Cyclopropanecarbonyl-amino)-methyl]-phenylboronic acid, pinacol ester

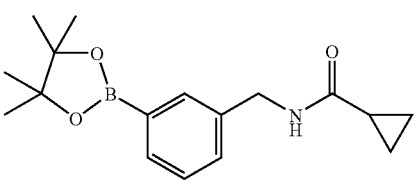

The title compound was synthesized in quantitative yield using cyclopropanecarbonyl chloride following the procedure described for the synthesis of Example 21a. $^1$H NMR (400 MHz, MeOD-$d_4$) δ 7.68 (s, 1H), 7.63 (d, J=7.6 Hz, 1H), 7.38 (d, J=7.6 Hz, 1H), 7.32 (t, J=7.6 Hz, 1H), 4.38 (s, 2H), 1.60-1.67 (m, 1H), 1.33 (s, 12H), 0.84-0.90 (m, 2H), 0.71-0.77 (m, 2H). [M+H] calc'd for $C_{17}H_{24}NO_3B$, 302; found, 302.

Example 22

Cyclopropanecarboxylic acid 3-[5-(5-cyclopropyl-1H-pyrazol-3-ylamino)-imidazo[1,2-c]pyrimidin-7-yl]-benzylamide

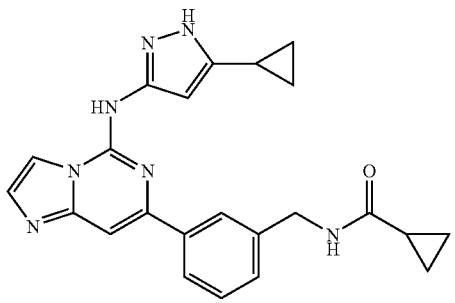

The title compound was synthesized in 33% yield using 3-[(cyclopropanecarbonyl-amino)-methyl]-phenylboronic acid, pinacol ester following the procedure described in the synthesis of Example 12. $^1$H NMR (400 MHz, MeOD-$d_4$) δ 8.50 (d, J=2.0 Hz, 1H), 8.02-8.12 (m, 3H), 7.85 (s, 1H), 7.50-7.56 (m, 2H), 6.57 (s, 1H), 4.48 (s, 2H), 2.11-2.18 (m, 1H), 1.61-1.68 (m, 1H), 1.20-1.26 (m, 2H), 0.94-1.01 (m, 2H), 0.81-0.87 (m, 2H), 0.73-0.79 (m, 2H). [M+H] calc'd for $C_{23}H_{23}N_7O$, 414; found, 414.

Example 23a 3-(3-Bromo-benzyl)-imidazolidine-2-one

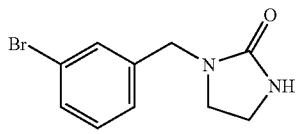

3-Bromobenzyl bromide (1.0 g, 4.0 mmol) was added to a solution of 2-imidazolidone (1.03 g, 12.0 mmol) and potassium carbonate (1.66 g, 12.0 mmol) in 2-propanol (10 mL), and the reaction stirred at reflux for 40 h. The cooled solution was partitioned between EtOAc and water. Organics were washed with brine, dried (MgSO$_4$) and concentrated in vacuo. Purification by silica gel chromatography (100% EtOAc) gave 446 mg (44%) of the title compound as a white solid. $^1$H NMR (400 MHz, MeOD-d$_4$) δ 7.40-7.48 (m, 2H), 7.21-7.28 (m, 2H), 4.30 (s, 2H), 3.29-3.41 (m, 4H). [M+H] calc'd for $C_{10}H_{11}BrN_2O$, 255, 257; found, 255, 257.

Example 23b 3-(2-Oxo-imidazolidin-1-ylmethyl)-phenylboronic acid, pinacol ester

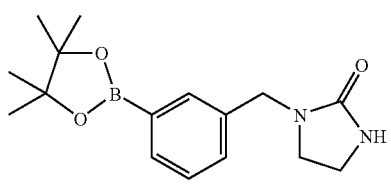

The title compound was synthesized in 77% yield using 3-(3-bromo-benzyl)-imidazolidine-2-one following the procedure for the synthesis of Example 15b. $^1$H NMR (400 MHz, MeOD-d$_4$) δ 7.63-7.69 (m, 2H), 7.31-7.39 (m, 2H), 4.32 (s, 2H), 3.24-3.36 (m, 4H), 1.32 (s, 12H). [M+H] calc'd for $C_{16}H_{23}BN_2O_3$, 317; found, 317.

Example 23

1-{3-[5-(5-Cyclopropyl-1H-pyrazol-3-ylamino)-imidazo[1,2-c]pyrimidin-7-yl]-benzyl}-imidazolidin-2-one

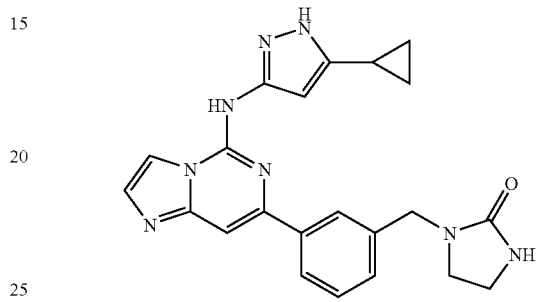

The title compound was synthesized in 25% yield using 3-(2-oxo-imidazolidin-1-ylmethyl)-phenylboronic acid, pinacol ester following the procedure described in the synthesis of Example 12. $^1$H NMR (400 MHz, MeOD-d$_4$) δ 8.07 (s, 1H), 7.98-8.05 (m, 2H), 7.59 (s, 1H), 7.42-7.50 (m, 2H), 7.37 (s, 1H), 6.56 (s, 1H), 4.43 (s, 2H), 3.39 (s, 2H), 3.33 (s, 2H), 1.98-2.04 (m, 1H), 1.00-1.08 (m, 2H), 0.76-0.84 (m, 2H). [M+H] calc'd for $C_{22}H_{22}N_8O$, 415; found, 415.

Example 24

Cyclopropanecarboxylic acid 3-[5-(5-methyl-1H-pyrazol-3-ylamino)-imidazo[1,2-c]pyrimidin-7-yl]-benzylamide

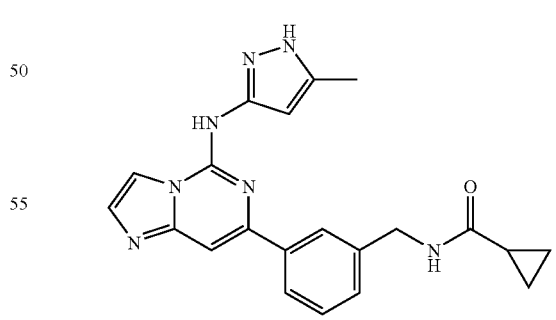

The title compound was synthesized in 32% yield using 3-[(cyclopropanecarbonyl-amino)-methyl]-phenylboronic acid, pinacol ester following the procedure described in the synthesis of Example 12. $^1$H NMR (400 MHz, MeOD-d$_4$) δ 8.60 (d, J=2.0 Hz, 1H), 8.10-8.16 (m, 2H), 8.05 (d, J=7.6 Hz, 1H), 7.94 (s, 1H), 7.50-7.58 (m, 2H), 6.80 (s, 1H), 4.49 (s,

Example 25

N-(5-cyclopropyl-1H-pyrazol-3-yl)-7-(2-methoxyphenyl)imidazo[1,2-f]pyrimidin-5-amine

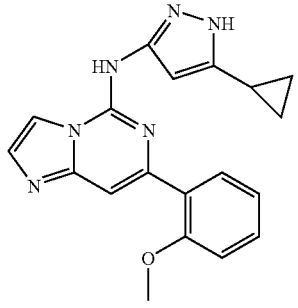

The title compound was synthesized using 7-chloro-N-(5-cyclopropyl-1H-pyrazol-3-yl)imidazo[1,2-f]pyrimidin-5-amine and 2-methoxyphenylboronic acid following the procedure described in the synthesis of Example 12. $^1$H NMR (400 MHz, DMSO) δ 8.57 (s, 1H) 8.06 (m, 2H) 7.83 (s, 1H) 7.51 (m, 1H) 7.24 (d, J=8 Hz, 1H) 7.14 (m, 1H) 6.96 (s, 1H) 3.94 (s, 3H) 1.95 (m, 1H) 0.97 (m, 2H) 0.71 (m, 2H). [M+H] calc'd for $C_{19}H_{19}N_6O$, 347; found, 347.

Example 26

3-(5-(5-cyclopropyl-1H-pyrazol-3-ylamino)imidazo[1,2-f]pyrimidin-7-yl)benzonitrile

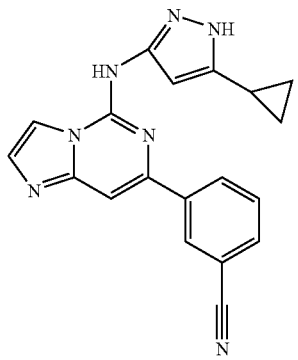

The title compound was synthesized using 7-chloro-N-(5-cyclopropyl-1H-pyrazol-3-yl)imidazo[1,2-f]pyrimidin-5-amine and 3-cyanophenylboronic acid following the procedure described in the synthesis of Example 12. $^1$H NMR (400 MHz, DMSO) δ 8.59 (s, 1H) 8.55 (s, 1H) 8.48 (d, J=8.0 Hz, 1H) 7.97 (m, 2H) 7.87 (s, 1H) 7.76 (m, 1H) 7.11 (s, 1H) 6.48 (s, 1H) 1.97 (m, 1H) 1.02 (m, 2H) 0.77 (m, 2H). [M+H] calc'd for $C_{19}H_{16}N_7$, 342; found, 342.

Example 27

N-(5-cyclopropyl-1H-pyrazol-3-yl)-7-(3,5-dimethylphenyl)imidazo[1,2-f]pyrimidin-5-amine

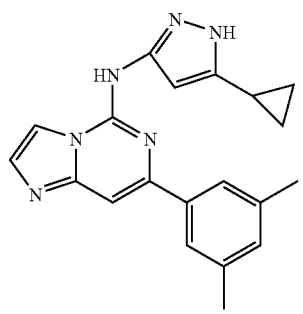

The title compound was synthesized using 7-chloro-N-(5-cyclopropyl-1H-pyrazol-3-yl)imidazo[1,2-f]pyrimidin-5-amine and 3,5-dimethylphenylboronic acid following the procedure described in the synthesis of Example 12. $^1$H NMR (400 MHz, DMSO) δ 8.55 (s, 1H) 7.99 (s, 1H) 7.80 (s, 2H) 7.68 (s, 1H) 7.17 (s, 1H) 6.55 (s, 1H) 2.37 (s, 6H) 1.97 (m, 1H) 1.02 (m, 2H) 0.74 (m, 2H). [M+H] calc'd for $C_{20}H_{21}N_6$, 345; found, 345.

Example 28

N-(5-cyclopropyl-1H-pyrazol-3-yl)-7-p-tolylimidazo[1,2-f]pyrimidin-5-amine

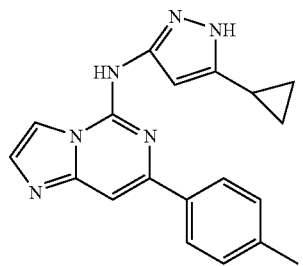

The title compound was synthesized using 7-chloro-N-(5-cyclopropyl-1H-pyrazol-3-yl)imidazo[1,2-f]pyrimidin-5-amine and 4-methylphenylboronic acid following the procedure described in the synthesis of Example 12. $^1$H NMR (400 MHz, DMSO) δ 8.55 (s, 1H) 8.06 (d, J=8.0 Hz, 2H) 8.00 (s, 1H) 7.66 (s, 1H) 7.38 (d, J=8.0 Hz, 2H) 6.52 (s, 1H) 2.38 (s, 3H) 1.98 (m, 1H) 1.01 (m, 2H) 0.74 (m, 2H). [M+H] calc'd for $C_{19}H_{19}N_6$, 331; found, 331.

Example 29

7-(5-chloro-2-methoxyphenyl)-N-(5-cyclopropyl-1H-pyrazol-3-yl)imidazo[1,2-f]pyrimidin-5-amine

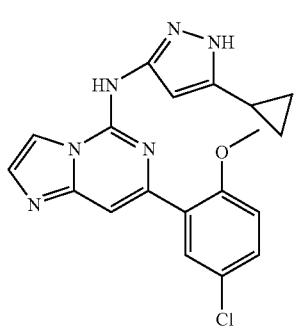

The title compound was synthesized using 7-chloro-N-(5-cyclopropyl-1H-pyrazol-3-yl)imidazo[1,2-f]pyrimidin-5-amine and 5-chloro-2-methoxyphenylboronic acid following the procedure described in the synthesis of Example 12. $^1$H NMR (400 MHz, DMSO) δ 8.58 (s, 1H) 8.18 (s, 1H) 8.07 (s, 1H), 7.94 (s, 1H) 7.56 (d, J=8.0 Hz, 1H) 7.28 (d, J=8.0 Hz, 1H) 6.40 (s, 1H) 3.97 (s, 3H) 1.97 (m, 1H) 1.02 (m, 2H) 0.75 (m, 2H). [M+H] calc'd for $C_{19}H_{18}ClN_6O$, 381; found, 381.

Example 30

N-(5-cyclopropyl-1H-pyrazol-3-yl)-7-(2-methoxy-5-methylphenyl)imidazo[1,2-f]pyrimidin-5-amine

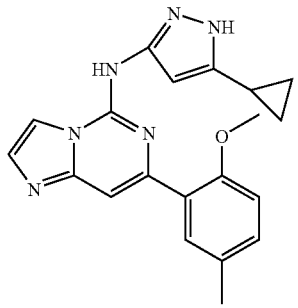

The title compound was synthesized using 7-chloro-N-(5-cyclopropyl-1H-pyrazol-3-yl)imidazo[1,2-f]pyrimidin-5-amine and 2-methoxy-5-methylphenylboronic acid following the procedure described in the synthesis of Example 12. $^1$H NMR (400 MHz, DMSO) δ 8.57 (s, 1H) 8.07 (s, 1H) 7.97 (s, 1H), 7.89 (s, 1H) 7.35 (d, J=8.0 Hz, 1H) 7.15 (d, J=8.0 Hz, 1H) 6.49 (s, 1H) 3.91 (s, 3H) 2.34 (s, 1H) 1.95 (m, 1H) 1.01 (m, 2H) 0.71 (m, 2H). [M+H] calc'd for $C_{20}H_{21}N_6O$, 361; found, 361.

Example 31

N-(5-cyclopropyl-1H-pyrazol-3-yl)-7-(3,5-dimethoxyphenyl)imidazo[1,2-f]pyrimidin-5-amine

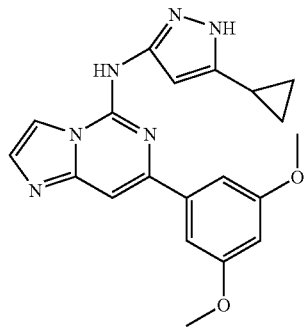

The title compound was synthesized using 7-chloro-N-(5-cyclopropyl-1H-pyrazol-3-yl)imidazo[1,2-f]pyrimidin-5-amine and 3,5-dimethoxyphenylboronic acid following the procedure described in the synthesis of Example 12. $^1$H NMR (400 MHz, DMSO) δ 8.56 (s, 1H) 8.01 (s, 1H) 7.77 (s, 1H) 7.36 (s, 2H) 6.66 (s, 1H) 6.57 (s, 1H) 3.86 (s, 6H) 1.95 (m, 1H) 0.98 (m, 2H) 0.73 (m, 2H). [M+H] calc'd for $C_{20}H_{21}N_6O_2$, 377; found, 377.

Example 32

N-(5-cyclopropyl-1H-pyrazol-3-yl)-7-(4-methoxyphenyl)imidazo[1,2-f]pyrimidin-5-amine

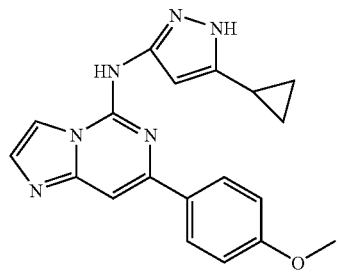

The title compound was synthesized using 7-chloro-N-(5-cyclopropyl-1H-pyrazol-3-yl)imidazo[1,2-f]pyrimidin-5-amine and 4-methoxyphenylboronic acid following the procedure described in the synthesis of Example 12. $^1$H NMR (400 MHz, DMSO) δ 8.55 (s, 1H) 8.13 (d, J=8.0 Hz, 2H) 8.02 (s, 1H) 7.62 (s, 1H) 7.11 (d, J=8.0 Hz, 2H) 6.52 (s, 1H) 3.85

(s, 3H) 1.98 (m, 1H) 1.01 (m, 2H) 0.74 (m, 2H). [M+H] calc'd for $C_{19}H_{19}N_6O$, 347; found, 347.

Example 33

N-(5-cyclopropyl-1H-pyrazol-3-yl)-7-(pyrimidin-5-yl)imidazo[1,2-f]pyrimidin-5-amine

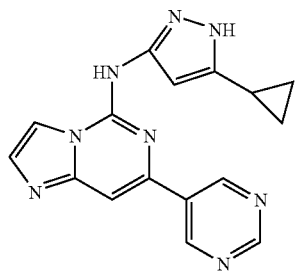

The title compound was synthesized using 7-chloro-N-(5-cyclopropyl-1H-pyrazol-3-yl)imidazo[1,2-f]pyrimidin-5-amine and 5-pyrimidinylboronic acid following the procedure described in the synthesis of Example 12. $^1$H NMR (400 MHz, DMSO) δ 9.49 (s, 2H) 9.28 (s, 1H) 8.57 (s, 1H) 7.96 (s, 1H) 7.94 (s, 1H) 6.50 (s, 1H) 1.99 (m, 1H) 1.00 (m, 2H) 0.75 (m, 2H). [M+H] calc'd for $C_{16}H_{15}N_8$, 319; found, 319.

Example 34

N-(5-cyclopropyl-1H-pyrazol-3-yl)-7-(pyridin-3-yl)imidazo[1,2-f]pyrimidin-5-amine

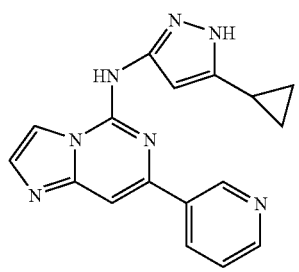

The title compound was synthesized using 7-chloro-N-(5-cyclopropyl-1H-pyrazol-3-yl)imidazo[1,2-f]pyrimidin-5-amine and 3-pyridineboronic acid following the procedure described in the synthesis of Example 12. $^1$H NMR (400 MHz, DMSO) δ 9.37 (s, 1H) 8.75 (d, J=4.0 Hz, 1H) 8.62 (m, 2H) 8.08 (s, 1H) 7.88 (s, 1H) 7.69 (m, 1H) 6.51 (s, 1H) 1.99 (m, 1H) 1.00 (m, 2H) 0.75 (m, 2H). [M+H] calc'd for $C_{17}H_{16}N_7$, 318; found, 318.

Example 35

N-(5-cyclopropyl-1H-pyrazol-3-yl)-7-(3,4-dimethoxyphenyl)imidazo[1,2-f]pyrimidin-5-amine

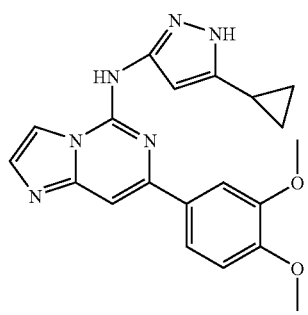

The title compound was synthesized using 7-chloro-N-(5-cyclopropyl-1H-pyrazol-3-yl)imidazo[1,2-f]pyrimidin-5-amine and 3,4-dimethoxyphenylboronic acid following the procedure described in the synthesis of Example 12. $^1$H NMR (400 MHz, DMSO) δ 8.56 (s, 1H) 8.03 (s, 1H) 7.79 (m, 2H) 7.69 (s, 1H) 7.14 (d, J=8.0 Hz, 1H) 6.59 (s, 1H) 3.90 (s, 3H) 3.85 (s, 3H) 1.96 (m, 1H) 0.98 (m, 2H) 0.74 (m, 2H). [M+H] calc'd for $C_{20}H_{21}N_6O_2$, 377; found, 377.

Example 36

N-(5-cyclopropyl-1H-pyrazol-3-yl)-7-(2,3-dimethylphenyl)imidazo[1,2-f]pyrimidin-5-amine

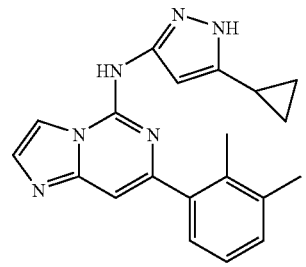

The title compound was synthesized using 7-chloro-N-(5-cyclopropyl-1H-pyrazol-3-yl)imidazo[1,2-f]pyrimidin-5-amine and 2,3-dimethylphenylboronic acid following the procedure described in the synthesis of Example 12. $^1$H NMR (400 MHz, DMSO) δ 8.58 (s, 1H) 8.05 (s, 1H) 7.30 (m, 2H)

7.23 (m, 2H) 6.35 (s, 1H) 2.32 (s, 3H) 2.27 (s, 3H) 1.90 (m, 1H) 0.93 (m, 2H) 0.64 (m, 2H). [M+H] calc'd for $C_{20}H_{21}N_6$, 345; found, 345.

Example 37

7-(benzo[d][1,3]dioxol-5-yl)-N-(5-cyclopropyl-1H-pyrazol-3-yl)imidazo[1,2-f]pyrimidin-5-amine

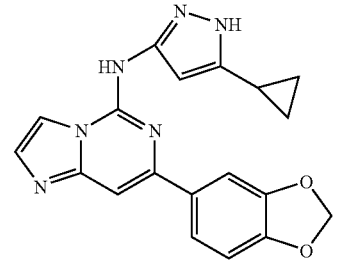

The title compound was synthesized using 7-chloro-N-(5-cyclopropyl-1H-pyrazol-3-yl)imidazo[1,2-f]pyrimidin-5-amine and 3,4-methylenedioxyphenylboronic acid following the procedure described in the synthesis of Example 12. $^1$H NMR (400 MHz, DMSO) δ 8.53 (s, 1H) 8.00 (s, 1H) 7.75 (d, J=8.0 Hz, 1H) 7.71 (s, 1H) 7.62 (s, 1H) 7.10 (d, J=8.0 Hz, 1H) 6.46 (s, 1H) 6.14 (s, 2H) 3.90 (s, 3H) 3.85 (s, 3H) 1.96 (m, 1H) 1.01 (m, 2H) 0.74 (m, 2H). [M+H] calc'd for $C_{19}H_{17}N_6O_2$, 361; found, 361.

Example 38

N-(5-cyclopropyl-1H-pyrazol-3-yl)-7-(2,6-dimethylphenyl)imidazo[1,2-f]pyrimidin-5-amine

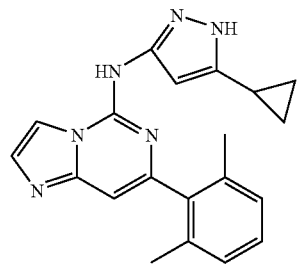

The title compound was synthesized using 7-chloro-N-(5-cyclopropyl-1H-pyrazol-3-yl)imidazo[1,2-f]pyrimidin-5-amine and 2,6-dimethylphenylboronic acid following the procedure described in the synthesis of Example 12. $^1$H NMR (400 MHz, DMSO) δ 8.58 (s, 1H) 8.07 (s, 1H) 7.24 (m, 2H) 7.15 (m, 2H) 6.21 (s, 1H) 2.15 (s, 3H) 2.07 (s, 3H) 1.80 (m, 1H) 0.90 (m, 2H) 0.61 (m, 2H). [M+H] calc'd for $C_{20}H_{21}N_6$, 345; found, 345.

Example 39

N-(5-cyclopropyl-1H-pyrazol-3-yl)-7-(2,6-dimethoxyphenyl)imidazo[1,2-f]pyrimidin-5-amine

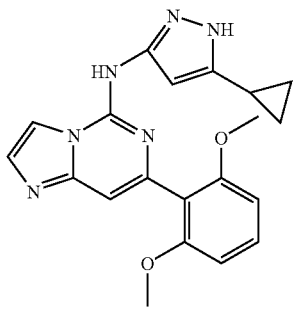

The title compound was synthesized using 7-chloro-N-(5-cyclopropyl-1H-pyrazol-3-yl)imidazo[1,2-f]pyrimidin-5-amine and 2,6-dimethoxyphenylboronic acid following the procedure described in the synthesis of Example 12. $^1$H NMR (400 MHz, DMSO) δ 8.48 (s, 1H) 7.99 (s, 1H) 7.43 (t, J=8.0 Hz, 1H) 7.07 (s, 1H) 6.81 (d, J=8.0 Hz, 2H) 6.29 (s, 1H) 3.74 (s, 3H) 3.67 (s, 3H) 1.87 (m, 1H) 0.92 (m, 2H) 0.61 (m, 2H). [M+H] calc'd for $C_{20}H_{21}N_6O_2$, 377; found, 377.

Example 40

N-(5-cyclopropyl-1H-pyrazol-3-yl)-7-(2-methoxypyridin-4-yl)imidazo[1,2-f]pyrimidin-5-amine

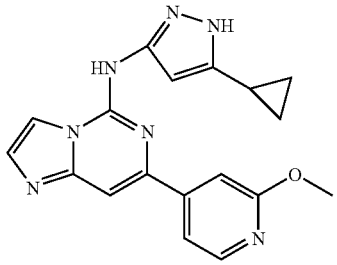

The title compound was synthesized using 7-chloro-N-(5-cyclopropyl-1H-pyrazol-3-yl)imidazo[1,2-f]pyrimidin-5-amine and 2-methoxypyridin-4-ylboronic acid following the procedure described in the synthesis of Example 12. $^1$H NMR (400 MHz, DMSO) δ 8.59 (s, 1H) 8.50 (d, J=8.0 Hz, 1H) 8.34 (d, J=4.0 Hz, 1H) 8.07 (s, 1H) 7.94 (s, 1H) 7.25 (m, 1H) 6.44

(s, 1H) 4.05 (s, 3H) 1.97 (m, 1H) 0.98 (m, 2H) 0.74 (m, 2H). [M+H] calc'd for $C_{18}H_{18}N_7O$, 348; found, 348.

Example 41

N-(5-cyclopropyl-1H-pyrazol-3-yl)-7-(4-phenoxyphenyl)imidazo[1,2-f]pyrimidin-5-amine

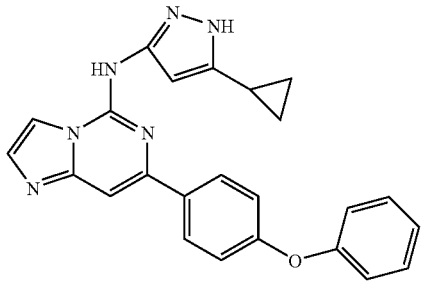

The title compound was synthesized using 7-chloro-N-(5-cyclopropyl-1H-pyrazol-3-yl)imidazo[1,2-f]pyrimidin-5-amine and 4-phenoxyphenylboronic acid following the procedure described in the synthesis of Example 12. $^1$H NMR (400 MHz, DMSO) δ 8.54 (s, 1H) 8.16 (d, J=8.0 Hz, 2H) 7.97 (s, 1H) 7.63 (s, 1H) 7.45 (m, 2H) 7.21 (m, 1H) 7.13 (m, 4H) 6.52 (s, 1H) 1.98 (m, 1H) 0.98 (m, 2H) 0.74 (m, 2H). [M+H] calc'd for $C_{24}H_{21}N_6O$, 409; found, 409.

Example 42

N-(5-cyclopropyl-1H-pyrazol-3-yl)-7-(3-biphenyl)imidazo[1,2-f]pyrimidin-5-amine

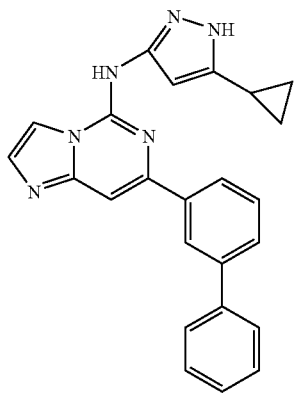

The title compound was synthesized using 7-chloro-N-(5-cyclopropyl-1H-pyrazol-3-yl)imidazo[1,2-f]pyrimidin-5-amine and 3-biphenylboronic acid following the procedure described in the synthesis of Example 12. $^1$H NMR (400 MHz, DMSO) δ 8.61 (s, 1H) 8.48 (s, 1H) 8.16 (d, J=8.0 Hz, 1H) 8.06 (s, 1H) 7.87 (s, 1H) 7.82 (d, J=8.0 Hz, 1H) 7.75 (m, 2H) 7.66 (m, 1H) 7.53 (m, 2H) 7.43 (m, 1H) 6.60 (s, 1H) 1.96 (m, 1H) 0.96 (m, 2H) 0.69 (m, 2H). [M+H] calc'd for $C_{24}H_{21}N_6$, 393; found, 393.

Example 43

N-(5-cyclopropyl-1H-pyrazol-3-yl)-7-(4-biphenyl)imidazo[1,2-f]pyrimidin-5-amine

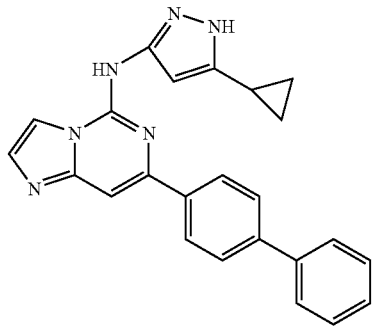

The title compound was synthesized using 7-chloro-N-(5-cyclopropyl-1H-pyrazol-3-yl)imidazo[1,2-f]pyrimidin-5-amine and 4-biphenylboronic acid following the procedure described in the synthesis of Example 12. $^1$H NMR (400 MHz, DMSO) δ 8.58 (s, 1H) 8.25 (d, J=8.0 Hz, 2H) 8.03 (s, 1H) 7.87-7.35 (m, 8H) 6.57 (s, 1H) 2.00 (m, 1H) 1.01 (m, 2H) 0.78 (m, 2H). [M+H] calc'd for $C_{24}H_{21}N_6$, 393; found, 393.

Example 44

N-(5-cyclopropyl-1H-pyrazol-3-yl)-7-(2-biphenyl)imidazo[1,2-f]pyrimidin-5-amine

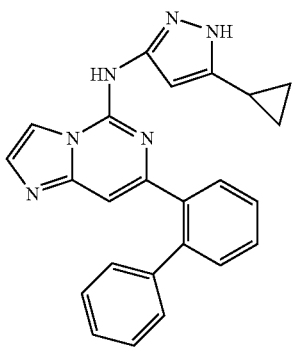

The title compound was synthesized using 7-chloro-N-(5-cyclopropyl-1H-pyrazol-3-yl)imidazo[1,2-f]pyrimidin-5-amine and 2-biphenylboronic acid following the procedure described in the synthesis of Example 12. $^1$H NMR (400 MHz, DMSO) δ 8.48 (s, 1H) 7.93 (s, 1H) 7.57-7.17 (m, 10H)

5.63 (s, 1H) 1.12 (m, 1H) 0.93 (m, 2H) 0.64 (m, 2H). [M+H] calc'd for $C_{24}H_{21}N_6$, 393; found, 393.

Example 45

N-(5-cyclopropyl-1H-pyrazol-3-yl)-7-(2-fluorophenyl)imidazo[1,2-f]pyrimidin-5-amine

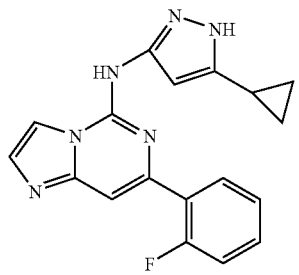

The title compound was synthesized using 7-chloro-N-(5-cyclopropyl-1H-pyrazol-3-yl)imidazo[1,2-f]pyrimidin-5-amine and 2-fluorophenylboronic acid following the procedure described in the synthesis of Example 12. $^1$H NMR (400 MHz, DMSO) δ 8.59 (s, 1H) 8.09 (m, 1H) 8.01 (s, 1H) 7.57 (m, 2H) 7.42 (m, 2H) 6.50 (s, 1H) 1.96 (m, 1H) 0.97 (m, 2H) 0.71 (m, 2H). [M+H] calc'd for $C_{18}H_{16}FN_6$, 335; found, 335.

Example 46

N-(5-cyclopropyl-1H-pyrazol-3-yl)-7-(3,5-difluorophenyl)imidazo[1,2-f]pyrimidin-5-amine

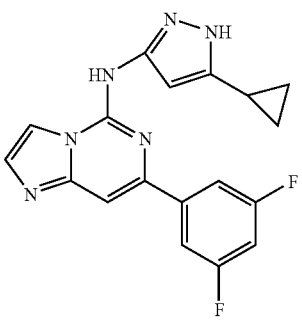

The title compound was synthesized using 7-chloro-N-(5-cyclopropyl-1H-pyrazol-3-yl)imidazo[1,2-f]pyrimidin-5-amine and 3,5-difluorophenylboronic acid following the procedure described in the synthesis of Example 12. $^1$H NMR (400 MHz, DMSO) δ 8.52 (s, 1H) 7.90 (m, 3H) 7.38 (m, 2H) 6.44 (s, 1H) 1.96 (m, 1H) 1.01 (m, 2H) 0.72 (m, 2H). [M+H] calc'd for $C_{18}H_{15}F_2N_6$, 353; found, 353.

Example 47

3-(5-(5-cyclopropyl-1H-pyrazol-3-ylamino)imidazo[1,2-f]pyrimidin-7-yl)-N-methylbenzamide

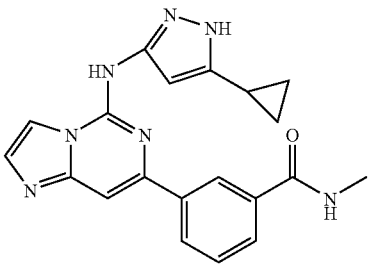

The title compound was synthesized using 7-chloro-N-(5-cyclopropyl-1H-pyrazol-3-yl)imidazo[1,2-f]pyrimidin-5-amine and 3-(N-methylaminocarbonyl)phenylboronic acid following the procedure described in the synthesis of Example 12. $^1$H NMR (400 MHz, DMSO) δ 8.61 (b, 2H) 8.29 (d, J=8.36 Hz, 1H) 8.04 (s, 1H) 7.93 (d, J=8.36 Hz, 1H) 7.78 (s, 1H) 7.65 (m, 1H) 6.58 (s, 1H) 2.84 (d, J=3.2 Hz, 3H) 1.96 (m, 1H) 1.00 (m, 2H) 0.79 (m, 2H). [M+H] calc'd for $C_{20}H_{20}N_7O$, 374; found, 374.

Example 48

3-(5-(5-cyclopropyl-1H-pyrazol-3-ylamino)imidazo[1,2-f]pyrimidin-7-yl)-N-ethylbenzamide

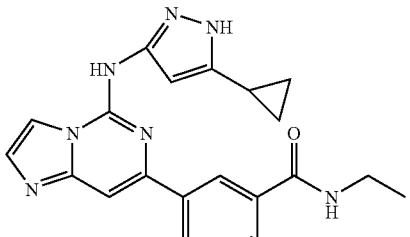

The title compound was synthesized using 7-chloro-N-(5-cyclopropyl-1H-pyrazol-3-yl)imidazo[1,2-f]pyrimidin-5-amine and 3-(N-ethylaminocarbonyl)phenylboronic acid following the procedure described in the synthesis of Example 12. $^1$H NMR (400 MHz, DMSO) δ 8.65-8.60 (b, 2H) 8.29 (d, J=7.8 Hz, 1H) 8.04 (s, 1H) 7.93 (d, J=7.8 Hz, 1H) 7.78 (s, 1H)

7.65 (m, 1H) 6.57 (s, 1H) 3.33 (m, 2H) 1.96 (m, 1H) 1.16 (t, J=7.0 Hz, 3H) 0.99 (m, 2H) 0.79 (m, 2H). [M+H] calc'd for $C_{21}H_{22}N_7O$, 388; found, 388.

Example 49

N-cyclopropyl-3-(5-(5-cyclopropyl-1H-pyrazol-3-ylamino)imidazo[1,2-f]pyrimidin-7-yl)benzamide

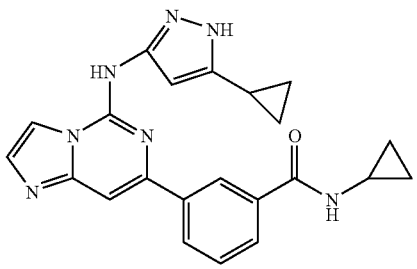

The title compound was synthesized using 7-chloro-N-(5-cyclopropyl-1H-pyrazol-3-yl)imidazo[1,2-f]pyrimidin-5-amine and 3-(cyclopropylaminocarbonyl)phenylboronic acid following the procedure described in the synthesis of Example 12. $^1$H NMR (400 MHz, DMSO) δ 8.60 (s, 1H) 8.57 (s, 1H) 8.29 (d, J=8.6 Hz, 1H) 8.05 (s, 1H) 7.93 (d, J=8.6 Hz, 1H) 7.78 (s, 1H) 7.65 (m, 1H) 6.57 (s, 1H) 2.88 (m, 1H) 1.96 (m, 1H) 0.98 (m, 2H) 0.79 (m, 2H) 0.74 (m, 2H) 0.61 (m, 2H). [M+H] calc'd for $C_{22}H_{22}N_7O$, 400; found, 400.

Example 50

N-(2-cyanoethyl)-3-(5-(5-cyclopropyl-1H-pyrazol-3-ylamino)imidazo[1,2-f]pyrimidin-7-yl)benzamide

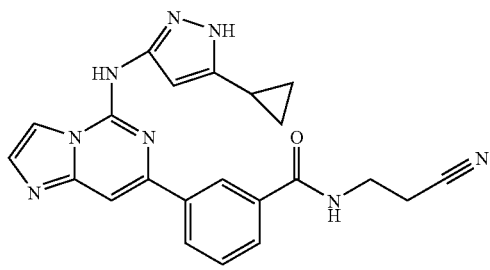

The title compound was synthesized using 7-chloro-N-(5-cyclopropyl-1H-pyrazol-3-yl)imidazo[1,2-f]pyrimidin-5-amine and 3-(2-cyanoethylaminocarbonyl)phenylboronic acid following the procedure described in the synthesis of Example 12. $^1$H NMR (400 MHz, DMSO) δ 8.64 (s, 1H) 8.61 (s, 1H) 8.33 (d, J=7.8 Hz, 1H) 8.05 (s, 1H) 7.97 (d, J=7.8 Hz, 1H) 7.78 (s, 1H) 7.68 (m, 1H) 6.57 (s, 1H) 3.55 (q, J=6.28 Hz, 2H) 2.82 (t, J=6.28 Hz, 2H) 1.96 (m, 1H) 0.98 (m, 2H) 0.81 (m, 2H). [M+H] calc'd for $C_{22}H_{21}N_8O$, 413; found, 413.

Example 51

(3-(5-(5-cyclopropyl-1H-pyrazol-3-ylamino)imidazo[1,2-f]pyrimidin-7-yl)phenyl)(pyrrolidin-1-yl)methanone

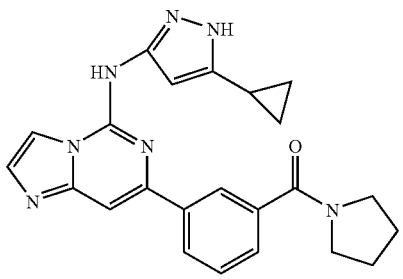

The title compound was synthesized using 7-chloro-N-(5-cyclopropyl-1H-pyrazol-3-yl)imidazo[1,2-f]pyrimidin-5-amine and 3-(pyrrolidine-1-carbonyl)phenylboronic acid following the procedure described in the synthesis of Example 12. $^1$H NMR (400 MHz, DMSO) δ 8.61 (s, 1H) 8.31 (s, 1H) 8.25 (d, J=7.56 Hz, 1H) 8.09 (s, 1H) 7.83 (s, 1H) 7.64 (m, 2H) 6.48 (s, 1H) 3.52 (t, J=6.84 Hz, 2H) 3.39 (t, J=6.84 Hz, 2H) 1.90 (m, 1H) 0.98 (m, 2H) 0.73 (m, 2H). [M+H] calc'd for $C_{23}H_{24}N_7O$, 414; found, 414.

Example 52

Methyl 3-(5-(5-cyclopropyl-1H-pyrazol-3-ylamino)imidazo[1,2-f]pyrimidin-7-yl)benzoate

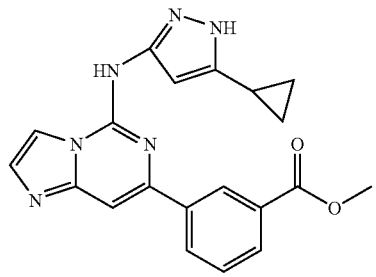

The title compound was synthesized using 7-chloro-N-(5-cyclopropyl-1H-pyrazol-3-yl)imidazo[1,2-f]pyrimidin-5-amine and 3-methoxycarbonylboronic acid following the procedure described in the synthesis of Example 12. $^1$H NMR (400 MHz, DMSO) δ 8.78 (s, 1H) 8.61 (s, 1H) 8.42 (d, J=8.08 Hz, 1H) 8.11 (d, J=8.08 Hz, 1H) 8.03 (s, 1H) 7.82 (s, 1H) 7.72

(m, 1H) 6.57 (s, 1H) 3.93 (s, 3H) 1.98 (m, 1H) 1.00 (m, 2H) 0.79 (m, 2H). [M+H] calc'd for $C_{20}H_{19}N_6O_2$, 375; found, 375.

Example 53

(3-(5-(5-cyclopropyl-1H-pyrazol-3-ylamino)imidazo[1,2-f]pyrimidin-7-yl)phenyl)methanol

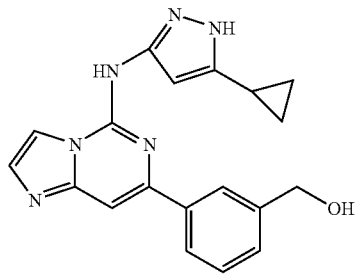

The title compound was synthesized using 7-chloro-N-(5-cyclopropyl-1H-pyrazol-3-yl)imidazo[1,2-f]pyrimidin-5-amine and 3-(hydroxymethyl)phenylboronic acid following the procedure described in the synthesis of Example 12. $^1$H NMR (400 MHz, DMSO) δ 8.61 (s, 1H) 8.17 (s, 1H) 8.07 (s, 1H) 8.03 (d, J=7.08 Hz, 1H) 7.73 (s, 1H) 7.50 (m, 2H) 6.57 (s, 1H) 4.62 (s, 2H) 1.97 (m, 1H) 1.00 (m, 2H) 0.78 (m, 2H). [M+H] calc'd for $C_{19}H_{19}N_6O$, 347; found, 347.

Example 54

(E)-N-(5-cyclopropyl-1H-pyrazol-3-yl)-7-styrylimidazo[1,2-f]pyrimidin-5-amine

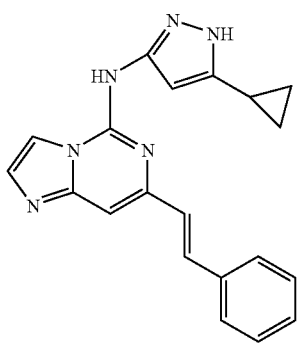

The title compound was synthesized using 7-chloro-N-(5-cyclopropyl-1H-pyrazol-3-yl)imidazo[1,2-f]pyrimidin-5-amine and trans-2-phenylvinylboronic acid following the procedure described in the synthesis of Example 12. $^1$H NMR (400 MHz, DMSO) δ 8.58 (s, 1H) 8.02 (s, 1H) 7.73-7.65 (m, 3H) 7.49-7.41 (m, 4H) 7.25 (s, 1H) 6.60 (s, 1H) 2.02 (m, 1H) 1.00 (m, 2H) 0.78 (m, 2H). [M+H] calc'd for $C_{20}H_{19}N_6$, 343; found, 343.

Example 55

N-(5-methyl-1H-pyrazol-3-yl)-7-phenylimidazo[1,2-f]pyrimidin-5-amine

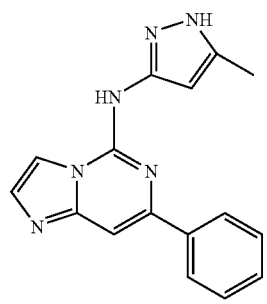

The title compound was synthesized using the procedure as Example 12. $^1$H NMR (400 MHz, MeOD) δ 8.35 (s, 1H) 8.17-8.14 (m, 2H) 7.95 (d, J=2.3 Hz, 1H) 7.62 (s, 1H) 7.55-7.54 (m, 3H) 6.61 (s, 1H) 2.39 (s, 3H). [M+H] calc'd for $C_{16}H_{14}N_6$, 291; found, 291.

Example 56

N-(4-(5-(5-cyclopropyl-1H-pyrazol-3-ylamino)imidazo[1,2-f]pyrimidin-7-yl)phenyl)acetamide

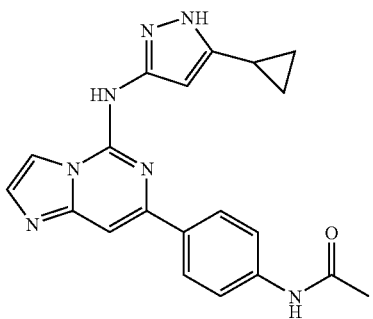

The title compound was synthesized using the procedure as Example 12. $^1$H NMR (400 MHz, MeOD) δ 8.32 (s, 1H) 8.12-8.10 (d, J=8.4 Hz, 2H) 7.94 (s, 1H) 7.76-7.74 (d, J=8.4 Hz, 2H) 7.58 (s, 1H) 6.47 (s, 1H) 2.11 (s, 1H) 2.02-1.99 (m, 1H) 1.29 (s, 3H) 1.09-1.05 (m, 1H) 0.82-0.78 (m, 1H). [M+H] calc'd for $C_{20}H_{19}N_7O$, 374; found, 374.

Example 57

7-(2-chlorophenyl)-N-(5-cyclopropyl-1H-pyrazol-3-yl)imidazo[1,2-f]pyrimidin-5-amine

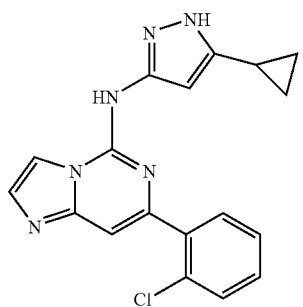

The title compound was synthesized using the procedure as Example 12. $^1$H NMR (400 MHz, MeOD) δ 8.42 (s, 1H) 8.02 (s, 1H) 7.79-7.77 (d, J=9.3 Hz, 1H) 7.62-7.59 (d, J=8.8 Hz, 1H) 7.50 (s, 3H) 6.46 (s, 1H) 1.93 (m, 1H) 1.0-0.99 (m, 2H) 0.71-0.69 (m, 2H). [M+H] calc'd for $C_{18}H_{15}ClN_6$, 351; found, 351.

Example 58

N-(5-cyclopropyl-1H-pyrazol-3-yl)-7-o-tolylimidazo[1,2-f]pyrimidin-5-amine

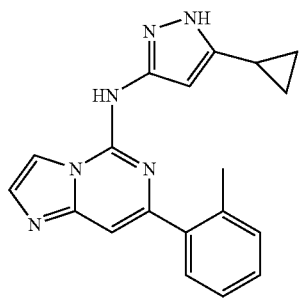

The title compound was synthesized using the procedure as Example 12. $^1$H NMR (400 MHz, MeOD) δ 8.35 (s, 1H) 7.97 (s, 1H) 7.59-7.56 (d, J=12.0 Hz, 1H) 7.41-7.40 (d, J=6.0 Hz, 1H) 7.36-7.34 (d, J=11.1 Hz, 2H) 7.22 (s, 2H) 6.30 (s, 1H) 2.46 (s, 3H) 2.31 (s, 3H) 1.96-1.89 (m, 1H) 1.01-0.98 (m, 2H) 0.71-0.68 (m, 2H). [M+H] calc'd for $C_{19}H_{18}N_6$, 331; found, 331.

Example 59

N-(5-cyclopropyl-1H-pyrazol-3-yl)-7-m-tolylimidazo[1,2-f]pyrimidin-5-amine

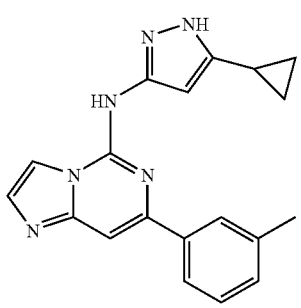

The title compound was synthesized using the procedure as Example 12. $^1$H NMR (400 MHz, MeOD) δ 8.35 (s, 1H) 8.00 (s, 1H) 7.96-7.95 (d, J=2.28 Hz, 2H) 7.62 (s, 1H) 7.39 (m, 1H) 7.24-7.20 (m, 2H) 6.51 (s, 1H) 2.46 (s, 3H) 2.33 (s, 3H) 2.02-1.98 (m, 1H) 1.09-1.06 (m, 2H) 0.82-0.78 (m, 2H). [M+H] calc'd for $C_{19}H_{18}N_6$, 331; found, 331.

Example 60

N-(5-cyclopropyl-1H-pyrazol-3-yl)-7-(4-(dimethylamino)phenyl)imidazo[1,2-f]pyrimidin-5-amine

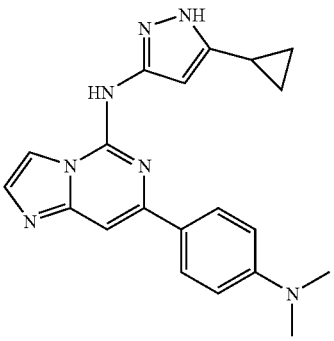

The title compound was synthesized using the procedure as Example 12. $^1$H NMR (400 MHz, MeOD) δ 8.23 (s, 1H) 8.02-8.00 (d, J=8.84 Hz, 2H) 7.84 (s, 1H) 7.35 (s, 1H) 6.85-

6.83 (d, J=8.84 Hz, 2H) 6.45 (s, 1H) 3.08 (s, 6H) 2.00 (m, 1H) 1.09-1.05 (m, 2H) 0.82-0.78 (m, 2H). [M+H] calc'd for $C_{20}H_{21}N_7$, 360; found, 360.

Example 61

N-(5-cyclopropyl-1H-pyrazol-3-yl)-7-(1H-indol-5-yl)imidazo[1,2-f]pyrimidin-5-amine

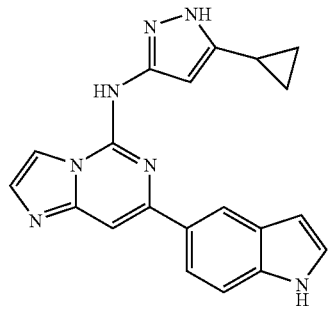

The title compound was synthesized using the procedure as Example 12. $^1$H NMR (400 MHz, MeOD) δ 8.40 (s, 1H) 8.23 (s, 1H) 7.89 (s, 1H) 7.86-7.85 (d, J=2.52 Hz, 1H) 7.50-7.49 (d, J=3.04 Hz, 2H) 7.3472 (m, 1H) 6.57 (s, 1H) 6.49 (s, 1H) 2.01 (m, 1H) 1.11-1.98 (m, 2H) 0.85-0.81 (m, 2H). [M+H] calc'd for $C_{20}H_{17}N_7$, 356; found, 356.

Example 62

7-(3-chlorophenyl)-N-(5-cyclopropyl-1H-pyrazol-3-yl)imidazo[1,2-f]pyrimidin-5-amine

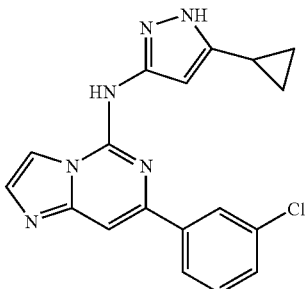

The title compound was synthesized using the procedure as Example 12. $^1$H NMR (400 MHz, MeOD) δ 8.39 (s, 1H) 8.23 (s, 1H) 8.08 (m, 1H) 8.00-7.99 (d, J=2.28 Hz, 1H) 7.71 (s, 1H) 7.55 (m, 3H) 6.48 (s, 1H) 2.00 (m, 1H) 1.09-1.05 (m, 2H) 0.84-0.80 (m, 2H). [M+H] calc'd for $C_{18}H_{15}ClN_6$, 351; found, 351.

Example 63

7-(3-(1H-pyrazol-1-yl)phenyl)-N-(5-cyclopropyl-1H-pyrazol-3-yl)imidazo[1,2-f]pyrimidin-5-amine

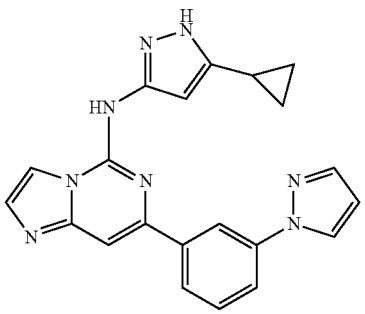

The title compound was synthesized using the procedure as Example 12. $^1$H NMR (400 MHz, MeOD) δ 8.67 (s, 1H) 8.41 (s, 1H) 8.33-8.32 (d, J=2.52 Hz, 1H) 8.12-8.10 (d, J=7.8 Hz, 1H) 8.01 (s, 1H) 7.92-7.91 (d, J=7.84 Hz, 1H) 7.81 (s, 1H) 7.78 (s, 1H) 6.60 (m, 2H) 1.99 (m, 1H) 1.07-1.02 (m, 2H) 0.85-0.82 (m, 2H). [M+H] calc'd for $C_{21}H_{18}N_8$, 383; found, 383.

Example 64

(3-(5-(5-cyclopropyl-1H-pyrazol-3-ylamino)imidazo[1,2-f]pyrimidin-7-yl)phenyl)(morpholino)methanone

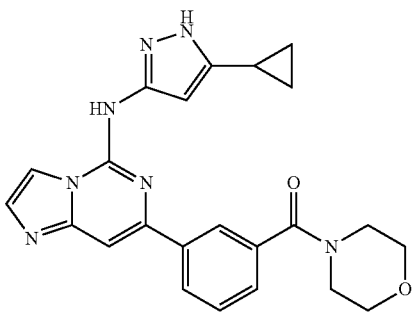

The title compound was synthesized using the procedure as Example 12. $^1$H NMR (400 MHz, MeOD) δ 8.40 (s, 1H) 8.28-8.25 (d, J=10.6 Hz, 2H) 8.02-8.01 (d, J=2.56 Hz, 1H) 7.75 (s, 1H) 7.68-7.60 (m, 2H) 6.47 (s, 1H) 3.81 (s, 4H) 3.62

(s, 2H) 3.49 (s, 1H) 2.00 (m, 1H) 1.09-1.05 (m, 2H) 0.83-0.79 (m, 2H). [M+H] calc'd for $C_{23}H_{23}N_7O_2$, 430; found, 430.

Example 65

(4-(5-(5-cyclopropyl-1H-pyrazol-3-ylamino)imidazo[1,2-f]pyrimidin-7-yl)phenyl)(morpholino)methanone

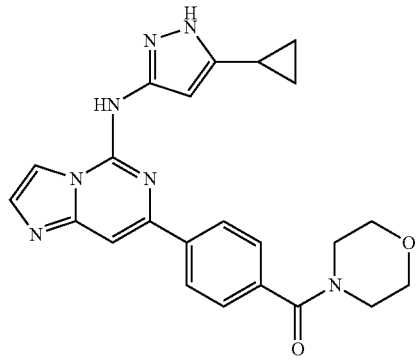

The title compound was synthesized using the procedure as Example 12. $^1$H NMR (400 MHz, MeOD) δ 8.40 (s, 1H) 8.28-8.26 (d, J=8.6 Hz, 2H) 8.01-8.01 (d, J=2.52 Hz, 1H) 7.73 (s, 1H) 7.62-7.61 (d, J=8.6 Hz, 2H) 6.49 (s, 1H) 3.79 (s, 4H) 3.65 (s, 1H) 3.48 (s, 1H) 2.01 (m, 1H) 1.09-1.04 (m, 2H) 0.82-0.78 (m, 2H). [M+H] calc'd for $C_{23}H_{23}N_7O_2$, 430; found, 430.

Example 66

N-(5-cyclopropyl-1H-pyrazol-3-yl)-7-(4-morpholinophenyl)imidazo[1,2-f]pyrimidin-5-amine

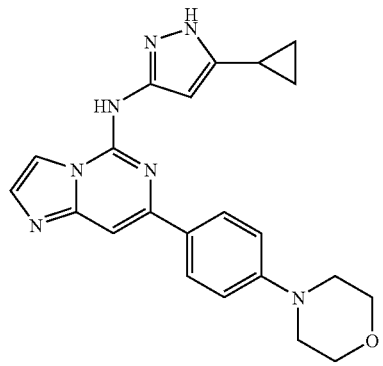

The title compound was synthesized using the procedure as Example 12. $^1$H NMR (400 MHz, MeOD) δ 8.27 (s, 1H) 8.08-8.05 (d, J=9.3 Hz, 2H) 7.89 (s, 1H) 7.46 (s, 1H) 7.09-7.07 (d, J=8.84 Hz, 2H) 6.47 (s, 1H) 3.85 (s, 4H) 3.30 (s, 4H) 2.01 (m, 1H) 1.08-1.05 (m, 2H) 0.81 (m, 2H). [M+H] calc'd for $C_{22}H_{23}N_7O$, 402; found, 402.

Example 67

N-(5-cyclopropyl-1H-pyrazol-3-yl)-7-(3-morpholinophenyl)imidazo[1,2-f]pyrimidin-5-amine

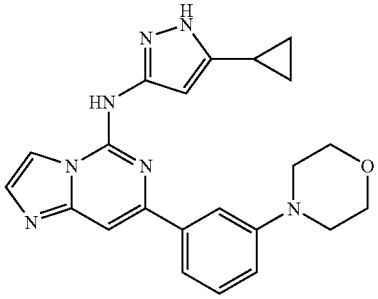

The title compound was synthesized using the procedure as Example 12. $^1$H NMR (400 MHz, MeOD) δ 8.35 (s, 1H) 7.97 (s, 1H) 7.81 (s, 1H) 7.63 (m, 2H) 7.42 (m, 1H) 7.18 (m, 1H) 6.52 (s, 1H) 3.88 (m, 4H) 3.24 (m, 4H) 1.99 (m, 1H) 1.08-1.04 (m, 2H) 0.80-0.76 (m, 2H). [M+H] calc'd for $C_{22}H_{23}N_7O$, 402; found, 402.

Example 68

N-(5-cyclopropyl-1H-pyrazol-3-yl)-7-(4-(piperidin-1-yl)phenyl)imidazo[1,2-f]pyrimidin-5-amine

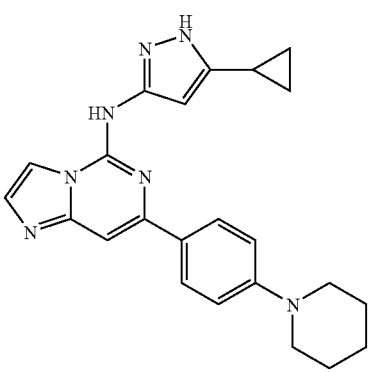

The title compound was synthesized using the procedure as Example 12. $^1$H NMR (400 MHz, MeOD) δ 8.29 (s, 1H) 8.12-8.10 (d, J=8.84 Hz, 2H) 7.90 (s, 1H) 7.50 (s, 1H) 7.26-7.24 (d, J=8.84 Hz, 2H) 6.45 (s, 1H) 3.47 (m, 4H) 2.00 (m, 1H) 1.80 (s, 4H) 1.73 (s, 2H) 1.09-1.04 (m, 2H) 0.82-0.78 (m, 2H). [M+H] calc'd for C$_{23}$H$_{25}$N$_7$, 400; found, 400.

Example 69a 1-(3-(4,4,5,5-tetramethyl-1,3,2-dioxaborolan-2-yl) benzyl)-4-methylpiperazine

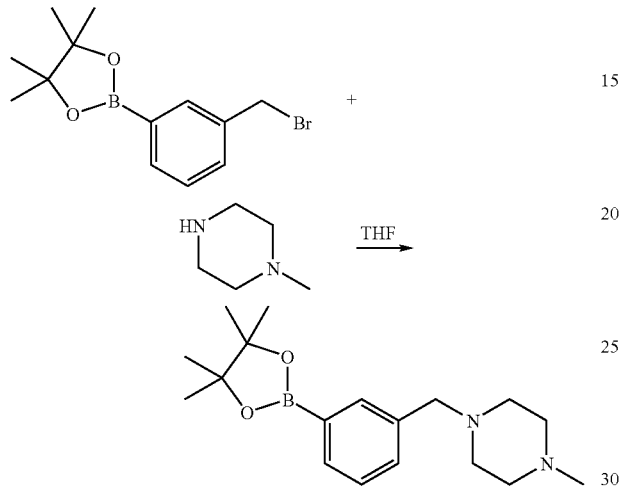

1-(3-(4,4,5,5-tetramethyl-1,3,2-dioxaborolan-2-yl)benzyl)-4-methylpiperazine was prepared by reacting 2-(3-(bromomethyl)phenyl)-4,4,5,5-tetramethyl-1,3,2-dioxaborolane (100 mg, 0.35 mmol) with methyl piperazine (196 μl, 1.76 mmol) in THF at room temperature for 2 hours. The intermediate product was purified by flash chromatography to afford 68 mg of colorless oil.

Example 69

N-(5-cyclopropyl-1H-pyrazol-3-yl)-7-(3-((4-methylpiperazin-1-yl)methyl)phenyl) imidazo[1,2-f]pyrimidin-5-amine

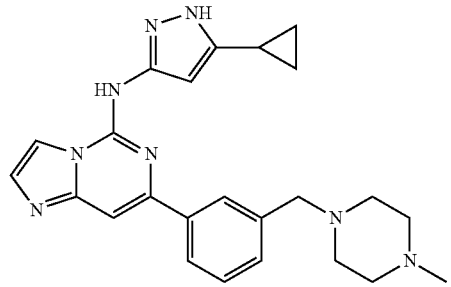

The title compound was synthesized from Example 69a using the procedure as Example 12. $^1$H NMR (400 MHz, MeOD) δ 8.38 (s, 1H) 8.19 (s, 1H) 8.16-8.14 (d, J=7.56 Hz, 1H) 8.00 (s, 1H) 7.72 (s, 1H) 7.60 (m, 2H) 6.49 (s, 1H) 5.48 (s, 2H) 3.94 (s, 2H) 3.38 (s, 4H) 3.34 (s, 2H) 2.99 (s, 3H) 2.90 (s, 4H) 2.03 (m, 1H) 1.10-1.06 (m, 2H) 0.83-0.79 (m, 2H). [M+H] calc'd for C$_{24}$H$_{28}$N$_8$, 429; found, 429.

Example 70

N-{3-[5-(5-Cyclopropyl-2H-pyrazol-3-ylamino)-imidazo[1,2-c]pyrimidin-7-yl]-phenyl}-methanesulfonamide

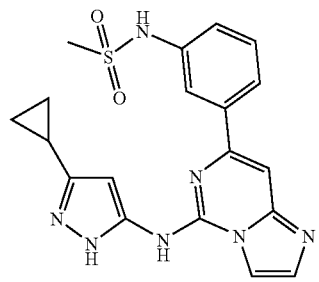

The title compound was prepared following a procedure analogous to that described in Example 12. $^1$H NMR (400 MHz, DMSO-D6) δ ppm 0.76-0.83 (m, 2H) 0.93-1.01 (m, 2H) 2.00 (ddd, J=13.52, 8.34, 4.93 Hz, 1H) 3.04 (s, 3H) 6.63 (s, 1H) 7.19 (d, J=8.34 Hz, 2H) 7.32 (m, 2H) 7.62 (s, 1H) 8.06 (d, J=7.33 Hz, 2H) 8.62 (s, 1H) 9.98 (s, 1H) 10.96 (s, 1H) 12.37 (s, 1H); ESI-MS: m/z 410.3 (M+H)$^+$

Example 71

N-{3-[5-(5-Cyclopropyl-2H-pyrazol-3-ylamino)-imidazo[1,2-c]pyrimidin-7-yl]-phenyl}-acetamide

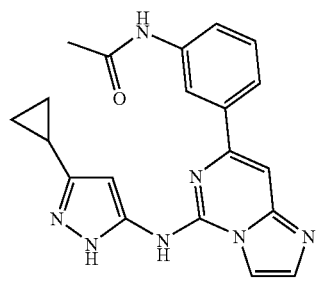

The title compound was prepared following a procedure analogous to that described in Example 12. $^1$H NMR (400 MHz, DMSO-D6) δ ppm 0.80 (ddd, J=6.13, 4.74, 4.55 Hz, 2H) 0.93-1.00 (m, 2H) 1.98-2.05 (m, 1H) 2.09 (s, 3H) 6.66 (s, 1H) 7.45-7.54 (m, 2H) 7.59 (s, 1H) 7.80 (d, J=7.33 Hz, 1H)

8.05 (s, 1H) 8.63 (d, J=10.36 Hz, 2H) 10.16 (s, 1H) 10.97 (s, 1H) 12.40 (s, 1H); ESI-MS: m/z 374.4 (M+H)+

Example 72

N-{3-[5-(5-Methyl-2H-pyrazol-3-ylamino)-imidazo[1,2-c]pyrimidin-7-yl]-phenyl}-methanesulfonamide

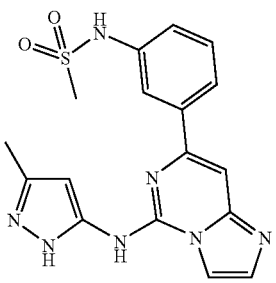

The title compound was prepared following a procedure analogous to that described in Example 12. ¹H NMR (400 MHz, DMSO-D6) δ ppm 2.32 (s, 3H) 3.05 (s, 3H) 6.75 (s, 1H) 7.30 (dd, J=8.72, 1.39 Hz, 1H) 7.52 (t, J=7.83 Hz, 1H) 7.66 (s, 1H) 7.88 (d, J=7.83 Hz, 1H) 8.06 (d, J=1.77 Hz, 1H) 8.15 (s, 1H) 8.64 (s, 1H) 10.03 (s, 1H) 11.00 (s, 1H) 12.38 (s, 1H); ESI-MS: m/z 384.3 (M+H)+

Example 73

[7-(3-Ethanesulfonyl-phenyl)-imidazo[1,2-c]pyrimidin-5-yl]-(5-methyl-2H-pyrazol-3-yl)-amine

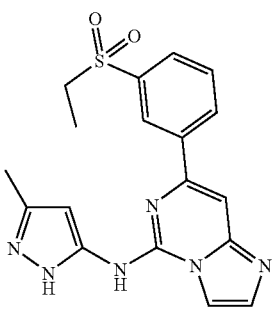

The title compound was prepared following a procedure analogous to that described in Example 12. ¹H NMR (400 MHz, DMSO-D6) δ ppm 1.15 (t, J=7.33 Hz, 3H) 3.38 (q, J=7.33 Hz, 2H) 3.56 (s, 3H) 6.68 (s, 1H) 7.81-7.90 (m, 2H) 7.98-8.03 (m, 2H) 8.53 (d, J=7.83 Hz, 1H) 8.60 (s, 1H) 8.73 (s, 1H) 10.95 (s, 1H) 12.39 (s, 1H); ESI-MS: m/z 383.3 (M+H)+

Example 74

N-{3-[5-(5-Cyclopropyl-2H-pyrazol-3-ylamino)-2-hydroxymethyl-imidazo[1,2-c]pyrimidin-7-yl]-phenyl}-methanesulfonamide

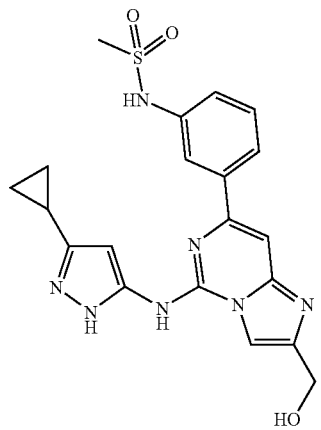

The title compound was prepared following a procedure analogous to that described in Example 12. ¹H NMR (400 MHz, DMSO-D6) δ ppm 0.78 (dd, J=4.93, 2.15 Hz, 2H) 0.97 (dd, J=8.34, 2.27 Hz, 2H) 1.95-2.03 (m, 1H) 3.04 (s, 3H) 4.68 (s, 2H) 6.61 (s, 1H) 7.32 (d, J=6.32 Hz, 1H) 7.48-7.55 (m, 2H) 7.86 (d, J=7.83 Hz, 1H) 8.05 (s, 1H) 8.52 (s, 1H) 9.96 (s, 1H) 10.87 (s, 1H) 12.35 (s, 1H); ESI-MS: m/z 440.3 (M+H)+

Example 75

(5-Cyclopropyl-2H-pyrazol-3-yl)-[7-(3-ethanesulfonyl-phenyl)-imidazo[1,2-c]pyrimidin-5-yl]-amine

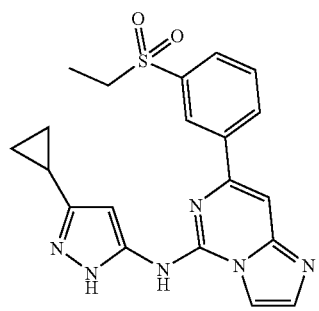

The title compound was prepared following a procedure analogous to that described in Example 12. ¹H NMR (400 MHz, DMSO-D6) δ ppm 0.83 (ddd, J=6.76, 4.74, 4.42 Hz, 2H) 0.95-1.00 (m, 2H) 1.15 (t, J=7.33 Hz, 3H) 1.95 (ddd, J=13.39, 8.34, 5.05 Hz, 1H) 3.38 (q, J=7.33 Hz, 2H) 6.53 (s, 1H) 7.81-7.90 (m, 2H) 8.00-8.05 (m, 2H) 8.53 (d, J=8.08 Hz, 1H) 8.62 (d, J=1.52 Hz, 1H) 8.67 (s, 1H) 10.97 (s, 1H) 12.48 (s, 1H); ESI-MS: m/z 409.3 (M+H)+

Example 76

[7-(4-Methyl-piperazin-1-yl)-imidazo[1,2-c]pyrimidin-5-yl]-(5-methyl-1H-pyrazol-3-yl)-amine

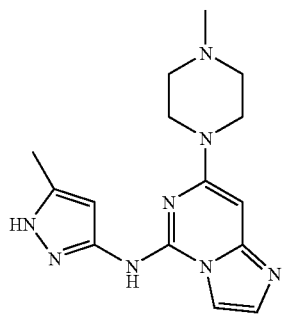

Referring to Scheme 6, (7-Chloro-imidazo[1,2-c]pyrimidin-5-yl)-(5-methyl-1H-pyrazol-3-yl)-amine (0.12 mol) and 1-methyl-piperazine (1.2 mol) were dissolved in DMF (0.3 mL) This solution was heated at between 150-200° C. for 1-25 minutes using a microwave reactor. Purification by preparative HPLC afforded the product as a solid. ¹H NMR (400 MHz, DMSO-D6) δ ppm 2.27 (s, 3H) 2.84 (s, 3H) 3.13 (bs, 2H) 3.32-3.49 (m, 4H) 4.41 (bs, 2H) 6.31 (s, 1H) 6.38 (s, 1H) 7.78 (d, J=2.53 Hz, 1H) 8.29 (d, J=2.27 Hz, 1H) 10.83 (s, 1H) 12.41 (s, 1H); ESI-MS: m/z 313.3 (M+H)+

Example 77

(5-Methyl-1H-pyrazol-3-yl)-(7-piperidin-1-yl-imidazo[1,2-c]pyrimidin-5-yl)-amine

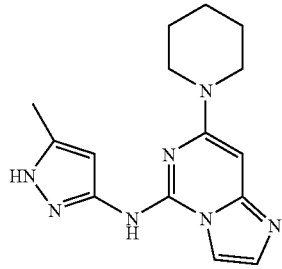

The title compound was prepared following a procedure analogous to that described in Example 76. ¹H NMR (400 MHz, DMSO-D6) δ ppm 1.56-164 (m, 6H) 2.26 (s, 3H) 3.63 (bs, 4H) 6.17 (s, 1H) 6.31 (s, 1H) 7.65 (d, J=2.27 Hz, 1H) 8.19 (d, J=2.27 Hz, 1H) 10.64 (s, 1H) 12.38 (s, 1H); ESI-MS: m/z 298.3 (M+H)+

Example 78

(5-Cyclopropyl-1H-pyrazol-3-yl)-[7-(2,3-dihydro-indol-1-yl)-imidazo[1,2-c]pyrimidin-5-yl]-amine

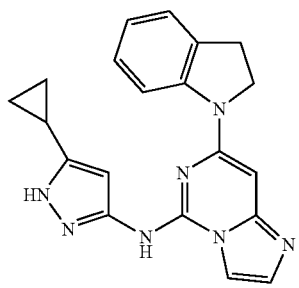

The title compound was prepared following a procedure analogous to that described in Example 76. ¹H NMR (400 MHz, DMSO-D6) δ ppm 0.71 (td, J=5.37, 4.17 Hz, 2H) 0.94-1.03 (m, 2H) 1.91-2.02 (m, 1H) 3.22 (t, J=8.46 Hz, 2H) 4.05 (t, J=8.59 Hz, 2H) 6.16 (s, 1H) 6.22 (s, 1H) 6.92-7.04 (m, 2H) 7.24 (d, J=7.33 Hz, 1H) 7.81 (d, J=2.02 Hz, 1H) 8.02 (d, J=7.83 Hz, 1H) 8.22 (s, 1H) 10.59 (s, 1H) 12.61 (s, 1H); ESI-MS: m/z 358.4 (M+H)+

Example 79

(5-Cyclopropyl-1H-pyrazol-3-yl)-[7-(3,4-dihydro-1H-isoquinolin-2-yl)-imidazo[1,2-c]pyrimidin-5-yl]-amine

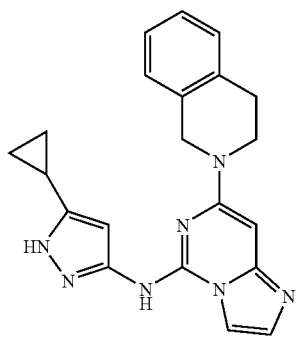

The title compound was prepared following a procedure analogous to that described in Example 76. ¹H NMR (400 MHz, DMSO-D6) δ ppm 0.71-0.79 (m, 2H) 0.98-1.05 (m, 2H) 1.98 (ddd, J=13.20, 8.53, 5.31 Hz, 1H) 2.95 (t, J=5.81 Hz, 2H) 3.86 (bs, 2H) 4.79 (s, 2H) 6.20 (s, 1H) 6.34 (s, 1H) 7.24

(s, 4H) 7.70 (d, J=1.77 Hz, 1H) 8.22 (d, J=1.77 Hz, 1H) 10.76 (s, 1H) 12.47 (s, 1H); ESI-MS: m/z 372.4 (M+H)+

Example 80

Ethyl 5-(5-cyclopropyl-1H-pyrazol-3-ylamino)-7-(4-((2,5-dioxoimidazolidin-1-yl)methyl)phenyl) imidazo[1,2-f]pyrimidine-2-carboxylate

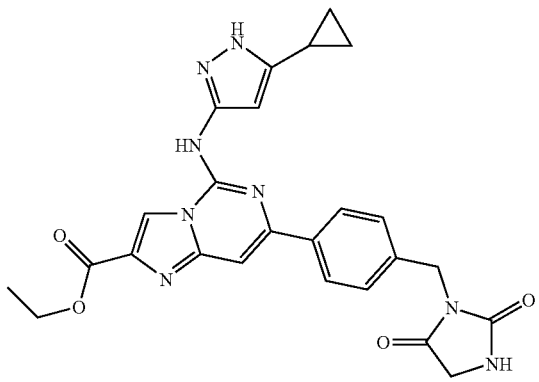

The title compound was prepared following a procedure analogous to that described in Example 12. $^1$H NMR (400 MHz, DMSO-D6) δ ppm 0.77-0.87 (m, 2H) 0.94-1.03 (m, 2H) 1.27 (s, 1H) 1.35 (t, J=7.20 Hz, 2H) 1.99-2.10 (m, 1H) 4.00 (s, 2H) 4.33 (q, J=7.16 Hz, 2H) 4.63 (s, 2H) 6.64 (s, 1H) 7.33 (d, J=7.83 Hz, 1H) 7.47 (t, J=7.83 Hz, 1H) 7.55 (s, 1H) 8.01 (d, J=7.58 Hz, 1H) 8.06 (s, 1H) 8.15 (s, 1H) 9.13 (s, 1H) 10.54 (s, 1H) 12.28 (s, 1H). MS [m+H] calc'd for $C_{25}H_{24}N_8O_4$, 501.19; found 501.19.

Example 81

Ethyl 5-(5-cyclopropyl-1H-pyrazol-3-ylamino)-7-(4-(pyrrolidine-1-carbonyl)phenyl) imidazo[1,2-f]pyrimidine-2-carboxylate

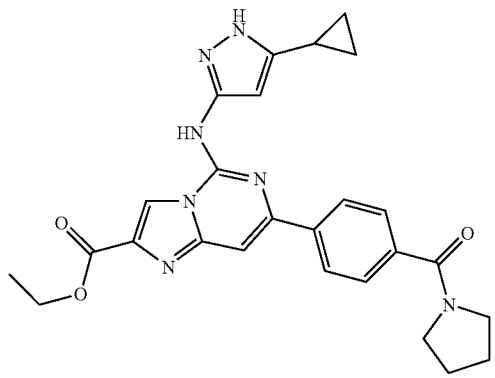

The title compound was prepared following a procedure analogous to that described in Example 12. $^1$H NMR (400 MHz, MeOD) δ ppm 0.74-0.83 (m, 2H) 1.00-1.09 (m, 2H) 1.25-1.36 (m, 5H) 1.43 (t, J=7.07 Hz, 3H) 1.92-1.97 (m, 2H) 2.00-2.06 (m, 2H) 4.40-4.47 (m, 2H) 6.46 (s, 1H) 7.53-7.63 (m, 3H) 8.14-8.21 (m, 1H) 8.29 (s, 1H) 8.71 (s, 1H). MS [m+H] calc'd for $C_{26}H_{27}N_7O_3$, 486.18; found 486.18.

Example 82

Ethyl 5-(5-cyclopropyl-1H-pyrazol-3-ylamino)-7-(4-(cyclopropylcarbamoyl)phenyl)imidazo[1,2-f]pyrimidine-2-carboxylate

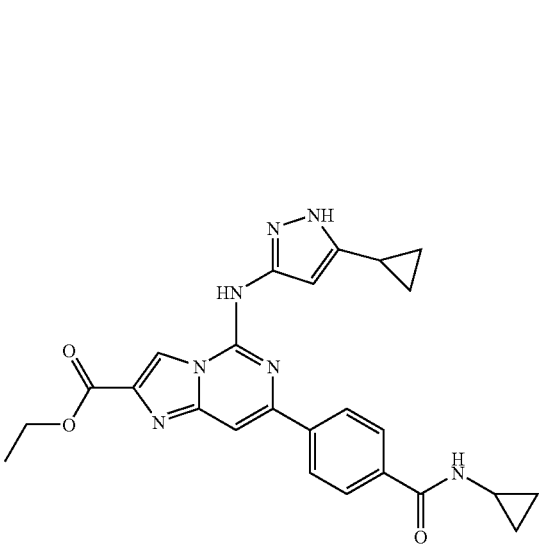

The title compound was prepared following a procedure analogous to that described in Example 12. $^1$H NMR (400 MHz, MeOD) δ ppm 0.67-0.72 (m, 2H) 0.76-0.79 (m, 2H) 0.84 (td, J=7.14, 4.93 Hz, 2H) 0.98 (td, J=7.45, 4.29 Hz, 2H) 1.42 (t, J=7.07 Hz, 3H) 1.91-1.99 (m, 1H) 2.85-2.95 (m, 1H) 4.41 (q, J=7.07 Hz, 2H) 6.21 (s, 1H) 7.30 (s, 1H) 7.57 (t, J=7.71 Hz, 1H) 7.85 (d, J=7.83 Hz, 1H) 8.20 (d, J=7.33 Hz, 1H) 8.46 (s, 1H) 8.60 (s, 1H). MS [m+H] calc'd for $C_{25}H_{25}N_7O_3$, 472.21; found 472.21.

Example 83a

3-[(Cyclopentanecarbonyl-amino)-methyl]-phenyl-boronic acid, pinacol ester

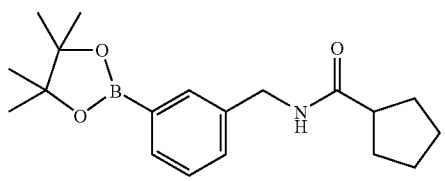

The title compound was synthesized in quantitative yield using cyclopentanecarbonyl chloride following the procedure described for the synthesis of Example 21a. $^1$H NMR (400 MHz, MeOD-d$_4$) δ 7.67 (s, 1H), 7.62 (d, J=7.6 Hz, 1H), 7.37 (d, J=7.6 Hz, 1H), 7.31 (t, J=7.6 Hz, 1H), 4.36 (s, 2H), 2.62-2.71 (m, 1H), 1.53-1.90 (m, 8H), 1.33 (s, 12H). [M+H] calc'd for $C_{19}H_{28}BNO_3$, 330; found, 330.

Example 83

Cyclopentanecarboxylic acid 3-[5-(5-cyclopropyl-1H-pyrazol-3-ylamino)-imidazo[1,2-c]pyrimidin-7-yl]-benzylamide

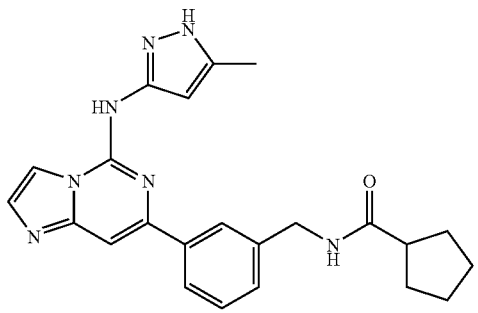

The title compound was synthesized in 34% yield using 3-[(cyclopentanecarbonyl-amino)-methyl]-phenylboronic acid, pinacol ester following the procedure described in the synthesis of Example 12. $^1$H NMR (400 MHz, MeOD-$d_4$) δ 8.51 (d, J=2.0 Hz, 1H), 8.01-8.11 (m, 3H), 7.84 (s, 1H), 7.45-7.53 (m, 2H), 6.73 (s, 1H), 4.47 (s, 2H), 2.62-2.72 (m, 1H), 2.51 (s, 3H), 1.80-1.90 (m, 2H), 1.52-1.76 (m, 6H). [M+H] calc'd for $C_{23}H_{25}N_7O$, 416; found 416.

Example 84

N-(5-cyclopropyl-1H-pyrazol-3-yl)-7-phenylimidazo[1,2-f]pyrimidin-5-amine

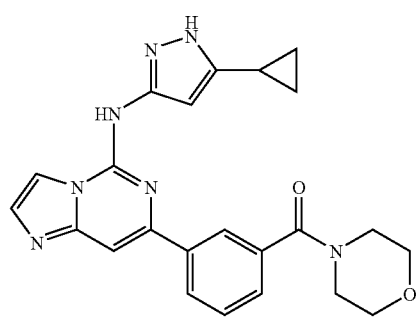

The title compound was synthesized using 3-(morpholine-4-carbonyl)phenylboronic acid following the procedure described in the synthesis of Example 12. $^1$H NMR (400 MHz, CD$_3$OD) 8.39 (s, 1H) 8.27 (d, J=7.56 Hz, 2H) 8.01 (s, 1H) 7.75 (s, 1H) 7.62 (m, 2H) 6.48 (s, 1H) 3.97 (s, 1H) 3.81 (s, 4H) 3.62 (s, 2H) 3.50 (s, 2H) 2.01 (m, 1H) 1.08 (m, 2H) 0.81 (m, 2H). [M+H] calc'd for $C_{23}H_{23}N_7O_2$, 429; found, 429.

Example 85

N-cyclopropyl-3-(5-(5-methyl-1H-pyrazol-3-ylamino)imidazo[1,2-f]pyrimidin-7-yl)benzamide

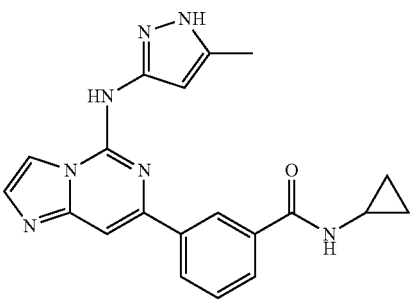

The title compound was synthesized using 3-(cyclopropylcarbamoyl)phenylboronic acid following the procedure described in the synthesis of Example 12. $^1$H NMR (400 MHz, CD$_3$OD) 8.64 (s, 1H) 8.41 (s, 1H) 8.35 (d, J=6.8 Hz, 1H) 8.02 (s, 1H) 7.92 (d, J=6.84 Hz, 1H) 7.76 (s, 1H) 7.65 (t, 1H) 6.67 (s, 1H) 5.50 (s, 1H) 2.92 (m, 1H) 2.42 (s, 3H) 0.86 (m, 2H) 0.69 (m, 2H). [M+H] calc'd for $C_{20}H_{19}N_7O$, 374; found, 374.

Example 86

(3-(5-(5-methyl-1H-pyrazol-3-ylamino)imidazo[1,2-f]pyrimidin-7-yl)phenyl)(4-methylpiperazin-1-yl)methanone

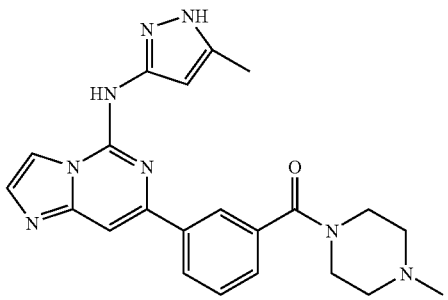

The title compound was synthesized using (4-methylpiperazin-1-yl)(3-(4,4,5,5-tetramethyl-1,3,2-dioxaborolan-2-yl)phenyl)methanone following the procedure described in the synthesis of Example 12. $^1$H NMR (400 MHz, CD$_3$OD) 8.41 (s, 1H) 8.29 (m, 2H) 8.02 (s, 1H) 7.79 (s, 1H) 7.67 (s, 2H)

6.60 (s, 1H) 3.99 (s, 1H) 3.53 (s, 3H) 3.36 (d, J=5.4 Hz 4H) 3.18 (s, 2H) 2.96 (s, 3H) 2.40 (s, 3H). [M+H] calc'd for $C_{22}H_{24}N_8O$, 417; found, 417.

Example 87

(4-aminopiperidin-1-yl)(3-(5-(5-methyl-1H-pyrazol-3-ylamino)imidazo[1,2-f]pyrimidin-7-yl)phenyl)methanone

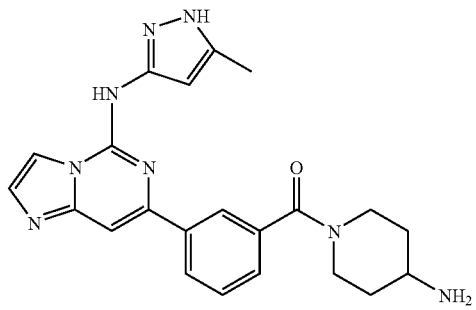

The title compound was synthesized using tert-butyl 1-(3-(4,4,5,5-tetramethyl-1,3,2-dioxaborolan-2-yl)benzoyl)piperidin-4-ylcarbamate following the procedure described in the synthesis of Example 12. The protecting group was then removed by stirring in trifluoroacetic acid for 30 minutes before purification. $^1$H NMR (400 MHz, CD$_3$OD) 8.40 (s, 1H) 8.30 (d, J=7.84 Hz 1H) 8.24 (s, 1H) 8.01 (s, 1H) 7.77 (s, 1H) 7.67 (t, 1H) 7.61 (d, J=7.84 Hz 1H) 6.60 (s, 1H) 3.45 (m, 1H) 3.31 (s, 4H) 2.39 (s, 3H) 1.62 (s, 2H). [M+H] calc'd for $C_{22}H_{24}N_8O$, 417; found, 417.

Example 88

3-(5-(5-Methyl-1H-pyrazol-3-ylamino)imidazo[1,2-f]pyrimidin-7-yl)-N-(piperidin-4-yl)benzamide

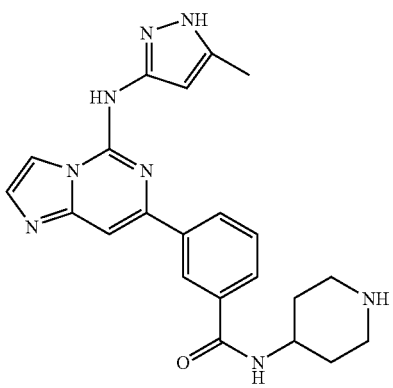

The title compound was synthesized using tert-butyl 4-(3-(4,4,5,5-tetramethyl-1,3,2-dioxaborolan-2-yl)benzamido)piperidine-1-carboxylate following the procedure described in the synthesis of Example 12. The protecting group was then removed by stirring in trifluoroacetic acid for 30 minutes before purification. $^1$H NMR (400 MHz, CD$_3$OD) 8.64 (s, 1H) 8.40 (s, 1H) 8.35 (d, J=8.0 Hz, 1H) 8.00 (s, 1H) 7.99 (d, J=8.0 Hz, 1H) 7.77 (s, 1H) 7.65 (t, J=8.0 Hz, 1H) 6.64 (s, 1H) 4.19-4.26 (m, 1H) 3.31-3.52 (m, 2H) 3.14-3.22 (m, 2H) 2.40 (s, 3H) 2.15-2.30 (m, 2H) 1.80-2.00 (m, 2H). [M+H] calc'd for $C_{22}H_{24}N_8O$, 417; found, 417.

Example 89

(3-(5-(5-Cyclopropyl-1H-pyrazol-3-ylamino)imidazo[1,2-f]pyrimidin-7-yl)phenyl)(piperazin-1-yl)methanone

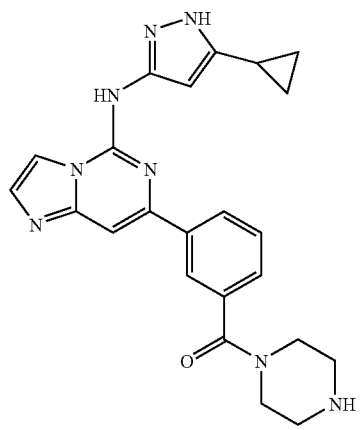

The title compound was synthesized using tert-butyl tert-butyl 4-(3-(4,4,5,5-tetramethyl-1,3,2-dioxaborolan-2-yl)benzoyl)piperazine-1-carboxylate following the procedure described in the synthesis of Example 12. The protecting group was then removed by stirring in trifluoroacetic acid for 30 minutes before purification. $^1$H NMR (400 MHz, CD$_3$OD) 8.40 (s, 1H) 8.27-8.31 (m, 2H) 8.02 (s, 1H) 7.79 (s, 1H) 7.66-7.68 (m, 2H) 6.48 (s, 1H) 3.70-4.20 (m, 2H) 3.20-3.40 (m, 2H) 1.94-2.03 (m, 1H) 1.06-1.10 (m, 2H) 0.75-0.90 (m, 2H). [M+H] calc'd for $C_{23}H_{25}N_8O$, 429; found, 429.

Example 90a (S)-3-{[(N-(tert-butylcarbonyl-pyrrolidine-2-carbonyl)-amino)-methyl]-phenylboronic acid, pinacol ester

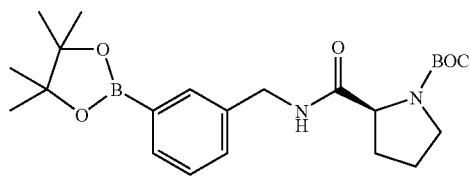

(3-Aminomethylphenyl)boronic acid pinacol ester, hydrochloride (200 mg, 0.74 mmol) and BOC-L-proline (160 mg, 0.74 mmol) were stirred with DIEA (260 mL, 1.48 mmol) in CH$_2$Cl$_2$ (5 mL) PyBOP (578 mg, 1.11 mmol) was added, and the reaction stirred at r.t for 16 h. The solution was washed with 1N HCl and brine, dried (MgSO$_4$), and concentrated in vacuo. Purification by silica gel chromatography (33% to 100% EtOAc/hexanes) gave 222 mg (70%) of the title compound as a clear oil. $^1$H NMR (400 MHz, MeOD-d$_4$) δ 7.72 (s, 1H), 7.62 (d, J=7.6 Hz, 1H), 7.40 (d, J=7.6 Hz, 1H), 7.31 (t, J=7.6 Hz, 1H), 4.330-4.45 (m, 2H), 4.15-4.20 (m, 1H), 3.49-

3.46 (m, 1H), 3.37-4.13 (m, 1H), 2.16-2.24 (m, 1H), 1.82-1.98 (m, 3H), 1.33 (s, 12H), 1.28 (s, 4.5H), 1.19 (s, 4.5H). [M+H] calc'd for $C_{23}H_{35}BN_2O_5$, 431; found, 431.

Example 90

(S)-Pyrrolidine-2-carboxylic acid 3-[5-(5-methyl-1H-pyrazol-3-ylamino)-imidazo[1,2-c]pyrimidin-7-yl]-benzylamide

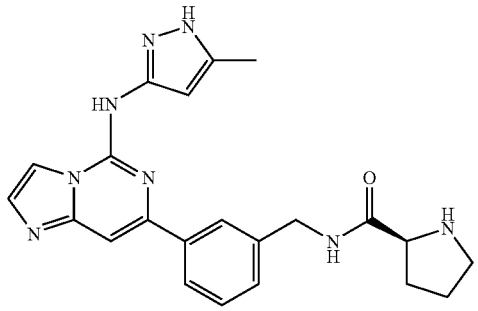

The title compound was synthesized in 34% yield using (S)-3-{[(N-(tert-butylcarbonyl-pyrrolidine-2-carbonyl)-amino)-methyl]-phenylboronic acid, pinacol ester following the procedure described in the synthesis of Example 12, followed by deprotection using 50% TFA/CH$_2$Cl$_2$. $^1$H NMR (400 MHz, MeOD-d$_4$) δ 8.38 (d, J=2.0 Hz, 1H), 8.13 (s, 1H), 8.09 (d, J=7.6 Hz, 1H), 7.99 (s, 1H), 7.68 (s, 1H), 7.49-7.56 (m, 2H), 6.61 (s, 1H), 4.54 (d, J=5.6 Hz, 2H), 4.26-4.31 (m, 1H), 3.30-3.40 (m, 2H), 2.39-2.45 (m, 1H), 2.39 (s, 3H), 1.98-2.08 (m, 3H). [M+H] calc'd for $C_{22}H_{24}N_8O$, 417; found, 417.

Example 91

N-{3-[5-(5-Cyclopropyl-1H-pyrazol-3-ylamino)-2-(4-methyl-piperazin-1-ylmethyl)-imidazo[1,2-c]pyrimidin-7-yl]-phenyl}-methanesulfonamide

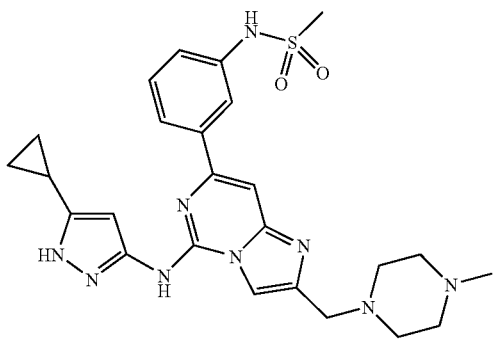

The title compound was synthesized following a procedure analogous to that described in Example 12. $^1$H NMR (400 MHz, DMSO-D6) δ ppm 0.74-0.81 (m, 2H) 0.96 (dd, J=8.46, 2.15 Hz, 2H) 1.99 (ddd, J=13.52, 8.46, 5.05 Hz, 1H) 2.66 (bs, 2H) 2.81 (s, 3H) 3.04 (s, 3H) 3.21 (bs, 2H) 3.45 (bs, 2H) 3.55 (bs, 2H) 3.96 (s, 2H) 6.61 (s, 1H) 7.24-7.34 (m, 1H) 7.45-7.55 (m, 2H) 7.83 (d, J=7.83 Hz, 1H) 8.04 (s, 1H) 8.49 (s, 1H) 9.96 (s, 1H) 10.72 (bs, 1H); ESI-MS: m/z 522.4 (M+H)$^+$

Example 92

[7-(3-Methanesulfonyl-phenyl)-imidazo[1,2-c]pyrimidin-5-yl]-(5-methyl-1H-pyrazol-3-yl)-amine

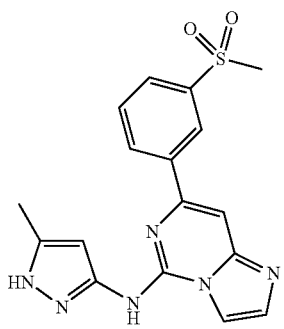

The title compound was synthesized following a procedure analogous to that described in Example 12. $^1$H NMR (400 MHz, DMSO-D6) δ ppm 2.32 (s, 3H) 3.31 (s, 3H) 6.69 (s, 1H) 7.85 (t, J=7.83 Hz, 1H) 7.91 (s, 1H) 8.04-8.10 (m, 2H) 8.53 (d, J=7.83 Hz, 1H) 8.63 (d, J=1.77 Hz, 1H) 8.78 (s, 1H) 11.03 (s, 1H) 12.40 (bs, 1H); ESI-MS: m/z 369.3 (M+H)$^+$

Example 93

[5-(5-Cyclopropyl-1H-pyrazol-3-ylamino)-7-(3-ethanesulfonyl-phenyl)-imidazo[1,2-c]pyrimidin-2-yl]-methanol

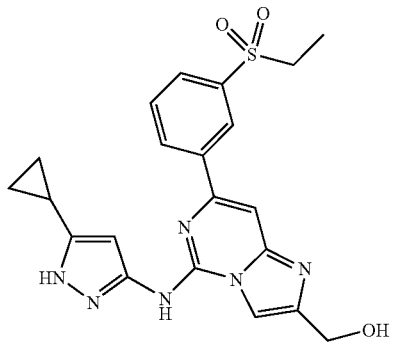

The title compound was synthesized following a procedure analogous to that described in Example 12. $^1$H NMR (400 MHz, DMSO-D6) δ ppm 0.82 (ddd, J=6.69, 4.67, 4.29 Hz, 2H) 0.94-1.00 (m, 2H) 1.15 (t, J=7.33 Hz, 3H) 1.95 (ddd, J=13.58, 8.40, 5.31 Hz, 1H) 3.38 (q, J=7.49 Hz, 2H) 4.69 (s, 3H) 6.51 (s, 1H) 7.77-7.86 (m, 2H) 8.02 (d, J=8.08 Hz, 1H) 8.52-8.53 (m, 2H) 8.66 (s, 1H) 10.90 (s, 1H) 12.45 (bs. 1H); ESI-MS: m/z 439.3 (M+H)+

Example 94

(5-Cyclopropyl-1H-pyrazol-3-yl)-[7-(3-ethanesulfonyl-phenyl)-2-(4-methyl-piperazin-1-ylmethyl)-imidazo[1,2-c]pyrimidin-5-yl]-amine

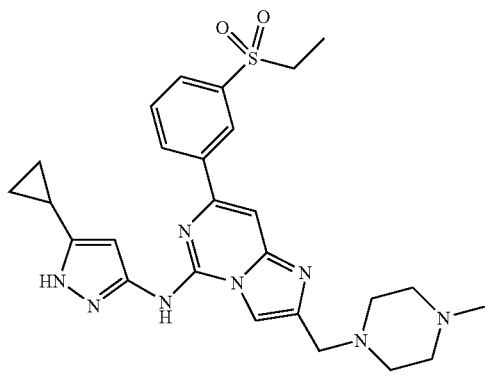

The title compound was synthesized following a procedure analogous to that described in Example 12. $^1$H NMR (400 MHz, DMSO-D6) δ ppm 0.82 (ddd, J=6.57, 4.67, 4.42 Hz, 2H) 0.94-1.00 (m, 2H) 1.16 (t, J=7.33 Hz, 3H) 1.94 (ddd, J=13.39, 8.34, 5.05 Hz, 1H) 2.66 (bs, 2H) 2.79 (s, 3H) 3.05 (bs, 2H) 3.21 (bs, 3H) 3.37 (q, J=7.33 Hz, 2H) 3.55 (bs, 2H) 3.95 (s, 2H) 6.52 (s, 1H) 7.73-7.83 (m, 2H) 7.96 (d, J=7.83 Hz, 1H) 8.42-8.50 (m, 2H) 8.65 (s, 1H) 10.57 (s, 1H) 12.37 (bs, 1H); ESI-MS: m/z 521.4 (M+H)+

Example 95

[7-(3-Ethanesulfonyl-phenyl)-5-(5-methyl-1H-pyrazol-3-ylamino)-imidazo[1,2-c]pyrimidin-2-yl]-methanol

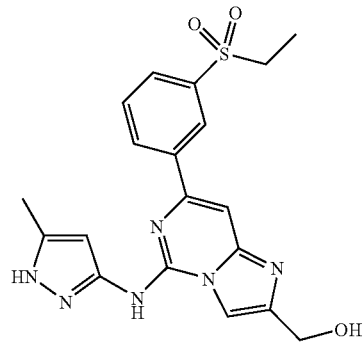

The title compound was synthesized following a procedure analogous to that described in Example 12. $^1$H NMR (400 MHz, DMSO-D6) δ ppm 1.14 (t, J=7.33 Hz, 3H) 2.31 (s, 3H) 3.38 (q, J=7.16 Hz, 2H) 4.68 (s, 2H) 6.66 (s, 1H) 7.78 (s, 1H) 7.83 (t, J=7.83 Hz, 1H) 8.00 (d, J=8.08 Hz, 1H) 8.47-8.56 (m, 2H) 8.72 (s, 1H) 10.87 (s, 1H) 12.35 (bs, 1H); ESI-MS: m/z 413.3 (M+H)+

Example 96

[7-(3-Ethanesulfonyl-phenyl)-2-(4-methyl-piperazin-1-ylmethyl)-imidazo[1,2-c]pyrimidin-5-yl]-(5-methyl-1H-pyrazol-3-yl)-amine

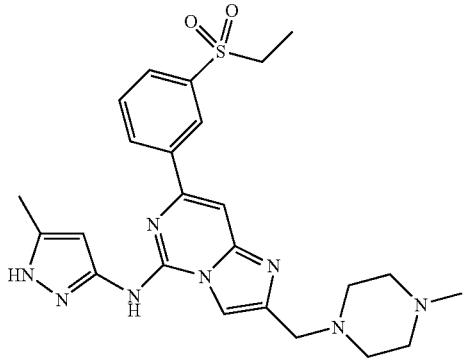

The title compound was synthesized following a procedure analogous to that described in Example 12. $^1$H NMR (400 MHz, DMSO-D6) δ ppm 1.15 (t, J=7.45 Hz, 3H) 2.30 (s, 3H) 2.78 (s, 3H) 3.03 (bs, 2H) 3.20 (bs, 2H) 3.37 (q, J=7.33 Hz, 2H) 3.45 (s, 2H) 3.64 (s, 2H) 3.91 (s, 2H) 6.67 (s, 1H) 7.72-7.83 (m, 2H) 7.95 (d, J=7.83 Hz, 1H) 8.42 (s, 1H) 8.48 (d, J=8.08 Hz, 1H) 8.71 (s, 1H) 10.56 (s, 1H) 12.30 (s, 1H); ESI-MS: m/z 495.4 (M+H)+

Example 97

$N^5$-(5-methyl-1H-pyrazol-3-yl)-$N^7$-(2-(piperidin-1-yl)ethyl)imidazo[1,2-f]pyrimidine-5,7-diamine

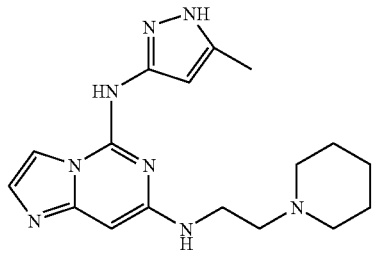

The title compound was synthesized following a procedure analogous to that described in Example 76. $^1$H NMR (400 MHz, CDCl$_3$/CD$_3$OD 10:1) δ ppm 8.22 (s, 1H) 7.22 (d, J=1.768 Hz, 1H) 6.50 (s, 1H) 3.72 (t, J=6.3 Hz, 2H) 3.51 (d, J=12.4 Hz, 2H) 3.24 (t, J=6.6 Hz, 2H) 2.80 (d, J=10.1 Hz, 2H) 2.34 (s, 3H) 1.85 (s, 5H). MS (ES) [m+H] calc'd for $C_{17}H_{24}N_8$, 341; found 341.

Example 98

N[7]-(2-(diethylamino)ethyl)-N[5]-(5-methyl-1H-pyrazol-3-yl)imidazo[1,2-f]pyrimidine-5,7-diamine

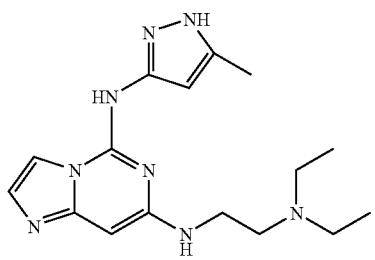

The title compound was synthesized following a procedure analogous to that described in Example 76. $^1$H NMR (400 MHz, CDCl$_3$/CD$_3$OD 10:1) δ ppm 8.38 (s, 1H) 7.26 (s, 1H) 6.57 (s, 1H) 3.72-3.78 (m, 3H) 3.26 (t, J=7.3 Hz, 4H) 3.18 (m, 2H) 2.39 (s, 3H) 1.32 (t, J=7.3 Hz, 6H). MS (ES) [m+H] calc'd for $C_{16}H_{25}N_8$, 329; found 329.

Example 99

N[7]-(2,5-difluorobenzyl)-N[5]-(5-methyl-1H-pyrazol-3-yl)imidazo[1,2-f]pyrimidine-5,7-diamine

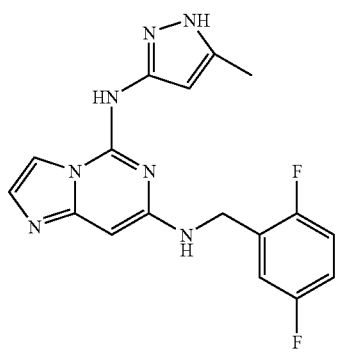

The title compound was synthesized following a procedure analogous to that described in Example 76. $^1$H NMR (400 MHz, CDCl$_3$/CD$_3$OD 10:1) δ ppm 8.08 (s, 1H) 7.24 (m, 1H) 6.96 (m, 2H) 6.88 (s, 1H) 6.24 (s, 1H) 4.46 (s, 2H) 2.30 (s, 3H). MS (ES) [m+H] calc'd for $C_{17}H_{16}F_2N_7$, 356; found 356.

Example 100

N[5]-(5-methyl-1H-pyrazol-3-yl)-N[7]-(thiophen-2-ylmethyl)imidazo[1,2-f]pyrimidine-5,7-diamine

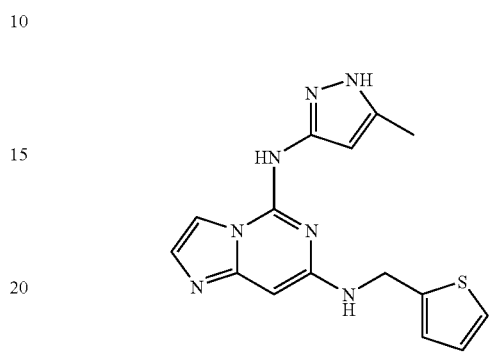

The title compound was synthesized following a procedure analogous to that described in Example 76. $^1$H NMR (400 MHz, CDCl$_3$/CD$_3$OD 10:1) δ ppm 8.04 (s, 1H) 7.21 (d, J=2.5 Hz, 1H) 7.13-7.17 (dd, J=1.0 and 5.1 Hz, 1H) 6.96 (s, 1H) 6.88 (dd, J=5.1, 3.5 Hz, 1H) 6.30 (s, 1H) 5.23 (s, 1H) 4.59 (s, 2H) 2.29 (s, 3H). MS (ES) [m+H] calc'd for $C_{15}H_{16}N_7S$, 326; found 326.

Example 101

N[7]-(2-chlorophenethyl)-N[5]-(5-methyl-1H-pyrazol-3-yl)imidazo[1,2-f]pyrimidine-5,7-diamine

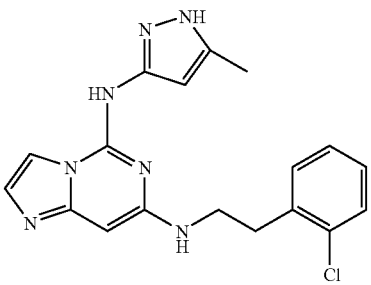

The title compound was synthesized following a procedure analogous to that described in Example 76. $^1$H NMR (400 MHz, CDCl$_3$/CD$_3$OD 10:1) δ ppm 8.08 (s, 1H) 7.27-7.32 (m, 1H) 7.17-7.22 (m, 2H) 7.08-7.16 (m, 3H) 6.31 (s, 1H) 3.38-

3.40 (m, 2H) 2.91 (t, J=7.2 Hz, 2H) 2.31 (s, 3H). MS (ES) [m+H] calc'd for $C_{16}H_{25}N_8$, 368; found 368.

Example 102

N[7]-(3-chlorophenethyl)-N[5]-(5-methyl-1H-pyrazol-3-yl)imidazo[1,2-f]pyrimidine-5,7-diamine

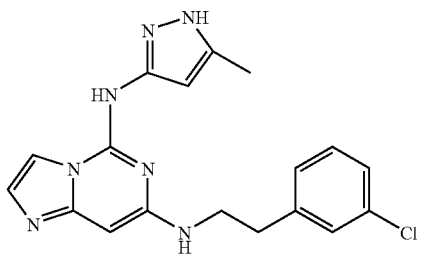

The title compound was synthesized following a procedure analogous to that described in Example 76. $^1$H NMR (400 MHz, CDCl$_3$/CD$_3$OD 10:1) δ ppm 7.99 (s, 1H) 7.11-7.22 (m, 5H) 6.31 (s, 1H) 3.45 (s, 2H) 2.80-2.91 (m, 2H) 2.30 (s, 3H). MS (ES) [m+H] calc'd for $C_{16}H_{25}N_8$, 368; found 368.

Example 103

N[7]-(4-chlorophenethyl)-N[5]-(5-methyl-1H-pyrazol-3-yl)imidazo[1,2-f]pyrimidine-5,7-diamine

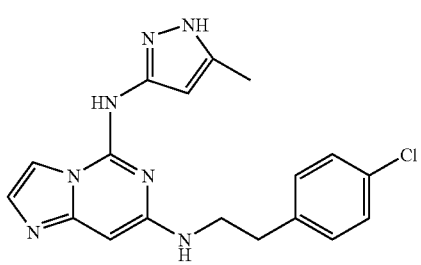

The title compound was synthesized following a procedure analogous to that described in Example 76. $^1$H NMR (400 MHz, CDCl$_3$/CD$_3$OD 10:1) δ ppm 7.98 (s, 1H) 7.16-7.21 (m, 4H) 7.06-7.11 (m, 2H) 6.28 (s, 1H) 3.40 (m, 2H) 2.84 (m, 2H) 2.31 (s, 3H). MS (ES) [m+H] calc'd for $C_{18}H_{19}ClN_7$, 368; found 368.

Example 104

N[5]-(5-methyl-1H-pyrazol-3-yl)-N[7]-phenethylimidazo[1,2-f]pyrimidine-5,7-diamine

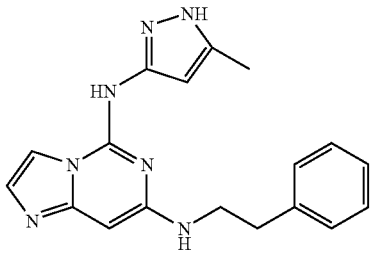

The title compound was synthesized following a procedure analogous to that described in Example 76. $^1$H NMR (400 MHz, CDCl$_3$/CD$_3$OD 10:1) δ ppm 8.05 (s, 1H) 7.24-7.14 (m, 7H) 6.29 (s, 1H) 3.33 (m, 2H) 2.89 (t, J=7.5 Hz, 2H) 2.31 (s, 3H). MS (ES) [m+H] calc'd for $C_{18}H_{20}N_7$, 334; found 334.

Example 105

N[5]-(5-methyl-1H-pyrazol-3-yl)-N[7]-(3-phenylpropyl)imidazo[1,2-f]pyrimidine-5,7-diamine

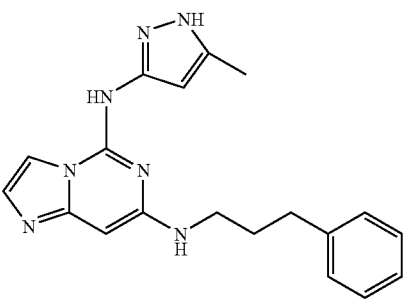

The title compound was synthesized following a procedure analogous to that described in Example 76. $^1$H NMR (400 MHz, CDCl$_3$/CD$_3$OD 10:1) δ ppm 8.04 (s, 1H) 7.19 (m, 3H) 7.07-7.14 (m, 3H) 6.28 (s, 1H), 5.23 (1s, 1H) 3.60 (m, 2H)

3.32 (s, 2H) 2.66 (t, J=7.2 Hz, 2H) 2.30 (s, 3H) 1.88-1.97 (m, 2H). MS (ES) [m+H] calc'd for $C_{19}H_{22}N_7$, 348; found 348.

Example 106

$N^5$-(5-methyl-1H-pyrazol-3-yl)-$N^7$-(2-phenoxyethyl) imidazo[1,2-f]pyrimidine-5,7-diamine

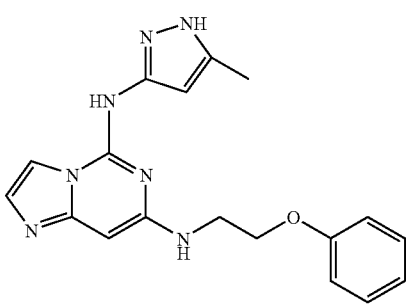

The title compound was synthesized following a procedure analogous to that described in Example 76. $^1$H NMR (400 MHz, CDCl$_3$/CD$_3$OD 10:1) δ ppm 8.04 (s, 1H) 7.14-7.23 (m, 3H) 6.88 (t, J=7.3 Hz, 1H) 6.81 (d, J=7.8 Hz, 2H) 6.31 (s, 1H) 6.03 (s, 1H) 4.08 (t, J=5.3 Hz, 2H) 3.55 (m, 2H) 2.28 (s, 3H). MS (ES) [m+H] calc'd for $C_{18}H_{20}N_7O$, 350; found 350.

Example 107

(R)-2-(5-(5-methyl-1H-pyrazol-3-ylamino)imidazo [1,2-f]pyrimidin-7-ylamino)-1-phenylethanol

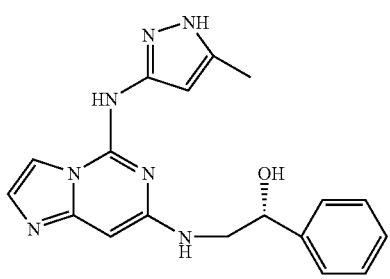

The title compound was synthesized following a procedure analogous to that described in Example 76. $^1$H NMR (400 MHz, CDCl$_3$/CD$_3$OD 10:1) δ ppm 7.97 (s, 1H) 7.20-7.37 (m, 6H) 7.12 (d, J=2.3 Hz, 1H) 6.27 (s, 1H) 4.86 (s, 1H) 3.36 (m, 2H) 2.26 (s, 3H). MS (ES) [m+H] calc'd for $C_{18}H_{20}N_7O$, 350; found 350.

Example 108

(S)-2-(5-(5-methyl-1H-pyrazol-3-ylamino)imidazo [1,2-f]pyrimidin-7-ylamino)-1-phenylethanol

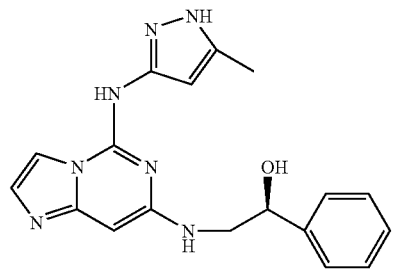

The title compound was synthesized following a procedure analogous to that described in Example 76. $^1$H NMR (400 MHz, CDCl$_3$/CD$_3$OD 10:1) δ ppm 7.96 (s, 1H) 7.2-7.37 (m, 6H) 7.16 (d, J=2.3 Hz, 1H) 6.32 (s, 1H) 4.86 (s, 1H) 3.41 (m, 2H) 2.27 (s, 3H). MS (ES) [m+H] calc'd for $C_{18}H_{20}N_7O$, 350; found 350.

Example 109

2-(methyl(5-(5-methyl-1H-pyrazol-3-ylamino)imi-dazo[1,2-f]pyrimidin-7-yl)amino)-1-phenylethanol

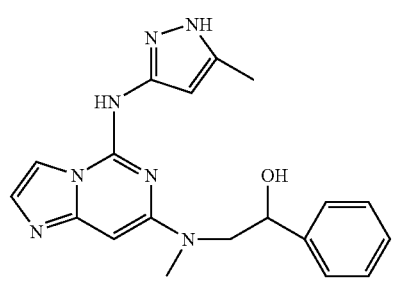

The title compound was synthesized following a procedure analogous to that described in Example 76. $^1$H NMR (400 MHz, CDCl$_3$/CD$_3$OD 10:1) δ ppm 7.88 (s, 1H) 7.08-7.20 (m, 6H) 6.22 (s, 1H) 3.75 (dd, J=12.8, 2.7 Hz, 1H) 3.54-3.61 (m, 2H) 2.28 (s, 3H). MS (ES) [m+H] calc'd for $C_{19}H_{22}N_7O$, 364; found 364.

Example 110

(R)-2-(5-(5-methyl-1H-pyrazol-3-ylamino)imidazo[1,2-f]pyrimidin-7-ylamino)-4-phenylbutan-1-ol

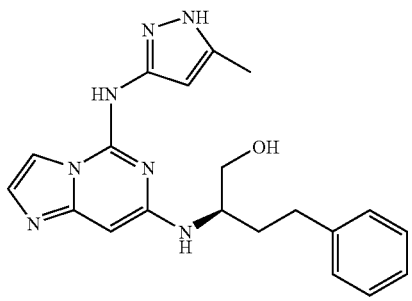

The title compound was synthesized following a procedure analogous to that described in Example 76. $^1$H NMR (400 MHz, CDCl$_3$/CD$_3$OD 10:1) δ ppm 7.77 (s, 1H) 7.16-7.30 (m, 6H) 6.28 (s, 1H) 4.60 (s, 1H) 3.56 (s, 1H) 3.05-3.11 (m, 1H) 3.01 (m, 3H) 2.26 (s, 3H) 1.95 (m, 2H). MS (ES) [m+H] calc'd for $C_{20}H_{23}N_7O$, 378; found 378.

Example 111

N$^5$-(5-methyl-1H-pyrazol-3-yl)-N$^7$-(pyridin-2-ylmethyl)imidazo[1,2-f]pyrimidine-5,7-diamine

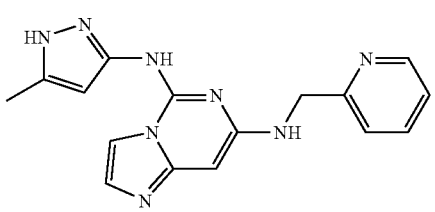

The title compound was synthesized following a procedure analogous to that described in Example 76. $^1$H NMR (400 MHz, DMSO-D6) δ ppm 1.99 (s, 3H) 3.17 (s, 2H) 7.27-7.39 (m, 4H) 7.71-7.83 (m, 3H) 8.15-8.28 (m, 2H) 8.51-8.62 (m, 2H). MS [m+H] calc'd for $C_{16}H_{16}N_8$, 321.3; found 321.3.

Example 112

N$^7$-(3-fluorobenzyl)-N$^7$-methyl-N$^5$-(5-methyl-1H-pyrazol-3-yl)imidazo[1,2-f]pyrimidine-5,7-diamine

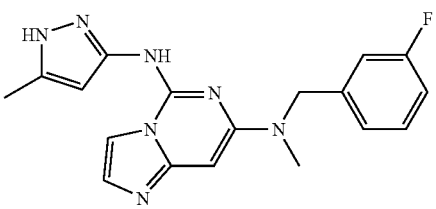

The title compound was synthesized following a procedure analogous to that described in Example 76. $^1$H NMR (400 MHz, DMSO-D6) δ ppm 2.14 (s, 3H) 3.18 (s, 3H) 4.89 (s, 2H) 6.05 (s, 2H) 7.03-7.13 (m, 3H) 7.34-7.44 (m, 1H) 7.69 (d, J=2.27 Hz, 1H) 8.23 (d, J=2.27 Hz, 1H) 10.71 (s, 1H) 12.31 (s, 1H) 12.87 (s, 1H). MS [m+H] calc'd for $C_{18}H_{18}FN_7$, 352.4; found 352.4.

Example 113

N$^7$-(3-chlorobenzyl)-N$^7$-methyl-N$^5$-(5-methyl-1H-pyrazol-3-yl)imidazo[1,2-f]pyrimidine-5,7-diamine

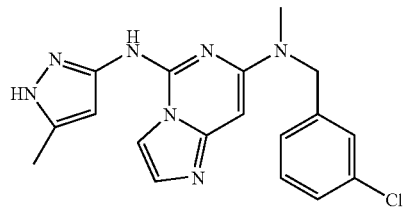

The title compound was synthesized following a procedure analogous to that described in Example 76. $^1$H NMR (400 MHz, DMSO-D6) δ ppm 2.16 (s, 3H) 3.18 (s, 3H) 4.88 (s, 2H) 6.06 (s, 2H) 7.18 (d, J=7.33 Hz, 1H) 7.29-7.40 (m, 3H) 7.70 (d, J=2.27 Hz, 1H) 8.24 (d, J=2.27 Hz, 1H) 10.71 (s, 1H) 12.32 (s, 1H) 12.92 (s, 1H). MS [m+H] calc'd for $C_{18}H_{18}ClN_7$, 368.3; found 368.3.

Example 114

N$^7$-(3,4-dimethoxybenzyl)-N$^5$-(5-methyl-1H-pyrazol-3-yl)imidazo[1,2-f]pyrimidine-5,7-diamine

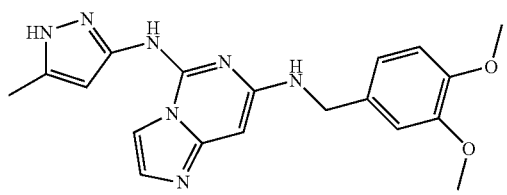

The title compound was synthesized following a procedure analogous to that described in Example 76. $^1$H NMR (400 MHz, DMSO-D6) δ ppm 2.22 (s, 3H) 3.72 (s, 8H) 6.81-6.93 (m, 4H) 6.97 (s, 2H) 7.63 (d, J=2.53 Hz, 2H) 8.20 (b, 4H) 10.68 (b, 2H) 12.32 (s, 2H). MS [m+H] calc'd for $C_{19}H_{21}N_7O_2$, 380.17; found 380.17.

Example 115

$N^7$-(2-Methoxy-benzyl)-$N^5$-(5-methyl-1H-pyrazol-3-yl)-imidazo[1,2-c]pyrimidine-5,7-diamine

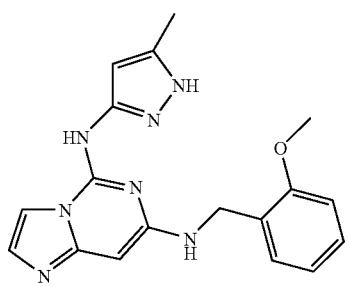

The title compound was synthesized following a procedure analogous to that described in Example 76. $^1$H NMR (400 MHz, DMSO-D6) δ ppm 2.15 (s, 3H) 3.84 (s, 3H) 3.85 (s, 2H) 6.07 (s, 1H) 6.85-6.96 (m, 1H) 7.05 (d, J=7.58 Hz, 1H) 7.17 (s, 1H) 7.21-7.31 (m, 1H) 7.63 (d, J=2.53 Hz, 1H) 8.19 (s, 2H) 10.68 (s, 1H) 12.27 (s, 1H) 12.58 (s, 1H). MS [m+H] calc'd for $C_{18}H_{19}N_7O$, 350.3; found 350.3.

Example 116

$N^7$-(4-Methoxy-benzyl)-$N^5$-(5-methyl-1H-pyrazol-3-yl)-imidazo[1,2-c]pyrimidine-5,7-diamine

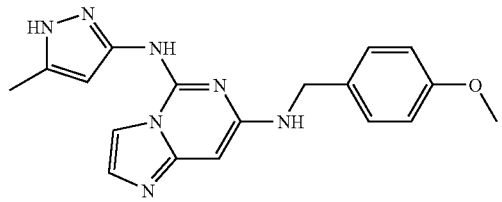

The title compound was synthesized following a procedure analogous to that described in Example 76. $^1$H NMR (400 MHz, DMSO-D6) δ ppm 2.22 (s, 3H) 3.72 (s, 3H) 3.735 (s, 2H) 6.91 (d, J=8.59 Hz, 2H) 6.99 (d, J=8.59 Hz, 1H) 7.25 (s, 2H) 7.32-7.41 (m, 1H) 7.62 (d, J=2.53 Hz, 1H) 8.20 (s, 1H) 8.25 (s, 1H) 10.67 (s, 1H) 12.31 (s, 1H).). MS [m+H] calc'd for $C_{18}H_{19}N_7O$, 350.3; found 350.3.

Example 117

N-(4-(5-(5-methyl-1H-pyrazol-3-ylamino)imidazo[1,2-f]pyrimidin-7-ylthio)phenyl)thiophene-2-sulfonamide

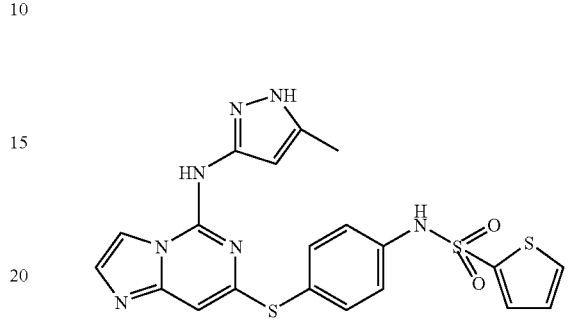

The title compound was synthesized following a procedure analogous to that described in Example 1. $^1$H NMR (400 MHz, CDCl$_3$/CD$_3$OD 10:1) δ ppm 8.13 (s, 1H) 7.73 (dd, J=3.9, 1.4 Hz, 1H) 7.70 (dd, J=5.1, 1.3 Hz, 1H) 7.61 (s, 1H) 7.28 (d, J=8.3 Hz, 2H) 7.08 (dd, J=4.9, 3.9 Hz, 1H) 6.75 (d, J=7.8 Hz, 2H) 6.62 (s, 1H) 6.49 (s, 1H) 2.51 (s, 3H). MS (ES) [m+H] calc'd for $C_{20}H_{18}N_7O_2S_3$, 484; found 484.

Example 118

N-(4-(5-(5-methyl-1H-pyrazol-3-ylamino)imidazo[1,2-f]pyrimidin-7-ylthio)phenyl)cyclopropanesulfonamide

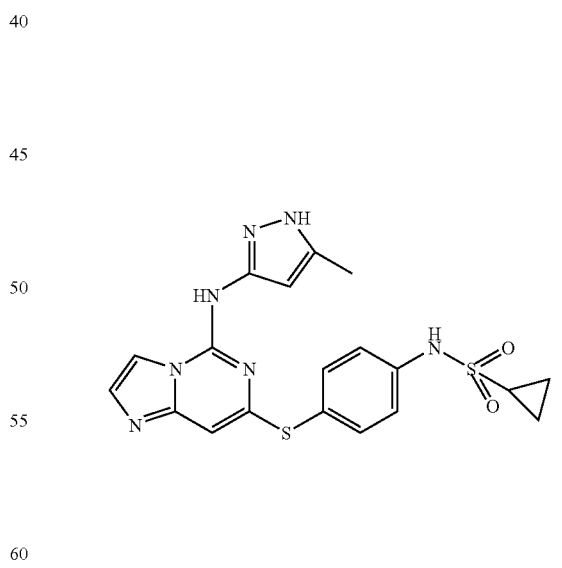

The title compound was synthesized following a procedure analogous to that described in Example 1. $^1$H NMR (400 MHz, CDCl$_3$/CD$_3$OD 10:1) δ ppm 8.10 (d, J=2.0 Hz, 1H) 7.61 (d, J=2.3 Hz, 1H) 7.26-7.31 (m, 2H) 6.72-6.77 (m, 2H) 6.65 (s, 1H) 6.50 (s, 1H) 2.64-2.71 (m, 1H) 2.46 (s, 3H) 2.40

(d, J=5.1 Hz, 1H) 1.33-1.38 (m, 2H) 1.11 (m, J=8.0, 1.9 Hz, 3H). MS (ES) [m+H] calc'd for $C_{19}H_{20}N_7O_2S_2$, 442; found 442.

Example 119

N-(4-(5-(5-methyl-1H-pyrazol-3-ylamino)imidazo[1,2-f]pyrimidin-7-ylthio)phenyl)propane-2-sulfonamide

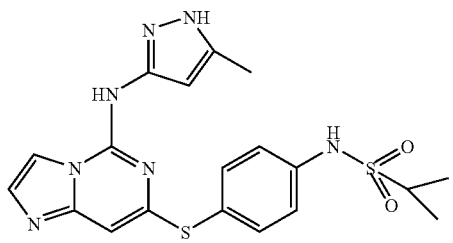

The title compound was synthesized following a procedure analogous to that described in Example 1. $^1$H NMR (400 MHz, CDCl$_3$/CD$_3$OD 10:1) δ ppm 8.06 (s, 1H) 7.45 (d, J=2.0 Hz, 1H) 7.35 (d, J=8.6 Hz, 2H) 7.17-7.22 (d, J=8.6 Hz, 2H) 6.47 (s, 1H) 5.89 (s, 1H) 3.15-3.20 (m, 1H) 2.11 (s, 3H) 1.20 (d, J=6.8 Hz, 6H). MS (ES) [m+H] calc'd for $C_{19}H_{21}N_7O_2S_2$, 444; found 444.

Example 120

1-amino-N-(4-(5-(5-methyl-1H-pyrazol-3-ylamino)imidazo[1,2-f]pyrimidin-7-ylthio)phenyl)cyclopropanecarboxamide

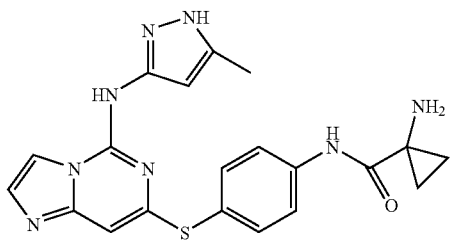

The title compound was synthesized following a procedure analogous to that described in Example 1. $^1$H NMR (400 MHz, CDCl$_3$/CD$_3$OD 10:1) δ ppm 8.02 (s, 1H) 7.56-7.61 (m, 2H) 7.38-7.42 (m, 3H) 6.37 (s, 1H) 5.99 (s, 1H) 2.09 (m, 4H) 1.49-1.55 (m, 2H) 1.27-1.33 (m, 2H). MS (ES) [m+H] calc'd for $C_{20}H_{21}N_8OS$, 421; found 421.

Example 121

(R)-2-amino-3-methyl-N-(4-(5-(5-methyl-1H-pyrazol-3-ylamino)imidazo[1,2-f]pyrimidin-7-ylthio)phenyl)butanamide

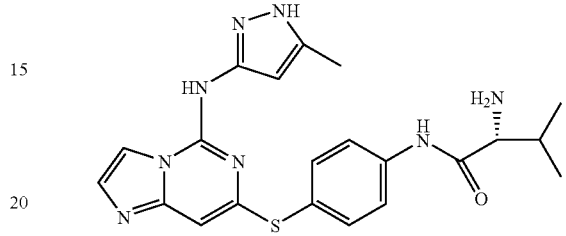

The title compound was synthesized following a procedure analogous to that described in Example 1. $^1$H NMR (400 MHz, CDCl$_3$/CD$_3$OD 10:1) δ ppm 7.94 (d, J=1.8 Hz, 1H) 7.52 (d, J=8.6 Hz, 2H) 7.36 (d, J=2.3 Hz, 1H) 7.31 (d, J=8.6 Hz, 2H) 6.30 (s, 1H) 5.85 (s, 1H) 3.61 (d, J=5.8 Hz, 1H) 1.97 (s, 4H) 0.82 (dd, J=13.0, 6.9 Hz, 6H). MS (ES) [m+H] calc'd for $C_{21}H_{25}N_8OS$, 437; found 437.

Example 122

N-(4-(5-(5-cyclopropyl-1H-pyrazol-3-ylamino)imidazo[1,2-f]pyrimidin-7-ylthio)phenyl)-2-methoxyacetamide

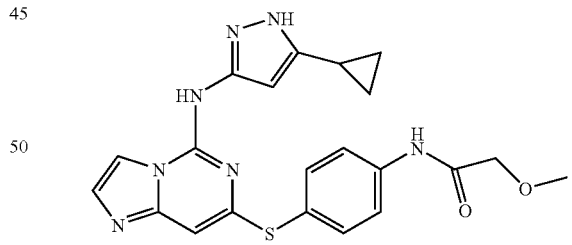

The title compound was synthesized following a procedure analogous to that described in Example 1. $^1$H NMR (400 MHz, CDCl$_3$/CD$_3$OD 10:1) δ ppm 7.96 (d, J=2.0 Hz, 1H) 7.52 (ddd, J=8.9, 2.5, 2.2 Hz, 2H) 7.37 (d, J=2.5 Hz, 1H) 7.32-7.36 (m, 2H) 6.32 (s, 1H) 5.78 (s, 1H) 3.80 (s, 2H) 3.25 (s, 3H) 1.59 (ddd, J=13.5, 8.3, 4.9 Hz, 1H) 0.70-0.76 (m, 2H)

0.46 (dt, J=6.8, 4.7 Hz, 2H). MS (ES) [m+H] calc'd for $C_{21}H_{22}N_7O_2S$, 436; found 436.

Example 123

N-(4-(5-(5-methyl-1H-pyrazol-3-ylamino)imidazo[1,2-f]pyrimidin-7-ylthio)phenyl)picolinamide

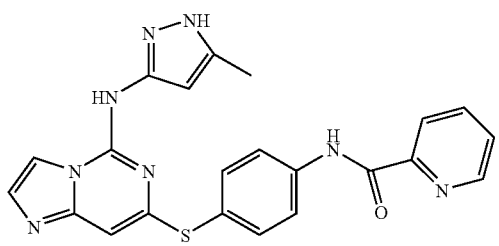

The title compound was synthesized following a procedure analogous to that described in Example 1. $^1$H NMR (400 MHz, CDCl$_3$/CD$_3$OD 10:1) δ ppm 8.43 (d, J=4.3 Hz, 1H) 7.96-8.04 (m, 2H) 7.70-7.77 (m, 3H) 7.37-7.44 (m, 3H) 7.34 (ddd, J=7.6, 4.8, 1.0 Hz, 1H) 6.44 (s, 1H) 5.73 (s, 1H) 1.95 (s, 3H). MS (ES) [m+H] calc'd for $C_{22}H_{19}N_8OS$, 443; found 433.

Example 124

N-(4-(5-(5-cyclopropyl-1H-pyrazol-3-ylamino)imidazo[1,2-f]pyrimidin-7-ylthio)phenyl)morpholine-4-carboxamide

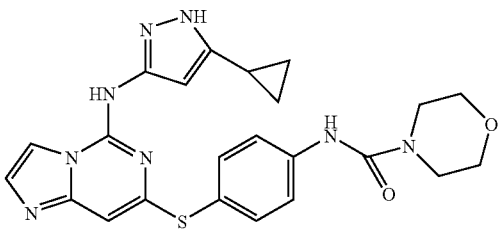

The title compound was synthesized following a procedure analogous to that described in Example 1. $^1$H NMR (400 MHz, CDCl$_3$/CD$_3$OD 10:1) δ ppm 8.09 (s, 1H) 7.47 (d, J=2.3 Hz, 1H) 7.16-7.21 (d, J=6.6 Hz, 2H) 6.64-6.69 (d, J=6.6 Hz, 2H) 6.27 (s, 1H) 6.23 (s, 1H) 3.60-3.68 (m, 4H) 3.56 (m, 4H) 2.07 (m, 1H) 0.87-0.98 (m, 2H) 0.59-0.66 (m, 2H). MS (ES) [m+H] calc'd for $C_{23}H_{25}N_8O_2S$, 477; found 477.

Example 125

2-methoxyethyl 4-(5-(5-methyl-1H-pyrazol-3-ylamino)imidazo[1,2-f]pyrimidin-7-ylthio)phenylcarbamate

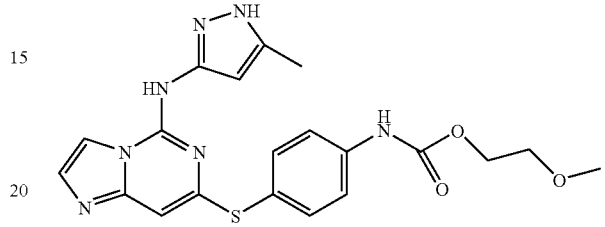

The title compound was synthesized following a procedure analogous to that described in Example 1. $^1$H NMR (400 MHz, CDCl$_3$/CD$_3$OD 10:1) δ ppm 8.15 (s, 1H) 7.60 (s, 1H) 7.27 (s, 2H) 6.73 (d, J=8.1 Hz, 2H) 6.63 (s, 1H) 6.37 (s, 1H) 4.49 (m, 2H) 4.47 (s, 3H) 3.64-3.72 (m, 2H) 3.34 (s, 3H) 3.25 (s, 1H) 2.47 (s, 3H). MS (ES) [m+H] calc'd for $C_{20}H_{22}N_7O_3S$, 440; found 440.

Example 126

Ethyl 4-(5-(5-methyl-1H-pyrazol-3-ylamino)imidazo[1,2-f]pyrimidin-7-ylthio)phenylcarbamate

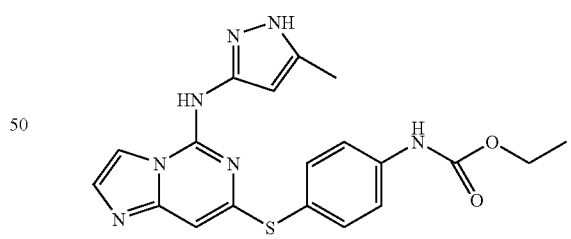

The title compound was synthesized following a procedure analogous to that described in Example 1. $^1$H NMR (400 MHz, CDCl$_3$/CD$_3$OD 10:1) δ ppm 8.07 (d, J=1.5 Hz, 1H) 7.44-7.50 (m, 3H) 7.38-7.44 (m, 2H) 6.53 (s, 1H) 5.96 (s, 1H)

4.10 (q, J=7.1 Hz, 2H) 2.13 (s, 3H) 1.20 (t, J=7.1 Hz, 3H). MS (ES) [m+H] calc'd for $C_{19}H_{20}N_7O_2S$, 410; found 410.

Example 127

Isobutyl 4-(5-(5-methyl-1H-pyrazol-3-ylamino)imidazo[1,2-f]pyrimidin-7-ylthio)phenylcarbamate

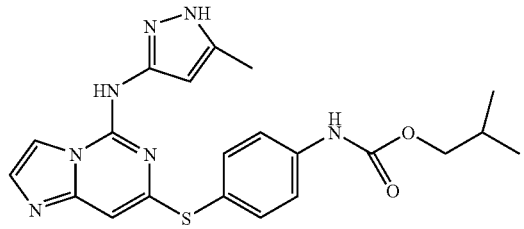

The title compound was synthesized following a procedure analogous to that described in Example 1. $^1$H NMR (400 MHz, CDCl$_3$/CD$_3$OD 10:1) δ ppm 8.12 (d, J=2.0 Hz, 1H) 7.53 (d, J=2.3 Hz, 1H) 7.25 (d, J=8.3 Hz, 2H) 6.75 (d, J=8.6 Hz, 2H) 6.55 (s, 1H) 6.41 (s, 1H) 4.08-4.14 (d, J=6.8 Hz, 2H) 2.42 (s, 3H) 1.95-2.06 (m, 1H) 0.88-0.96 (d, J=6.8, Hz, 6H). MS (ES) [m+H] calc'd for $C_{21}H_{23}N_7O_2S$, 438; found 438.

Example 128

Ethyl 4-(5-(5-cyclopropyl-1H-pyrazol-3-ylamino)imidazo[1,2-f]pyrimidin-7-ylthio) phenylcarbamate

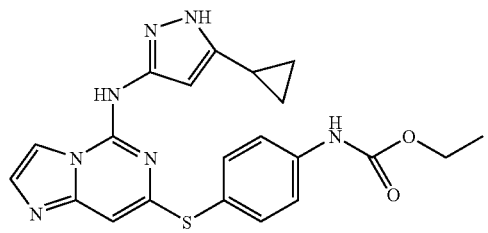

The title compound was synthesized following a procedure analogous to that described in Example 1. $^1$H NMR (400 MHz, CDCl$_3$/CD$_3$OD 10:1) δ ppm 8.94 (s, 1H) 8.35 (s, 1H) 7.52 (d, J=8.6 Hz, 2H) 7.33-7.40 (d, J=8.6 Hz, 2H) 6.58 (s, 1H) 5.97 (s, 1H) 4.09 (q, J=7.2 Hz, 2H) 1.74 (s, 1H) 1.19 (t, J=7.1 Hz, 3H) 0.83 (dd, J=8.3, 1.8 Hz, 2H) 0.56-0.68 (m, 2H). MS (ES) [m+H] calc'd for $C_{21}H_{22}N_7O_2S$, 436; found 436.

Example 129

{4-[5-(5-Cyclopropyl-1H-pyrazol-3-ylamino)-imidazo[1,2-c]pyrimidin-7-ylsulfanyl]-phenyl}-carbamic acid but-2-ynyl ester

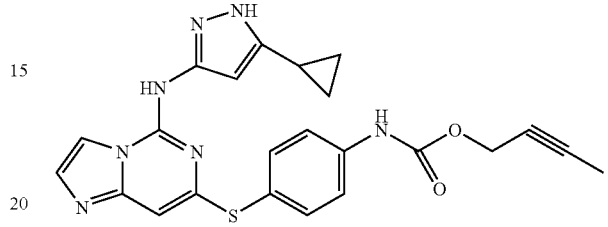

The title compound was synthesized following a procedure analogous to that described in Example 1. $^1$H NMR (400 MHz, CDCl$_3$/CD$_3$OD 10:1) δ ppm 8.05 (d, J=2.3 Hz, 1H) 7.47 (d, J=2.3 Hz, 1H) 7.17 (d, J=8.1 Hz, 2H) 6.63 (d, J=8.3 Hz, 2H) 6.49 (s, 1H) 6.30 (s, 1H) 4.82-4.86 (m, 2H) 2.25 (m, 1H) 1.71 (t, J=2.0 Hz, 3H) 0.91-0.99 (m, 2H) 0.58-0.65 (m, 2H). MS (ES) [m+H] calc'd for $C_{21}H_{22}N_7O_2S$, 460; found 460.

Example 130

{4-[5-(5-Cyclopropyl-1H-pyrazol-3-ylamino)-imidazo[1,2-c]pyrimidin-7-ylsulfanyl]-phenyl}-carbamic acid allyl ester

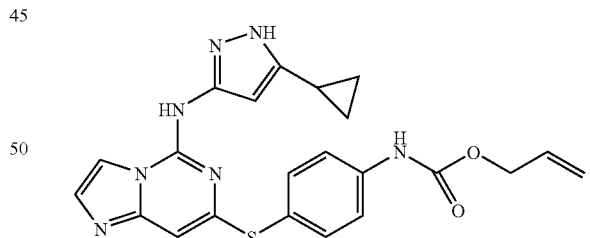

The title compound was synthesized following a procedure analogous to that described in Example 1. $^1$H NMR (400 MHz, CDCl$_3$/CD$_3$OD 10:1) δ ppm 8.15 (s, 1H) 7.49-7.55 (m, 3H) 7.40-7.48 (m, 2H) 6.60 (s, 1H) 6.09 (s, 1H) 5.84-5.94 (m, 1H) 5.29 (dd, J=17.2, 1.5 Hz, 1H) 5.18 (d, J=10.4 Hz, 1H) 4.59 (d, J=5.6 Hz, 2H) 3.32 (s, 2H) 1.74-1.84 (m, 1H) 1.17 (s, 2H) 0.90-1.00 (m, 2H) 0.65-0.74 (m, 2H). MS (ES) [m+H] calc'd for $C_{22}H_{22}N_7O_2S$, 448; found 448.

Example 131

Propyl 4-(5-(5-cyclopropyl-1H-pyrazol-3-ylamino) imidazo[1,2-f]pyrimidin-7-ylthio)phenylcarbamate

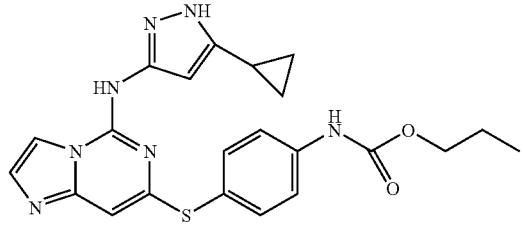

The title compound was synthesized following a procedure analogous to that described in Example 1. $^1$H NMR (400 MHz, CDCl$_3$/CD$_3$OD 10:1) δ ppm 8.09 (s, 1H) 7.49 (m, 3H) 7.39-7.45 (d, J=8.6 Hz, 2H) 6.52 (s, 1H) 6.02 (s, 1H) 4.02 (t, J=6.7 Hz, 2H) 1.71-1.81 (m, 1H) 1.54-1.65 (m, 2H) 1.13 (s, 3H) 0.83-0.93 (m, 5H) 0.61-0.68 (m, 2H). MS (ES) [m+H] calc'd for $C_{22}H_{24}N_7O_2S$, 450; found 450.

Example 132

N-(4-(5-(5-methyl-1H-pyrazol-3-ylamino)imidazo[1,2-f]pyrimidin-7-ylthio)phenyl)pyrrolidine-2-carboxamide

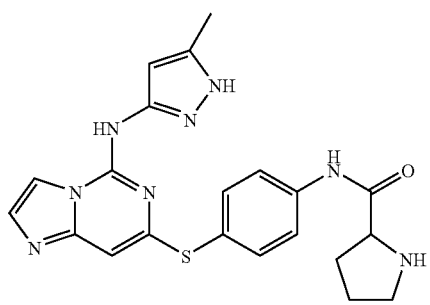

The title compound was synthesized following a procedure analogous to that described in Example 1. $^1$H NMR (400 MHz, MeOD) δ ppm 1.94 (s, 3H) 2.11-2.23 (m, 4H) 2.36-2.45 (m, 2H) 4.79-4.80 (m, 1H) 6.04 (s, 1H) 6.23 (s, 1H) 7.22 (d, J=7.83 Hz, 2H) 7.34 (s, 2H) 7.54 (s, 1H) 7.95 (s, 1H). MS [m+H] calc'd for, $C_{21}H_{22}N_8OS$ 435.3; found 435.3

Example 133

N-(4-(5-(5-methyl-1H-pyrazol-3-ylamino)imidazo[1,2-f]pyrimidin-7-ylthio)phenyl)butyramide

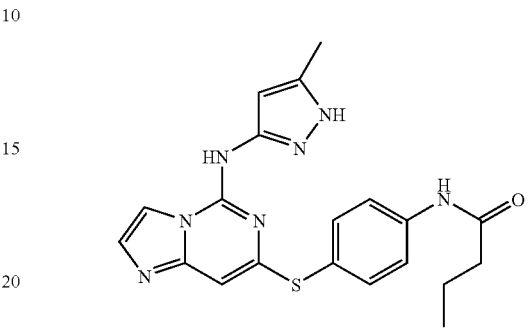

The title compound was synthesized following a procedure analogous to that described in Example 1. $^1$H NMR (400 MHz, MeOD) δ ppm 1.02 (t, J=7.45 Hz, 3H) 1.68-1.79 (m, 2H) 2.21 (s, 3H) 2.40 (t, J=7.45 Hz, 2H) 5.95 (s, 1H) 6.72 (s, 1H) 7.51-7.62 (m, 2H) 7.71-7.82 (m, 3H) 8.24 (s, 1H). MS [m+H] calc'd for $C_{20}H_{21}N_7OS$, 408.3; found 408.3.

Example 134

N-(4-(5-(5-methyl-1H-pyrazol-3-ylamino)imidazo[1,2-f]pyrimidin-7-ylthio)phenyl)cyclobutanecarboxamide

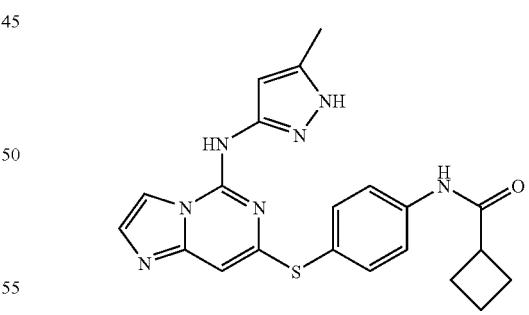

The title compound was synthesized following a procedure analogous to that described in Example 1. $^1$H NMR (400 MHz, DMSO-D6) δ ppm 1.79-1.88 (m, 2H) 1.98 (dt, J=17.49, 8.81 Hz, 2H) 2.12 (s, 3H) 2.16-2.27 (m, 4H) 3.25-3.32 (m, 1H) 5.85 (s, 1H) 6.67 (s, 1H) 7.58 (d, J=8.08 Hz, 2H)

7.83 (d, J=8.84 Hz, 3H) 8.46 (s, 1H) 10.09 (s, 1H) 10.98 (s, 1H) 12.32 (s, 1H). MS [m+H] calc'd for $C_{21}H_{21}N_7OS$, 420.4; found 420.4.

Example 135

N-(4-(5-(5-methyl-1H-pyrazol-3-ylamino)imidazo[1,2-f]pyrimidin-7-ylthio)phenyl)isobutyramide

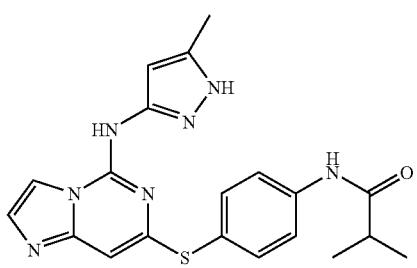

The title compound was synthesized following a procedure analogous to that described in Example 1. $^1$H NMR (400 MHz, DMSO-D6) δ ppm 1.12 (s, 3H) 1.13 (s, 3H) 2.12 (s, 3H) 2.59-2.71 (m, 2H) 5.84 (s, 1H) 6.70 (s, 1H) 7.58 (d, J=8.08 Hz, 2H) 7.82-7.93 (m, 3H) 8.48 (s, 1H) 10.20 (s, 1H) 11.06 (s, 1H) 12.36 (s, 1H). MS [m+H] calc'd for $C_{20}H_{21}N_7OS$, 408.15; found 408.15.

Example 136

2-methoxy-N-(4-(5-(5-methyl-1H-pyrazol-3-ylamino)imidazo[1,2-f]pyrimidin-7-ylthio)phenyl)acetamide

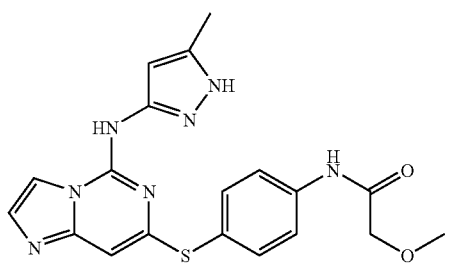

The title compound was synthesized following a procedure analogous to that described in Example 1. $^1$H NMR (400 MHz, DMSO-D6) δ ppm 2.14 (s, 3H) 3.39 (s, 3H) 4.05 (s, 2H) 5.90 (s, 1H) 6.65 (s, 2H) 7.60 (d, J=7.58 Hz, 3H) 7.85-7.95 (m, 5H) 8.46 (s, 2H) 10.15 (s, 1H) 10.99 (s, 1H) 12.30 (s, 1H). MS [m+H] calc'd for $C_{19}H_{19}N_7O_2S$, 410.3; found 410.3.

Example 137

N-(4-(5-(5-methyl-1H-pyrazol-3-ylamino)imidazo[1,2-f]pyrimidin-7-ylthio)phenyl)-2-propoxyacetamide

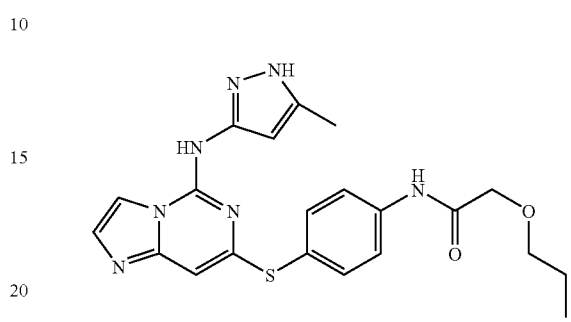

The title compound was synthesized following a procedure analogous to that described in Example 1. $^1$H NMR (400 MHz, MeOD) δ ppm 1.00 (t, J=7.45 Hz, 3H) 1.66-1.76 (m, 2H) 2.22 (s, 3H) 3.58 (t, J=6.69 Hz, 2H) 4.12 (s, 2H) 5.96 (s, 1H) 6.73 (s, 1H) 7.63 (d, J=8.59 Hz, 2H) 7.78-7.88 (m, 3H) 8.24 (d, J=2.02 Hz, 1H). MS [m+H] calc'd for $C_{21}H_{23}N_7O_2S$ 438.3; found 438.3.

Example 138

2-ethoxy-N-(4-(5-(5-methyl-1H-pyrazol-3-ylamino)imidazo[1,2-f]pyrimidin-7-ylthio)phenyl)acetamide

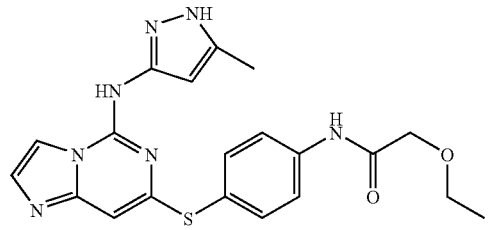

The title compound was synthesized following a procedure analogous to that described in Example 1. $^1$H NMR (400 MHz, MeOD) δ ppm 1.30 (t, J=7.07 Hz, 3H) 2.21 (s, 3H) 3.67 (q, J=6.91 Hz, 3H) 4.11 (s, 2H) 6.00 (s, 1H) 6.53 (s, 1H) 7.41

(s, 2H) 7.60 (d, J=8.8 Hz, 2H) 7.80 (d, J=8.8, 2H) 7.93 (s, 1H). MS [m+H] calc'd for $C_{20}H_{21}N_7O_2S$, 424.82; found 424.82.

Example 139

2-(allyloxy)-N-(4-(5-(5-methyl-1H-pyrazol-3-ylamino)imidazo[1,2-f]pyrimidin-7-ylthio)phenyl)acetamide

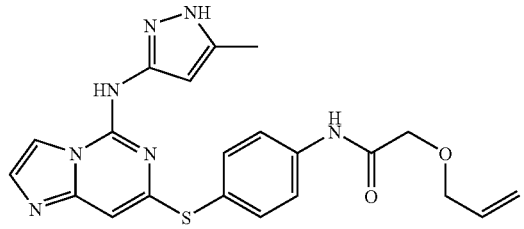

The title compound was synthesized following a procedure analogous to that described in Example 1. $^1$H NMR (400 MHz, MeOD) δ ppm 2.22 (s, 3H) 4.13 (s, 3H) 4.17 (d, J=5.81 Hz, 2H) 5.27 (d, J=10.8 Hz, 1H) 5.37 (d, J=17.18 Hz, 1H) 5.97 (s, 1H) 6.72 (s, 1H) 7.62 (d, J=8.59 Hz, 2H) 7.81-7.86 (m, 3H) 8.24 (s, 1H). MS [m+H] calc'd for $C_{21}H_{21}N_7O_2S$, 436.3; found 436.3.

Example 140

2-(dimethylamino)-N-(4-(5-(5-methyl-1H-pyrazol-3-ylamino)imidazo[1,2-f]pyrimidin-7-ylthio)phenyl)acetamide

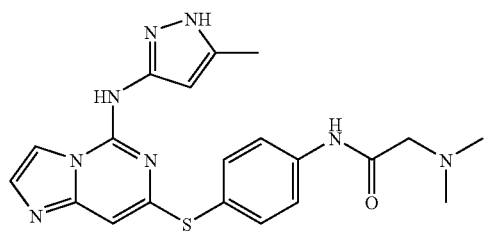

The title compound was synthesized following a procedure analogous to that described in Example 1. $^1$H NMR (400 MHz, MeOD) δ ppm 2.24 (s, 3H) 3.02 (s, 6H) 4.22 (s, 2H) 6.02 (s, 1H) 6.72 (s, 1H) 7.66 (d, J=8.59 Hz, 2H) 7.80-7.89 (m, 3H) 8.25 (s, 1H). MS [m+H] calc'd for $C_{20}H_{22}N_8OS$, 423; found 423.3.

Example 141

2-(cyclopropylamino)-N-(4-(5-(5-methyl-1H-pyrazol-3-ylamino)imidazo[1,2-f]pyrimidin-7-ylthio)phenyl)acetamide

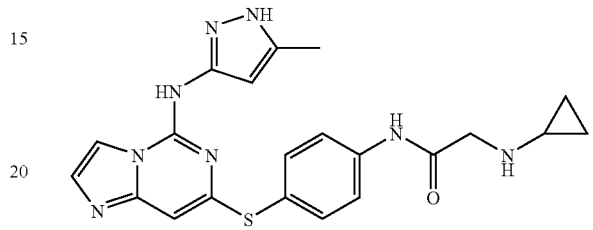

The title compound was synthesized following a procedure analogous to that described in Example 1. $^1$H NMR (400 MHz, MeOD) δ ppm 0.91-0.98 (m, 4H) 2.24 (s, 3H) 2.83-2.90 (m, 1H) 4.15 (s, 2H) 6.01 (s, 1H) 6.72 (s, 1H) 7.66 (d, J=8.34 Hz, 2H) 7.76-7.86 (m, 3H) 8.25 (s, 1H). MS [m+H] calc'd for $C_{21}H_{22}N_8OS$, 435.8; found 435.8.

Example 142

2-(1H-imidazol-1-yl)-N-(4-(5-(5-methyl-1H-pyrazol-3-ylamino)imidazo[1,2-f]pyrimidin-7-ylthio)phenyl)acetamide

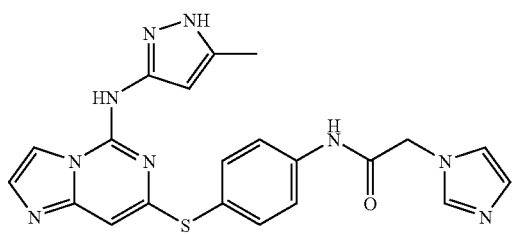

The title compound was synthesized following a procedure analogous to that described in Example 1. $^1$H NMR (400 MHz, MeOD) δ ppm 2.22 (s, 3H) 5.16 (s, 2H) 6.08 (s, 1H) 6.53 (s, 1H) 7.38 (s, 1H) 7.50 (d, J=11.87 Hz, 2H) 7.61 (d, J=8.84 Hz, 2H) 7.76 (d, J=8.84 Hz, 2H) 8.01 (s, 1H) 8.51 (s, 1H). MS [m+H] calc'd for $C_{21}H_{19}N_9OS$, 446.3; found 446.3.

Example 143

N-(4-(5-(5-cyclopropyl-1H-pyrazol-3-ylamino)imidazo[1,2-f]pyrimidin-7-ylthio)phenyl)-2-(ethyl(methyl)amino)acetamide

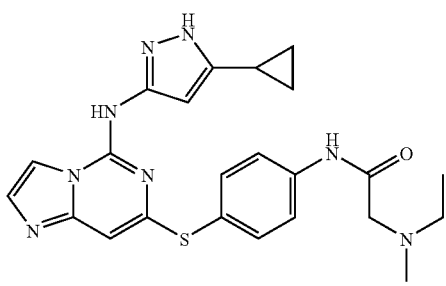

The title compound was synthesized following a procedure analogous to that described in Example 1. $^1$H NMR (400 MHz, MeOD) δ ppm 0.62-0.71 (m, 2H) 0.94 (q, J=6.32 Hz, 2H) 1.14 (t, J=7.20 Hz, 3H) 1.75-1.89 (m, 1H) 2.38 (s, 3H) 2.60 (q, J=7.07 Hz, 2H) 3.20 (s, 2H) 3.34 (s, 3H) 5.99 (s, 1H) 6.53 (s, 1H) 7.42 (s, 1H) 7.57 (d, J=8.59 Hz, 2H) 7.76 (d, J=8.34 Hz, 2H) 7.93 (s, 1H). MS [m+H] calc'd for $C_{23}H_{26}N_8OS$, 463.43; found 463.43.

Example 144

N-(4-(5-(5-cyclopropyl-1H-pyrazol-3-ylamino)imidazo[1,2-f]pyrimidin-7-ylthio)phenyl)-2-(dimethylamino)acetamide

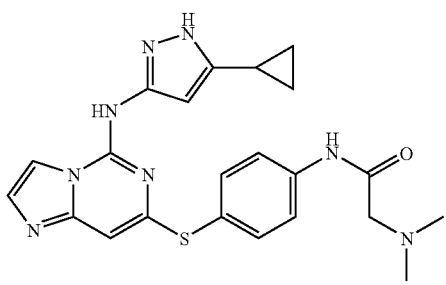

The title compound was synthesized following a procedure analogous to that described in Example 1. $^1$H NMR (400 MHz, MeOD) δ ppm 0.67 (ddd, J=6.76, 4.74, 4.42 Hz, 2H) 0.99 (ddd, J=8.40, 6.51, 4.29 Hz, 2H) 1.86-1.91 (m, 1H) 2.69 (s, 3H) 3.02 (s, 6H) 4.20 (s, 2H) 6.07 (s, 1H) 6.64 (s, 1H) 7.66 (d, J=8.59 Hz, 2H) 7.78-7.88 (m, 3H) 8.24 (d, J=2.27 Hz, 1H). MS [m+H] calc'd for $C_{22}H_{24}N_8OS$, 449.1; found 449.1.

Example 145

N-(4-(5-(5-cyclopropyl-1H-pyrazol-3-ylamino)imidazo[1,2-f]pyrimidin-7-ylthio)phenyl)-2-(cyclopropylamino)acetamide

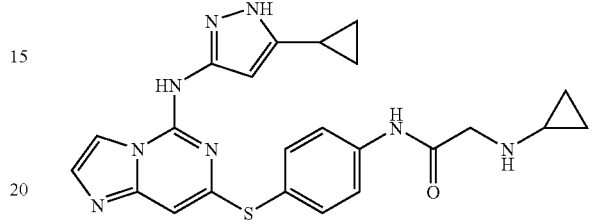

The title compound was synthesized following a procedure analogous to that described in Example 1. $^1$H NMR (400 MHz, MeOD) δ ppm 0.63-0.70 (m, 2H) 0.91-1.02 (m, 6H) 1.84-1.93 (m, 1H) 3.48 (td, J=7.39, 6.19 Hz, 1H) 4.14 (s, 2H) 6.08 (s, 1H) 6.63 (s, 1H) 7.65 (d, J=8.84 Hz, 2H) 7.82 (d, J=8.59 Hz, 3H) 8.24 (s, 1H). MS [m+H] calc'd for $C_{23}H_{24}N_8OS$, 461.2; found 461.2.

Example 146

N-(4-(5-(5-cyclopropyl-1H-pyrazol-3-ylamino)imidazo[1,2-f]pyrimidin-7-ylthio)phenyl)-2-ethoxyacetamide

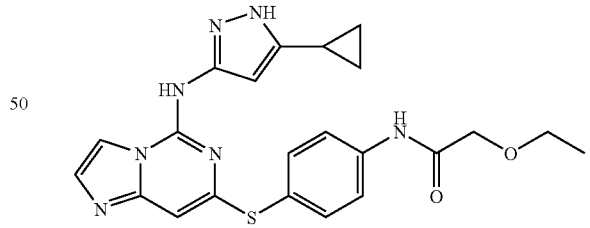

The title compound was synthesized following a procedure analogous to that described in Example 1. $^1$H NMR (400 MHz, MeOD) δ ppm 0.68 (dd, J=4.93, 1.89 Hz, 2H) 0.98 (dd, J=8.34, 2.02 Hz, 2H) 1.30 (t, J=7.2 Hz, 3H) 1.79-1.91 (m, 1H) 3.67 (q, J=6.99 Hz, 2H) 4.11 (s, 2H) 6.02 (s, 1H) 6.67 (s, 1H)

7.63 (d, J=8.84 Hz, 2H) 7.79-7.90 (m, 3H) 8.24 (s, 1H). MS [m+H] calc'd for C₂₂H₂₃N₇O₂S, 450.1; found 450.1.

Example 147

2-(ethyl(methyl)amino)-N-(4-(5-(5-methyl-1H-pyrazol-3-ylamino)imidazo[1,2-f]pyrimidin-7-ylthio)phenyl)acetamide

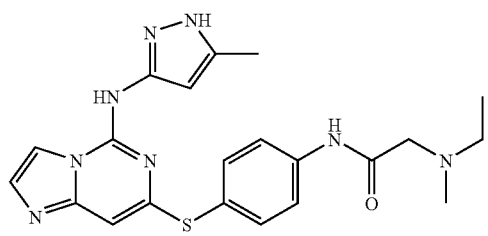

The title compound was synthesized following a procedure analogous to that described in Example 1. ¹H NMR (400 MHz, MeOD) δ ppm 1.07 (t, J=7.33 Hz, 3H) 2.20 (s, 3H) 2.38 (s, 3H) 2.60 (q, J=7.07 Hz, 2H) 3.20 (s, 2H) 5.94 (s, 1H) 6.44 (s, 1H) 7.37 (s, 1H) 7.58 (d, J=8.59 Hz, 2H) 7.75 (d, J=8.59 Hz, 2H) 7.89 (s, 1H). MS [m+H] calc'd for C₂₁H₂₄N₈OS, 437.46; found 437.46.

Example 148

N-(4-(2-(hydroxymethyl)-5-(5-methyl-1H-pyrazol-3-ylamino)imidazo[1,2-f]pyrimidin-7-ylthio)phenyl)-2-methoxyacetamide

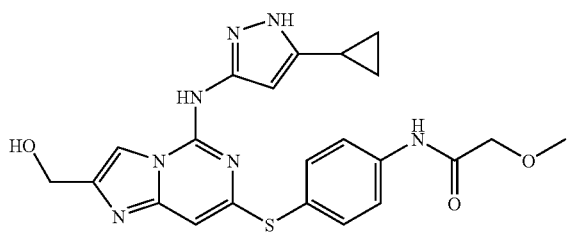

The title compound was synthesized following a procedure analogous to that described in Example 1. ¹H NMR (400 MHz, MeOD) δ ppm 0.67 (ddd, J=6.76, 4.74, 4.42 Hz, 2H) 0.95-1.00 (m, 2H) 1.82-1.89 (m, 1H) 3.50 (s, 3H) 4.07 (s, 2H) 4.74 (d, J=1.01 Hz, 2H) 6.00 (s, 1H) 6.61 (s, 1H) 7.62 (d, J=8.84 Hz, 2H) 7.86 (d, J=8.84 Hz, 2H) 8.08 (s, 1H). MS [m+H] calc'd for C₂₂H₂₃N₇O₃S, 466.42; found 466.42.

Example 149

N-(4-(5-(5-cyclopropyl-1H-pyrazol-3-ylamino)imidazo[1,2-f]pyrimidin-7-ylthio) phenyl)nicotinamide

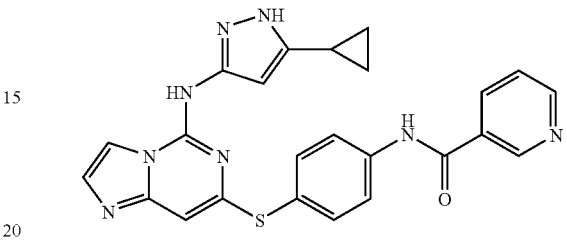

The title compound was synthesized following a procedure analogous to that described in Example 1. ¹H NMR (400 MHz, MeOD) δ ppm 0.63-0.73 (m, 2H) 0.90-0.93 (m, 2H) 1.82-1.90 (m, 1H) 6.04 (s, 1H) 6.71 (s, 1H) 7.69-7.7 (m, 3H) 7.98 (d, J=8.84 Hz, 2H) 8.24 (s, 2H) 8.40 (d, J=7.33 Hz, 1H) 8.78 (s, 1H) 9.11 (s, 1H). MS [m+H] calc'd for C₂₄H₂₀N₈OS, 469.09; found 469.09.

Example 150

N-(4-(5-(5-cyclopropyl-1H-pyrazol-3-ylamino)imidazo[1,2-f]pyrimidin-7-ylthio)phenyl)-2-methylcyclopropanecarboxamide

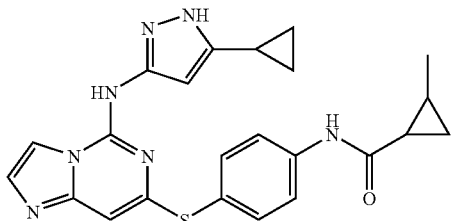

The title compound was synthesized following a procedure analogous to that described in Example 1. ¹H NMR (400 MHz, MeOD) δ ppm 0.66-0.76 (m, 3H) 0.91-1.03 (m, 2H) 1.17 (s, 3H) 1.28-1.39 (m, 2H) 1.53 (dt, J=8.15, 4.14 Hz, 1H) 1.81-1.88 (m, 1H) 5.97 (s, 1H) 6.68 (s, 1H) 7.59 (d, J=8.59

Hz, 2H) 7.76 (s, 3H) 8.21 (s, 1H). MS [m+H] calc'd for C$_{23}$H$_{23}$N$_7$OS, 446.16; found 446.16.

Example 151

N-(4-(5-(5-cyclopropyl-1H-pyrazol-3-ylamino)imidazo[1,2-f]pyrimidin-7-ylthio)phenyl)pyrrolidine-1-carboxamide

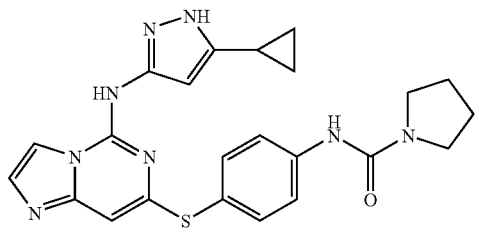

The title compound was synthesized following a procedure analogous to that described in Example 1. $^1$H NMR (400 MHz, MeOD) δ ppm 0.68-0.77 (m, 3H) 1.03-1.06 (m, 2H) 1.93-2.05 (m, 5H) 3.51-3.57 (m, 4H) 6.19 (s, 1H) 6.79 (d, J=8.4 Hz, 2H) 7.32 (d, J=8.84 Hz, 3H) 8.09 (s, 1H) 8.31 (s, 1H). MS [m+H] calc'd for C$_{23}$H$_{24}$N$_8$OS, 461.17; found 461.17.

Example 152

N-(4-(5-(5-cyclopropyl-1H-pyrazol-3-ylamino)imidazo[1,2-f]pyrimidin-7-ylthio)phenyl)-3-methylbutanamide

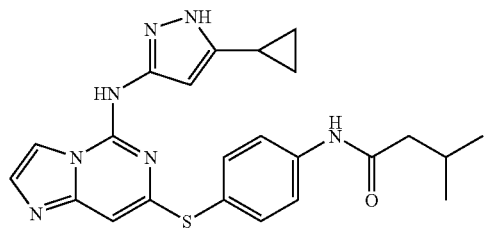

The title compound was synthesized following a procedure analogous to that described in Example 1. $^1$H NMR (400 MHz, MeOD) δ ppm 0.66-0.71 (m, 2H) 0.94-1.00 (m, 2H) 1.02 (s, 3H) 1.3 (s, 3H) 1.83-1.90 (m, 1H) 2.11-2.21 (m, 1H) 2.27-2.30 (m, 2H) 6.06 (s, 1H) 6.63 (s, 1H) 7.61 (d, J=8.84 Hz, 2H) 7.78-7.82 (m, 3H) 8.24 (s, 1H). MS [m+H] calc'd for C$_{23}$H$_{25}$N$_7$OS, 448.09; found 448.09.

Example 153

N-(4-(5-(5-cyclopropyl-1H-pyrazol-3-ylamino)-2-(methoxymethyl)imidazo[1,2-f]pyrimidin-7-ylthio)phenyl)acetamide

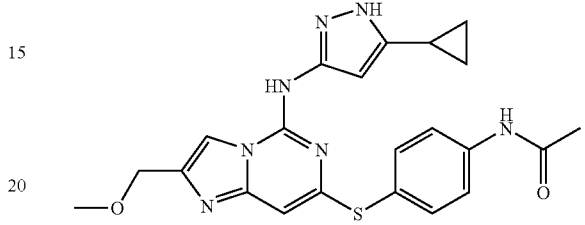

The title compound was synthesized following a procedure analogous to that described in Example 1. $^1$H NMR (400 MHz, MeOD) δ ppm 0.65-0.70 (m, 2H) 0.95-1.04 (m, 2H) 1.82-1.91 (m, 1H) 2.17 (s, 3H) 3.45 (s, 3H) 4.62 (s, 2H) 6.01 (s, 1H) 6.60 (s, 1H) 7.61 (d, J=8.84 Hz, 2H) 7.79 (d, J=8.59 Hz, 2H) 8.14 (s, 1H). MS [m+H] calc'd for C$_{22}$H$_{23}$H$_7$O$_2$S, 450.13; found 450.13.

Example 154

N-(4-(5-(5-cyclopropyl-1H-pyrazol-3-ylamino)imidazo[1,2-f]pyrimidin-7-ylthio)phenyl) isonicotinamide

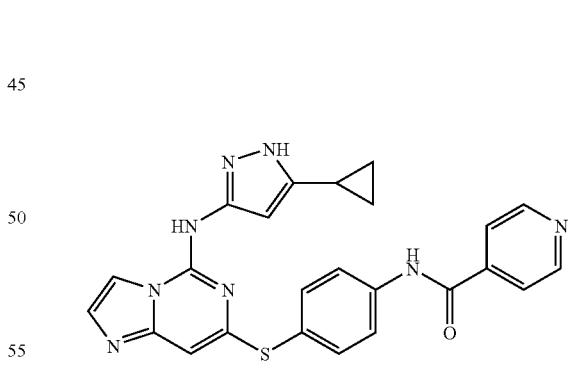

The title compound was synthesized following a procedure analogous to that described in Example 1. $^1$H NMR (400 MHz, MeOD) δ ppm 0.67 (ddd, J=6.69, 4.80, 4.67 Hz, 2H) 0.91-1.00 (m, 2H) 1.84-1.91 (m, 1H) 6.03 (s, 1H) 6.72 (s, 1H)

7.66-7.74 (m, 3H) 7.82 (d, J=2.27 Hz, 1H) 7.98-8.00 (m, 3H) 8.25 (s, 1H) 8.82 (s, 2H). MS [m+H] calc'd for $C_{24}H_{20}N_8OS$, 469.35; found 469.35.

Example 155

6-chloro-N-(4-(5-(5-cyclopropyl-1H-pyrazol-3-ylamino)imidazo[1,2-f]pyrimidin-7-ylthio)phenyl)nicotinamide

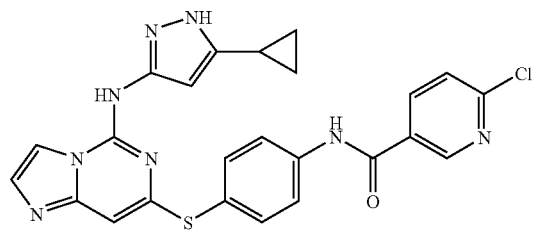

The title compound was synthesized following a procedure analogous to that described in Example 1. $^1$H NMR (400 MHz, MeOD) δ ppm 0.67-0.68 (m, 2H) 0.93-0.95 (m, 2H) 1.84-1.94 (m, 1H) 6.05 (s, 1H) 6.71 (s, 1H) 7.63-7.72 (m, 3H) 7.81 (s, 1H) 7.96 (d, J=8.0 Hz, 2H) 8.24 (s, 1H) 8.33 (dd, J=8.34, 2.53 Hz, 1H) 8.93 (s, 1H). MS [m+H] calc'd for $C_{24}H_{19}ClN_8OS$, 503.34, 505.24; found 503.34.

Example 156a

Ethyl 7-chloro-5-(5-methyl-1H-pyrazol-3-ylamino)imidazo[1,2-f]pyrimidine-2-carboxylate

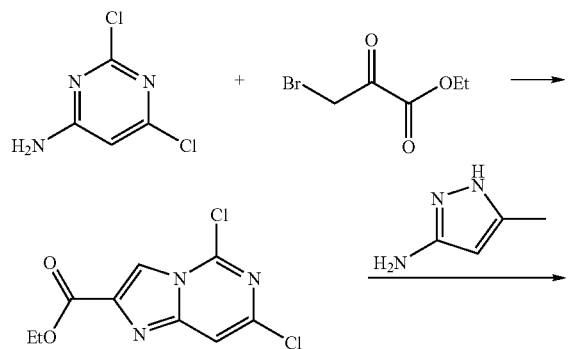

2,6-Dichloro-pyrimidin-4-ylamine and 3-bromo-2-oxo-propionic acid ethyl ester were reacted to provide 5,7-dichloro-imidazo[1,2-c]pyrimidine-2-carboxylic acid ethyl ester. The title compound was prepared from 5,7-dichloro-imidazo[1,2-c]pyrimidine-2-carboxylic acid ethyl ester and 5-methyl-1H-pyrazol-3-ylamine according to the procedure described in Scheme 7. $^1$H NMR (400 MHz, DMSO) 10.81 (s, 1H) 9.10 (s, 1H) 7.10 (s, 1H) 6.48 (s, 1H) 4.37 (q, J=7.2 Hz 2H) 2.28 (s, 3H) 1.33 (t, J=7.2 Hz, 3H). [M+H] calc'd for $C_{13}H_{14}ClN_6O_2$, 321; found, 321.

Example 156b

Ethyl 7-(4-acetamidophenylthio)-5-(5-methyl-1H-pyrazol-3-ylamino)imidazo[1,2-f]pyrimidine-2-carboxylate

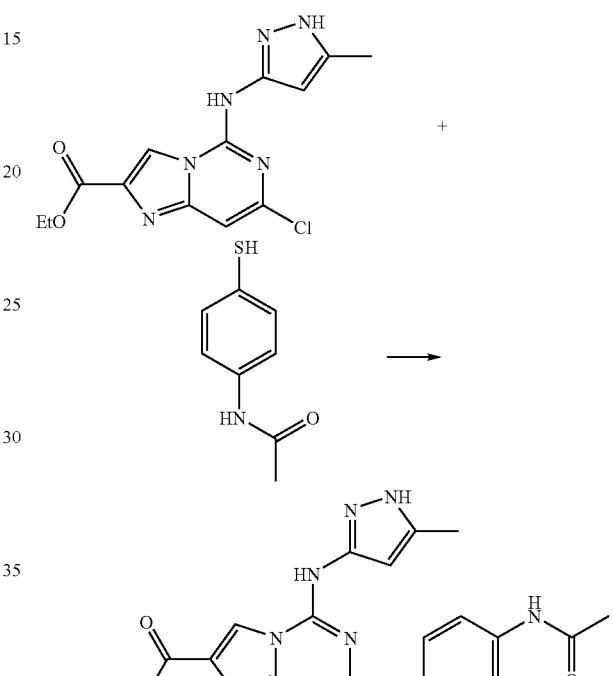

The title compound was synthesized following a procedure analogous to that described in Scheme 1. $^1$H NMR (400 MHz, CD$_3$OD) 8.60 (s, 1H) 7.71-7.74 (m, 2H) 7.56-7.58 (m, 2H) 6.54 (s, 1H) 6.03 (s, 1H) 4.38 (q, J=7.2 Hz 2H) 2.21 (s, 3H) 2.16 (s, 3H) 1.38 (t, J=7.2 Hz, 3H). [M+H] calc'd for $C_{21}H_{22}N_7O_3S$, 452; found, 452.

Example 156

N-(4-(2-(Hydroxymethyl)-5-(5-methyl-1H-pyrazol-3-ylamino)imidazo[1,2-f]pyrimidin-7-ylthio)phenyl)acetamide

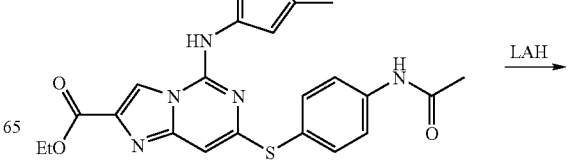

-continued

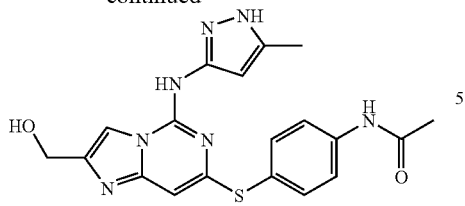

Ethyl 7-(4-acetamidophenylthio)-5-(5-methyl-1H-pyrazol-3-ylamino)imidazo[1,2-f]pyrimidine-2-carboxylate (10 mg, 0.022 mmol, 1 eq) was dissolved in anhydrous THF under nitrogen at 0° C. 1.0M lithium aluminum hydride in THF (220 μl) was added dropwise. Upon completion of addition the solution was stirred for 2 hours. Reaction was seen to be complete by LCMS. Sodium sulfate decahydrate was slowly added until bubbling stopped and the reaction mixture was filtered. The solid was triturated in 20% methanol in methylene chloride and filtered. This was repeated a further two times. The solvent was removed in vacuo to leave a brown oil which was purified by flash chromatography to leave the desired as an off-white solid. [M+H] calc'd for $C_{19}H_{20}N_7O_2S$, 410; found, 410.

Example 157a

Ethyl 7-(4-(Cyclopropanecarboxamido)phenylthio)-5-(5-methyl-1H-pyrazol-3-ylamino)imidazo[1,2-f]pyrimidine-2-carboxylate

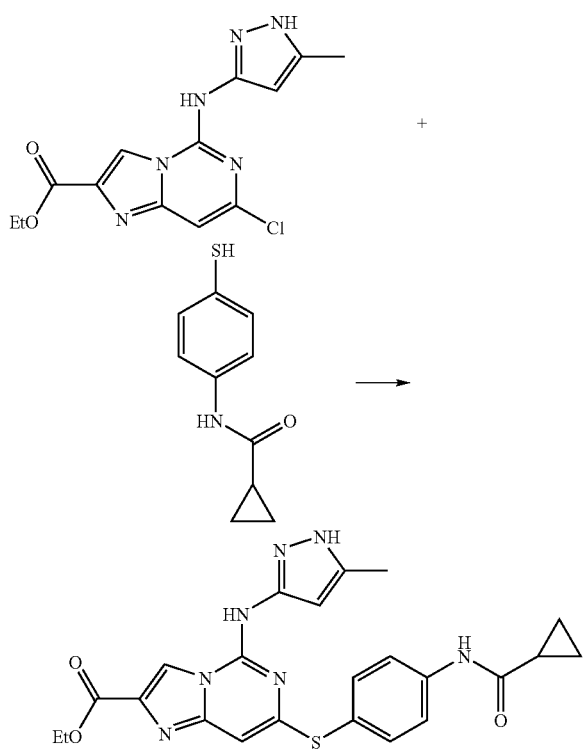

The title compound was synthesized following a procedure analogous to that described in Example 156b. $^1$H NMR (400 MHz, DMSO) 10.51 (s, 1H) 9.05 (s, 1H) 7.76-7.79 (m, 2H) 7.54-7.57 (m, 2H) 6.52 (s, 1H) 5.86 (s, 1H) 4.30 (q, J=7.2 Hz, 2H) 2.12 (s, 3H) 1.80-1.84 (m, 1H) 1.32 (t, J=7.2 Hz, 3H), 0.82-0.84 (m, 4H). [M+H] calc'd for $C_{23}H_{23}N_7O_3S$, 478; found, 478.

Example 157

N-(4-(2-(Hydroxymethyl)-5-(5-methyl-1H-pyrazol-3-ylamino)imidazo[1,2-f]pyrimidin-7-ylthio)phenyl)cyclopropanecarboxamide

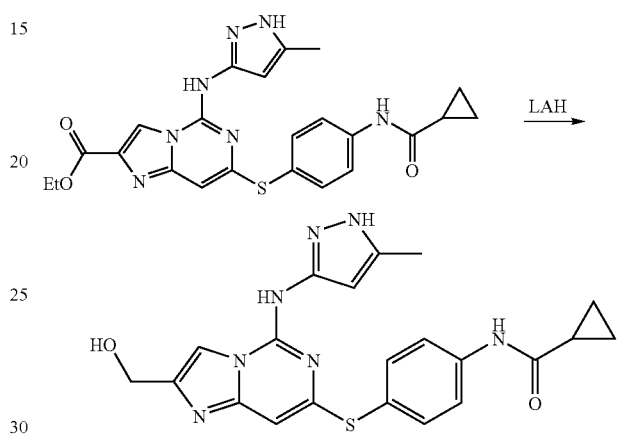

The title compound was synthesized following a procedure analogous to that described in Example 156. $^1$H NMR (400 MHz, CD$_3$OD) 8.09 (s, 1H) 7.76-7.80 (m, 2H) 7.57-7.60 (m, 2H) 6.68 (s, 1H) 5.90 (s, 1H) 4.74 (s, 2H) 2.20 (s, 3H) 1.80-1.84 (m, 1H) 0.95-1.00 (m, 2H), 0.87-0.92 (m, 2H). [M+H] calc'd for $C_{21}H_{22}N_7O_2S$, 436; found, 436.

Example 158

N-{4-[5-(5-Cyclopropyl-1H-pyrazol-3-ylamino)-2-dimethylaminomethyl-imidazo[1,2-c]pyrimidin-7-ylsulfanyl]-phenyl}acetamide

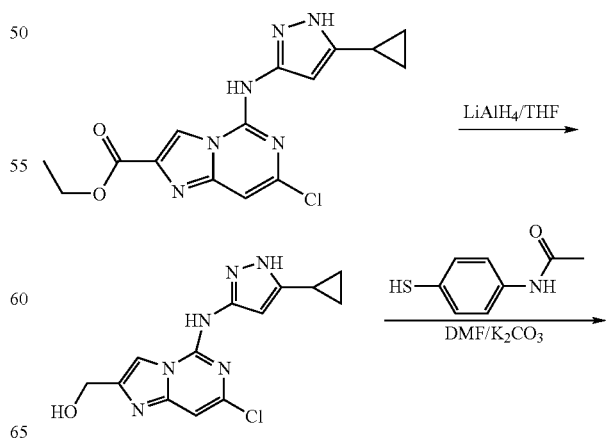

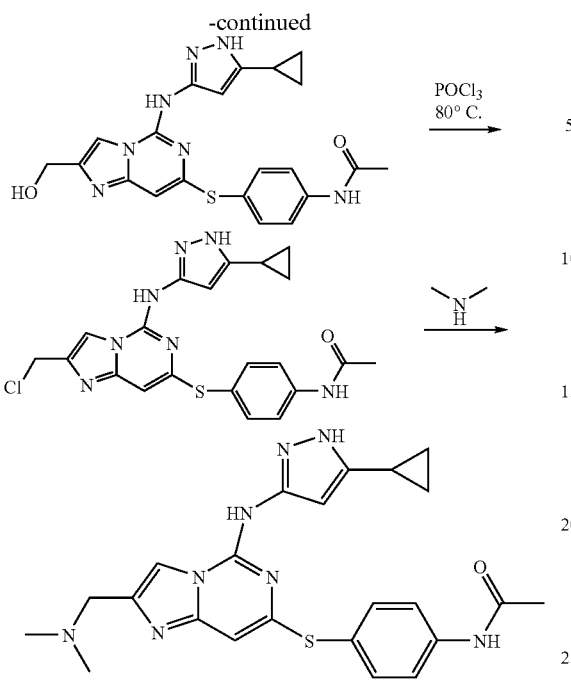
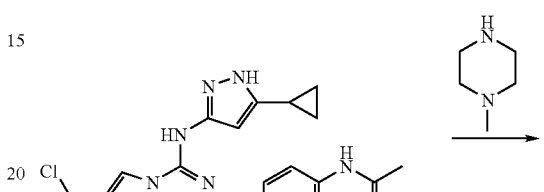

Referring to Scheme 11, ethyl 7-chloro-5-(5-cyclopropyl-1H-pyrazol-3-ylamino)imidazo[1,2-f]pyrimidine-2-carboxylate (3.59 g, 10.4 ml 1 eq) was dissolved in anhydrous THF under nitrogen at 0° C. 1.0M lithium aluminum hydride in THF (15.5 ml, 15.5 mmol, 1.5 eq) was added dropwise. Upon completion of addition the solution was stirred for 2 hours. Reaction was seen to be complete by LCMS. Sodium sulfate decahydrate was slowly added until bubbling stopped and the reaction mixture was filtered. The solid was triturated in 20% methanol in methylene chloride and filtered. This was repeated a further two times. The solvent was removed in vacuo to leave a brown oil which was purified by flash chromatography to leave (7-chloro-5-(5-cyclopropyl-1H-pyrazol-3-ylamino) imidazo[1,2-f]pyrimidin-2-yl)methanol as an off-white solid. 1.4 g (41%). [M+H] calc'd for $C_{13}H_{13}ClN_6O$, 305; found, 305.

(7-chloro-5-(5-cyclopropyl-1H-pyrazol-3-ylamino) imidazo[1,2-f]pyrimidin-2-yl)methanol (928 mg, 30.5 mmol, 1 eq), N-(4-mercaptophenyl)acetamide (1.02 g, 61 mmol, 2 eq) and potassium carbonate (421 mg, 30.5 mmol, 1 eq) were dissolved in DMF. The mixture was placed in a microwave reactor at 160° C. for 15 minutes. LCMS confirmed the product. The solvent was evaporated and the residue purified by flash chromatography to leave N-(4-(5-(5-cyclopropyl-1H-pyrazol-3-ylamino)-2-(hydroxymethyl)imidazo[1,2-f]pyrimidin-7-ylthio)phenyl)acetamide, 383 mg (29%). $^1$H NMR (400 MHz, CDCl$_3$) 7.75 (s, 1H) 7.68-7.70 (m, 2H) 7.55-7.58 (m, 2H) 6.55 (br.s., 1H) 4.70 (s, 2H) 2.18 (s, 3H) 1.84-1.87 (m, 1H) 0.93-0.98 (m, 2H), 0.70-0.73 (m, 2H). [M+H] calc'd for $C_{21}H_{22}N_7O_2S$, 436; found, 436.

N-(4-(5-(5-cyclopropyl-1H-pyrazol-3-ylamino)-2-(hydroxymethyl) imidazo[1,2-f]pyrimidin-7-ylthio)phenyl)acetamide (50 mg, 0.11 mmol, 1 eq) and 2.0M methylamine in THF (1 ml, 22 mmol, 180 eq) were mixed in DMF and stirred at room temperature. The reaction was followed by LCMS. Upon completion the reaction mixture was evaporated and the residue purified by high-performance liquid chromatography to leave the title compound as an off-white solid. 4 mg (8%). $^1$H NMR (400 MHz, CD$_3$OD) 7.87 (s, 1H) 7.72 (d, J=8.84 Hz, 2H) 7.56 (d, J=8.84 Hz, 2H) 6.50 (s, 1H) 5.99 (s, 1H) 4.67 (s, 2H) 2.15 (s, 2H) 1.85 (m, 1H) 1.29 (s, 6H) 0.96 (m, 3H) 0.66 (m, 2H). [M+H] calc'd for $C_{23}H_{26}N_8OS$, 463; found, 463.

Example 159

N-(4-(5-(5-Cyclopropyl-1H-pyrazol-3-ylamino)-2-((4-methylpiperazin-1-yl)methyl)imidazo[1,2-f]pyrimidin-7-ylthio)phenyl)acetamide The title compound was synthesized following a procedure analogous to that described in Example 158. [M+H] calc'd for $C_{26}H_{32}N_9OS$, 518; found, 518.

Example 160

N-(5-methyl-1H-pyrazol-3-yl)-7-(o-tolylthio)imidazo[1,2-f]pyrimidin-5-amine

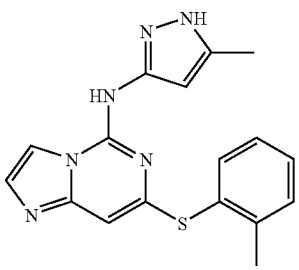

The title compound was synthesized using 2-methylbenzenethiol following the procedure described in the synthesis of Example 1. $^1$H NMR (400 MHz, CD$_3$OD) 8.25 (s, 1H) 7.80 (s, 1H) 7.66 (d, J=7.84 Hz, 1H) 7.54 (m, 1H) 7.49 (m, 1H)

7.37 (m, 1H) 6.67 (s, 1H) 5.86 (s, 1H) 2.44 (s, 3H) 2.24 (s, 3H). [M+H] calc'd for $C_{17}H_{16}N_6S$, 337; found, 337.

Example 161

((5-fluoro-2-(5-(5-methyl-1H-pyrazol-3-ylamino)imidazo[1,2-f]pyrimidin-7-ylthio)phenyl)methanol

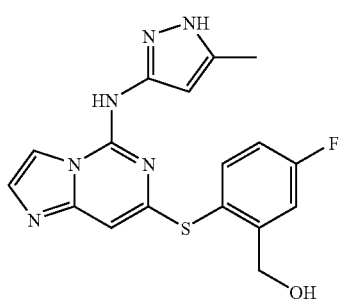

The title compound was synthesized using (5-fluoro-2-mercaptophenyl)methanol following the procedure described in the synthesis of Example 1. $^1$H NMR (400 MHz, DMSO) 7.64 (m, 1H) 7.42 (m, 1H) 7.22 (m, 1H) 5.45 (s, 1H) 4.60 (s, 2H) 3.61 (s, 1H) 2.08 (s, 3H). [M+H] calc'd for $C_{17}H_{15}FN_6OS$, 371; found, 371.

Example 162

7-(3-aminophenylthio)-N-(5-methyl-1H-pyrazol-3-yl)imidazo[1,2-f]pyrimidin-5-amine

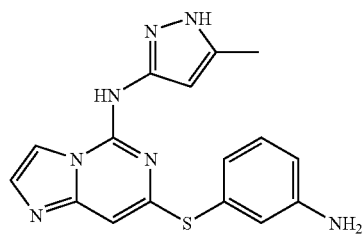

The title compound was synthesized using 3-aminobenzenethiol following the procedure described in the synthesis of Example 1. $^1$H NMR (400 MHz, CD$_3$OD) 8.25 (s, 1H) 7.81 (s, 1H) 7.38 (t, 1H) 7.09 (d, J=9.08 Hz, 1H) 6.72 (s, 1H) 6.09 (s, 1H) 3.34 (s, 2H) 2.66 (s, 1H) 2.28 (s, 3H). [M+H] calc'd for $C_{16}H_{15}N_7S$, 338; found, 338.

Example 163

Methyl 3-(5-(5-methyl-1H-pyrazol-3-ylamino)imidazo[1,2-f]pyrimidin-7-ylthio)benzoate

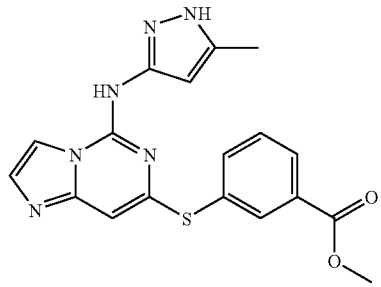

The title compound was synthesized using methyl 3-mercaptobenzoate following the procedure described in the synthesis of Example 1. However, the reaction mixture contained the intended (example 8) and the corresponding carboxylic acid (example 9). The two compounds were separated by HPLC. $^1$H NMR (400 MHz, CD$_3$OD) 8.2 (m, 3H) 7.91 (d, J=8.84 Hz, 1H) 7.81 (m, 1H) 7.67 (t, 1H) 6.87 (s, 1H) 5.68 (s, 1H) 3.91 (s, 3H) 3.29 (s, 1H) 2.17 (s, 3H). [M+H] calc'd for $C_{18}H_{16}N_6O_2S$, 381; found, 381.

Example 164

3-(5-(5-methyl-1H-pyrazol-3-ylamino)imidazo[1,2-f]pyrimidin-7-ylthio)benzoic acid

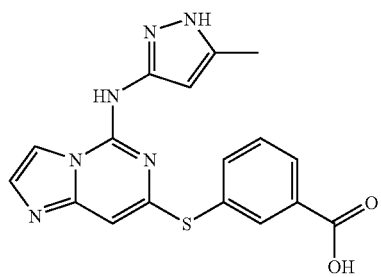

The title compound was synthesized following a procedure analogous to that described in Example 1. $^1$H NMR (400 MHz, CD$_3$OD) 8.2 (m, 3H) 7.89 (d, J=7.8 Hz, 1H) 7.82 (s, 1H) 7.66 (t, 1H) 6.86 (s, 1H) 5.71 (s, 1H) 2.19 (s, 3H). [M+H] calc'd for $C_{17}H_{14}N_6O_2S$, 367; found, 367.

Example 165

Methyl 4-(5-(5-methyl-1H-pyrazol-3-ylamino)imidazo[1,2-f]pyrimidin-7-ylthio)benzoate

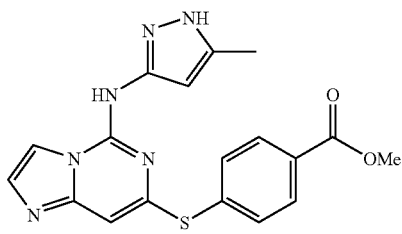

The title compound was synthesized using methyl 3-mercaptobenzoate following the procedure described in the synthesis of Example 1. The two compounds were separated by HPLC. $^1$H NMR (400 MHz, CD$_3$OD) 8.26 (m, 1H) 8.11-8.26 (m, 2H) 7.84 (s, 1H) 7.76-7.78 (m, 2H) 6.94 (s, 1H) 5.73 (s, 1H) 3.96 (s, 3H) 2.13 (s, 3H). [M+H] calc'd for $C_{18}H_{17}N_6O_2S$, 381; found, 381.

Example 166

4-(5-(5-Methyl-1H-pyrazol-3-ylamino)imidazo[1,2-f]pyrimidin-7-ylthio)benzoic acid

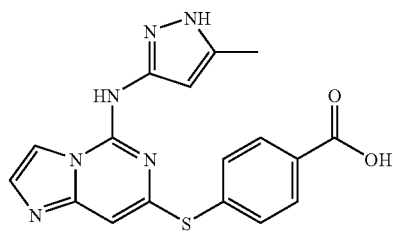

The title compound was synthesized following a procedure analogous to that described in Example 1. $^1$H NMR (400 MHz, CD$_3$OD) 8.27 (s, 1H) 8.13-8.15 (m, 2H) 7.84 (s, 1H) 7.75-7.78 (m, 2H) 7.33 (m, 1H) 6.94 (s, 1H) 5.73 (s, 1H) 2.15 (s, 3H). [M+H] calc'd for $C_{17}H_{15}N_6O_2S$, 367; found, 367.

Example 167

(E)-methyl 3-(4-(5-(5-methyl-1H-pyrazol-3-ylamino)imidazo[1,2-f]pyrimidin-7-ylthio)phenyl)acrylate

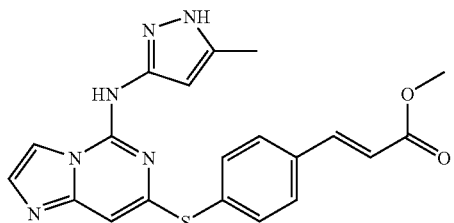

The title compound was synthesized using (E)-methyl 3-(4-mercaptophenyl)acrylate following the procedure described in the synthesis of Example 1. $^1$H NMR (400 MHz, CD$_3$OD) 8.2 (s, 1H) 7.79 (m, 4H) 7.71 (d, J=8.32 Hz, 2H) 6.83 (s, 1H) 6.71 (d, J=16.2 Hz, 1H) 5.87 (s, 1H) 3.81 (s, 3H) 2.15 (s, 1H). [M+H] calc'd for $C_{20}H_{18}N_6O_2S$, 407; found, 407.

Example 168

3-(5-(5-methyl-1H-pyrazol-3-ylamino)imidazo[1,2-f]pyrimidin-7-ylthio)benzamide

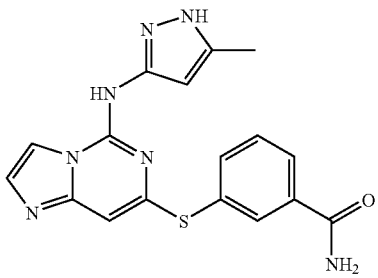

The title compound was synthesized using 3-mercaptobenzamide following the procedure described in the synthesis of Example 1. $^1$H NMR (400 MHz, CD$_3$OD) 8.2 (s, 1H) 8.19 (m, 1H) 8.10 (m, 1H) 7.82 (m, 2H) 7.62 (m, 1H) 6.81 (s, 1H) 5.79

(s, 1H) 2.65 (s, 1H) 2.20 (s, 3H). [M+H] calc'd for C₁₇H₁₅N₇OS, 366; found, 366.

Example 169

7-(2-Amino-4-chlorophenylthio)-N-(5-methyl-1H-pyrazol-3-yl)imidazo[1,2-f]pyrimidin-5-amine

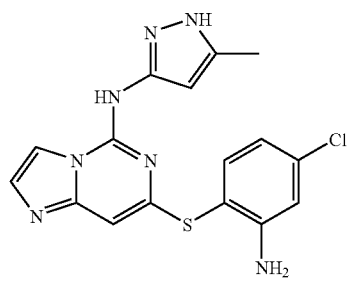

The title compound was synthesized using 2-amino-4-chlorobenzenethiol following the procedure described in the synthesis of Example 1. [M+H] calc'd for C₁₆H₁₅ClN₇S, 372; found, 372.

Example 170

2-(3-(5-(5-methyl-1H-pyrazol-3-ylamino)imidazo[1,2-f]pyrimidin-7-ylthio)phenyl)acetic acid

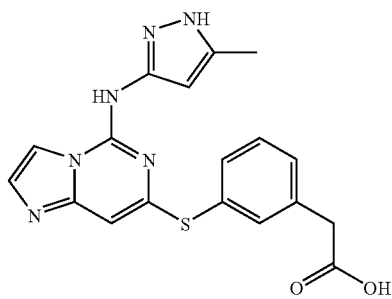

The title compound was synthesized using 2-(3-mercaptophenyl)acetic acid following the procedure described in the synthesis of Example 1. ¹H NMR (400 MHz, CD₃OD) 8.46 (s, 1H) 7.86 (s, 1H) 7.58 (s, 1H) 7.53 (m, 3H) 6.66 (s, 1H) 5.89 (s, 1H) 3.67 (s, 2H) 2.89 (s, 1H) 2.73 (s, 1H) 2.17 (s, 3H). [M+H] calc'd for C₁₈H₁₆N₆O₂S, 381; found, 381.

Example 171

N-cyclopropyl-2-(3-(5-(5-methyl-1H-pyrazol-3-ylamino)imidazo[1,2-f]pyrimidin-7-ylthio)phenyl)acetamide

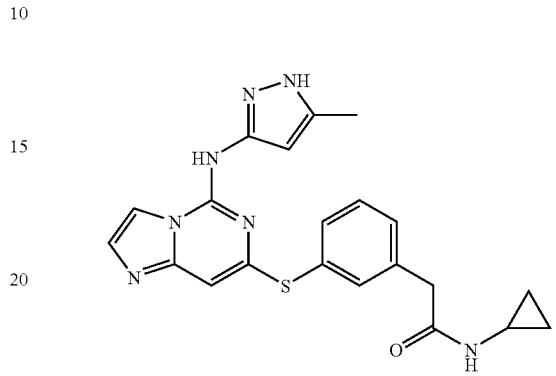

Referring to Scheme 8, 2-(3-(5-(5-methyl-1H-pyrazol-3-ylamino)imidazo[1,2-f]pyrimidin-7-ylthio)phenyl)acetic acid (30 mg, 0.078 mmol, 1 eq), hydroxybenzotriazole (11 mg, 0.078 mmol, 1 eq), 1-ethyl-(3-dimethylaminopropyl)carbodiimide hydrochloride (16 mg, 0.078 mmol, 1 eq), triethylamine (16 μl, 0.15 mmol, 2 eq) and cyclopropylamine (27 μl, 0.39 mmol, 5 eq) were stirred in DMF (2 ml) for 8 hours. The solvent was removed and the residue purified by high-performance liquid chromatography to leave N-cyclopropyl-2-(3-(5-(5-methyl-1H-pyrazol-3-ylamino)imidazo[1,2-f]pyrimidin-7-ylthio)phenyl)acetamide, 29 mg (88% yield). ¹H NMR (400 MHz, CD₃OD) 8.24 (s, 1H) 7.81 (s, 1H) 7.61 (s, 1H) 7.58 (m, 1H) 7.51 (m, 2H) 6.70 (s, 1H) 5.89 (s, 1H) 3.98 (s, 1H) 3.51 (s, 1H) 3.34 (s, 1H) 2.61 (m, 1H) 2.25 (s, 3H) 0.69 (m, 2H) 0.44 (m, 2H). [M+H] calc'd for C₂₁H₂₁N₇OS, 420; found, 420.

Example 172

N-methyl-2-(3-(5-(5-methyl-1H-pyrazol-3-ylamino)imidazo[1,2-f]pyrimidin-7-ylthio)phenyl)acetamide

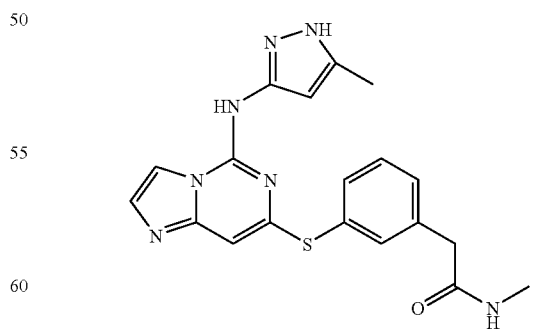

The title compound was synthesized following a procedure analogous to that described in Example 171. ¹H NMR (400 MHz, CD₃OD) 8.24 (s, 1H) 7.81 (s, 1H) 7.62 (s, 1H) 7.58 (s, 1H) 7.52 (s, 2H) 6.70 (s, 1H) 5.97 (s, 1H) 3.98 (s, 1H) 3.55 (s, 2H) 3.34 (s, 1H) 2.68 (s, 3H) 2.25 (s, 3H). [M+H] calc'd for $C_{19}H_{19}N_7OS$, 394; found, 394.

Example 173

N-ethyl-2-(3-(5-(5-methyl-1H-pyrazol-3-ylamino)imidazo[1,2-f]pyrimidin-7-ylthio)phenyl)acetamide

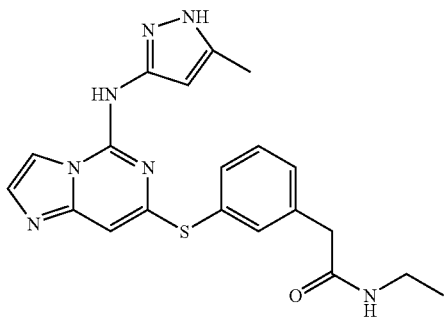

The title compound was synthesized following a procedure analogous to that described in Example 171. $^1$H NMR (400 MHz, CD$_3$OD) 8.24 (s, 1H) 7.80 (s, 1H) 7.62 (s, 1H) 7.57 (s, 1H) 7.52 (s, 2H) 6.70 (s, 1H) 5.97 (s, 1H) 3.54 (s, 2H) 3.17 (m, 2H) 2.24 (s, 2H) 2.14 (s, 3H) 1.07 (m, 3H). [M+H] calc'd for $C_{20}H_{21}N_7OS$, 408; found, 408.

Example 174

4-(5-(5-cyclopropyl-1H-pyrazol-3-ylamino)imidazo[1,2-f]pyrimidin-7-ylthio)-N-ethylbenzamide

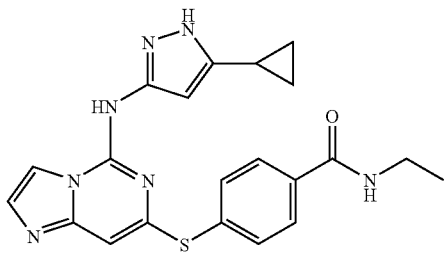

Referring to Scheme 9, 4-(5-(5-cyclopropyl-1H-pyrazol-3-ylamino) imidazo[1,2-f]pyrimidin-7-ylthio)benzoic acid (40 mg, 0.1 mmol, 1 eq), hydroxybenzotriazole (14 mg, 0.1 mmol, 1 eq), 1-ethyl-(3-dimethylaminopropyl) carbodiimide hydrochloride (19.5 mg, 0.1 mmol, 1 eq), triethylamine (29 µl, 0.2 mmol, 2 eq) and ethanamine (50 µl, 0.15 mmol, 1.5 eq) were stirred in DMF (2 ml) for 8 hours. The solvent was removed and the residue purified by high-performance liquid chromatography to leave 4-(5-(5-cyclopropyl-1H-pyrazol-3-ylamino) imidazo[1,2-f]pyrimidin-7-ylthio)-N-ethylbenzamide. 21 mg (51% yield). $^1$H NMR (400 MHz, DMSO) 8.66 (s, 1H) 8.51 (s, 1H) 8.03 (d, J=8.32 Hz, 1H) 7.93 (s, 1H) 7.74 (d, J=8.36 Hz, 1H) 6.88 (s, 1H) 5.78 (s, 1H) 3.31 (m, 3H) 3.17 (s, 2H) 1.13 (m, 1H) 0.86 (m, 2H) 0.54 (m, 2H). [M+H] calc'd for $C_{21}H_{21}N_7OS$, 420; found, 420.

Example 175

(4-(5-(5-cyclopropyl-1H-pyrazol-3-ylamino)imidazo[1,2-f]pyrimidin-7-ylthio)phenyl)(piperazin-1-yl)methanone

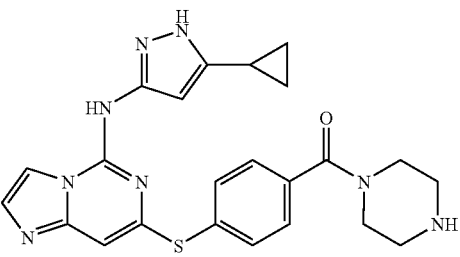

The title compound was synthesized using tert-butyl piperazine-1-carboxylate following the procedure described in the synthesis of Example 174. The protecting group was then removed by stirring in trifluoroacetic acid for 30 minutes before purification. $^1$H NMR (400 MHz, CD$_3$OD) 8.23 (s, 1H) 7.79 (m, 2H) 7.66 (m, 2H) 6.71 (s, 1H) 6.12 (s, 1H) 3.98 (s, 1H) 3.34 (s, 2H) 1.93 (m, 1H) 0.99 (m, 2H) 0.70 (m, 2H). [M+H] calc'd for $C_{23}H_{24}N_8OS$, 461; found, 461.

Example 176

N-cyclopropyl-4-(5-(5-cyclopropyl-1H-pyrazol-3-ylamino)imidazo[1,2-f]pyrimidin-7-ylthio)benzamide

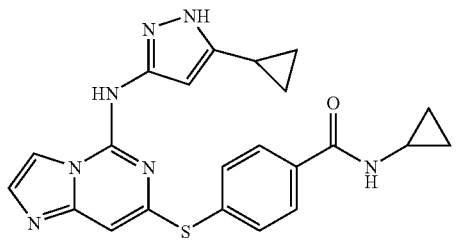

The title compound was synthesized using cyclopropanamine following the procedure described in the synthesis of Example 174. $^1$H NMR (400 MHz, CD$_3$OD) 8.52 (s, 1H) 8.34 (s, 2H) 7.89 (m, 2H) 7.60 (s, 2H) 7.53 (s, 1H) 6.87 (s, 1H) 5.76

(s, 1H) 2.84 (m, 1H) 1.68 (m, 2H) 0.82 (m, 2H) 0.69 (m, 2H) 0.57 (m, 2H) 0.43 (m, 2H). [M+H] calc'd for $C_{22}H_{21}N_7OS$, 432; found, 432.

Example 177

Azetidin-1-yl(4-(5-(5-cyclopropyl-1H-pyrazol-3-ylamino)imidazo[1,2-f]pyrimidin-7-ylthio)phenyl)methanone

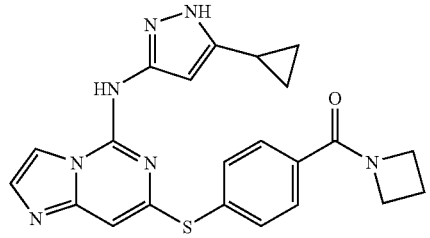

The title compound was synthesized using azetidine following the procedure described in the synthesis of Example 174. $^1$H NMR (400 MHz, CD$_3$OD) 8.26 (s, 1H) 7.77 (m, 4H) 6.80 (s, 1H) 5.95 (s, 1H) 4.42 (m, 2H) 4.23 (m, 2H) 3.98 (s, 1H) 2.99 (s, 1H) 2.86 (s, 2H) 2.40 (m, 2H) 1.86 (m, 1H) 0.98 (m, 2H) 0.66 (m, 2H). [M+H] calc'd for $C_{22}H_{21}N_7OS$, 432; found, 432.

Example 178

4-(5-(5-cyclopropyl-1H-pyrazol-3-ylamino)imidazo[1,2-f]pyrimidin-7-ylthio)-N-(pyrrolidin-3-yl)benzamide

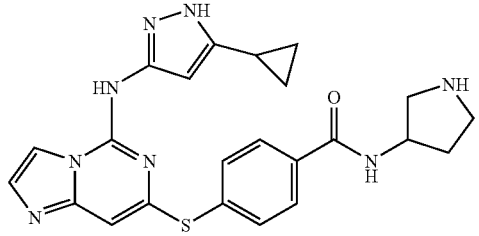

The title compound was synthesized using tert-butyl 3-aminopyrrolidine-1-carboxylate following the procedure described in the synthesis of Example 174. The protecting group was then removed by stirring in trifluoroacetic acid for 30 minutes before purification. $^1$H NMR (400 MHz, CD$_3$OD) 8.27 (s, 1H) 8.01 (m, 2H) 7.85 (s, 1H) 7.77 (m, 2H) 6.85 (s, 1H) 5.91 (s, 1H) 4.65 (m, 1H) 3.61 (m, 2H) 3.39 (m, 1H) 2.42 (m, 2H) 2.19 (m, 2H) 1.81 (m, 1H) 1.29 (s, 1H) 0.96 (m, 2H) 0.60 (m, 2H). [M+H] calc'd for $C_{23}H_{24}N_8OS$, 461; found, 461.

Example 179

4-(5-(5-cyclopropyl-1H-pyrazol-3-ylamino)imidazo[1,2-f]pyrimidin-7-ylthio)-N-(piperidin-4-yl)benzamide

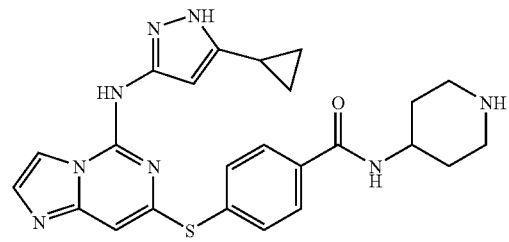

The title compound was synthesized using tert-butyl 4-aminopiperidine-1-carboxylate following the procedure described in the synthesis of Example 174. The protecting group was then removed by stirring in trifluoroacetic acid for 30 minutes before purification. $^1$H NMR (400 MHz, CD$_3$OD) 8.27 (s, 1H) 7.99 (m, 2H) 7.84 (s, 1H) 7.77 (m, 2H) 6.87 (s, 1H) 5.87 (s, 1H) 4.21 (m, 1H) 3.47 (m, 2H) 3.17 (m, 2H) 2.65 (s, 2H) 2.20 (m, 2H) 1.81 (m, 3H) 0.94 (m, 2H) 0.60 (s, 2H). [M+H] calc'd for $C_{24}H_{26}N_8OS$, 475; found, 475.

Example 180

4-(5-(5-cyclopropyl-1H-pyrazol-3-ylamino)imidazo[1,2-f]pyrimidin-7-ylthio)-N-(piperidin-3-yl)benzamide

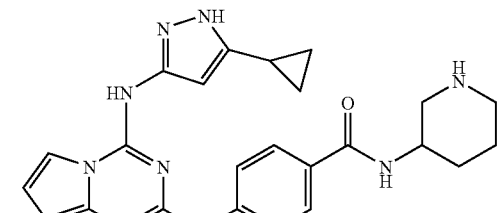

The title compound was synthesized using tert-butyl 3-aminopiperidine-1-carboxylate following the procedure described in the synthesis of Example 174. The protecting group was then removed by stirring in trifluoroacetic acid for 30 minutes before purification. $^1$H NMR (400 MHz, CD$_3$OD) 8.27 (s, 1H) 8.00 (m, 2H) 7.85 (s, 1H) 7.77 (m, 2H) 6.87 (s, 1H) 5.88 (s, 1H) 4.29 (m, 1H) 3.98 (s, 1H) 3.53 (m, 1H) 3.34

(s, 2H) 2.95 (m, 2H) 2.07 (m, 2H) 1.80 (m, 3H) 0.94 (m, 2H) 0.60 (s, 2H). [M+H] calc'd for $C_{24}H_{26}N_8OS$, 475; found, 475.

Example 181

4-(5-(5-cyclopropyl-1H-pyrazol-3-ylamino)imidazo[1,2-f]pyrimidin-7-ylthio)-N-methoxybenzamide

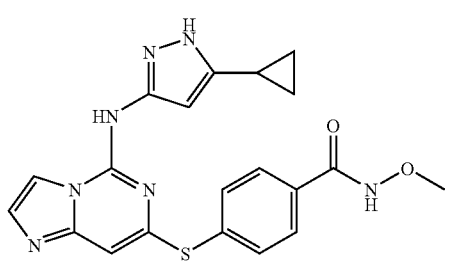

The title compound was synthesized using methoxyamine following the procedure described in the synthesis of Example 174. $^1$H NMR (400 MHz, CD$_3$OD) 8.28 (s, 1H) 7.92 (d, J=8.08 Hz, 2H) 7.85 (s, 1H) 7.76 (d, J=8.32 Hz, 2H) 6.91 (s, 1H) 5.83 (s, 1H) 3.83 (s, 3H) 3.31 (s, 2H) 1.80 (m, 1H) 0.98 (m, 2H) 0.61 (m, 2H). [M+H] calc'd for $C_{20}H_{19}N_7O_2S$, 422; found, 422.

Example 182

4-(5-(5-cyclopropyl-1H-pyrazol-3-ylamino)imidazo[1,2-f]pyrimidin-7-ylthio)-N',N'-dimethylbenzohydrazide

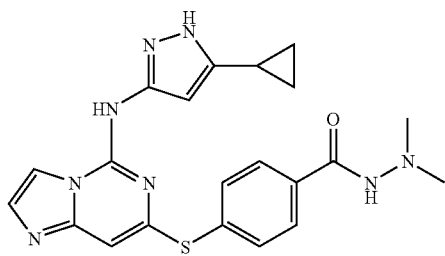

The title compound was synthesized using 1,1-dimethylhydrazine following the procedure described in the synthesis of Example 174. $^1$H NMR (400 MHz, CD$_3$OD) 8.27 (s, 1H) 7.97 (d, J=7.56 Hz, 2H) 7.85 (s, 1H) 7.77 (d, J=7.78 Hz, 2H) 6.89 (s, 1H) 5.85 (s, 1H) 2.77 (s, 4H) 1.80 (m, 1H) 0.96 (m, 2H) 0.60 (m, 2H). [M+H] calc'd for $C_{21}H_{22}N_8OS$, 435; found, 435.

Example 183

4-(5-(5-cyclopropyl-1H-pyrazol-3-ylamino)imidazo[1,2-f]pyrimidin-7-ylthio)-N-(2-(dimethylamino)ethyl)benzamide

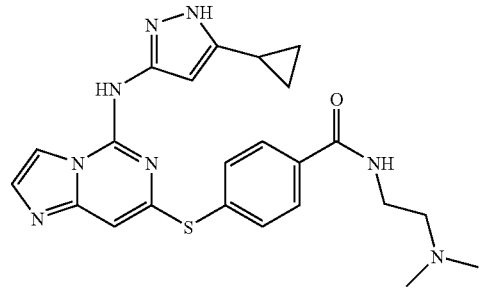

The title compound was synthesized using N1,N1-dimethylethane-1,2-diamine following the procedure described in the synthesis of Example 174. $^1$H NMR (400 MHz, CD$_3$OD) 8.27 (s, 1H) 8.03 (d, J=8.32 Hz, 2H) 7.85 (s, 1H) 7.79 (d, J=8.36 Hz, 2H) 6.85 (s, 1H) 5.92 (s, 1H) 3.79 (m, 2H) 3.40 (m, 2H) 3.00 (s, 6H) 1.81 (m, 1H) 0.95 (m, 2H) 0.60 (m, 2H). [M+H] calc'd for $C_{23}H_{26}N_8OS$, 463; found, 463.

Example 184

4-(5-(5-cyclopropyl-1H-pyrazol-3-ylamino)imidazo[1,2-f]pyrimidin-7-ylthio)-N-(2-hydroxyethyl)benzamide

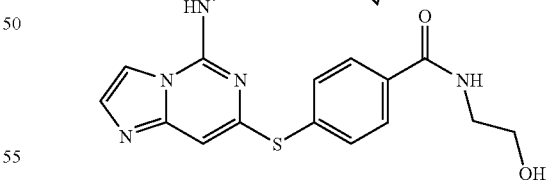

The title compound was synthesized using 2-aminoethanol following the procedure described in the synthesis of Example 174. $^1$H NMR (400 MHz, CD$_3$OD) 8.26 (s, 1H) 7.99 (m, 2H) 7.84 (s, 1H) 7.74 (d, J=8.36 Hz, 2H) 6.85 (s, 1H) 5.87

(s, 1H) 3.98 (m, 1H) 3.72 (m, 2H) 3.53 (m, 2H) 1.80 (m, 1H) 0.95 (m, 2H) 0.59 (m, 2H). [M+H] calc'd for $C_{21}H_{21}N_7O_2S$, 436; found, 436.

Example 185

(4-(5-(5-cyclopropyl-1H-pyrazol-3-ylamino)imidazo[1,2-f]pyrimidin-7-ylthio)phenyl)(morpholino)methanone

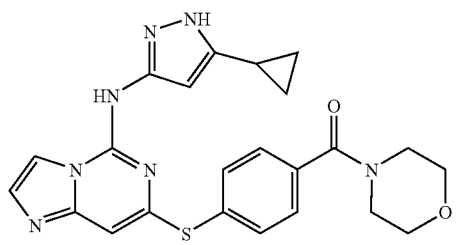

The title compound was synthesized using morpholine following the procedure described in the synthesis of Example 174. $^1$H NMR (400 MHz, CD$_3$OD) 8.23 (s, 1H) 7.89 (s, 1H) 7.79 (d, J=8.32 Hz, 2H) 7.61 (d, J=8.32 Hz, 2H) 6.67 (s, 1H) 6.14 (s, 1H) 3.78-3.65 (d, J=50.7 Hz, 6H) 3.48 (s, 2H) 1.94 (m, 1H) 1.00 (m, 2H) 0.72 (m, 2H). [M+H] calc'd for $C_{23}H_{23}N_7O_2S$, 462; found, 462.

Example 186

N-cyclopropyl-4-(5-(5-methyl-1H-pyrazol-3-ylamino)imidazo[1,2-f]pyrimidin-7-ylthio)benzamide

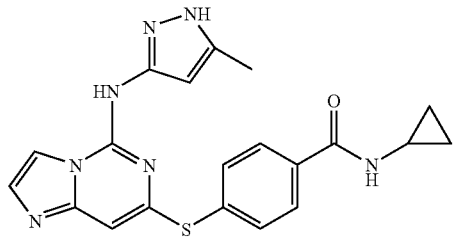

The title compound was synthesized using cyclopropanamine following the procedure described in the synthesis of Example 174. $^1$H NMR (400 MHz, CD$_3$OD) 8.26 (s, 1H) 7.79 (d, J=7.84 Hz, 2H) 7.84 (s, 1H) 7.76 (d, J=8.08 Hz, 2H) 6.89 (s, 1H) 5.75 (s, 1H) 2.88 (m, 1H) 2.15 (s, 3H) 0.85 (m, 2H) 0.66 (m, 2H). [M+H] calc'd for $C_{23}H_{23}N_7O_2S$, 462; found, 462.

Example 187

N-ethyl-4-(5-(5-methyl-1H-pyrazol-3-ylamino)imidazo[1,2-f]pyrimidin-7-ylthio)benzamide

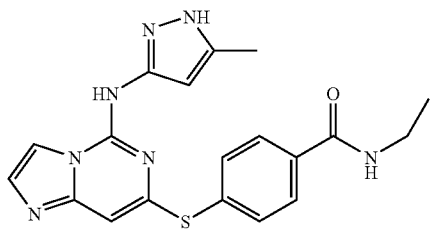

The title compound was synthesized using ethanamine following the procedure described in the synthesis of Example 174. $^1$H NMR (400 MHz, CD$_3$OD) 8.27 (s, 1H) 8.00 (d, J=8.56 Hz, 2H) 7.84 (s, 1H) 7.78 (d, J=8.6 Hz, 2H) 6.89 (s, 1H) 5.78 (s, 1H) 3.47 (m, 2H) 2.16 (s, 3H) 1.26 (m, 3H). [M+H] calc'd for $C_{19}H_{19}N_7OS$, 394; found, 394.

Example 188

N-(5-cyclopropyl-1H-pyrazol-3-yl)-7-(4-(5-ethyl-1,3,4-oxadiazol-2-yl)phenylthio)imidazo[1,2-f]pyrimidin-5-amine

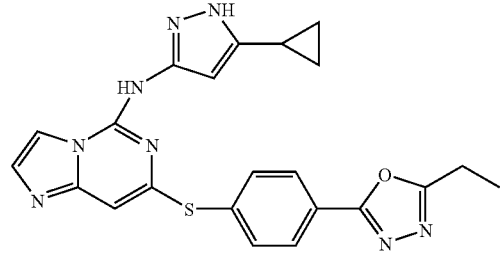

Referring to Scheme 10, 4 4-(tritylthio)benzohydrazide (407 mg, 0.99 mmol, 1 eq), is reacted with Triethyl orthopropionate (2 ml, 10.0 ml 10 eq) in a microwave reactor at 120° C. for 20 minutes. LCMS confirmed the product. Excess propionate was removed under a stream of nitrogen to leave Compound D that was used without further purification. Compound D was dissolved in dioxane (2 ml) and 3 drops of acetic acid was added. This mixture was reacted in a microwave reactor at 170° C. for 20 minutes. TLC and LCMS confirmed the intended product. The solvent was removed and the residue purified by flash chromatography to leave 2-ethyl-5-(4-(tritylthio)phenyl)-1,3,4-oxadiazole-Compound E. 220 mg (49% yield). [M+H] calc'd for $C_{29}H_{24}N_2OS$, 449; found, 449.

2-Ethyl-5-(4-(tritylthio)phenyl)-1,3,4-oxadiazole was dissolved in trifluoroacetic acid (5 ml) and a large excess of triethyl silane (500 µl) was added. The solution was stirred for 10 minutes then the solvent was removed under a stream of nitrogen to leave 4-(5-ethyl-1,3,4-oxadiazol-2-yl)benzenethiol-Compound F 98 mg (99%).

4-(5-Ethyl-1,3,4-oxadiazol-2-yl)benzenethiol (53 mg, 0.26 mmol, 1.3 eq) and 7-chloro-N-(5-cyclopropyl-1H-pyrazol-3-yl)imidazo[1,2-f]pyrimidin-5-amine (50 mg, 0.20 mmol, 1 eq) were dissolved in DMF (2 ml) and reacted in a microwave reactor at 190° C. for 15 minutes. The solvent was removed in vacuo and the residue purified by high-performance liquid chromatography to leave N-(5-cyclopropyl-1H-pyrazol-3-yl)-7-(4-(5-ethyl-1,3,4-oxadiazol-2-yl)phenylthio)imidazo[1,2-f]pyrimidin-5-amine as a tan solid, 30 mg (37%). $^1$H NMR (400 MHz, CD$_3$OD) 8.27 (s, 1H) 8.17 (d, J=8.6 Hz, 2H) 7.85 (m, 3H) 6.98 (s, 1H) 5.81 (s, 1H) 3.03 (m, 2H) 1.69 (m, 1H) 1.44 (m, 3H) 0.78 (m, 2H) 0.51 (m, 2H). [M+H] calc'd for C$_{22}$H$_{20}$N$_8$OS, 445; found, 445.

Example 189

7-(4-(5-ethyl-1,3,4-oxadiazol-2-yl)phenylthio)-N-(5-methyl-1H-pyrazol-3-yl)imidazo[1,2-f]pyrimidin-5-amine

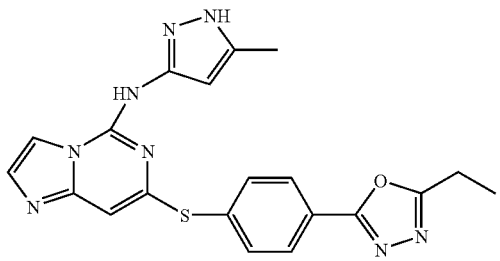

The title compound was synthesized using 7-chloro-N-(5-methyl-1H-pyrazol-3-yl)imidazo[1,2-f]pyrimidin-5-amine following the procedure described in the synthesis of Example 188. $^1$H NMR (400 MHz, CD$_3$OD) 8.27 (s, 1H) 8.19 (d, J=8.56 Hz, 2H) 7.86 (m, 3H) 6.97 (s, 1H) 5.83 (s, 1H) 3.05 (m, 2H) 2.06 (s, 3H) 1.46 (m, 3H). [M+H] calc'd for C$_{20}$H$_{18}$N$_8$OS, 419; found, 419.

Example 190

7-(4-(1,3,4-Oxadiazol-2-yl)phenylthio)-N-(5-cyclopropyl-1H-pyrazol-3-yl)imidazo[1,2-f]pyrimidin-5-amine

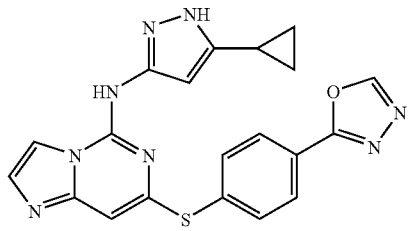

The title compound was synthesized using 7-chloro-N-(5-cyclopropyl-1H-pyrazol-3-yl)imidazo[1,2-f]pyrimidin-5-amine following the procedure described in the synthesis of Example 188. $^1$H NMR (400 MHz, CD$_3$OD) 9.10 (s, 1H) 8.28 (s, 1H) 8.19-8.21 (m, 2H) 7.84-7.87 (m, 3H) 7.00 (s, 1H) 5.81 (s, 1H) 1.64-1.69 (m, 1H) 0.76-0.80 (m, 2H) 0.40-0.60 (m, 2H). [M+H] calc'd for C$_{20}$H$_{17}$N$_8$OS, 417; found, 417.

Example 191

7-(4-(1,3,4-oxadiazol-2-yl)phenylthio)-N-(5-methyl-1H-pyrazol-3-yl)imidazo[1,2-f]pyrimidin-5-amine

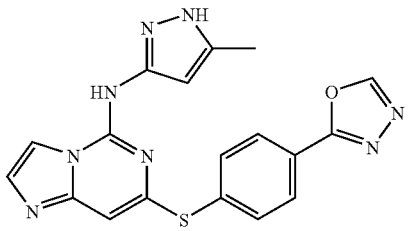

The title compound was synthesized using 7-chloro-N-(5-methyl-1H-pyrazol-3-yl)imidazo[1,2-f]pyrimidin-5-amine following the procedure described in the synthesis of Example 188. $^1$H NMR (400 MHz, CD$_3$OD) 9.07 (s, 1H) 8.12-8.15 (m, 2H) 8.01 (s, 1H) 7.78-7.80 (m, 2H) 7.51 (s, 1H) 6.88 (s, 1H) 5.90 (s, 1H) 5.49 (s, 1H) 2.03 (s, 3H). [M+H] calc'd for C$_{18}$H$_{15}$N$_8$OS, 391; found, 391.

Example 192

7-(4-(5-Methyl-1,3,4-oxadiazol-2-yl)phenylthio)-N-(5-methyl-1H-pyrazol-3-yl)imidazo[1,2-f]pyrimidin-5-amine

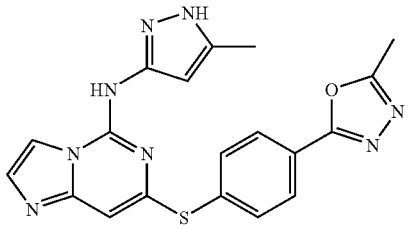

The title compound was synthesized using 7-chloro-N-(5-methyl-1H-pyrazol-3-yl)imidazo[1,2-f]pyrimidin-5-amine following the procedure described in the synthesis of Example 188. $^1$H NMR (400 MHz, CD$_3$OD) 8.27 (br.s., 1H)

8.15-8.27 (m, 2H) 7.83-7.86 (m, 3H) 6.95 (s, 1H) 5.84 (s, 1H) 2.65 (s, 3H) 2.07 (s, 3H). [M+H] calc'd for $C_{19}H_{17}N_8OS$, 405; found, 405.

Example 193

N-(5-Cyclopropyl-1H-pyrazol-3-yl)-7-(4-(5-methyl-1,3,4-oxadiazol-2-yl)phenylthio)imidazo[1,2-f]pyrimidin-5-amine

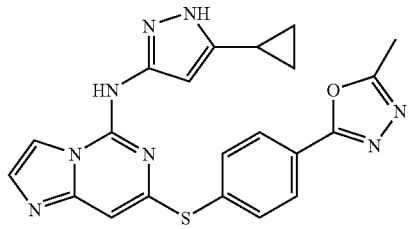

The title compound was synthesized using 7-chloro-N-(5-cyclopropyl-1H-pyrazol-3-yl)imidazo[1,2-f]pyrimidin-5-amine following the procedure described in the synthesis of Example 188. $^1$H NMR (400 MHz, CD$_3$OD) 8.28 (br.s., 1H) 8.13-8.16 (m, 2H) 7.82-7.87 (m, 3H) 6.98 (s, 1H) 5.83 (s, 1H) 2.66 (s, 3H) 1.68-1.72 (m, 1H), 0.80-0.83 (m, 2H), 0.45-0.60 (m, 2H). [M+H] calc'd for $C_{21}H_{19}N_8OS$, 431; found, 431.

Example 194

N-(4-(5-(5-Methyl-1H-pyrazol-3-ylamino)imidazo[1,2-f]pyrimidin-7-yloxy)phenyl)acetamide

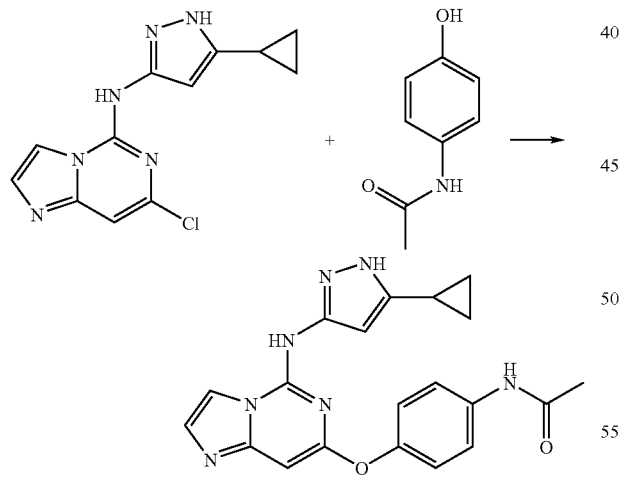

Referring to Scheme 12, a mixture of (7-Chloro-imidazo[1,2-c]pyrimidin-5-yl)-(5-cyclopropyl-1H-pyrazol-3-yl)-amine (125 mg, 0.46 mmol), N-(4-Hydroxy-phenyl)-acetamide (689 mg, 4.56 mmol) and K$_2$CO$_3$ (630 mg) was mixed in DMF (1 ml) was heated at 200° C. in microwave for 15 minutes. The reaction mixture was then purified with HPLC to give the title compound (30 mg) as a solid. $^1$H NMR (400 MHz, CD$_3$OD) 7.97 (s, 1H) 7.68-7.70 (m, 2H) 7.45 (s, 1H) 7.10-7.12 (m, 2H) 6.35 (s, 1H) 5.74 (s, 1H) 2.15 (s, 3H) 1.75 (m, 1H) 0.87-0.89 (m, 2H) 0.49 (m, 2H). [M+H] calc'd for $C_{20}H_{20}N_7O_2S$, 390; found, 390.

Example 195

2-methyl-N-(5-methyl-1H-pyrazol-3-yl)-7-phenylimidazo[1,2-f]pyrimidin-5-amine

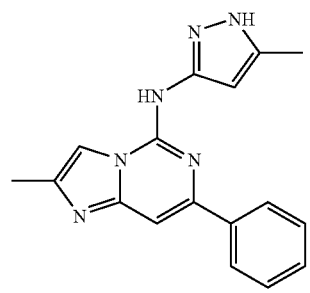

The title compound was synthesized following a procedure analogous to that described in Example 12. $^1$H NMR (400 MHz, CD$_3$OD) 8.15 (m, 2H) 8.05 (s, 1H) 7.58 (s, 1H) 7.54 (m, 3H) 6.60 (s, 1H) 2.55 (s, 3H) 2.39 (s, 3H). [M+H] calc'd for $C_{17}H_{16}N_6$, 304; found, 304.

Example 196

N-cyclopropyl-2-(3-(2-methyl-5-(5-methyl-1H-pyrazol-3-ylamino)imidazo[1,2-f]pyrimidin-7-yl)phenyl)acetamide

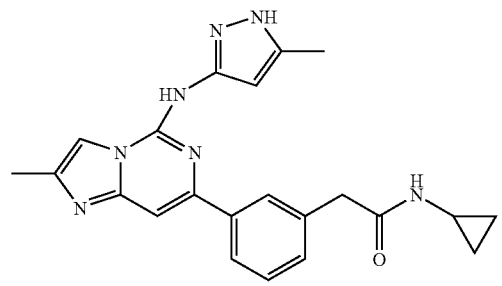

The title compound was synthesized following a procedure analogous to that described in Example 12. $^1$H NMR (400 MHz, CD$_3$OD) 7.99 (m, 2H) 7.75 (s, 1H) 7.44 (s, 1H) 7.40 (d, J=32.84 Hz, 3H) 6.64 (s, 1H) 3.55 (s, 2H) 3.34 (s, 1H) 2.67

(m, 1H) 2.40 (d, J=17.44 Hz, 6H) 1.28 (s, 2H) 0.70 (m, 2H) 0.49 (m, 2H). [M+H] calc'd for C$_{22}$H$_{18}$N$_7$O, 402; found, 402.

Example 197

7-(3-(ethylsulfonyl)phenyl)-2-methyl-N-(5-methyl-1H-pyrazol-3-yl)imidazo[1,2-f]pyrimidin-5-amine

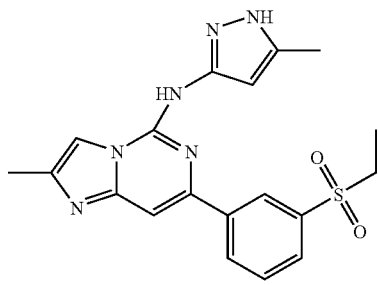

The title compound was synthesized following a procedure analogous to that described in Example 12. $^1$H NMR (400 MHz, CD$_3$OD) 8.80 (s, 1H) 8.49 (d, J=7.56 Hz, 1H) 8.10 (s, 1H) 8.06 (d, J=6.84 Hz 1H) 7.82 (m, 1H) 7.76 (s, 1H) 6.65 (s, 1H) 2.57 (s, 3H) 2.40 (s, 3H) 1.25 (m, 3H). [M+H] calc'd for C$_{19}$H$_{20}$N$_6$O$_2$S, 396; found, 397.

Example 198

2-methyl-N-(5-methyl-1H-pyrazol-3-yl)-7-(3-methylsulfonyl)phenyl) imidazo[1,2-f]pyrimidin-5-amine

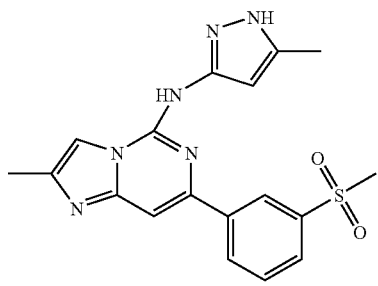

The title compound was synthesized following a procedure analogous to that described in Example 12. $^1$H NMR (400 MHz, CD$_3$OD) 8.84 (s, 1H) 8.47 (s, 1H) 8.09 (s, 1H) 7.80 (m, 2H) 6.65 (s, 1H) 3.19 (s, 3H) 2.57 (s, 3H) 2.40 (s, 3H). [M+H] calc'd for C$_{18}$H$_{18}$N$_6$O$_2$S, 383; found, 383.

Example 199

2-methoxy-N-methyl-5-(2-methyl-5-(5-methyl-1H-pyrazol-3-ylamino) imidazo[1,2-f]pyrimidin-7-yl) benzenesulfonamide

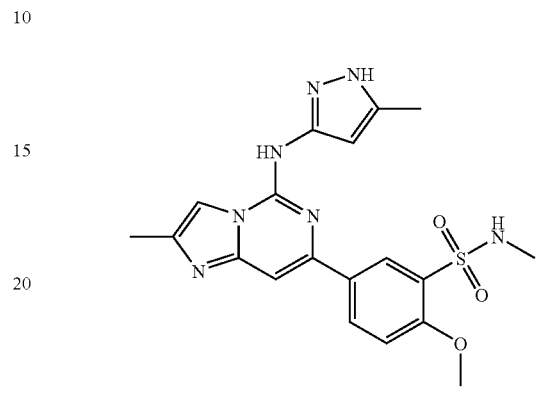

The title compound was synthesized following a procedure analogous to that described in Example 12. $^1$H NMR (400 MHz, CD$_3$OD) 8.76 (s, 1H) 8.37 (d, J=8.6 Hz, 1H) 8.03 (s, 1H) 7.57 (m, 1H) 7.35 (d, J=8.84 Hz, 1H) 6.69 (s, 1H) 4.06 (s, 3H) 2.53 (s, 6H) 2.40 (s, 3H). [M+H] calc'd for C$_{19}$H$_{21}$N$_7$O$_3$S, 428; found, 428.

Example 200

2-methoxy-N-methyl-5-(2-methyl-5-(5-methyl-1H-pyrazol-3-ylamino) imidazo[1,2-f]pyrimidin-7-yl) benzenesulfonamide

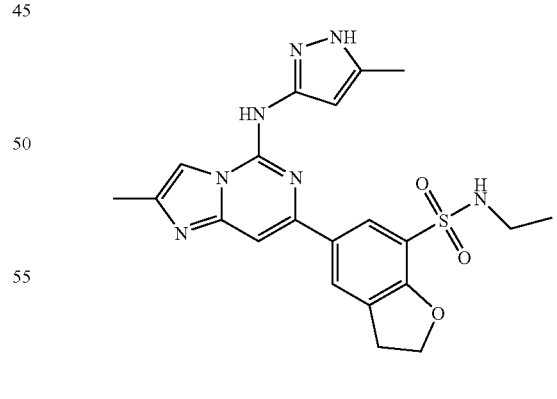

The title compound was synthesized following a procedure analogous to that described in Example 12. $^1$H NMR (400 MHz, CD$_3$OD) 8.57 (s, 1H) 8.24 (s, 1H) 8.04 (s, 1H) 7.56 (s, 1H) 6.66 (s, 1H) 2.98 (m, 2H) 2.54 (s, 3H) 2.39 (s, 3H) 1.08 (m, 3H). [M+H] calc'd for $C_{21}H_{23}N_7O_3S$, 454; found, 454.

Example 201

N-ethyl-N-methyl-3-(2-methyl-5-(5-methyl-1H-pyrazol-3-ylamino) imidazo[1,2-f]pyrimidin-7-yl) benzenesulfonamide

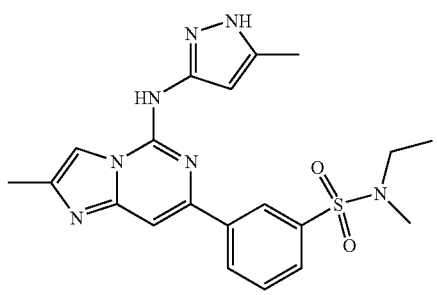

The title compound was synthesized following a procedure analogous to that described in Example 12. $^1$H NMR (400 MHz, CD$_3$OD) 8.58 (s, 1H) 8.32 (d, J=8.08 Hz, 1H) 8.05 (s, 1H) 7.87 (d, J=8.56 Hz, 1H) 7.72 (d, J=7.84 Hz, 1H) 7.67 (s, 1H) 6.57 (s, 1H) 3.31 (s, 3H) 3.09 (m, 2H) 2.73 (s, 3H) 2.56 (s, 3H) 2.38 (s, 3H) 1.10 (m, 3H). [M+H] calc'd for $C_{20}H_{23}N_7O_2S$, 426; found, 426.

Example 202

N-ethyl-N-methyl-3-(2-methyl-5-(5-methyl-1H-pyrazol-3-ylamino) imidazo[1,2-f]pyrimidin-7-yl) benzenesulfonamide

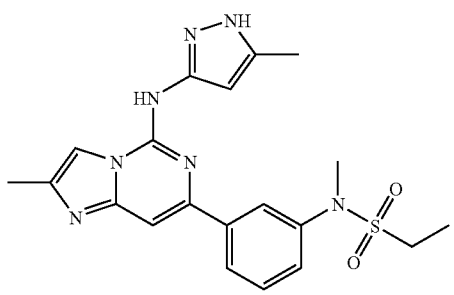

The title compound was synthesized following a procedure analogous to that described in Example 12. $^1$H NMR (400 MHz, CD$_3$OD) 8.35 (s, 1H) 8.06 (s, 1H) 7.88 (d, J=7.84 Hz, 1H) 7.56 (s, 1H) 7.42 (d, J=8.36 Hz, 1H) 6.77 (s, 1H) 3.17 (m, 2H) 2.55 (s, 3H) 2.43 (d, J=13.12 Hz, 6H) 1.36 (m, 3H). [M+H] calc'd for $C_{20}H_{23}N_7O_2S$, 426; found, 426.

Example 203

N-(3-(2-Methyl-5-(5-methyl-1H-pyrazol-3-ylamino) imidazo[1,2-f]pyrimidin-7-yl)phenyl)cyclopropane-sulfonamide

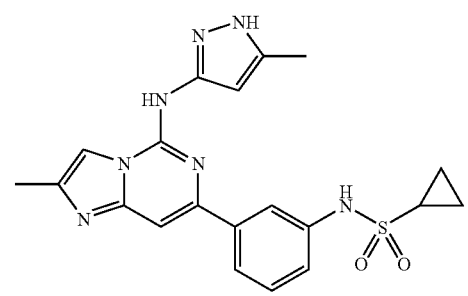

The title compound was synthesized following a procedure analogous to that described in Example 12. $^1$H NMR (400 MHz, CD$_3$OD) 8.19 (br.s., 1H) 7.80 (br.d., 1H) 7.24-7.44 (m, 4H) 6.75 (br.s., 1H) 2.56-2.62 (m, 1H) 2.43 (s, 3H) 2.38 (s, 3H) 1.06-1.09 (m, 2H), 0.94-0.97 (m, 2H). [M+H] calc'd for $C_{20}H_{22}N_7O_2S$, 424; found, 424

Example 204

N-Ethyl-2-methoxy-5-(2-methyl-5-(5-methyl-1H-pyrazol-3-ylamino) imidazo[1,2-f]pyrimidin-7-yl) benzenesulfonamide

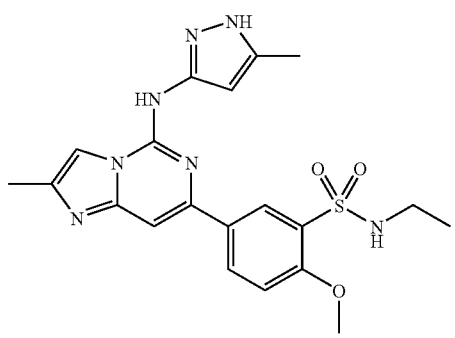

The title compound was synthesized following a procedure analogous to that described in Example 12. $^1$H NMR (400 MHz, CD$_3$OD) 8.68 (d, J=2.4, 1H) 8.27 (dd, J=8.8, 2.4, 1H) 7.97 (s., 1H) 7.52 (s, 1H) 7.28 (d, J=8.8, 1H) 6.61 (s, 1H) 4.05

(s, 3H) 2.91 (q, J=7.2, 2H) 2.53 (s, 3H) 2.38 (s, 3H) 1.05 (t, J=7.2, 3H). [M+H] calc'd for $C_{20}H_{23}N_7O_3S$, 442; found, 442.

Example 205

N-(3-(2-Methyl-5-(5-methyl-1H-pyrazol-3-ylamino)imidazo[1,2-f]pyrimidin-7-yl)phenyl)ethanesulfonamide

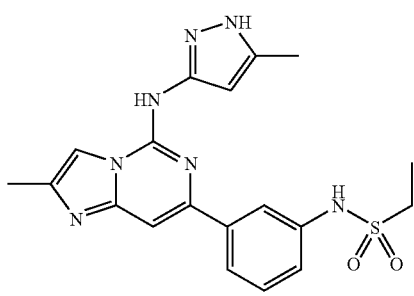

The title compound was synthesized following a procedure analogous to that described in Example 12. $^1$H NMR (400 MHz, CD$_3$OD) 8.21 (s, 1H) 8.04 (s, 1H) 7.80 (d, J=7.6, 1H) 7.55 (s, 1H) 7.45 (t, J=8.0, 1H) 7.24-7.26 (m, 1H) 6.72 (s, 1H) 3.98 (s, 1H) 3.14 (q, J=7.6, 2H) 2.54 (s, 3H) 2.39 (s, 3H) 1.31 (t, J=7.6, 3H). [M+H] calc'd for $C_{19}H_{22}N_7O_2S$, 412; found, 412.

Example 206

N-(2-Methoxy-5-(2-methyl-5-(5-methyl-1H-pyrazol-3-ylamino) imidazo[1,2-f]pyrimidin-7-yl)phenyl) cyclopropanesulfonamide

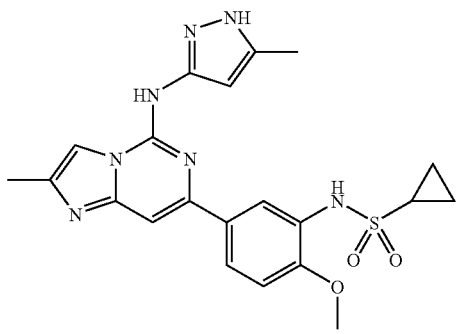

The title compound was synthesized following a procedure analogous to that described in Example 12. $^1$H NMR (400 MHz, CD$_3$OD) 8.83 (d, J=2.4, 1H) 8.39 (dd, J=8.8, 2.4, 1H) 8.05 (s., 1H) 7.59 (s, 1H) 7.37 (d, J=8.8, 1H) 6.69 (s, 1H) 4.07 (s, 3H) 2.55 (s, 3H) 2.41 (s, 3H) 2.11-2.15 (m, 1H) 0.43-0.65 (m, 4H). [M+H] calc'd for $C_{21}H_{24}N_7O_3S$, 454; found, 454.

Example 207

N-(3-(2-Methyl-5-(5-methyl-1H-pyrazol-3-ylamino)imidazo[1,2-f]pyrimidin-7-yl)phenyl)methanesulfonamide

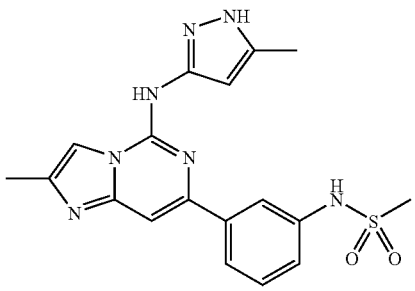

The title compound was synthesized following a procedure analogous to that described in Example 12. $^1$H NMR (400 MHz, CD$_3$OD) 8.26 (m, 1H) 8.07 (s, 1H) 7.87 (d, J=8.0, 1H) 7.58 (s, 1H) 7.49 (t, J=8.0, 1H) 6.74 (s, 1H) 3.01 (s, 3H) 2.57 (s, 3H) 2.40 (s, 3H). [M+H] calc'd for $C_{18}H_{20}N_7O_2S$, 398; found, 398.

Example 208

N-(4-(2-Methyl-5-(5-methyl-1H-pyrazol-3-ylamino)imidazo[1,2-f]pyrimidin-7-yl)phenyl)methanesulfonamide

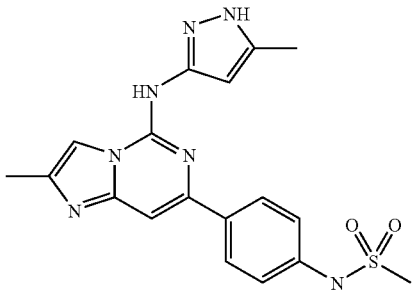

The title compound was synthesized following a procedure analogous to that described in Example 12. $^1$H NMR (400 MHz, CD$_3$OD) 8.14 (d, J=8.8, 2H) 8.03 (s, 1H) 7.54 (s, 1H)

7.39 (d, J=8.8, 2H) 6.58 (s, 1H) 3.05 (s, 3H) 2.54 (s, 3H) 2.39 (s, 3H). [M+H] calc'd for $C_{18}H_{20}N_7O_2S$, 398; found, 398.

Example 209

Cyclopropanecarboxylic acid 4-fluoro-3-[5-(5-methyl-1H-pyrazol-3-ylamino)-imidazo[1,2-c]pyrimidin-7-yl]-benzylamide

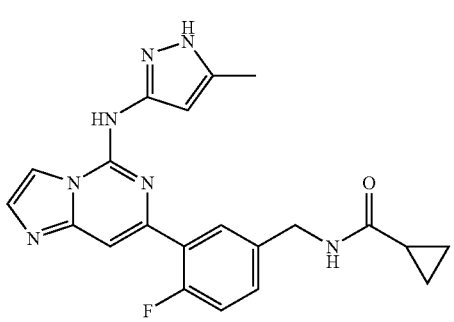

The title compound was synthesized following a procedure analogous to that described in Example 12. $^1$H NMR (400 MHz, MeOD-d$_4$) δ 8.39 (s, 1H), 8.15 (d, J=7.2 Hz, 1H), 7.99 (s, 1H), 7.67 (s, 1H), 7.45-7.51 (m, 1H), 7.25-7.31 (m, 1H), 6.62 (s, 1H), 4.45 (s, 2H), 2.39 (s, 3H), 1.57-1.62 (m, 1H), 0.82-0.88 (m, 2H), 0.71-0.78 (m, 2H). [M+H] calc'd for $C_{21}H_{20}FN_7O$, 406; found, 406.

Example 210

Cyclopropanecarboxylic acid 4-fluoro-3-[2-methyl-5-(5-methyl-1H-pyrazol-3-ylamino)-imidazo[1,2-c]pyrimidin-7-yl]-benzylamide

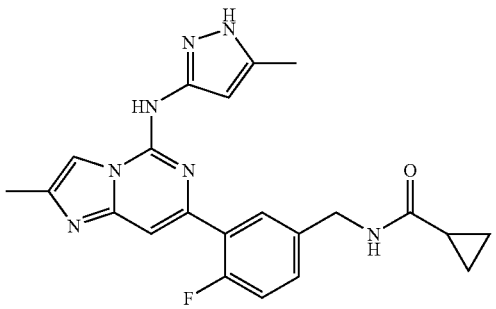

The title compound was synthesized following a procedure analogous to that described in Example 12. $^1$H NMR (400 MHz, MeOD-d$_4$) δ 8.14 (d, J=7.2 Hz, 1H), 8.09 (s, 1H), 7.58 (s, 1H), 7.45-7.51 (m, 1H), 7.24-7.30 (m, 1H), 6.61 (s, 1H), 4.43 (s, 2H), 2.55 (s, 3H), 2.38 (s, 3H), 1.54-1.61 (m, 1H), 0.82-0.88 (m, 2H), 0.70-0.77 (m, 2H). [M+H] calc'd for $C_{22}H_{22}FN_7O$, 420; found, 420.

Example 211

5-[2-Methyl-5-(5-methyl-1H-pyrazol-3-ylamino)-imidazo[1,2-c]pyrimidin-7-yl]-1,3-dihydro-benzoimidazol-2-one

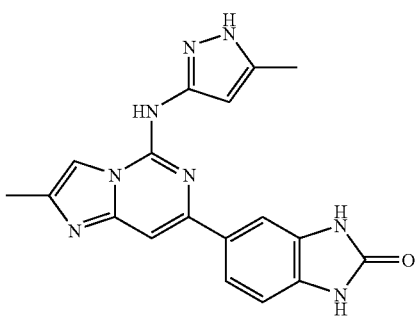

The title compound was synthesized following a procedure analogous to that described in Example 12. $^1$H NMR (400 MHz, DMSO-d$_6$) δ 12.39 (s, 1H), 10.97 (s, 1H), 10.94 (s, 1H), 10.77 (s, 1H), 8.29 (s, 1H), 7.82 (d, J=7.6 Hz, 1H), 7.75 (s, 1H), 7.55 (s, 1H), 7.07 (d, J=7.6 Hz, 1H), 6.60 (s, 1H), 2.43 (s, 3H), 2.34 (s, 3H). [M+H] calc'd for $C_{18}H_{16}N_8O$, 361; found, 361.

Example 212

Cyclopropanesulfonic acid methyl-{3-[2-methyl-5-(5-methyl-1H-pyrazol-3-ylamino)-imidazo[1,2-c]pyrimidin-7-yl]-phenyl}-amide

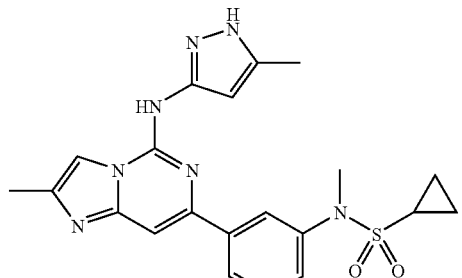

The title compound was synthesized following a procedure analogous to that described in Example 12. $^1$H NMR (400 MHz, MeOD-d$_4$) δ 8.28 (s, 1H), 7.96 (s, 1H), 7.76 (s, 1H), 7.45-7.51 (m, 2H), 7.40 (s, 1H), 6.69 (s, 1H), 3.41 (s, 3H), 2.51-2.60 (m, 1H), 2.42 (s, 3H), 2.35 (s, 3H), 0.90-0.98 (m, 4H). [M+H] calc'd for $C_{21}H_{23}N_7O_2S$, 438; found, 438.

Example 213

(5-Methyl-1H-pyrazol-3-yl)-(2-methyl-7-pyridin-2-yl-imidazo[1,2-c]pyrimidin-5-yl)-amine

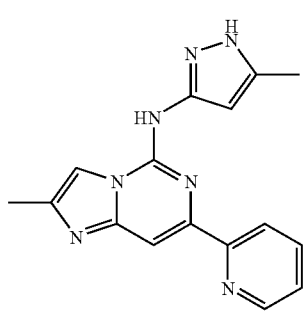

The title compound was synthesized following a procedure analogous to that described in Example 12. $^1$H NMR (400 MHz, MeOD-d$_4$) δ 8.63 (s, 1H), 8.20-8.33 (m, 2H), 7.91 (t, J=7.6 Hz, 1H), 7.79 (s, 1H), 7.38-7.45 (m, 1H), 6.51 (s, 1H), 2.42 (s, 3H), 2.35 (s, 3H). [M+H] calc'd for $C_{16}H_{15}N_7$, 306; found, 306.

Example 214

[7-(1-Ethanesulfonyl-1H-indol-6-yl)-2-methyl-imidazo[1,2-c]pyrimidin-5-yl]-(5-(5-methyl-1H-pyrazol-3-yl)-amine

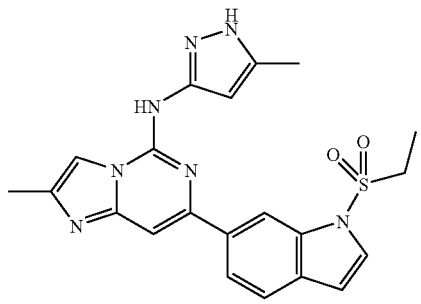

The title compound was synthesized following a procedure analogous to that described in Example 12. $^1$H NMR (400 MHz, MeOD-d$_4$) δ 8.89 (s, 1H), 7.96 (d, J=8.4 Hz, 1H), 7.79 (s, 1H), 7.71 (d, J=8.4 Hz, 1H), 7.59 (d, J=3.6 Hz, 1H), 7.46 (s, 1H), 6.86 (s, 1H), 6.79 (d, J=3.6 Hz, 1H), 3.48 (q, J=7.2 Hz, 2H), 2.42 (s, 6H), 1.15 (t, J=7.2 Hz, 3H). [M+H] calc'd for $C_{21}H_{21}N_7O_2S$, 436; found, 436.

Example 215

Ethanesulfonic acid methyl-{3-[2-methyl-5-(5-methyl-1H-pyrazol-3-ylamino)-imidazo[1,2-c]pyrimidin-7-yl]-benzyl}-amide

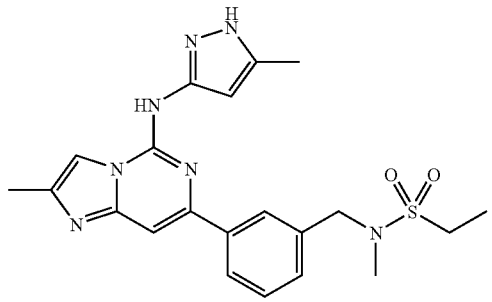

The title compound was synthesized following a procedure analogous to that described in Example 12. $^1$H NMR (400 MHz, MeOD-d$_4$) δ 8.09 (s, 1H), 7.92 (s, 1H), 7.71 (s, 1H), 7.26-7.45 (m, 3H), 6.61 (s, 1H), 4.40 (s, 2H), 3.11 (q, J=7.2 Hz, 2H), 2.80 (s, 3H), 2.39 (s, 3H), 2.36 (s, 3H), 1.36 (t, J=7.2 Hz, 3H). [M+H] calc'd for $C_{21}H_{25}N_7O_2S$, 440; found, 440.

Example 216

Ethanesulfonic acid {5-[2-methyl-5-(5-methyl-1H-pyrazol-3-ylamino)-imidazo[1,2-c]pyrimidin-7-yl]-1H-indol-7-yl}-amide

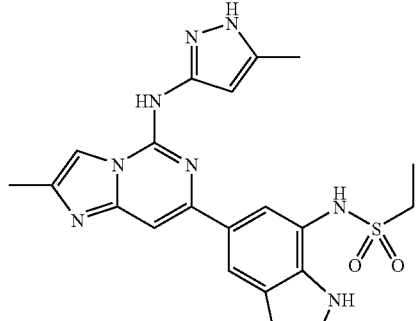

The title compound was synthesized following a procedure analogous to that described in Example 12. $^1$H NMR (400 MHz, MeOD-d$_4$) δ 8.14 (s, 1H), 7.97 (s, 1H), 7.72 (s, 1H), 7.30-7.39 (m, 2H), 6.75 (s, 1H), 6.59 (s, 1H), 3.16 (q, J=7.2

Hz, 2H), 2.41 (s, 3H), 2.38 (s, 3H), 1.35 (t, J=7.2 Hz, 3H). [M+H] calc'd for $C_{21}H_{22}N_8O_2S$, 451; found, 451.

Example 217

N-ethyl-2-methoxy-N-methyl-5-(2-methyl-5-(5-methyl-1H-pyrazol-3-ylamino)imidazo[1,2-f]pyrimidin-7-yl)benzenesulfonamide

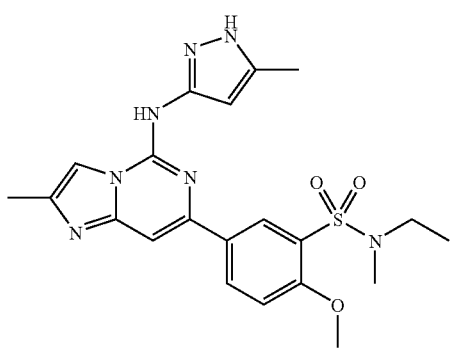

The title compound was synthesized following a procedure analogous to that described in Example 12. $^1$H NMR (400 MHz, DMSO) δ 8.72 (s, 1H) 8.41 (d, J=9.1 Hz, 1H) 8.36 (s, 1H) 7.71 (s, 1H) 7.41 (d, J=9.1 Hz, 1H) 6.66 (s, 1H) 3.98 (s, 3H) 3.16 (q, J=6.8 Hz, 2H) 2.78 (s, 3H) 2.44 (s, 3H) 2.29 (s, 3H) 1.03 (t, J=6.8 Hz, 3H). [M+H] calc'd for $C_{21}H_{25}N_7O_3S$, 455; found, 456.

Example 218

N-(cyclopropylmethyl)-2-methoxy-5-(2-methyl-5-(5-methyl-1H-pyrazol-3-ylamino) imidazo[1,2-f]pyrimidin-7-yl)benzenesulfonamide

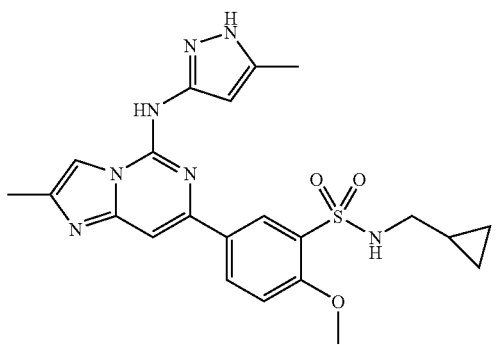

The title compound was synthesized following a procedure analogous to that described in Example 12. $^1$H NMR (400 MHz, DMSO) δ 8.71 (s, 1H) 8.40 (d, J=8.8 Hz, 1H) 8.36 (s, 1H) 7.69 (s, 1H) 7.38 (d, J=8.8 Hz, 1H) 6.67 (s, 1H) 3.99 (s, 3H) 2.72 (br, 2H) 2.45 (s, 3H) 2.31 (s, 3H) 0.71 (m, 1H) 0.24 (m, 2H) 0.02 (m, 2H). [M+H] calc'd for $C_{22}H_{25}N_7O_3S$, 467; found, 468.

Example 219

N-cyclopropyl-3-(2-methyl-5-(5-methyl-1H-pyrazol-3-ylamino)imidazo[1,2-f]pyrimidin-7-yl)benzenesulfonamide

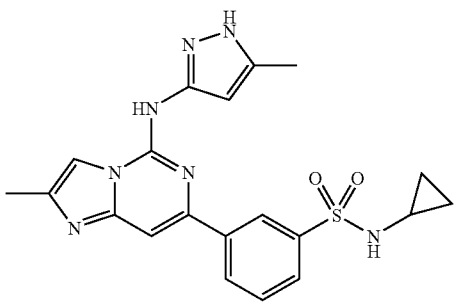

The title compound was synthesized following a procedure analogous to that described in Example 12. $^1$H NMR (400 MHz, DMSO) δ 8.69 (s, 1H) 8.44 (d, J=8.0 Hz, 1H) 8.32 (s, 1H) 7.90 (d, J=8.0 Hz, 1H) 7.77 (m, 1H) 7.73 (s, 1H) 6.67 (s, 1H) 2.42 (s, 3H) 2.29 (s, 3H) 2.12 (m, 1H) 0.46 (m, 2H), 0.38 (m, 2H). [M+H] calc'd for $C_{20}H_{21}N_7O_2S$, 423; found, 424.

Example 220

N-ethyl-3-(2-methyl-5-(5-methyl-1H-pyrazol-3-ylamino)imidazo[1,2-f]pyrimidin-7-yl)benzenesulfonamide

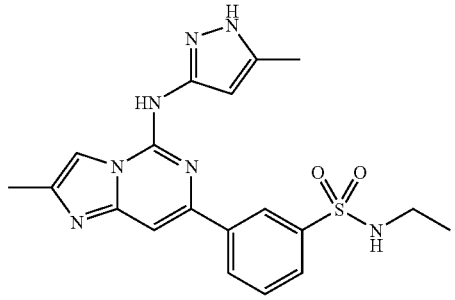

The title compound was synthesized following a procedure analogous to that described in Example 12. $^1$H NMR (400 MHz, DMSO) δ 8.65 (s, 1H) 8.43 (d, J=7.6 Hz, 1H) 8.37 (s, 1H) 7.92 (d, J=8.0 Hz, 1H) 7.77 (m, 1H) 7.67 (s, 1H) 6.65 (s, 1H) 2.83 (q, J=6.8 Hz, 2H) 2.45 (s, 3H) 2.30 (s, 3H) 0.97 (t, J=6.8 Hz, 3H). [M+H] calc'd for $C_{19}H_{21}N_7O_2S$, 411; found, 412.

Example 221

7-Chloro-N-(5-cyclopropyl-1H-pyrazol-3-yl)-2-(isopropoxymethyl) imidazo[1,2-f]pyrimidin-5-amine

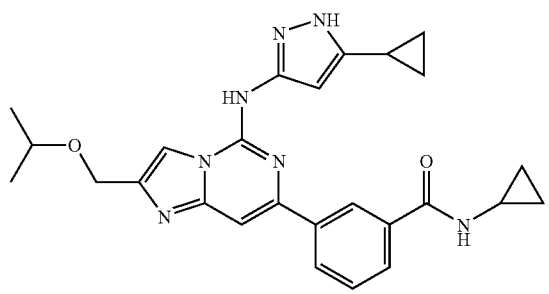

The title compound was synthesized following a procedure analogous to that described in Example 12. $^1$HNMR (400 MHz, MeOD) δppm 0.69 (m, 2H) 0.81-0.92 (m, 4H) 1.02-1.10 9 m, 2H) 1.24 (m, 7H) 2.44 s, 2H) 2.72-2.81 (m, 1H) 2.86-2.96 (m, 1H) 6.67 s, 1H) 7.50 (s, 1H) 7.62 (t, J=7.83 Hz, 1H) 7.90 (d, J=8.08 Hz, 1H) 8.27 (d, J=7.33 Hz, 1H) 8.59 (s, 1H). MS [m+H] calc'd, 472.4 and 473.4; found 472.4 and 473.4.

Example 222

7-Chloro-N-(5-cyclopropyl-1H-pyrazol-3-yl)-2-(isopropoxymethyl) imidazo[1,2-f]pyrimidin-5-amine

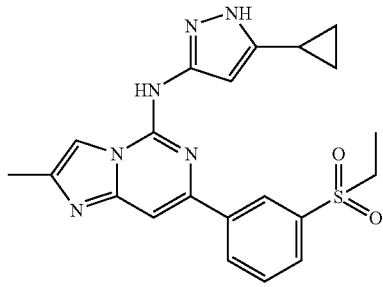

The title compound was synthesized following a procedure analogous to that described in Example 12. $^1$HNMR (400 MHz, MeOD) δppm 0.89 (s, 2H) 1.04 (s, 2H) 1.23-1.31 (m, 3H) 2.00 (s, 1H) 2.54 (s, 3H) 3.25-3.30 (m, 2H) 6.50 (s, 1H) 7.70 (s, 1H), 7.79 (s, 1H) 8.04 (s, 2H) 8.46 (s, 1H) 8.75 (s, 1H). MS [m+H] calc'd for $C_{21}H_{22}N_6O_2S$, 423.3 and 424.3; found 423.3 and 424.3.

Example 223

7-Chloro-N-(5-cyclopropyl-1H-pyrazol-3-yl)-2-(isopropoxymethyl) imidazo[1,2-f]pyrimidin-5-amine

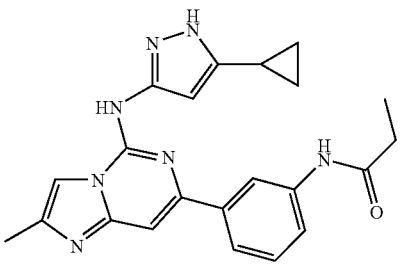

The title compound was synthesized following a procedure analogous to that described in Example 12. $^1$HNMR (400 MHz, MeOD) δppm 0.82 (ddd, J=6.63, 4.74, 4.55 Hz, 2H) 1.01-1.11 (m, 2H) 1.27 (t, J=7.20 Hz, 3H) 1.93-2.04 (m, 1H) 2.56 (s, 3H) 3.47 (q, J=7.24 Hz, 2H) 6.52 (s, 1H) 7.61-7.69 (m, 2H) 7.94 (d, J=7.58 Hz, 1H) 8.06 (s, 1H) 8.30 (d, J=8.08 Hz, 1H) 8.61 (s, 1H). MS [m+H] calc'd $C_{22}H_{23}N_7O$, 402.3 and 403.3; found 402.3 and 403.3.

Example 224

N-{3-[5-(5-Cyclopropyl-1H-pyrazol-3-ylamino)-2-methyl-imidazo[1,2-c]pyrimidin-7-ylsulfanyl]-phenyl}-acetamide

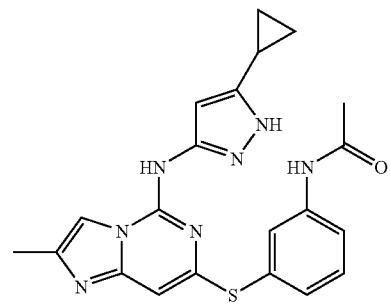

The title compound was synthesized following a procedure analogous to that described in Example 12. $^1$HNMR (400 MHz, MeOD) δppm 0.63-0.70 (m 2H) 0.94-1.02 (m, 2H) 1.82-1.88 (m, 1H) 2.16 (s, 3H) 2.44 (s, 3H) 5.98 (s, 1H) 6.57 (s, 1H) 7.20 (d, J=8.8 Hz, 1H) 7.41 (d, J=8.59 Hz, 1H) 7.59 (d, J=8.59 Hz, 1H), 7.77 (d, J=8.59 Hz, 1H) 7.9 (s, 1H). MS [m+H] calc'd $C_{21}H_{21}N_7OS$, 420.3 and 421.3; found 420.3 and 421.3.

Example 225

N-(5-methyl-1H-pyrazol-3-yl)-7-phenyl-2-(trifluoromethyl)imidazo[1,2-f]pyrimidin-5-amine

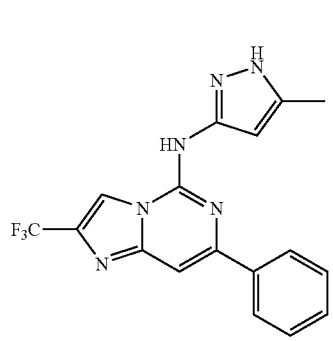

The title compound was synthesized following a procedure analogous to that described in Example 12. $^1$H NMR (400 MHz, DMSO-D6) δ ppm 2.31 (s, 3H) 6.65 (s, 1H) 7.45 (t, J=7.20 Hz, 1H) 7.52 (t, J=7.58 Hz, 2H) 7.64 (s, 1H) 8.13 (d, J=7.58 Hz, 2H) 8.98 (s, 1H) 10.48 (bs, 1H); ESI-MS: m/z 359.3 (M+H)$^+$.

Example 226

3-(2-(Chloromethyl)-5-(5-methyl-1H-pyrazol-3-ylamino)imidazo[1,2-f]pyrimidin-7-yl0-N-cyclopropylbenzamide

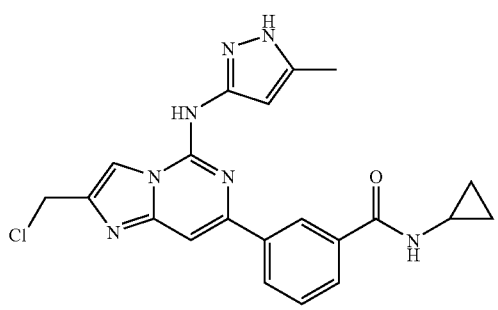

The title compound was synthesized following a procedure analogous to that described in Example 12. $^1$H NMR (400 MHz, DMSO-D6) δ ppm 0.56-0.63 (m, 2H) 0.69-0.77 (m, 2H) 2.31 (s, 3H) 2.88 (td, J=7.45, 3.79 Hz, 1H) 4.90 (s, 2H) 6.68 (s, 1H) 7.58 (t, J=7.71 Hz, 1H) 7.66 (s, 1H) 7.86 (d, J=7.58 Hz, 1H) 8.25 (d, J=7.83 Hz, 1H) 8.52 (d, J=8.84 Hz, 2H) 8.59 (d, J=3.79 Hz, 1H) 10.51 (s, 1H); ESI-MS: m/z 422.4 (M+H)$^+$

Example 227

2-Ethyl-7-(3-(ethylsulfonyl)phenyl)-N-(5-methyl-1H-pyrazol-3-yl)imidazo[1,2-f]pyrimidin-5-amine

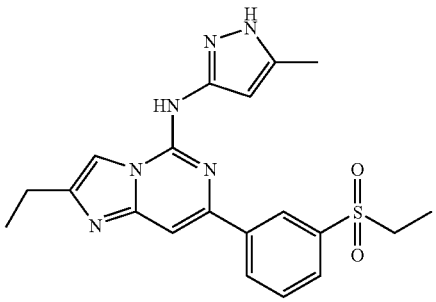

The title compound was synthesized following a procedure analogous to that described in Example 12. $^1$H NMR (400 MHz, DMSO-D6) δ ppm 1.14 (t, J=7.07 Hz, 3H) 1.32 (t, J=7.20 Hz, 3H) 2.31 (s, 3H) 2.83 (q, J=6.74 Hz, 2H) 3.35-3.43 (m, 2H) 6.66 (s, 1H) 7.82-7.89 (m, 2H) 8.03 (d, J=7.58 Hz, 1H) 8.46 (s, 1H) 8.55 (d, J=7.33 Hz, 1H) 8.73 (s, 1H) 10.95 (s, 1H) 12.42 (bs, 1H); ESI-MS: m/z 411.4 (M+H)$^+$.

Example 228

7-(3-(ethylsulfonyl)phenyl)-2-isopropyl-N-(5-methyl-1H-pyrazol-3-yl) imidazo[1,2-f]pyrimidin-5-amine

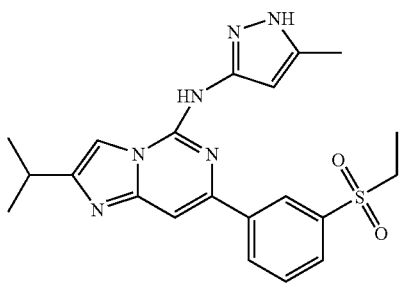

The title compound was synthesized following a procedure analogous to that described in Example 12. $^1$H NMR (400 MHz, DMSO-D6) 12.46 (bs, 1H) 10.94 (bs, 1H) 8.72 (s, 1H) 8.56 (d, J=7.56 Hz, 1H) 8.45 (s, 1H) 8.04 (d, J=7.04 Hz 1H) 7.88 (t, J=7.14 Hz 1H) 7.82 (s, 1H) 6.66 (s, 1H) 3.34 (t, J=7.12 Hz 2H) 3.18 (m, 1H) 2.32 (s, 3H) 1.36 (d, J=6.82 Hz 6H) 1.16

(t, J=7.33 Hz 2H) 1.09 (t, J=7.07 Hz 3H). [M+H] calc'd for C$_{21}$H$_{24}$N$_6$O$_2$S, 425.17; found, 425.40.

Example 229

N-(5-ethyl-1H-pyrazol-3-yl)-7-(3-(ethylsulfonyl)phenyl)-2-methylimidazo[1,2-f]pyrimidin-5-amine

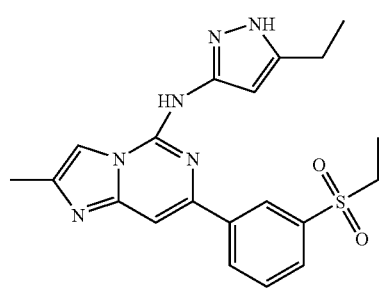

The title compound was synthesized following a procedure analogous to that described in Example 12. $^1$H NMR (400 MHz, DMSO-D6) 12.42 (bs, 1H) 10.92 (bs, 1H) 8.73 (s, 1H) 8.56 (d, J=7.56 Hz, 1H) 8.45 (s, 1H) 8.03 (d, J=8.59 Hz 1H) 7.86 (t, J=3.92 Hz 1H) 7.82 (s, 1H) 6.68 (s, 1H) 3.38 (q, J=7.41 Hz 2H) 2.68 (q, J=7.41 Hz 2H) 2.47 (s, 3H) 1.29 (t, J=7.58 Hz 3H) 1.14 (t, J=7.33 Hz 3H). [M+H] calc'd for C$_{20}$H$_{222}$N$_6$O$_2$S, 411.15; found, 411.20

Example 230

N-(methyl-N-(3-(2-methyl-5-(5-methyl-1H-pyrazol-3-ylamino) imidazo[1,2-f]pyrimidin-7-yl)phenyl) cycloprpanesulfonamide

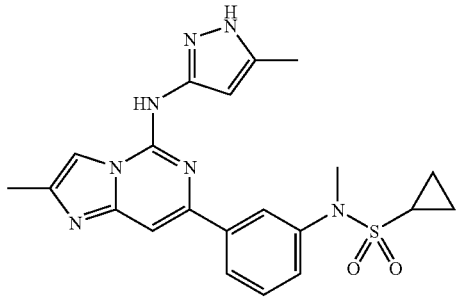

The title compound was synthesized following a procedure analogous to that described in Example 12. $^1$H NMR (400 MHz, DMSO-D6) δ 12.40 (bs, 1H) 10.96 (bs, 1H) 8.51 (s, 1H), 8.21 (s, 1H), 8.06-8.16 (m, 1H), 7.70 (s, 1H), 7.60-7.65 (m, 2H), 6.72 (s, 1H), 3.38 (s, 3H), 3.10-3-20 (m, 1H). 2.70-2.78 (m, 1H), 2.30 (s, 3H), 1.36 (d, J=6.82 Hz 6H), 0.92-0.98 (m, 2H) 0.80-0.86 (m, 2H). [M+H] calc'd for C$_{23}$H$_{27}$N$_7$O$_2$S, 466.19; found, 466.30.

Example 231

2-(3-(ethylsulfonyl)phenyl)-6-methyl-N-(5-methyl-1H-pyrazol-3-yl)pyrrolo[1,2-f][1,2,4]triazin-4-amine

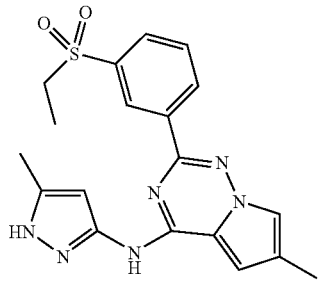

$^1$H NMR (400 MHz, DMSO-d$_6$) δ ppm 1.15 (t, J=7.33 Hz, 3H) 2.27 (s, 3H) 2.31 (s, 3H) 3.35-3.39 (m, 2H) 6.76 (s, 1H) 7.12 (s, 1H) 7.69 (s, 1H) 7.81 (t, J=7.83 Hz, 1H) 7.98 (d, J=7.83 Hz, 1H) 8.55 (d, J=7.83 Hz, 1H) 8.75 (s, 1H) 10.60 (s, 1H) 12.25 (s, 1H); ESI-MS: m/z calc'd for C19H20N6O2S 396.47; found 397.4 (M+H)$^+$

Example 232

2-(3-(ethylsulfonyl)phenyl)-N-(5-methyl-1H-pyrazol-3-yl)pyrrolo[1,2-f][1,2,4]triazin-4-amine

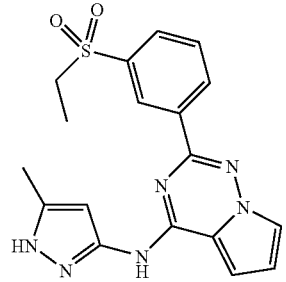

$^1$H NMR (400 MHz, DMSO-d$_6$) δ ppm 1.16 (t, J=7.33 Hz, 3H) 2.31 (s, 3H) 3.37 (q, J=7.24 Hz, 2H) 6.73-6.82 (m, 2H) 7.33 (s, 1H) 7.80-7.89 (m, 2H) 8.00 (d, J=7.58 Hz, 1H) 8.57

(d, J=7.83 Hz, 1H) 8.77 (s, 1H) 10.77 (s, 1H); ESI-MS: m/z calc'd for $C_{18}H_{18}N_6O_2S$ 382.44; found 383.3 (M+H)+

Example 233

N-(5-methyl-1H-pyrazol-3-yl)-2-(3-(methylsulfonyl)phenyl)pyrrolo[1,2-f][1,2,4]triazin-4-amine

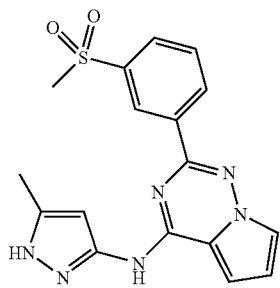

$^1$H NMR (400 MHz, DMSO-$d_6$) δ ppm 2.32 (s, 3H) 3.29 (s, 3H) 6.76 (dd, J=4.42, 2.65 Hz, 1H) 6.78 (s, 1H) 7.33 (s, 1H) 7.79-7.89 (m, 2H) 8.05 (d, J=8.34 Hz, 1H) 8.56 (d, J=7.83 Hz, 1H) 8.83 (s, 1H) 10.76 (s, 1H); ESI-MS: m/z calc'd for $C_{17}H_{16}N_6O_2S$ 368.41; found 369.3 (M+H)+

Example 234

N-(5-methyl-1H-pyrazol-3-yl)-2-phenylpyrrolo[1,2-f][1,2,4]triazin-4-amine

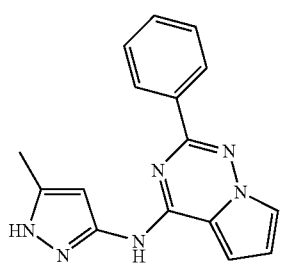

$^1$H NMR (400 MHz, DMSO-$d_6$) δ ppm 2.32 (s, 3H) 6.71 (dd, J=4.17, 2.65 Hz, 1H) 6.76 (s, 1H) 7.29 (s, 1H) 7.46-7.56 (m, 3H) 7.79 (d, J=2.27 Hz, 1H) 8.26 (d, J=7.07 Hz, 2H) 10.60 (s, 1H) 12.25 (s, 1H); ESI-MS: m/z calc'd for C16H14N6 290.32; found 291.4 (M+H)+

Example 235

2-(1-(Ethylsulfonyl)-1H-indol-6-yl)-N-(5-methyl-1H-pyrazol-3-yl)pyrrolo[1,2-f][1,2,4]triazin-4-amine

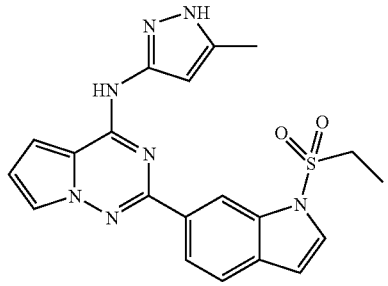

$^1$H NMR (400 MHz, DMSO-d6) δ ppm 1.14 (t, J=7.33 Hz, 3H) 2.35 (s, 3H) 3.76 (q, J=7.24 Hz, 2H) 6.73 (dd, J=4.29, 2.53 Hz, 1H) 6.94 (s, 1H) 7.33 (s, 1H) 7.83 (dd, J=2.53, 1.52 Hz, 1H) 8.00 (s, 1H) 8.06 (d, J=8.59 Hz, 1H) 8.33 (d, J=9.09 Hz, 1H) 8.97 (s, 1H) 9.77 (s, 1H) 10.71 (s, 1H) 12.25 (bs. 1H); ESI-MS: m/z calc'd for C20H196N7O2S 421.13; found 422.2 (M+H)+

Example 236

2-(1-(Ethylsulfonyl)-1H-indol-6-yl)-6-methyl-N-(5-methyl-1H-pyrazol-3-yl)pyrrolo[1,2-f][1,2,4]triazin-4-amine

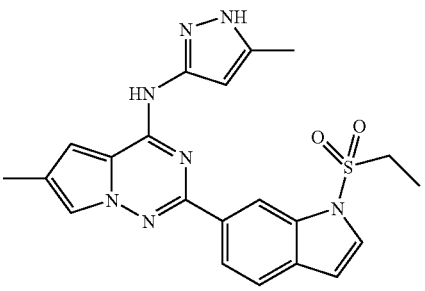

$^1$H NMR (400 MHz, DMSO-$d_6$) δ ppm 1.14 (t, J=7.30 Hz, 3H) 2.27 (s, 3H) 2.35 (s, 3H) 3.76 (q, J=7.24 Hz, 2H) 6.75 (dd, J=4.29, 2.55 Hz, 1H) 6.96 (s, 1H) 7.36 (s, 1H) 8.02 (s, 1H) 8.08 (d, J=8.59 Hz, 1H) 8.34 (d, J=9.10 Hz, 1H) 8.98 (s, 1H)

9.78 (s, 1H) 10.70 (s, 1H) 12.30 (bs. 1H); m/z calc'd for C$_{21}$H$_{21}$N$_7$O$_2$S 435.15; found 435.3 (M+H)$^+$.

Example 237

2-(3-((dimethylamino)methyl)-1-(ethylsulfonyl)-1H-indol-6-yl)-6-methyl-N-(5-methyl-1H-pyrazol-3-yl)pyrrolo[1,2-f][1,2,4]triazin-4-amine

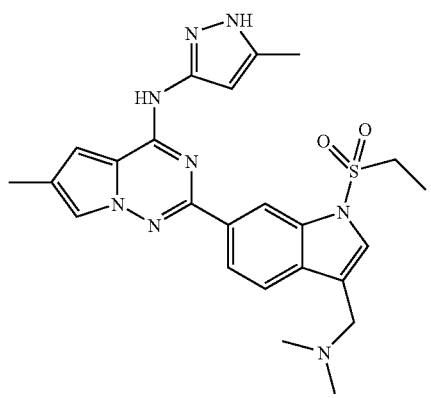

$^1$H NMR (400 MHz, DMSO-d$_6$) δ ppm 1.16 (t, J=7.33 Hz, 3H) 2.27 (s, 3H) 2.30 (s, 3H) 2.80 (d, J=4.55 Hz, 6H) 3.76 (q, J=7.24 Hz, 2H) 6.73 (dd, J=4.29, 2.53 Hz, 1H) 6.94 (s, 1H) 7.33 (s, 1H) 8.00 (s, 1H) 8.06 (d, J=8.59 Hz, 1H) 8.33 (d, J=9.09 Hz, 1H) 8.97 (s, 1H) 9.77 (s, 1H) 10.71 (s, 1H) 12.25 (bs. 1H); ESI-MS: m/z calc'd for C$_{24}$H$_{28}$N$_8$O$_2$S 492.21; found 493.3 (M+H)$^+$ Example 238

Cyclobutanecarboxylic acid 3-[5-(5-methyl-1H-pyrazol-3-ylamino)-imidazo[1,2-c]pyrimidin-7-yl]-benzylamide, TFA salt

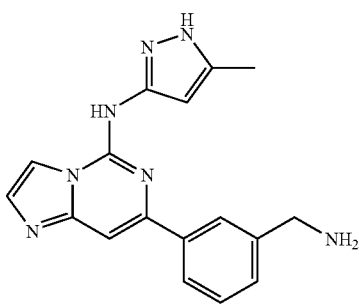

$^1$H NMR (400 MHz, MeOD-d$_4$) δ 7.90-8.07 (m, 3H), 7.57 (s, 1H), 7.39-7.49 (m, 2H), 7.28-7.34 (m, 1H), 6.61 (s, 1H), 4.42 (s, 2H), 3.10-3.20 (m, 2H), 2.39 (s, 3H), 1.80-2.32 (m, 6H). [M+H] calc'd for C$_{22}$H$_{23}$N$_7$O, 402; found, 402.

Example 239

Azetidine-3-carboxylic acid 3-[5-(5-methyl-1H-pyrazol-3-ylamino)-imidazo[1,2-c]pyrimidin-7-yl]-benzylamide, bis-TFA salt

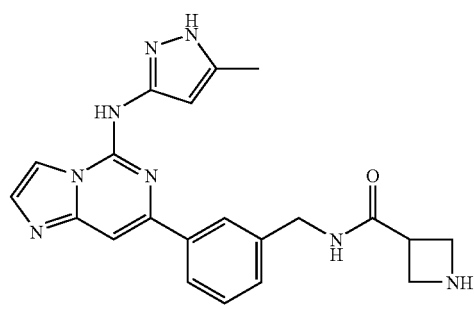

$^1$H NMR (400 MHz, MeOD-d$_4$) δ 8.70 (s, 1H), 8.37 (s, 1H), 8.06-8.11 (m, 2H), 7.98 (s, 1H), 7.49-7.53 (m, 2H), 6.61 (s, 1H), 4.51 (s, 2H), 4.18-4.23 (m, 4H), 3.56-3.63 (m, 1H), 2.40 (s, 3H). [M+H] calc'd for C$_{21}$H$_{22}$N$_8$O, 403; found, 403.

Example 240

[7-(3-Aminomethyl-phenyl)-imidazo[1,2-c]pyrimidin-5-yl]-(5-methyl-1H-pyrazol-3-yl)-amine, bis-TFA salt ¹H NMR (400 MHz, MeOD-d₄) δ 7.90-8.01 (m, 3H), 7.53 (s, 1H), 7.39-7.46 (m, 2H), 7.28 (s, 1H), 6.39 (s, 1H), 4.12 (s, 2H), 2.29 (s, 3H). [M+H] calc'd for $C_{17}H_{17}N_7$, 320; found, 320.

Example 241

Cyclopropanesulfonic acid 3-[5-(5-methyl-1H-pyrazol-3-ylamino)-imidazo[1,2-c]pyrimidin-7-yl]-benzylamide, TFA salt

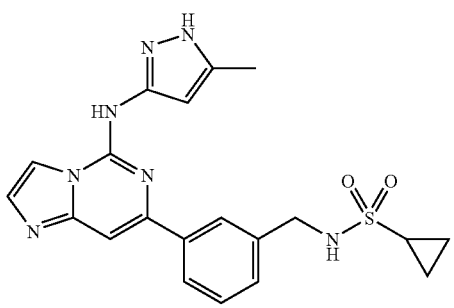

¹H NMR (400 MHz, MeOD-d₄) δ 7.95-8.18 (m, 3H), 7.58 (s, 1H), 7.39-7.49 (m, 3H), 6.62 (s, 1H), 4.36 (s, 2H), 2.30-2.42 (m, 4H), 0.80-1.06 (m, 4H). [M+H] calc'd for $C_{20}H_{21}N_7O_2S$, 424; found, 424.

Example 242

(7-{3-[(Cyclopropylmethyl-amino)-methyl]-phenyl}-imidazo[1,2-c]pyrimidin-5-yl)-(5-methyl-1H-pyrazol-3-yl)-amine, bis-TFA salt

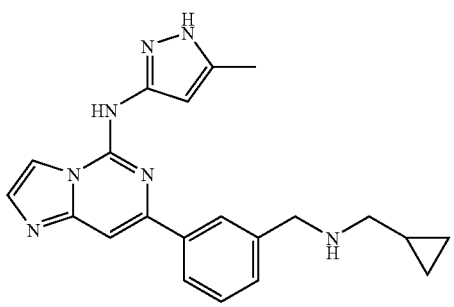

¹H NMR (400 MHz, MeOD-d₄) δ 8.01-8.13 (m, 3H), 7.38-7.59 (m, 4H), 6.52 (s, 1H), 4.17 (s, 2H), 2.85 (d, 2H, J=7.6 Hz), 2.35 (s, 3H), 1.05-1.12 (m, 1H), 0.60-0.68 (m, 2H), 0.30-0.36 (m, 2H). [M+H] calc'd for $C_{21}H_{23}N_7$, 374; found, 374.

Example 243

[7-(3-Methylaminomethyl-phenyl)-imidazo[1,2-c]pyrimidin-5-yl]-(5-methyl-1H-pyrazol-3-yl)-amine, bis-TFA salt

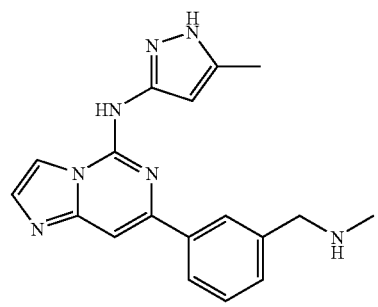

¹H NMR (400 MHz, MeOD-d₄) δ 8.40 (s, 1H), 8.26-8.30 (m, 2H), 8.00 (s, 1H), 7.74 (s, 1H), 7.64-7.69 (m, 2H), 6.59 (s, 1H), 4.12 (s, 2H), 2.29 (s, 3H). [M+H] calc'd for $C_{18}H_{19}N_7$, 334; found, 334.

Example 244

(5-Methyl-1H-pyrazol-3-yl)-[7-(1,2,3,4-tetrahydro-isoquinolin-7-yl)-imidazo[1,2-c]pyrimidin-5-yl]-amine, bis-TFA salt

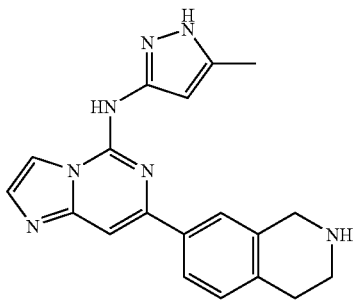

¹H NMR (400 MHz, MeOD-d₄) δ 8.37 (s, 1H), 7.98-8.12 (m, 3H), 7.70 (s, 1H), 7.44 (d, 1H, J=8.4 Hz), 6.58 (s, 1H), 4.48 (s, 2H), 3.50-3.58 (m, 2H), 3.12-3.20 (m, 2H), 2.39 (s, 3H). [M+H] calc'd for $C_{19}H_{19}N_7$, 346; found, 346.

Example 245

[7-(2-Methanesulfonyl-1,2,3,4-tetrahydro-isoquinolin-7-yl)-imidazo[1,2-c]pyrimidin-5-yl]-(5-methyl-1H-pyrazol-3-yl)-amine, bis-TFA salt

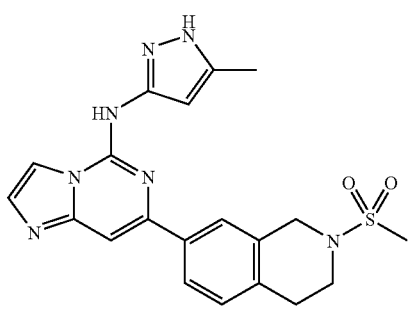

$^1$H NMR (400 MHz, MeOD-$d_4$) δ 8.33 (s, 1H), 7.90-8.01 (m, 3H), 7.61 (s, 1H), 7.36 (d, 1H, J=8.4 Hz), 6.57 (s, 1H), 4.53 (s, 2H), 3.58 (t, 2H, J=6.0 Hz), 3.06 (t, 2H, J=6.0 Hz), 2.93 (s, 3H), 2.39 (s, 3H). [M+H] calc'd for $C_{20}H_{21}N_7O_2S$, 424; found, 424.

Example 246

[7-(3-Ethanesulfonylmethyl-phenyl)-2-methyl-imidazo[1,2-c]pyrimidin-5-yl]-(5-methyl-1H-pyrazol-3-yl)-amine, TFA salt

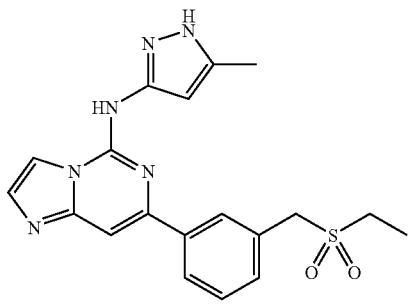

$^1$H NMR (400 MHz, MeOD-$d_4$) δ 8.21 (s, 1H), 8.02 (s, 1H), 7.74 (s, 1H), 7.45-7.51 (m, 2H), 7.34 (s, 1H), 6.68 (s, 1H), 4.46 (s, 2H), 3.04 (q, 2H, J=7.6 Hz), 2.40 (s, 3H), 2.35 (s, 3H), 1.17 (t, 3H, J=7.6 Hz). [M+H] calc'd for $C_{20}H_{22}N_6O_2S$, 411; found, 411.

Example 247

[7-(3-Ethanesulfonylmethyl-phenyl)-2-methyl-imidazo[1,2-c]pyrimidin-5-yl]-(5-methyl-1H-pyrazol-3-yl)-amine, TFA salt

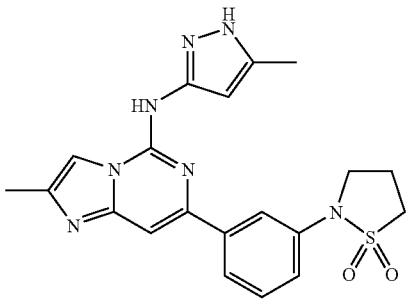

$^1$H NMR (400 MHz, MeOD-$d_4$) δ 8.13 (s, 1H), 7.95 (s, 1H), 7.70 (d, 1H, J=7.6 Hz), 7.38-7.49 (m, 2H), 7.24 (d, 1H, J=7.6 Hz), 6.67 (s, 1H), 3.82 (t, 2H, J=6.4 Hz), 3.51 (t, 2H, J=7.2 Hz), 2.50-2.59 (m, 2H), 2.49 (s, 3H), 2.35 (s, 3H). [M+H] calc'd for $C_{20}H_{21}N_7O_2S$, 424; found, 424.

Example 248

{2-Methyl-7-[3-(3-methyl-pyridin-4-yl)-phenyl]-imidazo[1,2-c]pyrimidin-5-yl}-(5-methyl-1H-pyrazol-3-yl)-amine, bis-TFA salt

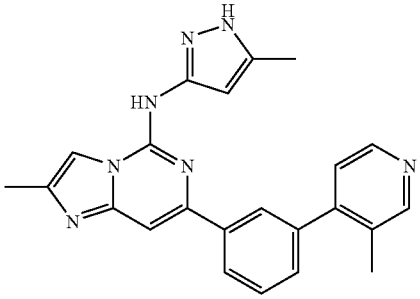

$^1$H NMR (400 MHz, MeOD-$d_4$) δ 8.85 (s, 1H), 8.77 (d, 1H, J=7.5 Hz), 8.31-8.36 (m, 2H), 8.08 (s, 1H), 7.99 (d, 1H, J=7.5

Hz), 7.68-7.80 (m, 3H), 6.54 (s, 1H), 2.56 (s, 3H), 2.54 (s, 3H), 2.35 (s, 3H). [M+H] calc'd for $C_{23}H_{21}N_7$, 396; found, 396.

Example 249

{7-[3-(3,5-Dimethyl-1H-pyrazol-4-yl)-phenyl]-2-methyl-imidazo[1,2-c]pyrimidin-5-yl}-(5-methyl-1H-pyrazol-3-yl)-amine, bis-TFA salt

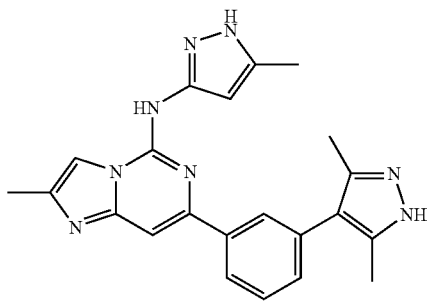

$^1$H NMR (400 MHz, MeOD-$d_4$) δ 8.10-8.14 (m, 2H), 8.06 (s, 1H), 7.69 (s, 2H), 7.66 (t, 1H, J=8.0 Hz), 7.53 (d, 1H, J=8.0 Hz), 6.52 (s, 1H), 2.56 (s, 3H), 2.41 (s, 6H), 2.35 (s, 3H). [M+H] calc'd for $C_{22}H_{22}N_8$, 399; found, 399.

Example 250

{2-Methyl-7-[3-(3-methyl-3H-imidazol-4-yl)-phenyl]-imidazo[1,2-c]pyrimidin-5-yl}-(5-methyl-1H-pyrazol-3-yl)-amine, TFA salt

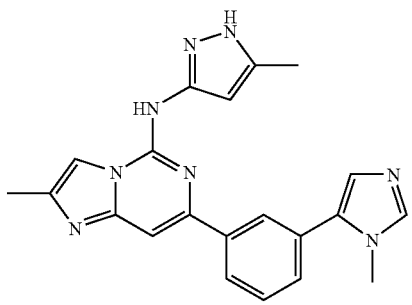

$^1$H NMR (400 MHz, MeOD-$d_4$) δ 9.05 (s, 1H), 8.30-8.41 (m, 2H), 8.09 (s, 1H), 7.70-7.79 (m, 4H), 6.59 (s, 1H), 3.95 (s, 3H), 2.56 (s, 3H), 2.37 (s, 3H). [M+H] calc'd for $C_{21}H_{20}N_8$, 385; found, 385.

Example 251

(5-Methyl-1H-pyrazol-3-yl)-{2-methyl-7-[3-(1,3,5-trimethyl-1H-pyrazol-4-yl)-phenyl]-imidazo[1,2-c]pyrimidin-5-yl}-amine, TFA salt

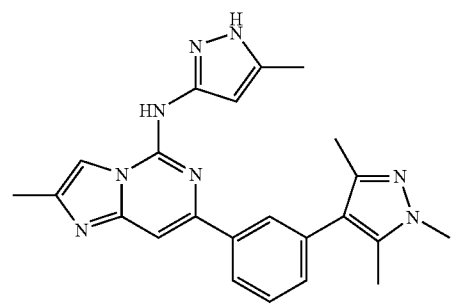

$^1$H NMR (400 MHz, MeOD-$d_4$) δ 8.06-8.12 (m, 3H), 7.58-7.65 (m, 2H), 7.46 (d, 1H, J=8.0 Hz), 6.55 (s, 1H), 3.84 (s, 3H), 2.55 (s, 3H), 2.35 (s, 3H), 2.32 (s, 3H), 2.26 (s, 3H). [M+H] calc'd for $C_{23}H_{24}N_8$, 413; found, 413.

Example 252

{7-[3-(3,5-Dimethyl-isoxazol-4-yl)-phenyl]-2-methyl-imidazo[1,2-c]pyrimidin-5-yl}-(5-methyl-1H-pyrazol-3-yl)-amine, bis-TFA salt

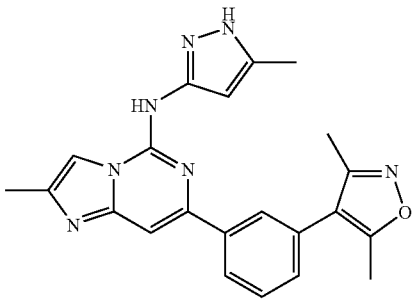

$^1$H NMR (400 MHz, MeOD-$d_4$) δ 8.10-8.18 (m, 2H), 8.05 (s, 1H), 7.62-7.69 (m, 2H), 7.52 (d, 1H, J=7.6 Hz), 6.52 (s,

1H), 2.56 (s, 3H), 2.45 (s, 3H), 2.34 (S, 3H), 2.29 (s, 3H). [M+H] calc'd for C$_{22}$H$_{22}$N$_7$O, 400; found, 4008.

Example 253

{7-[3-(5-Cyclopropyl-3-methyl-1H-pyrazol-4-yl)-phenyl]-2-methyl-imidazo[1,2-c]pyrimidin-5-yl}-(5-methyl-1H-pyrazol-3-yl)-amine, bis-TFA salt

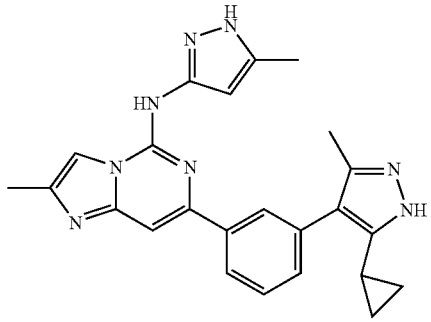

$^1$H NMR (400 MHz, MeOD-d$_4$) δ 8.23 (s, 1H), 8.04-8.10 (m, 2H), 7.59-7.65 (m, 3H), 6.54 (s, 1H), 2.55 (s, 3H), 2.34 (s, 3H), 2.32 (s, 3H), 1.88-1.95 (m, 1H), 0.78-0.94 (m, 4H). [M+H] calc'd for C$_{24}$H$_{24}$N$_8$, 425; found, 425.

Example 254

(5-Methyl-1H-pyrazol-3-yl)-{2-methyl-7-[3-(thiazole-2-sulfonyl)-phenyl]-imidazo[1,2-c]pyrimidin-5-yl}-amine, bis-TFA salt

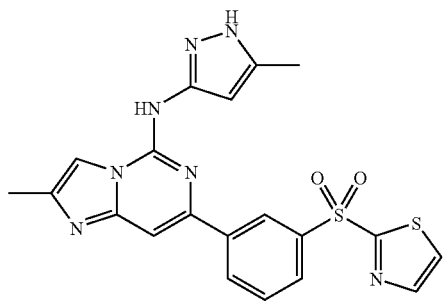

$^1$H NMR (400 MHz, MeOD-d$_4$) δ 9.01 (s, 1H), 8.49 (d, 1H, J=7.6 Hz), 8.19 (d, 1H, J=7.6 Hz), 8.10 (s, 1H), 8.02-8.09 (m, 2H), 7.80 (t, 1H, J=7.6 Hz), 7.75 (s, 1H), 6.70 (s, 1H), 2.56 (s, 3H), 2.44 (s, 3H). [M+H] calc'd for C$_{20}$H$_{17}$N$_7$O$_2$S$_2$, 438; found, 438.

Example 255

[7-(3-Dimethylaminomethyl-1-ethanesulfonyl-1H-indol-6-yl)-2-methyl-imidazo[1,2-c]pyrimidin-5-yl]-(5-methyl-1H-pyrazol-3-yl)-amine, TFA salt

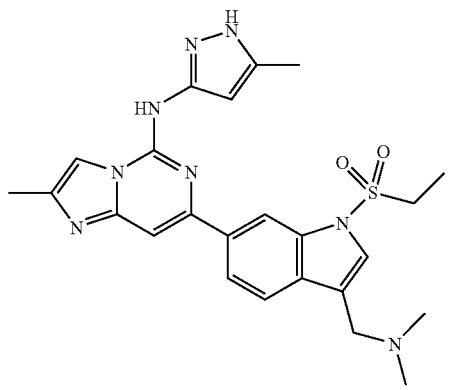

$^1$H NMR (400 MHz, MeOD-d$_4$) δ 8.88 (s, 1H), 7.92-8.10 (m, 4H), 7.67 (s, 1H), 6.74 (s, 1H), 4.58 (s, 2H), 3.50-3.58 (m, 2H), 3.12-3.20 (m, 2H), 2.39 (s, 3H). [M+H] calc'd for C$_{19}$H$_{19}$N$_7$, 346; found, 346.

Example 256

(5-Methyl-1H-pyrazol-3-yl)-{2-methyl-7-[3-(1H-pyrrolo[2,3-b]pyridin-4-yl)-phenyl]-imidazo[1,2-c]pyrimidin-5-yl}-amine, bis-TFA salt

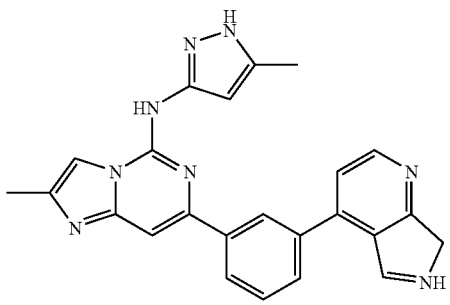

$^1$H NMR (400 MHz, MeOD-d$_4$) δ 8.62 (s, 1H), 8.28 (d, 1H, J=3.2 Hz), 8.13 (d, 1H, J=5.4 Hz), 7.72-7.81 (m, 2H), 7.63 (t, 1H, J=5.4 Hz), 7.47-7.50 (m, 2H), 7.29 (d, 1H, J=3.2 Hz), 6.72 (s, 1H), 6.63 (s, 1H), 2.43 (s, 3H), 2.22 (s, 3H). [M+H] calc'd for $C_{24}H_{20}N_8$, 421; found, 421.

Example 257

(5-Methyl-1H-pyrazol-3-yl)-{2-methyl-7-[3-(5)-(pyrrolidine-3-sulfonyl)-phenyl]-imidazo[1,2-c]pyrimidin-5-yl}-amine, bis-TFA salt

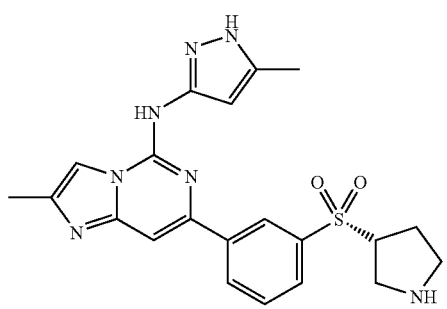

$^1$H NMR (400 MHz, MeOD-d$_4$) δ 8.79 (s, 1H), 8.51 (d, 1H, J=7.6 Hz), 8.07-8.12 (m, 2H), 7.78-7.87 (m, 2H), 6.60 (s, 1H), 4.26-4.34 (m, 1H), 3.40-3.79 (m, 4H), 2.57 (s, 3H), 2.42-2.53 (m, 1H), 2.39 (s, 3H), 2.31-2.48 (m, 1H). [M+H] calc'd for $C_{21}H_{23}N_7O_2S$, 438; found, 438.

Example 258

{7-[3-(3-Amino-propane-1-sulfonyl)-phenyl]-2-methyl-imidazo[1,2-c]pyrimidin-5-yl}-(5-methyl-1H-pyrazol-3-yl)-amine, bis-TFA salt

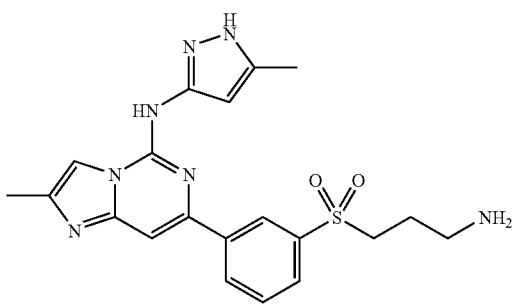

$^1$H NMR (400 MHz, MeOD-d$_4$) δ 8.81 (s, 1H), 8.10 (s, 1H), 8.8.50 (d, 1H, J=6.0 Hz), 8.05-8.10 (m, 2H), 7.77-7.84 (m, 2H), 6.64 (s, 1H), 3.41 (t, 2H, J=7.2 Hz), 3.09 (t, 2H, J=7.2 Hz), 2.57 (s, 3H), 2.39 (s, 3H), 2.06-2.11 (m, 2H). [M+H] calc'd for $C_{20}H_{23}N_7O_2S$, 426; found, 426.

Example 259

[7-(3-Ethylsulfanyl-phenyl)-2-methyl-imidazo[1,2-c]pyrimidin-5-yl]-(5-methyl-1H-pyrazol-3-yl)-amine, TFA salt

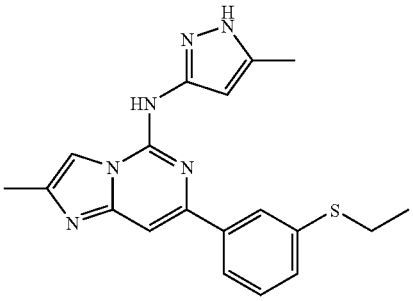

$^1$H NMR (400 MHz, DMSO-d$_6$) δ 12.20 (s, 1H), 10.09 (s, 1H), 8.10 (s, 1H), 8.07 (s, 1H), 7.87 (d, 1H, J=5.4 Hz), 7.51 (s, 1H), 7.29-7.40 (m, 2H), 6.64 (s, 1H), 3.07 (q, 2H, J=7.2 Hz), 2.32 (s, 3H), 2.29 (s, 3H), 1.29 (t, 3H, J=7.2 Hz). [M+H] calc'd for $C_{19}H_{20}N_6S$, 365; found, 365.

Example 260

[7-(3-Ethanesulfinyl-phenyl)-2-methyl-imidazo[1,2-c]pyrimidin-5-yl]-(5-methyl-1H-pyrazol-3-yl)-amine, TFA salt

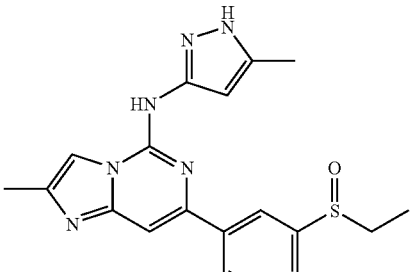

$^1$H NMR (400 MHz, MeOD-d$_4$) δ 8.45 (s, 1H), 8.24 (s, 1H), 7.78 (s, 1H), 7.63-7.71 (m, 2H), 7.47 (m, 1H), 6.64 (s, 1H), 3.01-3.11 (m, 1H), 2.88-2.98 (m, 1H), 2.43 (s, 3H), 2.30

(s, 3H), 1.22 (t, 3H, J=7.2 Hz). [M+H] calc'd for C$_{19}$H$_{20}$N$_6$OS, 381; found, 381.

Example 261

7-(3-(ethylsulfonyl)phenyl)-N-(5-methyl-1H-pyrazol-3-yl)-[1,2,4]triazolo[1,5-c]pyrimidin-5-amine

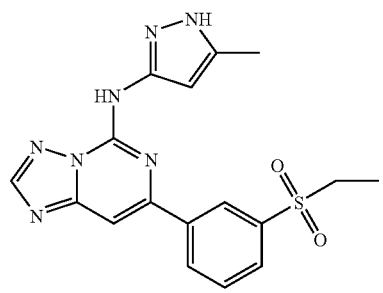

The title compound was synthesized following a procedure analogous to that described in Example 6. $^1$H NMR (400 MHz, MeOD-d$_4$) δ 8.72 (s, 1H) 8.63 (s, 1H) 8.52 (d, J=11.64 Hz, 1H) 8.01 (m, 2H) 7.81 (m, 1H) 6.60 (s, 1H) 2.49 (m, 2H) 2.30 (s, 3H) 1.15 (s, 3H). [M+H] calc'd for C$_{17}$H$_{17}$N$_7$O$_2$S, 384; found, 384.

Example 262

N-(5-(2-methyl-5-(5-methyl-1H-pyrazol-3-ylamino)imidazo[1,2-c]pyrimidin-7-yl)-2-(2-morpholinoethoxy)phenyl)cyclopropanesulfonamide

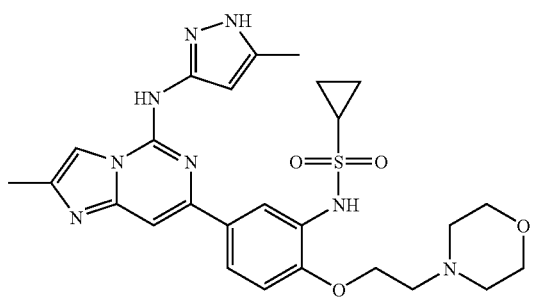

The title compound was synthesized following a procedure analogous to that described in Example 12. $^1$H NMR (400 MHz, MeOD-d$_4$) δ 8.44 (d, J=2.28 Hz, 1H) 8.05 (m, 2H) 7.56 (s, 1H) 7.29 (d, J=8.6 Hz, 2H) 6.69 (s, 1H) 4.56 (m, 2H) 3.74 (m, 2H) 2.65 (s, 2H) 2.54 (s, 3H) 2.39 (s, 3H) 1.07 (m, 2H) 0.98 (s, 2H). [M+H] calc'd for C$_{26}$H$_{32}$N$_8$O$_4$S, 553; found, 553.

Example 263

4-methyl-5-(3-(2-methyl-5-(5-methyl-1H-pyrazol-3-ylamino)imidazo[1,2-c]pyrimidin-7-yl)phenyl)thiazol-2-amine

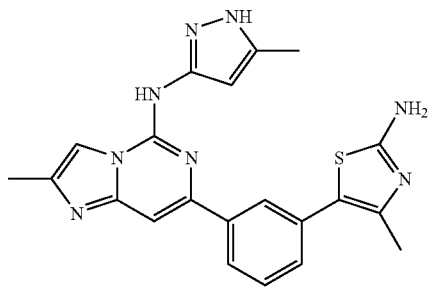

The title compound was synthesized following a procedure analogous to that described in Example 12. $^1$H NMR (400 MHz, MeOD-d$_4$) δ 8.29 (s, 1H) 8.22 (d, J=7.72 Hz, 1H) 8.08 (s, 2H) 7.71 (d, J=5.8 Hz, 1H) 7.67 (d, J=7.8 Hz, 1H) 7.63 (d, J=7.84 Hz, 1H) 6.57 (s, 1H) 2.57 (s, 3H) 2.38 (d, J=8.08 Hz, 2H)). [M+H] calc'd for C$_{21}$H$_{20}$N$_8$S, 417; found, 417.

Example 264

3-(2-methyl-5-(5-methyl-1H-pyrazol-3-ylamino)imidazo[1,2-c]pyrimidin-7-yl)-N-phenylbenzenesulfonamide

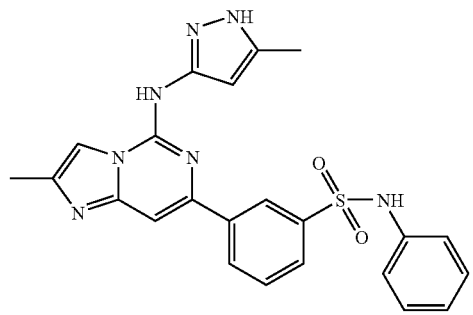

The title compound was synthesized following a procedure analogous to that described in Example 12. $^1$H NMR (400 MHz, MeOD-d$_4$) δ 8.63 (s, 1H) 8.29 (d, J=7.84 Hz, 1H) 8.06 (s, 1H) 7.87 (d, J=6.84 Hz, 1H) 7.63 (t, 1H) 7.59 (s, 1H) 7.10

(m, 4H) 6.99 (t, 1H) 6.61 (s, 1H) 2.69 (s, 1H) 2.55 (s, 3H) 2.42 (s, 6H). [M+H] calc'd for $C_{23}H_{21}N_7O_2S$, 460; found, 460.

Example 265

N-(4-(5-(5-cyclopropyl-1H-pyrazol-3-ylamino)-2-((dimethylamino)methyl)imidazo[1,2-c]pyrimidin-7-ylthio)phenyl)acetamide

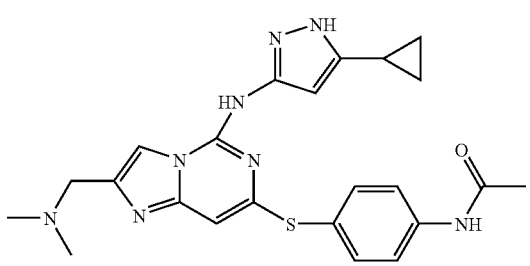

The title compound was synthesized following a procedure analogous to that described in Example 1. $^1$H NMR (400 MHz, MeOD-d$_4$) δ 7.87 (s, 1H) 7.72 (d, J=8.84 Hz, 2H) 7.56 (d, J=8.84 Hz, 2H) 6.50 (s, 1H) 4.66 (s, 2H) 2.15 (s, 3H) 1.28 (, 6H) 0.96 (d, J=6.32 Hz 3H) 0.66 (d, J=7.04 Hz, 2H). [M+H] calc'd for $C_{23}H_{26}N_8OS$, 463; found, 463.

Example 266

(4-hydroxypiperidin-1-yl)(3-(5-(5-methyl-1H-pyrazol-3-ylamino)imidazo[1,2-c]pyrimidin-7-yl)phenyl)methanone

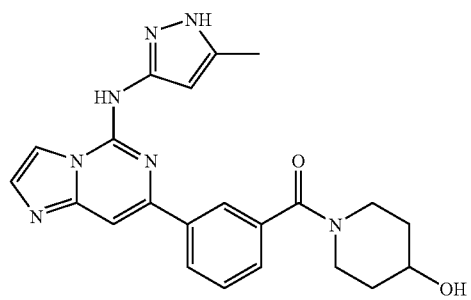

The title compound was synthesized following a procedure analogous to that described in Example 12. $^1$H NMR (400 MHz, MeOD-d$_4$) δ 8.39 (s, 1H) 8.27 (d, J=7.8 Hz, 1H) 8.23 (s, 1H) 8.01 (s, 1H) 7.74 (s, 1H) 7.65 (t, 1H) 7.59 (d, J=7.6 Hz, 1H) 6.58 (s, 1H) 4.20 (s, 1H) 3.93 (s, 1H) 3.66 (s, 1H) 2.39 (s, 3H) 1.97 (s, 1H) 1.81 (s, 1H) 1.60 (s, 1H) 1.47 (s, 1H). [M+H] calc'd for $C_{22}H_{23}N_7O_2$, 418; found, 418.

Example 267

N-isobutyl-3-(5-(5-methyl-1H-pyrazol-3-ylamino)imidazo[1,2-c]pyrimidin-7-yl)benzamide

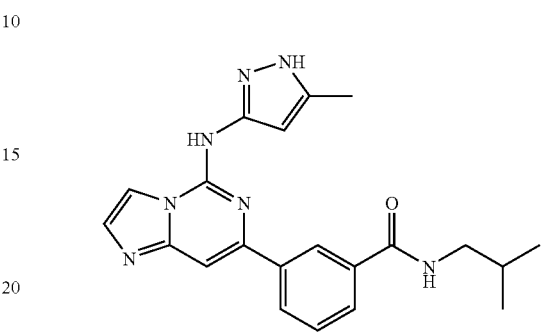

The title compound was synthesized following a procedure analogous to that described in Example 12. $^1$H NMR (400 MHz, MeOD-d$_4$) δ 8.62 (s, 1H) 8.40 (s, 1H) 8.35 (d, J=9.84 Hz, 1H) 8.01 (d, J=2.52 Hz, 1H) 7.97 (d, J=6.84 Hz, 1H) 7.73 (s, 1H) 7.65 (t, 1H) 6.64 (s, 1H) 3.25 (d, J=7.08 Hz, 2H) 2.39 (s, 3H) 1.96 (m, 1H) 1.00 (d, J=6.56 6H). [M+H] calc'd for $C_{21}H_{23}N_7O$, 389; found, 389.

Example 268

N-cyclopentyl-3-(5-(5-methyl-1H-pyrazol-3-ylamino)imidazo[1,2-c]pyrimidin-7-yl)benzamide

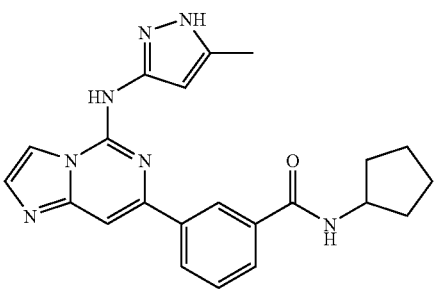

The title compound was synthesized following a procedure analogous to that described in Example 12. $^1$H NMR (400 MHz, MeOD-d$_4$) δ 8.61 (s, 1H) 8.40 (d, J=2.28 Hz, 1H) 8.34 (d, J=8.08 Hz, 1H) 8.01 (d, J=2.28 Hz, 1H) 7.96 (d, J=8.32 Hz, 1H) 7.74 (s, 1H) 7.64 (t, 1H) 6.65 (s, 1H) 4.36 (m, 1H)

2.40 (s, 3H) 2.07 (m, 2H) 1.80 (m, 2H) 1.65 (m, 4H). [M+H] calc'd for $C_{22}H_{23}N_7O$, 402; found, 402.

Example 269

3-(5-(5-methyl-1H-pyrazol-3-ylamino)imidazo[1,2-c]pyrimidin-7-yl)-N-(pyrrolidin-3-ylmethyl)benzamide

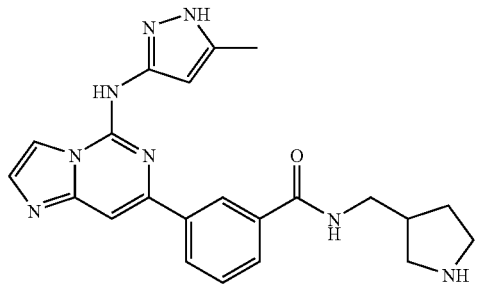

The title compound was synthesized following a procedure analogous to that described in Example 12. $^1$H NMR (400 MHz, MeOD-$d_4$) δ 8.66 (s, 1H) 8.40 (s, 1H) 8.37 (d, J=7.84 Hz, 1H) 8.01 (m, 2H) 7.77 (s, 1H) 7.66 (t, 1H) 6.66 (s, 1H) 3.53 (m, 2H) 3.44 (m, 2H) 3.08 (m, 1H) 2.74 (m, 1H) 2.40 (s, 3H) 2.21 (m, 1H) 1.85 (m, 1H). [M+H] calc'd for $C_{22}H_{24}N_8O$, 417; found, 417.

Example 270

3-(5-(5-methyl-1H-pyrazol-3-ylamino)imidazo[1,2-c]pyrimidin-7-yl)-N-(pyrrolidin-2-ylmethyl)benzamide

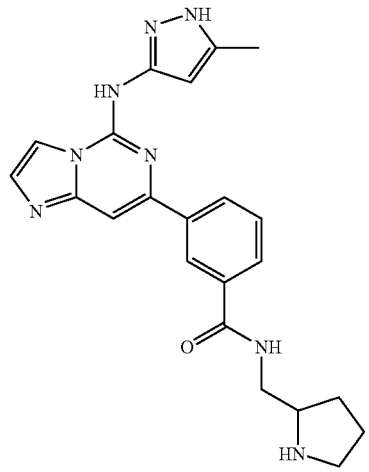

The title compound was synthesized following a procedure analogous to that described in Example 12. $^1$H NMR (400 MHz, MeOD-$d_4$) δ 8.69 (s, 1H) 8.40 (s, 1H) 8.37 (d, J=7.84 Hz, 1H) 8.03 (d, J=9.32 Hz, 2H) 7.78 (s, 1H) 7.66 (t, 1H) 6.64 (s, 1H) 3.84 (m, 1H) 3.75 (d, J=5.28 Hz, 2H) 3.39 (m, 1H) 2.39 (s, 3H) 2.23 (m, 1H) 2.09 (m, 2H) 1.86 (m, 1H). [M+H] calc'd for $C_{22}H_{24}N_8O$, 417; found, 417.

Example 271

N-isopropyl-3-(5-(5-methyl-1H-pyrazol-3-ylamino)imidazo[1,2-c]pyrimidin-7-yl)benzamide

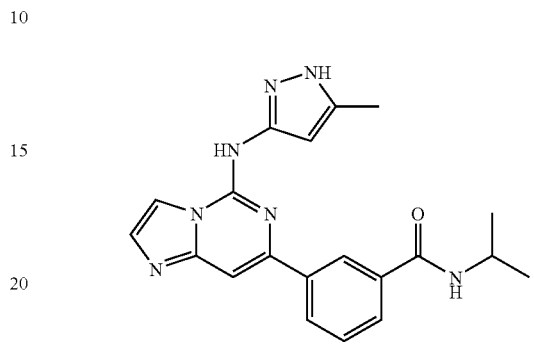

The title compound was synthesized following a procedure analogous to that described in Example 12. $^1$H NMR (400 MHz, MeOD-$d_4$) δ 8.60 (s, 1H) 8.40 (d, J=2.52 Hz, 1H) 8.33 (d, J=7.84 Hz, 1H) 8.0 (d, J=2.52 Hz, 1H) 7.96 (d, J=15.8 Hz, 1H) 7.74 (s, 1H) 7.63 (t, 1H) 6.64 (s, 1H) 4.25 (m, 1H) 2.39 (s, 3H) 1.30 (d, J=6.56 Hz, 6H). [M+H] calc'd for $C_{20}H_{21}N_7O$, 376; found, 376.

Example 272

3-(5-(5-methyl-1H-pyrazol-3-ylamino)imidazo[1,2-c]pyrimidin-7-yl)-N-phenylbenzamide

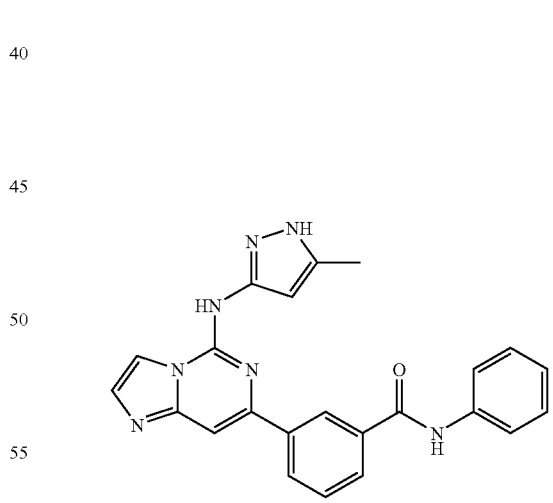

The title compound was synthesized following a procedure analogous to that described in Example 12. $^1$H NMR (400 MHz, MeOD-$d_4$) δ 8.72 (s, 1H) 8.38 (s, 1H) 8.35 (d, J=7.8 Hz, 1H) 8.06 (d, J=7.84 Hz, 1H) 7.99 (s, 1H) 7.76 (s, 1H) 7.69 (m, 4H) 7.38 (m, 3H) 7.17 (m, 1H) 6.65 (s, 1H) 4.25 (m, 1H) 2.30 (s, 3H). [M+H] calc'd for C₂₃H₁₉N₇O, 410; found, 410.

Example 273

N-benzyl-3-(5-(5-methyl-1H-pyrazol-3-ylamino)imidazo[1,2-c]pyrimidin-7-yl)benzamide

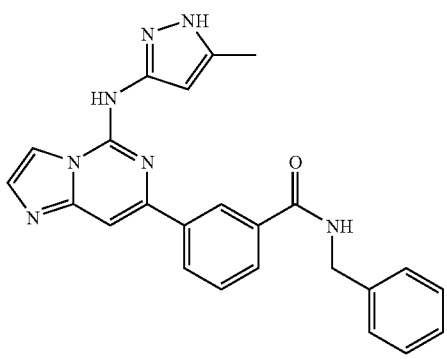

The title compound was synthesized following a procedure analogous to that described in Example 12. ¹H NMR (400 MHz, MeOD-d₄) δ 8.67 (s, 1H) 8.39 (s, 1H) 8.35 (d, J=9.88 Hz, 1H) 8.00 (s, 2H) 7.73 (s, 1H) 7.65 (t, 1H) 7.33 (m, 4H) 7.26 (m, 1H) 6.64 (s, 1H) 4.63 (m, 2H) 2.34 (s, 3H). [M+H] calc'd for C₂₄H₂₁N₇O, 424; found, 424.

Example 274

N-(4-(2-methyl-5-(5-methyl-1H-pyrazol-3-ylamino)imidazo[1,2-c]pyrimidin-7-ylthio)phenyl)cyclopropanecarboxamide

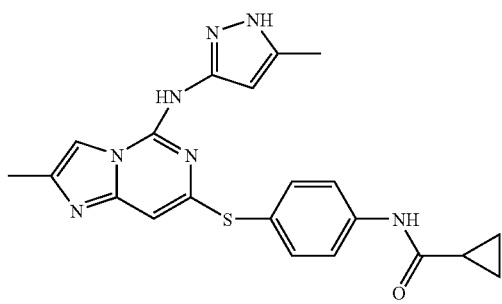

The title compound was synthesized following a procedure analogous to that described in Example 1. ¹H NMR (400 MHz, MeOD-d₄) δ 7.72 (d, J=8.84 Hz, 2H) 7.63 (s, 1H) 7.55 (d, J=8.56 Hz 2H) 6.46 (s, 1H) 5.96 (s, 1H) 2.33 (s, 3H) 2.20 (s, 2H) 2.15 (s, 2H) 1.80 (m, 1H) 0.97 (m, 2H) 0.86 (m, 2H). [M+H] calc'd for C₂₁H₂₁N₇OS, 420; found, 420.

Example 275

3-(2-methyl-5-(5-methyl-1H-pyrazol-3-ylamino)imidazo[1,2-c]pyrimidin-7-yl)-N-(thiazol-2-yl)benzenesulfonamide

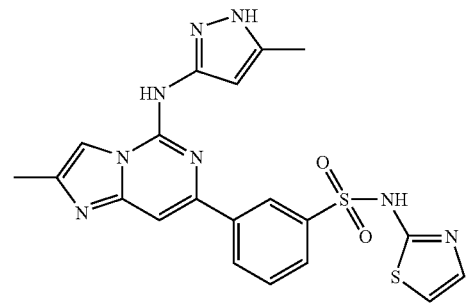

The title compound was synthesized following a procedure analogous to that described in Example 12. ¹H NMR (400 MHz, MeOD-d₄) δ 8.82 (s, 1H) 8.33 (d, J=7.56 Hz, 1H) 8.08 (s, 1H) 8.01 (d, J=7.32 Hz 1H) 7.68 (s, 2H) 7.10 (d, J=4.8 Hz, 1H) 6.71 (d, J=4.96 Hz, 1H) 6.69 (s, 1H) 2.65 (s, 3H) 2.56 (s, 3H) 2.42 (s, 3H). [M+H] calc'd for C₂₀H₁₈N₈O₂S₂, 467; found, 467.

Example 276

N-(2-aminoethyl)-3-(2-methyl-5-(5-methyl-1H-pyrazol-3-ylamino)imidazo[1,2-c]pyrimidin-7-yl)benzenesulfonamide

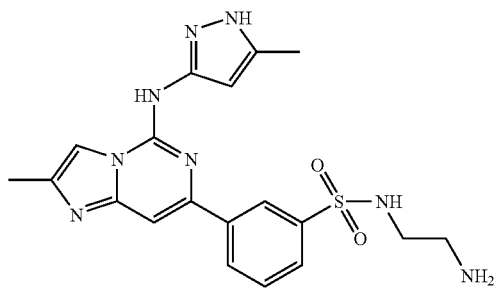

The title compound was synthesized following a procedure analogous to that described in Example 12. ¹H NMR (400 MHz, MeOD-d₄) δ 8.76 (s, 1H) 8.43 (d, J=8.6 Hz, 1H) 8.09 (s, 1H) 8.02 (d, J=9.6 Hz 1H) 7.79 (d, J=7.84 Hz, 1H) 7.75 (s, 1H) 6.64 (s, 1H) 3.13 (m, 2H) 3.07 (m, 2H) 2.56 (s, 3H) 2.39 (s, 3H). [M+H] calc'd for $C_{19}H_{22}N_8O_2S$, 427; found, 427.

Example 277

N-(4-(2-ethyl-5-(5-methyl-1H-pyrazol-3-ylamino) imidazo[1,2-c]pyrimidin-7-ylthio)phenyl)cyclopropanecarboxamide

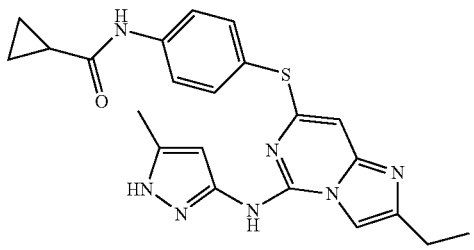

7-chloro-2-ethyl-N-(5-methyl-1H-pyrazol-3-yl)imidazo [1,2-c]pyrimidin-5-amine (0.22 mmol, 0.06 g) was dissolved in DMF (1 mL) N-(4-mercaptophenyl)cyclopropanecarboxamide (0.24 mmol, 0.046 g) and $K_2CO_3$ (0.24 mmol, 0.033 g) was added. The reaction mixture was heated to 160° C. using a microwave reactor for 20 minutes. The mixture was then concentrated and purified by LC-MS to give the title compound. $^1$H NMR (400 MHz, DMSO-$d_6$) δ ppm 0.83-0.84 (m, 4H) 1.25 (t, J=7.45 Hz, 3H) 1.79-1.86 (m, 1H) 2.12 (s, 3H) 2.73 (q, J=7.24 Hz, 2H) 5.80 (s, 1H) 6.65 (s, 1H) 7.58 (d, J=8.59 Hz, 2H) 7.81 (d, J=8.59 Hz, 2H) 8.31 (s, 1H) 10.55 (s, 1H) 10.97 (s, 1H) 12.30 (s, 1H); ESI-MS: m/z calc'd for $C_{22}H_{23}N_7OS$ 433.53; found 434.4 (M+H)$^+$ Example 278

N-ethyl-N-(3-(2-isopropyl-5-(5-methyl-1H-pyrazol-3-ylamino)imidazo[1,2-c]pyrimidin-7-yl)phenyl) methanesulfonamide

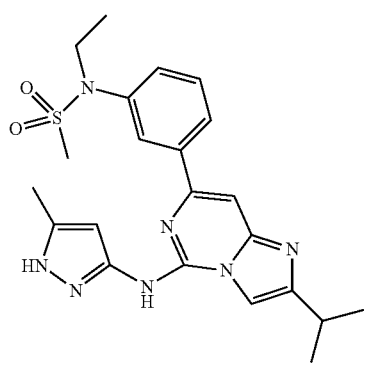

7-chloro-2-isopropyl-N-(5-methyl-1H-pyrazol-3-yl)imidazo[1,2-c]pyrimidin-5-amine (0.17 mmol, 0.05 g), 3-(N-ethylmethylsulfonamido)phenylboronic acid (0.35 mmol) and $(Ph_3)_4Pd(O)$ (0.086 mmol, 0.1 g) were stirred in dioxane (3 mL) and sat. $K_2CO_3$ (1.5 mL) The reaction mixture was heated to 150° C. using a microwave reactor for 20 minutes. The mixture was then concentrated and purified by LC-MS to give the title compound. $^1$H NMR (400 MHz, DMSO-$d_6$) δ ppm 1.06 (t, J=7.07 Hz, 3H) 1.35 (d, J=6.82 Hz, 6H) 2.29 (s, 3H) 3.04 (s, 3H) 3.76 (q, J=7.07 Hz, 2H) 6.70 (s, 1H) 7.57 (s, 1H) 7.59-7.67 (m, 2H) 8.11 (d, J=7.58 Hz, 1H) 8.17 (s, 1H) 8.45 (s, 1H) 10.80 (s, 1H) 12.35 (s, 1H); ESI-MS: m/z calc'd for C22H27N7O2S 453.56; found 454.4 (M+H)$^+$ Example 279

N-isopropyl-3-(5-(5-methyl-1H-pyrazol-3-ylamino)-2-(trifluoromethyl) imidazo[1,2-c]pyrimidin-7-yl) benzamide

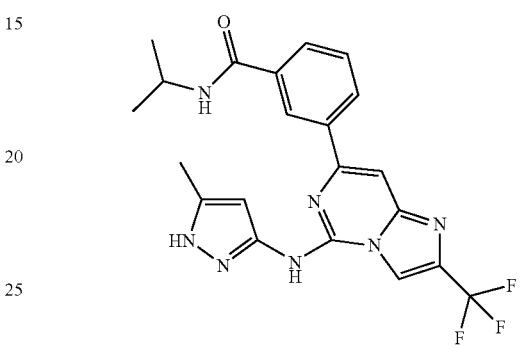

Title compound was synthesized from 7-chloro-N-(5-methyl-1H-pyrazol-3-yl)-2-(trifluoromethyl)imidazo[1,2-c]pyrimidin-5-amine and 3-(isopropylcarbamoyl)phenyl boronic acid using the procedure described in Example 278. $^1$H NMR (400 MHz, DMSO-$d_6$) δ ppm 1.21 (d, J=6.57 Hz, 6H) 2.32 (s, 3H) 4.15 (td, J=13.45, 6.69 Hz, 2H) 6.74 (s, 1H) 7.60 (t, J=7.71 Hz, 1H) 7.78 (s, 1H) 7.90 (d, J=7.83 Hz, 1H) 8.27 (d, J=8.08 Hz, 1H) 8.38 (d, J=7.58 Hz, 1H) 8.57 (s, 1H) 9.03 (s, 1H) 10.55 (s, 1H); ESI-MS: m/z calc'd for C21H20F3N7O 443.43; found 444.3 (M+H)$^+$ Example 280

N-(5-methyl-1H-pyrazol-3-yl)-2,7-diphenylimidazo [1,2-c]pyrimidin-5-amine

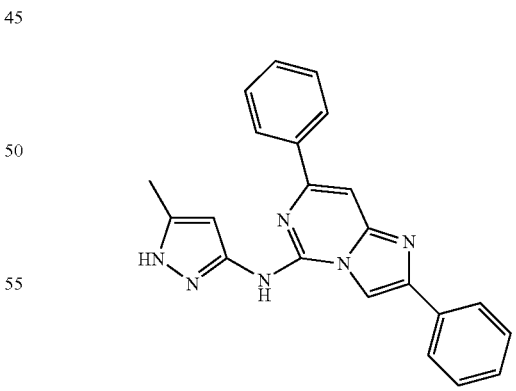

5-(methylthio)-2,7-diphenylimidazo[1,2-c]pyrimidines (0.13 mmol, 0.04 g), 3-amino-5-methylpyrazol (0.38 mmol, 0.037 g) and NaHCO3 (0.25 mmol, 0.021 g) were dissolved in DMF (1 mL) The reaction mixture was heated to 200° C. using a microwave reactor for 1 hour. The mixture was then concentrated and purified by LC-MS to give the title compound. $^1$H NMR (400 MHz, DMSO-$d_6$) δ ppm 2.33 (s, 3H)

6.71 (s, 1H) 7.35-7.50 (m, 6H) 7.63 (s, 1H) 7.93 (d, J=7.07 Hz, 2H) 8.15 (d, J=7.33 Hz, 2H) 8.90 (s, 1H) 10.22 (s, 1H) 12.24 (s, 1H); ESI-MS: m/z calc'd for C22H18N6 366.42; found 367.3 (M+H)+

Example 281

N-(4-(2-(hydroxymethyl)-5-(5-methyl-1H-pyrazol-3-ylamino)imidazo[1,2-c]pyrimidin-7-ylthio)phenyl)cyclopropanecarboxamide

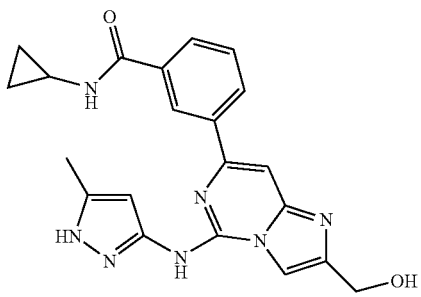

The title compound was synthesized using (7-chloro-5-(5-methyl-1H-pyrazol-3-ylamino)imidazo[1,2-c]pyrimidin-2-yl)methanol and 3-(cyclopropylcarbamoyl)phenyl boronic acid using the procedure described in Example 278. $^1$H NMR (400 MHz, DMSO-$d_6$) δ ppm 0.61 (d, J=6.57 Hz, 2H) 0.74 (d, J=6.57 Hz, 2H) 2.33 (s, 3H) 2.84-2.95 (m, 1H) 4.70 (s, 2H) 6.70 (s, 1H) 7.60-7.71 (m, 2H) 7.93 (d, J=7.33 Hz, 1H) 8.30 (d, J=7.07 Hz, 1H) 8.54 (d, J=17.68 Hz, 2H) 8.64 (s, 1H) 10.89 (s, 1H) 12.40 (s, 1H); ESI-MS: m/z calc'd for C21H21N7O2 403.44; found 404.4 (M+H)+

Example 282

N-(3-(2-(hydroxymethyl)-5-(5-methyl-1H-pyrazol-3-ylamino)imidazo[1,2-c]pyrimidin-7-yl)phenyl)methanesulfonamide

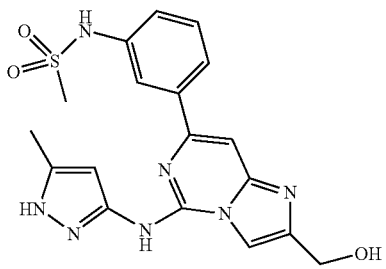

The title compound was synthesized using (7-chloro-5-(5-methyl-1H-pyrazol-3-ylamino)imidazo[1,2-c]pyrimidin-2-yl)methanol and 3-(methylsulfonamido)phenyl boronic acid using the procedure described in Example 278. $^1$H NMR (400 MHz, DMSO-$d_6$) δ ppm 2.32 (s, 3H) 3.06 (s, 3H) 4.70 (s, 2H) 6.75 (s, 1H) 7.31 (dd, J=7.96, 1.64 Hz, 1H) 7.50-7.61 (m, 2H) 7.89 (d, J=8.08 Hz, 1H) 8.15 (s, 1H) 8.57 (s, 1H) 10.02 (s, 1H) 10.97 (s, 1H) 12.37 (s, 1H); ESI-MS: m/z calc'd for C18H19N7O3S 413.45; found 414.3 (M+H)+

Example 283

N-(4-(2-((dimethylamino)methyl)-5-(5-methyl-1H-pyrazol-3-ylamino)imidazo[1,2-c]pyrimidin-7-ylthio)phenyl)cyclopropanecarboxamide

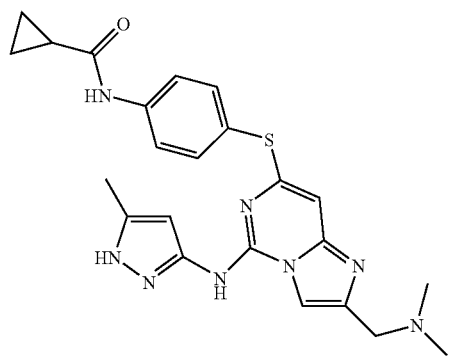

N-(4-(2-(hydroxymethyl)-5-(5-methyl-1H-pyrazol-3-ylamino)imidazo[1,2-c]pyrimidin-7-ylthio)phenyl)cyclopropanecarboxamide (0.18 mmol, 0.089 g) was treated with thionyl chloride (0.5 mL) at ambient temperature for 1 hour. After reaction mixture was concentrated in vacuo, excess dimethylamine in THF (1.5 mL) was added and heated to 60° C. Reaction mixture was concentrated and purified by LC-MS to give the title compound. $^1$H NMR (400 MHz, DMSO-$d_6$) δ ppm 0.82 (d, J=6.57 Hz, 4H) 1.81 (dt, J=12.19, 6.16 Hz, 1H) 2.12 (s, 3H) 3.17 (d, J=5.31 Hz, 6H) 4.10 (s, 1H) 5.89 (s, 1H) 6.42 (s, 1H) 7.52 (d, J=8.34 Hz, 2H) 7.74 (d, J=8.34 Hz, 2H) 8.17 (s, 1H) 10.21 (s, 1H) 10.46 (s, 1H) 12.09 (s, 1H); ESI-MS: m/z calc'd for C23H26N8OS 462.57; found 463.4 (M+H)+

Example 284

N-(4-(5-(5-methyl-1H-pyrazol-3-ylamino)-2-((methylamino)methyl) imidazo[1,2-c]pyrimidin-7-ylthio)phenyl)cyclopropanecarboxamide

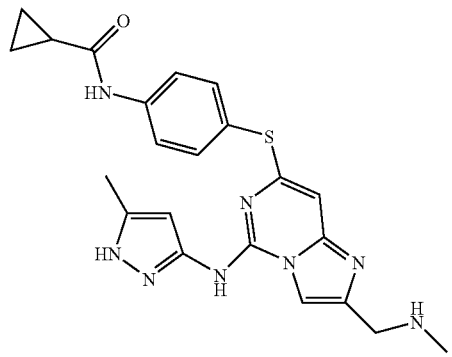

The title compound was synthesized using N-(4-(2-(hydroxymethyl)-5-(5-methyl-1H-pyrazol-3-ylamino)imidazo[1,2-c]pyrimidin-7-ylthio)phenyl)cyclopropanecarboxamide and methyl amine using the procedure described in Example 283. ¹H NMR (400 MHz, DMSO-d₆) δ ppm 0.82 (d, J=5.56 Hz, 4H) 1.82 (dt, J=12.06, 5.97 Hz, 1H) 2.11 (s, 3H) 3.28 (s, 3H) 4.03 (s, 2H) 5.84 (s, 1H) 6.49 (s, 1H) 7.53 (d, J=8.08 Hz, 2H) 7.75 (d, J=8.08 Hz, 2H) 8.27 (s, 1H) 10.48 (s, 1H) 12.12 (s, 1H); ESI-MS: m/z calc'd for C22H24N8OS 448.54; found 449.4 (M+H)⁺

Example 285

N-(4-(2-((2-hydroxyethylamino)methyl)-5-(5-methyl-1H-pyrazol-3-ylamino)imidazo[1,2-c]pyrimidin-7-ylthio)phenyl)cyclopropanecarboxamide

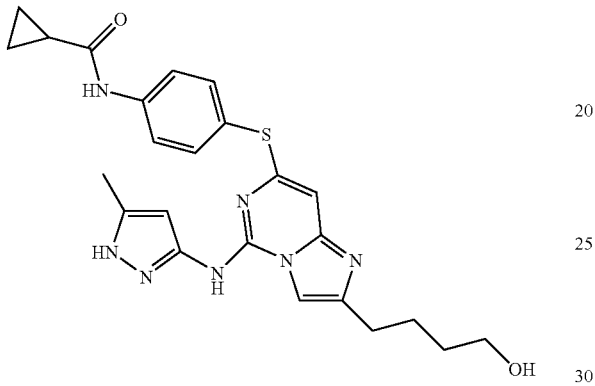

The title compound was synthesized using N-(4-(2-(hydroxymethyl)-5-(5-methyl-1H-pyrazol-3-ylamino)imidazo[1,2-c]pyrimidin-7-ylthio)phenyl)cyclopropanecarboxamide and ethanol amine using the procedure described in Example 283. ¹H NMR (400 MHz, DMSO-d₆) δ ppm 0.82 (d, J=6.32 Hz, 4H) 1.82 (dt, J=12.44, 6.28 Hz, 1H) 2.11 (s, 3H) 2.83-2.92 (m, 2H) 3.53-3.62 (m, 2H) 4.01 (s, 2H) 4.90 (s, 1H) 5.86 (s, 1H) 6.47 (s, 1H) 7.53 (d, J=8.08 Hz, 2H) 7.75 (d, J=7.83 Hz, 2H) 8.26 (s, 1H) 10.36 (s, 1H) 10.48 (s, 1H) 12.12 (s, 1H); ESI-MS: m/z calc'd for C23H26N8O2S 478.57; found 479.4 (M+H)⁺

Example 286

[7-(3-Ethanesulfonyl-phenyl)-2-methyl-imidazo[1,2-c]pyrimidin-5-yl]-(5-methyl-1H-pyrazol-3-yl)-amine

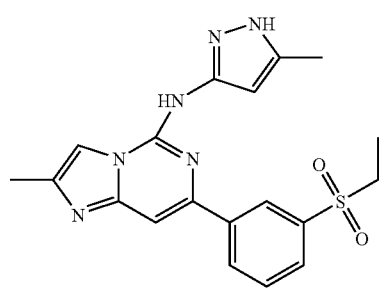

¹H NMR (400 MHz, DMSO-d₆) δ ppm 1.16 (t, J=7.33 Hz, 3H) 2.31 (s, 3H) 2.35 (s, 3H) 4.10 (q, J=5.22 Hz, 2H) 6.70 (s, 1H) 7.67 (s, 1H) 7.76 (t, J=7.83 Hz, 1H) 7.89 (d, J=7.83 Hz, 1H) 8.15 (s, 1H) 8.46 (d, J=7.83 Hz, 1H) 8.71 (s, 1H) 10.23 (s, 1H) 12.22 (s, 1H) MS [m+H] calc'd C₁₉H₂₀N₆O₂S 397.14 and 398.15; found 397.14 and 398.15.

Example 287

N⁷-(1-Benzyl-piperidin-4-yl)-2-methyl-N⁵-(5-methyl-1H-pyrazol-3-yl)-imidazo[1,2-c]pyrimidine-5,7-diamine

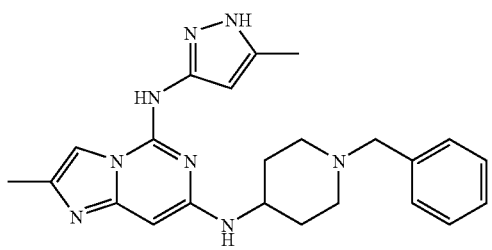

¹H NMR (400 MHz, MeOD) δ ppm 1.59-1.88 (m, 2H) 1.95-2.26 (m, 2H) 2.25-2.44 (m, 7H) 2.98-3.22 (m, 2H) 3.47-3.69 (m, 2H) 4.36 (s, 2H) 5.93 (s, 1H) 6.35 (s, 1H) 7.40-7.55 (m, 5H) 7.59 (s, 1H) MS [m+H] calc'd C₂₃H₂₈N₈ 417.25 and 418.26; found 417.25 and 418.26.

Example 288

[7-(3-Isopropoxy-phenyl)-2-methyl-imidazo[1,2-c]pyrimidin-5-yl]-(5-methyl-1H-pyrazol-3-yl)-amine

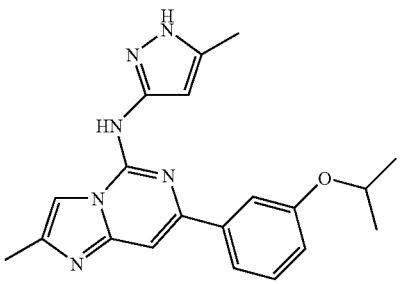

¹H NMR (400 MHz, MeOD) δ ppm 1.29 (d, J=6.06 Hz, 3H) 1.37 (d, J=6.06 Hz, 3H) 2.40 (s, 3H) 2.55 (s, 3H) 4.49-4.65 (m, 1H) 6.86-6.97 (m, 1H) 7.04-7.16 (m, 2H) 7.27 (d, J=16.67 Hz, 2H) 7.38-7.51 (m, 1H) 8.05 (s, 1H) MS [m+H] calc'd $C_{20}H_{22}N_6O$ 363.20, and 363.21; found 363.20, and 364.21.

Example 289

[2-Methyl-7-(3-propoxy-phenyl)-imidazo[1,2-c]pyrimidin-5-yl]-(5-methyl-1H-pyrazol-3-yl)-amine

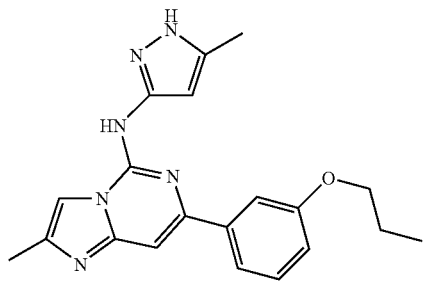

$^1$H NMR (400 MHz, MeOD) δ ppm 1.04 (t, J=7.45 Hz, 3H) 1.71-1.85 (m, 2H) 2.39 (s, 3H) 2.55 (s, 3H) 3.92 (t, J=6.57 Hz, 2H) 6.93 (dd, J=8.08, 2.02 Hz, 2H) 7.36-7.51 (m, 1H) 7.59 (s, 1H) 7.69 (d, J=7.83 Hz, 1H) 7.75 (d, J=2.02 Hz, 1H) 8.04 (s, 1H) MS [m+H] calc'd $C_{20}H_{22}N_6O$ 363.20 and 364.22; found 363.20 and 364.22.

Example 290

[7-(3-Ethanesulfonyl-phenyl)-2-imidazol-1-ylmethyl-imidazo[1,2-c]pyrimidin-5-yl]-(5-methyl-1H-pyrazol-3-yl)-amine

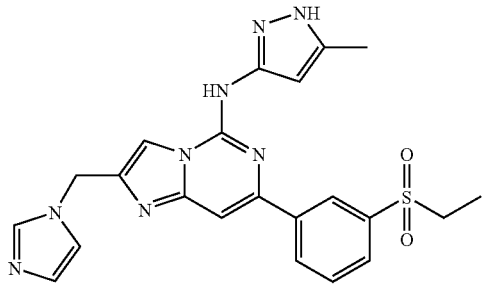

$^1$H NMR (400 MHz, MeOD) δ ppm 1.22-1.30 (m, 3H) 2.34 (s, 2H) 2.54 (s, 3H) 4.02-4.18 (m, 2H) 5.50-5.67 (s, 1H)) 7.16 (s, 1H) 7.59 (s, 1H) 7.76-7.82 (m, 2H) 8.06-8.7 (m, 2H) 8.24 (s, 1H) 8.41 (s, 1H) 9.08 (s, 1H) MS [m+H] calc'd $C_{22}H_{22}N_8O_2S$ 463.17 and 464.17; found 463.17 and 464.17.

Example 291

3-{3-[2-Methyl-5-(5-methyl-1H-pyrazol-3-ylamino)-imidazo[1,2-c]pyrimidin-7-yl]-phenyl}-propionic acid methyl ester

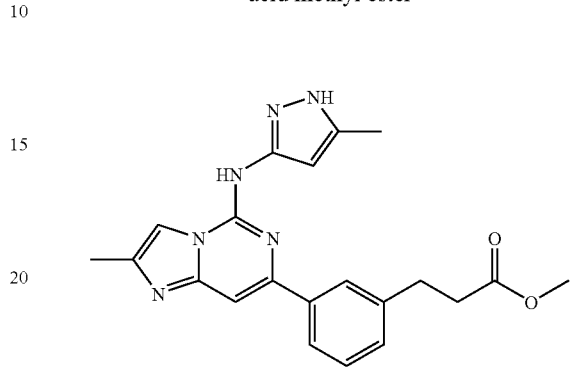

$^1$H NMR (400 MHz, DMSO-$d_6$) δ ppm 2.34 (s, 3H) 2.46 (s, 3H) 2.75 (t, J=7.45 Hz, 2H) 2.98 (t, J=7.71 Hz, 2H) 3.58 (s, 3H) 6.66 (s, 1H) 7.40 (d, J=8.08 Hz, 1H) 7.48 (t, J=7.71 Hz, 1H) 7.66 (s, 1H) 8.01 (d, J=9.60 Hz, 1H) 8.07 (s, 1H) 8.35 (s, 1H) 10.83 (s, 1H) 12.38 (s, 1H) MS [m+H] calc'd $C_{21}H_{22}N_6O_2$ 391.19 and 392.18; found 391.19 and 392.18.

Example 292

3-{3-[2-Methyl-5-(5-methyl-1H-pyrazol-3-ylamino)-imidazo[1,2-c]pyrimidin-7-yl]-phenyl}-propionic acid

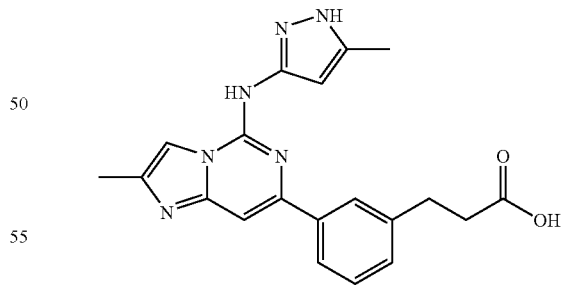

$^1$H NMR (400 MHz, DMSO-$d_6$) δ ppm 2.33 (s, 3H) 2.44 (s, 3H) 2.65 (t, J=7.58 Hz, 2H) 2.91-3.02 (m, 2H) 6.68 (s, 1H) 7.39 (d, J=8.08 Hz, 1H) 7.47 (t, J=7.33 Hz, 1H) 7.65 (s, 1H) 8.00 (d, J=7.33 Hz, 1H) 8.08 (s, 1H) 8.32 (s, 1H) 10.78 (s, 1H)

12.26 (s, 2H) MS [m+H] calc'd $C_{20}H_{20}N_6O_2$ 377.16 and 378.17; found 377.16 and 378.17.

Example 293

5-[2-Methyl-5-(5-methyl-1H-pyrazol-3-ylamino)-imidazo[1,2-c]pyrimidin-7-yl]-thiophene-2-carboxylic acid cyclopropylamide

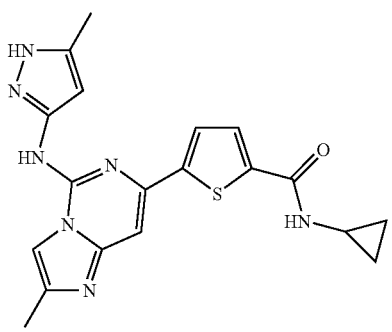

$^1$H NMR (400 MHz, MeOD) δ ppm 0.54-0.72 (m, 2H) 0.74-0.96 (m, 2H) 1.81-1.90 (m, 1H) 2.40 (s, 3H) 2.51 (s, 3H) 5.49 (s, 1H) 7.53 (s, 1H) 7.68 (s, 1H) 7.83 (s, 1H) 8.04 (s, 1H) MS [m+H] calc'd $C_{19}H_{19}N_7OS$ 394.15 and 395.15; found 394.15 and 395.15.

Example 294

[7-(1-Benzyl-1H-pyrazol-4-yl)-2-methyl-imidazo[1,2-c]pyrimidin-5-yl]-(5-cyclopropyl-1H-pyrazol-3-yl)-amine

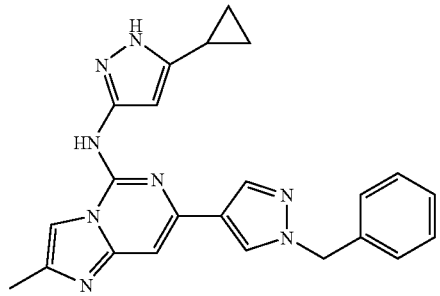

$^1$H NMR (400 MHz, MeOD) δ ppm 0.60-0.87 (m, 2H) 0.91-1.14 (m, 2H) 1.84-2.10 (m, 1H) 3.31 (s, 3H) 3.35 (s, 2H) 5.39 (s, 2H) 6.35 (s, 1H) 7.10-7.56 (m, 6H) 7.92 (s, 1H) 8.07 (s, 1H) 8.27 (s, 1H) MS [m+H] calc'd $C_{23}H_{22}N_8$ 411.2 and 412.2; found 411.2 and 412.2.

Example 295

[7-(1-Benzyl-1H-pyrazol-4-yl)-2-methyl-imidazo[1,2-c]pyrimidin-5-yl]-(5-methyl-1H-pyrazol-3-yl)-amine

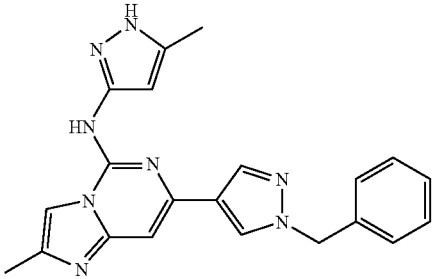

$^1$H NMR (400 MHz, MeOD) δ ppm 2.35 (s, 3H) 2.48 (s, 3H) 3.35 (s, 2H) 5.40 (s, 2H) 6.49 (s, 1H) 7.22-7.58 (m, 6H) 7.93 (s, 1H) 8.10 (s, 1H) 8.30 (s, 1H) MS [m+H] calc'd $C_{21}H_{20}N_8$ 385.19 and 386.19; found 385.19 and 386.19.

Example 296

N-{2-[2-Methyl-5-(5-methyl-1H-pyrazol-3-ylamino)-imidazo[1,2-c]pyrimidin-7-yl]-phenyl}-methanesulfonamide

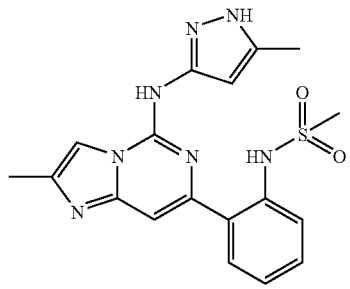

$^1$H NMR (400 MHz, DMSO-$d_6$) δ ppm 2.26 (s, 3H) 2.47 (s, 3H) 2.87 (s, 3H) 6.23 (s, 1H) 7.33 (t, J=7.33 Hz, 1H) 7.40-7.63 (m, 2H) 7.78 (d, J=7.83 Hz, 1H) 8.27 (s, 1H) 10.30 (s, 1H) 10.70 (s, 1H) 12.36 (s, 1H) MS [m+H] calc'd C$_{18}$H$_{19}$N$_7$O$_2$S 398.13 and 399.13; found 398.13 and 399.13.

Example 297

N-{2-[2-Methyl-5-(5-methyl-1H-pyrazol-3-ylamino)-imidazo[1,2-c]pyrimidin-7-yl]-phenyl}-acetamide

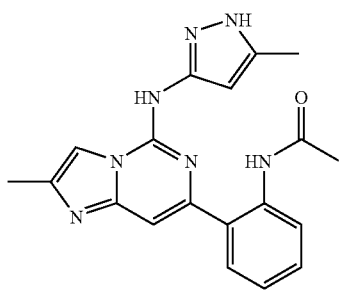

$^1$H NMR (400 MHz, DMSO-d$_6$) δ ppm 1.82 (s, 3H) 2.26 (s, 3H) 2.47 (s, 3H) 6.29 (s, 1H) 7.25 (t, J=7.45 Hz, 1H) 7.39 (s, 1H) 7.42-7.51 (m, 1H) 7.72 (d, J=7.83 Hz, 1H) 8.03 (d, J=8.08 Hz, 1H) 8.27 (s, 1H) 10.63 (s, 1H) 10.75 (s, 1H) 12.47 (s, 1H) MS [m+H] calc'd C$_{19}$H$_{19}$N$_7$O 362.18 and 363.18; found 362.18 and 363.18.

Example 298

[7-(1H-Indol-4-yl)-2-methyl-imidazo[1,2-c]pyrimidin-5-yl]-(5-methyl-1H-pyrazol-3-yl)-amine

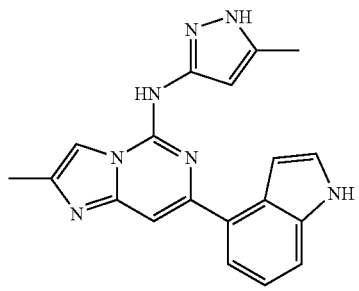

$^1$H NMR (400 MHz, DMSO-d$_6$) δ ppm 1.17 (t, J=7.20 Hz, 2H) 2.27 (s, 3H) 2.42-2.50 (m, 3H) 6.62 (s, 1H) 6.94 (s, 1H) 7.28 (t, J=7.83 Hz, 1H) 7.49-7.64 (m, 2H) 7.68-7.77 (m, 1H) 8.37 (s, 1H) 10.82 (s, 1H) 11.46 (s, 1H) 12.40 (s, 1H) MS [m+H] calc'd C$_{19}$H$_{17}$N$_7$ 344.15 and 345.15; found 344.15 and 345.15.

Example 299

N-{4-[2-Methyl-5-(5-methyl-1H-pyrazol-3-ylamino)-imidazo[1,2-c]pyrimidin-7-ylsulfanyl]-phenyl}-acetamide

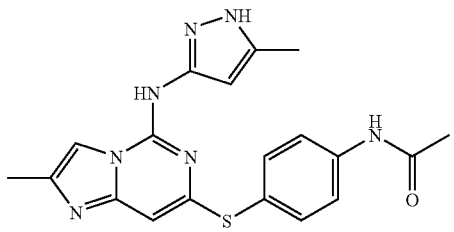

$^1$H NMR (400 MHz, MeOD) δ ppm 2.17 (s, 3H) 2.21 (s, 3H) 2.45 (s, 3H) 5.92 (s, 1H) 6.64 (s, 1H) 7.60 (d, J=7.58 Hz, 2H) 7.78 (d, J=9.85 Hz, 2H) 7.91 (s, 1H) MS [m+H] calc'd C$_{19}$H$_{19}$N$_7$OS 394.15 and 395.15; found 394.15 and 395.15.

Example 300

[7-(2-Amino-phenyl)-2-methyl-imidazo[1,2-c]pyrimidin-5-yl]-(5-methyl-1H-pyrazol-3-yl)-amine

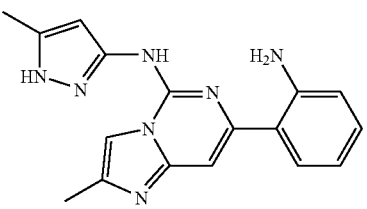

$^1$H NMR (400 MHz, MeOD) δ ppm 2.36 (s, 3H) 2.55 (s, 3H) 6.22 (s, 1H) 6.99 (t, J=8.97 Hz, 2H) 7.33 (t, J=7.71 Hz, 1H) 7.49 (s, 1H) 7.80 (d, J=8.08 Hz, 1H) 7.99 (s, 1H) MS [m+H] calc'd C17H17N7 320.17 and 321.18; found 320.17 and 321.18.

Example 301

[7-(1-Isobutyl-1H-pyrazol-4-yl)-2-methyl-imidazo[1,2-c]pyrimidin-5-yl]-(5-methyl-1H-pyrazol-3-yl)-amine

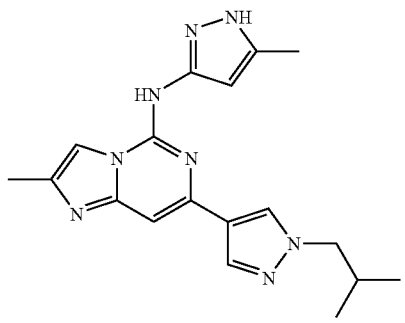

$^1$H NMR (400 MHz, DMSO-d$_6$) δ ppm 0.69-0.79 (m, 3H) 0.94-1.04 (m, 3H) 2.41 (s, 3H) 3.74 (s, 3H) 5.40 (d, J=7.5 Hz 2H) 6.49 (s, 1H) 6.79-6.99 (m, 2H) 7.22 (s, 1H) 8.27 (s, 1H) 8.47 (s, 1H) 10.74 (s, 1H) MS [m+H] calc'd C$_{18}$H$_{22}$N$_8$ 351.2 and 352.2; found 351.2 and 352.2.

Example 302

4-{4-[2-Methyl-5-(5-methyl-1H-pyrazol-3-ylamino)-imidazo[1,2-c]pyrimidin-7-yl]-pyrazol-1-ylmethyl}-benzoic acid methyl ester

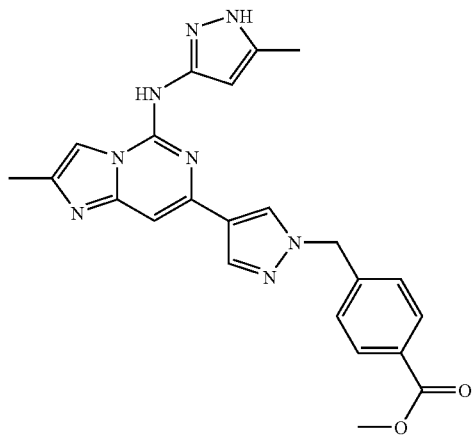

$^1$H NMR (400 MHz, DMSO-d$_6$) δ ppm 2.36 (s, 3H) 2.40 (s, 3H) 3.84 (s, 3H) 5.53 (s, 2H) 6.50 (s, 1H) 7.33 (s, 1H) 7.49-7.69 (m, 2H) 7.91 (s, 2H) 8.16 (s, 1H) 8.28 (s, 1H) 8.51 (s, 1H) 10.72 (s, 1H) 12.36 (s, 1H) MS [m+H] calc'd C$_{23}$H$_{22}$N$_8$O$_2$ 443.20 and 444.20; found 443.20 and 444.20.

Example 303

(5-Cyclopropyl-1H-pyrazol-3-yl)-{7-[1-(3-methoxy-benzyl)-1H-pyrazol-4-yl]-2-methyl-imidazo[1,2-c]pyrimidin-5-yl}-amine

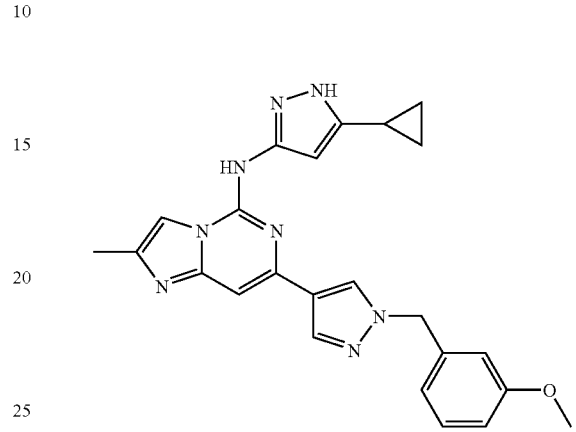

$^1$H NMR (400 MHz, DMSO-d$_6$) δ ppm 0.69-0.79 (m, 2H) 0.94-1.04 (m, 2H) 1.91-2.06 (m, 1H) 2.41 (s, 3H) 3.74 (s, 3H) 5.40 (s, 2H) 6.49 (s, 1H) 6.79-6.99 (m, 2H) 7.22-7.38 (m, 2H) 8.15 (s, 1H) 8.27 (s, 1H) 8.47 (s, 1H) 10.74 (s, 1H) MS [m+H] calc'd C$_{24}$H$_{24}$N$_8$O 441.22 and 442.22; found 441.22 and 442.22.

Example 304

(5-Cyclopropyl-1H-pyrazol-3-yl)-[2-methyl-7-(1-quinolin-8-ylmethyl-1H-pyrazol-4-yl)-imidazo[1,2-c]pyrimidin-5-yl]-amine

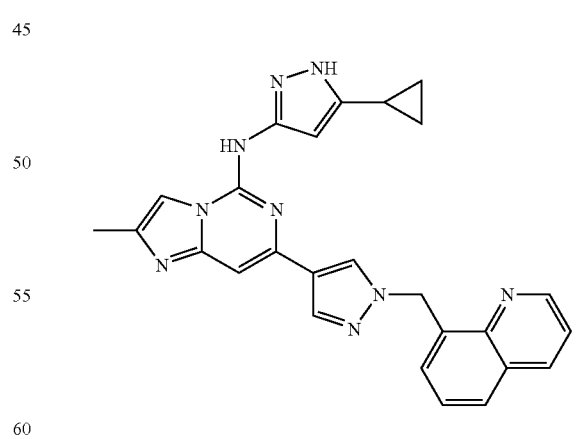

$^1$H NMR (400 MHz, DMSO-d$_6$) δ ppm 0.67-0.79 (m, 2H) 0.92-1.04 (m, 2H) 1.88-2.04 (m, 1H) 2.40 (s, 3H) 6.06 (s, 2H) 6.48 (s, 1H) 7.34 (s, 1H) 7.48 (d, J=6.82 Hz, 1H) 7.52-7.70 (m, 2H) 8.00 (d, J=8.08 Hz, 1H) 8.17 (s, 1H) 8.26 (s, 1H) 8.44

(d, J=9.09 Hz, 1H) 8.53 (s, 1H) 8.92-9.06 (m, 1H) MS [m+H] calc'd C$_{26}$H$_{23}$N$_9$ 462.23 and 463.23; found 462.23 and 463.23.

Example 305

3-{4-[5-(5-Cyclopropyl-1H-pyrazol-3-ylamino)-2-methyl-imidazo[1,2-c]pyrimidin-7-yl]-pyrazol-1-ylmethyl}-benzoic acid methyl ester

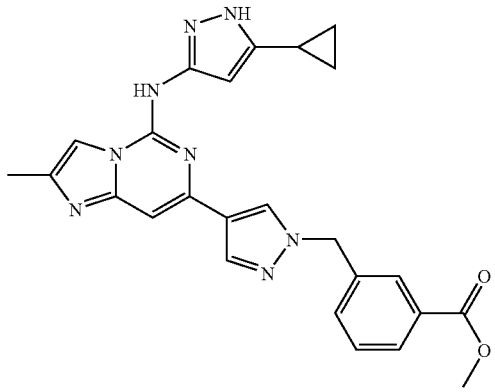

$^1$H NMR (400 MHz, DMSO-d$_6$) δ ppm 0.67-0.80 (m, 2H) 0.92-1.05 (m, 2H) 1.89-2.08 (m, 1H) 2.40 (s, 3H) 3.84 (s, 3H) 5.53 (s, 2H) 6.50 (s, 1H) 7.33 (s, 1H) 7.55 (t, J=7.20 Hz, 1H) 7.58-7.65 (m, 1H) 7.89-7.97 (m, 2H) 8.16 (s, 1H) 8.27 (s, 1H) 8.51 (s, 1H) MS [m+H] calc'd C$_{25}$H$_{24}$N$_8$O$_2$ 469.2 and 470.2; found 469.2 and 470.2.

Example 306

(5-Cyclopropyl-1H-pyrazol-3-yl)-{7-[1-(4-methanesulfonyl-benzyl)-1H-pyrazol-4-yl]-2-methyl-imidazo[1,2-c]pyrimidin-5-yl}-amine

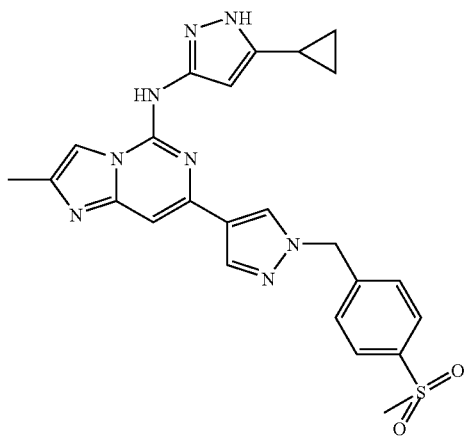

$^1$H NMR (400 MHz, DMSO-d$_6$) δ ppm 0.70-0.81 (m, 2H) 0.93-1.03 (m, 2H) 1.90-2.08 (m, 1H) 2.42 (s, 3H) 3.20 (s, 3H) 5.59 (s, 2H) 6.50 (s, 1H) 7.34 (s, 1H) 7.53 (d, J=8.34 Hz, 2H) 7.94 (d, J=8.34 Hz, 2H) 8.19 (s, 1H) 8.28 (s, 1H) 8.57 (s, 1H). MS [m+H] calc'd C$_{24}$H$_{24}$N$_8$O$_2$S 489.18 and 490.18; found 489.18 and 490.18.

Example 307

(5-Cyclopropyl-1H-pyrazol-3-yl)-{7-[1-(4-methoxy-benzyl)-1H-pyrazol-4-yl]-2-methyl-imidazo[1,2-c]pyrimidin-5-yl}-amine

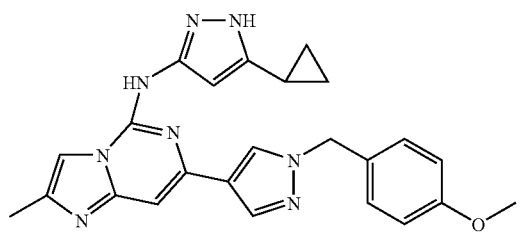

$^1$H NMR (400 MHz, MeOD) δ ppm 0.60-0.87 (m, 2H) 0.92-1.22 (m, 2H) 1.80-2.18 (m, 1H) 2.49 (s, 3H) 3.79 (s, 3H) 5.33 (s, 2H) 6.94 (d, J=8.34 Hz, 3H) 7.29 (d, J=8.84 Hz, 3H) 7.95 (s, 1H) 8.11 (s, 1H) 8.23 (s, 1H) MS [m+H] calc'd C$_{24}$H$_{24}$N$_8$O 441.21 and 442.21; found 441.21 and 442.21.

Example 308

(5-Cyclopropyl-1H-pyrazol-3-yl)-{7-[1-(2,3-dimethoxy-benzyl)-1H-pyrazol-4-yl]-2-methyl-imidazo[1,2-c]pyrimidin-5-yl}-amine

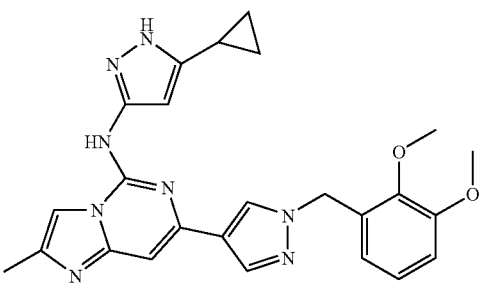

$^1$H NMR (400 MHz, MeOD) δ ppm 0.67-0.89 (m, 2H) 0.97-1.15 (m, 2H) 1.88-2.13 (m, 1H) 2.49 (s, 3H) 3.79 (s, 3H) 3.86 (s, 3H) 5.40 (s, 2H) 6.40 (s, 1H) 6.84 (dd, J=7.07, 1.77 Hz, 1H) 7.00-7.15 (m, 2H) 7.27 (s, 1H) 7.93 (s, 1H) 8.09 (s, 1H) 8.23 (s, 1H) MS [m+H] calc'd $C_{25}H_{26}N_8O_2$ 471.22 and 472.22; found 471.22 and 472.22.

Example 309

(5-Cyclopropyl-1H-pyrazol-3-yl)-{7-[1-(3,5-dimethoxy-benzyl)-1H-pyrazol-4-yl]-2-methyl-imidazo[1,2-c]pyrimidin-5-yl}-amine

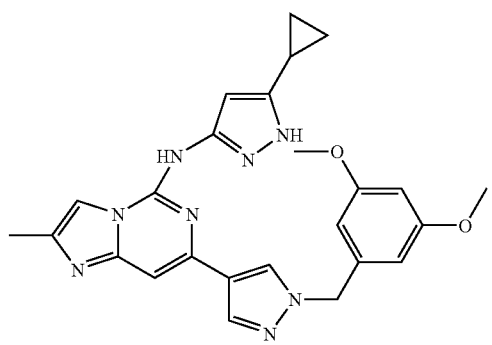

$^{1}$H NMR (400 MHz, MeOD) δ ppm 0.68-0.83 (m, 2H) 0.95-1.14 (m, 2H) 1.87-2.06 (m, 1H) 2.50 (s, 3H) 3.75 (s, 6H) 5.34 (s, 2H) 6.39 (s, 1H) 6.46 (s, 3H) 7.29 (s, 1H) 7.94 (s, 1H) 8.12 (s, 1H) 8.29 (s, 1H) MS [m+H] calc'd $C_{25}H_{26}N_8O_2$ 471.22 and 472.22; found 471.22 and 472.22.

Example 310

[7-(1-Benzo[1,2,5]oxadiazol-5-ylmethyl-1H-pyrazol-4-yl)-2-methyl-imidazo[1,2-c]pyrimidin-5-yl]-(5-cyclopropyl-1H-pyrazol-3-yl)-amine

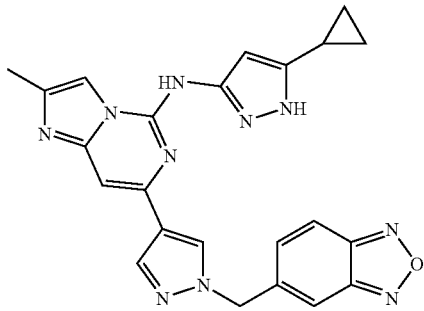

$^{1}$H NMR (400 MHz, MeOD) δ ppm 0.62-0.82 (m, 2H) 0.88-1.08 (m, 2H) 1.84-2.07 (m, 1H) 2.51 (s, 3H) 5.58 (s, 2H) 6.40 (s, 1H) 7.33 (s, 1H) 7.45 (dd, J=9.35, 1.26 Hz, 1H) 7.74 (s, 1H) 7.92 (d, J=9.35 Hz, 1H) 7.96 (s, 1H) 8.19 (s, 1H) 8.44 (s, 1H) MS [m+H] calc'd $C_{23}H_{20}N_{10}O$ 453.19 and 454.19; found 453.19 and 454.19.

Example 311

2-{4-[5-(5-Cyclopropyl-1H-pyrazol-3-ylamino)-2-methyl-imidazo[1,2-c]pyrimidin-7-yl]-pyrazol-1-ylmethyl}-benzonitrile

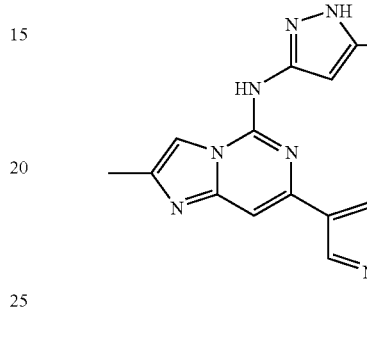

$^{1}$H NMR (400 MHz, MeOD) δ ppm 0.67-0.89 (m, 2H) 0.93-1.19 (m, 2H) 1.76-2.12 (m, 1H) 2.50 (s, 3H) 5.64 (s, 2H) 6.43 (s, 1H) 7.31 (s, 1H) 7.45 (d, J=8.34 Hz, 1H) 7.50-7.59 (m, 1H) 7.64-7.74 (m, 1H) 7.81 (dd, J=7.71, 1.14 Hz, 1H) 7.97 (s, 1H) 8.14 (s, 1H) 8.42 (s, 1H) MS [m+H] calc'd $C_{24}H_{21}N_9$ 436.19 and 437.19; found 436.19 and 437.19.

Example 312

(5-Cyclopropyl-1H-pyrazol-3-yl)-[2-methyl-7-(1-pyridin-2-ylmethyl-1H-pyrazol-4-yl)-imidazo[1,2-c]pyrimidin-5-yl]-amine

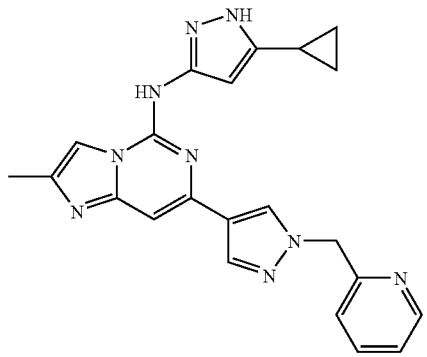

$^{1}$H NMR (400 MHz, MeOD) δ ppm 0.71-0.91 (m, 2H) 0.94-1.17 (m, 2H) 1.88-2.10 (m, 1H) 2.51 (s, 3H) 5.53 (s, 2H) 6.43 (s, 1H) 7.23-7.35 (m, 2H) 7.34-7.48 (m, 1H) 7.76-7.91

(m, 1H) 7.97 (s, 1H) 8.14 (s, 1H) 8.43 (s, 1H) 8.55 (d, J=4.29 Hz, 1H) MS [m+H] calc'd $C_{22}H_{21}N_9$ 412.19 and 413.19; found 412.19 and 413.19.

Example 313

3-{4-[5-(5-Cyclopropyl-1H-pyrazol-3-ylamino)-2-methyl-imidazo[1,2-c]pyrimidin-7-yl]-pyrazol-1-ylmethyl}-N-ethyl-benzamide

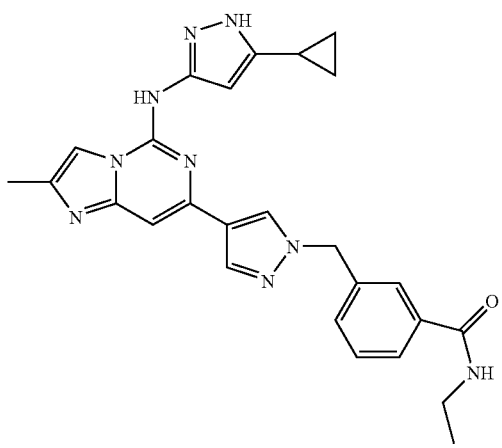

$^1$H NMR (400 MHz, MeOD) δ ppm 0.71-0.81 (m, 2H) 0.96-1.11 (m, 2H) 1.21 (t, J=7.20 Hz, 3H) 1.90-2.08 (m, 1H) 2.50 (s, 3H) 3.40 (q, J=7.24 Hz, 2H) 5.48 (s, 2H) 7.31 (s, 1H) 7.42-7.58 (m, 2H) 7.73-7.84 (m, 2H) 7.85-8.04 (m, 2H) 8.13 (s, 1H) 8.36 (s, 1H) MS [m+H] calc'd $C_{26}H_{27}N_9O$ 482.23 and 483.23; found 482.23 and 483.23.

Example 314

3-{4-[5-(5-Cyclopropyl-1H-pyrazol-3-ylamino)-2-methyl-imidazo[1,2-c]pyrimidin-7-yl]-pyrazol-1-ylmethyl}-benzonitrile

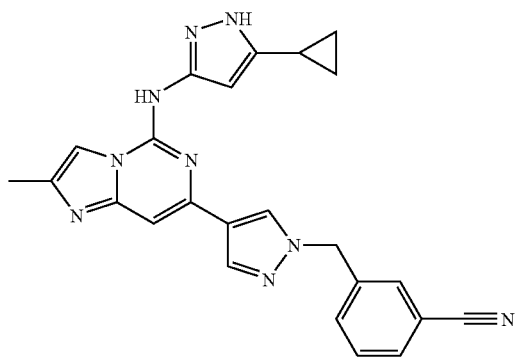

$^1$H NMR (400 MHz, DMSO-d$_6$) δ ppm 0.68-0.82 (m, 2H) 0.93-1.07 (m, 2H) 1.91-2.10 (m, 1H) 2.43 (s, 3H) 5.53 (s, 2H) 6.50 (s, 1H) 7.37 (s, 1H) 7.55-7.71 (m, 2H) 7.74-7.97 (m, 2H) 8.20 (s, 1H) 8.32 (s, 1H) 8.56 (s, 1H) 10.86 (s, 1H) 12.40 (s, 1H) MS [m+H] calc'd $C_{24}H_{21}N_9$ 436.19 and 437.19; found 436.19 and 437.19.

Example 315

3-{4-[5-(5-Cyclopropyl-1H-pyrazol-3-ylamino)-2-methyl-imidazo[1,2-c]pyrimidin-7-yl]-pyrazol-1-ylmethyl}-N-thiazol-2-yl-benzamide

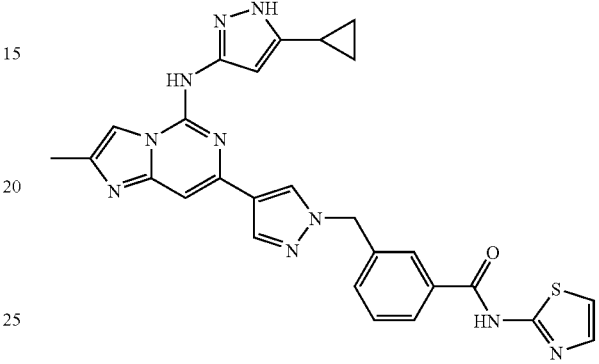

$^1$H NMR (400 MHz, MeOD) δ ppm 0.62-0.82 (m, 2H) 0.85-1.03 (m, 2H) 1.66-1.86 (m, 1H) 2.41 (s, 3H) 5.54 (s, 2H) 6.50 (s, 1H) 7.26-7.32 (m, 1H) 7.33-7.38 (m, 1H) 7.51-7.61 (m, 3H) 8.02 (s, 1H) 8.04-8.12 (m, 1H) 8.18 (s, 1H) 8.25-8.32 (m, 1H) 8.53 (s, 1H) MS [m+H] calc'd $C_{27}H_{24}N_{10}OS$ 537.19 and 538.19; found 537.19 and 538.19.

Example 316

(5-Cyclopropyl-1H-pyrazol-3-yl)-[2-methyl-7-(1-phenethyl-1H-pyrazol-4-yl)-imidazo[1,2-c]pyrimidin-5-yl]-amine

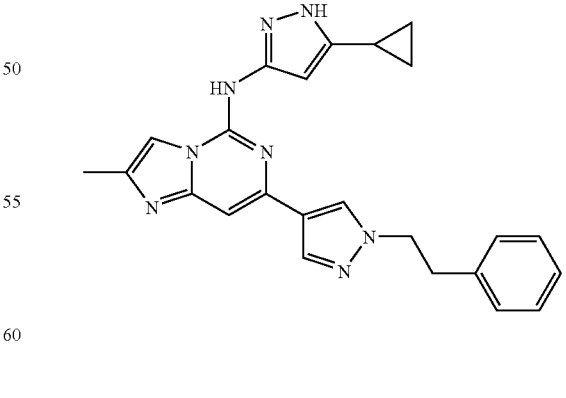

$^1$H NMR (400 MHz, MeOD) δ ppm 0.69-0.89 (m, 2H) 0.98-1.18 (m, 2H) 1.31 (t, J=7.33 Hz, 2H) 1.91-2.12 (m, 1H) 2.50 (s, 1H) 4.45 (t, J=6.82 Hz, 2H) 6.36 (s, 1H) 7.03-7.40 (m, 5H) 7.95 (s, 1H) 8.00 (s, 1H) 8.11 (s, 1H) MS [m+H] calc'd C$_{24}$H$_{24}$N$_8$ 425.21 and 426.2; found 425.21 and 426.2.

Example 317

(5-Cyclopropyl-1H-pyrazol-3-yl)-{2-methyl-7-[1-(4-pyrazol-1-yl-benzyl)-1H-pyrazol-4-yl]-imidazo[1,2-c]pyrimidin-5-yl}-amine

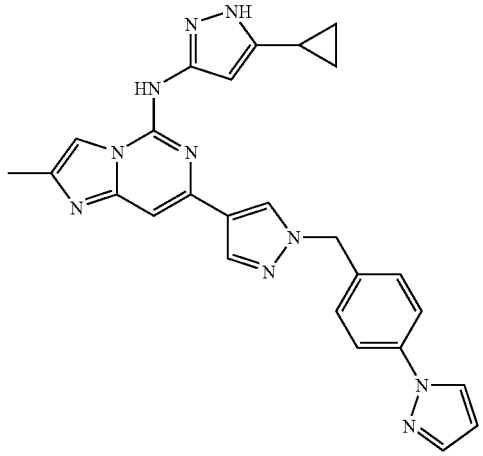

$^1$H NMR (400 MHz, MeOD) δ ppm 0.66-0.80 (m, 2H) 0.93-1.06 (m, 2H) 1.87-2.03 (m, 1H) 2.51 (s, 3H) 5.47 (s, 2H) 6.38 (s, 1H) 6.53 (dd, J=2.53, 1.77 Hz, 1H) 7.31 (s, 1H) 7.47 (d, J=8.84 Hz, 2H) 7.72 (d, J=1.52 Hz, 1H) 7.78 (d, J=8.59 Hz, 2H) 7.96 (s, 1H) 8.15 (s, 1H) 8.24 (d, J=2.53 Hz, 1H) 8.33 (s, 1H) MS [m+H] calc'd C$_{26}$H$_{24}$N$_{10}$ 477.22 and 478.22; found 477.22 and 478.22.

Example 318

2-{4-[2-Methyl-5-(5-methyl-1H-pyrazol-3-ylamino)-imidazo[1,2-c]pyrimidin-7-yl]-pyrazol-1-ylmethyl}-benzonitrile

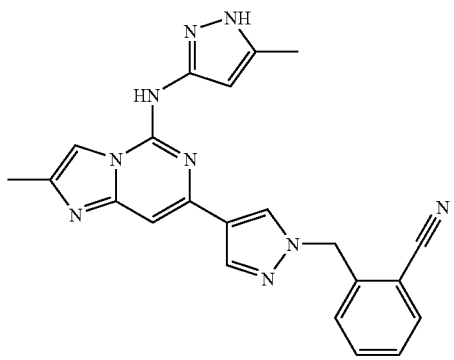

$^1$H NMR (400 MHz, MeOD) δ ppm 2.38 (s, 3H) 2.51 (s, 3H) 5.65 (s, 2H) 6.59 (s, 1H) 7.32 (s, 1H) 7.46 (d, J=7.33 Hz, 1H) 7.49-7.59 (m, 1H) 7.65-7.74 (m, 1H) 7.82 (d, J=0.51 Hz, 1H) 7.99 (s, 1H) 8.17 (s, 1H) 8.48 (s, 1H) MS [m+H] calc'd C$_{22}$H$_{19}$N$_9$ 410.18 and 411.19; found 410.18 and 411.19.

Example 319

(5-Cyclopropyl-1H-pyrazol-3-yl)-{2-methyl-7-[1-(3-pyrrol-1-yl-benzyl)-1H-pyrazol-4-yl]-imidazo[1,2-c]pyrimidin-5-yl}-amine

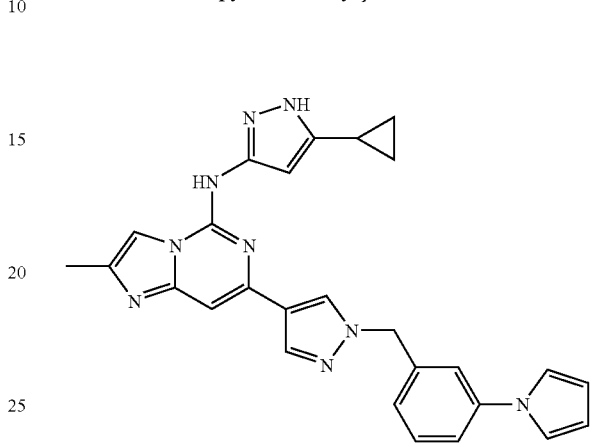

$^1$H NMR (400 MHz, MeOD) δ ppm 0.56-0.85 (m, 2H) 0.87-1.09 (m, 2H) 1.76-2.08 (m, 2H) 2.38 (s, 3H) 5.45 (s, 2H) 6.13-6.45 (m, 2H) 7.09-7.26 (m, 3H) 7.34-7.53 (m, 3H) 7.69 (s, 1H) 8.04 (s, 1H) 8.22 (s, 1H) MS [m+H] calc'd C$_{27}$H$_{25}$N$_9$ 476.22 and 477.22; found 476.22 and 477.22.

Example 320

N-Ethyl-4-{4-[2-methyl-5-(5-methyl-1H-pyrazol-3-ylamino)-imidazo[1,2-c]pyrimidin-7-yl]-pyrazol-1-ylmethyl}-benzamide

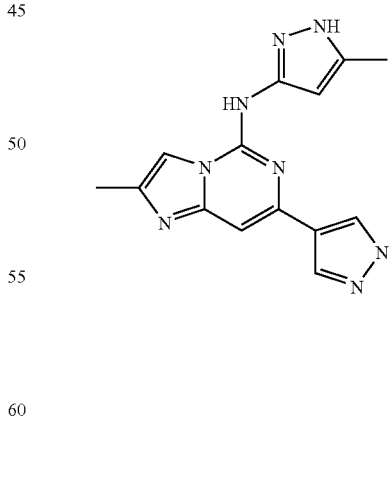

$^1$H NMR (400 MHz, MeOD) δ ppm 1.21 (t, J=7.20 Hz, 3H) 2.36 (s, 3H) 2.51 (s, 3H) 3.33-3.48 (m, 2H) 5.50 (s, 2H) 6.53 (s, 1H) 7.31 (s, 1H) 7.38 (d, J=8.59 Hz, 2H) 7.82 (d, J=8.59

Example 321

(5-Cyclopropyl-1H-pyrazol-3-yl)-{2-methyl-7-[1-(3-nitro-benzyl)-1H-pyrazol-4-yl]-imidazo[1,2-c]pyrimidin-5-yl}-amine

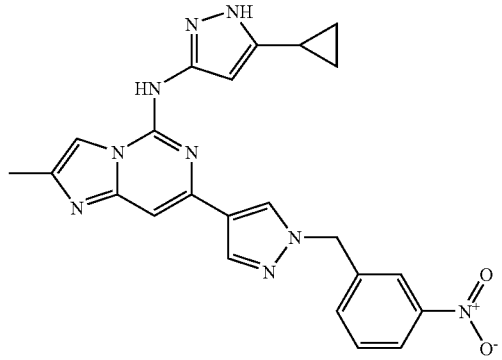

$^1$H NMR (400 MHz, MeOD) δ ppm 0.60-0.85 (m, 2H) 0.95-1.10 (m, 2H) 1.84-2.14 (m, 1H) 2.51 (s, 3H) 5.58 (s, 2H) 6.41 (s, 1H) 7.32 (s, 1H) 7.64 (t, J=7.83 Hz, 1H) 7.73 (d, J=8.34 Hz, 1H) 7.97 (s, 1H) 8.11-8.29 (m, 3H) 8.43 (s, 1H) MS [m+H] calc'd $C_{23}H_{21}N_9O_2$ 456.18 and 457.18; found 456.18 and 457.18.

Example 322

(5-Cyclopropyl-1H-pyrazol-3-yl)-{2-methyl-7-[1-(2-morpholin-4-yl-ethyl)-1H-pyrazol-4-yl]-imidazo[1,2-c]pyrimidin-5-yl}-amine

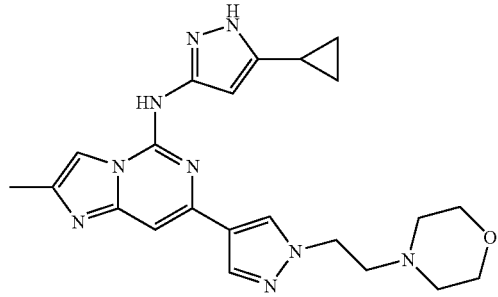

$^1$H NMR (400 MHz, MeOD) δ ppm 0.76-0.87 (m, 2H) 1.00-1.12 (m, 2H) 1.94-2.07 (m, 1H) 2.51 (s, 3H) 3.32-3.51 (m, 4H) 3.72 (t, J=5.81 Hz, 2H) 3.85-4.09 (m, 4H) 4.71 (t, J=5.81 Hz, 2H) 6.44 (s, 1H) 7.34 (s, 1H) 7.98 (s, 1H) 8.17 (s, 1H) 8.40 (s, 1H) MS [m+H] calc'd $C_{22}H_{27}N_9O$ 434.23 and 435.23; found 434.23 and 435.23.

Example 323

{7-[1-(3-Amino-benzyl)-1H-pyrazol-4-yl]-2-methyl-imidazo[1,2-c]pyrimidin-5-yl}-(5-cyclopropyl-1H-pyrazol-3-yl)-amine

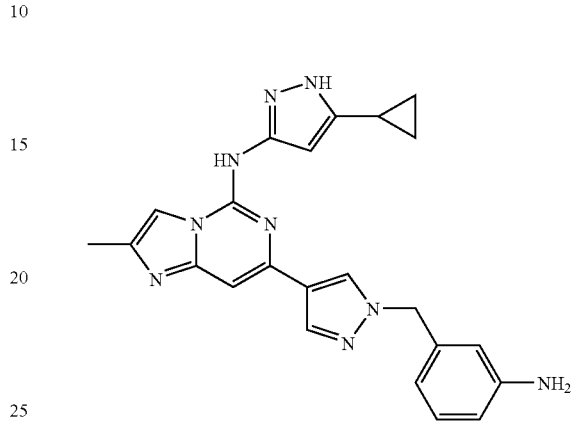

$^1$H NMR (400 MHz, MeOD) δ ppm 0.59-0.86 (m, 2H) 0.97-1.16 (m, 2H) 1.86-2.11 (m, 1H) 2.50 (s, 3H) 5.36 (s, 2H) 6.39 (d, J=1.77 Hz, 1H) 6.76-6.98 (m, 3H) 7.24 (t, J=7.83 Hz, 1H) 7.30 (s, 1H) 7.95 (s, 1H) 8.12 (s, 1H) 8.31 (s, 1H) MS [m+H] calc'd $C_{23}H_{23}N_9$ 426.21 and 427.21; found 426.21 and 427.21.

Example 324

{7-[1-(2,5-Dichloro-benzyl)-1H-pyrazol-4-yl]-2-methyl-imidazo[1,2-c]pyrimidin-5-yl}-(5-methyl-1H-pyrazol-3-yl)-amine

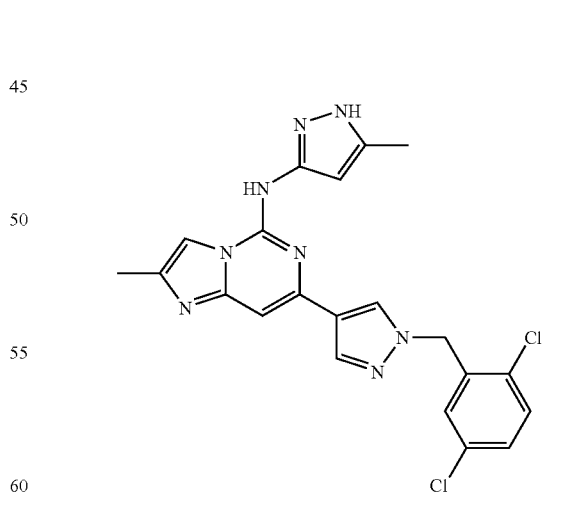

$^1$H NMR (400 MHz, MeOD) δ ppm 2.37 (s, 3H) 2.51 (s, 3H) 5.54 (s, 2H) 6.55 (s, 1H) 7.16 (d, J=2.02 Hz, 1H) 7.26-7.43 (m, 2H) 7.43-7.55 (m, 1H) 7.98 (s, 1H) 8.19 (s, 1H) 8.41

(s, 1H) MS [m+H] calc'd $C_{21}H_{18}C_{12}N_8$ 453.1, 454.1 and 455.1; found 453.1, 454.1 and 455.1.

Example 325

{2-Methyl-7-[1-(2-piperidin-1-yl-ethyl)-1H-pyrazol-4-yl]-imidazo[1,2-c]pyrimidin-5-yl}-(5-methyl-1H-pyrazol-3-yl)-amine

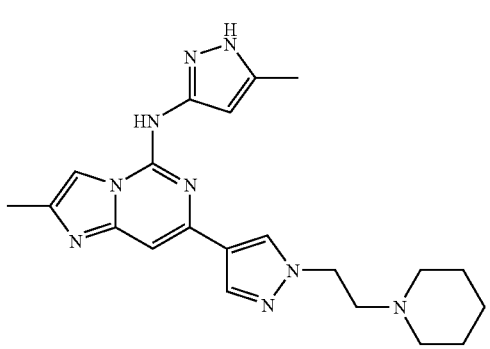

$^1$H NMR (400 MHz, MeOD) δ ppm 1.63-2.10 (m, 6H) 2.39 (s, 3H) 2.51 (s, 3H) 2.88-3.20 (m, 2H) 3.53-3.80 (m, 4H) 4.70 (t, J=6.19 Hz, 2H) 6.55 (s, 1H) 7.32 (s, 1H) 7.98 (s, 1H) 8.21 (s, 1H) 8.40 (s, 1H) MS [m+H] calc'd $C_{21}H_{27}N_9$ 406.24 and 407.24; found 406.24 and 407.24.

Example 326

2-{4-[2-Methyl-5-(5-methyl-1H-pyrazol-3-ylamino)-imidazo[1,2-c]pyrimidin-7-yl]-pyrazol-1-yl}-N-phenyl-acetamide

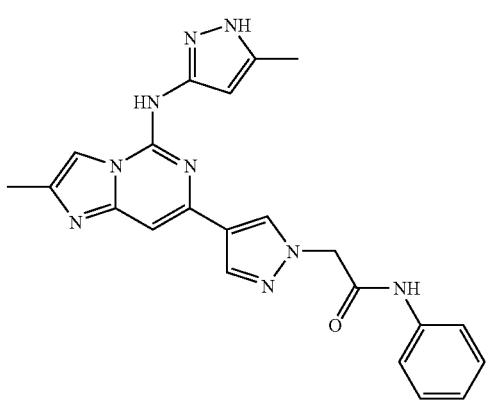

$^1$H NMR (400 MHz, MeOD) δ ppm 2.37 (s, 3H) 2.51 (s, 3H) 5.14 (s, 2H) 6.59 (s, 1H) 7.12 (t, J=7.45 Hz, 1H) 7.32 (t, J=8.08 Hz, 3H) 7.58 (d, J=7.33 Hz, 2H) 7.98 (s, 1H) 8.17 (s, 1H) 8.42 (s, 1H) MS [m+H] calc'd $C_{22}H_{21}N_9O$ 428.19 and 429.19; found 428.19 and 429.19.

Example 327

{2-Methyl-7-[1-(1-methyl-2-phenyl-ethyl)-1H-pyrazol-4-yl]-imidazo[1,2-c]pyrimidin-5-yl}-(5-methyl-1H-pyrazol-3-yl)-amine

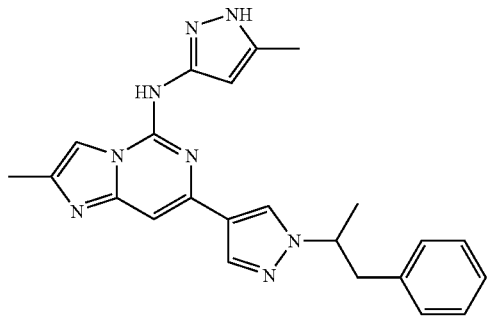

$^1$H NMR (400 MHz, MeOD) δ ppm 0.94 (m, Hz, 2H) 2.37 (s, 3H) 2.50 (s, 3H) 4.84 (d, J=10.11 Hz, 3H) 5.24-5.47 (m, 1H) 6.52 (s, 1H) 7.21-7.50 (m, 5H) 7.96 (s, 1H) 8.14 (s, 1H) 8.40 (s, 1H) MS [m+H] calc'd $C_{23}H_{24}N_8$ 413.21 and 414.21; found 413.21 and 414.21.

Example 328

N-(3-{4-[5-(5-Cyclopropyl-1H-pyrazol-3-ylamino)-2-methyl-imidazo[1,2-c]pyrimidin-7-yl]-pyrazol-1-ylmethyl}-phenyl)-2-methoxy-acetamide

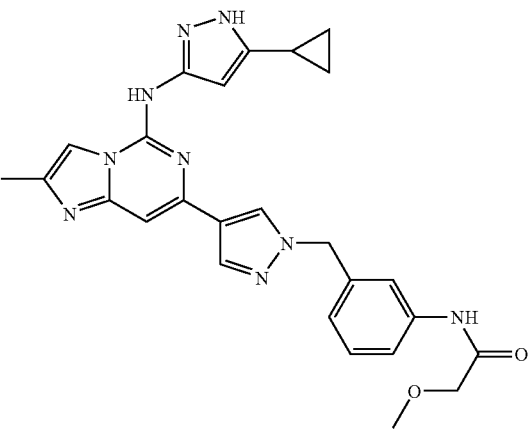

$^1$H NMR (400 MHz, MeOD) δ ppm 0.71-0.81 (m, 2H) 0.86-0.97 (m, 2H) 1.94-2.06 (m, 1H) 2.86 (s, 3H) 2.99 (s, 3H) 3.46 (s, 3H) 4.01 (s, 2H) 5.42 (s, 2H) 7.10 (d, J=7.33 Hz, 1H) 7.26-7.44 (m, 2H) 7.55 (d, J=8.34 Hz, 1H) 7.64 (s, 1H) 7.97

(d, J=8.08 Hz, 2H) 8.13 (s, 1H) 8.33 (s, 1H) MS [m+H] calc'd C$_{26}$H$_{27}$N$_9$O$_2$ 498.23 and 499.23; found 498.23 and 499.23.

Example 329

4-Fluoro-2-{4-[2-methyl-5-(5-methyl-1H-pyrazol-3-ylamino)-imidazo[1,2-c]pyrimidin-7-yl]-pyrazol-1-ylmethyl}-benzonitrile

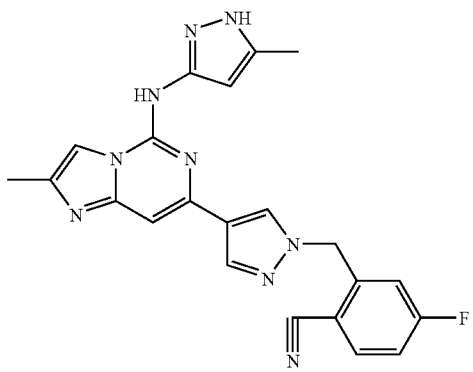

$^1$H NMR (400 MHz, MeOD) δ ppm 2.38 (s, 3H) 2.51 (s, 3H) 5.66 (s, 2H) 6.59 (s, 1H) 7.17 (dd, J=9.09, 2.53 Hz, 1H) 7.25-7.43 (m, 2H) 7.88 (dd, J=8.72, 5.18 Hz, 1H) 8.00 (s, 1H) 8.19 (s, 1H) 8.50 (s, 1H) MS [m+H] calc'd C$_{22}$H$_{18}$FN$_9$ 428.17 and 429.17; found 428.17 and 429.17.

Example 330

(5-Methyl-1H-pyrazol-3-yl)-{2-methyl-7-[1-(2-trifluoromethoxy-benzyl)-1H-pyrazol-4-yl]-imidazo[1,2-c]pyrimidin-5-yl}-amine

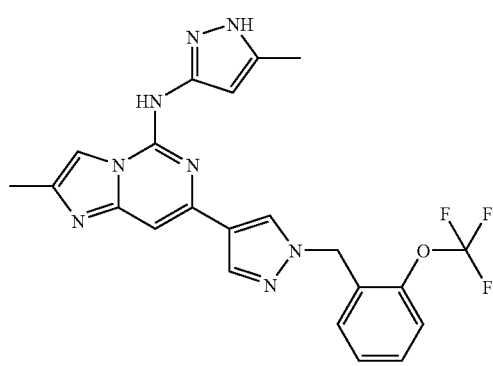

$^1$H NMR (400 MHz, MeOD) δ ppm 2.36 (s, 3H) 2.50 (s, 3H) 5.52 (s, 2H) 6.53 (s, 1H) 7.21-7.42 (m, 4H) 7.42-7.56 (m, 1H) 7.97 (s, 1H) 8.16 (s, 1H) 8.33 (s, 1H) MS [m+H] calc'd C$_{22}$H$_{19}$F$_3$N$_8$O 469.16 and 470.16; found 469.16 and 470.16.

Example 331

N-(5-cyclopropyl-1H-pyrazol-3-yl)-7-(2-methoxyphenyl)imidazo[1,2-f]pyrimidin-5-amine

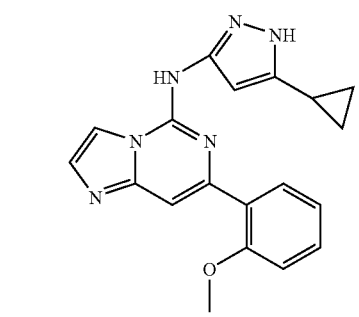

$^1$H NMR (400 MHz, DMSO) δ 8.57 (s, 1H) 8.06 (m, 2H) 7.83 (s, 1H) 7.51 (m, 1H) 7.24 (d, J=8 Hz, 1H) 7.14 (m, 1H) 6.96 (s, 1H) 3.94 (s, 3H) 1.95 (m, 1H) 0.97 (m, 2H) 0.71 (m, 2H). [M+H] calc'd for C$_{19}$H$_{19}$N$_6$O, 347; found, 347.

Example 332

3-(5-(5-cyclopropyl-1H-pyrazol-3-ylamino)imidazo[1,2-f]pyrimidin-7-yl)benzonitrile

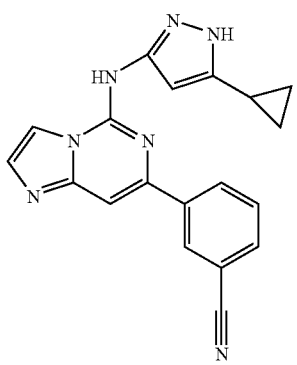

$^1$H NMR (400 MHz, DMSO) δ 8.59 (s, 1H) 8.55 (s, 1H) 8.48 (d, J=8.0 Hz, 1H) 7.97 (m, 2H) 7.87 (s, 1H) 7.76 (m, 1H)

7.11 (s, 1H) 6.48 (s, 1H) 1.97 (m, 1H) 1.02 (m, 2H) 0.77 (m, 2H). [M+H] calc'd for $C_{19}H_{16}N_7$, 342; found, 342.

Example 333

N-(5-cyclopropyl-1H-pyrazol-3-yl)-7-(3,5-dimethylphenyl)imidazo[1,2-f]pyrimidin-5-amine

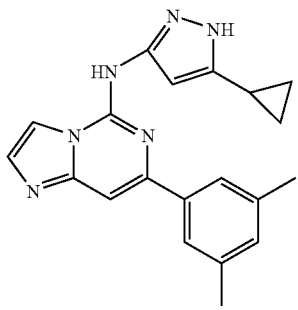

$^1$H NMR (400 MHz, DMSO) δ 8.55 (s, 1H) 7.99 (s, 1H) 7.80 (s, 2H) 7.68 (s, 1H) 7.17 (s, 1H) 6.55 (s, 1H) 2.37 (s, 6H) 1.97 (m, 1H) 1.02 (m, 2H) 0.74 (m, 2H). [M+H] calc'd for $C_{20}H_{21}N_6$, 345; found, 345.

Example 334

N-(5-cyclopropyl-1H-pyrazol-3-yl)-7-p-tolylimidazo[1,2-f]pyrimidin-5-amine

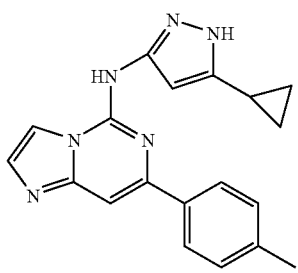

$^1$H NMR (400 MHz, DMSO) δ 8.55 (s, 1H) 8.06 (d, J=8.0 Hz, 2H) 8.00 (s, 1H) 7.66 (s, 1H) 7.38 (d, J=8.0 Hz, 2H) 6.52 (s, 1H) 2.38 (s, 3H) 1.98 (m, 1H) 1.01 (m, 2H) 0.74 (m, 2H). [M+H] calc'd for $C_{19}H_{19}N_6$, 331; found, 331.

Example 335

7-(5-chloro-2-methoxyphenyl)-N-(5-cyclopropyl-1H-pyrazol-3-yl)imidazo[1,2-f]pyrimidin-5-amine

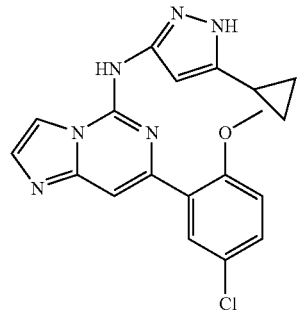

$^1$H NMR (400 MHz, DMSO) δ 8.58 (s, 1H) 8.18 (s, 1H) 8.07 (s, 1H), 7.94 (s, 1H) 7.56 (d, J=8.0 Hz, 1H) 7.28 (d, J=8.0 Hz, 1H) 6.40 (s, 1H) 3.97 (s, 3H) 1.97 (m, 1H) 1.02 (m, 2H) 0.75 (m, 2H). [M+H] calc'd for $C_{19}H_{18}ClN_6O$, 381; found, 381.

Example 336

N-(5-cyclopropyl-1H-pyrazol-3-yl)-7-(2-methoxy-5-methylphenyl)imidazo[1,2-f]pyrimidin-5-amine

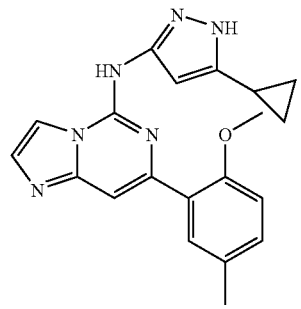

$^1$H NMR (400 MHz, DMSO) δ 8.57 (s, 1H) 8.07 (s, 1H) 7.97 (s, 1H), 7.89 (s, 1H) 7.35 (d, J=8.0 Hz, 1H) 7.15 (d, J=8.0

Hz, 1H) 6.49 (s, 1H) 3.91 (s, 3H) 2.34 (s, 1H) 1.95 (m, 1H) 1.01 (m, 2H) 0.71 (m, 2H). [M+H] calc'd for $C_{20}H_{21}N_6O$, 361; found, 361.

Example 337

N-(5-cyclopropyl-1H-pyrazol-3-yl)-7-(3,5-dimethoxyphenyl)imidazo[1,2-f]pyrimidin-5-amine

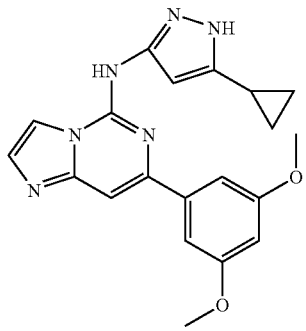

$^1$H NMR (400 MHz, DMSO) δ 8.56 (s, 1H) 8.01 (s, 1H) 7.77 (s, 1H) 7.36 (s, 2H) 6.66 (s, 1H) 6.57 (s, 1H) 3.86 (s, 6H) 1.95 (m, 1H) 0.98 (m, 2H) 0.73 (m, 2H). [M+H] calc'd for $C_{20}H_{21}N_6O_2$, 377; found, 377.

Example 338

N-(5-cyclopropyl-1H-pyrazol-3-yl)-7-(4-methoxyphenyl)imidazo[1,2-f]pyrimidin-5-amine

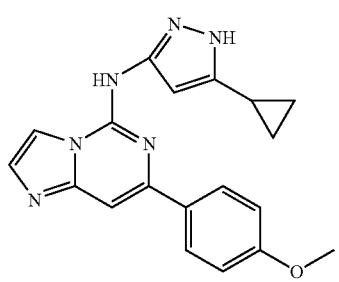

$^1$H NMR (400 MHz, DMSO) δ 8.55 (s, 1H) 8.13 (d, J=8.0 Hz, 2H) 8.02 (s, 1H) 7.62 (s, 1H) 7.11 (d, J=8.0 Hz, 2H) 6.52 (s, 1H) 3.85 (s, 3H) 1.98 (m, 1H) 1.01 (m, 2H) 0.74 (m, 2H). [M+H] calc'd for $C_{19}H_{19}N_6O$, 347; found, 347.

Example 339

N-(5-cyclopropyl-1H-pyrazol-3-yl)-7-(pyrimidin-5-yl)imidazo[1,2-f]pyrimidin-5-amine

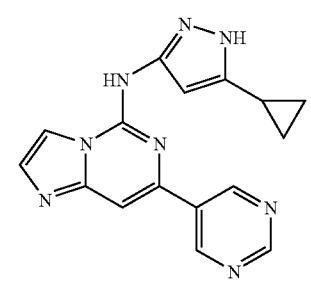

$^1$H NMR (400 MHz, DMSO) δ 9.49 (s, 2H) 9.28 (s, 1H) 8.57 (s, 1H) 7.96 (s, 1H) 7.94 (s, 1H) 6.50 (s, 1H) 1.99 (m, 1H) 1.00 (m, 2H) 0.75 (m, 2H). [M+H] calc'd for $C_{16}H_{15}N_8$, 319; found, 319.

Example 340

N-(5-cyclopropyl-1H-pyrazol-3-yl)-7-(pyridin-3-yl)imidazo[1,2-f]pyrimidin-5-amine

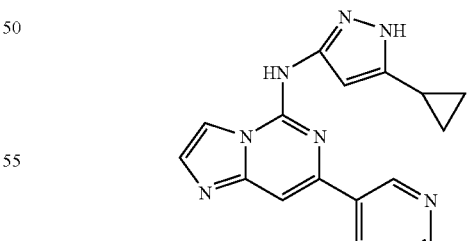

$^1$H NMR (400 MHz, DMSO) δ 9.37 (s, 1H) 8.75 (d, J=4.0 Hz, 1H) 8.62 (m, 2H) 8.08 (s, 1H) 7.88 (s, 1H) 7.69 (m, 1H)

6.51 (s, 1H) 1.99 (m, 1H) 1.00 (m, 2H) 0.75 (m, 2H). [M+H] calc'd for C$_{17}$H$_{16}$N$_{7}$, 318; found, 318.

Example 341

N-(5-cyclopropyl-1H-pyrazol-3-yl)-7-(3,4-dimethoxyphenyl)imidazo[1,2-f]pyrimidin-5-amine

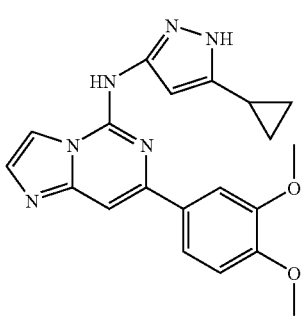

$^1$H NMR (400 MHz, DMSO) δ 8.56 (s, 1H) 8.03 (s, 1H) 7.79 (m, 2H) 7.69 (s, 1H) 7.14 (d, J=8.0 Hz, 1H) 6.59 (s, 1H) 3.90 (s, 3H) 3.85 (s, 3H) 1.96 (m, 1H) 0.98 (m, 2H) 0.74 (m, 2H). [M+H] calc'd for C$_{20}$H$_{21}$N$_{6}$O$_{2}$, 377; found, 377.

Example 342

N-(5-cyclopropyl-1H-pyrazol-3-yl)-7-(2,3-dimethylphenyl)imidazo[1,2-f]pyrimidin-5-amine

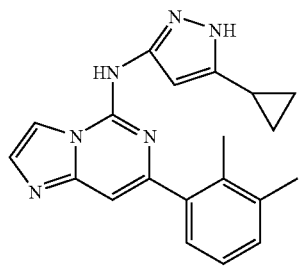

$^1$H NMR (400 MHz, DMSO) δ 8.58 (s, 1H) 8.05 (s, 1H) 7.30 (m, 2H) 7.23 (m, 2H) 6.35 (s, 1H) 2.32 (s, 3H) 2.27 (s, 3H) 1.90 (m, 1H) 0.93 (m, 2H) 0.64 (m, 2H). [M+H] calc'd for C$_{20}$H$_{21}$N$_{6}$, 345; found, 345.

Example 343

7-(benzo[d][1,3]dioxol-5-yl)-N-(5-cyclopropyl-1H-pyrazol-3-yl)imidazo[1,2-f]pyrimidin-5-amine

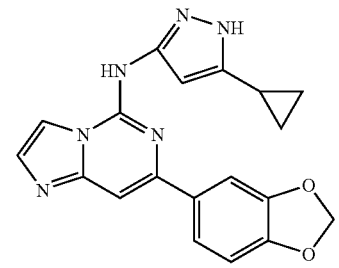

$^1$H NMR (400 MHz, DMSO) δ 8.53 (s, 1H) 8.00 (s, 1H) 7.75 (d, J=8.0 Hz, 1H) 7.71 (s, 1H) 7.62 (s, 1H) 7.10 (d, J=8.0 Hz, 1H) 6.46 (s, 1H) 6.14 (s, 2H) 3.90 (s, 3H) 3.85 (s, 3H) 1.96 (m, 1H) 1.01 (m, 2H) 0.74 (m, 2H). [M+H] calc'd for C$_{19}$H$_{17}$N$_{6}$O$_{2}$, 361; found, 361.

Example 344

N-(5-cyclopropyl-1H-pyrazol-3-yl)-7-(2,6-dimethylphenyl)imidazo[1,2-f]pyrimidin-5-amine

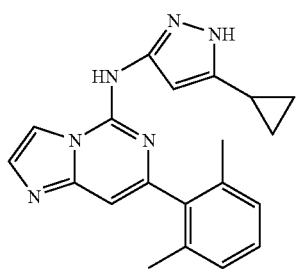

$^1$H NMR (400 MHz, DMSO) δ 8.58 (s, 1H) 8.07 (s, 1H) 7.24 (m, 2H) 7.15 (m, 2H) 6.21 (s, 1H) 2.15 (s, 3H) 2.07 (s, 3H) 1.80 (m, 1H) 0.90 (m, 2H) 0.61 (m, 2H). [M+H] calc'd for C$_{20}$H$_{21}$N$_6$, 345; found, 345.

Example 345

N-(5-cyclopropyl-1H-pyrazol-3-yl)-7-(2,6-dimethoxyphenyl)imidazo[1,2-f]pyrimidin-5-amine

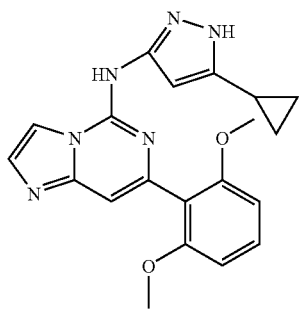

$^1$H NMR (400 MHz, DMSO) δ 8.48 (s, 1H) 7.99 (s, 1H) 7.43 (t, J=8.0 Hz, 1H) 7.07 (s, 1H) 6.81 (d, J=8.0 Hz, 2H) 6.29 (s, 1H) 3.74 (s, 3H) 3.67 (s, 3H) 1.87 (m, 1H) 0.92 (m, 2H) 0.61 (m, 2H). [M+H] calc'd for C$_{20}$H$_{21}$N$_6$O$_2$, 377; found, 377.

Example 346

N-(5-cyclopropyl-1H-pyrazol-3-yl)-7-(2-methoxypyridin-4-yl)imidazo[1,2-f]pyrimidin-5-amine

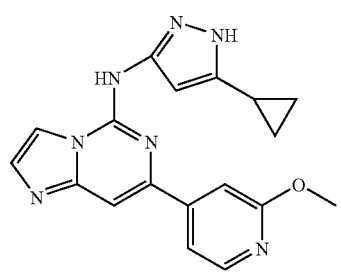

$^1$H NMR (400 MHz, DMSO) δ 8.59 (s, 1H) 8.50 (d, J=8.0 Hz, 1H) 8.34 (d, J=4.0 Hz, 1H) 8.07 (s, 1H) 7.94 (s, 1H) 7.25 (m, 1H) 6.44 (s, 1H) 4.05 (s, 3H) 1.97 (m, 1H) 0.98 (m, 2H) 0.74 (m, 2H). [M+H] calc'd for C$_{18}$H$_{18}$N$_7$O, 348; found, 348.

Example 347

N-(5-cyclopropyl-1H-pyrazol-3-yl)-7-(4-phenoxyphenyl)imidazo[1,2-f]pyrimidin-5-amine

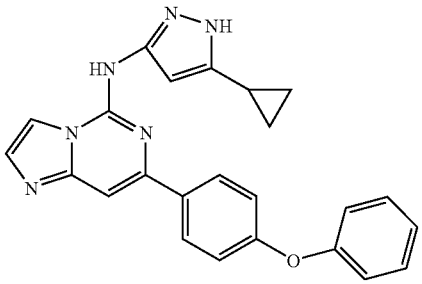

$^1$H NMR (400 MHz, DMSO) δ 8.54 (s, 1H) 8.16 (d, J=8.0 Hz, 2H) 7.97 (s, 1H) 7.63 (s, 1H) 7.45 (m, 2H) 7.21 (m, 1H) 7.13 (m, 4H) 6.52 (s, 1H) 1.98 (m, 1H) 0.98 (m, 2H) 0.74 (m, 2H). [M+H] calc'd for C$_{24}$H$_{21}$N$_6$O, 409; found, 409.

Example 348

N-(5-cyclopropyl-1H-pyrazol-3-yl)-7-(3-biphenyl)imidazo[1,2-f]pyrimidin-5-amine

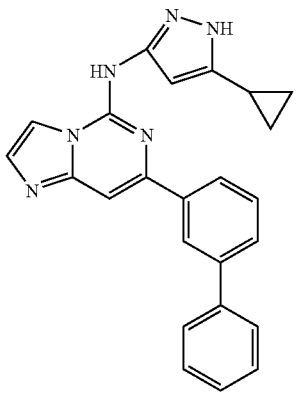

$^1$H NMR (400 MHz, DMSO) δ 8.61 (s, 1H) 8.48 (s, 1H) 8.16 (d, J=8.0 Hz, 1H) 8.06 (s, 1H) 7.87 (s, 1H) 7.82 (d, J=8.0 Hz, 1H) 7.75 (m, 2H) 7.66 (m, 1H) 7.53 (m, 2H) 7.43 (m, 1H)

6.60 (s, 1H) 1.96 (m, 1H) 0.96 (m, 2H) 0.69 (m, 2H). [M+H] calc'd for $C_{24}H_{21}N_6$, 393; found, 393.

Example 349

N-(5-cyclopropyl-1H-pyrazol-3-yl)-7-(4-biphenyl)imidazo[1,2-f]pyrimidin-5-amine

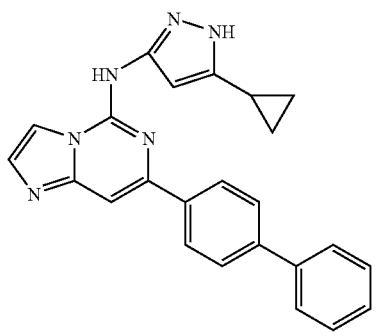

$^1$H NMR (400 MHz, DMSO) δ 8.58 (s, 1H) 8.25 (d, J=8.0 Hz, 2H) 8.03 (s, 1H) 7.87-7.35 (m, 8H) 6.57 (s, 1H) 2.00 (m, 1H) 1.01 (m, 2H) 0.78 (m, 2H). [M+H] calc'd for $C_{24}H_{21}N_6$, 393; found, 393.

Example 350

N-(5-cyclopropyl-1H-pyrazol-3-yl)-7-(2-biphenyl)imidazo[1,2-f]pyrimidin-5-amine

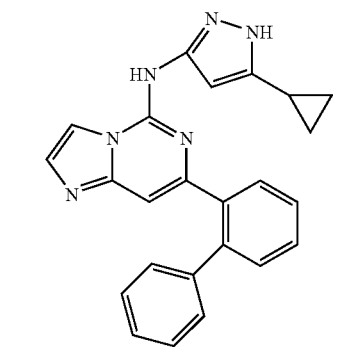

$^1$H NMR (400 MHz, DMSO) δ 8.48 (s, 1H) 7.93 (s, 1H) 7.57-7.17 (m, 10H) 5.63 (s, 1H) 1.12 (m, 1H) 0.93 (m, 2H) 0.64 (m, 2H). [M+H] calc'd for $C_{24}H_{21}N_6$, 393; found, 393.

Example 351

N-(5-cyclopropyl-1H-pyrazol-3-yl)-7-(2-fluorophenyl)imidazo[1,2-f]pyrimidin-5-amine

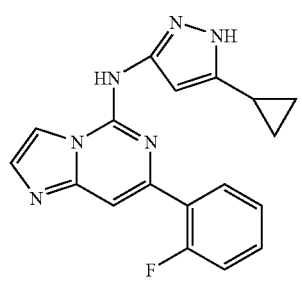

$^1$H NMR (400 MHz, DMSO) δ 8.59 (s, 1H) 8.09 (m, 1H) 8.01 (s, 1H) 7.57 (m, 2H) 7.42 (m, 2H) 6.50 (s, 1H) 1.96 (m, 1H) 0.97 (m, 2H) 0.71 (m, 2H). [M+H] calc'd for $C_{18}H_{16}FN_6$, 335; found, 335.

Example 352

N-(5-cyclopropyl-1H-pyrazol-3-yl)-7-(3,5-difluorophenyl)imidazo[1,2-f]pyrimidin-5-amine

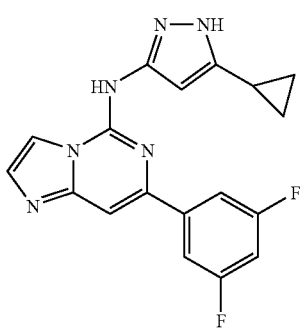

¹H NMR (400 MHz, DMSO) δ 8.52 (s, 1H) 7.90 (m, 3H) 7.38 (m, 2H) 6.44 (s, 1H) 1.96 (m, 1H) 1.01 (m, 2H) 0.72 (m, 2H). [M+H] calc'd for C$_{18}$H$_{15}$F$_2$N$_6$, 353; found, 353.

Example 353

3-(5-(5-cyclopropyl-1H-pyrazol-3-ylamino)imidazo[1,2-f]pyrimidin-7-yl)-N-methylbenzamide

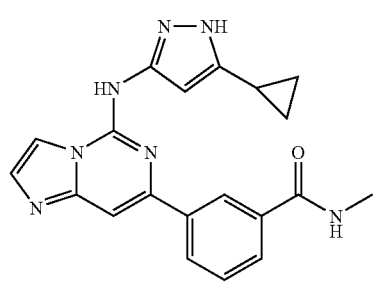

¹H NMR (400 MHz, DMSO) δ 8.61 (b, 2H) 8.29 (d, J=8.36 Hz, 1H) 8.04 (s, 1H) 7.93 (d, J=8.36 Hz, 1H) 7.78 (s, 1H) 7.65 (m, 1H) 6.58 (s, 1H) 2.84 (d, J=3.2 Hz, 3H) 1.96 (m, 1H) 1.00 (m, 2H) 0.79 (m, 2H). [M+H] calc'd for C$_{20}$H$_{20}$N$_7$O, 374; found, 374.

Example 354

3-(5-(5-cyclopropyl-1H-pyrazol-3-ylamino)imidazo[1,2-f]pyrimidin-7-yl)-N-ethylbenzamide

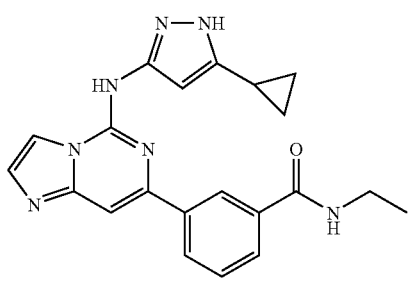

¹H NMR (400 MHz, DMSO) δ 8.65-8.60 (b, 2H) 8.29 (d, J=7.8 Hz, 1H) 8.04 (s, 1H) 7.93 (d, J=7.8 Hz, 1H) 7.78 (s, 1H) 7.65 (m, 1H) 6.57 (s, 1H) 3.33 (m, 2H) 1.96 (m, 1H) 1.16 (t, J=7.0 Hz, 3H) 0.99 (m, 2H) 0.79 (m, 2H). [M+H] calc'd for C$_{21}$H$_{22}$N$_7$O, 388; found, 388.

Example 355

N-cyclopropyl-3-(5-(5-cyclopropyl-1H-pyrazol-3-ylamino)imidazo[1,2-f]pyrimidin-7-yl)benzamide

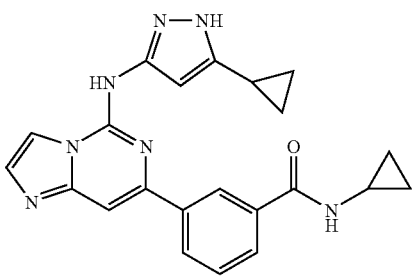

¹H NMR (400 MHz, DMSO) δ 8.60 (s, 1H) 8.57 (s, 1H) 8.29 (d, J=8.6 Hz, 1H) 8.05 (s, 1H) 7.93 (d, J=8.6 Hz, 1H) 7.78 (s, 1H) 7.65 (m, 1H) 6.57 (s, 1H) 2.88 (m, 1H) 1.96 (m, 1H) 0.98 (m, 2H) 0.79 (m, 2H) 0.74 (m, 2H) 0.61 (m, 2H). [M+H] calc'd for C$_{22}$H$_{22}$N$_7$O, 400; found, 400.

Example 356

N-(2-cyanoethyl)-3-(5-(5-cyclopropyl-1H-pyrazol-3-ylamino)imidazo[1,2-f]pyrimidin-7-yl)benzamide

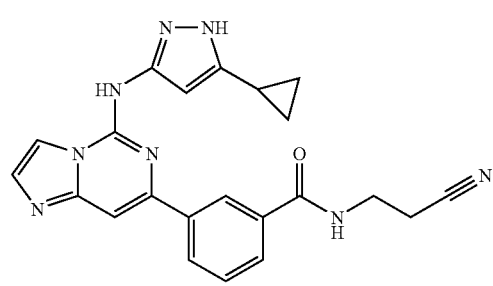

¹H NMR (400 MHz, DMSO) δ 8.64 (s, 1H) 8.61 (s, 1H) 8.33 (d, J=7.8 Hz, 1H) 8.05 (s, 1H) 7.97 (d, J=7.8 Hz, 1H) 7.78 (s, 1H) 7.68 (m, 1H) 6.57 (s, 1H) 3.55 (q, J=6.28 Hz, 2H) 2.82

(t, J=6.28 Hz, 2H) 1.96 (m, 1H) 0.98 (m, 2H) 0.81 (m, 2H). [M+H] calc'd for $C_{22}H_{21}N_8O$, 413; found, 413.

Example 357

(3-(5-(5-cyclopropyl-1H-pyrazol-3-ylamino)imidazo[1,2-f]pyrimidin-7-yl)phenyl)(pyrrolidin-1-yl)methanone

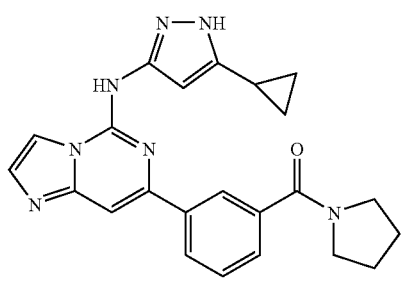

$^1$H NMR (400 MHz, DMSO) δ 8.61 (s, 1H) 8.31 (s, 1H) 8.25 (d, J=7.56 Hz, 1H) 8.09 (s, 1H) 7.83 (s, 1H) 7.64 (m, 2H) 6.48 (s, 1H) 3.52 (t, J=6.84 Hz, 2H) 3.39 (t, J=6.84 Hz, 2H) 1.90 (m, 1H) 0.98 (m, 2H) 0.73 (m, 2H). [M+H] calc'd for $C_{23}H_{24}N_7O$, 414; found, 414.

Example 358

Methyl 3-(5-(5-cyclopropyl-1H-pyrazol-3-ylamino)imidazo[1,2-f]pyrimidin-7-yl)benzoate

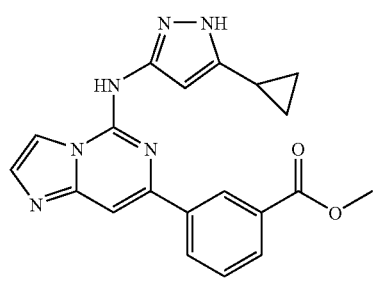

$^1$H NMR (400 MHz, DMSO) δ 8.78 (s, 1H) 8.61 (s, 1H) 8.42 (d, J=8.08 Hz, 1H) 8.11 (d, J=8.08 Hz, 1H) 8.03 (s, 1H) 7.82 (s, 1H) 7.72 (m, 1H) 6.57 (s, 1H) 3.93 (s, 3H) 1.98 (m, 1H) 1.00 (m, 2H) 0.79 (m, 2H). [M+H] calc'd for $C_{20}H_{19}N_6O_2$, 375; found, 375.

Example 359

(3-(5-(5-cyclopropyl-1H-pyrazol-3-ylamino)imidazo[1,2-f]pyrimidin-7-yl)phenyl)methanol

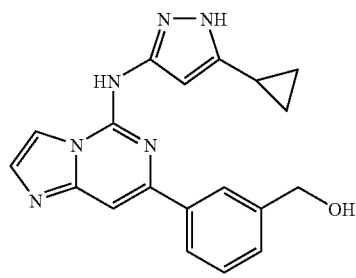

$^1$H NMR (400 MHz, DMSO) δ 8.61 (s, 1H) 8.17 (s, 1H) 8.07 (s, 1H) 8.03 (d, J=7.08 Hz, 1H) 7.73 (s, 1H) 7.50 (m, 2H) 6.57 (s, 1H) 4.62 (s, 2H) 1.97 (m, 1H) 1.00 (m, 2H) 0.78 (m, 2H). [M+H] calc'd for $C_{19}H_{19}N_6O$, 347; found, 347.

Example 360

N-ethyl-2-methoxy-N-methyl-5-(2-methyl-5-(5-methyl-1H-pyrazol-3-ylamino)imidazo[1,2-f]pyrimidin-7-yl)benzenesulfonamide

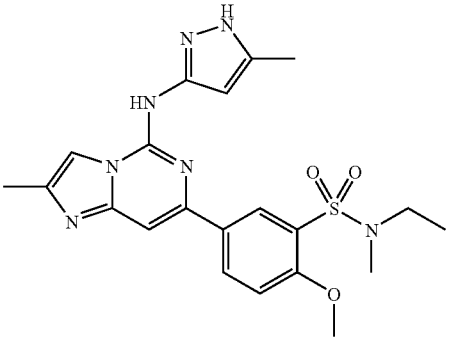

$^1$H NMR (400 MHz, DMSO) δ 8.72 (s, 1H) 8.41 (d, J=9.1 Hz, 1H) 8.36 (s, 1H) 7.71 (s, 1H) 7.41 (d, J=9.1 Hz, 1H) 6.66 (s, 1H) 3.98 (s, 3H) 3.16 (q, J=6.8 Hz, 2H) 2.78 (s, 3H) 2.44

(s, 3H) 2.29 (s, 3H) 1.03 (t, J=6.8 Hz, 3H). [M+H] calc'd for C$_{21}$H$_{26}$N$_7$O$_3$S, 456; found, 456.

Example 361

N-(cyclopropylmethyl)-2-methoxy-5-(2-methyl-5-(5-methyl-1H-pyrazol-3-ylamino) imidazo[1,2-f]pyrimidin-7-yl)benzenesulfonamide

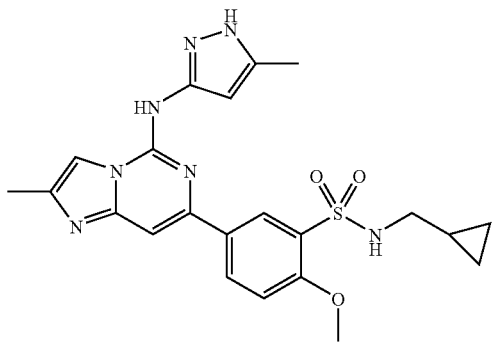

$^1$H NMR (400 MHz, DMSO) δ 8.71 (s, 1H) 8.40 (d, J=8.8 Hz, 1H) 8.36 (s, 1H) 7.69 (s, 1H) 7.38 (d, J=8.8 Hz, 1H) 6.67 (s, 1H) 3.99 (s, 3H) 2.72 (br, 2H) 2.45 (s, 3H) 2.31 (s, 3H) 0.71 (m, 1H) 0.24 (m, 2H) 0.02 (m, 2H). [M+H] calc'd for C$_{22}$H$_{26}$N$_7$O$_3$S, 468; found, 468.

Example 362

N-cyclopropyl-3-(2-methyl-5-(5-methyl-1H-pyrazol-3-ylamino)imidazo[1,2-f]pyrimidin-7-yl)benzenesulfonamide

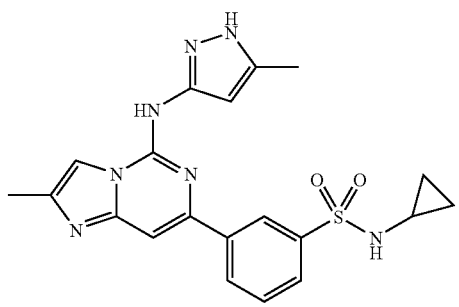

$^1$H NMR (400 MHz, DMSO) δ 8.69 (s, 1H) 8.44 (d, J=8.0 Hz, 1H) 8.32 (s, 1H) 7.90 (d, J=8.0 Hz, 1H) 7.77 (m, 1H) 7.73 (s, 1H) 6.67 (s, 1H) 2.42 (s, 3H) 2.29 (s, 3H) 2.12 (m, 1H) 0.46 (m, 2H), 0.38 (m, 2H). [M+H] calc'd for C$_{20}$H$_{22}$N$_7$O$_2$S, 424; found, 424.

Example 363

N-ethyl-3-(2-methyl-5-(5-methyl-1H-pyrazol-3-ylamino)imidazo[1,2-f]pyrimidin-7-yl)benzenesulfonamide

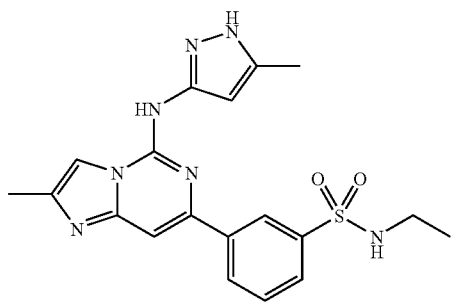

$^1$H NMR (400 MHz, DMSO) δ 8.65 (s, 1H) 8.43 (d, J=7.6 Hz, 1H) 8.37 (s, 1H) 7.92 (d, J=8.0 Hz, 1H) 7.77 (m, 1H) 7.67 (s, 1H) 6.65 (s, 1H) 2.83 (q, J=6.8 Hz, 2H) 2.45 (s, 3H) 2.30 (s, 3H) 0.97 (t, J=6.8 Hz, 3H). [M+H] calc'd for C$_{19}$H$_{22}$N$_7$O$_2$S, 412; found, 412.

Example 364

N-(2-hydroxyethyl)-2-methoxy-5-(2-methyl-5-(5-methyl-1H-pyrazol-3-ylamino) imidazo[1,2-c]pyrimidin-7-yl)benzenesulfonamide

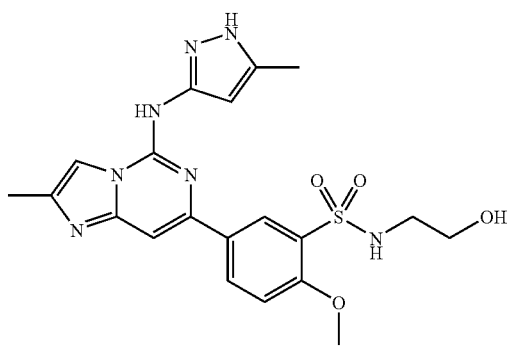

$^1$H NMR (400 MHz, DMSO) δ 8.70 (s, 1H) 8.41 (d, J=8.6 Hz, 1H) 8.35 (s, 1H) 7.70 (s, 1H) 7.40 (d, J=8.6 Hz, 1H) 6.67

(s, 1H) 3.98 (s, 3H) 3.34 (m, 2H) 2.84 (m, 2H) 2.44 (s, 3H) 2.31 (s, 3H). [M+H] calc'd for $C_{20}H_{24}N_7O_4S$, 458; found, 458.

Example 365

7-(4-methoxy-3-(morpholinosulfonyl)phenyl)-2-methyl-N-(5-methyl-1H-pyrazol-3-yl)imidazo[1,2-c]pyrimidin-5-amine

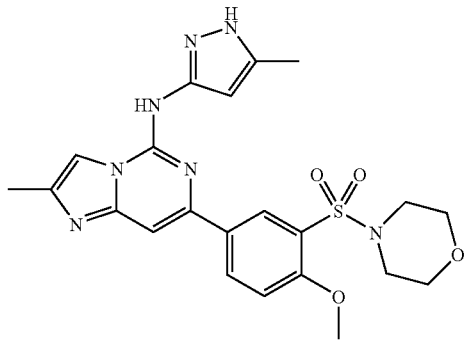

$^1$H NMR (400 MHz, DMSO) δ 8.71 (s, 1H) 8.46 (d, J=8.6 Hz, 1H) 8.35 (s, 1H) 7.71 (s, 1H) 7.44 (d, J=8.6 Hz, 1H) 6.66 (s, 1H) 3.98 (s, 3H) 3.60 (m, 4H) 3.10 (m, 4H) 2.44 (s, 3H) 2.29 (s, 3H). [M+H] calc'd for $C_{22}H_{26}N_7O_4S$, 484; found, 484.

Example 366

7-(4-methoxy-3-(tetrahydro-2H-pyran-4-ylsulfonyl)phenyl)-2-methyl-N-(5-methyl-1H-pyrazol-3-yl)imidazo[1,2-c]pyrimidin-5-amine

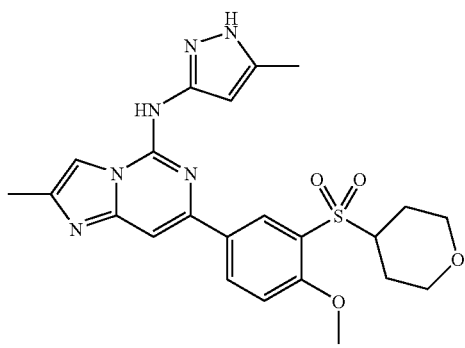

$^1$H NMR (400 MHz, DMSO) δ 8.73 (s, 1H) 8.42 (d, J=8.6 Hz, 1H) 8.35 (s, 1H) 7.70 (s, 1H) 7.37 (d, J=8.6 Hz, 1H) 6.66

(s, 1H) 3.99 (s, 3H) 3.68 (m, 2H) 3.17 (m, 3H) 2.45 (s, 3H) 2.30 (s, 3H) 1.46 (m, 4H). [M+H] calc'd for $C_{23}H_{27}N_6O_4S$, 483; found, 483.

Example 367

N-(2-(2-(dimethylamino)ethoxy)-5-(2-methyl-5-(5-methyl-1H-pyrazol-3-ylamino) imidazo[1,2-c]pyrimidin-7-yl)phenyl)cyclopropanesulfonamide

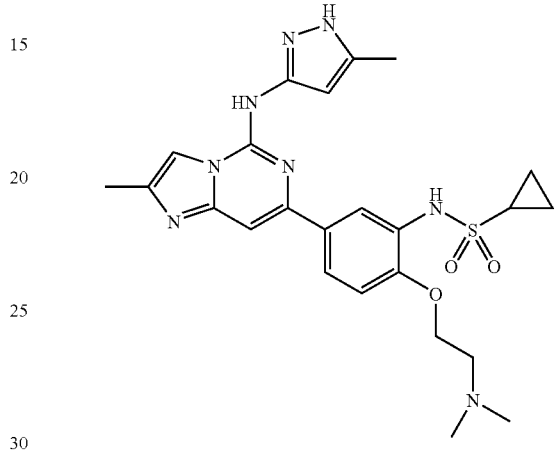

$^1$H NMR (400 MHz, CD$_3$OD) δ 8.49 (s, 1H) 8.06 (s, 1H) 8.01 (d, J=8.8 Hz, 1H) 7.56 (s, 1H) 7.27 (d, J=8.8 Hz, 1H) 6.73 (s, 1H) 4.54 (t, J=5.0 Hz, 2H) 3.69 (t, J=5.0 Hz, 2H) 3.05 (s, 6H) 2.66 (m, 1H) 2.55 (s, 3H) 2.39 (s, 3H) 1.05 (m, 2H) 0.95 (m, 2H). [M+H] calc'd for $C_{24}H_{31}N_8O_3S$, 511; found, 511.

Example 368

N-(2-hydroxyethyl)-3-(2-methyl-5-(5-methyl-1H-pyrazol-3-ylamino)imidazo[1,2-c]pyrimidin-7-yl)benzenesulfonamide

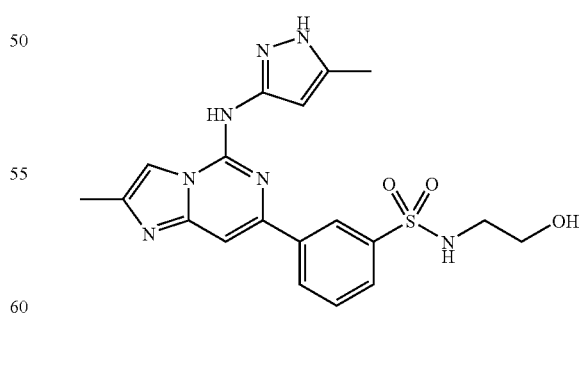

$^1$H NMR (400 MHz, Acetone-d$_6$) δ 8.80 (s, 1H) 8.38 (d, J=7.6 Hz, 1H) 8.23 (s, 1H) 8.04 (m, 2H) 7.78 (m, 1H) 6.76 (s, 1H) 3.63 (t, J=5.6, 2H) 3.14 (m, br, 2H) 2.57 (s, 3H) 2.40 (s, 3H). [M+H] calc'd for $C_{19}H_{22}N_7O_3S$, 428; found, 428.

Example 369

3-(2-methyl-5-(5-methyl-1H-pyrazol-3-ylamino) imidazo[1,2-c]pyrimidin-7-yl)-N-(2,2,2-trifluoroethyl)benzenesulfonamide

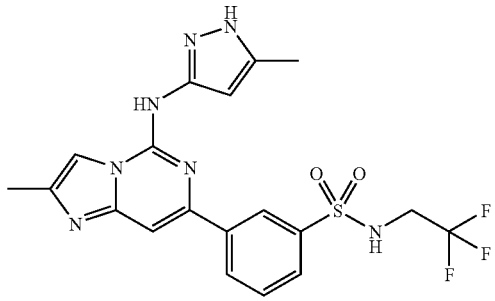

$^1$H NMR (400 MHz, Methanol-$d_6$) δ 8.75 (s, 1H) 8.40 (d, J=8.3 Hz, 1H) 8.09 (s, 1H) 7.98 (d, J=8.3 Hz, 1H) 7.74 (m, 1H) 7.72 (s, 1H) 6.64 (s, 1H) 3.68 (t, J=9.0 Hz, 2H) 2.57 (s, 3H) 2.40 (s, 3H). [M+H] calc'd for $C_{19}H_{19}F_3N_7O_2S$, 466; found, 466.

Example 370

7-(3-(2-(dimethylamino)ethoxy)phenyl)-2-methyl-N-(5-methyl-1H-pyrazol-3-yl)imidazo[1,2-c]pyrimidin-5-amine

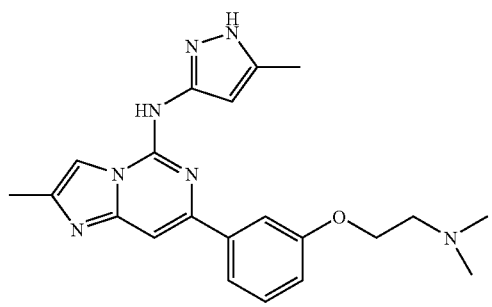

$^1$H NMR (400 MHz, DMSO-$d_6$) δ 8.29 (s, 1H) 7.79 (m, 2H) 7.66 (s, 1H) 7.49 (m, 1H) 7.14 (d, J=8.6 Hz, 1H) 6.63 (s, 1H) 4.42 (t, J=4.2 Hz, 2H) 3.55 (t, J=4.2 Hz, 2H) 2.89 (s, 6H) 2.42 (s, 3H) 2.30 (s, 3H). [M+H] calc'd for $C_{21}H_{26}N_7O$, 392; found, 392.

Example 371

2-methyl-N-(5-methyl-1H-pyrazol-3-yl)-7-(3-(pyrrolidin-1-ylsulfonyl)phenyl) imidazo[1,2-c]pyrimidin-5-amine

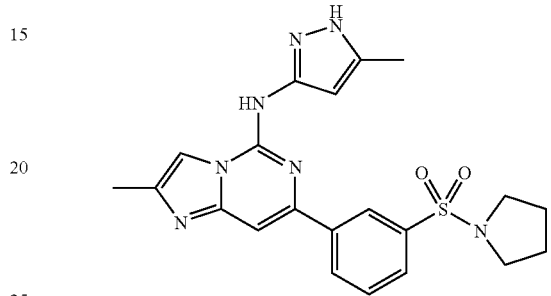

$^1$H NMR (400 MHz, DMSO-$d_6$) δ 8.64 (s, 1H) 8.49 (d, J=8.6 Hz, 1H) 8.37 (s, 1H) 7.93 (d, J=8.6 Hz, 1H) 7.82 (m, 2H) 6.62 (s, 1H) 3.20 (m, 4H) 2.46 (s, 3H) 2.30 (s, 3H) 1.65 (m, 4H). [M+H] calc'd for $C_{21}H_{24}N_7O_2S$, 438; found, 438.

Example 372

7-(3-(3-aminopyrrolidin-1-ylsulfonyl)phenyl)-2-methyl-N-(5-methyl-1H-pyrazol-3-yl)imidazo[1,2-c]pyrimidin-5-amine

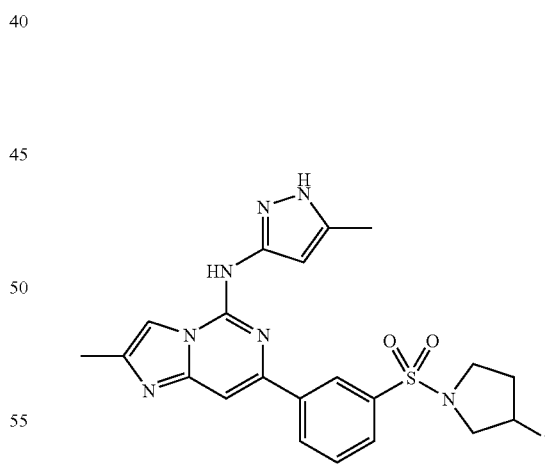

$^1$H NMR (400 MHz, DMSO-$d_6$) δ 8.66 (s, 1H) 8.53 (d, J=8.0 Hz, 1H) 8.38 (s, 1H) 7.93 (d, J=8.0 Hz, 1H) 7.84 (m, 2H) 6.64 (s, 1H) 3.73 (m, 1H) 3.45 (m, 2H) 3.32 (m, 1H) 3.20

(m, 2H) 2.46 (s, 3H) 2.30 (s, 3H) 1.82 (m, 1H). [M+H] calc'd for $C_{21}H_{25}N_8O_2S$, 453; found, 453.

Example 373

3-(2-methyl-5-(5-methyl-1H-pyrazol-3-ylamino) imidazo[1,2-c]pyrimidin-7-yl)-N-(3-(pyrrolidin-1-yl) propyl)benzenesulfonamide

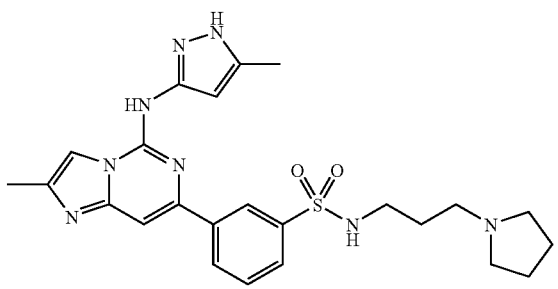

$^1$H NMR (400 MHz, Methanol-$d_4$) δ 8.75 (s, 1H) 8.40 (d, J=8.0 Hz, 1H) 8.07 (s, 1H) 7.98 (d, J=8.0 Hz, 1H) 7.78 (m, 1H) 7.76 (s, 1H) 6.66 (s, 1H) 3.62 (br, 2H) 3.25 (m, 2H) 3.01 (m, 4H) 2.56 (s, 3H) 2.40 (s, 3H) 2.12 (br, 2H) 2.00 (br, 2H) 1.93 (m, 2H). [M+H] calc'd for $C_{24}H_{31}N_8O_2S$, 495; found, 495.

Example 374

3-(2-methyl-5-(5-methyl-1H-pyrazol-3-ylamino) imidazo[1,2-c]pyrimidin-7-yl)-N-p-tolylbenzene-sulfonamide

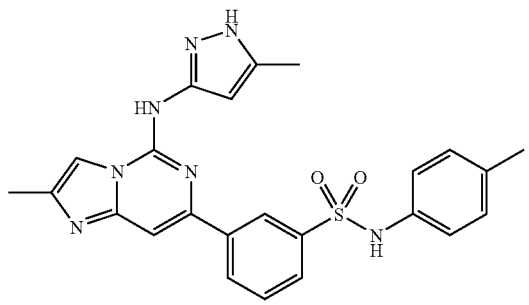

$^1$H NMR (400 MHz, Methanol-$d_4$) δ 8.21 (s, 1H) 8.05 (s, 1H) 7.73 (d, J=6.8 Hz, 1H) 7.65 (d, J=8.6 Hz, 2H) 7.50 (s, 1H) 7.33 (m, 1H) 7.21 (d, J=8.6 Hz, 2H) 7.02 (d, J=6.8 Hz, 1H) 6.77 (s, 1H) 2.56 (s, 3H) 2.40 (s, 3H) 2.30 (s, 3H). [M+H] calc'd for $C_{24}H_{24}N_7O_2S$, 474; found, 474.

Example 375

N-(5-methyl-1H-pyrazol-3-yl)-7-(3-(4-methylpiperazin-1-ylsulfonyl)phenyl)imidazo[1,2-c]pyrimidin-5-amine

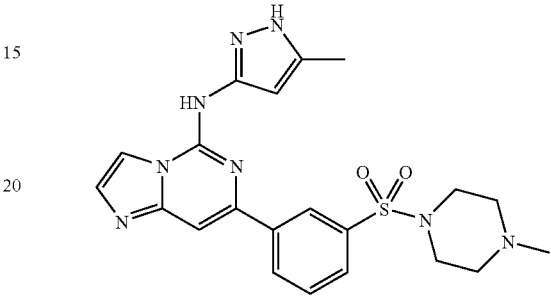

$^1$H NMR (400 MHz, DMSO) δ 8.60 (m, 3H) 8.02 (s, 1H) 7.95 (m, 3H) 6.63 (s, 1H) 3.81 (br, 2H) 3.46 (br, 2H) 3.21 (br, 2H) 2.77 (s, 3H) 2.60 (br, 2H) 2.31 (s, 3H). [M+H] calc'd for $C_{21}H_{25}N_8O_2S$, 453; found, 453.

Example 376

7-(1-(ethylsulfonyl)-1H-indol-6-yl)-2-methyl-N-(5-methyl-1H-pyrazol-3-yl)imidazo[1,2-c]pyrimidin-5-amine

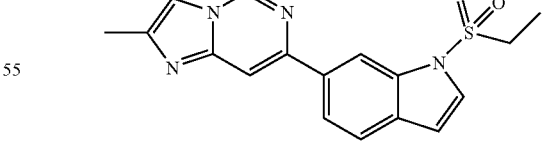

$^1$H NMR (400 MHz, DMSO-$d_6$) δ 8.90 (s, 1H) 8.31 (s, 1H) 8.09 (s, 1H) 8.02 (d, J=8.3 Hz, 1H) 7.84 (d, J=8.3 Hz, 1H) 7.70 (d, J=4.0 Hz, 1H) 6.90 (m, 2H) 3.64 (q, J=7.4 Hz, 2H) 2.56 (s,

Example 377

N-(6-(2-methyl-5-(5-methyl-1H-pyrazol-3-ylamino)imidazo[1,2-c]pyrimidin-7-yl)-1H-indol-3-yl)ethanesulfonamide

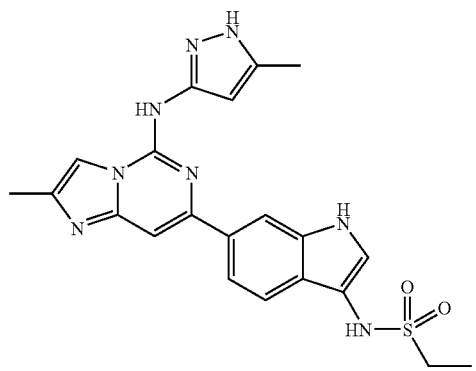

¹H NMR (400 MHz, Methanol-d₄) δ 8.90 (s, 1H) 8.02 (m, 2H) 7.89 (s, 1H) 7.60 (m, 2H) 6.81 (s, 1H) 2.95 (q, J=6.6 Hz, 2H) 2.54 (s, 3H) 2.45 (s, 3H) 1.03 (t, J=6.6 Hz, 3H). [M+H] calc'd for $C_{21}H_{23}N_8O_2S$, 451; found, 451.

Example 378

(3-(7-phenylimidazo[1,2-c]pyrimidin-5-ylamino)-1H-pyrazol-5-yl)methanol

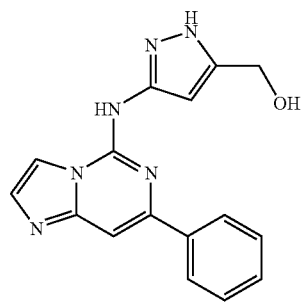

3H) 2.45 (s, 3H) 1.21 (t, J=7.4 Hz, 3H). [M+H] calc'd for $C_{21}H_{22}N_7O_2S$, 436; found, 436.

¹H NMR (400 MHz, DMSO-d₆) δ 8.59 (s, 1H) 8.18 (d, J=6.0 Hz, 2H) 8.02 (s, 1H) 7.70 (s, 1H) 7.54 (m, 3H) 6.78 (s, 1H) 4.55 (s, 2H). [M+H] calc'd for $C_{16}H_{15}N_6O$, 307; found, 307.

Example 379

7-(3-(5-amino-2-methylthiophen-3-yl)phenyl)-2-methyl-N-(5-methyl-1H-pyrazol-3-yl)imidazo[1,2-c]pyrimidin-5-amine

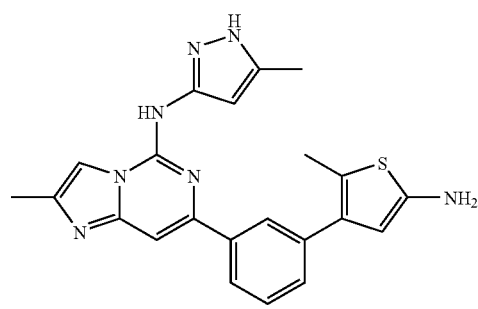

¹H NMR (400 MHz, Methanol-d₄) δ 8.35 (s, 1H) 8.30 (d, J=6.8 Hz, 1H) 8.08 (s, 1H) 7.74 (m, 3H) 7.52 (s, 1H) 6.56 (s, 1H) 2.57 (s, 3H) 2.38 (s, 6H). [M+H] calc'd for $C_{22}H_{22}N_7S$, 416; found, 416.

Example 380

2-Methyl-N-(5-methyl-1H-pyrazol-3-yl)-7-phenyl-2,3-dihydroimidazo[1,2-c]pyrimidin-5-amine

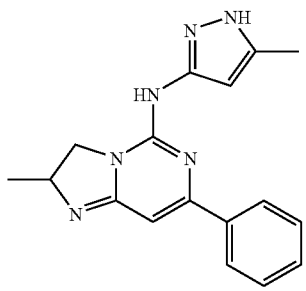

¹H NMR (400 MHz, CD₃OD) 8.04 (d, J=7.2 Hz, 2H) 7.48-7.58 (m, 3H) 6.67 (s, 1H) 6.40 (s, 1H) 4.51-4.62 (m, 2H) 4.02-4.07 (m, 1H) 2.34 (s, 3H). [M+H] calc'd for C₁₇H₁₉N₆, 307; found, 307.

Example 381

7-(3-(Ethylsulfonyl)phenyl)-N-(5-methyl-1H-pyrazol-3-yl)imidazo[1,2-c]pyrimidin-5-amine

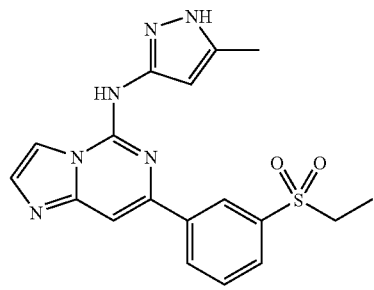

¹H NMR (400 MHz, CD₃OD) 8.69 (m, 1H) 8.46 (d, J=8.0 Hz, 1H) 8.30 (d, J=2.8 Hz, 1H) 8.24 (s, 1H) 8.11 (d, J=8.0 Hz, 1H) 8.02 (d, J=2.8 Hz, 1H) 7.82 (t, J=8.0 Hz, 1H) 6.14 (s, 1H) 3.28 (q, J=7.2 Hz, 2H) 2.38 (s, 3H) 1.25 (t, J=7.2 Hz, 3H). [M+H] calc'd for C₁₈H₁₉N₆O₂S, 383; found, 383.

Example 382

2-Methyl-N-(5-methyl-1H-pyrazol-3-yl)-7-(3-(piperazin-1-ylmethyl)phenyl) imidazo[1,2-c]pyrimidin-5-amine

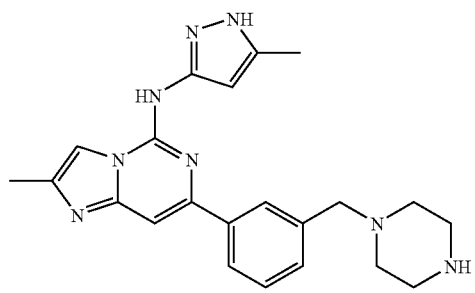

¹H NMR (400 MHz, CD₃OD) 8.24-8.26 (m, 2H) 8.08 (s, 1H) 7.61-7.69 (m, 3H) 6.58 (s, 1H) 3.47-3.50 (m, 4H) 3.36-3.78 (m, 4H) 2.57 (s, 3H) 2.39 (s, 3H). [M+H] calc'd for C₂₂H₂₇N₈, 403; found, 403.

Example 383

(S)-1-(3-(2-Methyl-5-(5-methyl-1H-pyrazol-3-ylamino)imidazo[1,2-c]pyrimidin-7-yl)phenylsulfonyl)pyrrolidin-3-ol

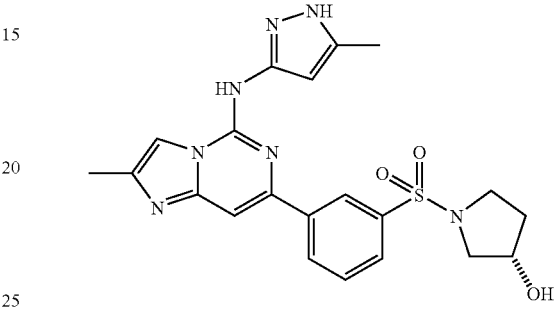

¹H NMR (400 MHz, CD₃OD) 8.64 (m, 1H) 8.33 (d, J=7.2 Hz, 1H) 8.05 (s, 1H) 7.93 (d, J=7.2 Hz, 2H) 7.68-7.73 (m, 2H) 6.60 (s, 1H) 4.25-4.27 (m, 1H) 3.18-3.40 (m, 4H) 2.56 (s, 3H) 2.39 (s, 3H) 1.72-1.87 (m, 2H). [M+H] calc'd for C₂₁H₂₄N₇O₃S, 453; found, 453.

Example 384

2-Methyl-N-(5-methyl-1H-pyrazol-3-yl)-7-(3-(3-(methylamino)pyrrolidin-1-ylsulfonyl)phenyl)imidazo[1,2-c]pyrimidin-5-amine

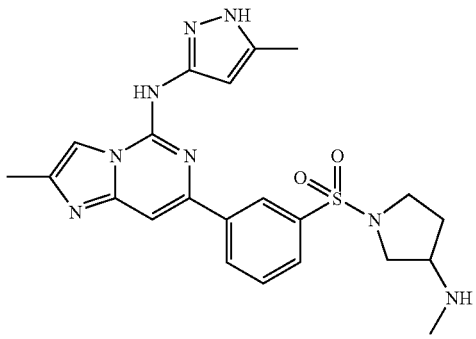

¹H NMR (400 MHz, CD₃OD) 8.68 (m, 1H) 8.42 (d, J=7.8 Hz, 1H) 8.08 (s, 1H) 7.96 (d, J=7.8 Hz, 1H) 7.79 (t, J=7.8 Hz, 1H) 7.75 (s, 1H) 6.60 (s, 1H) 3.70-3.75 (m, 1H) 3.39-3.57 (m, 3H) 3.14-3.19 (m, 1H) 2.67 (s, 3H) 2.57 (s, 3H) 2.40 (s, 3H)

2.20-2.29 (m, 1H) 1.93-2.06 (m, 1H). [M+H] calc'd for C$_{22}$H$_{27}$N$_8$O$_2$S, 467; found, 467.

Example 385

2-Methyl-N-(5-methyl-1H-pyrazol-3-yl)-7-(3-(piperidin-1-ylmethyl)phenyl) imidazo[1,2-c]pyrimidin-5-amine

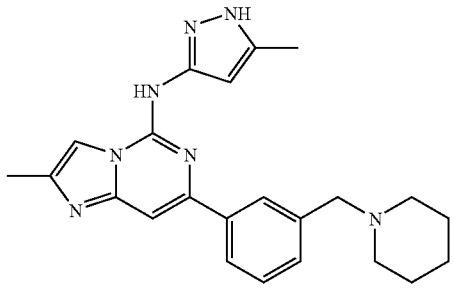

$^1$H NMR (400 MHz, CD$_3$OD) 8.28-8.32 (m, 2H) 8.09 (s, 1H) 7.67-7.70 (m, 3H) 6.57 (s, 1H) 4.42 (s, 2H) 3.49-3.53 (m, 2H) 2.98-3.05 (m, 2H) 2.57 (s, 3H) 2.39 (s, 3H) 1.71-1.98 (m, 5H) 1.50-1.54 (m, 1H). [M+H] calc'd for C$_{23}$H$_{28}$N$_7$, 402; found, 402.

Example 386

N,4-Dimethyl-5-(3-(2-methyl-5-(5-methyl-1H-pyrazol-3-ylamino)imidazo[1,2-c]pyrimidin-7-yl)phenyl) thiazol-2-amine

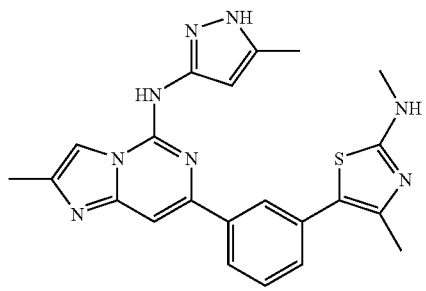

$^1$H NMR (400 MHz, CD$_3$OD) 8.23 (m, 1H) 8.16 (m, 1H) 8.06 (s, 1H) 7.72 (s, 1H) 7.61-7.64 (m, 2H) 6.54 (s, 1H) 3.15 (s, 3H) 2.56 (s, 3H) 2.39 (s, 3H) 2.38 (s, 3H). [M+H] calc'd for C$_{22}$H$_{23}$N$_8$S, 431; found, 431.

Example 387

2-Methyl-N-(5-methyl-1H-pyrazol-3-yl)-7-(3-(piperazin-1-ylsulfonyl)phenyl) imidazo[1,2-c]pyrimidin-5-amine

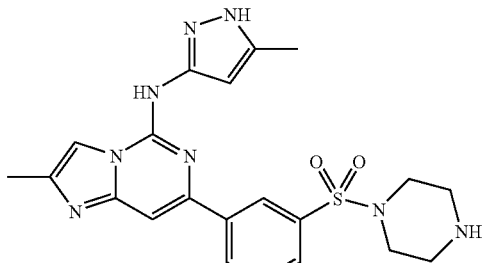

$^1$H NMR (400 MHz, CD$_3$OD) 8.72 (s, 1H) 8.50 (d, J=7.6 Hz, 1H) 8.11 (s., 1H) 7.97 (d, J=7.6 Hz, 1H) 7.84 (m, 1H) 7.79 (s, 1H) 6.62 (s, 1H) 3.30 (m, 8H) 2.58 (s, 3H), 2.40 (s, 3H). [M+H] calc'd for C$_{21}$H$_{25}$N$_8$O$_2$S, 453; found, 453.

Example 388

3-(2-Methyl-5-(5-methyl-1H-pyrazol-3-ylamino)imidazo[1,2-c]pyrimidin-7-yl)-N-(pyrrolidin-3-yl)benzenesulfonamide

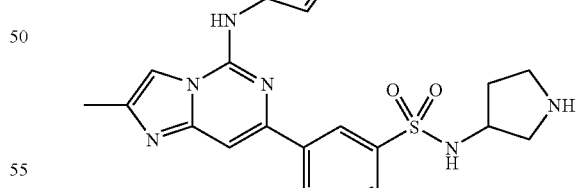

$^1$H NMR (400 MHz, CD$_3$OD) 8.71 (s, 1H) 8.37 (d, J=7.6 Hz, 1H) 8.08 (s., 1H) 7.99 (d, J=7.6 Hz, 1H) 7.73-7.76 (m, 2H) 6.63 (s, 1H) 3.89 (m, 1H) 3.24-3.39 (m, 4H) 2.57 (s, 3H)

2.40 (s, 3H) 2.07-2.15 (m, 1H) 1.89-1.94 (m, 1H). [M+H] calc'd for $C_{21}H_{25}N_8O_2S$, 453; found, 453.

Example 389

N-Cyclopropyl-2-(3-(7-phenylimidazo[1,2-c]pyrimidin-5-ylamino)-1H-pyrazol-5-yl)acetamide

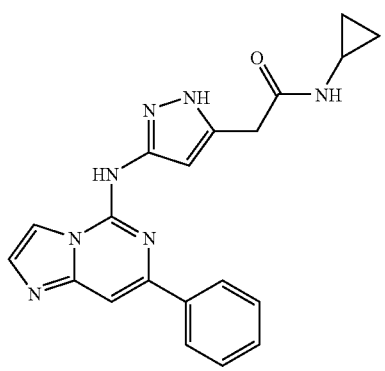

[M+H] calc'd for $C_{20}H_{20}N_7O$, 374; found, 374.

Example 390

N-(4-(5-(5-cyclopropyl-1H-pyrazol-3-ylamino)-2-(methoxymethyl)imidazo[1,2-c]pyrimidin-7-ylthio)phenyl)-2-methoxyacetamide

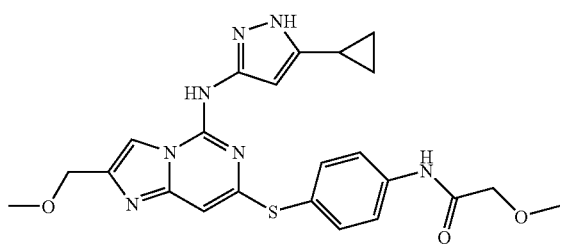

$^1$H NMR (400 MHz, CDCl3: MDOD 10:1) δ ppm 8.06 (s, 1H) 7.64 (d, J=8.6 Hz, 2H) 7.48 (d, J=8.6 Hz, 4H) 6.54 (s, 1H) 6.00 (s, 1H) 4.47 (s, 2H) 3.95 (s, 2H) 3.41 (s, 3H) 3.33 (s, 3H) 1.72-1.81 (m, 1H) 0.89-0.97 (m, 2H) 0.63-0.71 (m, 2H). LCMS (M+1) calcd for $C_{23}H_{26}H_7O_3S$ 480; found 480.

Example 391

Ethyl 2-(4-(5-(5-methyl-1H-pyrazol-3-ylamino)imidazo[1,2-c]pyrimidin-7-ylthio)phenylamino)-2-oxoacetate

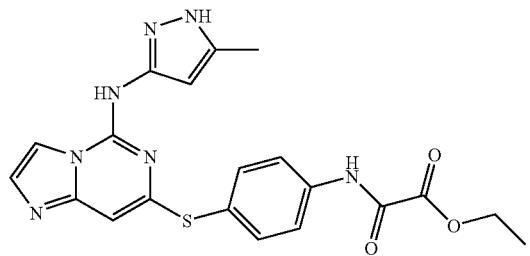

$^1$H NMR (400 MHz, CDCl3:CDOD 10:1) δ ppm 8.15 (s, 1H) 7.76 (d, J=8.3 Hz, 2H) 7.52 (m, 3H) 6.65 (s, 1H) 6.05 (s, 1H) 6.05 (s, 1H) 4.32 (q, J=7.2 Hz, 2H) 3.25 (s, 1H) 2.14 (s, 3H) 1.33 (t, J=7.2 Hz, 3H). LCMS (M+1) calcd for $C_{20}H_{20}N_7O_3S$ 438; found 438.

Example 392

N-(4-(5-(5-methyl-1H-pyrazol-3-ylamino)imidazo[1,2-c]pyrimidin-7-ylthio)phenyl)tetrahydrofuran-2-carboxamide

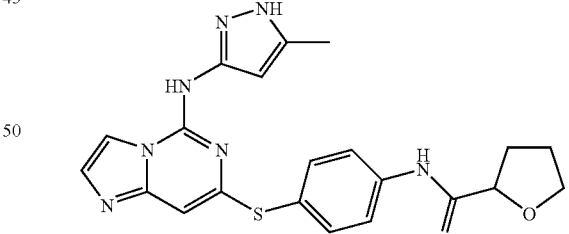

$^1$H NMR (400 MHz, CDCl3:CDOD 10:1) δ ppm 8.10 (s, 1H) 7.65 (d, J=8.6 Hz, 2H) 7.46-7.53 (m, 3H) 6.58 (s, 1H) 5.98 (s, 1H) 4.38 (dd, J=8.2, 6.2 Hz, 1H) 3.97-4.03 (m, 1H) 3.87 (q, J=7.4 Hz, 1H) 3.28 (s, 1H) 3.24 (s, 1H) 2.24-2.34 (m, 1H) 2.15 (s, 3H) 2.02 (ddd, J=13.5, 6.6, 6.4 Hz, 1H) 1.83-1.94 (m, 2H). LCMS (M+1) calcd for $C_{21}H_{22}N_7O_2S$, 436; found 436.

Example 393

N-(4-(2-methyl-5-(5-methyl-1H-pyrazol-3-ylamino)imidazo[1,2-c]pyrimidin-7-ylthio)phenyl)furan-2-carboxamide

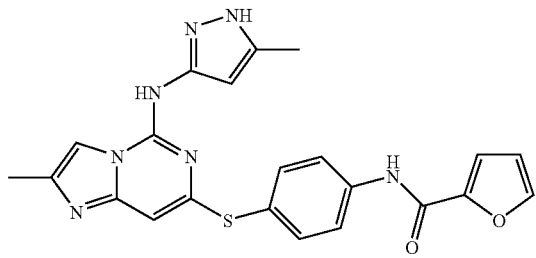

$^1$H NMR (400 MHz, DMSO-d$_6$) δ ppm 10.97 (s, 1H) 10.52 (s, 1H) 8.23 (s, 1H) 8.00 (s, 1H) 7.96-7.98 (m, 2H) 7.61 (d, J=8.8 Hz, 2H) 7.39 (dd, J=3.5, 0.8 Hz, 1H) 6.72 (dd, J=3.5, 1.8 Hz, 1H) 6.67 (s, 1H) 5.79 (s, 1H) 2.52 (s, 1H) 2.34 (s, 3H) 2.08 (s, 3H). LCMS (M+1) calcd for $C_{22}H_{20}N_7O_2S$, 446; found 446.

Example 394

(S)—N-(4-(2-methyl-5-(5-methyl-1H-pyrazol-3-ylamino)imidazo[1,2-c]pyrimidin-7-ylthio)phenyl)tetrahydrofuran-2-carboxamide

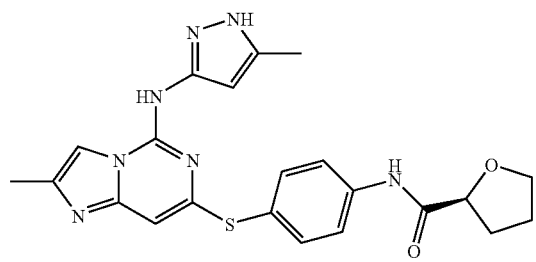

$^1$H NMR (400 MHz, CDCl3:CDOD 10:1) δ ppm 7.81 (s, 1H) 7.64 (d, J=8.6 Hz, 2H) 7.48 (d, J=8.6 Hz, 2H) 6.52 (s, 1H) 5.90 (s, 1H) 5.21 (s, 1H) 4.37 (dd, J=8.3, 6.1 Hz, 1H) 4.01-3.35 (m, 2H) 3.28 (s, 2H) 2.32 (s, 3H) 2.24-2.30 (m, 1H) 2.11 (s, 3H) 2.03 (m, 1H) 1.82-1.90 (m, 2H). LCMS (M+1) calcd for $C_{22}H_{24}N_7O_2S$, 450; found 450.

Example 395

N-(4-(2-methyl-5-(5-methyl-1H-pyrazol-3-ylamino)imidazo[1,2-c]pyrimidin-7-ylthio)phenyl)isoxazole-5-carboxamide

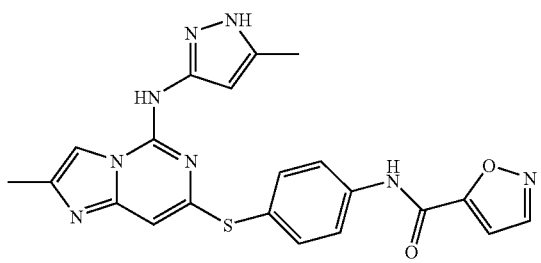

$^1$H NMR (400 MHz, CDCl3:CDOD 10:1) δ ppm 8.34 (s, 1H) 7.78-7.89 (m, 3H) 7.52 (d, J=8.1 Hz, 2H) 7.02 (s, 1H) 6.60 (s, 1H) 6.03 (s, 1H) 3.28 (s, 1H) 2.34 (s, 3H) 2.15 (s, 3H). LCMS (M+1) calcd for $C_{21}H_{19}N_8O_2S$, 447; found 447.

Example 396

5-methyl-N-(4-(2-methyl-5-(5-methyl-1H-pyrazol-3-ylamino)imidazo[1,2-c]pyrimidin-7-ylthio)phenyl)isoxazole-3-carboxamide

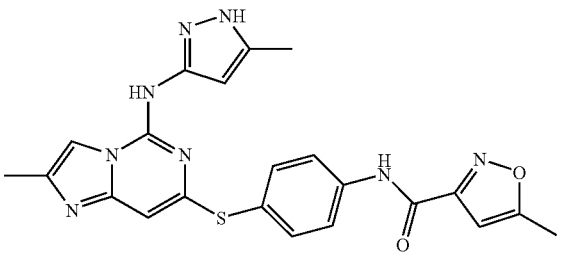

$^1$H NMR (400 MHz, CDCl3:CDOD 10:1) δ ppm 7.86 (s, 1H) 7.78 (d, J=6.8 Hz, 2H) 7.53 (d, J=7.8 Hz, 2H) 6.70 (s, 1H)

6.46 (s, 1H) 5.99 (s, 1H) 3.30 (s, 2H) 3.26 (s, 3H) 2.43 (s, 3H) 2.36 (s, 3H). LCMS (M+1) calcd for $C_{22}H_{21}N_8O_2S$, 461; found 461.

Example 397

4-methyl-N-(4-(2-methyl-5-(5-methyl-1H-pyrazol-3-ylamino)imidazo[1,2-c]pyrimidin-7-ylthio)phenyl)oxazole-5-carboxamide

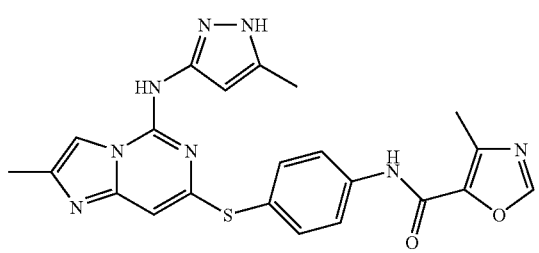

$^1$H NMR (400 MHz, CDCl3:CDOD 10:1) δ ppm 7.92 (s, 1H) 7.79 (s, 1H) 7.72-7.77 (m, 2H) 7.50 (d, J=8.6 Hz, 2H) 6.56 (s, 1H) 5.98 (s, 1H) 3.29 (s, 2H) 2.47 (s, 3H) 2.33 (s, 3H) 2.15 (s, 3H). LCMS (M+1) calcd for $C_{22}H_{21}N_8O_2S$, 461; found 461.

Example 398

N-(4-(5-(5-cyclopropyl-1H-pyrazol-3-ylamino)-2-methylimidazo[1,2-c]pyrimidin-7-ylthio)phenyl)-5-methylfuran-2-carboxamide

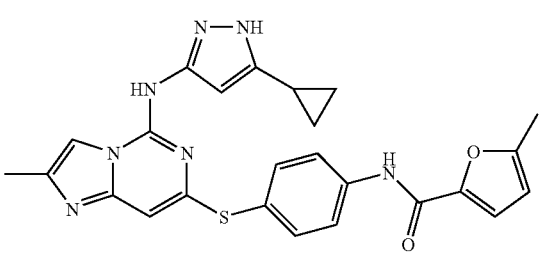

$^1$H NMR (400 MHz, CDCl3:CDOD 10:1) δ ppm 7.90 (s, 1H) 7.75 (d, J=8.3 Hz, 2H) 7.50 (d, J=8.3 Hz, 2H) 7.12 (d, J=3.3 Hz, 1H) 6.62 (s, 1H) 6.04-6.15 (m, 2H) 2.35 (s, 3H) 2.33 (s, 3H) 1.80 (s, 1H) 1.11-1.23 (m, 2H) 0.89-1.00 (m, 2H) 0.66-0.72 (m, 2H). LCMS (M+1) calcd for $C_{25}H_{24}N_7O_2S$, 486; found 486.

Example 399

N-(4-(5-(5-cyclopropyl-1H-pyrazol-3-ylamino)-2-methylimidazo[1,2-c]pyrimidin-7-ylthio)phenyl)-1,5-dimethyl-1H-pyrazole-3-carboxamide

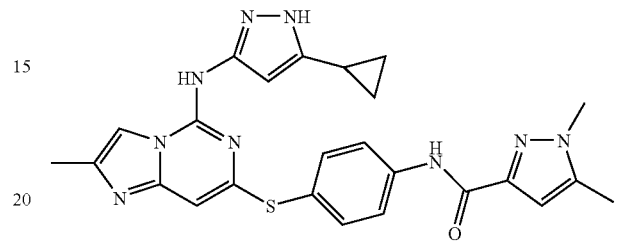

$^1$H NMR (400 MHz, CDCl3:CDOD 10:1) δ ppm 7.85 (s, 1H) 7.74 (d, J=8.6 Hz, 2H) 7.51 (d, J=8.3 Hz, 2H) 6.65 (s, 1H) 6.55 (s, 1H) 5.93 (s, 1H) 3.76 (s, 3H) 3.31 (s, 1H) 2.35 (s, 3H) 2.25 (s, 3H) 1.75 (m, 1H) 1.16 (s, 2H) 0.83-0.93 (m, 2H) 0.63 (t, J=5.4 Hz, 2H). LCMS (M+1) calcd for $C_{25}H_{26}N_9OS$, 500; found 500.

Example 400

N-(4-(5-(5-cyclopropyl-1H-pyrazol-3-ylamino)-2-methylimidazo[1,2-c]pyrimidin-7-ylthio)phenyl)-1,3-dimethyl-1H-pyrazole-5-carboxamide $^1$H NMR (400 MHz, CDCl3:CDOD 10:1) δ ppm 7.79 (s, 1H) 7.71-7.75 (m, 2H) 7.47-7.51 (m, 2H) 6.66 (s, 1H) 6.49 (s, 1H) 6.05 (s, 1H) 4.03 (s, 3H) 3.31 (m, 1H) 2.34 (s, 3H) 2.20

(s, 3H) 1.79 (s, 1H) 0.87-0.95 (m, 2H) 0.67 (dt, J=6.5, 4.8 Hz, 2H). LCMS (M+1) calcd for $C_{25}H_{26}N_9OS$, 500; found 500.

Example 401

N1-(4-(5-(5-cyclopropyl-1H-pyrazol-3-ylamino)-2-methylimidazo[1,2-c]pyrimidin-7-ylthio)phenyl)-N2-ethyl-N2-methyloxalamide

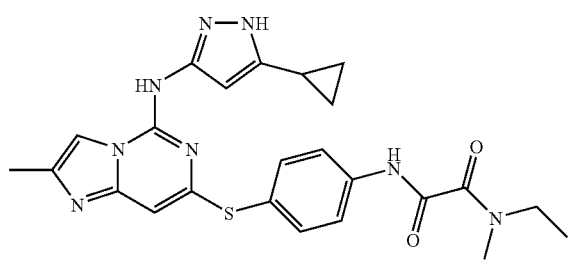

$^1$H NMR (400 MHz, CDCl3:CDOD 10:1) δ ppm 7.81 (s, 1H) 7.71 (d, J=7.8 Hz, 2H) 7.50 (d, J=8.3 Hz, 2H) 6.55 (s, 1H) 3.41 (q, J=7.3 Hz, 2H) 3.31 (s, 1H) 3.23 (s, 2H) 2.95 (s, 3H) 2.35 (s, 3H) 1.79 (m, 1H) 1.22 (t, J=6.9 Hz, 3H) 0.93 (d, J=10.1 Hz, 2H) 0.65 (d, J=1.3 Hz, 2H). LCMS (M+1) calcd for $C_{24}H_{27}N_8O_2S$, 491; found 491.

Example 402

N1-(4-(5-(5-cyclopropyl-1H-pyrazol-3-ylamino)-2-methylimidazo[1,2-c]pyrimidin-7-ylthio)phenyl)-N2-(thiazol-2-yl)oxalamide

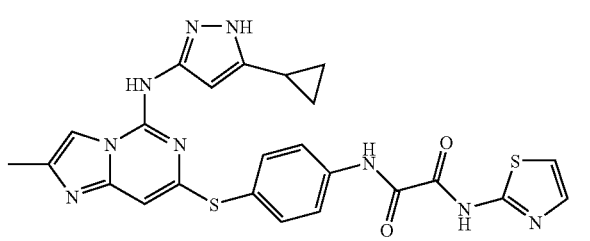

$^1$H NMR (400 MHz, CDCl3:CDOD 10:1) δ ppm 7.61-7.70 (m, 3H) 7.34 (d, J=8.6 Hz, 2H) 6.90 (d, J=3.5 Hz, 1H) 6.28 (s, 1H) 7.26 (m, 1H) 5.68 (s, 1H) 2.35 (s, 1H) 2.15 (s, 3H) 1.47-1.56 (m, 1H) 0.94 (s, 5H) 0.64 (q, J=6.6 Hz, 2H) 0.31-0.40 (m, 2H). LCMS (M+1) calcd for $C_{24}H_{22}N_9O_2S_2$, 532; found 532.

Example 403

N7,2-dimethyl-N-5-(5-methyl-1H-pyrazol-3-yl)-N-7-(1-methylpyrrolidin-3-yl)imidazo[1,2-c]pyrimidine-5,7-diamine

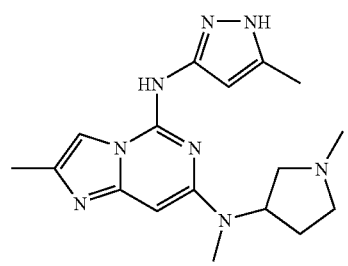

$^1$H NMR (400 MHz, CDCl3:CDOD 10:1) δ ppm 7.71 (s, 1H) 6.16 (m, 2H) 4.74 (m, 1H) 3.75-3.85 (m, 4H) 3.30 (s, 1H) 3.03 (s, 3H) 2.85 (s, 3H) 2.4-2.5 (m, 1H) 2.31 (m, 1H) 2.28 (s, 3H) 2.25 (s, 3H). LCMS (M+1) calcd for $C_{17}H_{25}N_8$, 341; found 341.

Example 404

N-(5-cyclopropyl-1H-pyrazol-3-yl)-2-(ethoxymethyl)-7-(3-(ethylsulfonyl)phenyl)imidazo[1,2-c]pyrimidin-5-amine

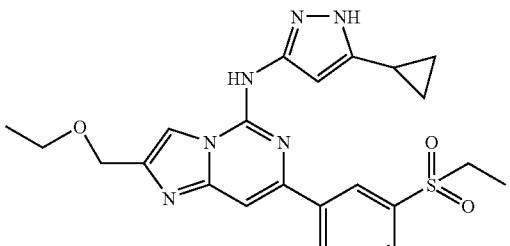

$^1$H NMR (400 MHz, MeOD) δ ppm 8.74 (s, 1H) 8.46 (d, J=6.3 Hz, 1H) 8.32 (s, 1H) 8.06 (d, J=7.1 Hz, 1H) 7.81 (t, J=7.8 Hz, 1H) 7.74 (s, 1H) 6.50 (s, 1H) 4.78 (s, 2H) 3.70 (q, J=7.1 Hz, 2H) 3.25-3.30 (m, 2H) 1.94-2.04 (m, 1H) 1.29 (m, 6H) 1.02-1.08 (m, 2H) 0.88 (m, 2H). LCMS (M+1) calcd for C$_{23}$H$_{27}$N$_6$O$_3$S, 467; found 467.

Example 405

N1-(3-(5-(5-cyclopropyl-1H-pyrazol-3-ylamino)-2-methylimidazo[1,2-c]pyrimidin-7-yl)phenyl)-N4-ethylsuccinamide

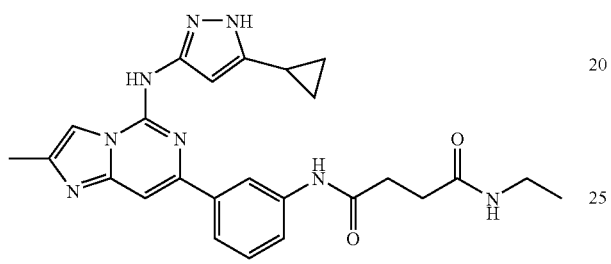

$^1$H NMR (400 MHz, MeOD) δ ppm 8.54 (s, 1H) 8.03 (s, 1H) 7.91 (s, 1H) 7.82 (d, J=7.8 Hz, 1H) 7.50-7.52 (m, 2H) 7.45 (m, J=7.8 Hz, 1H) 6.55 (s, 1H) 3.98 (s, 2H) 3.22 (q, J=7.3 Hz, 2H) 2.73 (t, J=6.7 Hz, 2H) 2.61 (t, J=6.7 Hz, 2H) 2.54 (s, 3H) 2.02 (m, 1H) 1.12 (t, J=7.3 Hz, 3H) 1.02-1.08 (m, 2H) 0.80-0.86 (m, 2H). LCMS (M+1) calcd for C$_{25}$H$_{29}$N$_8$O$_2$, 473; found 473.

Example 406

N-(5-cyclopropyl-1H-pyrazol-3-yl)-7-(1-isopentyl-1H-pyrazol-4-yl)-2-methylimidazo[1,2-c]pyrimidin-5-amine

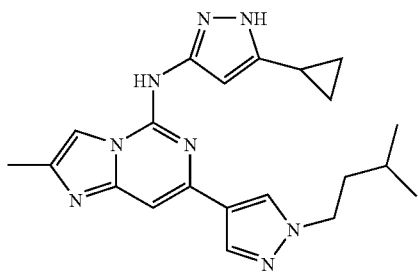

$^1$H NMR (400 MHz, CDCl3:CDOD 10:1) δ ppm 8.07 (s, 1H) 7.84-7.90 (m, 1H) 7.86 (s, 1H) 7.26 (s, 1H) 6.35 (s, 1H) 4.11 (t, J=7.452 Hz, 2H) 2.37 (s, 3H) 1.88 (m, 1H) 1.67-1.75 (m, 2H) 1.51 (m, 1H) 1.01 (q, J=6.2 Hz, 2H) 0.89 and 87 (s, 3H each) 0.74-0.78 (m, 2H). LCMS (M+1) calcd for C$_{21}$H$_{27}$N$_8$, 391; found 391.

Example 407

7-(3-(diethylamino)pyrrolidin-1-yl)-2-methyl-N-(5-methyl-1H-pyrazol-3-yl)imidazo[1,2-c]pyrimidin-5-amine

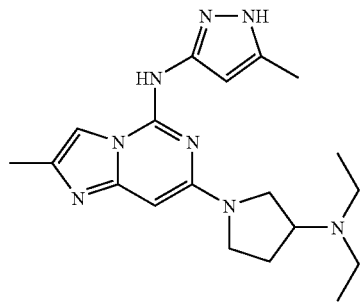

$^1$H NMR (400 MHz, CDCl3:CDOD 10:1) δ ppm 7.62 (s, 1H) 6.37 (s, 1H) 5.87 (s, 1H) 3.95-4.04 (m, 2H) 3.88-3.71 (s, 3H) 3.42 (m, 1H) 3.30-3.19 (s, 4H) 2.38 (s, 3H) 2.17-2.28 (m, 6H) 1.27 (q, J=7.1 Hz, 6H). LCMS (M+1) calcd for C$_{19}$H$_{29}$N$_8$, 369; found 369.

Example 408

2(3-(dimethylamino)methyl-1-(ethylsulfonyl)-1H-indol-6-yl)-N-(5-methyl-1H-pyrazol-3-yl)pyrrolo[1,2-f][1,2,4]triazin-4-amine

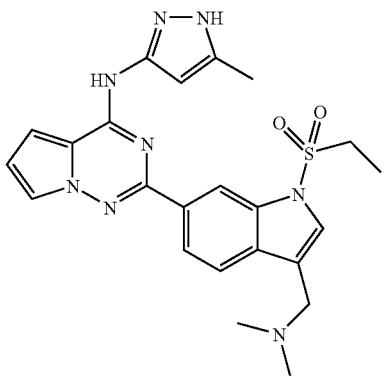

$^1$H NMR (400 MHz, DMSO-d$_6$) δ ppm 1.14 (t, J=7.33 Hz, 3H) 2.35 (s, 3H) 2.83 (d, J=4.55 Hz, 6H) 3.76 (q, J=7.24 Hz, 2H) 4.53 (d, J=4.80 Hz, 2H) 6.73 (dd, J=4.29, 2.53 Hz, 1H) 6.94 (s, 1H) 7.33 (s, 1H) 7.83 (dd, J=2.53, 1.52 Hz, 1H) 8.00 (s, 1H) 8.06 (d, J=8.59 Hz, 1H) 8.33 (d, J=9.09 Hz, 1H) 8.97

(s, 1H) 9.77 (s, 1H) 10.71 (s, 1H) 12.25 (bs. 1H); ESI-MS: m/z calc'd for C23H26N8O2S 478.57; found 479.4 (M+H)+

Example 409

N-(4-(4-(5-methyl-1H-pyrazol-3-ylamino)pyrrolo[1,2-f][1,2,4]triazin-2-ylthio)phenyl)acetamide

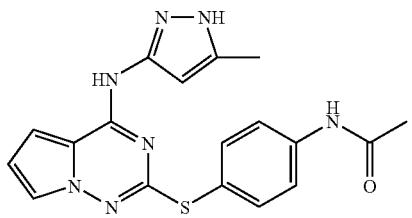

$^1$H NMR (400 MHz, DMSO) δ 10.15 (s, 1H) 8.03 (d, J=0.8 Hz, 1H) 7.98 (s, 1H) 7.76 (s, 1H) 7.69 (d, J=8.8 Hz, 2H) 7.51 (d, J=8.4 Hz, 2H) 7.47 (d, J=8.8 Hz, 1H) 7.21 (d, J=8.8 Hz, 1H) 6.05 (s, 1H) 2.16 (s, 3H) 2.06 (s, 3H). ESI-MS: m/z calc'd for C18H17N7OS 379.12; found 380.3 (M+H)+

Biological Testing

The activity of compounds as protein kinase inhibitors may be assayed in vitro, in vivo or in a cell line. In vitro assays include assays that determine inhibition of either the phosphorylation activity or ATPase activity of the activated protein kinase. Alternate in vitro assays quantitate the ability of the inhibitor to bind to the protein kinase Inhibitor binding may be measured by radiolabelling the inhibitor prior to binding, isolating the inhibitor/protein kinase complex and determining the amount of radiolabel bound. Alternatively, inhibitor binding may be determined by running a competition experiment where new inhibitors are incubated with the protein kinase bound to known radioligands.

A. Determination of Inhibition of AIK

The inhibitory properties of compounds relative to AIK may be determined by the Direct Fluorescence Polarization detection method (FP) using a Greiner small volume black 384-well-plate format under the following reaction conditions: 50 mM Hepes pH 7.3, 10 mM MgCl$_2$, 10 mM NaCl, 1 mM DTT, 0.01% Brij35, 100 nM Fluorescein-LRRASLG peptide (provided by SYNPEP), 5% DMSO, 2.5 uM ATP. Detection of the reaction product is performed by addition of IMAP binding reagent (Molecular Devices). Reaction product may be determined quantitatively by FP using an Analyst HT plate reader (Molecular Devices) with an excitation wavelength at 485 nm and emission at 530 nm and using a Fluorescein 505 dichroic mirror.

The assay reaction may be initiated as follows: 2 ul of (3×) 300 nM Fl-Peptide/7.5 uM ATP was added to each well of the plate, followed by the addition of 2 ul of (3×) inhibitor (2.5 fold serial dilutions for 11 data points for each inhibitor) containing 15% DMSO. 2 ul of (3×) 7.5 nM AIK solution may be added to initiate the reaction (final enzyme concentration was 2.5 nM for AIK). The reaction mixture may then be incubated at room temperature for 45 min, and quenched and developed by addition of 20 ul of 1 to 400 diluted IMAP binding reagent in 1× proprietary IMAP binding buffer. Fluorescence polarization readings of the resulting reaction mixtures may be measured after a 60-minute incubation at room temperature.

IC50 values may be calculated by non-linear curve fitting of the compound concentrations and fluorescent polarization values to the standard IC50 equation. As a reference point for this assay, Staurosporin showed an IC50 of <10 nM.

B. Determination of Inhibition of c-KIT

The inhibitory properties of compounds relative to c-Kit may be determined by the Time-Resolved Fluorescence Resonance Energy Transfer (TR-FRET) method using a small volume black 384-well-plate (Greiner) format under the following reaction conditions: 50 mM Hepes pH 7.3, 10 mM MgCl$_2$, 10 mM NaCl, 1 mM DTT, 0.01% Brij35, 250 nM Biotin-EGPWLEEEEEAYGWMDF peptide (provided by SYNPEP), 5% DMSO, 100 uM ATP. Detection of the reaction product may be performed by addition of Streptavidin-APC (Prozyme) and Eu-Anti-phosphotyrosine antibody (Perkin Elmer). Reaction product may be determined quantitatively by TR-FRET reading using an Analyst HT plate reader (Molecular Devices) with an excitation wavelength at 330 nm and emission at 615 nm (Europium) compared to 330 nm excitation (Europium) and emission 665 nm (APC) and using an Europium 400 dichroic mirror.

The assay reaction may be initiated as follows: 4 ul of (2.5×) 625 nM Biotin-Peptide/250 uM ATP was added to each well of the plate, followed by the addition of 2 ul of (5×) inhibitor (2.5 fold serial dilutions for 11 data points for each inhibitor) containing 25% DMSO. 4 ul of (2.5×) c-Kit solution may be added to initiate the reaction (final enzyme concentration was 0.13 nM for c-Kit). The reaction mixture may then be incubated at room temperature for 30 min, and quenched and developed by addition of 10 ul of (2×) 3.2 nM Eu-Antibody and 25 nM Streptavidin-APC in 50 mM Hepes pH 7.3, 30 mM EDTA, 0.1% Triton X-100 buffer. TR-FRET readings of the resulting reaction mixtures may be measured after a 60-minute incubation at room temperature on the Analyst HT.

IC50 values may be calculated by non-linear curve fitting of the compound concentrations and ratio metric Eu:APC values to the standard IC50 equation. As a reference point for this assay, Staurosporin showed an IC50 of <5 nM.

The following abbreviations have been used:
ATP Adenosine Triphophatase
BSA Bovine Serum Albumin
EDTA Ethylenediaminetetraacetic acid
GSK3 Glycogen synthase kinase 3
MOPS Morpholinepropanesulfonic acid
SPA Scintillation Proximity Assay It will be apparent to those skilled in the art that various modifications and variations can be made in the compounds, compositions, kits, and methods of the present invention without departing from the spirit or scope of the invention. Thus, it is intended that the present invention cover the modifications and variations of this invention provided they come within the scope of the appended claims and their equivalents.

What is claimed is:
1. A compound having the formula:

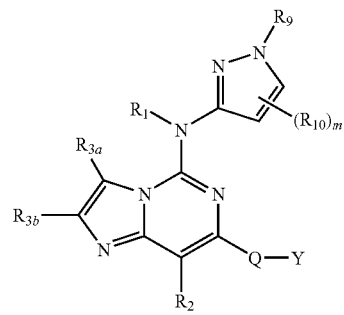

wherein:
  m is selected from the group consisting of 0, 1 and 2;
  Q is selected from the group consisting of S, SO, SO$_2$, O, NR$_6$, NR$_6$—(CR$_{21}$R$_{22}$)$_l$, NR$_6$—(CR$_{21}$R$_{22}$)$_l$—O, and a substituted or unsubstituted (C$_{2-5}$)alkylene, or Q is absent;
  l is selected from the group consisting of 1, 2, 3, 4 and 5;
  Y is selected from the group consisting of (C$_{3-12}$)cycloalkyl, hetero(C$_{3-12}$)cycloalkyl, (C$_{9-12}$)bicycloalkyl, hetero(C$_{3-12}$)bicycloalkyl, aryl, heteroaryl, (C$_{9-12}$)bicycloaryl, and hetero(C$_{4-12}$)bicycloaryl, each substituted or unsubstituted;
  R$_1$ is selected from the group consisting of hydrogen, nitro, thio, hydroxy, alkoxy, aryloxy, heteroaryloxy, amino, (C$_{1-10}$)alkyl, (C$_{3-12}$)cycloalkyl, hetero(C$_{3-12}$)cycloalkyl, (C$_{9-12}$)bicycloalkyl, hetero(C$_{3-12}$)bicycloalkyl, aryl(C$_{1-10}$)alkyl, heteroaryl(C$_{1-5}$)alkyl, (C$_{3-12}$)cycloalkyl(C$_{1-10}$)alkyl, halo(C$_{1-10}$)alkyl, aryl, heteroaryl, (C$_{9-12}$)bicycloaryl, and hetero(C$_{4-12}$)bicycloaryl, each substituted or unsubstituted, and substituted carbonyl, substituted sulfonamido, substituted imino, substituted sulfonyl, substituted sulfinyl, substituted carbonyl(C$_{1-3}$)alkyl, substituted thiocarbonyl(C$_{1-3}$)alkyl, substituted sulfonyl(C$_{1-3}$)alkyl, substituted sulfinyl(C$_{1-3}$)alkyl, and substituted imino(C$_{1-3}$)alkyl;
  R$_2$ is selected from the group consisting of hydrogen, halo, nitro, cyano, hydroxy, alkoxy, aryloxy, heteroaryloxy, amino, (C$_{1-10}$)alkylamino, (C$_{1-10}$)alkyl, (C$_{3-12}$)cycloalkyl, hetero(C$_{3-12}$)cycloalkyl, (C$_{9-12}$)bicycloalkyl, hetero(C$_{3-12}$)bicycloalkyl, aryl(C$_{1-10}$)alkyl, heteroaryl(C$_{1-5}$)alkyl, perhalo(C$_{1-10}$)alkyl, amino(C$_{1-10}$)alkyl, aryl, heteroaryl, (C$_{9-12}$)bicycloaryl, and hetero(C$_{4-12}$)bicycloaryl, each substituted or unsubstituted, and substituted carbonyl, substituted sulfonamido, substituted imino, substituted sulfonyl, substituted sulfinyl, substituted carbonyl(C$_{1-3}$)alkyl, substituted thiocarbonyl(C$_{1-3}$)alkyl, substituted sulfonyl(C$_{1-3}$)alkyl, substituted sulfinyl(C$_{1-3}$)alkyl, and substituted imino(C$_{1-3}$)alkyl;
  R$_{3a}$ and R$_{3b}$ are each independently selected from the group consisting of hydrogen, halo, nitro, cyano, hydroxy, alkoxy, aryloxy, heteroaryloxy, amino, (C$_{1-10}$)alkylamino, (C$_{1-10}$)alkyl, (C$_{3-12}$)cycloalkyl, hetero(C$_{3-12}$)cycloalkyl, (C$_{9-12}$)bicycloalkyl, hetero(C$_{3-12}$)bicycloalkyl, aryl(C$_{1-10}$)alkyl, heteroaryl(C$_{1-5}$)alkyl, perhalo(C$_{1-10}$)alkyl, amino(C$_{1-10}$)alkyl, heteroaryl, (C$_{9-12}$)bicycloaryl, and hetero(C$_{4-12}$)bicycloaryl, each substituted or unsubstituted, and substituted carbonyl, substituted sulfonamido, substituted imino, substituted sulfonyl, substituted sulfinyl, substituted carbonyl(C$_{1-3}$)alkyl, substituted thiocarbonyl(C$_{1-3}$)alkyl, substituted sulfonyl(C$_{1-3}$)alkyl, substituted sulfinyl(C$_{1-3}$)alkyl, and substituted imino(C$_{1-3}$)alkyl; or R$_{3a}$ and R$_{3b}$ are taken together to form a substituted or unsubstituted ring;
  R$_6$ is selected from the group consisting of hydrogen, (C$_{1-10}$)alkyl, (C$_{3-12}$)cycloalkyl, hetero(C$_{3-12}$)cycloalkyl, (C$_{9-12}$)bicycloalkyl, hetero(C$_{3-12}$)bicycloalkyl, aryl(C$_{1-10}$)alkyl, heteroaryl(C$_{1-5}$)alkyl, (C$_{3-12}$)cycloalkyl(C$_{1-10}$)alkyl, halo(C$_{1-10}$)alkyl, aryl, heteroaryl, (C$_{9-12}$)bicycloaryl, and hetero(C$_{4-12}$)bicycloaryl, each substituted or unsubstituted, and substituted carbonyl, substituted sulfonamido, substituted imino, substituted sulfonyl, substituted sulfinyl, substituted carbonyl(C$_{1-3}$)alkyl, substituted thiocarbonyl(C$_{1-3}$)alkyl, substituted sulfonyl(C$_{1-3}$)alkyl, substituted sulfinyl(C$_{1-3}$)alkyl, and substituted imino(C$_{1-3}$)alkyl;
  R$_9$ is selected from the group consisting of hydrogen, amino, (C$_{1-10}$)alkyl, (C$_{3-12}$)cycloalkyl, hetero(C$_{3-12}$)cycloalkyl, (C$_{9-12}$)bicycloalkyl, hetero(C$_{3-12}$)bicycloalkyl, aryl(C$_{1-10}$)alkyl, heteroaryl(C$_{1-5}$)alkyl, (C$_{3-12}$)cycloalkyl(C$_{1-10}$)alkyl, halo(C$_{1-10}$)alkyl, aryl, heteroaryl, (C$_{9-12}$)bicycloaryl, and hetero(C$_{4-12}$)bicycloaryl, each substituted or unsubstituted, and substituted carbonyl, substituted sulfonamido, substituted imino, substituted sulfonyl, substituted sulfinyl, substituted carbonyl(C$_{1-3}$)alkyl, substituted thiocarbonyl(C$_{1-3}$)alkyl, substituted sulfonyl(C$_{1-3}$)alkyl, substituted sulfinyl(C$_{1-3}$)alkyl, and substituted imino(C$_{1-3}$)alkyl;
  each R$_{10}$ is independently selected from the group consisting of hydrogen, halo, nitro, cyano, hydroxy, alkoxy, aryloxy, heteroaryloxy, amino, (C$_{1-10}$)alkylamino, (C$_{1-10}$)alkyl, (C$_{3-12}$)cycloalkyl, hetero(C$_{3-12}$)cycloalkyl, (C$_{9-12}$)bicycloalkyl, hetero(C$_{3-12}$)bicycloalkyl, aryl(C$_{1-10}$)alkyl, heteroaryl(C$_{1-5}$)alkyl, perhalo(C$_{1-10}$)alkyl, amino(C$_{1-10}$)alkyl, aryl, heteroaryl, (C$_{9-12}$)bicycloaryl, and hetero(C$_{4-12}$)bicycloaryl, each substituted or unsubstituted, and substituted carbonyl, substituted sulfonamido, substituted imino, substituted sulfonyl, substituted sulfinyl, substituted carbonyl(C$_{1-3}$)alkyl, substituted thiocarbonyl(C$_{1-3}$)alkyl, substituted sulfonyl(C$_{1-3}$)alkyl, substituted sulfinyl(C$_{1-3}$)alkyl, and substituted imino(C$_{1-3}$)alkyl; or R$_9$ and R$_{10}$ are taken together to form a ring; and
  R$_{21}$ and R$_{22}$ are each independently selected from the group consisting of hydrogen, halo, hydroxy, alkoxy, amino, (C$_{1-5}$)alkylamino, (C$_{1-5}$)alkyl, halo(C$_{1-5}$)alkyl, and amino(C$_{1-5}$)alkyl, each substituted or unsubstituted, and substituted carbonyl and substituted carbonyl(C$_{1-3}$)alkyl;
  or a pharmaceutically acceptable salt thereof.

2. A compound of claim 1 wherein the compound is of the formula:

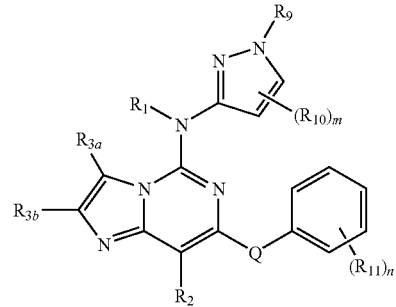

wherein:
  n is selected from the group consisting of 0, 1, 2, 3, 4, and 5; and
  each R$_{11}$ is selected from the group consisting of hydrogen, halo, nitro, cyano, hydroxy, alkoxy, aryloxy, heteroaryloxy, amino, (C$_{1-10}$)alkylamino, (C$_{1-10}$)alkyl, (C$_{3-12}$)cycloalkyl, hetero(C$_{3-12}$)cycloalkyl, (C$_{9-12}$)bicycloalkyl, hetero(C$_{3-12}$)bicycloalkyl, aryl(C$_{1-10}$)alkyl, heteroaryl(C$_{1-5}$)alkyl, perhalo(C$_{1-10}$)alkyl, amino(C$_{1-10}$)alkyl, aryl, heteroaryl, (C$_{9-12}$)bicycloaryl, and hetero(C$_{4-12}$)bicycloaryl, each substituted or unsubstituted, and substituted carbonyl, substituted sulfonamido, substituted imino, substituted sulfonyl, substituted sulfinyl, substituted carbonyl(C$_{1-3}$)alkyl, substituted thiocarbonyl(C$_{1-3}$)alkyl, substituted sulfonyl(C$_{1-3}$)alkyl, substituted sulfinyl(C$_{1-3}$)alkyl, and substituted imino(C$_{1-3}$)alkyl, or two R$_{11}$ are taken together to form a ring.

3. The compound of claim 2, wherein Q is absent, $R_1$ is hydrogen, $R_2$ is hydrogen, and $R_{3a}$ is hydrogen.

4. The compound of claim 2, wherein Q is S, $R_1$ is hydrogen, $R_2$ is hydrogen, and $R_{3a}$ is hydrogen.

5. The compound of any one of claims 1 or 2 to 4 wherein $R_{10}$ is selected from the group consisting of hydrogen, $(C_{1-6})$ alkyl, $(C_{3-12})$cycloalkyl and heteroaryl, each substituted or unsubstituted.

6. A compound of claim 1 selected from the group consisting of:

- N-(4-(5-(5-methyl-1H-1,2,4-triazol-3-ylamino)imidazo[1,2-f]pyrimidin-7-ylthio)phenyl)cyclopropane carboxamide;
- N-(4-(5-(5-cyclopropyl-1H-pyrazol-3-ylamino)imidazo[1,2-f]pyrimidin-7-ylthio)phenyl)thiophene-2-sulfonamide;
- N-(4-(5-(5-isopropyl-1H-pyrazol-3-ylamino)imidazo[1,2-f]pyrimidin-7-ylthio)phenyl)cyclopropane carboxamide;
- N-(4-(5-(5-isopropyl-1H-pyrazol-3-ylamino)imidazo[1,2-f]pyrimidin-7-ylthio)phenyl)acetamide;
- N-(4-(5-(5-ethyl-1H-pyrazol-3-ylamino)imidazo[1,2-f]pyrimidin-7-ylthio)phenyl)cyclopropane carboxamide;
- N-(4-(5-(5-ethyl-1H-pyrazol-3-ylamino)imidazo[1,2-f]pyrimidin-7-ylthio)phenyl)acetamide;
- N-(4-(5-(1H-pyrazol-3-ylamino)imidazo[1,2-f]pyrimidin-7-ylthio)phenyl)cyclopropane carboxamide;
- N-(4-(5-(5-propyl-1H-pyrazol-3-ylamino)imidazo[1,2-f]pyrimidin-7-ylthio)phenyl)cyclopropane carboxamide;
- N-(4-(5-(1H-indazol-3-ylamino)imidazo[1,2-f]pyrimidin-7-ylthio)phenyl)cyclopropane carboxamide;
- N-(4-(5-(5-(3-hydroxypropyl)-1H-pyrazol-3-ylamino)imidazo[1,2-f]pyrimidin-7-ylthio)phenyl)cyclopropane carboxamide;
- N-(4-(5-(5-(3-methoxypropyl)-1H-pyrazol-3-ylamino)imidazo[1,2-f]pyrimidin-7-ylthio)phenyl)cyclopropane carboxamide;
- N-(4-(5-(5-cyclobutyl-1H-pyrazol-3-ylamino)imidazo[1,2-f]pyrimidin-7-ylthio)phenyl)cyclopropane carboxamide;
- N-(4-(5-(5-cyclopentyl-1H-pyrazol-3-ylamino)imidazo[1,2-f]pyrimidin-7-ylthio)phenyl)cyclopropane carboxamide;
- N-(4-(3-methyl-5-(5-methyl-1H-pyrazol-3-ylamino)imidazo[1,2-f]pyrimidin-7-ylthio)phenyl)cyclopropane carboxamide;
- N-(4-(3-fluoro-5-(5-methyl-1H-pyrazol-3-ylamino)imidazo[1,2-f]pyrimidin-7-ylthio)phenyl)cyclopropane carboxamide;
- N-(4-(3-chloro-5-(5-methyl-1H-pyrazol-3-ylamino)imidazo[1,2-f]pyrimidin-7-ylthio)phenyl)cyclopropane carboxamide;
- N-(4-(3-bromo-5-(5-methyl-1H-pyrazol-3-ylamino)imidazo[1,2-f]pyrimidin-7-ylthio)phenyl)cyclopropane carboxamide;
- N-(4-(5-(5-methyl-1H-pyrazol-3-ylamino)-2-((4-methylpiperazin-1-yl)methyl)imidazo[1,2-f]pyrimidin-7-ylthio)phenyl)cyclopropane carboxamide;
- N-(4-(2-(aminomethyl)-5-(5-methyl-1H-pyrazol-3-ylamino)imidazo[1,2-f]pyrimidin-7-ylthio)phenyl)cyclopropane carboxamide;
- N-(4-(5-(5-methyl-1H-pyrazol-3-ylamino)-2-(morpholinomethyl)imidazo[1,2-f]pyrimidin-7-ylthio)phenyl)cyclopropane carboxamide;
- N-(4-(3-amino-5-(5-methyl-1H-pyrazol-3-ylamino)imidazo[1,2-f]pyrimidin-7-ylthio)phenyl)cyclopropane carboxamide;
- N-(4-(2-amino-5-(5-methyl-1H-pyrazol-3-ylamino)imidazo[1,2-f]pyrimidin-7-ylthio)phenyl)cyclopropane carboxamide;
- 7-(4-(cyclopropanecarboxamido)phenylthio)-N-methyl-5-(5-methyl-1H-pyrazol-3-ylamino)imidazo[1,2-f]pyrimidine-2-carboxamide;
- 7-(4-(dimethylamino)phenyl)-N-(5-methyl-1H-pyrazol-3-yl)imidazo[1,2-f]pyrimidin-5-amine;
- N-(5-methyl-1H-pyrazol-3-yl)-7-(pyridin-3-yl)imidazo[1,2-f]pyrimidin-5-amine;
- 1-(5-(5-methyl-1H-pyrazol-3-ylamino)imidazo[1,2-f]pyrimidin-7-yl)piperidin-4-ol;
- 7-(azepan-1-yl)-N-(5-methyl-1H-pyrazol-3-yl)imidazo[1,2-f]pyrimidin-5-amine;
- 7-(isoindolin-2-yl)-N-(5-methyl-1H-pyrazol-3-yl)imidazo[1,2-f]pyrimidin-5-amine;
- 7-(3,4-dihydroisoquinolin-2(1H)-yl)-N-(5-methyl-1H-pyrazol-3-yl)imidazo[1,2-f]pyrimidin-5-amine;
- 6-(5-(5-methyl-1H-pyrazol-3-ylamino)imidazo[1,2-f]pyrimidin-7-ylthio)-1,2-dihydroindazol-3-one;
- 6-(5-(5-methyl-1H-pyrazol-3-ylamino)imidazo[1,2-f]pyrimidin-7-ylamino)-1,2-dihydroindazol-3-one;
- N-(4-(5-(5-methyl-1H-pyrazol-3-ylamino)imidazo[1,2-f]pyrimidin-7-ylthio)phenyl)-2-morpholinoacetamide;
- 3-(dimethylamino)-N-(4-(5-(5-methyl-1H-pyrazol-3-ylamino)imidazo[1,2-f]pyrimidin-7-ylthio)phenyl)propanamide;
- N-(4-(5-(5-methyl-1H-pyrazol-3-ylamino)imidazo[1,2-f]pyrimidin-7-ylthio)phenyl)-2-(methylamino)acetamide;
- N-(2-(dimethylamino)ethyl)-4-(5-(5-methyl-1H-pyrazol-3-ylamino)imidazo[1,2-f]pyrimidin-7-ylthio)benzamide;
- 4-(5-(5-methyl-1H-pyrazol-3-ylamino)imidazo[1,2-f]pyrimidin-7-ylthio)-N-(2-morpholinoethyl)benzamide;
- N-(5-methyl-1H-pyrazol-3-yl)-7-(4-(methylamino)phenylthio)imidazo[1,2-f]pyrimidin-5-amine;
- 7-(4-(cyclopropylmethylamino)phenylthio)-N-(5-methyl-1H-pyrazol-3-yl)imidazo[1,2-f]pyrimidin-5-amine;
- 2-amino-2-methyl-N-(4-(5-(5-methyl-1H-pyrazol-3-ylamino)imidazo[1,2-f]pyrimidin-7-ylthio)phenyl)propanamide;
- N-(4-(5-(5-methyl-1H-pyrazol-3-ylamino)imidazo[1,2-f]pyrimidin-7-ylthio)phenyl)propionamide;
- 1-amino-N-(4-(5-(5-methyl-1H-pyrazol-3-ylamino)imidazo[1,2-f]pyrimidin-7-ylthio)phenyl)cyclobutanecarboxamide;
- 1-amino-N-(4-(5-(5-methyl-1H-pyrazol-3-ylamino)imidazo[1,2-f]pyrimidin-7-ylthio)phenyl)cyclopentanecarboxamide;
- N-(4-(5-(5-methyl-1H-pyrazol-3-ylamino)imidazo[1,2-f]pyrimidin-7-ylthio)phenyl)pyrrolidine-3-carboxamide;
- N-(4-(5-(5-methyl-1H-pyrazol-3-ylamino)imidazo[1,2-f]pyrimidin-7-ylthio)phenyl)-tetrahydro-2H-pyran-4-carboxamide;
- N-(4-(5-(5-methyl-1H-pyrazol-3-ylamino)imidazo[1,2-f]pyrimidin-7-ylthio)phenyl)piperidine-4-carboxamide;
- 2-amino-N-(4-(5-(5-methyl-1H-pyrazol-3-ylamino)imidazo[1,2-f]pyrimidin-7-ylthio)phenyl)cyclopentanecarboxamide;
- 3-amino-N-(4-(5-(5-methyl-1H-pyrazol-3-ylamino)imidazo[1,2-f]pyrimidin-7-ylthio)phenyl)cyclopentanecarboxamide;
- N-(4-(5-(5-methyl-1H-pyrazol-3-ylamino)imidazo[1,2-f]pyrimidin-7-ylthio)phenyl)piperidine-2-carboxamide;
- N-(4-(5-(5-methyl-1H-pyrazol-3-ylamino)imidazo[1,2-f]pyrimidin-7-ylthio)phenyl)piperidine-3-carboxamide;

N-(4-(5-(5-methyl-1H-pyrazol-3-ylamino)imidazo[1,2-f]
pyrimidin-7-ylthio)phenyl)morpholine-4-carboxamide;
N-(4-(5-(5-methyl-1H-pyrazol-3-ylamino)imidazo[1,2-f]
pyrimidin-7-ylthio)phenyl)piperazine-1-carboxamide;
1-cyclopropyl-3-(4-(5-(5-methyl-1H-pyrazol-3-ylamino)
imidazo[1,2-f]pyrimidin-7-ylthio)phenyl)urea;
1,1-diethyl-3-(4-(5-(5-methyl-1H-pyrazol-3-ylamino)
imidazo[1,2-f]pyrimidin-7-ylthio)phenyl)urea;
1-ethyl-3-(4-(5-(5-methyl-1H-pyrazol-3-ylamino)imidazo[1,2-f]pyrimidin-7-ylthio)phenyl)urea;
1-isopropyl-3-(4-(5-(5-methyl-1H-pyrazol-3-ylamino)
imidazo[1,2-f]pyrimidin-7-ylthio)phenyl)urea;
isopropyl 4-(5-(5-methyl-1H-pyrazol-3-ylamino)imidazo[1,2-f]pyrimidin-7-ylthio)phenylcarbamate;
cyclopropyl 4-(5-(5-methyl-1H-pyrazol-3-ylamino)imidazo[1,2-f]pyrimidin-7-ylthio)phenylcarbamate;
cyclobutyl 4-(5-(5-methyl-1H-pyrazol-3-ylamino)imidazo[1,2-f]pyrimidin-7-ylthio)phenylcarbamate;
cyclopentyl 4-(5-(5-methyl-1H-pyrazol-3-ylamino)imidazo[1,2-f]pyrimidin-7-ylthio)phenylcarbamate; and
pyrrolidin-3-yl 4-(5-(5-methyl-1H-pyrazol-3-ylamino)
imidazo[1,2-f]pyrimidin-7-ylthio)phenylcarbamate;
2-methyl-N-(4-(5-(5-methyl-1H-pyrazol-3-ylamino)imidazo[1,2-f]pyrimidin-7-ylthio)phenyl)propane-1-sulfonamide;
N-(4-(5-(5-methyl-1H-pyrazol-3-ylamino)imidazo[1,2-f]
pyrimidin-7-ylthio)phenyl)benzenesulfonamide;
N-(4-(5-(5-methyl-1H-pyrazol-3-ylamino)imidazo[1,2-f]
pyrimidin-7-ylthio)phenyl)thiazole-5-sulfonamide; and
1-methyl-N-(4-(5-(5-methyl-1H-pyrazol-3-ylamino)imidazo[1,2-f]pyrimidin-7-ylthio)phenyl)-1H-imidazole-5-sulfonamide; or a pharmaceutically acceptable salt of each of the above-mentioned compounds.

7. A compound of claim 1 selected from the group consisting of:

N-(4-(5-(5-Methyl-1H-pyrazol-3-ylamino)imidazo[1,2-f]
pyrimidin-7-ylthio)phenyl)cyclopropane carboxamide;
N-(4-(5-(5-Cyclopropyl-1H-pyrazol-3-ylamino)imidazo
[1,2-f]pyrimidin-7-ylthio)phenyl)cyclopropane carboxamide;
N-(4-(5-(3-Cyclopropyl-1H-pyrazol-5-ylamino)imidazo
[1,2-f]pyrimidin-7-ylthio)phenyl)acetamide;
N-(4-(5-(5-Methyl-1H-pyrazol-3-ylamino)imidazo[1,2-f]
pyrimidin-7-ylthio)phenyl)acetamide;
7-(4-Aminophenylthio)-N-(5-methyl-1H-pyrazol-3-yl)
imidazo[1,2-f]pyrimidin-5-amine;
N-(5-cyclopropyl-1H-pyrazol-3-yl)-7-phenylimidazo[1,2-f]pyrimidin-5-amine;
N-cyclopentyl-3-(5-(5-cyclopropyl-1H-pyrazol-3-ylamino)imidazo[1,2-f]pyrimidin-7-yl)benzamide;
N-(5-cyclopropyl-1H-pyrazol-3-yl)-7-(3-(piperazin-1-ylmethyl)phenyl)imidazo[1,2-f]pyrimidin-5-amine;
4-((3-(5-(5-Cyclopropyl-1H-pyrazol-3-ylamino)imidazo
[1,2-f]pyrimidin-7-yl)phenyl)methyl)piperazin-2-one;
4-((3-(5-(5-Methyl-1H-pyrazol-3-ylamino)imidazo[1,2-f]
pyrimidin-7-yl)phenyl)methyl)piperazin-2-one;
(5-Cyclopropyl-1H-pyrazol-3-yl)-[7-(2,3-dihydro-benzofuran-5-yl)-imidazo[1,2-c]pyrimidin-5-yl]-amine;
N-{3-[5-(5-Cyclopropyl-1H-pyrazol-3-ylamino)-imidazo
[1,2-c]pyrimidin-7-yl]-benzyl}-acetamide;
3-{3-[5-(5-Cyclopropyl-1H-pyrazol-3-ylamino)-imidazo
[1,2-c]pyrimidin-7-yl]-benzyl}-imidazolidine-2,4-dione;
(5-Cyclopropyl-1H-pyrazol-3-yl)-{7-[3-(3-methyl-3H-imidazol-4-yl)-phenyl]-imidazo[1,2-c]pyrimidin-5-yl}-amine;
N-{3-[5-(5-Cyclopropyl-1H-pyrazol-3-ylamino)-imidazo
[1,2-c]pyrimidin-7-yl]-benzyl}-methanesulfonamide;
Cyclopropanecarboxylic acid 3-[5-(5-cyclopropyl-1H-pyrazol-3-ylamino)-imidazo[1,2-c]pyrimidin-7-yl]-benzylamide;
1-{3-[5-(5-Cyclopropyl-1H-pyrazol-3-ylamino)-imidazo
[1,2-c]pyrimidin-7-yl]-benzyl}-imidazolidin-2-one;
Cyclopropanecarboxylic acid 3-[5-(5-methyl-1H-pyrazol-3-ylamino)-imidazo[1,2-c]pyrimidin-7-yl]-benzylamide;
N-(5-cyclopropyl-1H-pyrazol-3-yl)-7-(2-methoxyphenyl)
imidazo[1,2-f]pyrimidin-5-amine;
3-(5-(5-cyclopropyl-1H-pyrazol-3-ylamino)imidazo[1,2-f]pyrimidin-7-yl)benzonitrile;
N-(5-cyclopropyl-1H-pyrazol-3-yl)-7-(3,5-dimethylphenyl)imidazo[1,2-f]pyrimidin-5-amine;
N-(5-cyclopropyl-1H-pyrazol-3-yl)-7-p-tolylimidazo[1,2-f]pyrimidin-5-amine;
7-(5-chloro-2-methoxyphenyl)-N-(5-cyclopropyl-1H-pyrazol-3-yl)imidazo[1,2f]pyrimidin-5-amine;
N-(5-cyclopropyl-1H-pyrazol-3-yl)-7-(2-methoxy-5-methylphenyl)imidazo[1,2-f]pyrimidin-5-amine;
N-(5-cyclopropyl-1H-pyrazol-3-yl)-7-(3,5-dimethoxyphenyl)imidazo[1,2-f]pyrimidin-5-amine;
N-(5-cyclopropyl-1H-pyrazol-3-yl)-7-(4-methoxyphenyl)
imidazo[1,2-f]pyrimidin-5-amine;
N-(5-cyclopropyl-1H-pyrazol-3-yl)-7-(pyrimidin-5-yl)
imidazo[1,2-f]pyrimidin-5-amine;
N-(5-cyclopropyl-1H-pyrazol-3-yl)-7-(pyridin-3-yl)imidazo[1,2-f]pyrimidin-5-amine;
N-(5-cyclopropyl-1H-pyrazol-3-yl)-7-(3,4-dimethoxyphenyl)imidazo[1,2-f]pyrimidin-5-amine;
N-(5-cyclopropyl-1H-pyrazol-3-yl)-7-(2,3-dimethylphenyl)imidazo[1,2-f]pyrimidin-5-amine;
7-(benzo[d][1,3]dioxol-5yl)-N-(5-cyclopropyl-1H-pyrazol-3-yl)imidazo[1,2-f]pyrimidin-5-amine;
N-(5-cyclopropyl-1H-pyrazol-3-yl)-7-(2,6-dimethylphenyl)imidazo[1,2-f]pyrimidin-5-amine;
N-(5-cyclopropyl-1H-pyrazol-3-yl)-7-(2,6-dimethoxyphenyl)imidazo[1,2-f]pyrimidin-5-amine;
N-(5-cyclopropyl-1H-pyrazol-3-yl)-7-(2-methoxypyridin-4-yl)imidazo[1,2-f]pyrimidin-5-amine;
N-(5-cyclopropyl-1H-pyrazol-3-yl)-7-(4-phenoxyphenyl)
imidazo[1,2-f]pyrimidin-5-amine;
N-(5-cyclopropyl-1H-pyrazol-3-yl)-7-(3-biphenyl)imidazo[1,2-f]pyrimidin-5-amine;
N-(5-cyclopropyl-1H-pyrazol-3-yl)-7-(4-biphenyl)imidazo[1,2-f]pyrimidin-5-amine; N-(5-cyclopropyl-1H-pyrazol-3-yl)-7-(2-biphenyl)imidazo[1,2-f]pyrimidin-5-amine;
N-(5-cyclopropyl-1H-pyrazol-3-yl)-7-(2-fluorophenyl)
imidazo[1,2-f]pyrimidin-5-amine; N-(5-cyclopropyl-1H-pyrazol-3-yl)-7-(3,5-difluorophenyl)imidazo[1,2-f]
pyrimidin-5-amine;
3-(5-(5-cyclopropyl-1H-pyrazol-3-ylamino)imidazo[1,2-f]pyrimidin-7-yl)-N-methylbenzamide;
3-(5-(5-cyclopropyl-1H-pyrazol-3-ylamino)imidazo[1,2-f]pyrimidin-7-yl)-N-ethylbenzamide;
N-cyclopropyl-3-(5-(5-cyclopropyl-1H-pyrazol-3-ylamino)imidazo[1,2-f]pyrimidin-7-yl)benzamide;
N-(2-cyanoethyl)-3-(5-(5-cyclopropyl-1H-pyrazol-3-ylamino)imidazo[1,2-f]pyrimidin-7-yl)benzamide;
(3-(5-(5-cyclopropyl-1H-pyrazol-3-ylamino)imidazo[1,2-f]pyrimidin-7-yl)phenyl)(pyrrolidin-1-yl)methanone;
Methyl 3-(5-(5-cyclopropyl-1H-pyrazol-3-ylamino)imidazo[1,2-f]pyrimidin-7-yl)benzoate;

(3-(5-(5-cyclopropyl-1H-pyrazol-3-ylamino)imidazo[1,2-f]pyrimidin-7-yl)phenyl)methanol;
(E)-N-(5-cyclopropyl-1H-pyrazol-3-yl)-7-styrylimidazo[1,2-f]pyrimidin-5-amine;
N-(5-methyl-1H-pyrazol-3-yl)-7-phenylimidazo[1,2-f]pyrimidin-5-amine;
N-(4-(5-(5-cyclopropyl-1H-pyrazol-3-ylamino)imidazo[1,2-f]pyrimidin-7-yl)phenyl)acetamide; 7-(2-chlorophenyl)-N-(5-cyclopropyl-1H-pyrazol-3-yl)imidazo[1,2-f]pyrimidin-5-amine;
N-(5-cyclopropyl-1H-pyrazol-3-yl)-7-o-tolylimidazo[1,2-f]pyrimidin-5-amine;
N-(5-cyclopropyl-1H-pyrazol-3-yl)-7-m-tolylimidazo[1,2-f]pyrimidin-5-amine;
N-(5-cyclopropyl-1H-pyrazol-3-yl)-7-(4-(dimethylamino)phenyl)imidazo[1,2-f]pyrimidin-5-amine;
N-(5-cyclopropyl-1H-pyrazol-3-yl)-7-(1H-indol-5-yl)imidazo[1,2-f]pyrimidin-5-amine;
7-(3-chlorophenyl)-N-(5-cyclopropyl-1H-pyrazol-3-yl)imidazo[1,2-f]pyrimidin-5-amine;
7-(3-(1H-pyrazol-1-yl)phenyl)-N-(5-cyclopropyl-1H-pyrazol-3-yl)imidazo[1,2-f]pyrimidin-5-amine;
(3-(5-(5-cyclopropyl-1H-pyrazol-3-ylamino)imidazo[1,2-f]pyrimidin-7-yl)phenyl)(morpholino)methanone;
(4-(5-(5-cyclopropyl-1H-pyrazol-3-ylamino)imidazo[1,2-f]pyrimidin-7-yl)phenyl)(morpholino)methanone;
N-(5-cyclopropyl-1H-pyrazol-3-yl)-7-(4-morpholinophenyl)imidazo[1,2-f]pyrimidin-5-amine;
N-(5-cyclopropyl-1H-pyrazol-3-yl)-7-(3-morpholinophenyl)imidazo[1,2-f]pyrimidin-5-amine;
N-(5-cyclopropyl-1H-pyrazol-3-yl)-7-(4-(piperidin-1-yl)phenyl)imidazo[1,2-f]pyrimidin-5-amine;
N-(5-cyclopropyl-1H-pyrazol-3-yl)-7-(3((4-methylpiperazin-1-yl)methyl)phenyl)imidazo[1,2-f]pyrimidin-5-amine;
N-{3-[5-(5-Cyclopropyl-2H-pyrazol-3-ylamino)-imidazo[1,2-c]pyrimidin-7-yl]-phenyl}-methanesulfonamide;
N-{3-[5-(5-Cyclopropyl-2H-pyrazol-3-ylamino)-imidazo[1,2-c]pyrimidin-7-yl]-phenyl}-acetamide;
N-{3-[5-(5-Methyl-2H-pyrazol-3-ylamino)-imidazo[1,2-c]pyrimidin-7-yl]-phenyl}-methanesulfonamide;
[7-(3-Ethanesulfonyl-phenyl)-imidazo[1,2-c]pyrimidin-5-yl]-(5-methyl-2H-pyrazol-3-yl)-amine;
N-{3-[5-(5-Cyclopropyl-2H-pyrazol-3-ylamino)-2-hydroxymethyl-imidazo[1,2-c]pyrimidin-7-yl]-phenyl}-methanesulfonamide;
(5-Cyclopropyl-2H-pyrazol-3-yl)-[7-(3-ethanesulfonyl-phenyl)-imidazo[1,2-c]pyrimidin-5-yl]-amine;
[7-(4-Methyl-piperazin-1-yl)-imidazo[1,2-c]pyrimidin-5-yl]-(5-methyl-1H-pyrazol-3-yl)-amine;
(5-Methyl-1H-pyrazol-3-yl)-(7-piperidin-1-yl-imidazo[1,2-c]pyrimidin-5-yl)-amine;
(5-Cyclopropyl-1H-pyrazol-3-yl)-[7-(2,3-dihydro-indol-1-yl)-imidazo[1,2-c]pyrimidin-5-yl]-amine;
(5-Cyclopropyl-1H-pyrazol-3-yl)-[7-(3,4-dihydro-1H-isoquinolin-2-yl)-imidazo[1,2-c]pyrimidin-5-yl]-amine;
Ethyl 5-(5-cyclopropyl-1H-pyrazol-3-ylamino)-7-(4-((2,5-dioxoimidazolidin-1-yl)methyl)phenyl)imidazo[1,2-f]pyrimidine-2-carboxylate;
Ethyl 5-(5-cyclopropyl-1H-pyrazol-3-ylamino)-7-(4-(pyrrolidine-1-carbonyl)phenyl)imidazo[1,2-f]pyrimidine-2-carboxylate;
Ethyl 5-(5-cyclopropyl-1H-pyrazol-3-ylamino)-7-(4-(cyclopropylcarbamoyl)phenyl)imidazo[1,2-f]pyrimidine-2-carboxylate;
Cyclopentanecarboxylic acid 3-[5-(5-cyclopropyl-1H-pyrazol-3-ylamino)-imidazo[1,2-c]pyrimidin-7-yl]-benzylamide;
N-(5-cyclopropyl-1H-pyrazol-3-yl)-7-phenylimidazo[1,2-f]pyrimidin-5-amine;
N-cyclopropyl-3-(5-(5-methyl-1H-pyrazol-3-ylamino)imidazo[1,2-f]pyrimidin-7-yl)benzamide;
(3-(5-(5-methyl-1H-pyrazol-3-ylamino)imidazo[1,2-f]pyrimidin-7-yl)phenyl)(4-methylpiperazin-1-yl)methanone;
(4-aminopiperidin-1-yl)(3-(5-(5-methyl-1H-pyrazol-3-ylamino)imidazo[1,2-f]pyrimidin-7-yl)phenyl)methanone;
3-(5-(5-Methyl-1H-pyrazol-3-ylamino)imidazo[1,2-f]pyrimidin-7-yl)-N-(piperidin-4-yl)benzamide;
(3-(5-(5-Cyclopropyl-1H-pyrazol-3-ylamino)imidazo[1,2-f]pyrimidin-7-yl)phenyl)(piperazin-1-yl)methanone;
(S)-Pyrrolidine-2-carboxylic acid 3-[5-(5-methyl-1H-pyrazol-3-ylamino)-imidazo[1,2-c]pyrimidin-7-yl]-benzylamide;
N-{3-[5-(5-Cyclopropyl-1H-pyrazol-3-ylamino)-2-(4-methyl-piperazin-1-ylmethyl)-imidazo[1,2-c]pyrimidin-7-yl]-phenyl}-methanesulfonamide;
[7-(3-Methanesulfonyl-phenyl)-imidazo[1,2-c]pyrimidin-5-yl]-(5-methyl-1H-pyrazol-3-yl)-amine;
[5-(5-Cyclopropyl-1H-pyrazol-3-ylamino)-7-(3-ethanesulfonyl-phenyl)-imidazo[1,2-c]pyrimidin-2-yl]-methanol;
(5-Cyclopropyl-1H-pyrazol-3-yl)-[7-(3-ethanesulfonyl-phenyl)-2-(4-methyl-piperazin-1-ylmethyl)-imidazo[1,2-c]pyrimidin-5-yl]-amine;
[7-(3-Ethanesulfonyl-phenyl)-5-(5-methyl-1H-pyrazol-3-ylamino)-imidazo[1,2-c]pyrimidin-2-yl]-methanol;
[7-(3-Ethanesulfonyl-phenyl)-2-(4-methyl-piperazin-1-ylmethyl)-imidazo[1,2-c]pyrimidin-5-yl]-(5-methyl-1H-pyrazol-3-yl)-amine;
$N^5$-(5-methyl-1H-pyrazol-3-yl)-$N^7$-(2-(piperidin-1-yl)ethyl)imidazo[1,2-f]pyrimidine-5,7-diamine;
$N^7$-(2,5-difluorobenzyl)-$N^5$-(5-methyl-1H-pyrazol-3-yl)imidazo[1,2-f]pyrimidine-5,7-diamine;
$N^5$-(5-methyl-1H-pyrazol-3-yl)-$N^7$-(thiophen-2-ylmethyl)imidazo[1,2-f]pyrimidine-5,7-diamine;
$N^7$-(2-chlorophenethyl)-$N^5$-(5-methyl-1H-pyrazol-3-yl)imidazo[1,2-f]pyrimidine-5,7-diamine;
$N^7$-(3-chlorophenethyl)-$N^5$-(5-methyl-1H-pyrazol-3-yl)imidazo[1,2-f]pyrimidine-5,7-diamine;
$N^7$-(4-chlorophenethyl)-$N^5$-(5-methyl-1H-pyrazol-3-yl)imidazo[1,2-f]pyrimidine-5,7-diamine;
$N^5$-(5-methyl-1H-pyrazol-3-yl)-$N^7$-phenethylimidazo[1,2-f]pyrimidine-5,7-diamine;
$N^5$-(5-methyl-1H-pyrazol-3-yl)-$N^7$-(3-phenylpropyl)imidazo[1,2-f]pyrimidine-5,7-diamine;
$N^5$-(5-methyl-1H-pyrazol-3-yl)-$N^7$-(2-phenoxyethyl)imidazo[1,2-f]pyrimidine-5,7-diamine;
(R)-2-(5-(5-methyl-1H-pyrazol-3-ylamino)imidazo[1,2-f]pyrimidin-7-ylamino)-1-phenylethanol;
(S)-2-(5-(5-methyl-1H-pyrazol-3-ylamino)imidazo[1,2-f]pyrimidin-7-ylamino)-1-phenylethanol;
2-(methyl(5-(5-methyl-1H-pyrazol-3-ylamino)imidazo[1,2-f]pyrimidin-7-yl)amino)-1-phenylethanol
(R)-2-(5-(5-methyl-1H-pyrazol-3-ylamino)imidazo[1,2-f]pyrimidin-7-ylamino)-4-phenylbutan-1-ol;
$N^5$-(5-methyl-1H-pyrazol-3-yl)-$N^7$-(pyridin-2-ylmethyl)imidazo[1,2-f]pyrimidine-5,7-diamine;
$N^7$-(3-fluorobenzyl)-$N^7$-methyl-$N^5$-(5-methyl-1H-pyrazol-3-yl)imidazo[1,2-f]pyrimidine-5,7-diamine;

N[7]-(3-chlorobenzyl)-N[7]-methyl-N[5]-(5-methyl-1H-pyrazol-3-yl)imidazo[1,2-f]pyrimidine-5,7-diamine;
N[7]-(3,4-dimethoxybenzyl)-N[5]-(5-methyl-1H-pyrazol-3-yl)imidazo[1,2-f]pyrimidine-5,7-diamine;
N[7]-(2-Methoxy-benzyl)-N[5]-(5-methyl-1H-pyrazol-3-yl)-imidazo[1,2-c]pyrimidine-5,7-diamine;
N[7]-(4-Methoxy-benzyl)-N[5]-(5-methyl-1H-pyrazol-3-yl)-imidazo[1,2-c]pyrimidine-5,7-diamine;
N-(4-(5-(5-methyl-1H-pyrazol-3-ylamino)imidazo[1,2-f]pyrimidin-7-ylthio)phenyl)thiophene-2-sulfonamide;
N-(4-(5-(5-methyl-1H-pyrazol-3-ylamino)imidazo[1,2-f]pyrimidin-7-ylthio)phenyl)cyclopropanesulfonamide;
N-(4-(5-(5-methyl-1H-pyrazol-3-ylamino)imidazo[1,2-f]pyrimidin-7-ylthio)phenyl)propane-2-sulfonamide;
1-amino-N-(4-(5-(5-methyl-1H-pyrazol-3-ylamino)imidazo[1,2-f]pyrimidin-7-ylthio)phenyl)cyclopropanecarboxamide;
(R)-2-amino-3-methyl-N-(4-(5-(5-methyl-1H-pyrazol-3-ylamino)imidazo[1,2-f]pyrimidin-7-ylthio)phenyl)butanamide;
N-(4-(5-(5-cyclopropyl-1H-pyrazol-3-ylamino)imidazo[1,2-f]pyrimidin-7-ylthio)phenyl)-2-methoxyacetamide;
N-(4-(5-(5-methyl-1H-pyrazol-3-ylamino)imidazo[1,2-f]pyrimidin-7-ylthio)phenyl)picolinamide;
N-(4-(5-(5-cyclopropyl-1H-pyrazol-3-ylamino)imidazo[1,2-f]pyrimidin-7-ylthio)phenyl)morpholine-4-carboxamide;
2-methoxyethyl 4-(5-(5-methyl-1H-pyrazol-3-ylamino)imidazo[1,2-f]pyrimidin-7-ylthio)phenylcarbamate;
Ethyl 4-(5-(5-methyl-1H-pyrazol-3-ylamino)imidazo[1,2-f]pyrimidin-7-ylthio)phenylcarbamate;
Isobutyl 4-(5-(5-methyl-1H-pyrazol-3-ylamino)imidazo[1,2-f]pyrimidin-7-ylthio)phenylcarbamate;
Ethyl 4-(5-(5-cyclopropyl-1H-pyrazol-3-ylamino)imidazo[1,2-f]pyrimidin-7-ylthio)phenylcarbamate;
{4-[5-(5-Cyclopropyl-1H-pyrazol-3-ylamino)-imidazo[1,2-c]pyrimidin-7-ylsulfanyl]-phenyl}-carbamic acid but-2-ynyl ester;
{4-[5-(5-Cyclopropyl-1H-pyrazol-3-ylamino)-imidazo[1,2-c]pyrimidin-7-ylsulfanyl]-phenyl}-carbamic acid allyl ester;
Propyl 4-(5-(5-cyclopropyl-1H-pyrazol-3-ylamino)imidazo[1,2-f]pyrimidin-7-ylthio)phenylcarbamate;
N-(4-(5-(5-methyl-1H-pyrazol-3-ylamino)imidazo[1,2-f]pyrimidin-7-ylthio)phenyl)pyrrolidine-2-carboxamide;
N-(4-(5-(5-methyl-1H-pyrazol-3-ylamino)imidazo[1,2-f]pyrimidin-7-ylthio)phenyl)butyramide;
N-(4-(5-(5-methyl-1H-pyrazol-3-ylamino)imidazo[1,2-f]pyrimidin-7-ylthio)phenyl)cyclobutanecarboxamide;
N-(4-(5-(5-methyl-1H-pyrazol-3-ylamino)imidazo[1,2-f]pyrimidin-7-ylthio)phenyl)isobutyramide;
2-methoxy-N-(4-(5-(5-methyl-1H-pyrazol-3-ylamino)imidazo[1,2-f]pyrimidin-7-ylthio)phenyl)acetamide;
N-(4-(5-(5-methyl-1H-pyrazol-3-ylamino)imidazo[1,2-f]pyrimidin-7-ylthio)phenyl)-2-propoxyacetamide;
2-ethoxy-N-(4-(5-(5-methyl-1H-pyrazol-3-ylamino)imidazo[1,2-f]pyrimidin-7-ylthio)phenyl)acetamide;
2-(allyloxy)-N-(4-(5-(5-methyl-1H-pyrazol-3-ylamino)imidazo[1,2-f]pyrimidin-7-ylthio)phenyl)acetamide;
2-(dimethylamino)-N-(4-(5-(5-methyl-1H-pyrazol-3-ylamino)imidazo[1,2-f]pyrimidin-7-ylthio)phenyl)acetamide;
2-(cyclopropylamino)-N-(4-(5-(5-methyl-1H-pyrazol-3-ylamino)imidazo[1,2-f]pyrimidin-7-ylthio)phenyl)acetamide;
2-(1H-imidazol-1-yl)-N-(4-(5-(5-methyl-1H-pyrazol-3-ylamino)imidazo[1,2-f]pyrimidin-7-ylthio)phenyl)acetamide;
N-(4-(5-(5-cyclopropyl-1H-pyrazol-3-ylamino)imidazo[1,2-f]pyrimidin-7-ylthio)phenyl)-2-(ethyl(methyl)amino)acetamide;
N-(4-(5-(5-cyclopropyl-1H-pyrazol-3-ylamino)imidazo[1,2-f]pyrimidin-7-ylthio)phenyl)-2-(dimethylamino)acetamide;
N-(4-(5-(5-cyclopropyl-1H-pyrazol-3-ylamino)imidazo[1,2-f]pyrimidin-7-ylthio)phenyl)-2-(cyclopropylamino)acetamide;
N-(4-(5-(5-cyclopropyl-1H-pyrazol-3-ylamino)imidazo[1,2-f]pyrimidin-7-ylthio)phenyl)-2-ethoxyacetamide;
2-(ethyl(methyl)amino)-N-(4-(5-(5-methyl-1H-pyrazol-3-ylamino)imidazo[1,2-f]pyrimidin-7-ylthio)phenyl)acetamide;
N-(4-(2-(hydroxymethyl)-5-(5-methyl-1H-pyrazol-3-ylamino)imidazo[1,2-f]pyrimidin-7-ylthio)phenyl)-2-methoxyacetamide;
N-(4-(5-(5-cyclopropyl-1H-pyrazol-3-ylamino)imidazo[1,2-f]pyrimidin-7-ylthio)phenyl)nicotinamide; N-(4-(5-(5-cyclopropyl-1H-pyrazol-3-ylamino)imidazo[1,2-f]pyrimidin-7-ylthio)phenyl)-2-methylcyclopropanecarboxamide
N-(4-(5-(5-cyclopropyl-1H-pyrazol-3-ylamino)imidazo[1,2-f]pyrimidin-7-ylthio)phenyl)pyrrolidine-1-carboxamide;
N-(4-(5-(5-cyclopropyl-1H-pyrazol-3-ylamino)imidazo[1,2-f]pyrimidin-7-ylthio)phenyl)-3-methylbutanamide;
N-(4-(5-(5-cyclopropyl-1H-pyrazol-3-ylamino)-2-(methoxymethyl)imidazo[1,2-f]pyrimidin-7-ylthio)phenyl)acetamide;
N-(4-(5-(5-cyclopropyl-1H-pyrazol-3-ylamino)imidazo[1,2-f]pyrimidin-7-ylthio)phenyl)isonicotinamide;
6-chloro-N-(4-(5-(5-cyclopropyl-1H-pyrazol-3-ylamino)imidazo[1,2-f]pyrimidin-7-ylthio)phenyl)nicotinamide;
Ethyl 7-(4-acetamidophenylthio)-5-(5-methyl-1H-pyrazol-3-ylamino)imidazo[1,2-f]pyrimidine-2-carboxylate;
N-(4-(2-(Hydroxymethyl)-5-(5-methyl-1H-pyrazol-3-ylamino)imidazo[1,2-f]pyrimidin-7-ylthio)phenyl)acetamide;
Ethyl 7-(4-(Cyclopropanecarboxamido)phenylthio)-5-(5-methyl-1H-pyrazol-3-ylamino)imidazo[1,2-f]pyrimidine-2-carboxylate;
N-(4-(2-(Hydroxymethyl)-5-(5-methyl-1H-pyrazol-3-ylamino)imidazo[1,2-f]pyrimidin-7-ylthio)phenyl)cyclopropanecarboxamide;
N-{4-[5-(5-Cyclopropyl-1H-pyrazol-3-ylamino)-2-dimethylaminomethyl-imidazo[1,2-c]pyrimidin-7-ylsulfanyl]-phenyl}acetamide;
N-(4-(5-(5-Cyclopropyl-1H-pyrazol-3-ylamino)-2-((4-methylpiperazin-1-yl)methyl)imidazo[1,2-f]pyrimidin-7-ylthio)phenyl)acetamide;
N-(5-methyl-1H-pyrazol-3-yl)-7-(o-tolylthio)imidazo[1,2-f]pyrimidin-5-amine;
((5-fluoro-2-(5-(5-methyl-1H-pyrazol-3-ylamino)imidazo[1,2-f]pyrimidin-7-ylthio)phenyl)methanol;
7-(3-aminophenylthio)-N-(5-methyl-1H-pyrazol-3-yl)imidazo[1,2-f]pyrimidin-5-amine;
Methyl 3-(5-(5-methyl-1H-pyrazol-3-ylamino)imidazo[1,2-f]pyrimidin-7-ylthio)benzoate;
3-(5-(5-methyl-1H-pyrazol-3-ylamino)imidazo[1,2-f]pyrimidin-7-ylthio)benzoic acid;

Methyl 4-(5-(5-methyl-1H-pyrazol-3-ylamino)imidazo[1,2-f]pyrimidin-7-ylthio)benzoate
4-(5-(5-Methyl-1H-pyrazol-3-ylamino)imidazo[1,2-f]pyrimidin-7-ylthio)benzoic acid;
(E)-methyl 3-(4-(5-(5-methyl-1H-pyrazol-3-ylamino)imidazo[1,2-f]pyrimidin-7-ylthio)phenyl)acrylate;
3-(5-(5-methyl-1H-pyrazol-3-ylamino)imidazo[1,2-f]pyrimidin-7-ylthio)benzamide;
7-(2-Amino-4-chlorophenylthio)-N-(5-methyl-1H-pyrazol-3-yl)imidazo[1,2-f]pyrimidin-5-amine;
2-(3-(5-(5-methyl-1H-pyrazol-3-ylamino)imidazo[1,2-f]pyrimidin-7-ylthio)phenyl)acetic acid;
N-cyclopropyl-2-(3-(5-(5-methyl-1H-pyrazol-3-ylamino)imidazo[1,2-f]pyrimidin-7-ylthio)phenyl)acetamide;
N-methyl-2-(3-(5-(5-methyl-1H-pyrazol-3-ylamino)imidazo[1,2-f]pyrimidin-7-ylthio)phenyl)acetamide;
N-ethyl-2-(3-(5-(5-methyl-1H-pyrazol-3-ylamino)imidazo[1,2-f]pyrimidin-7-ylthio)phenyl)acetamide;
4-(5-(5-cyclopropyl-1H-pyrazol-3-ylamino)imidazo[1,2-f]pyrimidin-7-ylthio)-N-ethylbenzamide;
(4-(5-(5-cyclopropyl-1H-pyrazol-3-ylamino)imidazo[1,2-f]pyrimidin-7-ylthio)phenyl)(piperazin-1-yl)methanone;
N-cyclopropyl-4-(5-(5-cyclopropyl-1H-pyrazol-3-ylamino)imidazo[1,2-f]pyrimidin-7-ylthio)benzamide;
Azetidin-1-yl(4-(5-(5-cyclopropyl-1H-pyrazol-3-ylamino)imidazo[1,2-f]pyrimidin-7-ylthio)phenyl)methanone;
4-(5-(5-cyclopropyl-1H-pyrazol-3-ylamino)imidazo[1,2-f]pyrimidin-7-ylthio)-N-(pyrrolidin-3-yl)benzamide;
4-(5-(5-cyclopropyl-1H-pyrazol-3-ylamino)imidazo[1,2-f]pyrimidin-7-ylthio)-N-(piperidin-4-yl)benzamide;
4-(5-(5-cyclopropyl-1H-pyrazol-3-ylamino)imidazo[1,2-f]pyrimidin-7-ylthio)-N-(piperidin-3-yl)benzamide;
4-(5-(5-cyclopropyl-1H-pyrazol-3-ylamino)imidazo[1,2-f]pyrimidin-7-ylthio)-N-methoxybenzamide;
4-(5-(5-cyclopropyl-1H-pyrazol-3-ylamino)imidazo[1,2-f]pyrimidin-7-ylthio)-N',N'-dimethylbenzohydrazide;
4-(5-(5-cyclopropyl-1H-pyrazol-3-ylamino)imidazo[1,2-f]pyrimidin-7-ylthio)-N-(2-(dimethylamino)ethyl)benzamide;
4-(5-(5-cyclopropyl-1H-pyrazol-3-ylamino)imidazo[1,2-f]pyrimidin-7-ylthio)-N-(2-hydroxyethyl)benzamide;
(4-(5-(5-cyclopropyl-1H-pyrazol-3-ylamino)imidazo[1,2-f]pyrimidin-7-ylthio)phenyl)(morpholino)methanone;
N-cyclopropyl-4-(5-(5-methyl-1H-pyrazol-3-ylamino)imidazo[1,2-f]pyrimidin-7-ylthio)benzamide;
N-ethyl-4-(5-(5-methyl-1H-pyrazol-3-ylamino)imidazo[1,2-f]pyrimidin-7-ylthio)benzamide;
N-(5-cyclopropyl-1H-pyrazol-3-yl)-7-(4-(5-ethyl-1,3,4-oxadiazol-2-yl)phenylthio)imidazo[1,2-f]pyrimidin-5-amine;
7-(4-(5-ethyl-1,3,4-oxadiazol-2-yl)phenylthio)-N-(5-methyl-1H-pyrazol-3-yl)imidazo[1,2-f]pyrimidin-5-amine;
7-(4-(1,3,4-Oxadiazol-2-yl)phenylthio)-N-(5-cyclopropyl-1H-pyrazol-3-yl)imidazo[1,2-f]pyrimidin-5-amine;
7-(4-(1,3,4-oxadiazol-2-yl)phenylthio)-N-(5-methyl-1H-pyrazol-3-yl)imidazo[1,2-f]pyrimidin-5-amine;
7-(4-(5-Methyl-1,3,4-oxadiazol-2-yl)phenylthio)-N-(5-methyl-1H-pyrazol-3-yl)imidazo[1,2-f]pyrimidin-5-amine;
N-(5-Cyclopropyl-1H-pyrazol-3-yl)-7-(4-(5-methyl-1,3,4-oxadiazol-2-yl)phenylthio)imidazo[1,2-f]pyrimidin-5-amine;
N-(4-(5-(5-Methyl-1H-pyrazol-3-ylamino)imidazo[1,2-f]pyrimidin-7-yloxy)phenyl)acetamide;
2-methyl-N-(5-methyl-1H-pyrazol-3-yl)-7-phenylimidazo[1,2-f]pyrimidin-5-amine;
N-cyclopropyl-2-(3-(2-methyl-5-(5-methyl-1H-pyrazol-3-ylamino)imidazo[1,2-f]pyrimidin-7-yl)phenyl)acetamide;
7-(3-(ethylsulfonyl)phenyl)-2-methyl-N-(5-methyl-1H-pyrazol-3-yl)imidazo[1,2-f]pyrimidin-5-amine;
2-methyl-N-(5-methyl-1H-pyrazol-3-yl)-7-(3-(methylsulfonyl)phenyl)imidazo[1,2-f]pyrimidin-5-amine;
2-methoxy-N-methyl-5-(2-methyl-5-(5-methyl-1H-pyrazol-3-ylamino)imidazo[1,2-f]pyrimidin-7-yl)benzenesulfonamide;
N-ethyl-N-methyl-3-(2-methyl-5-(5-methyl-1H-pyrazol-3-ylamino)imidazo[1,2-f]pyrimidin-7-yl)benzenesulfonamide;
N-(3-(2-Methyl-5-(5-methyl-1H-pyrazol-3-ylamino)imidazo[1,2-f]pyrimidin-7-yl)phenyl)cyclopropanesulfonamide;
N-Ethyl-2-methoxy-5-(2-methyl-5-(5-methyl-1H-pyrazol-3-ylamino)imidazo[1,2-f]pyrimidin-7-yl)benzenesulfonamide;
N-(3-(2-Methyl-5-(5-methyl-1H-pyrazol-3-ylamino)imidazo[1,2-f]pyrimidin-7-yl)phenyl)ethanesulfonamide;
N-(2-Methoxy-5-(2-methyl-5-(5-methyl-1H-pyrazol-3-ylamino)imidazo[1,2-f]pyrimidin-7-yl)phenyl)cyclopropanesulfonamide;
N-(3-(2-Methyl-5-(5-methyl-1H-pyrazol-3-ylamino)imidazo[1,2-f]pyrimidin-7-yl)phenyl)methanesulfonamide;
N-(4-(2-Methyl-5-(5-methyl-1H-pyrazol-3-ylamino)imidazo[1,2-f]pyrimidin-7-yl)phenyl)methanesulfonamide;
Cyclopropanecarboxylic acid 4-fluoro-3-[5-(5-methyl-1H-pyrazol-3-ylamino)-imidazo[1,2-c]pyrimidin-7-yl]-benzylamide;
Cyclopropanecarboxylic acid 4-fluoro-3-[2-methyl-5-(5-methyl-1H-pyrazol-3-ylamino)-imidazo[1,2-c]pyrimidin-7-yl]-benzylamide;
5-[2-Methyl-5-(5-methyl-1H-pyrazol-3-ylamino)-imidazo[1,2-c]pyrimidin-7-yl]-1,3-dihydro-benzoimidazol-2-one;
Cyclopropanesulfonic acid methyl-{3-[2-methyl-5-(5-methyl-1H-pyrazol-3-ylamino)-imidazo[1,2-c]pyrimidin-7-yl]-phenyl}-amide;
(5-Methyl-1H-pyrazol-3-yl)-(2-methyl-7-pyridin-2-yl-imidazo[1,2-c]pyrimidin-5-yl)-amine;
[7-(1-Ethanesulfonyl-1H-indol-6-yl)-2-methyl-imidazo[1,2-c]pyrimidin-5-yl]-(5-methyl-1H-pyrazol-3-yl)-amine;
Ethanesulfonic acid methyl-{3-[2-methyl-5-(5-methyl-1H-pyrazol-3-ylamino)-imidazo[1,2-c]pyrimidin-7-yl]-benzyl}-amide;
Ethanesulfonic acid {5-[2-methyl-5-(5-methyl-1H-pyrazol-3-ylamino)-imidazo[1,2-c]pyrimidin-7-yl]-1H-indol-7-yl}-amide;
N-ethyl-2-methoxy-N-methyl-5-(2-methyl-5-(5-methyl-1H-pyrazol-3-ylamino)imidazo[1,2-f]pyrimidin-7-yl)benzenesulfonamide;
N-(cyclopropylmethyl)-2-methoxy-5-(2-methyl-5-(5-methyl-1H-pyrazol-3-ylamino)imidazo[1,2-f]pyrimidin-7-yl)benzenesulfonamide;
N-cyclopropyl-3-(2-methyl-5-(5-methyl-1H-pyrazol-3-ylamino)imidazo[1,2-f]pyrimidin-7-yl)benzenesulfonamide;

N-ethyl-3-(2-methyl-5-(5-methyl-1H-pyrazol-3-ylamino)imidazo[1,2-f]pyrimidin-7-yl)benzenesulfonamide;

N-{3-[5-(5-Cyclopropyl-1H-pyrazol-3-ylamino)-2-methyl-imidazo[1,2-c]pyrimidin-7-ylsulfanyl]-phenyl}-acetamide;

N-(5-methyl-1H-pyrazol-3-yl)-7-phenyl-2-(trifluoromethyl)imidazo[1,2-f]pyrimidin-5-amine;

3-(2-(Chloromethyl)-5-(5-methyl-1H-pyrazol-3-ylamino)imidazo[1,2-f]pyrimidin-7-yl0-N-cyclopropylbenzamide;

2-Ethyl-7-(3-(ethylsulfonyl)phenyl)-N-(5-methyl-1H-pyrazol-3-yl)imidazo[1,2-f]pyrimidin-5-amine;

7-(3-(ethylsulfonyl)phenyl)-2-isopropyl-N-(5-methyl-1H-pyrazol-3-yl)imidazo[1,2-f]pyrimidin-5-amine;

N-(5-ethyl-1H-pyrazol-3-yl)-7-(3-(ethylsulfonyl)phenyl)-2-methylimidazo[1,2-f]pyrimidin-5-amine;

N-(methyl-N-(3-(2-methyl-5-(5-methyl-1H-pyrazol-3-ylamino)imidazo[1,2-f]pyrimidin-7-yl)phenyl)cyclo-prpanesulfonamide;

Cyclobutanecarboxylic acid 3-[5-(5-methyl-1H-pyrazol-3-ylamino)-imidazo[1,2-c]pyrimidin-7-yl]-benzylamide;

Azetidine-3-carboxylic acid 3-[5-(5-methyl-1H-pyrazol-3-ylamino)-imidazo[1,2-c]pyrimidin-7-yl]-benzylamide;

[7-(3-Aminomethyl-phenyl)-imidazo[1,2-c]pyrimidin-5-yl]-(5-methyl-1H-pyrazol-3-yl)-amine;

Cyclopropanesulfonic acid 3-[5-(5-methyl-1H-pyrazol-3-ylamino)-imidazo[1,2-c]pyrimidin-7-yl]-benzylamide;

(7-{3-[(Cyclopropylmethyl-amino)-methyl]-phenyl}-imidazo[1,2-c]pyrimidin-5-yl)-(5-methyl-1H-pyrazol-3-yl)-amine;

[7-(3-Methylaminomethyl-phenyl)-imidazo[1,2-c]pyrimidin-5-yl]-(5-methyl-1H-pyrazol-3-yl)-amine;

(5-Methyl-1H-pyrazol-3-yl)-[7-(1,2,3,4-tetrahydro-isoquinolin-7-yl)-imidazo[1,2-c]pyrimidin-5-yl]-amine;

[7-(2-Methanesulfonyl-1,2,3,4-tetrahydro-isoquinolin-7-yl)-imidazo[1,2-c]pyrimidin-5-yl]-(5-methyl-1H-pyrazol-3-yl)-amine;

[7-(3-Ethanesulfonylmethyl-phenyl)-2-methyl-imidazo[1,2-c]pyrimidin-5-yl]-(5-methyl-1H-pyrazol-3-yl)-amine;

[7-(3-Ethanesulfonylmethyl-phenyl)-2-methyl-imidazo[1,2-c]pyrimidin-5-yl]-(5-methyl-1H-pyrazol-3-yl)-amine;

{2-Methyl-7-[3-(3-methyl-pyridin-4-yl)-phenyl]-imidazo[1,2-c]pyrimidin-5-yl}-(5-methyl-1H-pyrazol-3-yl)-amine;

{7-[3-(3,5-Dimethyl-1H-pyrazol-4-yl)-phenyl]-2-methyl-imidazo[1,2-c]pyrimidin-5-yl}-(5-methyl-1H-pyrazol-3-yl)-amine;

{2-Methyl-7-[3-(3-methyl-3H-imidazol-4-yl)-phenyl]-imidazo[1,2-c]pyrimidin-5-yl}-(5-methyl-1H-pyrazol-3-yl)-amine;

(5-Methyl-1H-pyrazol-3-yl)-{2-methyl-7-[3-(1,3,5-trimethyl-1H-pyrazol-4-yl)-phenyl]-imidazo[1,2-c]pyrimidin-5-yl}-amine;

{7-[3-(3,5-Dimethyl-isoxazol-4-yl)-phenyl]-2-methyl-imidazo[1,2-c]pyrimidin-5-yl}-(5-methyl-1H-pyrazol-3-yl)-amine;

{7-[3-(5-Cyclopropyl-3-methyl-1H-pyrazol-4-yl)-phenyl]-2-methyl-imidazo[1,2-c]pyrimidin-5-yl}-(5-methyl-1H-pyrazol-3-yl)-amine;

(5-Methyl-1H-pyrazol-3-yl)-{2-methyl-7-[3-(thiazole-2-sulfonyl)-phenyl]-imidazo[1,2-c]pyrimidin-5-yl}-amine;

[7-(3-Dimethylaminomethyl-1-ethanesulfonyl-1H-indol-6-yl)-2-methyl-imidazo[1,2-c]pyrimidin-5-yl]-(5-methyl-1H-pyrazol-3-yl)-amine;

(5-Methyl-1H-pyrazol-3-yl)-{2-methyl-7-[3-(1H-pyrrolo[2,3-b]pyridin-4-yl)-phenyl]-imidazo[1,2-c]pyrimidin-5-yl}-amine;

(5-Methyl-1H-pyrazol-3-yl)-{2-methyl-7-[3-(S)-(pyrrolidine-3-sulfonyl)-phenyl]-imidazo[1,2-c]pyrimidin-5-yl}-amine;

{7-[3-(3-Amino-propane-1-sulfonyl)-phenyl]-2-methyl-imidazo[1,2-c]pyrimidin-5-yl}-(5-methyl-1H-pyrazol-3-yl)-amine;

[7-(3-Ethylsulfanyl-phenyl)-2-methyl-imidazo[1,2-c]pyrimidin-5-yl]-(5-methyl-1H-pyrazol-3-yl)-amine;

[7-(3-Ethanesulfinyl-phenyl)-2-methyl-imidazo[1,2-c]pyrimidin-5-yl]-(5-methyl-1H-pyrazol-3-yl)-amine;

N-(5-(2-methyl-5-(5-methyl-1H-pyrazol-3-ylamino)imidazo[1,2-c]pyrimidin-7-yl)-2-(2-morpholinoethoxy)phenyl)cyclopropanesulfonamide;

4-methyl-5-(3-(2-methyl-5-(5-methyl-1H-pyrazol-3-ylamino)imidazo[1,2-c]pyrimidin-7-yl)phenyl)thiazol-2-amine;

3-(2-methyl-5-(5-methyl-1H-pyrazol-3-ylamino)imidazo[1,2-c]pyrimidin-7-yl)-N-phenylbenzenesulfonamide;

N-(4-(5-(5-cyclopropyl-1H-pyrazol-3-ylamino)-2-((dimethylamino)methyl)imidazo[1,2-c]pyrimidin-7-ylthio)phenyl)acetamide;

(4-hydroxypiperidin-1-yl)(3-(5-(5-methyl-1H-pyrazol-3-ylamino)imidazo[1,2-c]pyrimidin-7-yl)phenyl)methanone;

N-isobutyl-3-(5-(5-methyl-1H-pyrazol-3-ylamino)imidazo[1,2-c]pyrimidin-7-yl)benzamide;

N-cyclopentyl-3-(5-(5-methyl-1H-pyrazol-3-ylamino)imidazo[1,2-c]pyrimidin-7-yl)benzamide;

3-(5-(5-methyl-1H-pyrazol-3-ylamino)imidazo[1,2-c]pyrimidin-7-yl)-N-(pyrrolidin-3-ylmethyl)benzamide;

3-(5-(5-methyl-1H-pyrazol-3-ylamino)imidazo[1,2-c]pyrimidin-7-yl)-N-(pyrrolidin-2-ylmethyl)benzamide;

N-isopropyl-3-(5-(5-methyl-1H-pyrazol-3-ylamino)imidazo[1,2-c]pyrimidin-7-yl)benzamide;

3-(5-(5-methyl-1H-pyrazol-3-ylamino)imidazo[1,2-c]pyrimidin-7-yl)-N-phenylbenzamide;

N-benzyl-3-(5-(5-methyl-1H-pyrazol-3-ylamino)imidazo[1,2-c]pyrimidin-7-yl)benzamide;

N-(4-(2-methyl-5-(5-methyl-1H-pyrazol-3-ylamino)imidazo[1,2-c]pyrimidin-7-ylthio)phenyl)cyclopropanecarboxamide;

3-(2-methyl-5-(5-methyl-1H-pyrazol-3-ylamino)imidazo[1,2-c]pyrimidin-7-yl)-N-(thiazol-2-yl)benzenesulfonamide;

N-(2-aminoethyl)-3-(2-methyl-5-(5-methyl-1H-pyrazol-3-ylamino)imidazo[1,2-c]pyrimidin-7-yl)benzenesulfonamide;

N-(4-(2-ethyl-5-(5-methyl-1H-pyrazol-3-ylamino)imidazo[1,2-c]pyrimidin-7-ylthio)phenyl)cyclopropanecarboxamide;

N-ethyl-N-(3-(2-isopropyl-5-(5-methyl-1H-pyrazol-3-ylamino)imidazo[1,2-c]pyrimidin-7-yl)phenyl)methanesulfonamide;

N-isopropyl-3-(5-(5-methyl-1H-pyrazol-3-ylamino)-2-(trifluoromethyl)imidazo[1,2-c]pyrimidin-7-yl)benzamide;

N-(5-methyl-1H-pyrazol-3-yl)-2,7-diphenylimidazo[1,2-c]pyrimidin-5-amine;

N-(4-(2-(hydroxymethyl)-5-(5-methyl-1H-pyrazol-3-ylamino)imidazo[1,2-c]pyrimidin-7-ylthio)phenyl)cyclopropanecarboxamide;

N-(3-(2-(hydroxymethyl)-5-(5-methyl-1H-pyrazol-3-ylamino)imidazo[1,2-c]pyrimidin-7-yl)phenyl)methanesulfonamide;
N-(4-(2-((dimethylamino)methyl)-5-(5-methyl-1H-pyrazol-3-ylamino)imidazo[1,2-c]pyrimidin-7-ylthio)phenyl)cyclopropanecarboxamide;
N-(4-(5-(5-methyl-1H-pyrazol-3-ylamino)-2-((methylamino)methyl)imidazo[1,2-c]pyrimidin-7-ylthio)phenyl)cyclopropanecarboxamide;
N-(4-(2-((2-hydroxyethylamino)methyl)-5-(5-methyl-1H-pyrazol-3-ylamino)imidazo[1,2-c]pyrimidin-7-ylthio)phenyl)cyclopropanecarboxamide;
[7-(3-Ethanesulfonyl-phenyl)-2-methyl-imidazo[1,2-c]pyrimidin-5-yl]-(5-methyl-1H-pyrazol-3-yl)-amine;
$N^7$-(1-Benzyl-piperidin-4-yl)-2-methyl-$N^5$-(5-methyl-1H-pyrazol-3-yl)-imidazo[1,2-c]pyrimidine-5,7-diamine;
[7-(3-Isopropoxy-phenyl)-2-methyl-imidazo[1,2-c]pyrimidin-5-yl]-(5-methyl-1H-pyrazol-3-yl)-amine;
[2-Methyl-7-(3-propoxy-phenyl)-imidazo[1,2-c]pyrimidin-5-yl]-(5-methyl-1H-pyrazol-3-yl)-amine;
[7-(3-Ethanesulfonyl-phenyl)-2-imidazol-1-ylmethyl-imidazo[1,2-c]pyrimidin-5-yl]-(5-methyl-1H-pyrazol-3-yl)-amine;
3-{3-[2-Methyl-5-(5-methyl-1H-pyrazol-3-ylamino)-imidazo[1,2-c]pyrimidin-7-yl]-phenyl}-propionic acid methyl ester;
3-{3-[2-Methyl-5-(5-methyl-1H-pyrazol-3-ylamino)-imidazo[1,2-c]pyrimidin-7-yl]-phenyl}-propionic acid;
5-[2-Methyl-5-(5-methyl-1H-pyrazol-3-ylamino)-imidazo[1,2-c]pyrimidin-7-yl]-thiophene-2-carboxylic acid cyclopropylamide;
[7-(1-Benzyl-1H-pyrazol-4-yl)-2-methyl-imidazo[1,2-c]pyrimidin-5-yl]-(5-cyclopropyl-1H-pyrazol-3-yl)-amine;
[7-(1-Benzyl-1H-pyrazol-4-yl)-2-methyl-imidazo[1,2-c]pyrimidin-5-yl]-(5-methyl-1H-pyrazol-3-yl)-amine;
N-{2-[2-Methyl-5-(5-methyl-1H-pyrazol-3-ylamino)-imidazo[1,2-c]pyrimidin-7-yl]-phenyl}-methanesulfonamide;
N-{2-[2-Methyl-5-(5-methyl-1H-pyrazol-3-ylamino)-imidazo[1,2-c]pyrimidin-7-yl]-phenyl}-acetamide;
[7-(1H-Indol-4-yl)-2-methyl-imidazo[1,2-c]pyrimidin-5-yl]-(5-methyl-1H-pyrazol-3-yl)-amine;
N-{4-[2-Methyl-5-(5-methyl-1H-pyrazol-3-ylamino)-imidazo[1,2-c]pyrimidin-7-ylsulfanyl]-phenyl}-acetamide;
[7-(2-Amino-phenyl)-2-methyl-imidazo[1,2-c]pyrimidin-5-yl]-(5-methyl-1H-pyrazol-3-yl)-amine;
[7-(1-Isobutyl-1H-pyrazol-4-yl)-2-methyl-imidazo[1,2-c]pyrimidin-5-yl]-(5-methyl-1H-pyrazol-3-yl)-amine;
4-{4-[2-Methyl-5-(5-methyl-1H-pyrazol-3-ylamino)-imidazo[1,2-c]pyrimidin-7-yl]-pyrazol-1-ylmethyl}-benzoic acid methyl ester;
(5-Cyclopropyl-1H-pyrazol-3-yl)-{7-[1-(3-methoxy-benzyl)-1H-pyrazol-4-yl]-2-methyl-imidazo[1,2-c]pyrimidin-5-yl}-amine;
(5-Cyclopropyl-1H-pyrazol-3-yl)-[2-methyl-7-(1-quinolin-8-ylmethyl-1H-pyrazol-4-yl)-imidazo[1,2-c]pyrimidin-5-yl]-amine;
3-{4-[5-(5-Cyclopropyl-1H-pyrazol-3-ylamino)-2-methyl-imidazo[1,2-c]pyrimidin-7-yl]-pyrazol-1-ylmethyl}-benzoic acid methyl ester;
(5-Cyclopropyl-1H-pyrazol-3-yl)-{7-[1-(4-methanesulfonyl-benzyl)-1H-pyrazol-4-yl]-2-methyl-imidazo[1,2-c]pyrimidin-5-yl}-amine;
(5-Cyclopropyl-1H-pyrazol-3-yl)-{7-[1-(4-methoxy-benzyl)-1H-pyrazol-4-yl]-2-methyl-imidazo[1,2-c]pyrimidin-5-yl}-amine;
(5-Cyclopropyl-1H-pyrazol-3-yl)-{7-[1-(2,3-dimethoxy-benzyl)-1H-pyrazol-4-yl]-2-methyl-imidazo[1,2-c]pyrimidin-5-yl}-amine;
(5-Cyclopropyl-1H-pyrazol-3-yl)-{7-[1-(3,5-dimethoxy-benzyl)-1H-pyrazol-4-yl]-2-methyl-imidazo[1,2-c]pyrimidin-5-yl}-amine;
[7-(1-Benzo[1,2,5]oxadiazol-5-ylmethyl-1H-pyrazol-4-yl)-2-methyl-imidazo[1,2-c]pyrimidin-5-yl]-(5-cyclopropyl-1H-pyrazol-3-yl)-amine;
2-{4-[5-(5-Cyclopropyl-1H-pyrazol-3-ylamino)-2-methyl-imidazo[1,2-c]pyrimidin-7-yl]-pyrazol-1-ylmethyl}-benzonitrile;
(5-Cyclopropyl-1H-pyrazol-3-yl)-[methyl-7-(1-pyridin-2-ylmethyl-1H-pyrazol-4-yl)-imidazo[1,2-c]pyrimidin-5-yl]-amine;
3-{4-[5-(5-Cyclopropyl-1H-pyrazol-3-ylamino)-2-methyl-imidazo[1,2-c]pyrimidin-7-yl]-pyrazol-1-ylmethyl}-N-ethyl-benzamide;
3-{4-[5-(5-Cyclopropyl-1H-pyrazol-3-ylamino)-2-methyl-imidazo[1,2-c]pyrimidin-7-yl]-pyrazol-1-ylmethyl}-benzonitrile;
3-{4-[5-(5-Cyclopropyl-1H-pyrazol-3-ylamino)-2-methyl-imidazo[1,2-c]pyrimidin-7-yl]-pyrazol-1-ylmethyl}-N-thiazol-2-yl-benzamide;
(5-Cyclopropyl-1H-pyrazol-3-yl)-[2-methyl-7-(1-phenethyl-1H-pyrazol-4-yl)-imidazo[1,2-c]pyrimidin-5-yl]-amine;
(5-Cyclopropyl-1H-pyrazol-3-yl)-{2-methyl-7-[1-(4-pyrazol-1-yl-benzyl)-1H-pyrazol-4-yl]-imidazo[1,2-c]pyrimidin-5-yl}-amine;
2-{4-[2-Methyl-5-(5-methyl-1H-pyrazol-3-ylamino)-imidazo[1,2-c]pyrimidin-7-yl]-pyrazol-1-ylmethyl}-benzonitrile;
(5-Cyclopropyl-1H-pyrazol-3-yl)-{2-methyl-7-[1-(3-pyrrol-1-yl-benzyl)-1H-pyrazol-4-yl]-imidazo[1,2-c]pyrimidin-5-yl}-amine;
N-Ethyl-4-{4-[2-methyl-5-(5-methyl-1H-pyrazol-3-ylamino)-imidazo[1,2-c]pyrimidin-7-yl]-pyrazol-1-ylmethyl}-benzamide;
(5-Cyclopropyl-1H-pyrazol-3-yl)-{2-methyl-7-[1-(3-nitro-benzyl)-1H-pyrazol-4-yl]-imidazo[1,2-c]pyrimidin-5-yl}-amine;
(5-Cyclopropyl-1H-pyrazol-3-yl)-{2-methyl-7-[1-(2-morpholin-4-yl-ethyl)-1H-pyrazol-4-yl]-imidazo[1,2-c]pyrimidin-5-yl}-amine;
{7-[1-(3-Amino-benzyl)-1H-pyrazol-4-yl]-2-methyl-imidazo[1,2-c]pyrimidin-5-yl}-(5-cyclopropyl-1H-pyrazol-3-yl)-amine;
{7-[1-(2,5-Dichloro-benzyl)-1H-pyrazol-4-yl]-2-methyl-imidazo[1,2-c]pyrimidin-5-yl}-(5-methyl-1H-pyrazol-3-yl)-amine;
{2-Methyl-7-[1-(2-piperidin-1-yl-ethyl)-1H-pyrazol-4-yl]-imidazo[1,2-c]pyrimidin-5-yl}-(5-methyl-1H-pyrazol-3-yl)-amine;
2-{4-[2-Methyl-5-(5-methyl-1H-pyrazol-3-ylamino)-imidazo[1,2-c]pyrimidin-7-yl]-pyrazol-1-yl}-N-phenyl-acetamide;
{2-Methyl-7-[1-(1-methyl-2-phenyl-ethyl)-1H-pyrazol-4-yl]-imidazo[1,2-c]pyrimidin-5-yl}-(5-methyl-1H-pyrazol-3-yl)-amine;
N-(3-{4-[5-(5-Cyclopropyl-1H-pyrazol-3-ylamino)-2-methyl-imidazo[1,2-c]pyrimidin-7-yl]-pyrazol-1-ylmethyl}-phenyl)-2-methoxy-acetamide;

Fluoro-2-{4-[2-methyl-5-(5-methyl-1H-pyrazol-3-ylamino)-imidazo[1,2-c]pyrimidin-7-yl]-pyrazol-1-ylmethyl}-benzonitrile;
(5-Methyl-1H-pyrazol-3-yl)-{2-methyl-7-[1-(2-trifluoromethoxy-benzyl)-1H-pyrazol-4-yl]-imidazo[1,2-c]pyrimidin-5-yl}-amine;
7-(5-chloro-2-methoxyphenyl)-N-(5-cyclopropyl-1H-pyrazol-3-yl)imidazo[1,2-f]pyrimidin-5-amine;
N-(2-hydroxyethyl)-2-methoxy-5-(2-methyl-5-(5-methyl-1H-pyrazol-3-ylamino)imidazo[1,2-c]pyrimidin-7-yl)benzenesulfonamide;
7-(4-methoxy-3-(morpholinosulfonyl)phenyl)-2-methyl-N-(5-methyl-1H-pyrazol-3-yl)imidazo[1,2-c]pyrimidin-5-amine;
7-(4-methoxy-3-(tetrahydro-2H-pyran-4-ylsulfonyl)phenyl)-2-methyl-N-(5-methyl-1H-pyrazol-3-yl)imidazo[1,2-c]pyrimidin-5-amine;
N-(2-(2-(dimethylamino)ethoxy)-5-(2-methyl-5-(5-methyl-1H-pyrazol-3-ylamino)imidazo[1,2-c]pyrimidin-7-yl)phenyl)cyclopropanesulfonamide;
N-(2-hydroxyethyl)-3-(2-methyl-5-(5-methyl-1H-pyrazol-3-ylamino)imidazo[1,2-c]pyrimidin-7-yl)benzenesulfonamide;
3-(2-methyl-5-(5-methyl-1H-pyrazol-3-ylamino)imidazo[1,2-c]pyrimidin-7-yl)-N-(2,2,2-trifluoroethyl)benzenesulfonamide;
7-(3-(2-(dimethylamino)ethoxy)phenyl)-2-methyl-N-(5-methyl-1H-pyrazol-3-yl)imidazo[1,2-c]pyrimidin-5-amine;
2-methyl-N-(5-methyl-1H-pyrazol-3-yl)-7-(3-(pyrrolidin-1-ylsulfonyl)phenyl)imidazo[1,2-c]pyrimidin-5-amine;
7-(3-(3-aminopyrrolidin-1-ylsulfonyl)phenyl)-2-methyl-N-(5-methyl-1H-pyrazol-3-yl)imidazo[1,2-c]pyrimidin-5-amine;
3-(2-methyl-5-(5-methyl-1H-pyrazol-3-ylamino)imidazo[1,2-c]pyrimidin-7-yl)-N-(3-(pyrrolidin-1-yl)propyl)benzenesulfonamide;
3-(2-methyl-5-(5-methyl-1H-pyrazol-3-ylamino)imidazo[1,2-c]pyrimidin-7-yl)-N-p-tolylbenzenesulfonamide;
N-(5-methyl-1H-pyrazol-3-yl)-7-(3-(4-methylpiperazin-1-ylsulfonyl)phenyl)imidazo[1,2-c]pyrimidin-5-amine;
7-(1-(ethylsulfonyl)-1H-indol-6-yl)-2-methyl-N-(5-methyl-1H-pyrazol-3-yl)imidazo[1,2-c]pyrimidin-5-amine;
N-(6-(2-methyl-5-(5-methyl-1H-pyrazol-3-ylamino)imidazo[1,2-c]pyrimidin-7-yl)-1H-indol-3-yl)ethanesulfonamide;
(3-(7-phenylimidazo[1,2-c]pyrimidin-5-ylamino)-1H-pyrazol-5-yl)methanol;
7-(3-(5-amino-2-methylthiophen-3-yl)phenyl)-2-methyl-N-(5-methyl-1H-pyrazol-3-yl)imidazo[1,2-c]pyrimidin-5-amine;
7-(3-(Ethylsulfonyl)phenyl)-N-(5-methyl-1H-pyrazol-3-yl)imidazo[1,2-c]pyrimidin-5-amine;
2-Methyl-N-(5-methyl-1H-pyrazol-3-yl)-7-(3-(piperazin-1-ylmethyl)phenyl)imidazo[1,2-c]pyrimidin-5-amine;
(S)-1-(3-(2-Methyl-5-(5-methyl-1H-pyrazol-3-ylamino)imidazo[1,2-c]pyrimidin-7-yl)phenylsulfonyl)pyrrolidin-3-ol;
2-Methyl-N-(5-methyl-1H-pyrazol-3-yl)-7-(3-(3-(methylamino)pyrrolidin-1-ylsulfonyl)phenyl)imidazo[1,2-c]pyrimidin-5-amine;
2-Methyl-N-(5-methyl-1H-pyrazol-3-yl)-7-(3-(piperidin-1-ylmethyl)phenyl)imidazo[1,2-c]pyrimidin-5-amine;
N,4-Dimethyl-5-(3-(2-methyl-5-(5-methyl-1H-pyrazol-3-ylamino)imidazo[1,2-c]pyrimidin-7-yl)phenyl)thiazol-2-amine;
2-Methyl-N-(5-methyl-1H-pyrazol-3-yl)-7-(3-(piperazin-1-ylsulfonyl)phenyl)imidazo[1,2-c]pyrimidin-5-amine;
3-(2-Methyl-5-(5-methyl-1H-pyrazol-3-ylamino)imidazo[1,2-c]pyrimidin-7-yl)-N-(pyrrolidin-3-yl)benzenesulfonamide;
N-Cyclopropyl-2-(3-(7-phenylimidazo[1,2-c]pyrimidin-5-ylamino)-1H-pyrazol-5-yl)acetamide;
N-(4-(5-(5-cyclopropyl-1H-pyrazol-3-ylamino)-2-(methoxymethyl)imidazo[1,2-c]pyrimidin-7-ylthio)phenyl)-2-methoxyacetamide;
Ethyl 2-(4-(5-(5-methyl-1H-pyrazol-3-ylamino)imidazo[1,2-c]pyrimidin-7-ylthio)phenylamino)-2-oxoacetate;
N-(4-(5-(5-methyl-1H-pyrazol-3-ylamino)imidazo[1,2-c]pyrimidin-7-ylthio)phenyl)tetrahydrofuran-2-carboxamide;
N-(4-(2-methyl-5-(5-methyl-1H-pyrazol-3-ylamino)imidazo[1,2-c]pyrimidin-7-ylthio)phenyl)furan-2-carboxamide;
(S)—N-(4-(2-methyl-5-(5-methyl-1-pyrazol-3-ylamino)imidazo[1,2-c]pyrimidin-7-ylthio)phenyl)tetrahydrofuran-2-carboxamide;
N-(4-(2-methyl-5-(5-methyl-1H-pyrazol-3-ylamino)imidazo[1,2-c]pyrimidin-7-ylthio)phenyl)isoxazole-5-carboxamide;
5-methyl-N-(4-(2-methyl-5-(5-methyl-1H-pyrazol-3-ylamino)imidazo[1,2-c]pyrimidin-7-ylthio)phenyl)isoxazole-3-carboxamide;
4-methyl-N-(4-(2-methyl-5-(5-methyl-1H-pyrazol-3-ylamino)imidazo[1,2-c]pyrimidin-7-ylthio)phenyl)oxazole-5-carboxamide;
N-(4-(5-(5-cyclopropyl-1H-pyrazol-3-ylamino)-2-methylimidazo[1,2-c]pyrimidin-7-ylthio)phenyl)-5-methylfuran-2-carboxamide;
N-(4-(5-(5-cyclopropyl-1H-pyrazol-3-ylamino)-2-methylimidazo[1,2-c]pyrimidin-7-ylthio)phenyl)-1,5-dimethyl-1H-pyrazole-3-carboxamide;
N-(4-(5-(5-cyclopropyl-1H-pyrazol-3-ylamino)-2-methylimidazo[1,2-c]pyrimidin-7-ylthio)phenyl)-1,3-dimethyl-1H-pyrazole-5-carboxamide;
N1-(4-(5-(5-cyclopropyl-1H-pyrazol-3-ylamino)-2-methylimidazo[1,2-c]pyrimidin-7-ylthio)phenyl)-N2-ethyl-N2-methyloxalamide;
N1-(4-(5-(5-cyclopropyl-1H-pyrazol-3-ylamino)-2-methylimidazo[1,2-c]pyrimidin-7-ylthio)phenyl)-N2-(thiazol-2-yl)oxalamide;
N7,2-dimethyl-N5-(5-methyl-1H-pyrazol-3-yl)-N7-(1-methylpyrrolidin-3-yl)imidazo[1,2-c]pyrimidine-5,7-diamine;
N-(5-cyclopropyl-1H-pyrazol-3-yl)-2-(ethoxymethyl)-7-(3-(ethylsulfonyl)phenyl)imidazo[1,2-c]pyrimidin-5-amine;
N1-(3-(5-(5-cyclopropyl-1H-pyrazol-3-ylamino)-2-methylimidazo[1,2-c]pyrimidin-7-yl)phenyl)-N4-ethylsuccinamide; and
N-(5-cyclopropyl-1H-pyrazol-3-yl)-7-(1-isopentyl-1H-pyrazol-4-yl)-2-methylimidazo[1,2-c]pyrimidin-5-amine; or a pharmaceutically acceptable salt of each of the above-mentioned compounds.

8. A pharmaceutical composition, consisting of a compound of claim 1, and at least one pharmaceutical excipient.

* * * * *